United States Patent [19]
Galemmo, Jr. et al.

[11] Patent Number: 6,060,462
[45] Date of Patent: May 9, 2000

[54] ELECTROPHILIC PEPTIDE ANALOGS AS INHIBITORS OF TRYPSIN-LIKE ENZYMES

[75] Inventors: Robert Anthony Galemmo, Jr., Collegeville, Pa.; Matthew Mark Abelman, Solana Beach, Calif.; Eugene Cruz Amparo, West Chester, Pa.; John Matthew Fevig, Lincoln University, Pa.; Robert Madara Knabb, Avondale, Pa.; William Henry Miller, Schwenksville, Pa.; Gregory James Pacofsky, Raleigh, N.C.; Patricia Carol Weber, Yardley, Pa.; Joseph Cacciola, Newark, Del.

[73] Assignee: DuPont Pharmaceuticals Company, Wilmington, Del.

[21] Appl. No.: 08/904,881

[22] Filed: Aug. 1, 1997

Related U.S. Application Data

[62] Division of application No. 08/642,817, May 3, 1996, abandoned, which is a continuation of application No. 08/318,028, Oct. 4, 1994, abandoned, which is a continuation-in-part of application No. 08/139,445, Oct. 20, 1993, abandoned.

[51] Int. Cl.$^7$ .............................. A61K 31/69; C07F 5/04; C07F 5/02
[52] U.S. Cl. ............................. 514/64; 546/13; 548/110; 549/4; 558/5; 558/288; 558/298; 562/7
[58] Field of Search ................. 514/64; 546/13; 548/110; 549/4; 558/5, 288, 298; 562/7

[56] References Cited

U.S. PATENT DOCUMENTS

| | | |
|---|---|---|
| 4,499,082 | 2/1985 | Shenvi et al. . |
| 5,169,841 | 12/1992 | Kleeman et al. . |
| 5,187,157 | 2/1993 | Kettner et al. . |
| 5,252,566 | 10/1993 | Shuman . |

FOREIGN PATENT DOCUMENTS

| | | |
|---|---|---|
| B52881/86 | 7/1986 | Australia . |
| 195212A2 | 9/1986 | European Pat. Off. . |
| 363284A2 | 4/1990 | European Pat. Off. . |
| 364344A2 | 4/1990 | European Pat. Off. . |
| 0369391A2 | 5/1990 | European Pat. Off. . |
| 417721A2 | 3/1991 | European Pat. Off. . |
| 471651A2 | 2/1992 | European Pat. Off. . |
| WO 07869 | 5/1992 | WIPO . |
| WO 92/12140 | 7/1992 | WIPO . |

OTHER PUBLICATIONS

Gesellchen and Shuman J. Med. Chem 36, 314–319 (1993).

Balasubramanian, et al. (J. Med. Chem 36, 300, (1993)).

*Primary Examiner*—Michael G. Ambrose
*Attorney, Agent, or Firm*—Norbert F. Reinert

[57] ABSTRACT

This invention relates to electrophilic dipeptide analogs conjugated to an N,N-disubstituted α-amino acid as inhibitors of trypsin-like serine protease enzymes.

12 Claims, No Drawings

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 1

Leu Ser Asn Leu Ser Asn Leu Ser Asn Leu Ser Asn Gly
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 2

Leu Ser Asn Leu Ser Asn Leu Ser Asn Leu Ser Asn Gly
 1               5                  10

<210> SEQ ID NO 3
<211> LENGTH: 13
<212> TYPE: PRT
<213> ORGANISM: Artificial Sequence

```
<220> FEATURE:
<223> OTHER INFORMATION: Description of Artificial Sequence:Synthetic
      Peptide

<400> SEQUENCE: 3

Leu Ser Asn Leu Ser Asn Leu Ser Asn Leu Ser Asn Gly
 1               5                  10
```

ELECTROPHILIC PEPTIDE ANALOGS AS INHIBITORS OF TRYPSIN-LIKE ENZYMES

CROSS-REFERENCE TO EARLIER FILED APPLICATIONS

This application is a division of U.S. patent application Ser. No. 08/642,817 filed May 3, 1996, now abandoned, which is a continuation of U.S. patent application Ser. No. 08/318,028 filed Oct. 4, 1994, now abandoned, which is continuation-in-part of U.S. patent application Ser. No. 08/139,445 filed Oct. 20, 1993 now abandoned.

FIELD OF THE INVENTION

This invention relates generally to electrophilic peptide analogs as inhibitors of trypsin-like serine proteases. These compounds are dipeptides in which an electrophilic derivative of an α-amino acid is conjugated with an N,N-disubstituted α-amino acid. The N,N-disubstituted α-amino acid conjugates of the electrophilic amino acid analog are derivatives of an amino acid where the α-amino group is alkylated and acylated or diacylated to give alicyclic or cyclic substituents. The electrophilic functional groups used to derivatize these peptide analogs are: boronic acids and their esters, α-mono- and α-perhaloketones, aldehydes, vicinal di- and tricarbonyl compounds, α-mono- and α,α-dihalo-β-ketoesters.

BACKGROUND OF THE INVENTION

Electrophilic tripeptide analogs containing the ((D-phenylalanyl)prolyl)-arginyl-sequence are well known as effective inhibitors of the trypsin-like serine protease thrombin. H-(D)Phe-Pro-ArgCH$_2$Cl was first reported by Kettner and Shaw (*Thromb. Res.* 14, 969 (1979)) to be a selective but irreversible inhibitor of human thrombin. A number of studies looking for alternatives to the electrophilic P$_1$ argininechloromethylketones that would yield a reversible protease inhibitor have been reported. Bajuez et al. (*Folia Haematol.* 109, s. 16 (1982)) found the corresponding aldehyde, D-phenylalanyl-prolyl-arginal, to be a reversible thrombin inhibitor with a K$_i$=75 nM for human thrombin. The nitrile analog, D-phenylalanyl-prolyl-NHCH((CH$_2$)$_3$NHC(=NH)NH$_2$)—CN, was found to be substantially less potent with a K$_i$=700 nM (Kaiser et al., *Pharmazie* 46, 128 (1991)). A retroamide inhibitor, with the D-phenylalanyl-prolyl-sequence and 2-(4-guanidinophenylalanyl)-N-acetyl-2,2-difluoroethylamine substituting for an electrophilic arginine derivative, is a good inhibitor with a K$_i$ of 70 nM for thrombin (Altenburger and Schirlin, *Tetrahedron Lett.* 32, 7255 (1991)). Cheng et al. claim that the substitution of racemic diphenyl 1-amino-4-methoxybutylphosphonate for an electrophilic arginine derivative gives very good inhibitors with a K$_i$=4.8 nM (*Tetrahedron Lett.* 32, 7333 (1991)). Iwanowicz et al. (*Bioorgan. Med. Chem. Lett.* 2, 1607 (1992)) has studied the efficacy of (D-phenylalanine)prolyl-conjugated to —NHCH[(CH$_2$)$_4$NH$_2$]CH(OH)CO$_2$Me) and —NHCH[(CH$_2$)$_4$NH$_2$]C(=O)CO$_2$Me derivatives. The most effective inhibitor of human thrombin reported to date is the boropeptide acetyl-D-phenylalanyl-prolyl-boro arginine with a K$_i$=0.041 nM (Kettner et al., *J. Biol. Chem.* 265, 18289 (1990)).

Walker et al. (*Biochem. J.* 230, 645 (1985)) published a comparative study of irreversible thrombin inhibitors based on the D-pherlylalarlyl-prolyl-argininyl sequence confirming the earlier report by Kettner and Shaw (1979). H-(D)Phe-Pro-ArgCH$_2$Cl was found to be the most effective inhibitor (K$_i$=25 nM) while replacing the D-phenylalanine with 4-amino-D-phenylalanine or ω-benzoyl-D-lysine gave less active analogs. Compounds in development include -(prolyl) arginal derivatives with a variety of unusual P$_3$ amino acids including D-N-methylphenylglycine, Boc-D-fluorophenylglycine as well as constrained cyclized derivatives of D-phenylglycine and D-phenylalanine (Shuman et. al., *J. Med. Chem.* 36, 314 (1993)). Balasubramanian et al. (*J. Med. Chem.* 36, 300 (1993)) has reported an extensive study of replacements for the P$_3$ D-phenylalanine of D-phenylalanyl-prolyl-arginal and found the dihydrocinnamoyl group to be effective, although somewhat less potent.

Patent disclosures in this area have centered around suitably protected peptides composed of natural and unnatural amino acids. In U.S. Pat. No. 5,187,157 DuPont Merck has disclosed peptides comprised of C-terminal boronic acid derivatives of lysine, ornithine and arginine as reversible inhibitors of trypsin-like serine proteases, as well as a series of boropeptides active as elastase inhibitors in U.S. Pat. No. 4,499,082. In European Patent Application EP 471 651 A2 Sandoz disclosed borolysine and boroarginine peptide analogs containing at least one unnatural hydrophobic α-amino acid substituted with groups such as the trimethylsilyl- or naphthyl-. In U.S. Pat. No. 5,106,948 was disclosed a series of boropeptides that are effective as cytotoxic agents. In PCT Application WO 92/07869, Thrombosis Research Institute has disclosed tripeptide analogs containing a P$_2$ proline and an unnatural disubstituted amino acid at P$_3$. A variety of electrophilic and non-electrophilic α-amino acid analogs were claimed as suitable P$_1$ substituents. Tripeptide antithrombotic agents limited to α-alkyl and α-aryl or heteroaryl substituted glycines at P$_3$ conjugated to -(prolyl)arginal were been disclosed by Lilly (European Patent Application EP 479 489 A2). Marion Merrell Dow disclosed a series of activated electrophilic ketone analogs of peptidase substrates useful for inhibiting serine-, carboxylic acid- and metallo-proteolytic enzymes; compounds are peptides composed of suitably protected α-amino acids conjugated to an electrophilic ketone derivative of an α-amino acid (European Patent Applications EP 417 721 A2, EP 364 344 A2, EP 363 284 A2, EP 195 212 A2). Astra has disclosed a series of α-((trifluoroethyl)oxymethyl)-arginine tripeptides (European Patent Application EP 0 530 167 A). Georgia Tech Research Corporation disclosed peptidyl ketoamides, -ketoacids and -ketoesters as inhibitors of serine and cysteine proteases (WO 92/12140). Boehringer Ingelheim disclosed a series of trifluoromethyl- and α,α-difluoromethyl-β-ketoesterpeptide derivatives as elastase inhibitors (EP 0 369 391 A2).

The present invention concerns dipeptides which contain an electrophilic derivative of an α-amino acid at P$_1$ conjugated with an N,N-disubstituted α-amino acid at P$_2$. The electrophilic functional groups used to derivatize the P$_1$ amino acid analog are: boronic acids and their esters, α-mono- and α-perhaloketones, vicinal di- and tricarbonyl compounds, and α,α-dihalo-g-ketoesters. The N,N-disubstituted α-amino acids are derivatives of an amino acid other than proline where the α-amino group is alkylated and acylated or diacylated to give alicyclic or cyclic substituents. As a result these compounds are found to have the advantage of an improved toxicological profile as well as the selectivity and inhibition activity for thrombin required for a useful therapeutic agent.

SUMMARY OF THE INVENTION

[1] There is provided by this invention a compound of the formula (I):

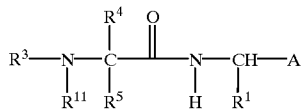
(I)

or a pharmaceutically acceptable salt, hydrate or prodrug thereof, wherein:

$R^1$ is
a) -($C_1$–$C_{12}$ alkyl)-X,
b) -($C_1$–$C_{12}$ alkenyl)-X, or
c)

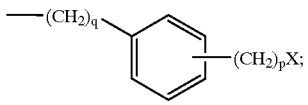

X is
a) halogen,
b) —CN,
c) —$NO_2$,
d) —$CF_3$,
e) —$NH_2$,
f) —$NHOR^2$,
g) —NHC(=NH)$R^2$,
h) —NHC(=NH)NHOH,
i) —NHC—(=NH)$NHNH_2$,
j) —NHC(=NH) NHCN,
) —NHC(=NH)$NHR^2$,
j) —NHC(=NH)$NHCOR^2$,
k) —C(=NH)$NHR^2$,
l) —C(=NH)$NHCOR^2$,
m) —C(=C)$NHR^2$,
n) —$CO_2R^2$,
o) —$OR^2$,
p) —$OCF_3$,
q) —S(O)$_vR^2$,
r) —SC(=NH)$NHR^2$, or
s) —SC(=NH)NHC(=O)$R^2$;

$R^2$ is
a) hydrogen, or
b) $C_1$–$C_4$ alkyl;

$R^3$ is:
a) —C((=O)-aryl,
b) —C(=O)—$(CH_2)_p$—$CR^6R^7$—$(CH_2)_q$-aryl,
c) —C(=O)-($C_2$–$C_5$ alkenyl)-aryl,
d) —C(=O)—W—$CR^8R^9$-aryl, with the proviso that W cannot be a bivalent oxygen atom,
e) —C(=O)—$CR^8R^9$—W—$(CH_2)_r$-aryl, with the proviso that W cannot be —$NR^4$— or —NC(=O)$R^4$—,
f) —C(=O)-heteroaryl,
g) —C(=O)—$(CH_2)_p$—$CR^6R^7$—$(CH_2)_q$- heteroaryl,
h) —C(=O)-($C_2$–$C_5$ alkenyl)-heteroaryl,
i) —C(=O)—W—$CR^8R^9$-heteroaryl,
j) —C(=O)—$CR^8R^9$—W—$(CH_2)_r$-heteroaryl, with the proviso that W cannot be —$NR^4$— or —NC(=O)$R^4$—,
k) —C(=O)-heterocycle,
l) —C(=O)—$(CH_2)_p$—$CR^6R^7$—$(CH_2)_q$- heterocycle,
m) —C((=O)-($C_2$–$C_5$ alkenyl)-heterocycle,
n) —C(=O)—W—$CR^8R^9$-heterocycle,
o) —C(=O)—$CR^8R^9$—W—$(CH_2)_r$-heterocycle, with the proviso that W cannot be —$NR^4$— or —$NCOR^4$—,
p) —C(=O)—$(CH_2)_t$-adamantyl,
q) —C(=O)—$(CH_2)_t$-($C_5$–$C_7$ cycloalkyl)
r) —C(=O)—$(CH_2)_t$—W—($C_5$–$C_7$ cycloalkyl), s)

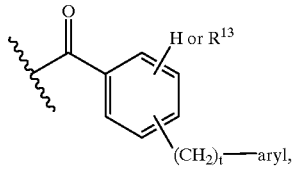

wherein aryl is limited to phenyl, t)

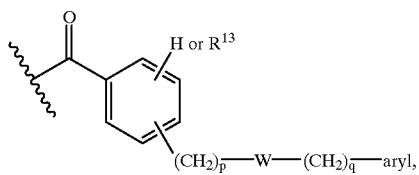

wherein aryl is limited to phenyl, u)

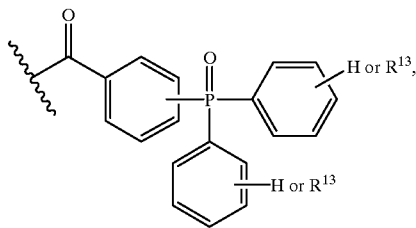

v)

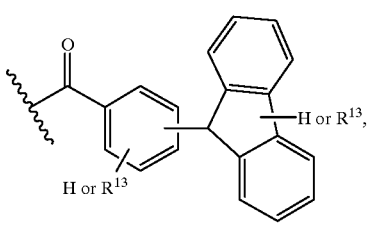

w)

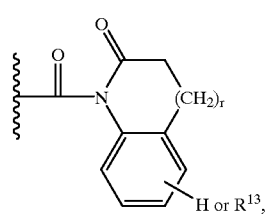

x) 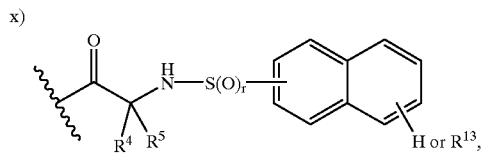
with the proviso that $R^{13}$ cannot be $-N(C_1-C_4$ alkyl$)_2$ when A is $-C(=O)R^{14}$,
y) 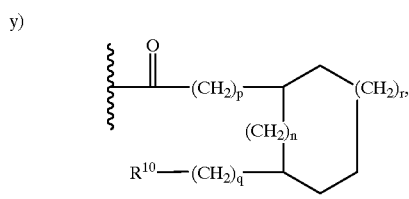
z) 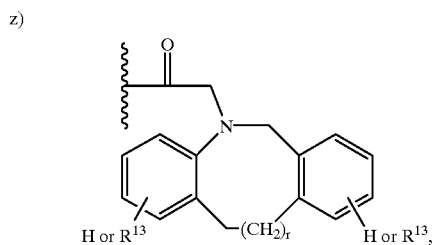
aa) 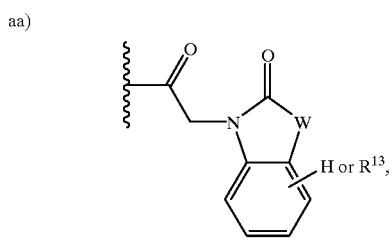
bb) 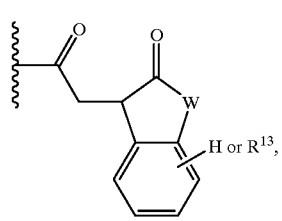
cc) 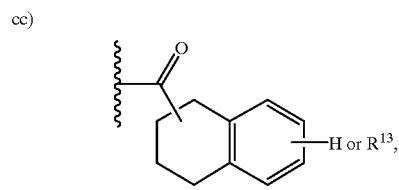
dd) 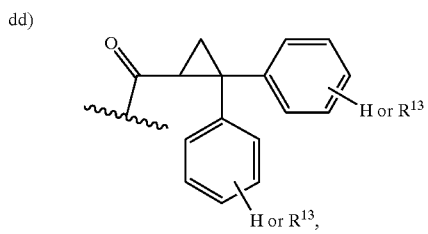
ee) 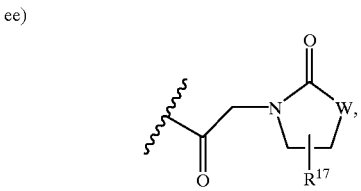
ff) 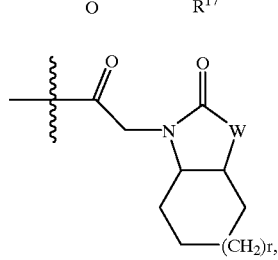
gg) 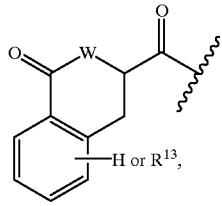
hh) 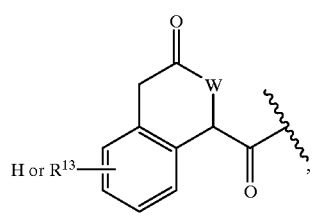
ii) 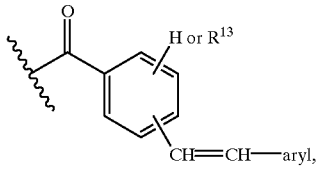
wherein aryl is limited to phenyl;
jj) $-(C(=O)-(CR^8R^9)-NR^{11'})_v-R^{11}$;
kk) $-(C(=O)-(CR^8R^9)-NR^{11'})_v-C(=O)R^{11}$;
ll) $-(C(=O)-(CR^8R^9)-NR^{11'})_v-C(=S)R^{11}$;
mm) 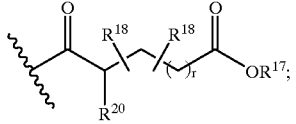
nn) 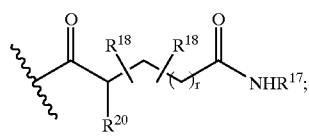
oo) 

pp)

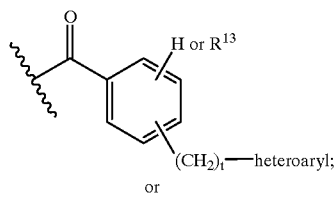

or qq)

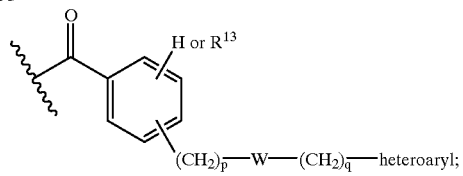

$R^4$ and $R^5$ are independently selected at each occurrence from the group consisting of:
a) hydrogen,
b) $C_1$–$C_4$ alkyl,
c) -($C_1$–$C_4$ alkyl)-aryl, or
d) $C_5$–$C_7$ cycloalkyl;

$R^6$, $R^7$, $R^8$ and $R^9$ are independently selected at each occurrence from the group consisting of:
a) hydrogen,
b) $C_1$–$C_4$ alkyl,
c) $C_1$–$C_4$ alkoxy,
d) aryl,
e) -($C_1$–$C_4$ alkyl)-aryl,
f) -($C_1$–$C_4$ alkyl)-heterocycle,
g) —O-aryl,
h) —$(CH_2)_p$—$CO_2R^4$,
i) $R^6$ and $R^7$ can be taken together to form a ($C_2$–$C_7$) alkyl, or
j) $R^8$ and $R^9$ can be taken together to form a ($C_2$–$C_7$) alkyl;

$R^{10}$ is:
phenyl, wherein phenyl is optionally substituted with one to three substituents selected from the group consisting of halogen, $C_1$–$C_4$ alkyl, $C_1$–$C_4$ alkoxy, $C_7$–$C_{15}$ alkylaryl, $C_7$–$C_{11}$ alkoxyaryl, methylenedioxy, —$NO_2$, —$CF_3$, —SH, —S(O)$_r$—($C_1$–$C_4$ alkyl), CN, —OH, —$NH_2$, —NH($C_1$–$C_4$ alkyl), —N($C_1$–$C_4$ alkyl)$_2$, —NHCOR$^4$, —$(CH_2)_p$—$CO_2R^4$, —C(=NH)NHR$^4$), —NHC(=NR$^4$)R$^4$, —NHC(=NH)NHR$^4$;

$R^{11}$ is:
a) $C_1$–$C_4$ alkyl,
b) $C_3$–$C_6$ cycloalkyl,
c) —OR$^4$,
d) —NR$^{15}$R$^{16}$,
e) —NC(=O)R$^{15}$R$^{16}$,
f) —NR$^{15}$C(=O)OR$^4$,
g) aryl,
h) -($C_1$–$C_4$ alkyl)-aryl,
i) heteroaryl,
j) -($C_1$–$C_4$ alkyl)-heteroaryl,
k) -($C_1$–$C_4$ alkyl)-$CO_2R^4$,
l) heterocycle,
m) -($C_1$–$C_4$ alkyl)heterocycle, n)

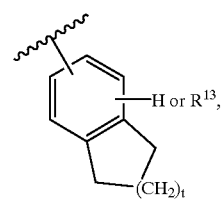

o)

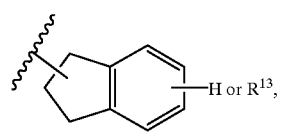

p)

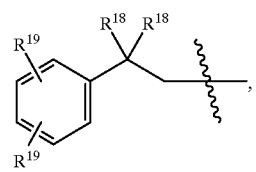

q)

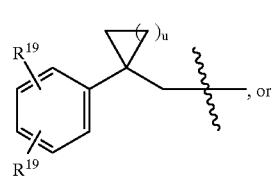

r)

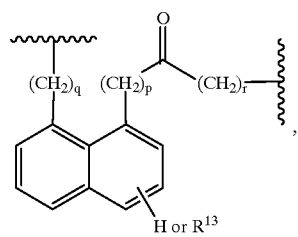

$R^3$ arid $R^{11}$, when taken together to form a ring bonded to the nitrogen:

a)

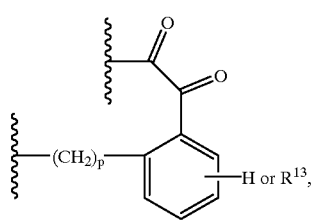

b)

c)

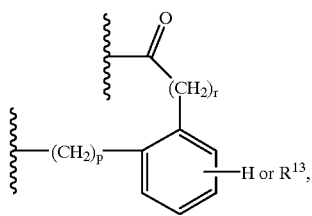

d)

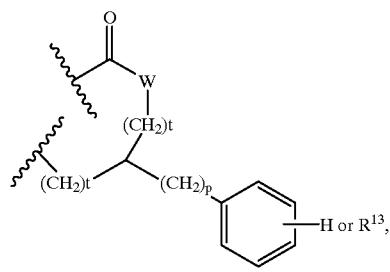

e)

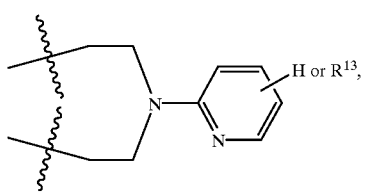

f)

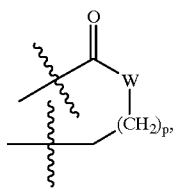

g)

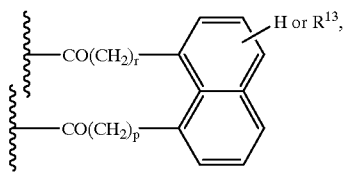

h)

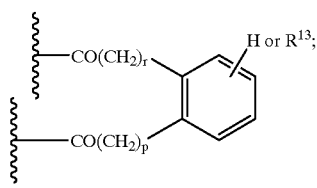

$R^{11'}$ is independently selected at each occurrence from the group consisting of:
a) hydrogen;
b) $C_1$–$C_4$ alkyl
c) —$OR^4$
d) —$NR^{15}R^{16}$
e) —NC(=O)$R^{15}R^{16}$
f) —$NR^{15}$C(=O)$OR^4$
g) aryl,
h) -($C_1$–$C_4$ alkyl)-aryl,
i) heteroaryl,
j) -($C_1$–$C_4$ alkyl)-heteroaryl,
k) -($C_1$–$C_4$ alkyl)—$CO_2R^4$,
l) heterocycle,
m) -($C_1$–$C_4$ alkyl)heterocycle, $R^{13}$ is independently selected at each occurrence from the group consisting of:
a) hydrogen
b) halogen,
c) $C_1$–$C_4$ alkyl,
d) $C_1$–$C_4$ alkoxy,
e) methylenedioxy,
f) —$NO_2$,
g) —$CF_3$,
h) —SH,
i) —S(O)$_r$—($C_1$–$C_4$ alkyl),
j) —CN,
k) —OH,
l) —$NH_2$,
m) —NH($C_1$–$C_4$ alkyl),
n) —N($C_1$–$C_4$ alkyl)$_2$,
o) —NHC(=O)$R^4$, or
p) —($CH_2$)$_p$—$CO_2R^4$;
q) —C(=NH)$NHR^4$
r) —NHC(=$NR^4$)$R^4$
s) —NHC(=NH)$NHR^4$ $R^{14}$ is:
a) —$CF_3$,
b) —$CHF_2$,
c) —$CH_2F$,
d) —$CH_2Cl$,
e) —C(=O)$OR^4$,
f) —C(=O)$NR^{15}R^{16}$,
g) —C(=O)$R^4$,
h) —C(=O)$COOR^4$,
i) —C(=O)C(=O)$NR^{15}R^{16}$,
j) —C(=O)C(=O)$R^4$
k) —$CY^3Y^4COOR^4$,
l) —$CY^3Y^4$C(=O)$NR^{15}R^{16}$, or
m) —$CY^3Y^4$C(=O)$R^4$;

$R^{15}$ and $R^{16}$ are independently selected at each occurrence from the group consisting of:
a) hydrogen,
b) $C_1$–$C_4$ alkyl,
c) -($C_1$–$C_4$ alkyl)-aryl, where aryl is defined above,
d) $C_5$–$C_7$ cycloalkyl, or
e) phenyl, unsubstituted or substituted by $R^{13}$,
f) $C_1$–$C_4$ alkoxy;

$R^{15}$ and $R^{16}$ taken together to form a ring can also include:

a)

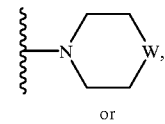

or b)

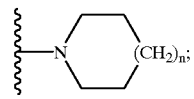

$R^{17}$ is:
a) hydrogen,
b) $C_1$–$C_4$ alkyl,
c) aryl, wherein aryl is defined above,
d) -($C_1$–$C_4$ alkyl)-aryl, wherein aryl is defined above, or e) $C_5$–$C_7$ cycloalkyl;

$R^{18}$ is:
a) hydrogen,
b) -($C_1$–$C_5$) alkyl, or
c) -($C_1$–$C_5$) haloalkyl,
d) -($C_1$–$C_5$) alkoxy;

$R^{19}$ is:
a) hydrogen,
b) -($C_1$–$C_5$) alkyl,
c) halo, or
d) -($C_1$–$C_5$) haloalkyl,
e) —$NO_2$,
f) —$NR^4R^5$,
g) —CN,
h) -($C_1$–$C_5$) alkoxy;

$R^{20}$ is
a) hydrogen; or
b) —$N^2$ with amine protecting;

A is:
a) —$BY^1Y^2$, or
b) —C(=O)$R^{14}$,
c) C(OH) $R^{14}R^{18}$;

W is:
a) —O—,
b) —S(O)$_r$—,
c) —$NR^4$—, or
d) —NC(=O)$R^4$—;

$Y^1$ and $Y^2$ are:
a) —OH,
b) —F,
c) —$NR^4R^5$,
d) $C_1$–$C_8$ alkoxy, or
when taken together $Y^1$ and $Y^2$ form:
e) a cyclic boron ester where said chain or ring contains from 2 to 20 carbon atoms and, optionally, 1–3 heteroatoms which can be N, S, or O,
f) a cyclic boron amide where said chain or ring contains from 2 to 20 carbon atoms and, optionally, 1–3 heteroatoms which can be N, S, or O,
g) a cyclic boron amide-ester where said chain or ring contains from 2 to 20 carbon atoms and, optionally, 1–3 heteroatoms which can be N, S, or O;

$Y^3$ and $Y^4$ are
a) —OH or
b) —F;

n is 0 or 1;
p is 0 to 3;
q is 0 to 4;
r is 0 to 2;
t is 1 to 3;
u is 1 to 4;
v is 1 to 17.

Specifically preferred compounds of this invention include:

Hydrocinnamoyl-[N-(Phenethyl)-Gly]-boroOrn-C10H16 HCl
Hydrocinnamoyl-[N-(Phenethyl)-Gly]-boroOrn(CH=NH)-C10H16 HCl
Hydrocinnamoyl-[N-(Phenethyl)-Gly]-boroOrn(CH=NH)—OH HCl
Hydrocinnamoyl-[N-(Phenethyl)-Gly]-boroArg(CH3)-C10H16 HCl
Hydrocinnamoyl-[N-(N(CH3)2)-Gly]-boroLys-C10H16 HCl
Hydrocinnamoyl-[N-(N(CH3)2)-Gly]-boroLys—OH HCl
Hydrocinnamoyl-[N-(N(CH3)2)-Gly]-boroOrn-C10H16 HCl
Hydrocinnamoyl-[N-(N(CH3)2)-Gly]-boroOrn(CH=NH)-C10H16 HCl
Methanesulfonyl-Sar-[N-(Phenethyl)-Gly]-boroLys-C10H16 HCl
Methanesulfonyl-Sar-[N-(Phenethyl)-Gly]-boroLys—OH HCl
Methanesulfonyl-Gly-[N-(Phenethyl)-Gly]-boroLys-C10H16 HCl
Hydrocinnamoyl-[N-(3-(Trifluoromethyl)-Phenethyl)-Gly]-boroLys-C10H16 HCl
Hydrocinnamoyl-[N-(3-(Trifluoromethyl)-Phenethyl)-Gly]-boroLys—OH HCl
Hydrocinnamoyl-[N-(3-(Methyl)-Phenethyl)-Gly]-boroLys-C10H16 HCl
Hydrocinnamoyl-[N-(3-(Methyl)-Phenethyl)-Gly]-boroLys—OH HCl
Succinyl-[N-(3-(Methyl)-Phenethyl)-Gly]-boroLys-C10H16 HCl
Hydrocinnamoyl-[N-(2,2-(Dimethyl)-Phenethyl)-Gly]-boroLys—OH HCl
Hydrocinnamoyl-[N-(2—(Cyclopropyl)-Phenethyl)-Gly]-boroLys-C10H16 HCl
Hydrocinnamoyl-[N-(2—(Cyclopropyl)-Phenethyl)-Gly]-boroLys—OH HCl
Hydrocinnamoyl-[N-(2—(Cyclopropyl)-Pheriethyl)-Gly]-boroOrn(CH=NH)—OH HCl
Hydrocinnamoyl-[N-(2,2-(Diethyl)-Phenethyl)-Gly]-boroLys-C10H16 HCl
Hydrocinnamoyl-Sar-Lys[C(=O)—C(=O)—OH]
(2-(2-Cyano)-Thiophenyl)-Benzoyl-Sar-boroGly[CH2)3-Br]-C10H16
(2-(2-Cyano)-Thiophenyl)-Benzoyl-Sar-boroGly[CH2)4)-Br]-C10H16
(2-(2-Cyano)-Thiophenyl)-Benzoyl-Sar-boroIrg-C10H16 HBr
(2-(2-Cyano)-Thiophenyl)-Benzoyl-Sar-boroGly[CH2)3-N3]-C10H16
(2-(2-Cyano)-Thiophenyl)-Benzoyl-Sar-borohomoIrg-C10H16 HBr
(2-(2-Cyano)-Thiophenyl)-Benzoyl-Sar-boroGly[CH2)4)—N3]-C10H16
(2-(2-Cyano)-Thiophenyl)-Benzoyl-Sar-boroOrn-C10H16 HCl
(2-(2-Cyano)-Thiophenyl)-Benzoyl-Sar-borohomoArg-C10H16 HC
(2-(2-Cyano)-Thiophenyl)-Benzoyl-Sar-boroArg-C10H16 HCl
(2-(2-Cyano)-Thiophenyl)-Benzoyl-Sar-boroOrn(CH=NH)-C10H16 HCl
(2-(2-Cyano)-Thiophenyl)-Benzoyl-Sar-boroLys(CH=NH)-C10H16 HCl
2-Benzyl-(N-Benzyl)-Sar-boroLys-C10H16 HCl
2-Thiophenyl-Benzoyl-Sar-boroLys(CH=NH)-C10H16
2-(Thiophenyl)-Benzoyl-Sar-boroIrg-C10H16 HBr
2-(Thiophenyl)-Benzoyl-Sar-boroOrn-C10H16 HCl
2-(Thiophenyl)-Benzoyl-Sar-boroOr-n(CH=NH)-C10H16 HCl
Pinanediol N-{N-methyl-N-[2-(Thiophenyl)-Benzoyl]Sar}-1-amido-5-thiocyanatobutane boronate
(2-(2-Cyano)-Thiophenyl)-Benzoyl-Sar-boroLys-C10H16 HCl
Acetyl-Gly[N-(2-(Berizyl)-Benzyl)]-boroLys-C10H16 HCl
Pinanediol N-{N-methyl-N-[2-(pyrrol-1-ylmethyl)-Benzyl-]glycyl}-1-amido-5-aminopentaneboronate, hydrochloride salt N-{N-methyl-N-[2-(pyrrol-1-ylmethyl)-Benzyl]glycyl}-1-amido-5-aminopentaneboronic acid, hydrochloride salt
2-(2-(Trifluoromethyl)-Benzyl)-Benzoyl-Sar-Lys—C(=O)—NHNH2 2 HCl
2-(Benzyl)-Benzoyl-Sar-Lys—C(=O)—NHNH2 2 HCl
[3-(Trifluoromethyl)-Benzyl]-Benzoyl-Sar-boroLys-C10H16 HCl
3-(3—(Chloro)-Benzyl)-Benzoyl-Sar-boroLys-C10H16 HCl
Hydrocinnamoyl-Sar-Lys(Z)—C(=O)—O-(CH2)2—NH(Z)
Hydrocinnamoyl-Sar-Lys—C(=O)—O—(CH2)2—NH2 2 HCl
Hydrocinnamoyl-Sar-Lys(Z)—C(=O)—OCH3
Hydrocinnamoyl-Sar-Lys—C(=O)—OCH3 HCl
Hydrocinnamoyl-Sar-Lys—C(=O)—CH3 HCl
Hydrocinnamoyl-Sar-Lys(Z)—H
Hydrocinnamoyl-Sar-NHCH(CH2OH)(CH2)4—NH(Z)
Hydrocinnamoyl-Sar-NHCH(CH2OH)(CH2)4—NH2
Hydrocinnamoyl-Sar-Lys[CH(OH)(OCH3)—C(=O)—OCH3] HCl
Hydrocinnamoyl-[N—(Cyclopropyl)-Gly]-boroOrn-C10H16 HCl
Hydrocinnamoyl-[N—(Cyclopropyl)-Gly]-boroLys—OH HCl
Hydrocinnamoyl-[N—(Cyclopropyl)-Gly]-boroOrn(CH=NH)—OH HCl
Hydrocinnamoyl-[N—(Cyclopropyl)-Gly]-boroOrn(CH=NH)-C10H16 HCl
Hydrocinnamoyl-[N—(Cyclopropyl)-Gly]-boroLys(CH=NH)-C10H16 HCl
Hydrocinnamoyl-[N—(Cyclopropyl)-Gly]-boroLys(CH=NH)—OH HCl
Phenoxyacetyl-[N—(Cyclopropyl)-Gly]-boroLys-C10H16 HCl
Thiophenacetyl-[N—(Cyclopropyl)-dly]-boroLys-C10H16 HCl
Phenoxyacetyl-[N—(Cyclopropyl)-Gly]-boroLys—OH HCl
Thiophenacetyl-[N—(Cyclopropyl)-Gly]-boroLys—OH HCl
Hydrocinnamoyl-[N-(N-(Methyl)-Phenyl)-Gly]-boroLys-C10H16 HCl
Hydrocinnamoyl-[N-(N-(Methyl)-Phenyl)-Gly]-boroLys—OH HCl
Hydrocinnamoyl-[N-(N-(Methyl)-Benzyl)-Gly]-boroLys-C10H16 HCl
Glutaryl-[N-(Phenethyl)-Gly]-boroLys—OH HCl
Glutaryl(3,3-Dimethyl)-[N-(Phenethyl)-Gly]-boroLys-C10H16
Methyl Glutaryl(3,3-Dimethyl)-[N-(Phenethyl)-Gly]-boroLys-C10H16 HCl
Glutaryl(3,3-Dimethyl)-[N-(Phenethyl)-Gly]-boroLys—OH
Methyl Glutaryl(3,3-Dimethyl)-[N-(Phenethyl)-Gly]-boroLys—OH HCl
Boc-Asp-[N-(Phenethyl)-Gly]-boroLys-C10H16
Boc-Glu-[N-(Phenethyl)-Gly]-boroLys-C10H16
Boc-Glu(OCH3)-[N-(Phenethyl)-Gly]-boroLys-C10H16 HCl
Boc-Glu-[N-(Phenethyl)-Gly]-boroLys—OH
Hydrocinnamoyl-[N-(N-(Methyl)-Benzyl)-Gly]-boroLys—OH HCl
Methanesylfonyl-Gly-[N-(N-(Methyl)-Benzyl)-Gly]-boroLys—C10H16 HCl
Methanesulfonyl-Gly-[N-(N-(Methyl)-Benzyl)-Gly]-boroLys—OH HCl
Hydrocinnamoyl-[N-(Succinyl)-Gly]-boroLys-C10H16
Hydrocinnamoyl-[N-(Methyl Succinyl)-Gly]-boroLys-C10H16 HCl
Succinyl-[N-(Phenethyl)-Gly]-boroLys—OH
Methyl Succinyl-[N-(Phenethyl)-Gly]-boroLys—OH HCl
Glutaryl-[N-(Phenethyl)-Gly]-boroLys-C10H16
Methyl Glutaryl-[N-(Pheriethyl)-Gly]-boroLys-C10H16 HCl
Methyl Glutaryl-[N-(Phenethyl)-Gly]-boroLys—OH HCl
Hydrocinnamoyl-[N-(2—(Cyclopropyl)-Phenethyl)-Gly]-boroArg-C10H16 HCl
Hydrocinnamoyl-[N-(2—(Cyclopentyl)-Phenethyl)-Gly]-boroLys-C10H16 HCl
(2-(2-Cyano)-Thiophenyl)-Benzoyl-Sar-boroArg—OH HCl
Hydrocinnamoyl-[N-(2,2-(Dimethyl)-Phenethyl)-Gly]-boroLys-C10H16 HCl
Hydrocinnamoyl-[N-(2,2-(Dimethyl)-Phenethyl)-Gly]-boroOrn-C10H16 HCl
Hydrocinnamoyl-[N-(2,2-(Dimethyl)-Phenethyl)-Gly]-boroArg-C10H16 HCl
Hydrocinnamoyl-[N-(2,2-(Dimethyl)-Phenethyl)-Gly]-boroOrn(CH=NH)-C10H16 HCl
Hydrocinnamoyl-[N-(2,2-(Dimethyl)-Phenethyl)-Gly]-boroArg—OH HCl
Hydrocinnamoyl-[N-(2,2-(Dimethyl)-Phenethyl)-Gly]-boroOrn(CH=NH)—OH HCl
Hydrocinnamoyl-[N-(2,2-(Dimethyl)-Phenethyl)-Gly]-boroOrn-C10H16 HCl
Hydrocinnamoyl-[N-(2,2-(Dimethyl)-Phenethyl)-Gly]-boroLys-C10H16 HCl
Hydrocinnamoyl-{N-[2-(3,5-dimethylphenyl)-ethyl]-Gly}-boroOrn-C10H16 HCl
Hydrocinnamoyl-{N-[2-(3,5-dimethylphenyl)-ethyl]-Gly}-boroLys-C10H16 HCl
Hydrocinnamoyl-{N-[2,2-(Dimethyl)-2-(3,5-dimethylphenyl)-ethyl]-Gly}-boroArg-C10H16 HCl
Hydrocinnamoyl-{N-[2,2-(Dimethyl)-2-(3,5-dimethylphenyl)-ethyl]-Gly}-boroOrn(CH=NH)-C10H16 HCl
Hydrocinnamoyl-{N-[2-(3,5-dimethylphenyl)-ethyl]-Gly}-boroArg-C10H16 HCl
Hydrocinnamoyl-{N-[2-(3,5-dimethylphenyl)-ethyl]-Gly}-boroOrn(CH=NH)-C10H16 HCl
Hydrocinnamoyl-[N—(Cyclohexyl)-Gly]-boroLys-C10H16 HCl
Hydrocinnamoyl-[N—(Cyclopropyl)-Gly]-boroLys-C10H16 HCl
Hydrocinnamoyl-[N—(Cyclohexyl)-Gly]-boroLys—OH HCl
Hydrocinnamoyl-[N-(Phenethyl)-Gly]-boroOrn(CH=NH)-C10H16 HCl
Hydrocinnamoyl-[N-(2—(Cyclopentyl)-Phenethyl)-Gly]-boroOrn(CH=NH)-C10H16 HCl
Hydrocinnamoyl-[N-(2—(Cyclopentyl)-Phenethyl)-Gly]-boroArg-C10H16 HCl
[N—(—C(S)(CH$_2$)$_2$Ph)—N—(CH$_3$)]Gly-boroLys—OH
[N—(—C(O)(CH$_2$)$_2$Ph)—N—(CH$_2$)$_2$Ph]Gly-boroLys—OH
[N—(—C(O)(CH$_2$)$_2$Ph)—N—Ph]Gly-boroLys—OH
[N—(—C(O)N(CH$_3$)CH$_2$Ph)—N—Ph]Gly-boroLys—OH
[N—(—C(O)Ph-3-CH=CHPh)—N—(CH$_3$)]Gly-boroLys—OH
[N—(—C(O)Ph-3-CH$_2$CH$_2$Ph)—N—(CH$_3$)]Gly-boroLys—OH
[N—(—C(O)Ph-3-SPh-2-OCH$_3$)—N—(CH$_3$)]Gly-boroLys—OH
[N—(—C(O)Ph-2-CH$_2$Ph-2-Ph)—N—(CH$_3$)]Gly-boroLys—OH

[N―(―C(O)Ph-4-CH₂Ph)―N―(CH₃)]Gly-boroLys―OH
[N―(―C(O)Ph-2-CH₂Ph)―N―(CH₃)]Gly-boroLys―OH
[N―(―C(O)Ph-3-CH₂Ph)―N―(CH₃)]Gly-boroLys―OH
[N―(―C(O)Ph-3-CH₂Ph-2-CF₃)―N―(CH₃)]Gly-boroLys―OH
[N―(―C(O)CH₂Ph-3,4-Cl₂)―N―(CH₃)]Gly-boroLys―OH
[N―(―C(O)(CH₂)₂Ph)―N―(i-C₃H₇)]Gly-boroLys―OH
[N―(―C(O)(CH₂)₂Ph)―N―(C₆H₁₂)]Gly-boroLys―OH
[N―(―C(O)(CH₂)₂Ph)―N―(N(CH₃)₂)]Gly-boroLys―OH
[N―(―C(O)CH₂Ph)―N―(CH₃)]Gly-boroLys―OH
[N―(―C(O)(CH₂)₃Ph)―N―(CH₃)]Gly-boroLys―OH
[N―(―C(O)Ph)―N―(CH₃)]Gly-boroLys―OH
[N―(―C(O)(CH₂)₂Ph)―N―CH₂Ph)]Gly-boroLys―OH
[N―(―C(O)(CH₂)₂Ph-3,4-Cl₂)―N―(CH₃)]Gly-boroLys―OH
[N―(―C(O)(CH₂)₂Ph-4-Cl)―N―(CH₃)]Gly-boroLys―OH
[N―(―C(O)(CH₂)₂Ph-4-CH₃)―N―(CH₃)]Gly-boroLys―OH
[N―(―C(O)(CH₂)₂Ph-4-OCH₃)―N―(CH₃)]Gly-boroLys―OH
[N―(―C(O)(CH₂)₂Ph)―N―(CH₃)]Gly-boroLys―C₁₀H₁₆
[N―(―C(O)(CH₂)₂Ph)―N―(CH₂)₂Ph]Gly-boroLys―C₁₀H₁₆
[N―(―C(O)(CH₂)₂Ph)―N―Ph]Gly-borolys―C₁₀H₁₆
[N―(―C(O)N(CH₃)CH₂Ph)―N―Ph]Gly-borolys―C₁₀H₁₆
[N―(―C(O)Ph-3-CH=CHPh)―N―(CH₃)]Gly-boroLys―C₁₀H₁₆
[N―(―C(O)Ph-3-CH₂CH₂Ph)―N―(CH₃)]Gly-boroLys―C₁₀H₁₆
[N―(―C(O)Ph-3-SPh-2-OCH₃)―N―(CH₃)]Gly-boroLys―C₁₀H₁₆
[N―(―C(O)Ph-2-CH₂Ph-2-Ph)―N―(CH₃)]Gly-boroLys―C₁₀H₁₆
[N―(―C(O)Ph-4-CH₂Ph)―N―(CH₃)]-Gly-boroLys―C₁₀H₁₆
[N―(―C(O)Ph-2-CH₂Ph)―N―(CH₃)]Gly-boroLys―C₁₀H₁₆
[N―(―C(O)Ph-3-CH₂Ph)―N―(CH₃)]Gly-boroLys―C₁₀H₁₆
[N―(―C(O)Ph-3-CH₂Ph-2-CF₃)―N―(CH₃)]Gly-boroLys―C₁₀H₁₆
[N―(―C(O)CH₂Ph-3,4-Cl₂)―N―(CH₃)]Gly-boroLys―C₁₀H₁₆
[N―(―C(O)(CH₂)₂Ph)―N―(i-C₃H₇)]Gly-boroLys―C₁₀H₁₆
[N―(―C(O)(CH₂)₂Ph)―N―(C₆H₁₂)]Gly-boroLys―C₁₀H₁₆
[N―(―C(O)CH₂Ph)―N―(CH₃)]Gly-boroLys―C₁₀H₁₆
[N―(―C(O)(CH₂)₃Ph)―N―(CH₃)]Gly-boroLys―C₁₀H₁₆
[N―(―C(O)Ph)―N―(CH₃)]Gly-boroLys―C₁₀H₁₆
[N―(―C(O)(CH₂)₂Ph)―N―CH₂Ph)]Gly-boroLys―C₁₀H₁₆
[N―(―C(O)(CH₂)₂Ph-3,4-Cl₂)―N―(CH₃)]Gly-boroLys―C₁₀H₁₆
[N―(―C(O)(CH₂)₂Ph-4-Cl)―N―(CH₃)]Gly-boroLys―C₁₀H₁₆
[N―(―C(O)(CH₂)₂Ph-4-CH₃)―N―(CH₃)]Gly-boroLys―C₁₀H₁₆
[N―(―C(O)(CH₂)₂Ph-4-OCH₃)―N―(CH₃)]Gly-boroLys―C₁₀H₁₆
[N―(―C(O)CH₃](D)-Phe[N―(CH₃)]Gly-boroLys―C₁₀H₁₆
[N-(SO₂CH₃](D)-Phe[N―(CH₃)]Gly-boroLys―C₁₀H₁₆
[N―(―C(O)(CH₂)₂Ph)―N―(CH₃)]Gly-Lys―OCH₃
[N―(―C(O)(CH₂)₂Ph)―N―(CH₃)]Gly-boroArg―OH
[N―(―C(O)CH₂Ph-3,4-Cl₂)―N―(CH₃)]Gly-boroArg―OH
[N―(―C(O)(CH₂)₂Ph)―N―(CH₃)]Gly-boroArg―C₁₀H₁₆
[N―(―C(O)CH₂Ph-3,4-Cl₂)―N―(CH₃)]Gly-boroArg―C₁₀H₁₆
[N―(―C(O)CH₂Ph-3,4-Cl₂)―N―(CH₃)]Gly-boroPhe(mCN)―C₁₀H₁₆
[N―(―C(O)(CH₂)₂Ph)―N―(CH₃)]Gly-boroOrn(N-methylamidino)―OH
[N―(―C(O)CH₂Ph-3,4-Cl₂)―N―(CH₃)]Gly-boroOrn(N-methylamidino)―OH
[N―(―C(O)(CH₂)₂Ph)―N―(CH₃)]Gly-boroOrn(N-methylamidino)―C₁₀H₁₆
[N―(―C(O)CH₂Ph-3,4-Cl₂)―N―(CH₃)]Gly-boroOrn(N-methylamidino)―C₁₀H₁₆
[N―(―C(O)(CH₂)₂Ph)―N―(CH₃)]Gly-boroOrn(formamidino)―OH
[N―(―C(O)CH₂Ph-3,4-Cl₂)―N―(CH₃)]Gly-boroOrn(formamidino)―OH
[N―(―C(O)CH₂Ph)―N―(CH₃)]Gly-boroOrn(formamidino)―OH
[N―(―C(O)(CH₂)₂Ph-4-OCH₃)―N―(CH₃)]Gly-boroOrn(formamidino)―OH
[N―(―C(O)Ph-4-CH₂Ph)―N―(CH₃)]Gly-boroOrn(formamidino)―C₁₀H₁₆
[N―(―C(O)CH₂Ph-3,4-Cl₂)―N―(CH₃)]Gly-boroOrn(formamidino)―C₁₀H₁₆
[N―(―C(O)(CH₂)₂Ph)―N―(OH)]Gly-boroOrn(formamidino)―C₁₀H₁₆
[N―(―C(O)(CH₂)₂Ph-3,4-Cl₂)―N―(CH₃)]Gly-boroOrn(formamidino)―C₁₀H₁₆
[N―(―C(O)(CH₂)₂Ph)―N―(CH₂C(CH₂CH₃)₂Ph)]-Gly-boroLys―OH
[N―(―C(O)(CH₂)₂Ph)―N―(CH₂CH(i-C₃H₇)Ph)]-Gly-boroLys―OH
[N―(―C(O)(CH₂)₂Ph)―N―(CH₂C(butane-1,4-diyl)Ph)]-Gly-boroLys―OH
[N―(―C(O)(CH₂)₂Ph)―N―(CH₂C(CH₃)₂Ph-3-CH₃)]-Gly-boroLys―OH
[N―(―C(O)(CH₂)₂Ph)―N―(CH₂C(CH₂CH₃)₂Ph-3-CH₃)]-Gly-boroLys―OH
[N―(―C(O)(CH₂)₂Ph)―N―(CH₂C(butane-1,4-diyl)Ph)]-Gly-boroArg―OH
[N―(―C(O)(CH₂)₂Ph)―N―(CH₂C(CH₃)₂Ph-3-NO₂)]-Gly-boroLys―OH
[N―(―C(O)(CH₂)₂Ph)―N―(CH₂C(CH₂CH₃)₂Ph-3-NO₂)]-Gly-boroLys―OH
[N―(―C(O)(CH₂)₂Ph)―N―(CH₂CH₂Ph-3,5―(CH₃)₂)]-Gly-boroArg―OH
[N―(―C(O)(CH₂)₂Ph)―N―(CH₂C(CH₃)₂Ph-3,5―(CH₃)₂)]-Gly-boroArg―OH
[N―(―C(O)(CH₂)₂Ph)―N―(CH₂C(butane-1,4-diyl)Ph)]-Gly-boroOrn(formamidino)―OH
[N―(―C(O)(CH₂)₂Ph)―N―(CH₂C(CH₃)₂Ph-3-CH₃)]-Gly-boroOrn(formamidino)―OH
[N―(―C(O)(CH₂)₂Ph)―N―(CH₂C(CH₂CH₃)₂Ph-3-CH₃)]-Gly-boroOrn(formamidino)―OH Illustrative of the preferred compounds of this invention are the following:
[N―(―C(O)(CH₂)₂Ph)―N―(C₂H₅)]Gly-boroLys―OH
[N―(―C(O)(CH₂)₂Ph)―N―(N―C₃H₇)]Gly-boroLys―OH
[N―(―C(O)(CH₂)₂Ph)―N―(OH)]Gly-boroLys―OH

[N—(—C(O)(CH$_2$)$_2$Ph)—N—(OCH$_3$)]Gly-boroLys—OH
[N—(—C(O)(CH$_2$)$_2$Ph)—N—(OCH$_2$Ph)]Gly-boroLys—OH
[N—(—C(O)(CH$_2$)$_2$Ph)—N—(NH$_2$)]Gly-boroLys—OH
[N—(—C(O)(CH$_2$)$_2$Ph)—N—(NHBoc)]Gly-boroLys—OH
[N—(—C(O)(CH$_2$)$_2$Ph)—N—(CH$_2$CO$_2$H)]Gly-boroLys—OH
[N—(—C(O)(CH$_2$)$_2$Ph)—N—(CH$_2$CO$_2$CH$_3$)]Gly-boroLys—OH
[N—(—C(O)(OCH$_2$)Ph)](D)-Phe[N—(CH$_3$)]Gly-boroLys—OH
[N—(—C(O)(OCH$_2$)Ph)](D)-Phe[N—(CH$_3$)]Ala-boroLys—OH
[N—(—C(O)(OCH$_2$)Ph)](D)-Phe[N-(Ph)]Gly-boroLys—OH
[N—(—C(O)(OCH$_2$)Ph)](D)-Phe[N—(CH$_2$Ph)]Gly-boroLys—OH
[N—(—C(O)(CH$_2$)$_2$Ph)—N—(C$_2$H$_5$)]Gly-boroLys—C$_{10}$H$_{16}$
[N—(—C(O)(CH$_2$)$_2$Ph)—N—(n-C$_3$H$_7$)]Gly-boroLys—C$_{10}$H$_{16}$
[N—(—C(O)(CH$_2$)$_2$Ph)—N—(OH)]Gly-boroLys—C$_{10}$H$_{16}$
[N—(—C(O)(CH$_2$)$_2$Ph)—N—(OCH$_3$)]Gly-boroLys—C$_{10}$H$_{16}$
[N—(—C(O)(CH$_2$)$_2$Ph)—N—(OCH$_2$Ph)]Gly-boroLys—C$_{10}$H$_{16}$
[N—(—C(O)(CH$_2$)$_2$Ph)—N—(NH$_2$)]Gly-boroLys—C$_{10}$H$_{16}$
[N—(—C(O)(CH$_2$)$_2$Ph)—N—(NHBoc)]Gly-boroLys—C$_{10}$H$_{16}$
[N—(—C(O)(CH$_2$)$_2$Ph)—N—(CH$_2$CO$_2$H)]Gly-boroLys—C$_{10}$H$_{16}$
[N—(—C(O)(CH$_2$)$_2$Ph)—N—(CH$_2$CO$_2$CH$_3$)]Gly-boroLys—C$_{10}$H$_{16}$
(N—CO$_2$CH$_2$Ph)[Leu-Ser(O'Bu)-Asn]$_4$-[N—(CH$_3$)]Gly-boroLys—C$_{10}$H$_{16}$ [Sequence No. 1]
(H)-[Leu-Ser(O'Bu)-Asn]$_4$-[N—(CH$_3$)]Gly-borolys—C$_{10}$H$_{16}$ [Sequence No. 2]
(H)-[Leu-Ser-Asn]$_4$-[N—(CH$_3$)]Gly-boroLys—C$_{10}$H$_{16}$ [Sequence No. 3]
[N—(—C(O)(OCH$_2$)Ph)](D)-Phe[N—(CH$_3$)]Gly-boroLys—C$_{10}$H$_{16}$
[N—(—C(O)(CH$_3$)](D)-(β-Cyclohexyl)Ala[N—(CH$_3$)]Gly-boroLys—C$_{10}$H$_1$
[N—(—C(O)(CH$_2$)$_2$Ph)—N—(CH$_3$)]Gly-Lys—CF$_3$
[N—(—C(O)(CH$_2$)$_2$Ph)—N—(CH$_2$)$_2$Ph]Gly-Lys—CF$_3$
[N—(—C(O)(CH$_2$)$_2$Ph)—N—Ph]Gly-Lys—CF$_3$
[N—(—C(O)N(CH$_3$)CH$_2$Ph)—N—Ph]Gly-Lys—CF$_3$
[N—(—C(O)Ph-3-CH=CHPh)—N—(CH$_3$)]Gly-Lys—CF$_3$
[N—(—C(O)Ph-3-CH$_2$CH$_2$Ph)—N—(CH$_3$)]Gly-Lys—CF$_3$
[N—(—C(O)Ph-3-SPh-3-OCH$_3$)—N—(CH$_3$)]Gly-Lys—CF$_3$
[N—(—C(O)Ph-2-CH$_2$Ph-2-Ph)—N—(CH$_3$)]Gly-Lys—CF$_3$
[N—(—C(O)Ph-4-CH$_2$Ph)—N—(CH$_3$)]Gly-Lys—CF$_3$
[N—(—C(O)Ph-2-CH$_2$Ph)—N—(CH$_3$)]Gly-Lys—CF$_3$
[N—(—C(O)Ph-3-CH$_2$Ph)—N—(CH$_3$)]Gly-Lys—CF$_3$
[N—(—C(O)Ph-3-CH$_2$Ph-2-CF$_3$)—N—(CH$_3$)]Gly-Lys—CF$_3$
[N—(—C(O)CH$_2$Ph-3,4-Cl$_2$)—N—(CH$_3$)]Gly-Lys—CF$_3$
[N—(—C(O)(CH$_2$)$_2$Ph)—N—(C$_2$H$_5$)]Gly-Lys—CF$_3$
[N—(—C(O)(CH$_2$)$_2$Ph)—N—(n-C$_3$H$_7$)]Gly-Lys—CF$_3$
[N—(—C(O)(CH$_2$)$_2$Ph)—N—(i-C$_3$H$_7$)]Gly-Lys—CF$_3$
[N—(—C(O)(CH$_2$)$_2$Ph)—N—(C$_6$H$_{12}$)]Gly-Lys—CF$_3$
[N—(—C(O)(CH$_2$)$_2$Ph)—N—(OH)]Gly-Lys—CF$_3$
[N—(—C(O)(CH$_2$)$_2$Ph)—N—(OCH$_3$)]Gly-Lys—CF$_3$
[N—(—C(O)(CH$_2$)$_2$Ph)—N—(OCH$_2$Ph)]Gly-Lys—CF$_3$
[N—(—C(O)(CH$_2$)$_2$Ph)—N—(NH$_2$)]Gly-Lys—CF$_3$
[N—(—C(O)(CH$_2$)$_2$Ph)—N—(N(CH$_3$)$_2$)]Gly-Lys—CF$_3$
[N—(—C(O)(CH$_2$)$_2$Ph)—N—(NHBoc)]Gly-Lys—CF$_3$
[N—(—C(O)(CH$_2$)$_2$Ph)—N—(CH$_2$CO$_2$H)]Gly-Lys—CF$_3$
[N—(—C(O)(CH$_2$)$_2$Ph)—N—(CH$_2$CO$_2$CH$_3$)]Gly-Lys—CF$_3$
[N—(—C(O)CH$_2$Ph)—N—(CH$_3$)]Gly-Lys—CF$_3$
[N—(—C(O)(CH$_2$)$_3$Ph)—N—(CH$_3$)]Gly-Lys—CF$_3$
[N—(—C(O)Ph)—N—(CH$_3$)]Gly-Lys—CF$_3$
[N—(—C(O)(CH$_2$)$_2$Ph)—N—CH$_2$Ph]Gly-Lys—CF$_3$
[N—(—C(O)(CH$_2$)$_2$Ph-3,4-C$_2$)—N—(CH$_3$)]Gly-Lys—CF$_3$
[N—(—C(O)(CH$_2$)$_2$Ph-4-Cl)—N—(CH$_3$)]Gly-Lys—CF$_3$
[N—(—C(O)(CH$_2$)$_2$Ph-4-CH$_3$)—N—(CH$_3$)]Gly-Lys—CF$_3$
[N—(—C(O)(CH$_2$)$_2$Ph-4-OCH$_3$)—N—(CH$_3$)]Gly-Lys—CF$_3$
[N—(—C(O)(CH$_2$)$_2$Ph)—N—(CH$_2$)$_2$Ph]Gly-Lys—OCH$_3$
[N—(—C(O)(CH$_2$)$_2$Ph)—N—Ph]Gly-Lys—OCH$_3$
[N—(—C(O)N(CH$_3$)CH$_2$Ph)—N—Ph]Gly-Lys—OCH$_3$
[N—(—C(O)Ph-3-CH=CHPh)—N—(CH$_3$)]Gly-Lys—OCH$_3$
[N—(—C(O)Ph-3-CH$_2$CH$_2$Ph)—N—(CH$_3$)]Gly-Lys—OCH$_3$
[N—(—C(O)Ph-3-SPh-3-OCH$_3$)—N—(CH$_3$)]Gly-Lys—OCH$_3$
[N—(—C(O)Ph-2-CH$_2$Ph-2-Ph)—N—(CH$_3$)]Gly-Lys—OCH$_3$
[N—(—C(O)Ph-4-CH$_2$Ph)—N—(CH$_3$)]Gly-Lys—OCH$_3$
[N—(—C(O)Ph-2-CH$_2$Ph)—N—(CH$_3$)]Gly-Lys—OCH$_3$
[N—(—C(O)Ph-3-CH$_2$Ph)—N—(CH$_3$)]Gly-Lys—OCH$_3$
[N—(—C(O)Ph-3-CH$_2$Ph-2-CF$_3$)—N—(CH$_3$)]Gly-Lys—OCH$_3$
[N—(—C(O)CH$_2$Ph-3,4-Cl$_2$)—N—(CH$_3$)]Gly-Lys—OCH$_3$
[N—(—C(O)(CH$_2$)$_2$Ph)—N—(C$_2$H$_5$)]Gly-Lys—OCH$_3$
[N—(—C(O)(CH$_2$)$_2$Ph)—N—(n-C$_3$H$_7$)]Gly-Lys—OCH$_3$
[N—(—C(O)(CH$_2$)$_2$Ph)—N—(i-C$_3$H$_7$)]Gly-Lys—OCH$_3$
[N—(—C(O)(CH$_2$)$_2$Ph)—N—(C$_6$H$_{12}$)]Gly-Lys—OCH$_3$
[N—(—C(O)(CH$_2$)$_2$Ph)—N—(OH)]Gly-Lys—OCH$_3$
[N—(—C(O)(CH$_2$)$_2$Ph)—N—(OCH$_3$)]Gly-Lys—OCH$_3$
[N—(—C(O)(CH$_2$)$_2$Ph)—N—(OCH$_2$Ph)]Gly-Lys—OCH$_3$
[N—(—C(O)(CH$_2$)$_2$Ph)—N—(NH$_2$)]Gly-Lys—OCH$_3$
[N—(—C(O)(CH$_2$)$_2$Ph)—N—(N(CH$_3$)$_2$)]Gly-Lys—OCH$_3$
[N—(—C(O)(CH$_2$)$_2$Ph)—N—(NHBoc)]Gly-Lys—OCH$_3$
[N—(—C(O)(CH$_2$)$_2$Ph)—N—(CH$_2$CO$_2$H)]Gly-Lys—OCH$_3$
[N—(—C(O)(CH$_2$)$_2$Ph)—N—(CH$_2$CO$_2$CH$_3$)]Gly-Lys—OCH$_3$
[N—(—C(O)CH$_2$Ph)—N—(CH$_3$)]Gly-Lys—OCH$_3$
[N—(—C(O)(CH$_2$)$_3$Ph)—N—(CH$_3$)]Gly-Lys—OCH$_3$
[N—(—C(O)Ph)—N—(CH$_3$)]Gly-Lys—OCH$_3$
[N—(—C(O)(CH$_2$)$_2$Ph)—N—CH$_2$Ph]Gly-Lys—OCH$_3$
[N—(—C(O)(CH$_2$)$_2$Ph-3,4-Cl$_2$)—N—(CH$_3$)]Gly-Lys—OCH$_3$
[N—(—C(O)(CH$_2$)$_2$Ph-4-Cl)—N—(CH$_3$)]Gly-Lys—OCH$_3$
[N—(—C(O)(CH$_2$)$_2$Ph-4-CH$_3$)—N—(CH$_3$)]Gly-Lys—OCH$_3$
[N—(—C(O)(CH$_2$)$_2$Ph-4-OCH$_3$)—N—(CH$_3$)]Gly-Lys—OCH$_3$
[N—(—C(O)(CH$_2$)$_2$Ph)—N—(CH$_3$)]C Gly-Lys—CO$_2$CH$_3$
[N—(—C(O)(CH$_2$)$_2$Ph)—N—(CH$_2$)$_2$Ph]Gly-Lys—CO$_2$CH$_3$
[N—(—C(O)(CH$_2$)$_2$Ph)—N—Ph]Gly-Lys—CO$_2$CH$_3$
[N—(—C(O)N(CH$_3$)CH$_2$Ph)—N—Ph]Gly-Lys—CO$_2$CH$_3$
[N—(—C(O)Ph-3-CH=CHPh)—N—(CH$_3$)]Gly-Lys—CO$_2$CH$_3$

[N—(—C(O)Ph-3-CH₂CH₂Ph)—N—(CH₃)]Gly-Lys—CO₂CH₃
[N—(—C(O)Ph-3-SPh-3-OCH₃)—N—(CH₃)]Gly-Lys—CO₂CH₃
[N—(—C(O)Ph-2-CH₂Ph-2-Ph)—N—(CH₃)]Gly-Lys—CO₂CH₃
[N—(—C(O)Ph-4-CH₂Ph)—N—(CH₃)]Gly-Lys—CO₂CH₃
[N—(—C(O)Ph-2-CH₂Ph)—N—(CH₃)]Gly-Lys—CO₂CH₃
[N—(—C(O)Ph-3-CH₂Ph)—N—(CH₃)]Gly-Lys—CO₂CH₃
[N—(—C(O)Ph-3-CH₂Ph-2-CF₃)—N—(CH₃)]Gly-Lys—CO₂CH₃
[N—(—C(O)CH₂Ph-3,4-Cl₂)—N—(CH₃)]Gly-Lys—CO₂CH₃
[N—(—C(O)(CH₂)₂Ph)—N—(C₂H₅)]Gly-Lys—CO₂CH₃
[N—(—C(O)(CH₂)₂Ph)—N—(n-C₃H₇)]Gly-Lys—CO₂CH₃
[N—(—C(O)(CH₂)₂Ph)—N—(i-C₃H₇)]Gly-Lys—CO₂CH₃
[N—(—C(O)(CH₂)₂Ph)—N—(C₆H₁₂)]Gly-Lys—CO₂CH₃
[N—(—C(O)(CH₂)₂Ph)—N—(OH)]Gly-Lys—CO₂CH₃
[N—(—C(O)(CH₂)₂Ph)—N—(OCH₃)]Gly-Lys—CO₂CH₃
[N—(—C(O)(CH₂)₂Ph)—N—(OCH₂Ph)]Gly-Lys—CO₂CH₃
[N—(—C(O)(CH₂)₂Ph)—N—(NH₂)]Gly-Lys—CO₂CH₃
[N—(—C(O)(CH₂)₂Ph)—N—(N(CH₃)₂)]Gly-Lys—CO₂CH₃
[N—(—C(O)(CH₂)₂Ph)—N—(NHBoc)]Gly-Lys—CO₂CH₃
[N—(—C(O)(CH₂)₂Ph)—N—(CH₂CO₂H)]Gly-Lys—CO₂CH₃
[N—(—C(O)(CH₂)₂Ph)—N—(CH₂CO₂CH₃)]Gly-Lys—CO₂CH₃
[N—(—C(O)CH₂Ph)—N—(CH₃)]Gly-Lys—CO₂CH₃
[N—(—C(O)(CH₂)₃Ph)—N—(CH₃)]Gly-Lys—CO₂CH₃
[N—(—C(O)Ph)—N—(CH₃)]Gly-Lys—CO₂CH₃
[N—(—C(O)(CH₂)₂Ph)—N—CH₂Ph)]Gly-Lys—CO₂CH₃
[N—(—C(O)(CH₂)₂Ph-3,4-C₁₂)—N—(CH₃)]Gly-Lys—CO₂CH₃
[N—(—C(O)(CH₂)₂Ph-4-Cl)—N—(CH₃)]Gly-Lys—CO₂CH₃
[N—(—C(O)(CH₂)₂Ph-4-CH₃)—N—(CH₃)]Gly-Lys—CO₂CH₃
[N—(—C(O)(CH₂)₂Ph-4-OCH₃)—N—(CH₃)]Gly-Lys—CO₂CH₃
[N—(—C(O)(CH₂)₂Ph)—N—(CH₂)₂Ph]Gly-boroArg—OH
[N—(—C(O)(CH₂)₂Ph)—N—Ph]Gly-boroArg—OH
[N—(—C(O)N(CH₃)CH₂Ph)—N—Ph]Gly-boroArg—OH
[N—(—C(O)Ph-3-CH=CHPh)—N—(CH₃)]Gly-boroArg—OH
[N—(—C(O)Ph-3-CH₂CH₂Ph)—N—(CH₃)]Gly-boroArg—OH
[N—(—C(O)Ph-3-SPh-3-OCH₃)—N—(CH₃)]Gly-boroArg—OH
[N—(—C(O)Ph-2-CH₂Ph-2-Ph)—N—(CH₃)]Gly-boroArg—OH
[N—(—C(O)Ph-4-CH₂Ph)—N—(CH₃)]Gly-boroArg—OH
[N—(—C(O)Ph-2-CH₂Ph)—N—(CH₃)]Gly-boroArg—OH
[N—(—C(O)Ph-3-CH₂Ph)—N—(CH₃)]Gly-boroArg—OH
[N—(—C(O)Ph-3-CH₂Ph-2-CF₃)—N—(CH₃)]Gly-boroArg—OH
[N—(—C(O)(CH₂)₂Ph)—N—(C₂H₅)]Gly-boroArg—OH
[N—(—C(O)(CH₂)₂Ph)—N—(n-C₃H₇)]Gly-boroArg—OH
[N—(—C(O)(CH₂)₂Ph)—N—(i-C₃H₇)]Gly-boroArg—OH
[N—(—C(O)(CH₂)₂Ph)—N—(C₆H₁₂)]Gly-boroArg—OH
[N—(—C(O)(CH₂)₂Ph)—N—(OH)]Gly-boroArg—OH
[N—(—C(O)(CH₂)₂Ph)—N—(OCH₃)]Gly-boroArg—OH
[N—(—C(O)(CH₂)₂Ph)—N—(OCH₂Ph)]Gly-boroArg—OH
[N—(—C(O)(CH₂)₂Ph)—N—(NH2)]Gly-boroArg—OH
[N—(—C(O)(CH₂)₂Ph)—N—(N(CH₃)₂)]Gly-boroArg—OH
[N—(—C(O)(CH₂)₂Ph)—N—(NHBoc)]Gly-boroArg—OH
[N—(—C(O)(CH₂)₂Ph)—N—(CH₂CO₂H)]Gly-boroArg—OH
[N—(—C(O)(CH₂)₂Ph)—N—(CH₂CO₂CH₃)]Gly-boroArg—OH
[N—(—C(O)CH₂Ph)—N—(CH₃)]Gly-boroArg—OH
[N—(—C(O)(CH₂)₃Ph)—N—(CH₃)]Gly-boroArg—OH
[N—(—C(O)Ph)—N—(CH₃)]Gly-boroArg—OH
[N—(—C(O)(CH₂)₂Ph)—N—CH₂Ph]Gly-boroArg—OH
[N—(—C(O)(CH₂)₂Ph-3,4-Cl₂)—N—(CH₃)]Gly-boroArg—OH
[N—(—C(O)(CH₂)₂Ph-4-Cl)—N—(CH₃)]Gly-boroArg—OH
[N—(—C(O)(CH₂)₂Ph-4-CH₃)—N—(CH₃)]Gly-boroArg—OH
[N—(—C(O)(CH₂)₂Ph-4-OCH₃)—N—(CH₃)]Gly-boroArg—OH
[N—(—C(O)(CH₂)₂Ph)—N—(CH₂)₂Ph]Gly-boroArg—C₁₀H₁₆
[N—(—C(O)(CH₂)₂Ph)—N—Ph]Gly-boroArg—C₁₀H₁₆
[N—(—C(O) N(CH₃)CH₂Ph)—N—Ph]Gly-boroArg—C₁₀H₁₆
[N—(—C(O)Ph-3-CH=CHPh)—N—(CH₃)]Gly-boroArg—C₁₀H₁₆
[N—(—C(O)Ph-3-CH₂CH₂Ph)—N—(CH₃)]Gly-boroArg—C₁₀H₁₆
[N—(—C(O)Ph-3-SPh-3-OCH₃)—N—(CH₃)]Gly-boroArg—C₁₀H₁₆
[N—(—C(O)Ph-2-CH₂Ph-2-Ph)—N—(CH₃)]Gly-boroArg—C₁₀H₁₆
[N—(—C(O)Ph-4-CH₂Ph)—N—(CH₃)]Gly-boroArg—C₁₀H₁₆
[N—(—C(O)Ph-2-CH₂Ph)—N—(CH₃)]Gly-boroArg—C₁₀H₁₆
[N—(—C(O)Ph-3-CH₂Ph)—N—(CH₃)]Gly-boroArg—C₁₀H₁₆
[N—(—C(O)Ph-3-CH₂Ph-2-CF₃)—N—(CH₃)]Gly-boroArg—C₁₀H₁₆
[N—(—C(O)(CH₂)₂Ph)—N—(C₂H₅)]Gly-boroArg—C₁₀H₁₆
[N—(—C(O)(CH₂)₂Ph)—N—(n-C₃H₇)]Gly-boroArg—C₁₀H₁₆
[N—(—C(O)(CH₂)₂Ph)—N—(i-C₃H₇)]Gly-boroArg—C₁₀H₁₆
[N—(—C(O)(CH₂)₂Ph)—N—(C₆H₁₂)]Gly-boroArg—C₁₀H₁₆
[N—(—C(O)(CH₂)₂Ph)—N—(OH)]Gly-boroArg—C₁₀H₁₆
[N—(—C(O)(CH₂)₂Ph)—N—(OCH₃)]Gly-boroArg—C₁₀H₁₆
[N—(—C(O)(CH₂)₂Ph)—N—(OCH₂Ph)]Gly-boroArg—C₁₀H₁₆
[N—(—C(O)(CH₂)₂Ph)—N—(NH₂)]Gly-boroArg—C₁₀H₁₆
[N—(—C(O)(CH₂)₂Ph)—N—(N(CH₃)₂)]Gly-boroArg—C₁₀H₁₆
[N—(—C(O)(CH₂)₂Ph)—N—(NHBoc)]Gly-boroArg-C₁₀H₁₆
[N—(—C(O)(CH₂)₂Ph)—N—(CH₂CO₂H)]Gly-boroArg—C₁₀H₁₆

[N—(—C(O)(CH$_2$)$_2$Ph)—N—(CH$_2$CO$_2$CH$_3$)]Gly-boroArg—C$_{10}$H$_{16}$
[N—(—C(O)CH$_2$Ph)—N—(CH$_3$)]Gly-boroArg—C$_{10}$H$_{16}$
[N—(—C(O)(CH$_2$)$_3$Ph)—N—(CH$_3$)]Gly-boroArg—C$_{10}$H$_{16}$
[N—(—C(O)Ph)—N—(CH$_3$)]Gly-boroArg—C$_{10}$H$_{16}$
[N—(—C(O)(CH$_2$)$_2$Ph)—N—CH$_2$Ph)]Gly-boroArg—C$_{10}$H$_{16}$
[N—(—C(O)(CH$_2$)$_2$Ph-3,4-Cl$_2$)—N—(CH$_3$)]Gly-boroArg—C$_{10}$H$_{16}$
[N—(—C(O)(CH$_2$)$_2$Ph-4-Cl)—N—(CH$_3$)]Gly-boroArg—C$_{10}$H$_{16}$
[N—(—C(O)(CH$_2$)$_2$Ph-4-CH$_3$)—N—(CH$_3$)]Gly-boroArg—C$_{10}$H$_{16}$
[N—(—C(O)(CH$_2$)$_2$Ph-4-OCH$_3$)—N—(CH$_3$)]Gly-boroArg—C$_{10}$H$_{16}$
[N—(—C(O)CH$_3$](D)-Phe[N—(CH$_3$)]Gly-boroArg—C$_{10}$H$_{16}$
[N—(—C(O)CH$_3$](D)-Phe[N—(CH$_3$)]Gly-boroIrg—C$_{10}$H$_{16}$
[N—(—C(O)(CH$_2$)$_2$Ph)—N—(CH$_3$)]Gly-Arg—CF$_3$
[N—(—C(O)(CH$_2$)$_2$Ph)—N—(CH$_2$)$_2$Ph]Gly-Arg—CF$_3$
[N—(—C()(CH$_2$)$_2$Ph)—N—Ph]Gly-Arg—CF$_3$
[N—(—C(O)N(CH$_3$)CH$_2$Ph)—N—Ph]Gly-Arg—CF$_3$
[N—(—C(O)Ph-3-CH=CHPh)—N—(CH$_3$)]ly-Arg—CF$_3$
[N—(—C(O)Ph-3-CH$_2$CH$_2$Ph)—N—(CH$_3$)]Gly-Arg—CF$_3$
[N—(—C(O)Ph-3-SPh-3-OCH$_3$)—N—(CH$_3$)]Gly-Arg—CF$_3$
[N—(—C(O)Ph-2-CH$_2$Ph-2-Ph)—N—(CH$_3$)]Gly-Arg—CF$_3$
[N—(—C(O)Ph-4-CH$_2$Ph)—N—(CH$_3$)]Gly-Arg—CF$_3$
[N—(—C(O)Ph-2-CH$_2$Ph)—N—(CH$_3$)]Gly-Arg—CF$_3$
[N—(—C(O)Ph-3-CH$_2$Ph)—N—(CH$_3$)]Gly-Arg—CF$_3$
[N—(—C(O)Ph-3-CH$_2$Ph-2-CF$_3$)—N—(CH$_3$)]Gly-Arg—CF$_3$
[N—(—C(O)CH$_2$Ph-3,4-Cl$_2$)—N—(CH$_3$)]Gly-Arg—CF$_3$
[N—(—C(O)(CH$_2$)$_2$Ph)—N—(C$_2$H)]Gly-Arg—CF$_3$
[N—(—C(O)(CH$_2$)$_2$Ph)—N—(n-C$_3$H$_7$)]Gly-Arg—CF$_3$
[N—(—C(O)(CH$_2$)$_2$Ph)—N—(i-C$_3$H$_7$)]Gly-Arg—CF$_3$
[N—(—C(O)(CH$_2$)$_2$Ph)—N—(C$_6$H$_{12}$)]Gly-Arg—CF$_3$
[N—(—C(O)(CH$_2$)$_2$Ph)—N—(OH)]Gly-Arg—CF$_3$
[N—(—C(O)(CH$_2$)$_2$Ph)—N—(OCH$_3$)]Gly-Arg—CF$_3$
[N—(—C(O)(CH$_2$)$_2$Ph)—N—(OCH$_2$Ph)]Gly-Arg—CF$_3$
[N—(—C(O)(CH$_2$)$_2$Ph)—N—(NH2)]Gly-Arg—CF$_3$
[N—(—C(O)(CH$_2$)$_2$Ph)—N—(N(CH$_3$)$_2$)]Gly-Arg—CF$_3$
[N—(—C(O)(CH$_2$)$_2$Ph)—N—(NHBoc)]Gly-Arg—CF$_3$
[N—(—C(O)(CH$_2$)$_2$Ph)—N—(CH$_2$CO$_2$H)]Gly-Arg—CF$_3$
[N—(—C(O)(CH$_2$)$_2$Ph)—N—(CH$_2$CO$_2$CH$_3$)]Gly-Arg—CF$_3$
[N—(—C(O)CH$_2$Ph)—N—(CH$_3$)]Gly-Arg—CF$_3$
[N—(—C(O)(CH$_2$)$_3$Ph)—N—(CH$_3$)]Gly-Arg—CF$_3$
[N—(—C(O)Ph)—N—(CH$_3$)]Gly-Arg—CF$_3$
[N—(—C(O)(CH$_2$)$_2$Ph)—N—CH$_2$Ph)]Gly-Arg—CF$_3$
[N—(—C(O)(CH$_2$)$_2$Ph-3,4-Cl$_2$)—N—(CH$_3$)]Gly-Arg—CF$_3$
[N—(—C(O)(CH$_2$)$_2$Ph-4-Cl)—N—(CH$_3$)]Gly-Arg—CF$_3$
[N—(—C(O)(CH$_2$)$_2$Ph-4-CH$_3$)—N—(CH$_3$)]Gly-Arg—CF$_3$
[N—(—C(O)(CH$_2$)$_2$Ph-4-OCH$_3$)—N—(CH$_3$)]Gly-Arg—CF$_3$
[N—(—C(O)(CH$_2$)$_2$Ph)—N—(CH$_3$)]Gly-Arg—OCH$_3$
[N—(—C(O)(CH$_2$)$_2$Ph)—N—(CH$_2$)$_2$Ph]Gly-Arg—OCH$_3$
[N—(—C(O)(CH$_2$)$_2$Ph)—N—Ph]Gly-Arg—OCH$_3$
[N—(—C(O)N(CH$_3$)CH$_2$Ph)—N—Ph]Gly-Arg—OCH$_3$
[N—(—C(O)Ph-3-CH=CHPh)—N—(CH$_3$)]Gly-Arg—OCH$_3$
[N—(—C(O)Ph-3-CH$_2$CH$_2$Ph)—N—(CH$_3$)]Gly-Arg—OCH$_3$
[N—(—C(O)Ph-3-SPh-3-OCH$_3$)—N—(CH$_3$)]Gly-Arg—OCH$_3$
[N—(—C(O)Ph-2-CH$_2$Ph-2-Ph)—N—(CH$_3$)]Gly-Arg—OCH$_3$
[N—(—C(O)Ph-4-CH$_2$Ph)—N—(CH$_3$)]Gly-Arg—OCH$_3$
[N—(—C(O)Ph-2-CH$_2$Ph)—N—(CH$_3$)]Gly-Arg—OCH$_3$
[N—(—C(O)Ph-3-CH$_2$Ph)—N—(CH$_3$)]Gly-Arg—OCH$_3$
[N—(—C(O)Ph-3-CH$_2$Ph-2-CF$_3$)—N—(CH$_3$)]Gly-Arg—OCH$_3$
[N—(—C(O)CH$_2$Ph-3,4-Cl$_2$)—N—(CH$_3$)]Gly-Arg—OCH$_3$
[N—(—C(O)(CH$_2$)$_2$Ph)—N—(C$_2$H$_5$)]Gly-Arg—OCH$_3$
[N—(—C(O)(CH$_2$)$_2$Ph)—N—(n-C$_3$H$_7$)]Gly-Arg—OCH$_3$
[N—(—C(O)(CH$_2$)$_2$Ph)—N—(i-C$_3$H$_7$)]Gly-Arg—OCH$_3$
[N—(—C(O)(CH$_2$)$_2$Ph)—N—(C$_6$H$_{12}$)]Gly-Arg—OCH$_3$
[N—(—C(O)(CH$_2$)$_2$Ph)—N—(OH)]Gly-Arg—OCH$_3$
[N—(—C(O)(CH$_2$)$_2$Ph)—N—(OCH$_3$)]Gly-Arg—OCH$_3$
[N—(—C(O)(CH$_2$)$_2$Ph)—N—(OCH$_2$Ph)]Gly-Arg—OCH$_3$
[N—(—C(O)(CH$_2$)$_2$Ph)—N—(NH$_2$)]Gly-Arg—OCH$_3$
[N—(—C(O)(CH$_2$)$_2$Ph)—N—(N(CH$_3$)$_2$)]Gly-Arg—OCH$_3$
[N—(—C(O)(CH$_2$)$_2$Ph)—N—(NHBoc)]Gly-Arg—OCH$_3$
[N—(—C(O)(CH$_2$)$_2$Ph)—N—(CH$_2$CO$_2$H)]Gly-Arg—OCH$_3$
[N—(—C(O)(CH$_2$)$_2$Ph)—N—(CH$_2$CO$_2$CH$_3$)]Gly-Arg—OCH$_3$
[N—(—C(O)CH$_2$Ph)—N—(CH$_3$)]Gly-Arg—OCH$_3$
[N—(—C(O)(CH$_2$)$_3$Ph)—N—(CH$_3$)]Gly-Arg—OCH$_3$
[N—(—C(O)Ph)—N—(CH$_3$)]Gly-Arg—OCH$_3$
[N—(—C(O)(CH$_2$)$_2$Ph)—N—CH$_2$Ph)]Gly-Arg—OCH$_3$
[N—(—C(O)(CH$_2$)$_2$Ph-3,4-C$_{12}$)—N—(CH$_3$)]Gly-Arg—OCH$_3$
[N—(—C(O)(CH$_2$)$_2$Ph-4-Cl)—N—(CH$_3$)]Gly-Arg—OCH$_3$
[N—(—C(O)(CH$_2$)$_2$Ph-4-CH$_3$)—N—(CH$_3$)]Gly-Arg—OCH$_3$
[N—(—C(O)(CH$_2$)$_2$Ph-4-OCH$_3$)—N—(CH$_3$)]Gly-Arg—OCH$_3$
[N—(—C(O)(CH$_2$)$_2$Ph)—N—(CH$_3$)]Gly-Arg—CO$_2$CH$_3$
[N—(—C(O)(CH$_2$)$_2$Ph)—N—(CH$_2$)$_2$Ph]Gly-Arg—CO$_2$CH$_3$
[N—(—C(O)(CH$_2$)$_2$Ph)—N—Ph]Gly-Arg—CO$_2$CH$_3$
[N—(—C(O)N(CH$_3$)CH$_2$Ph)—N—Ph]Gly-Arg—CO$_2$CH$_3$
[N—(—C(O)Ph-3-CH=CHPh)—N—(CH$_3$)]Gly-Arg—CO$_2$CH$_3$
[N—(—C(O)Ph-3-CH$_2$CH$_2$Ph)—N—(CH$_3$)]Gly-Arg—CO$_2$CH$_3$
[N—(—C(O)Ph-3-SPh-3-OCH$_3$)—N—(CH$_3$)]Gly-Arg—CO$_2$CH$_3$
[N—(—C(O)Ph-2-CH$_2$Ph-2-Ph)—N—(CH$_3$)]Gly-Arg—CO$_2$CH$_3$
[N—(—C(O)Ph-4-CH$_2$Ph-N)—N—(CH$_3$)]Gly-Arg—CO$_2$CH$_3$
[N—(—C(O)Ph-2-CH$_2$Ph)—N—(CH$_3$)]Gly-Arg—CO$_2$CH$_3$
[N—(—C(O)Ph-3-CH$_2$Ph)—N—(CH$_3$)]Gly-Arg—CO$_2$CH$_3$
[N—(—C(O)Ph-3-CH$_2$Ph-2-CF$_3$)—N—(CH$_3$)]Gly-Arg—CO$_2$CH$_3$
[N—(—C(O)CH$_2$Ph-3,4-Cl$_2$)—N—(CH$_3$)]Gly-Arg—CO$_2$CH$_3$
[N—(—C(O)(CH$_2$)$_2$Ph)—N—(C$_2$H))]Gly-Arg—CO$_2$CH$_3$
[N—(—C(O)(CH$_2$)$_2$Ph)—N—(n-C$_3$H$_7$)]Gly-Arg—CO$_2$CH$_3$
[N—(—C(O)(CH$_2$)$_2$Ph)—N—(i-C$_3$H$_7$)]Gly-Arg—CO$_2$CH$_3$

[N—(—C(O)(CH₂)₂Ph)—N—(C₆H₁₂)]Gly-Arg—CO₂CH₃
[N—(—C(O)(CH₂)₂Ph)—N—(OH)]Gly-Arg—CO₂CH₃
[N—(—C(O)(CH₂)₂Ph)—N—(OCH₃)]Gly-Arg—CO₂CH₃
[N—(—C(O)(CH₂)₂Ph)—N—(OCH₂Ph)]Gly-Arg—CO₂CH₃
[N—(—C(O)(CH₂)₂Ph)—N—(NH₂)]Gly-Arg—CO₂CH₃
[N—(—C(O)(CH₂)₂Ph)—N—(N(CH₃)₂)]Gly-Arg—CO₂CH₃
[N—(—C(O)(CH₂)₂Ph)—N—(NHBoc)]Gly-Arg—CO₂CH₃
[N—(—C(O)(CH₂)₂Ph)—N—(CH₂CO₂H)]Gly-Arg—CO₂CH₃
[N—(—C(O)(CH₂)₂Ph)—N—(CH₂CO₂CH₃)]Gly-Arg—CO₂CH₃
[N—(—C(O)CH₂Ph)—N—(CHC CH₃)]Gly-Arg—CO₂CH₃
[N—(—C(O)(CH₂)₃Ph)—N—(CH₃)]Gly-Arg—CO₂CH₃
[N—(—C(O)Ph)—N—(CH₃)]Gly-Arg—CO₂CH₃
[N—(—C(O)(CH₂)₂Ph)—N—CH₂Ph]Gly-Arg—CO₂CH₃
[N—(—C(O)(CH₂)₂Ph-3,4-Cl₂)—N—(CH₃)]Gly-Arg—CO₂CH₃
[N—(—C(O)(CH₂)₂Ph-4-Cl)—N—(CH₃)]Gly-Arg—CO₂CH₃
[N—(—C(O)(CH₂)₂Ph-4-CH₃)—N—(CH₃)]Gly-Arg—CO₂CH₃
[N—(—C(O)(CH₂)₂Ph-4-OCH₃)—N—(CH₃)]Gly-Arg—CO₂CH₃
[N—(—C(O)(CH₂)₂Ph)—N—(CH₃)]Gly-boroPhe(mCN)—OH
[N—(—C(O)(CH₂)₂Ph)—N—(CH₂)₂Ph]Gly-boroPhe(mCN)—OH
[N—(—C(O)(CH₂)₂Ph)—N—Ph]Gly-boroPhe(mCN)—OH
[N—(—C(O)N(CH₃)CH₂Ph)—N—Ph]Gly-boroPhe(mCN)—OH
[N—(—C(O)Ph-3-CH=CHPh)—N—(CH₃)]Gly-boroPhe(mCN)—OH
[N—(—C(O)Ph-3-CH₂CH₂Ph)—N—(CH₃)]Gly-boroPhe(mCN)—OH
[N—(—C(O)Ph-3-SPh-3-OCH₃)—N—(CH₃)]Gly-boroPhe(mCN)—OH
[N—(—C(O)Ph-2-CH₂Ph-2-Ph)—N—(CH₃)]Gly-boroPhe(mCN)—OH
[N—(—C(O)Ph-4-CH₂Ph)—N—(CH₃)]Gly-boroPhe(mCN)—OH
[N—(—C(O)Ph-2-CH₂Ph)—N—(CH₃)]Gly-borophe(mCN)—OH
[N—(—C(O)Ph-3-CH₂Ph)—N—(CH₃)]Gly-boroPhe(mCN)—OH
[N—(—C(O)Ph-3-CH₂Ph-2-CF₃)—N—(CH₃)]Gly-borophe(mCN)—OH
[N—(—C(O)CH₂Ph-3,4-Cl₂)—N—(CH₃)]Gly-borophe(mCN)—OH
[N—(—C(O)(CH₂)₂Ph)—N—(C₂H₅)]Gly-boroPhe(mCN)—OH
[N—(—C(O)(CH₂)₂Ph)—N—(n-C₃H₇)]Gly-boroPhe(mCN)—OH
[N—(—C(O)(CH₂)₂Ph)—N—(i-C₃H₇)]Gly-boroPhe(mCN)—OH
[N—(—C(O)(CH₂)₂Ph)—N—(C₆H₁₂)]Gly-boroPhe(mCN)—OH
[N—(—C(O)(CH₂)₂Ph)—N—(OH)]Gly-boroPhe(mCN)—OH
[N—(—C(O)(CH₂)₂Ph)—N—(OCH₃)]Gly-boroPhe(mCN)—OH
[N—(—C(O)(CH₂)₂Ph)—N—(OCH₂Ph)]Gly-boroPhe(mCN)—OH
[N—(—C(O)(CH₂)₂Ph)—N—(NH₂)]Gly-boroPhe(mCN)—OH
[N—(—C(O)(CH₂)₂Ph)—N—(N(CH₃)₂)]Gly-boroPhe(mCN)—OH
[N—(—C(O)(CH₂)₂Ph)—N—(NHBoc)]Gly-borophe(mCN)—OH
[N—(—C(O)(CH₂)₂Ph)—N—(CH₂CO₂H)]Gly-boroPhe(mCN)—OH
[N—(—C(O)(CH₂)₂Ph)—N—(CH₂CO₂CH₃)]Gly-boroPhe(mCN)—OH
[N—(—C(O)CH₂Ph)—N—(CH₃)]Gly-boroPhe(mCN)—OH
[N—(—C(O)(CH₂)₃Ph)—N—(CH₃)]Gly-boroPhe(mCN)—OH
[N—(—C(O)Ph)—N—(CH₃)]Gly-boroPhe(mCN)—OH
[N—(—C(O)(CH₂)₂Ph)—N—CH₂Ph]Gly-boroPhe(mCN)—OH
[N—(—C(O)(CH₂)₂Ph-3,4-Cl₂)—N—(CH₃)]Gly-boroPhe(mCN)—OH
[N—(—C(O)(CH₂)₂Ph-4-Cl)—N—(CH₃)]Gly-boroPhe(mCN)—OH
[N—(—C(O)(CH₂)₂Ph-4-CH₃)—N—(CH₃)]Gly-boroPhe(mCN)—OH
[N—(—C(O)(CH₂)₂Ph-4-OCH₃)—N—(CH₃)]Gly-boroPhe(mCN)—OH
[N—(—C(O)(CH₂)₂Ph)—N—(CH₃)]Gly-boroPhe(mCN)—C₁₀H₁₆
[N—(—C(O)(CH₂)₂Ph)—N—(CH₂)₂Ph]Gly-boroPhe(mCN)—C₁₀H₁₆
[N—(—C(O)(CH₂)₂Ph)—N—Ph]Gly-borophe(mCN)—C₁₀H₁₆
[N—(—C(O)N(CH₃)CH₂Ph)—N—Ph]Gly-boroPhe(mCN)—C₁₀H₁₆
[N—(—C(O)Ph-3-CH=CHPh)—N—(CH₃)]Gly-boroPhe(mCN)—C₁₀H₁₆
[N—(—C(O)Ph-3-CH₂CH₂Ph)—N—(CH₃)]Gly-boroPhe(mCN)—C₁₀H₁₆
[N—(—C(O)Ph-3-SPh-3-OCH₃)—N—(CH₃)]Gly-boroPhe(mCN)—C₁₀H₁₆
[N—(—C(O)Ph-2-CH₂Ph-2-Ph)—N—(CH₃)]Gly-boroPhe(mCN)—C₁₀H₁₆
[N—(—C(O)Ph-4-CH₂Ph)—N—(CH₃)]Gly-boroPhe(mCN)—C₁₀H₁₆
[N—(—C(O)Ph-2-CH₂Ph)—N—(CH₃)]Gly-boroPhe(mCN)—C₁₀H₁₆
[N—(—C(O)Ph-3-CH₂Ph)—N—(CH₃)]Gly-boroPhe(mCN)—C₁₀H₁₆
[N—(—C(O)Ph-3-CH₂Ph-2-CF₃)—N—(CH₃)]Gly-boroPhe(mCN)—C₁₀H₁₆
[N—(—C(O)(CH₂)₂Ph)—N—(C₂H₅)]Gly-boroPhe(mCN)—C₁₀H₁₆
[N—(—C(O)(CH₂)₂Ph)—N—(n-C₃H₇)]Gly-boroPhe(mCN)—C₁₀H₁₆
[N—(—C(O)(CH₂)₂Ph)—N—(i-C₃H₇)]Gly-boroPhe(mCN)—C₁₀H₁₆
[N—(—C(O)(CH₂)₂Ph)—N—(C₆H₁₂)]Gly-boroPhe(mCN)—C₁₀H₁₆
[N—(—C(O)(CH₂)₂Ph)—N—(OH)]Gly-boroPhe(mCN)—C₁₀H₁₆
[N—(—C(O)(CH₂)₂Ph)—N—(OCH₃)]Gly-boroPhe(mCN)—C₁₀H₁₆
[N—(—C(O)(CH₂)₂Ph)—N—(OCH₂Ph)]Gly-boroPhe(mCN)—C₁₀H₁₆
[N—(—C(O)(CH₂)₂Ph)—N—(NH₂)]Gly-boroPhe(mCN)—C₁₀H₁₆
[N—(—C(O)(CH₂)₂Ph)—N—(N(CH₃)₂)]Gly-boroPhe(mCN)—C₁₀H₁₆

[N—(—C(O)(CH₂)₂Ph)—N—(NHBoc)]Gly-boroPhe(mCN)—C₁₀H₁₆
[N—(—C(O)(CH₂)₂Ph)—N—(CH₂CO₂H)]Gly-boroPhe(raCN)—C₁₀H₁₆
[N—(—C(O)(CH₂)₂Ph)—N—(CH₂CO₂CH₃)]Gly-boroPhe(mCN)—C₁₀H₁₆
[N—(—C(O)CH₂Ph)—N—(CH₃)]Gly-boroPhe(mCN)—C₁₀H₁₆
[N—(—C(O)(CH₂)₃Ph)—N—(CH₃)]Gly-boroPhe(mCN)—C₁₀H₁₆
[N—(—C(O)Ph)—N—(CH₃)]Gly-borophe(mCN)—C₁₀H₁₆
[N—(—C(O)(CH₂)₂Ph)—N—CH₂Ph]Gly-boroPhe(mCN)—C₁₀H₁₆
[N—(—C(O)(CH₂)₂Ph-3,4-Cl₂)—N—(CH₃)]Gly-boroPhe(mCN)—C₁₀H₁₆
[N—(—C(O)(CH₂)₂Ph-4-Cl)—N—(CH₃)]Gly-boroPhe(mCN)—C₁₀H₁₆
[N—(—C(O)(CH₂)₂Ph-4-CH₃)—N—(CH₃)]Gly-boroPhe(mCN)—C₁₀H₁₆
[N—(—C(O)(CH₂)₂Ph-4-OCH₃)—N—(CH₃)]Gly-boroPhe(mCN)—C₁₀H₁₆
[N—(—C(O)(CH₂)₂Ph)—N—(CH₃)]Gly-Phe(mCN)—CF₃
[N—(—C(O)(CH₂)₂Ph)—N—(CH₂)Ph]Gly-Phe(mCN)—CF₃
[N—(—C(O)(CH₂)₂Ph)—N—Ph]Gly-Phe(mCN)—CF₃
[N—(—C(O)N(CH₃)CH₂Ph)—N—Ph]Gly-Phe(mCN)—CF₃
[N—(—C(O)Ph-3-CH=CHPh)—N—(CH₃)]Gly-Phe(mCN)—CF₃
[N—(—C(O)Ph-3-CH₂CH₂Ph)—N—(CH₃)]Gly-Phe(mCN)—CF₃
[N—(—C(O)Ph-3-SPh-3-OCH₃)—N—(CH₃)]Gly-Phe(mCN)—CF₃
[N—(—C(O)Ph-2-CH₂Ph-2-Ph)—N—(CH₃)]Gly-Phe(mCN)—CF₃
[N—(—C(O)Ph-4-CH₂Ph)—N—(CH₃)]Gly-Phe(mCN)—CF₃
[N—(—C(O)Ph-2-CH₂Ph)—N—(CH₃)]Gly-Phe(mCN)—CF₃
[N—(—C(O)Ph-3-CH₂Ph)—N—(CH₃)]Gly-Phe(mCN)—CF₃
[N—(—C(O)Ph-3-CH₂Ph-2-CF₃)—N—(CH₃)]Gly-Phe(mCN)—CF₃
[N—(—C(O)CH₂Ph-3,4-Cl₂)—N—(CH₃)]Gly-Phe(mCN)—CF₃
[N—(—C(O)(CH₂)₂Ph)—N—(C₂H₅)]Gly-Phe(mCN)—CF₃
[N—(—C(O)(CH₂)₂Ph)—N—(n-C₃H₇)]Gly-Phe(mCN)—CF₃
[N—(—C(O)(CH₂)₂Ph)—N—(i-C₃H₇)]Gly-Phe(mCN)—CF₃
[N—(—C(O)(CH₂)₂Ph)—N—(C₆H₁₂)]Gly-Phe(mCN)—CF₃
[N—(—C(O)(CH₂)₂Ph)—N—(OH)]Gly-Phe(mCN)—CF₃
[N—(—C(O)(CH₂)₂Ph)—N—(OCH₃)]Gly-Phe(mCN)—CF₃
[N—(—C(O)(CH₂)₂Ph)—N—(OCH₂Ph)]Gly-Phe(mCN)—CF₃
[N—(—C(O)(CH₂)₂Ph)—N—(NH₂)]Gly-Phe(mCN)—CF₃
[N—(—C(O)(CH₂)₂Ph)—N—(N(CH₃)₂)]Gly-Phe(mCN)—CF₃
[N—(—C(O)(CH₂)₂Ph)—N—(NHBoc)]Gly-Phe(mCN)—CF₃
[N—(—C(O)(CH₂)₂Ph)—N—(CH₂CO₂H)]Gly-Phe(mCN)—CF₃
[N—(—C(O)(CH₂)₂Ph)—N—(CH₂CO₂CH₃)]Gly-Phe(mCN)—CF₃
[N—(—C(O)CH₂Ph)—N—(CH₃)]Gly-Phe(mCN)—CF₃
[N—(—C(O)(CH₂)₃Ph)—N—(CH₃)]Gly-Phe(mCN)—CF₃
[N—(—C(O)Ph)—N—(CH₃)]Gly-Phe(mCN)—CF₃
[N—(—C(O)(CH₂)₂Ph)—N—CH₂Ph]Gly-Phe(mCN)—CF₃
[N—(—C(O)(CH₂)₂Ph-3,4-Cl₂)—N—(CH₃)]Gly-Phe(mCN)—CF₃
[N—(—C(O)(CH₂)₂Ph-4-Cl)—N—(CH₃)]Gly-Phe(mCN)—CF₃
[N—(—C(O)(CH₂)₂Ph-4-CH₃)—N—(CH₃)]Gly-Phe(mCN)—CF₃
[N—(—C(O)(CH₂)₂Ph-4-OCH₃)—N—(CH₃)]Gly-Phe(mCN)—CF₃
[N—(—C(O)(CH₂)₂Ph)—N—(CH₃)]Gly-Phe(mCN)—OCH₃
[N—(—C(O)(CH₂)₂Ph)—N—(CH₂)₂Ph]Gly-Phe(mCN)—OCH₃
[N—(—C(O)(CH₂)₂Ph)—N—Ph]Gly-Phe(mCN)—OCH₃
[N—(—C(O)N(CH₃)CH₂Ph)—N—Ph]Gly-Phe(mCN)—OCH₃
[N—(—C(O)Ph-3-CH=CHPh)—N—(CH₃)]Gly-Phe(mCN)—OCH₃
[N—(—C(O)Ph-3-CH₂CH₂Ph)—N—(CH₃)]Gly-Phe(mCN)—OCH₃
[N—(—C(O)Ph-3-SPh-3-OCH₃)—N—(CH₃)]Gly-Phe(mCN)—OCH₃
[N—(—C(O)Ph-2-CH₂Ph-2-Ph)—N—(CH₃)]Gly-Phe(mCN)—OCH₃
[N—(—C(O)Ph-4-CH₂Ph)—N—(CH₃)]Gly-Phe(mCN)—OCH₃
[N—(—C(O)Ph-2-CH₂Ph)—N—(CH₃)]Gly-Phe(mCN)—OCH₃
[N—(—C(O)Ph-3-CH₂Ph)—N—(CH₃)]Gly-Phe(mCN)—OCH₃
[N—(—C(O)Ph-3-CH₂Ph-2-CF₃)—N—(CH₃)]Gly-Phe(mCN)—OCH₃
[N—(—C(O)CH₂Ph-3,4-Cl₂)—N—(CH₃)]Gly-Phe(mCN)—OCH₃
[N—(—C(O)(CH₂)₂Ph)—N—(C₂H₅)]Gly-Phe(mCN)—OCH₃
[N—(—C(O)(CH₂)₂Ph)—N—(n-C₃H₇)]Gly-Phe(mCN)—OCH₃
[N—(—C(O)(CH₂)₂Ph)—N—(i-C₃H₇)]Gly-Phe(mCN)—OCH₃
[N—(—C(O)(CH₂)₂Ph)—N—(C₆H₁₂)]Gly-Phe(mCN)—OCH₃
[N—(—C(O)(CH₂)₂Ph)—N—(OH)]Gly-Phe(mCN)—OCH₃
[N—(—C(O)(CH₂)₂Ph)—N—(OCH₃)]Gly-Phe(mCN)—OCH₃
[N—(—C(O)(CH₂)₂Ph)—N—(OCH₂Ph)]Gly-Phe(mCN)—OCH₃
[N—(—C(O)(CH₂)₂Ph)—N—(NH₂)]Gly-Phe(mCN)—OCH₃
[N—(—C(O)(CH₂)₂Ph)—N—(N(CH₃)₂)]Gly-Phe(mCN)—OCH₃
[N—(—C(O)(CH₂)₂Ph)—N—(NHBoc)]Gly-Phe(mCN)—OCH₃
[N—(—C(O)(CH₂)₂Ph)—N—(CH₂CO₂H)]Gly-Phe(mCN)—OCH₃
[N—(—C(O)(CH₂)₂Ph)—N—(CH₂CO₂CH₃)]Gly-Phe(mCN)—OCH₃
[N—(—C(O)CH₂Ph)—N—(CH₃)]Gly-Phe(mCN)—OCH₃
[N—(—C(O)(CH₂)₃Ph)—N—(CH₃)]Gly-Phe(mCN)—OCH₃
[N—(—C(O)Ph)—N—(CH₃)]Gly-Phe(mCN)—OCH₃
[N—(—C(O)(CH₂)₂Ph)—N—CH₂Ph]Gly-Phe(mCN)—OCH₃

[N—(—C(O)(CH$_2$)$_2$Ph-3,4-Cl$_2$)—N—(CH$_3$)]Gly-Phe
(mCN)—OCH$_3$
[N—(—C(O)(CH$_2$)$_2$Ph-4-Cl)—N—(CH$_3$)]Gly-Phe
(mCN)—OCH$_3$
[N—(—C(O)(CH$_2$)$_2$Ph-4-CH$_3$)—N—(CH$_3$)]Gly-Phe
(mCN)—OCH$_3$
[N—(—C(O)(CH$_2$)$_2$Ph-4-OCH$_3$)—N—(CH$_3$)]Gly-Phe
(mCN)—OCH$_3$
[N—(—C(O)(CH$_2$)$_2$Ph)—N—(CH$_3$)]Gly-Phe(mCN)—
CO$_2$CH$_3$
[N—(—C(O)(CH$_2$)$_2$Ph)—N—(CH$_2$)$_2$Ph]Gly-Phe(mCN)—
CO$_2$CH$_3$
[N—(—C(O)(CH$_2$)$_2$Ph)—N—Ph]Gly-Phe(mCN)—
CO$_2$CH$_3$
[N—(—C(O) N(CH$_3$)CH$_2$Ph)—N—Ph]Gly-Phe(mCN)—
CO$_2$CH$_3$
[N—(—C(O)Ph-3-CH=CHPh)—N—(CH$_3$)]Gly-Phe
(mCN)—CO$_2$CH$_3$
[N—(—C(O)Ph-3-CH$_2$CH$_2$Ph)—N—(CH$_3$)]Gly-Phe
(mCN)—CO$_2$CH$_3$
[N—(—C(O)Ph-3-SPh-3-OCH$_3$)—N—(CH$_3$)]Gly-Phe
(mCN)—CO$_2$CH$_3$
[N—(—C(O)Ph-2-CH$_2$Ph-2-Ph)—N—(CH$_3$)]Gly-Phe
(mCN)—CO$_2$CH$_3$
[N—(—C(O)Ph-4-CH$_2$Ph)—N—(CH$_3$)]Gly-Phe(mCN)—
CO$_2$CH$_3$
[N—(—C(O)Ph-2-CH$_2$Ph)—N—(CH$_3$)]Gly-Phe(mCN)—
CO$_2$CH$_3$
[N—(—C(O)Ph-3-CH$_2$Ph)—N—(CH$_3$)]Gly-Phe(mCN)—
CO$_2$CH$_3$
[N—(—C(O)Ph-3-CH$_2$Ph-2-CF$_3$)—N—(CH$_3$)]Gly-Phe
(mCN)—CO$_2$CH$_3$
[N—(—C(O)CH$_2$Ph-3,4-Cl$_2$)—N—(CH$_3$)]Gly-Phe
(mCN)—CO$_2$CH$_3$
[N—(—C(O)(CH$_2$)$_2$Ph)—N—(C$_2$H$_5$)]Gly-Phe(mCN)—
CO$_2$CH$_3$
[N—(—C(O)(CH$_2$)$_2$Ph)—N—(n-C$_3$H$_7$)]Gly-Phe(mCN)—
CO$_2$CH$_3$
[N—(—C(O)(CH$_2$)$_2$Ph)—N—(i-C$_3$H$_7$)]Gly-Phe(mCN)—
CO$_2$CH$_3$
[N—(—C(O)(CH$_2$)$_2$Ph)—N—(C$_6$H$_{12}$)]Gly-Phe(mCN)—
CO$_2$CH$_3$
[N—(—C(O)(CH$_2$)$_2$Ph)—N—(OH)]Gly-Phe(mCN)—
CO$_2$CH$_3$
[N—(—C(O)(CH$_2$)$_2$Ph)—N—(OCH$_3$)]Gly-Phe(mCN)—
CO$_2$CH$_3$
[N—(—C(O)(CH$_2$)$_2$Ph)—N—(OCH$_2$Ph)]Gly-Phe
(mCN)—CO$_2$CH$_3$
[N—(—C(O)(CH$_2$)$_2$Ph)—N—(NH$_2$)]Gly-Phe(mCN)—
CO$_2$CH$_3$
[N—(—C(O)(CH$_2$)$_2$Ph)—N—(N(CH$_3$)$_2$)]Gly-Phe
(mCN)—CO$_2$CH$_3$
[N—(—C(O)(CH$_2$)$_2$Ph)—N—(NHBoc)]Gly-Phe(mCN)—
CO$_2$CH$_3$
[N—(—C(O)(CH$_2$)$_2$Ph)—N—(CH$_2$CO$_2$H)]Gly-Phe
(mCN)—CO$_2$CH$_3$
[N—(—C(O)(CH$_2$)$_2$Ph)—N—(CH$_2$CO$_2$CH$_3$)]Gly-Phe
(mCN)—CO$_2$CH$_3$
[N—(—C(O)CH$_2$ Ph)—N—(CH$_3$)]Gly-Phe(mCN)—
CO$_2$CH$_3$
[N—(—C(O)(CH$_2$)$_3$Ph)—N—(CH$_3$)]Gly-Phe(mCN)—
CO$_2$CH$_3$
[N—(—C(O)Ph)—N—(CH$_3$)]Gly-Phe(mCN)—CO$_2$CH$_3$
[N—(—C(O)(CH$_2$)$_2$ Ph)—N—CH$_2$Ph]Gly-Phe(mCN)—
CO$_2$CH$_3$
[N—(—C(O)(CH$_2$)$_2$Ph-3,4-Cl$_2$)—N—(CH$_3$)]Gly-Phe
(mCN)—CO$_2$CH$_3$
[N—(—C(O)(CH$_2$)$_2$Ph-4-Cl)—N—(CH$_3$)]Gly-Phe
(mCN)—CO$_2$CH$_3$
[N—(—C(O)(CH$_2$)$_2$Ph-4-CH$_3$)—N—(CH$_3$)]Gly-Phe
(mCN)—CO$_2$CH$_3$
[N—(—C(O)(CH$_2$)$_2$Ph-4-OCH$_3$)—N—(CH$_3$)]Gly-Phe
(mCN)—CO$_2$CH$_3$
[N—(—C(O)(CH$_2$)$_2$Ph)—N—(CH$_2$)$_2$Ph]Gly-boroOrn(N-methylamidino)—OH
[N—(—C(O)(CH$_2$)$_2$Ph)—N—Ph]Gly-boroOrn(N-methylamidino)—OH
[N—(—C(O)N(CH$_3$)CH$_2$Ph)—N—Ph]Gly-boroOrn(N-methylamidino)—OH
[N—(—C(O)Ph-3-CH=CHPh)—N—(CH$_3$)]Gly-boroOrn
(N-methylamidino)—OH
[N—(—C(O)Ph-3-CH$_2$CH$_2$Ph)—N—(CH$_3$)]Gly-boroOrn
(N-methylamidino)—OH
[N—(—C(O)Ph-3-SPh-3-OCH$_3$)—N—(CH$_3$)]Gly-boroOrn
(N-methylamidino)—OH
[N—(—C(O)Ph-2-CH$_2$Ph-2-Ph)—N—(CH$_3$)]Gly-boroOrn
(N-methylamidino)—OH
[N—(—C(O)Ph-4-CH$_2$Ph)—N—(CH$_3$)]Gly-boroOrn(N-methylamidino)—OH
[N—(—C(O)Ph-2-CH$_2$Ph)—N—(CH$_3$)]Gly-boroOrn
(N-methylamidino)—OH
[N—(—C(O)Ph-3-CH$_2$Ph)—N—(CH$_3$)]Gly-boroOrn(N-methylamidino)—OH
[N—(—C(O)Ph-3-CH$_2$Ph-2-CF$_3$)—N—(CH$_3$)]Gly-boroOrn(N-methylamidino)—OH
[N—(—C(O)(CH$_2$)$_2$Ph)—N—(C$_2$H$_5$)]Gly-boroOrn(N-methylamidino)—OH
[N—(—C(O)(CH$_2$)$_2$Ph)—N—(n-C$_3$H$_7$)]Gly-boroOrn(N-methylamidino)—OH
[N—(—C(O)(CH$_2$)$_2$Ph)—N—(i-C$_3$H$_7$)]Gly-boroOrn(N-methylamidino)—OH
[N—(—C(O)(CH$_2$)$_2$Ph)—N—(C$_6$H$_{12}$)]Gly-boroOrn(N-methylamidino)—OH
[N—(—C(O)(CH$_2$)$_2$Ph)—N—(OH)]Gly-boroOrn(N-methylamidino)—OH
[N—(—C(O)(CH$_2$)$_2$Ph)—N—(OCH$_3$)]Gly-boroOrn(N-methylamidino)—OH
[N—(—C(O)(CH$_2$)$_2$Ph)—N—(OCH$_2$Ph)]Gly-boroOrn(N-methylamidino)—OH
[N—(—C(O)(CH$_2$)$_2$Ph)—N—(NH2)]Gly-boroOrn(N-methylamidino)—OH
[N—(—C(O)(CH$_2$)$_2$Ph)—N—(N(CH$_3$)$_2$)]Gly-boroOrn(N-methylamidino)—OH
[N—(—C(O)(CH$_2$)$_2$Ph)—N—(NHBoc)]Gly-boroOrn(N-methylamidino)—OH
[N—(—C(O)(CH$_2$)$_2$Ph)—N—(CH$_2$CO$_2$H)]Gly-boroOrn
(N-methylamidino)—OH
[N—(—C(O)(CH$_2$)$_2$Ph)—N—(CH$_2$CO$_2$CH$_3$)]Gly-boroOrn
(N-methylamidino)—OH
[N—(—C(O)CH$_2$Ph)—N—(CH$_3$)]Gly-boroOrn(N-methylamidino)—OH
[N—(—C(O)(CH$_2$)$_3$Ph)—N—(CH$_3$)]Gly-boroOrn(N-methylamidino)—OH
[N—(—C(O)Ph)—N—(CH$_3$)]Gly-boroOrn(N-methylamidino)—OH
[N—(—C(O)(CH$_2$)$_2$Ph)—N—CH$_2$Ph)]Gly-boroOrn(N-methylamidino)—OH
[N—(—C(O)(CH$_2$)$_2$Ph-3,4-Cl$_2$)—N—(CH$_3$)]Gly-boroOrn
(N-methylamidino)—OH
[N—(—C(O)(CH$_2$)$_2$Ph-4-Cl)—N—(CH$_3$)]Gly-boroOrn(N-methylamidino)—OH
[N—(—C(O)(CH$_2$)$_2$Ph-4-CH$_3$)—N—(CH$_3$)]Gly-boroOrn
(N-methylamidino)—OH
[N—(—C(O)(CH$_2$)$_2$Ph-4-OCH$_3$)—N—(CH$_3$)]Gly-boroOrn(N-methylamidino)—OH

[N—(—C(O)(CH₂)₂Ph)—N—Ph]Gly-boroOrn(N-methylamidino)—C₁₀H₁₆
[N—(—C(O)N(CH₃)CH₂Ph)—N—Ph]Gly-boroOrn(N-methylamidino)—C₁₀H₁₆
[N—(—C(O)Ph-3-CH=CHPh)—N—(CH₃)]Gly-boroOrn(N-methylamidino)—C₁₀H₁₆
[N—(—C(O)Ph-3-CH₂CH₂Ph)—N—(CH₃)]Gly-boroOrn(N-methylamidino)—C₁₀H₁₆
[N—(—C(O)Ph-3-SPh-3-OCH₃)—N—(CH₃)]Gly-boroOrn(N-methylamidino)—C₁₀H₁₆
[N—(—C(O)Ph-2-CH₂Ph-2-Ph)—N—(CH₃)]Gly-boroOrn(N-methylamidino)—C₁₀H₁₆
[N—(—C(O)Ph-4-CH₂Ph)—N—(CH₃)]Gly-boroOrn(N-methylamidino)—C₁₀H₁₆
[N—(—C(O)Ph-2-CH₂Ph)—N—(CH₃)]Gly-boroOrn(N-methylamidino)—C₁₀H₁₆
[N—(—C(O)Ph-3-CH₂Ph)—N—(CH₃)]Gly-boroOrn(N-nmethylamidino)—C₁₀H₁₆
[N—(—C(O)Ph-3-CH₂Ph-2-CF₃)—N—(CH₃)]Gly-boroOrn(N-methylamidino)—C₁₀H₁₆
[N—(—C(O)(CH₂)₂Ph)—N—(C₂H₅)]Gly-boroOrn(N-methylamidino)—C₁₀H₁₆
[N—(—C(O)(CH₂)₂Ph)—N—(n-C₃H₇)]Gly-boroOrn(N-methylamidino)—C₁₀H₁₆
[N—(—C(O)(CH₂)₂Ph)—N—(i-C₃H₇)]Gly-boroOrn(N-methylamidino)—C₁₀H₁₆
[N—(—C(O)(CH₂)₂Ph)—N—(C₆H₁₂)]Gly-boroOrn(N-methylamidino)—C₁₀H₁₆
[N—(—C(O)(CH₂)₂Ph)—N—(OH)]Gly-boroOrn(N-methylamidino)—C₁₀H₁₆
[N—(—C(O)(CH₂)₂Ph)—N—(OCH₃)]Gly-boroOrn(N-methylamidino)—C₁₀H₁₆
[N—(—C(O)(CH₂)₂Ph)—N—(OCH₂Ph)]Gly-boroOrn(N-methylamidino)—C₁₀H₁₆
[N—(—C(O)(CH₂)₂Ph)—N—(NH₂)]Gly-boroOrn(N-inethylamidino)—C₁₀H₁₆
[N—(—C(O)(CH₂)₂Ph)—N—(N(CH₃)₂)]Gly-boroOrn(N-methylamidino)—C₁₀H₁₆
[N—(—C(O)(CH₂)₂Ph)—N—(NHBoc)]Gly-boroOrn(N-methylamidino)—C₁₀H₁₆
[N—(—C(O)(CH₂)₂Ph)—N—(CH₂CO₂H)]Gly-boroOrn(N-methylamidino)—C₁₀H₁₆
[N—(—C(O)(CH₂)₂Ph)—N—(CH₂CO₂CH₃)]Gly-boroOrn(N-methylamidino)—C₁₀H₁₆
[N—(—C(O)CH₂Ph)—N—(CH₃)]Gly-boroOrn(N-methylamidino)—C₁₀H₁₆
[N—(—C(O)(CH₂)₃Ph)—N—(CH₃)]Gly-boroOrn(N-methylamidino)—C₁₀H₁₆
[N—(—C(O)Ph)—N—(CH₃)]Gly-boroOrn(N-methylamidino)—C₁₀H₁₆
[N—(—C(O)(CH₂)₂Ph)—N—CH₂Ph)]Gly-boroOrn(N-methylamidino)—C₁₀H₁₆
[N—(—C(O)(CH₂)₂Ph-3,4-Cl₂)—N—(CH₃)]Gly-boroOrn(N-methylamidino)—C₁₀H₁₆
[N—(—C(O)(CH₂)₂Ph-4-Cl)—N—(CH₃)]Gly-boroOrn(N-methylamidino)—C₁₀H₁₆
[N—(—C(O)(CH₂)₂Ph-4-CH₃)—N—(CH₃)]Gly-boroOrn(N-methylamidino)—C₁₀H₁₆
[N—(—C(O)(CH₂)₂Ph-4-OCH₃)—N—(CH₃)]Gly-boroOrn(N-methylamidino)—C₁₀H₁₆
[N—(—C(O)(CH₂)₂Ph)—N—(CH₃)]Gly-Orn(N-methylamidino)—CF₃
[N—(—C(O)(CH₂)₂Ph)—N—(CH₂)₂Ph]Gly-Orn(N-methylamidino)—CF₃
[N—(—C(O)(CH₂)₂Ph)—N—Ph]Gly-Orn(N-methylamidino)—CF₃
[N—(—C(O)N(CH₃)CH₂Ph)—N—Ph]Gly-Orn(N-methylamidino)—CF₃
[N—(—C(O)Ph-3-CH=CHPh)—N—(CH₃)]Gly-Orn(N-methylamidino)—CF₃
[N—(—C(O)Ph-3-CH₂CH₂Ph)—N—(CH₃)]Gly-Orn(N-methylamidino)—CF₃
[N—(—C(O)Ph-3-SPh-3-OCH₃)—N—(CH₃)]Gly-Orn(N-methylamidino)—CF₃
[N—(—C(O)Ph-2-CH₂Ph-2-Ph)—N—(CH₃)]Gly-Orn(N-methylamidino)—CF₃
[N—(—C(O)Ph-4-CH₂Ph)—N—(CH₃)]Gly-Orn(N-methylamidino)—CF₃
[N—(—C(O)Ph-2-CH₂Ph)—N—(CH₃)]Gly-Orn(N-methylamidino)—CF₃
[N—(—C(O)Ph-3-CH₂Ph)—N—(CH₃)]Gly-Orn(N-methylamidino)—CF₃
[N—(—C(O)Ph-3-CH₂Ph-2-CF₃)—N—(CH₃)]Gly-Orn(N-methylamidino)—CF₃
[N—(—C(O)CH₂Ph-3,4-Cl₂)—N—(CH₃)]Gly-Orn(N-methylamidino)—CF₃
[N—(—C(O)(CH₂)₂Ph)—N—(C₂H₅)]Gly-Orn(N-methylamidino)—CF₃
[N—(—C(O)(CH₂)₂Ph)—N—(n-C₃H₇)]Gly-Orn(N-methylamidino)—CF₃
[N—(—C(O)(CH₂)₂Ph)—N—(i-C₃H₇)]Gly-Orn(N-methylamidino)—CF₃
[N—(—C(O)(CH₂)₂Ph)—N—(C₆H₁₂)]Gly-Orn(N-methylamidino)—CF₃
[N—(—C(O)(CH₂)₂Ph)—N—(OH)]Gly-Orn(N-methylamidino)—CF₃
[N—(—C(O)(CH₂)₂Ph)—N—(OCH₃)]Gly-Orn(N-methylamidino)—CF₃
[N—(—C(O)(CH₂)₂Ph)—N—(OCH₂Ph)]Gly-Orn(N-methylamidino)—CF₃
[N—(—C(O)(CH₂)₂Ph)—N—(NH₂)]Gly-Orn(N-methylamidino)—CF₃
[N—(—C(O)(CH₂)₂Ph)—N—(N(CH₃)₂)]Gly-Orn(N-methylamidino)—CF₃
[N—(—C(O)(CH₂)₂Ph)—N—(NHBoc)]Gly-Orn(N-methylamidino)—CF₃
[N—(—C(O)(CH₂)₂Ph)—N—(CH₂CO₂H)]Gly-Orn(N-methylamidino)—CF₃
[N—(—C(O)(CH₂)₂Ph)—N—(CH₂CO₂CH₃)]Gly-Orn(N-methylamidino)—CF₃
[N—(—C(O)CH₂Ph)—N—(CH₃)]Gly-Orn(N-methylamidino)—CF₃
[N—(—C(O)(CH₂)₃Ph)—N—(CH₃)]Gly-Orn(N-methylamidino)—CF₃
[N—(—C(O)Ph)—N—(CH₃)]Gly-Orn(N-methylamidino)—CF₃
[N—(—C(O)(CH₂)₂Ph)—N—CH₂Ph)]Gly-Orn(N-methylamidino)—CF₃
[N—(—C(O)(CH₂)₂Ph-3,4-Cl₂)—N—(CH₃)]Gly-Orn(N-methylamidino)—CF₃
[N—(—C(O)(CH₂)₂Ph-4-Cl)—N—(CH₃)]Gly-Orn(N-methylamidino)—CF₃
[N—(—C(O)(CH₂)₂Ph-4-CH₃)—N—(CH₃)]Gly-Orn(N-methylamidino)—CF₃
[N—(—C(O)(CH₂)₂Ph-4-OCH₃)—N—(CH₃)]Gly-Orn(N-methylamidino)—CF₃
[N—(—C(O)(CH₂)₂Ph)—N—(CH₃)]Gly-Orn(N-methylamidino)—OCH₃
[N—(—C(O)(CH₂)₂Ph)—N—(CH₂)₂Ph]Gly-Orn(N-methylamidino)—OCH₃
[N—(—C(O)(CH₂)₂Ph)—N—Ph]Gly-Orn(N-methylamidino)—OCH₃
[N—(—C(O)N(CH₃)CH₂Ph)—N—Ph]Gly-Orn(N-methylamidino)—OCH₃
[N—(—C(O)Ph-3-CH=CHPh)—N—(CH₃)]Gly-Orn(N-methylamidino)—OCH₃

[N—(—C(O)Ph-3-CH₂CH₂Ph)—N—(CH₃)]Gly-Orn(N-methylamidino)—OCH₃
[N—(—C(O)Ph-3-SPh-3-OCH₃)—N—(CH₃)]Gly-Orn(N-methylamidino)—OCH₃
[N—(—C(O)Ph-2-CH₂Ph-2-Ph)—N—(CH₃)]Gly-Orn(N-methylamidino)—OCH₃
[N—(—C(O)Ph-4-CH₂Ph)—N—(CH₃)]Gly-Orn(N-methylamidino)—OCH₃
[N—(—C(O)Ph-2-CH₂Ph)—N—(CH₃)]Gly-Orn(N-methylamidino)—OCH₃
[N—(—C(O)Ph-3-CH₂Ph)—N—(CH₃)]Gly-Orn(N-methylamidino)—OCH₃
[N—(—C(O)Ph-3-CH₂Ph-2-CF₃)—N—(CH₃)]Gly-Orn(N-methylamidino)—OCH₃
[N—(—C(O)CH₂Ph-3,4-Cl₂)—N—(CH₃)]Gly-Orn(N-methylamidino)—OCH₃
[N—(—C(O)(CH₂)₂Ph)—N—(C₂H₅)]Gly-Orn(N-methylamidino)—OCH₃
[N—(—C(O)(CH₂)₂Ph)—N—(n-C₃H₇)]Gly-Orn(N-methylamidino)—OCH₃
[N—(—C(O)(CH₂)₂Ph)—N—(i-C₃H₇)]Gly-Orn(N-methylamidino)—OCH₃
[N—(—C(O)(CH₂)₂Ph)—N—(C₆H₁₂)]Gly-Orn(N-methylamidino)—OCH₃
[N—(—C(O)(CH₂)₂Ph)—N—(OH)]Gly-Orn(N-methylamidino)—OCH₃
[N—(—C(O)(CH₂)₂Ph)—N—(OCH₃)]Gly-Orn(N-methylamidino)—OCH₃
[N—(—C(O)(CH₂)₂Ph)—N—(OCH₂Ph)]Gly-Orn(N-methylamidino)—OCH₃
[N—(—C(O)(CH₂)₂Ph)—N—(NH₂)]Gly-Orn(N-methylamidino)—OCH₃
[N—(—C(O)(CH₂)₂Ph)—N—(N(CH₃)₂)]Gly-Orn(N-methylamidino)—OCH₃
[N—(—C(O)(CH₂)₂Ph)—N—(NHBoc)]Gly-Orn(N-methylamidino)—OCH₃
[N—(—C(O)(CH₂)₂Ph)—N—(CH₂CO₂H)]Gly-Orn(N-methylamidino)—OCH₃
[N—(—C(O)(CH₂)₂Ph)—N—(CH₂CO₂CH₃)]Gly-Orn(N-methylamidino)—OCH₃
[N—(—C(O)CH₂Ph)—N—(CH₃)]Gly-Orn(N-methylamidino)—OCH₃
[N—(—C(O)(CH₂)₃Ph)—N—(CH₃)]Gly-Orn(N-methylamidino)—OCH₃
[N—(—C(O)Ph)—N—(CH₃)]Gly-Orn(N-methylamidino)—OCH₃
[N—(—C(O)(CH₂)₂Ph)—N—CH₂Ph]Gly-Orn(N-methylamidino)—OCH₃
[N—(—C(O)(CH₂)₂Ph-3,4-Cl₂)—N—(CH₃)]Gly-Orn(N-methylamidino)—OCH₃
[N—(—C(O)(CH₂)₂Ph-4-Cl)—N—(CH₃)]Gly-Orn(N-methylamidino)—OCH₃
[N—(—C(O)(CH₂)₂Ph-4-CH₃)—N—(CH₃)]Gly-Orn(N-methylamidino)—OCH₃
[N—(—C(O)(CH₂)₂Ph-4-OCH₃)—N—(CH₃)]Gly-Orn(N-methylamidino)—OCH₃
[N—(—C(O)(CH₂)₂Ph)—N—(CH₃)]Gly-Orn(N-methylamidino)—CO₂CH₃
[N—(—C(O)(CH₂)₂Ph)—N—(CH₂)₂Ph]Gly-Orn(N-methylamidino)—CO₂CH₃
[N—(—C(O)(CH₂)₂Ph)—N—Ph]Gly-Orn(N-methylamidino)—CO₂CH₃
[N—(—C(O) N (CH₃)CH₂Ph)—N—Ph]Gly-Orn(N-methylamidino)—CO₂CH₃
[N—(—C(O)Ph-3-CH=CHPh)—N—(CH₃)]Gly-Orn(N-methylamidino)—CO₂CH₃
[N—(—C(O)Ph-3-CH₂CH₂Ph)—N—(CH₃)]Gly-Orn(N-methylamidino)—CO₂CH₃
[N—(—C(O)Ph-3-SPh-3-OCH₃)—N—(CH₃)]Gly-Orn(N-methylamidino)—CO₂CH₃
[N—(—C(O)Ph-2-CH₂Ph-2-Ph)—N—(CH₃)]Gly-Orn(N-methylamidino)—CO₂CH₃
[N—(—C(O)Ph-4-CH₂Ph)—N—(CH₃)]Gly-Orn(N-methylamidino)—CO₂CH₃
[N—(—C(O)Ph-2-CH₂Ph)—N—(CH₃)]Gly-Orn(N-methylamidino)—CO₂CH₃
[N—(—C(O)Ph-3-CH₂Ph)—N—(CH₃)]Gly-Orn(N-methylamidino)—CO₂CH₃
[N—(—C(O)Ph-3-CH₂Ph-2-CF₃)—N—(CH₃)]Gly-Orn(N-methylamidino)—CO₂CH₃
[N—(—C(O)CH₂Ph-3,4-Cl₂)—N—(CH₃)]Gly-Orn(N-methylamidino)—CO₂CH₃
[N—(—C(O)(CH₂)₂Ph)—N—(C₂H₅)]Gly-Orn(N-methylamidino)—CO₂CH₃
[N—(—C(O)(CH₂)₂Ph)—N—(n-C₃H₇)]Gly-Orn(N-methylamidino)—CO₂CH₃
[N—(—C(O)(CH₂)₂Ph)—N—(i-C₃H₇)]Gly-Orn(N-methylamidino)—CO₂CH₃
[N—(—C(O)(CH₂)₂Ph)—N—(C₆H₁₂)]Gly-Orn(N-methylamidino)—CO₂CH₃
[N—(—C(O)(CH₂)₂Ph)—N—(OH)]Gly-Orn(N-methylamidino)—CO₂CH₃
[N—(—C(O)(CH₂)₂Ph)—N—(OCH₃)]Gly-Orn(N-methylamidino)—CO₂CH₃
[N—(—C(O)(CH₂)₂Ph)—N—(OCH₂Ph)]Gly-Orn(N-methylamidino)—CO₂CH₃
[N—(—C(O)(CH₂)₂Ph)—N—(NH₂)]Gly-Orn(N-methylamidino)—CO₂CH₃
[N—(—C(O)(CH₂)₂Ph)—N—(N(CH₃)₂)]Gly-Orn(N-methylamidino)—CO₂CH₃
[N—(—C(O)(CK₂)₂Ph)—N—(NHBoc)]Gly-Orn(N-methylamidino)—CO₂CH₃
[N—(—C(O)(CH₂)₂Ph)—N—(CH₂CO₂H)]Gly-Orn(N-methylamidino)—CO₂CH₃
[N—(—C(O)(CH₂)₂Ph)—N—(CH₂CO₂CH₃)]Gly-Orn(N-methylamidino)—CO₂CH₃
[N—(—C(O)CH₂Ph)—N—(CH₃)]Gly-Orn(N-methylamidino)—CO₂CH₃
[N—(—C(O)(CH₂)₃Ph)—N—(CH₃)]Gly-Orn(N-methylamidino)—CO₂CH₃
[N—(—C(O)Ph)—N—(CH₃)]Gly-Orn(N-methylamidino)—CO₂CH₃
[N—(—C(O)(CH₂)₂Ph)—N—CH₂Ph]Gly-Orn(N-methylamidino)—CO₂CH₃
[N—(—C(O)(CH₂)₂Ph-3,4-Cl₂)—N—(CH₃)]Gly-Orn(N-methylamidino)—CO₂CH₃
[N—(—C(O)(CH₂)₂Ph-4-Cl)—N—(CH₃)]Gly-Orn(N-methylamidino)—CO₂CH₃
[N—(—C(O)(CH₂)₂Ph-4-CH₃)—N—(CH₃)]Gly-Orn(N-methylamidino)—CO₂CH₃
[N—(—C(O)(CH₂)₂Ph-4-OCH₃)—N—(CH₃)]Gly-Orn(N-methylamidino)—CO₂CH₃
[N—(—C(O)(CH₂)₂Ph)—N—Ph]Gly-boroOrn(formamidino)—OH
[N—(—C(O)N(CH₃)CH₂Ph)—N—Ph]Gly-boroOrn(formamidino)—OH
[N—(—C(O)Ph-3-CH=CHPh)—N—(CH₃)]Gly-boroOrn(formamidino)—OH
[N—(—C(O)Ph-3-CH₂CH₂Ph)—N—(CH₃)]Gly-boroOrn(formamidino)—OH
[N—(—C(O)Ph-3-SPh-3-OCH₃)—N—(CH₃)]Gly-boroOrn(formamidino)—OH
[N—(—C(O)Ph-2-CH₂Ph-2-Ph)—N—(CH₃)]Gly-boroOrn(formamidino)—OH
[N—(—C(O)Ph-4-CH₂Ph)—N—(CH₃)]Gly-boroOrn(formamidino)—OH

[N—(—C(O)Ph-2-CH₂Ph)—N—(CH₃)]Gly-boroOrn(formamidino)—OH
[N—(—C(O)Ph-3-CH₂Ph)—N—(CH₃)]Gly-boroOrn(formamidino)—OH
[N—(—C(O)Ph-3-CH₂Ph-2-CF₃)—N—(CH₃)]Gly-boroOrn(formamidino)—OH
[N—(—C(O)(CH₂)₂Ph)—N—(C₂H₅)]Gly-boroOrn(formamidino)—OH
[N—(—C(O)(CH₂)₂Ph)—N—(n-C₃H₇)]Gly-boroOrn(formamidino)—OH
[N—(—C(O)(CH₂)₂Ph)—N—(i-C₃H₇)]Gly-boroOrn(formamidino)—OH
[N—(—C(O)(CH₂)₂Ph)—N—(C₆H₁₂)]Gly-boroOrn(formamidino)—OH
[N—(—C(O)(CH₂)₂Ph)—N—(OH)]Gly-boroOrn(formamidino)—OH
[N—(—C(O)(CH₂)₂Ph)—N—(OCH₃)]Gly-boroOrn(formamidino)—OH
[N—(—C(O)(CH₂)₂Ph)—N—(OCH₂Ph)]Gly-boroOrn(formamidino)—OH
[N—(—C(O)(CH₂)₂Ph)—N—(NH₂)]Gly-boroOrn(formamidino)—OH
[N—(—C(O)(CH₂)₂Ph)—N—(N(CH₃)₂)]Gly-boroOrn(formamidino)—OH
[N—(—C(O)(CH₂)₂Ph)—N—(NHBoc)]Gly-boroOrn(formamidino)—OH
[N—(—C(O)(CH₂)₂Ph)—N—(CH₂CO₂H)]Gly-boroOrn(formamidino)—OH
[N—(—C(O)(CH₂)₂Ph)—N—(CH₂CO₂CH₃)]Gly-boroOrn(formamidino)—OH
[N—(—C(O)(CH₂)₃Ph)—N—(CH₃)]Gly-boroOrn(formamidino)—OH
[N—(—C(O)Ph))—N—(CH₃)]Gly-boroOrn(formamidino)—OH
[N—(—C(O)(CH₂)₂Ph)—N—CH₂Ph)]Gly-boroOrn(formamidino)—OH
[N—(—C(O)(CH₂)₂Ph-3,4-Cl₂)—N—(CH₃)]Gly-boroOrn(formamidino)—OH
[N—(—C(O)(CH₂)₂Ph-4-Cl)—N—(CH₃)]Gly-boroOrn(formamidino)—OH
[N—(—C(O)(CH₂)₂Ph-4-CH₃)—N—(CH₃)]Gly-boroOrn(formamidino)—OH
[N—(—C(O)(CH₂)₂Ph)—N—(CH₃)]Gly-boroOrn(formamidino)—C₁₀H₁₆
[N—(—C(O)(CH₂)₂Ph)—N—(CH₂)₂Ph]Gly-boroOrn(formamidino)—C₁₀H₁₆
[N—(—C(O)(CH₂)₂Ph)—N—Ph]Gly-boroOrn(formamidino)—C₁₀H₁₆
[N—(—C(O)N(CH₃)CH₂Ph)—N—Ph]Gly-boroOrn(formamidino)—C₁₀H₁₆
[N—(—C(O)Ph-3-CH=CHPh)—N—(CH₃)]Gly-boroOrn(formamidino)—C₁₀H₁₆
[N—(—C(O)Ph-3-CH₂CH₂Ph)—N—(CH₃)]Gly-boroOrn(formamidino)—C₁₀H₁₆
[N—(—C(O)Ph-3-SPh-3-OCH₃)—N—(CH₃)]Gly-boroOrn(formamidino)—C₁₀H₁₆
[N—(—C(O)Ph-2-CH₂Ph-2-Ph)—N—(CH₃)]Gly-boroOrn(formamidino)—C₁₀H₁₆
[N—(—C(O)Ph-3-CH₂Ph)—N—(CH₃)]Gly-boroOrn(formamidino)—C₁₀H₁₆
[N—(—C(O)Ph-3-CH₂Ph-2-CF₃)—N—(CH₃)]Gly-boroOrn(formamidino)—C₁₀H₁₆
[N—(—C(O)(CH₂)₂Ph)—N—(C₂H₅)]Gly-boroOrn(formamidino)—C₁₀H₁₆
[N—(—C(O)(CH₂)₂Ph)—N—(n-C₃H₇)]Gly-boroOrn(formamidino)—C₁₀H₁₆
[N—(—C(O)(CH₂)₂Ph)—N—(i-C₃H₇)]Gly-boroOrn(formamidino)—C₁₀H₁₆
[N—(—C(O)(CH₂)₂Ph)—N—(C₆H₁₂)]Gly-boroOrn(formamidino)—C₁₀H₁₆
[N—(—C(O)(CH₂)₂Ph)—N—(OCH₃)]Gly-boroOrn(formamidino)—C₁₀H₁₆
[N—(—C(O)(CH₂)₂Ph)—N—(OCH₂Ph)]Gly-boroOrn(formamidino)—C₁₀H₁₆
[N—(—C(O)(CH₂)₂Ph)—N—(NH₂)]Gly-boroOrn(formamidino)—C₁₀H₁₆
[N—(—C(O)(CH₂)₂Ph)—N—(N(CH₃)₂)]Gly-boroOrn(formamidino)—C₁₀H₁₆
[N—(—C(O)(CH₂)₂Ph)—N—(NHBoc)]Gly-boroOrn(formamidino)—C₁₀H₁₆
[N—(—C(O)(CH₂)₂Ph)—N—(CH₂CO₂H)]Gly-boroOrn(formamidino)—C₁₀H₁₆
[N—(—C(O)(CH₂)₂Ph)—N—(CH₂CO₂CH₃)]Gly-boroOrn(formamidino)—C₁₀H₁₆
[N—(—C(O)CH₂Ph)—N—(CH₃)]Gly-boroOrn(formamidino)—C₁₀H₁₆
[N—(—C(O)(CH₂)₃Ph)—N—(CH₃)]Gly-boroOrn(formamidino)—C₁₀H₁₆
[N—(—C(O)Ph)—N—(CH₃)]Gly-boroOrn(formamidino)—C₁₀H₁₆
[N—(—C(O)(CH₂)₂Ph)—N—CH₂Ph]Gly-boroOrn(formamidino)—C₁₀H₁₆
[N—(—C(O)(CH₂)₂Ph-4-Cl)—N—(CH₃)]Gly-boroOrn(formamidino)—C₁₀H₁₆
[N—(—C(O)(CH₂)₂Ph-4-CH₃)—N—(CH₃)]Gly-boroOrn(formamidino)—C₁₀H₁₆
[N—(—C(O)(CH₂)₂Ph-4-OCH₃)—N—(CH₃)]Gly-boroOrn(formamidino)—C₁₀H₁₆
[N—(—C(O)(CH₂)₂Ph)—N—(CH₃)]Gly-Orn(formamidino)—CF₃
[N—(—C(O)(CH₂)₂Ph)—N—(CH₂)₂Ph]Gly-Orn(formamidino)—CF₃
[N—(—C(O)(CH₂)₂Ph)—N—Ph]Gly-Orn(formamidino)—CF₃
[N—(—C(O)N(CH₃)CH₂Ph)—N—Ph]Gly-Orn(formamidino)—CF₃
[N—(—C(O)Ph-3-CH=CHPh)—N—(CH₃)]Gly-Orn(formamidino)—CF₃
[N—(—C(O)Ph-3-CH₂CH₂Ph)—N—(CH₃)]Gly-Orn(formamidino)—CF₃
[N—(—C(O)Ph-3-SPh-3-OCH₃)—N—(CH₃)]Gly-Orn(formamidino)—CF₃
[N—(—C(O)Ph-2-CH₂Ph-2-Ph)—N—(CH₃)]Gly-Orn(formamidino)—CF₃
[N—(—C()Ph-4-CH₂Ph)—N—(CH₃)]Gly-Orn(formamidino)—CF₃
[N—(—C(O)Ph-2-CH₂Ph)—N—(CH₃)]Gly-Orn(formamidino)—CF₃
[N—(—C(O)Ph-3-CH₂Ph)—N—(CH₃)]Gly-Orn(formamidino)—CF₃
[N—(—C(O)Ph-3-CH₂Ph-2-CF₃)—N—(CH₃)]Gy-Orn(formamidino)—CF₃
[N—(—C(O)CH₂Ph-3,4-Cl₂)—N—(CH₃)]Gly-Orn(formamidino)—CF₃
[N—(—C(O)(CH₂)₂Ph)—N—(C₂H₅)]Gly-Orn(formamidino)—CF₃
[N—(—C(O)(CH₂)₂Ph)—N—(n-C₃H₇)]Gly-Orn(formamidino)—CF₃
[N—(—C(O)(CH₂)₂Ph)—N—(i-C₃H₇)]Gly-Orn(formamidino)—CF₃
[N—(—C(O)(CH₂)₂Ph)—N—(C₆H₁₂)]Gly-Orn(formamidino)—CF₃
[N—(—C(O)(CH₂)₂Ph)—N—(OH)]Gly-Orn(formamidino)—CF₃
[N—(—C(O)(CH₂)₂Ph)—N—(OCH₃)]Gly-Orn(formamidino)—CF₃

[N—(—C(O)(CH₂)₂Ph)—N—(OCH₂Ph)]Gly-Orn(formamidino)—CF₃
[N—(—C(O)(CH₂)₂Ph)—N—(NH₂)]Gly-Orn(formamidino)—CF₃
[N—(—C(O)(CH₂)₂Ph)—N—(N(CH₃)₂)]Gly-Orn(formamidino)—CF₃
[N—(—C(O)(CH₂)₂Ph)—N—(NHBoc)]Gly-Orn(formamidino)—CF₃
[N—(—C(O)(CH₂)₂Ph)—N—(CH₂CO₂H)]Gly-Orn(formamidino)—CF₃
[N—(—C(O)(CH₂)₂Ph)—N—(CH₂CO₂CH₃)]Gly-Orn(formamidino)—CF₃
[N—(—C(O)CH₂Ph)—N—(CH₃)]Gly-Orn(formamidino)—CF₃
[N—(—C(O)(CH₂)₃Ph)—N—(CH₃)]Gly-Orn(formamidino)—CF₃
[N—(—C(O)Ph)—N—(CH₃)]Gly-Orn(formamidino)—CF₃
[N—(—C(O)(CH₂)₂Ph)—N—CH₂Ph]Gly-Orn(formamidino)—CF₃
[N—(—C(O)(CH₂)₂Ph-3,4-Cl₂)—N—(CH₃)]Gly-Orn(formamidino)—CF₃
[N—(—C(O)(CH₂)₂Ph-4-Cl)—N—(CH₃)]Gly-Orn(formamidino)—CF₃
[N—(—C(O)(CH₂)₂Ph-4-CH₃)—N—(CH₃)]Gly-Orn(formamidino)—CF₃
[N—(—C(O)(CH₂)₂Ph-4-OCH₃)—N—(CH₃)]Gly-Orn(formamidino)—CF₃
[N—(—C(O)(CH₂)₂Ph)—N—(CH₃)]Gly-Orn(formamidino)—OCH₃
[N—(—C(O)(CH₂)₂Ph)—N—(CH₂)₂Ph]Gly-Orn(formamidino)—OCH₃
[N—(—C(O)(CH₂)₂Ph)—N—Ph]Gly-Orn(formamidino)—OCH₃
[N—(—C(O)N(CH₃)CH₂Ph)—N—Ph]Gly-Orn(formamidino)—OCH₃
[N—(—C(O)Ph-3-CH=CHPh)—N—(CH₃)]Gly-Orn(formamidino)—OCH₃
[N—(—C(O)Ph-3-CH₂CH₂Ph)—N—(CH₃)]Gly-Orn(formamidino)—OCH₃
[N—(—C(O)Ph-3-SPh-3-OCH₃)—N—(CH₃)]Gly-Orn(formamidino)—OCH₃
[N—(—C(O)Ph-2-CH₂Ph-2-Ph)—N—(CH₃)]Gly-Orn(formamidino)—OCH₃
[N—(—C(O)Ph-4-CH₂Ph)—N—(CH₃)]Gly-Orn(formamidino)—OCH₃
[N—(—C(O)Ph-2-CH₂Ph)—N—(CH₃)]Gly-Orn(formamidino)—OCH₃
[N—(—C(O)Ph-3-CH₂Ph)—N—(CH₃)]Gly-Orn(formamidino)—OCH₃
[N—(—C(O)Ph-3-CH₂Ph-2-CF₃)—N—(CH₃)]Gly-Orn(formamidino)—OCH₃
[N—(—C(O)CH₂Ph-3,4-Cl₂)—N—(CH₃)]Gly-Orn(formamidino)—OCH₃
[N—(—C(O)(CH₂)₂Ph)—N—(C₂H₅)]Gly-Orn(formamidino)—OCH₃
[N—(—C(O)(CH₂)₂Ph)—N—(n-C₃H₇)]Gly-Orn(formamidino)—OCH₃
[N—(—C(O)(CH₂)₂Ph)—N—(i-C₃H₇)]Gly-Orn(formamidino)—OCH₃
[N—(—C(O)(CH₂)₂Ph)—N—(C₆H₁₂)]Gly-Orn(formamidino)—OCH₃
[N—(—C(O)(CH₂)₂Ph)—N—(OH)]Gly-Orn(formamidino)—OCH₃
[N—(—C(O)(CH₂)₂Ph)—N—(OCH₃)]Gly-Orn(formamidino)—OCH₃
[N—(—C(O)(CH₂)₂Ph)—N—(OCH₂Ph)]Gly-Orn(formamidino)—OCH₃
[N—(—C(O)(CH₂)₂Ph)—N—(NH₂)]Gly-Orn(formamidino)—OCH₃
[N—(—C(O)(CH₂)₂Ph)—N—(N(CH₃)₂)]Gly-Orn(formamidino)—OCH₃
[N—(—C(O)(CH₂)₂Ph)—N—(NHBoc)]Gly-Orn(formamidino)—OCH₃
[N—(—C(O)(CH₂)₂Ph)—N—(CH₂CO₂H)]Gly-Orn(formamidino)—OCH₃
[N—(—C(O)(CH₂)₂Ph)—N—(CH₂CO₂CH₃)]Gly-Orn(formamidino)—OCH₃
[N—(—C(O)CH₂Ph)—N—(CH₃)]Gly-Orn(formamidino)—OCH₃
[N—(—C(O)(CH₂)₃Ph)—N—(CH₃)]Gly-Orn(formamidino)—OCH₃
[N—(—C(O)Ph)—N—(CH₃)]Gly-Orn(formamidino)—OCH₃
[N—(—C(O)(CH₂)₂Ph)—N—CH₂Ph]Gly-Orn(formamidino)—OCH₃
[N—(—C(O)(CH₂)₂Ph-3,4-Cl₂)—N—(CH₃)]Gly-Orn(formamidino)—OCH₃
[N—(—C(O)(CH₂)₂Ph-4-Cl)—N—(CH₃)]Gly-Orn(formamidino)—OCH₃
[N—(—C(O)(CH₂)₂Ph-4-CH₃)—N—(CH₃)]Gly-Orn(formamidino)—OCH₃
[N—(—C(O)(CH₂)₂Ph-4-OCH₃)—N—(CH₃)]Gly-Orn(formamidino)—OCH₃
[N—(—C(O)(CH₂)₂Ph)—N—(CH₃)]Gly-Orn(formamidino)—CO₂CH₃
[N—(—C(O)(CH₂)₂Ph)—N—(CH₂)₂Ph]Gly-Orn(formamidino)—CO₂CH₃
[N—(—C(O)(CH₂)₂Ph)—N—Ph]Gly-Orn(formamidino)—CO₂CH₃
[N—(—C(O)N(CH₃)CH₂Ph)—N—Ph]Gly-Orn(formamidino)—CO₂CH₃
[N—(—C(O)Ph-3-CH=CHPh)—N—(CH₃)]Gly-Orn(formamidino)—CO₂CH₃
[N—(—C(O)Ph-3-CH₂CH₂Ph)—N—(CH₃)]Gly-Orn(formamidino)—CO₂CH₃
[N—(—C(O)Ph-3-SPh-3-OCH₃)—N—(CH₃)]Gly-Orn(formamidino)—CO₂CH₃
[N—(—C(O)Ph-2-CH₂Ph-2-Ph)—N—(CH₃)]Gly-Orn(formamidino)—CO₂CH₃
[N—(—C()Ph-4-CH₂Ph)—N—(CH₃)]Gly-Orn(formamidino)—CO₂CH₃
[N—(—C(O)Ph-2-CH₂Ph)—N—(CH₃)]Gly-Orn(formamidino)—CO₂CH₃
[N—(—C(O)Ph-3-CH₂Ph)—N—(CH₃)]Gly-Orn(formamidino)—CO₂CH₃
[N—(—C(O)Ph-3-CH₂Ph-2-CF₃)—N—(CH₃)]Gly-Orn(formamidino)—CO₂CH₃
[N—(—C(O)CH₂Ph-3,4-Cl₂)—N—(CH₃)]Gly-Orn(formamidino)—CO₂CH₃
[N—(—C(O)(CH₂)₂Ph)—N—(C₂H₅)]Gly-Orn(formamidino)—CO₂CH₃
[N—(—C(O)(CH₂)₂Ph)—N—(n-C₃H₇)]Gly-Orn(formamidino)—CO₂CH₃
[N—(—C(O)(CH₂)₂Ph)—N—(i-C₃H₇)]Gly-Orn(formamidino)—CO₂CH₃
[N—(—C(O)(CH₂)₂Ph)—N—(C₆H₁₂)]Gly-Orn(formamidino)—CO₂CH₃
[N—(—C(O)(CH₂)₂Ph)—N—(OH)]Gly-Orn(formamidino)—CO₂CH₃
[N—(—C(O)(CH₂)₂Ph)—N—(OCH₃)]Gly-Orn(formamidino)—CO₂CH₃
[N—(—C(O)(CH₂)₂Ph)—N—(OCH₂Ph)]Gly-Orn(formamidino)—CO₂CH₃
[N—(—C(O)(CH₂)₂Ph)—N—(NH₂)]Gly-Orn(formamidino)—CO₂CH₃

[N—(—C(O)(CH$_2$)$_2$Ph)—N—(N(CH$_3$)$_2$)]Gly-Orn(formamidino)—CO$_2$CH$_3$
[N—(—C(O)(CH$_2$)$_2$Ph)—N—(NHBoc)]Gly-Orn(formamidino)—CO$_2$CH$_3$
[N—(—C(O)(CH$_2$)$_2$Ph)—N—(CH$_2$CO$_2$H)]Gly-Orn(formamidino)—CO$_2$CH$_3$
[N—(—C(O)(CH$_2$)$_2$Ph)—N—(CH$_2$CO$_2$CH$_3$)]Gly-Orn(formamidino)—CO$_2$CH$_3$
[N—(—C(O)CH$_2$Ph)—N—(CH$_3$)]Gly-Orn(formamidino)—CO$_2$CH$_3$
[N—(—C(O)(CH$_2$)$_3$Ph)—N—(CH$_3$)]Gly-Orn(formamidino)—CO$_2$CH$_3$
[N—(—C(O)Ph)—N—(CH$_3$)]Gly-Orn(formamidino)—CO$_2$CH$_3$
[N—(—C(O)(CH$_2$)$_2$Ph)—N—CH$_2$Ph)]Gly-Orn(formamidino)—CO$_2$CH$_3$
[N—(—C(O)(CH$_2$)$_2$Ph-3,4-Cl$_2$)—N—(CH$_3$)]Gly-Orn(formamidino)—CO$_2$CH$_3$
[N—(—C(O)(CH$_2$)$_2$Ph-4-Cl)—N—(CH$_3$)]Gly-Orn(formamidino)—CO$_2$CH$_3$
[N—(—C(O)(CH$_2$)$_2$Ph-4-CH$_3$)—N—(CH$_3$)]Gly-Orn(formamidino)—CO$_2$CH$_3$
[N—(—C(O)(CH$_2$)$_2$Ph-4-OCH$_3$)—N—(CH$_3$)]Gly-Orn(formamidino)—CO$_2$CH$_3$
[N—(—C(O)(CH$_2$)$_2$Ph)—N—(CH$_2$C(propane-1,3-diyl)Ph)]-Gly-boroLys—OH
[N—(—C(O)(CH$_2$)$_2$Ph)—N—(CH$_2$CH(i-C$_3$H$_7$)Ph-3-CH$_3$)]-Gly-boroLys—OH
[N—(—C(O)(CH$_2$)$_2$Ph)—N—(CH$_2$C(ethanediyl)Ph-3-CH$_3$)]-Gly-boroLys—OH
[N—(—C(O)(CH$_2$)$_2$Ph)—N—(CH$_2$C(propane-1,3-diyl)Ph-3-CH$_3$)]-Gly-boroLys—OH
[N—(—C(O)(CH$_2$)$_2$Ph)—N—(CH$_2$C(butane-1,4-diyl)Ph-3-CH$_3$)]-Gly-boroLys—OH
[N—(—C(O)(CH$_2$)$_2$Ph)—N—(CH$_2$C(CH$_2$CH$_3$)$_2$Ph-3,5—(CH$_3$)$_2$)]-Gly-boroLys—OH
[N—(—C(O)(CH$_2$)$_2$Ph)—N—(CH$_2$CH(i-C$_3$H$_7$)Ph-3,5—(CH$_3$)$_2$)]-Gly boroLys—OH
[N—(—C(O)(CH$_2$)$_2$Ph)—N—(CH$_2$C(ethanediyl)Ph-3,5—(CH$_3$)$_2$)]-Gly-boroLys—OH
[N—(—C(O)(CH$_2$)$_2$Ph)—N—(CH$_2$C(propane-1,3-diyl)Ph-3,5-(CH$_3$)$_2$)]-Gly-boroLys—OH
[N—(—C(O)(CH$_2$)$_2$Ph)—N—(CH$_2$C(butane-1,4-diyl)Ph-3,5—(CH$_3$)$_2$)]-Gly-boroLys—OH
[N—(—C(O)(CH$_2$)$_2$Ph)—N—(CH$_2$CH$_2$Ph-3-NH$_2$)]-Gly-boroLys—OH
[N—(—C(O)(CH$_2$)$_2$Ph)—N—(CH$_2$C(CH$_3$)$_2$Ph-3-NH$_2$)]-Gly-boroLys—OH
[N—(—C(O)(CH$_2$)$_2$Ph)—N—(CH$_2$C(CH$_2$CH$_3$)$_2$Ph-3-NH$_2$)]-Gly-boroLys—OH
[N—(—C(O)(CH$_2$)$_2$Ph)—N—(CH$_2$CH(i-C$_3$H$_7$)Ph-3-NH$_2$)]-Gly-boroLys—OH
[N—(—C(O)(CH$_2$)$_2$Ph)—N—(CH$_2$C(ethanediyl)Ph-3-NH$_2$)]-Gly-boroLys—OH
[N—(—C(O)(CH$_2$)$_2$Ph)—N—(CH$_2$C(propane-1,3-diyl)Ph-3-NH$_2$)]-Gly-boroLys—OH
[N—(—C(O)(CH$_2$)$_2$Ph)—N—(CH$_2$C(butane-1,4-diyl)Ph-3-NH$_2$)]-Gly-boroLys—OH
[N—(—C(O)(CH$_2$)$_2$Ph)—N—(CH$_2$CH$_2$Ph-3-NO$_2$)]-Gly-boroLys—OH
[N—(—C(O)(CH$_2$)$_2$Ph)—N—(CH$_2$CH(i-C$_3$H$_7$)Ph-3-NO$_2$)]-Gly-boroLys—OH
[N—(—C(O)(CH$_2$)$_2$Ph)—N—(CH$_2$C(ethanediyl)Ph-3-NO$_2$)]-Gly-boroLys—OH
[N—(—C(O)(CH$_2$)$_2$Ph)—N—(CH$_2$C(propane-1,3-diyl)Ph-3-NO$_2$)]-Gly-boroLys—OH
[N—(—C(O)(CH$_2$)$_2$Ph)—N—(CH$_2$C(butane-1,4-diyl)Ph-3-NO$_2$)]-Gly-boroLys—OH

[N—(—C(O)(CH$_2$)$_2$Ph)—N—(CH$_2$CH$_2$Ph)]-Gly-boroArg—OH
[N—(—C(O)(CH$_2$)$_2$Ph)—N—(CH$_2$C(CH$_2$CH$_3$)$_2$Ph)]-Gly-boroArg—OH
[N—(—C(O)(CH$_2$)$_2$Ph)—N—(CH$_2$CH(i-C$_3$H$_7$)Ph)]-Gly-boroArg—OH
[N—(—C(O)(CH$_2$)$_2$Ph)—N—(CH$_2$C(propane-1,3-diyl)Ph)]-Gly-boroArg—OH
[N—(—C(O)(CH$_2$)$_2$Ph)—N—(CH$_2$CH$_2$Ph-3-CH$_3$)]-Gly-boroArg—OH
[N—(—C(O)(CH$_2$)$_2$Ph)—N—(CH$_2$C(CH$_3$)$_2$Ph-3-CH$_3$)]-Gly-boroArg—OH
[N—(—C(O)(CH$_2$)$_2$Ph)—N—(CH$_2$C(CH$_2$CH$_3$)$_2$Ph-3-CH$_3$)]-Gly-boroArg—OH
[N—(—C(O)(CH$_2$)$_2$Ph)—N—(CH$_2$CH(i-C$_3$H$_7$)Ph-3-CH$_3$)]-Gly-boroArg—OH
[N—(—C(O)(CH$_2$)$_2$Ph)—N—(CH$_2$C(ethanediyl)Ph-3-CH$_3$)$_3$-Gly-boroArg—OH
[N—(—C(O)(CH$_2$)$_2$Ph)—N—(CH$_2$C(propeae-1,3-diyl)Ph-3-CH$_3$)]-Gly-boroArg—OH
[N—(—C(O)(CH$_2$)$_2$Ph)—N—(CH$_2$C(butane-1,4-diyl)Ph-3-CH$_3$)]-Gly-boroArg—OH
[N—(—C(O)(CH$_2$)$_2$Ph)—N—(CH$_2$C(CH$_2$CH$_3$)$_2$Ph-3,5—(CH$_3$)$_2$)]-Gly-boroArg—OH
[N—(—C(O)(CH$_2$)$_2$Ph)—N—(CH$_2$CH(i-C$_3$H$_7$)Ph-3,5—(CH$_3$)$_2$)]-Gly-boroArg—OH
[N—(—C(O)(CH$_2$)$_2$Ph)—N—(CH$_2$C(ethanediyl)Ph-3,5—(CH$_3$)$_2$)]-Gly-boroArg—OH
[N—(—C(O)(CH$_2$)$_2$Ph)—N—(CH$_2$C(propane-1,4-diyl)Ph-3,5-(CH$_3$)$_2$)]-Gly-boroArg—OH
[N—(—C(O)(CH$_2$)$_2$Ph)—N—(CH$_2$C(butane-1,4-diyl)Ph-3,5-(CH$_3$)$_2$)]-Gly-boroArg—OH
[N—(—C(O)(CH$_2$)$_2$Ph)—N—(CH$_2$CH$_2$Ph-3-NH$_2$)]-Gly-boroArg—OH
[N—(—C(O)(CH$_2$)$_2$Ph)—N—(CH$_2$C(CH$_3$)$_2$Ph-3-NH$_2$)]-Gly-boroArg—OH
[N—(—C(O)(CH$_2$)$_2$Ph)—N—(CH$_2$C(CH$_2$CH$_3$)$_2$Ph-3-NH$_2$)]-Gly-boroArg—OH
[N—(—C(O)(CH$_2$)$_2$Ph)—N—(CH$_2$CH(i-C$_3$H$_7$)Ph-3-NH$_2$)]-Gly-boroArg—OH
[N—(—C(O)(CH$_2$)$_2$Ph)—N—(CH$_2$C(ethanediyl)Ph-3-NH$_2$)]-Gly-boroArg—OH
[N—(—C(O)(CH$_2$)$_2$Ph)—N—(CH$_2$C(propane-1,3-diyl)Ph-3-NH$_2$)]-Gly-boroArg—OH
[N—(—C(O)(CH$_2$)$_2$Ph)—N—(CH$_2$C(butane-1,4-diyl)Ph-3-NH$_2$)]-Gly-boroArg—OH
[N—(—C(O)(CH$_2$)$_2$Ph)—N—(CH$_2$C$_2$Ph-3-NO$_2$)]-Gly-boroArg—OH
[N—(—C(O)(CH$_2$)$_2$Ph)—N—(CH$_2$C(CH$_3$)$_2$Ph-3-NO$_2$)]-Gly-boroArg—OH
[N—(—C(O)(CH$_2$)$_2$Ph)—N—(CH$_2$C(CH$_2$CH$_3$)$_2$Ph-3-NO$_2$)]-Gly-boroArg—OH
[N—(—C(O)(CH$_2$)$_2$Ph)—N—(CH$_2$CH(i-C$_3$H$_7$)Ph-3-NO$_2$)]-Gly-boroArg—OH
[N—(—C(O)(CH$_2$)$_2$Ph)—N—(CH$_2$C(ethanediyl)Ph-3-NO$_2$)]-Gly-boroArg—OH
[N—(—C(O)(CH$_2$)$_2$Ph)—N—(CH$_2$C(propane-1,3-diyl)Ph-3-NO$_2$)]-Gly-boroArg—OH
[N—(—C(O)(CH$_2$)$_2$Ph)—N—(CH$_2$C(butane-1,4-diyl)Ph-3-NO$_2$)]-Gly-boroArg—OH
[N—(—C(O)(CH$_2$)$_2$Ph)—N—(CH$_2$C(CH$_2$CH$_3$)$_2$Ph)]-Gly-boroOrn (formamidino)—OH
[N—(—C(O)(CH$_2$)$_2$Ph)—N—(CH$_2$CH(i-C$_3$H$_7$)Ph)]-Gly-boroOrn (formamidino)—OH
[N—(—C(O)(CH$_2$)$_2$Ph)—N—(CH$_2$C(propane-1,3-diyl)Ph)]-Gly-boroOrn(formamidino)—OH
[N—(—C(O)(CH$_2$)$_2$Ph)—N—(CH$_2$CH$_2$Ph-3-CH$_3$)]-Gly-boroOrn (formamidino)—OH

[N—(—C(O)(CH$_2$)$_2$Ph)—N—(CH$_2$CH(i-C$_3$H$_7$)Ph-3-CH$_3$)]-Gly-boroOrn(formamidino)—OH
[N—(—C(O)(CH$_2$)$_2$Ph)—N—(CH$_2$C(ethanediyl)Ph-3-CH$_3$)]-Gly-boroOrn(formamidino)—OH
[N—(—C(O)(CH$_2$)$_2$Ph)—N—(CH$_2$C(propane-1,4-diyl)Ph-3-CH$_3$)]-Gly-boroOrn(formamidino)—OH
[N—(—C(O)(CH$_2$)$_2$Ph)—N—(CH$_2$C(butane-1,4-diyl)Ph-3-CH$_3$)]-Gly-boroOrn(formamidino)—OH
[N—(—C(O)(CH$_2$)$_2$Ph)—N—(CH$_2$CH$_2$Ph-3,5—(CH$_3$)$_2$)]-Gly-boroOrn(formamidino)—OH
[N—(—C(O)(CH$_2$)$_2$Ph)—N—(CH$_2$C(CH$_3$)$_2$Ph-3,5—(CH$_3$)$_2$)]-Gly-boroOrn(formamidino)—OH
[N—(—C(O)(CH$_2$)$_2$Ph)—N—(CH$_2$C(CH$_2$CH$_3$)$_2$Ph-3,5—(CH$_3$)$_2$)]-Gly-boroOrn(formamidino)—OH
[N—(—C(O)(CH$_2$)$_2$Ph)—N—(CH$_2$CH(i-C$_3$H$_7$)Ph-3,5—(CH$_3$)$_2$)]-Gly-boroOrn(formamidino)—OH
[N—(—C(O)(CH$_2$)$_2$Ph)—N—(CH$_2$C(ethanediyl)Ph-3,5—(CH$_3$)$_2$)]-Gly-boroOrn(formamidino)—OH
[N—(—C(O)(CH$_2$)$_2$Ph)—N—(CH$_2$C(propane-1,3-diyl)Ph-3,5-(CH$_3$)$_2$)]-Gly-boroOrn(formamidino)—OH
[N—(—C(O)(CH$_2$)$_2$Ph)—N—(CH$_2$C(butane-1,4-diyl)Ph-3,5—(CH$_3$)$_2$)]-Gly-boroOrn(formamidino)—OH
[N—(—C(O)(CH$_2$)$_2$Ph)—N—(CH$_2$C(CH$_2$CH$_3$)$_2$Ph-3-NH$_2$)]-Gly-boroOrn(formamidino)—OH
[N—(—C(O)(CH$_2$)$_2$Ph)—N—(CH$_2$CH(i-C$_3$H$_7$)Ph-3-NH$_2$)]-Gly-boroOrn(formamidino)—OH
[N—(—C(O)(CH$_2$)$_2$Ph)—N—(CH$_2$C(ethanediyl)Ph-3-NH$_2$)]-Gly-boroOrn(formamidino)—OH
[N—(—C(O)(CH$_2$)$_2$Ph)—N—(CH$_2$C(propane-1,3-diyl)Ph-3-NH$_2$)]-Gly-boroOrn(formamidino)—OH
[N—(—C(O)(CH$_2$)$_2$Ph)—N—(CH$_2$C(butane-1,4-diyl)Ph-3-NH$_2$)]-Gly-boroOrn(formamidino)—OH
[N—(—C(O)(CH$_2$)$_2$Ph)—N—(CH$_2$CH$_2$Ph-3-NO$_2$)]-Gly-boroOrn (formamidino)—OH
[N—(—C(O)(CH$_2$)$_2$Ph)—N—(CH$_2$C(CH$_3$)$_2$Ph-3-NO$_2$)]-Gly-boroOrn(formamidino)—OH
[N—(—C(O)(CH$_2$)$_2$Ph)—N—(CH$_2$C(CH$_2$CH$_3$)$_2$Ph-3-NO$_2$)]-Gly-boroOrn(formamidino)—OH
[N—(—C(O)(CH$_2$)$_2$Ph)—N—(CH$_2$CH(i-C$_3$H$_7$)Ph-3-NO$_2$)]-Gly-boroOrn(formamidino)—OH
[N—(—C(O)(CH$_2$)$_2$Ph)—N—(CH$_2$C(ethanediyl)Ph-3-NO$_2$)]-Gly-boroOrn(formamidino)—OH
[N—(—C(O)(CH$_2$)$_2$Ph)—N—(CH$_2$C(propane-1,3-diyl)Ph-3-NO$_2$)]-Gly-boroOrn(formamidino)—OH
[N—(—C(O)(CH$_2$)$_2$Ph)—N—(CH$_2$C(butane-1,4-diyl)Ph-3-NO$_2$)]-Gly-boroOrn(formamidino)—OH
[N—(—C(O)(CH$_2$)$_2$-2-pyridyl)—N—(CH$_2$CH$_2$Ph)]-Gly-boroLys—OH
[N—(—C(O)(CH$_2$)$_2$-2-pyridyl)—N—(CH$_2$C(CH$_3$)$_2$Ph)]-Gly-boroLys—OH
[N—(—C(O)(CH$_2$)$_2$-2-pyridyl)—N—(CH$_2$C(CH$_2$CH$_3$)$_2$Ph)]-Gly-boroLys—OH
[N—(—C(O)(CH$_2$)$_2$-2-pyridyl)—N—(CH$_2$CH(i-C$_3$H$_7$)Ph)]-Gly-boroLys—OH
[N—(—C(O)(CH$_2$)$_2$-2-pyridyl)—N—(CH$_2$C(ethanediyl)Ph)]-Gly-boroLys—OH
[N—(—C(O)(CH$_2$)$_2$-2-pyridyl)—N—(CH$_2$C(propane-1,3-diyl)Ph)]-Gly-boroLys—OH
[N—(—C(O)(CH$_2$)$_2$-2-pyridyl)—N—(CH$_2$C(butane-1,4-diyl)Ph)]-Gly-boroLys—OH
[N—(—C(O)(CH$_2$)$_2$-3-pyridyl)—N—(CH$_2$CH$_2$Ph)]-Gly-boroLys—OH
[N—(—C(O)(CH$_2$)$_2$-3-pyridyl)—N—(CH$_2$C(CH$_3$)$_2$Ph)]-Gly-boroLys—OH
[N—(—C(O)(CH$_2$)$_2$-3-pyridyl)—N—(CH$_2$C(CH$_2$CH$_3$)$_2$Ph)]-Gly-boroLys—OH
[N—(—C(O)(CH$_2$)$_2$-3-pyridyl)—N—(CH$_2$CH(i-C$_3$H$_7$)Ph)]-Gly-boroLys—OH
[N—(—C(O)(CH$_2$)$_2$-3-pyridyl)—N—(CH$_2$C(ethanediyl)Ph)]-Gly-boroLys—OH
[N—(—C(O)(CH$_2$)$_2$-3-pyridyl)—N—(CH$_2$C(propane-1,3-diyl)Ph)]-Gly-boroLys—OH
[N—(—C(O)(CH$_2$)$_2$-3-pyridyl)—N—(CH$_2$C(butane-1,4-diyl)Ph)]-Gly-boroLys—OH
[N—(—C(O)(CH$_2$)$_2$Ph-3-OH)—N—(CH$_2$CH$_2$Ph)]-Gly-boroLys—OH
[N—(—C(O)(CH$_2$)$_2$Ph-3-OH)—N—(CH$_2$C(CH$_3$)$_2$Ph)]-Gly-boroLys—OH
[N—(—C(O)(CH$_2$)$_2$Ph-3-OH)—N—(CH$_2$C(CH$_2$CH$_3$)$_2$Ph)]-Gly-boroLys—OH
[N—(—C(O)(CH$_2$)$_2$Ph-3-OH)—N—(CH$_2$CH(i-C$_3$H$_7$)Ph)]-Gly-boroLys—OH
[N—(—C(O)(CH$_2$)$_2$Ph-3-OH)—N—(CH$_2$C(ethanediyl)Ph)]-Oly-boroLys—OH
[N—(—C(O)(CH$_2$)$_2$Ph-3-OH)—N—(CH$_2$C(propane-1,3-diyl)Ph)]-Gly-boroLys—OH
[N—(—C(O)(CH$_2$)$_2$Ph-3-OH)—N—(CH$_2$C(butane-1,4-diyl)Ph)]-Gly-boroLys—OH
[N—(—C(O)(CH$_2$)$_2$Ph-3-OMe)—N—(CH$_2$CH$_2$Ph)]-Gly-boroLys—OH
[N—(—C(O)(CH$_2$)$_2$Ph-3-OMe)—N—(CH$_2$C(CH$_3$)$_2$Ph)]-Gly-boroLys—OH
[N—(—C(O)(CH$_2$)$_2$Ph-3-OMe)—N—(CH$_2$C(CH$_2$CH$_3$)$_2$Ph)]-Gly-boroLys—OH
[N—(—C(O)(CH$_2$)$_2$Ph-3-OMe)—N—(CH$_2$CH(i-C$_3$H$_7$)Ph)]-Gly-boroLys—OH
[N—(—C(O)(CH$_2$)$_2$Ph-3-OMe)—N—(CH$_2$C(ethanediyl)Ph)]-Gly-boroLys—OH
[N—(—C(O)(CH$_2$)$_2$Ph-3-OMe)—N—(CH$_2$C(propane-1,3-diyl)Ph)]-Gly-boroLys—OH
[N—(—C(O)(CH$_2$)$_2$Ph-3-OMe)—N—(CH$_2$C(butane-1,4-diyl)Ph)]-Gly-boroLys—OH
[N—(—C(O)(CH$_2$)$_2$Ph-3-NO$_2$)—N—(CH$_2$CH$_2$Ph)]-Gly-boroLys—OH
[N—(—C(O)(CH$_2$)$_2$Ph-3-NO$_2$)—N—(CH$_2$C(CH$_3$)$_2$Ph)]-Gly-boroLys—OH
[N—(—C(O)(CH$_2$)$_2$Ph-3-NO$_2$)—N—(CH$_2$C(CH$_2$CH$_3$)$_2$Ph)]-Gly-boroLys—OH
[N—(—C(O)(CH$_2$)$_2$Ph-3-NO$_2$)—N—(CH$_2$CH(i-C$_3$H$_7$)Ph)]-Gly-boroLys—OH
[N—(—C(O)(CH$_2$)$_2$Ph-3-NO$_2$)—N—(CH$_2$C(ethanediyl)Ph)]-Gly-boroLys—OH
[N—(—C(O)(CH$_2$)$_2$Ph-3-NO$_2$)—N—(CH$_2$C(propane-1,3-diyl)Ph)]-Gly-boroLys—OH
[N—(—C(O)(CH$_2$)$_2$Ph-3-NO$_2$)—N—(CH$_2$C(butane-1,4-diyl)Ph)]-Gly-boroLys—OH
[N—(—C(O)(CH$_2$)$_2$Ph-3-CO$_2$H)—N—(CH$_2$CH$_2$Ph)]-Gly-boroLys—OH
[N—(—C(O)(CH$_2$)$_2$Ph-3-CO$_2$H)—N—(CH$_2$C(CH$_3$)$_2$Ph)]-Gy-boroLys—OH
[N—(—C(O)(CH$_2$)$_2$Ph-3-CO$_2$H)—N—(CH$_2$C(CH$_2$CH$_3$)$_2$Ph)]-Gly-boroLys—OH
[N—(—C(O)(CH$_2$)$_2$Ph-3-CO$_2$H)—N—(CH$_2$CH(i-C$_3$H$_7$)Ph)]-Gly-boroLys—OH
[N—(—C(O)(CH$_2$)$_2$Ph-3-CO$_2$H)—N—(CH$_2$C(ethanediyl)Ph)]-Gly-boroLys—OH
[N—(—C(O)(CH$_2$)$_2$Ph-3-CO$_2$H)—N—(CH$_2$C(propane-1,3-diyl)Ph)]-Gly-boroLys—OH
[N—(—C(O)(CH$_2$)$_2$Ph-3-CO$_2$H)—N—(CH$_2$C(butane-1,4-diyl)Ph)]-Gly-boroLys—OH
[N—(—C(O)(CH$_2$)$_2$Ph-3-CO$_2$Me)—N—(CH$_2$CH$_2$Ph)]-Gly-boroLys—OH
[N—(—C(O)(CH$_2$)$_2$Ph-3-CO$_2$Me)—N—(CH$_2$C(CH$_3$)$_2$Ph)]-Gly-boroLys—OH
[N—(—C(O)(CH$_2$)$_2$Ph-3-CO$_2$Me)—N—(CH$_2$C(CH$_2$CH$_3$)$_2$Ph)]-Gly-boroLys—OH

[N—(—C(O)(CH₂)₂Ph-3-CO₂Me)—N—(CH₂CH(i-C₃H₇)Ph)]-Gly-boroLys—OH
[N—(—C(O)(CH₂)₂Ph-3-CO₂Me)—N—(CH₂C(ethanediyl)Ph)]-Gly-boroLys—OH
[N—(—C(O)(CH₂)₂Ph-3-CO₂Me)—N—(CH₂C(propane-1,3-diyl)Ph)]-Gly-boroLys—OH
[N—(—C(O)(CH₂)₂Ph-3-CO₂Me)—N—(CH₂C(butane-1,4-diyl)Ph)]-Gly-boroLys—OH
[N—(—C(O)(CH₂)₂Ph-3-NH₂)—N—(CH₂CH₂Ph)]-Gly-boroLys—OH
[N—(—C(O)(CH₂)₂Ph-3-NH₂)—N—(CH₂C(CH₃)₂Ph)]-Gly-boroLys—OH
[N—(—C(O)(CH₂)₂Ph-3-NH₂)—N—(CH₂C(CH₂CH₃)₂Ph)]-Gly-boroLys—OH
[N—(—C(O)(CH₂)₂Ph-3-NH₂)—N—(CH₂CH(i-C₃H₇)Ph)]-Gly-boroLys—OH
[N—(—C(O)(CH₂)₂Ph-3-NH₂)—N—(CH₂C(ethanediyl)Ph)]-Gly-boroLys—OH
[N—(—C(O)(CH₂)₂Ph-3-NH₂)—N—(CH₂C(propane-1,4-diyl)Ph)]-Gly-boroLys—OH
[N—(—C(O)(CH₂)₂Ph-3-NH₂)—N—(CH₂C(butane-1,4-diyl)Ph)]-Gly-boroLys—OH This invention also provides compositions comprising one or more of the foregoing compounds and methods of using such compositions in the treatment of aberrant proteolysis such as thrombosis in mammals.

DETAIL DESCRIPTION OF THE INVENTION

As used throughout the specifications, the following abbreviations for amino acid residues or amino acids apply:
Ala=L-alanine
Arg=L-arginine
Asn=L-asparagine
Asp=L-aspartic acid
Cys=L-cysteine
Gln=L-glutamine
Glu=L-glutamic acid
Gly=glycine
His=L-histidine
Ile=L-isoleucine
Leu=L-leucine
Lys=L-lysine
Met=L-methionine
Phe=L-phenylalanine
Pro=L-proline
Ser=L-serine
Thr=L-threonine
Trp=L-tryptophan
Tyr=L-tyrosine
Val=L-valine
Sar=L-sarcosine
Irg=L-arginine where the guanidine is replaced with an isothiouronium (—SC(=NH)NH₂)

The "D" prefix for the foregoing abbreviations indicates the amino acid is in the D-configuration. "D, L" indicates the amino is present in mixture of the D- and the L-configuration. The prefix "boro" indicates amino acid residues where the carboxyl is replaced by a boronic acid or a boronic acid ester. For example, if R¹ is isopropyl and Y¹ and Y² are OH, the C-terminal residue is abbreviated "boroVal—OH" where "—OH" indicates the boronic acid is in the form of the free acid. The pinanediol boronic acid ester and the pinacol boronic acid ester are abbreviated "—C₁₀H₁₆" and "—C₆H₁₂", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Other abbreviations are: formamidino, HC(=NH)—; N-methylamidino, CH₃NHC(=NH)—; Z, benzyloxycarbonyl; BSA, benzene sulfonic acid; THF, tetrahydrofuran; Boc-, t-butoxycarbonyl-; Ac-, acetyl; pNA, p-nitro-aniline; DMAP, 4-N,N-dimethylaminopyridine; Tris, Tris(hydroxymethyl)aminomethane; MS, mass spectrometry; FAB/MS, fast atom bombardment mass spectrometry. LRMS(NH₃-CI) and HRMS(NH₃-CI) are low and high resolution mass spectrometry, respectively, using NH₃ as an ion source. Thus, an example of the chemical structure based on the nomenclature used herein is:

N—(—C(O)(CH₂)₂Ph)—N—(CH₃)]Gly-Orn(formamidino)—CO₂CH₃ represents

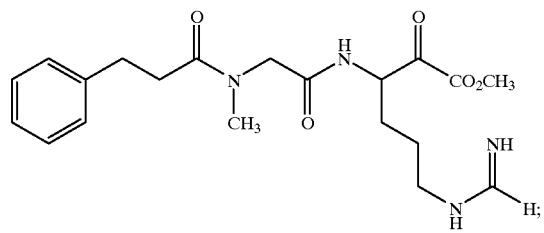

and [N—(—C(O)(CH₂)₂Ph-4-OCH₃)—N—(CH₃)]Gly-boroPhe(mCN)—OH represents

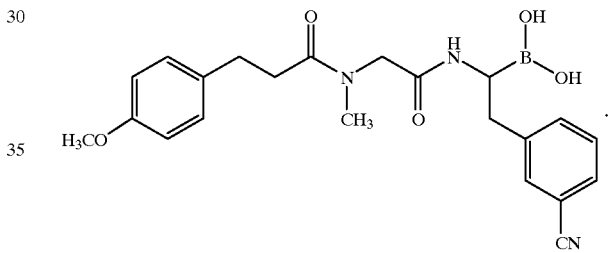

It is understood that many of the compounds of the present invention contain one or more chiral centers and that these stereoisomers may possess distinct physical and biological properties. The present invention comprises all of the stereoisomers or mixtures thereof. If the pure enantiomers or diasteromers are desired, they may be prepared using starting materials with the appropriate stereochemistry, or may be separated from mixtures of undesired stereoisomers by standard techniques, including chiral chromatography and recrystalization of diastereomeric salts.

The term "amine-blocking group" or "amine-protecting group" as used herein, refers to various acyl, thioacyl, alkyl, sulfonyl, phosphoryl, and phosphinyl groups comprised of 1 to 20 carbon atoms. Substituents on these groups maybe either alkyl, aryl, alkaryl which may contain the heteroatoms, O, S, and N as a substituent or as inchain component. A number of amine-blocking groups are recognized by those skilled in the art of organic synthesis. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meienhofer, eds., *The Peptides*, Vol 3; 3–88 (1981), Academic Press, New York, and Greene and Wuts *Protective Groups in Organic Synthesis*, 315–405 (1991), J. Wiley and Sons, Inc., New York disclose numerous suitable amine protecting groups and they are incorporated herein by reference for that purpose.

"Amino acid residues" as used herein, refers to natural or unnatural amino acids of either D- or L-configuration. Natural amino acids residues are Ala, Arg, Asn, Asp, Cys, Gln, Glu, Gly, His, Ile, Leu, Lys, Met, Phe, Pro, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose.

"Amino acids residues" also refers to various amino acids where sidechain functional groups are coupled with appropriate protecting groups known to those skilled in the art. "The Peptides", Vol 3, 3–88 (1981) discloses numerous suitable protecting groups and is incorporated herein by reference for that purpose.

As used herein, "alkyl" is intended to include both branched and straight-chain saturated aliphatic hydrocarbon groups having the specified number of carbon atoms.

"Alkoxyl" represents an alkyl group of indicated number of carbon atoms attached through an oxygen bridge.

"Cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl, and so forth.

"Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo.

The term "aryl" is defined as phenyl, fluorenyl, biphenyl and naphthyl, which may be unsubstituted or include optional substitution with one to three substituents.

The term "heteroaryl" is meant to include 5-, 6-, 9-, or 10-membered mono- or bicyclic aromatic rings which can optionally contain from 1 to 3 heteroatoms selected from the group consisting of O, N, and S; said ring(s) may be unsubstituted or include optional substitution with one to three substituents. Included in the definition of the group heteroaryl, but not limited to, are the following: 2-, or 3-, or 4-pyridyl; 2-or 3-furyl; 2- or 3-benzofuranyl; 2—, or 3-thiophenyl; 2- or 3-benzo[b]thiophenyl; 2—, or 3-, or 4-quinolinyl; 1-, or 3-, or 4-isoquinolinyl; 2- or 3-pyrrolyl; 1- or 2- or 3-indolyl; 2-, or 4-, or 5-oxazolyl; 2-benzoxazolyl; 2- or 4- or-5-imidazolyl; 1- or 2-benzimidazolyl; 2- or 4- or 5-thiazolyl; 2-benzothiazolyl; 3- or 4- or 5-isoxazolyl; 3- or 4- or 5-pyrazolyl; 3- or 4- or 5-isothiazolyl; 3- or 4-pyridazinyl; 2- or 4- or 5-pyrimidinyl; 2-pyrazinyl; 2-triazinyl; 3- or 4-cinnolinyl; 1-phthalazinyl; 2- or 4-quinazolinyl; or 2-quinoxalinyl ring. Particularly preferred are 2-, 3-, or 4-pyridyl; 2-, or 3-furyl; 2- or 3-thiophenyl; 2-, 3-, or 4-quinolinyl; or 1-, 3-, or 4-isoquinolinyl.

The term "heterocycle" is meant to include 5-, 6-, 9-, or 10-membered mono- or bicyclic rings which can optionally contain from 1 to 3 heteroatoms selected from the group consisting of N, O, or S, with the proviso that proline is excluded from this group; said ring(s) may be unsubstituted or include optional substitution with one to three substituents. Included in the definition of the group heterocycle, but not limited to, are tetrahydroisoquinoline, tetrahydroquinoline, tetrahydrofuran, tetrahydrothiophene, piperidine, piperazine, morpholine. Particularly preferred are 1-, 3-, or 4-tetrahdroisoquinolinyl.

Unless otherwise specified, the substituents that may be attached to the aryl, heteroaryl or heterocycle ring(s) may be independently selected at each occurrence from the group consisting of:

halogen, $C_1$–$C_4$ alkyl, $C_1$–$C_4$ alkoxy, methylenedioxy, —$NO_2$, —$CF_3$, —SH, —S(O)$_r$-($C_1$–$C_4$ alkyl), CN, —OH, —$NH_2$, —NH($C_1$–$C_4$ alkyl), —N($C_1$–$C_4$ alkyl)$_2$, —C(=NH)NHR$^4$, —NHC(=NR$^4$), —NHC(=NH)NHR$^4$, —NHC(=O)R$^4$, —(CH$_2$)$_p$—CO$_2$R$^4$, —NHCO $C_1$–$C_4$ alkoxy), —NH($C_1$–$C_4$ alkoxy)$_2$, —N($C_1$–$C_4$ alkoxy), phenyl which may be unsubstituted or substituted with R$^{13}$.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Reminaton's Pharmaceutical Sciences*, 17th ed., Mack Publishing Company, Easton, Pa., 1985, p. 1418, the disclosure of which is hereby incorporated by reference.

Synthesis

The compounds of Formula (I) can be prepared using the reactions and techniques described below, in addition to synthetic procedures described in Applicant's Assignee's commonly assigned patent applications U.S. Ser. No. 08/010,731 (filed Jan. 29, 1993), U.S. Ser. No. 08/036,378 (filed Mar. 24, 1993), and U.S. Ser. No. 08/052,835 (filed Apr. 27, 1993), all of which are hereby incorporated by reference. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts, *Protective Groups In Organic Synthesis*, Wiley and Sons (1991).

Scheme 1

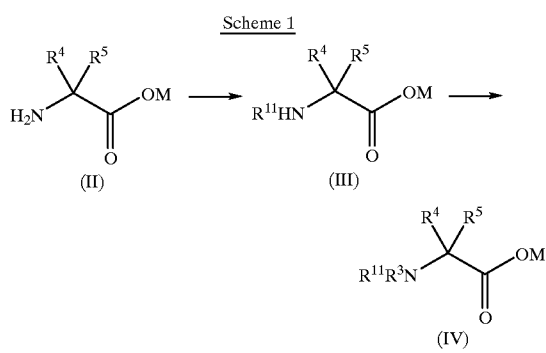

M is a carboxylic acid protecting group

The preparation of the required N,N-disubstituted amino acid subunit can be accomplished by the sequence outlined in Scheme 1. A variety of methods for the asymmetric synthesis of the amino acids required for the amino acid ester substrate (II) is reviewed by Morrison and Mosher (*Asymmetric Organic Reactions*, American Chemical Society, 297–334 (1976) and references there in). The appropriate ester (II), where M is the ester residue, can be conjugated to give the N-substituted intermediate (III) by N-monoalkylation with an alkyl halide related to $R^{11}$. Typical conditions for N-monoalkylation include the admixture of an excess of (II), the required alkyl bromide or iodide and a base in an anhydrous polar aprotic solvent, such as acetone, acetonitrile, N,N-dimethylformamide or methyl sulfoxide. The option exists for stirring this mixture at room temperature or heating at temperatures up to the reflux point of the selected solvent. The base added is chosen so that it will not interfere with the ester functionality of (II); among those recommended are non-nucleophilic bases such as sodium hydride or potassium carbonate. Another general route for the preparation of compounds of this type is the reductive amination of (II) with a selected aldehyde related to $R^{11}$. In this procedure, a mixture of (II) and the aldehyde are heated in an anhydrous non polar solvent, such as benzene, toluene or xylene, with continuous removal of evolved water by drying agents or azeotropic distillation. This process causes condensation of the aldehyde with amine (II). The condensation product is reduced to monoalkylated (III) by treatment with a selective hydride reducing agent such as sodium cyanoborohydride or sodium borohydride, according to the method of Getson et. al., *J. Heterocycl. Chem.* 1, 300 (1964), or by catalytic hydrogenation with platinum, palladium, nickel or Raney nickel in an alcohol solvent like propanol, ethanol or methanol, according to the method of Hudlicky, *Reductions In Organic Synthesis*, John Wiley and Sons, pp. 134 (1984).

While a number of coupling or acylation methods can be contemplated for the preparation of the disubstituted derivative (IV) from (III), (see Bodanszky and Bodanszky, *The Practice of Peptide Synthesis*, Springer-Verlag, p. 87–150 (1984)), three methods are preferred. In the first, a solution of (III) in an anhydrous non polar solvent, such as tetrahydrofuran or dichloromethane, at −78° C. or higher is treated sequentially with a selected acid chloride related to $R^3$ followed by a trialkylamine base. This mixture is allowed to warm to ambient temperature over several hours if required. The second method is the mixed anhydride procedure of Anderson et al. reported in *J. Am. Chem. Soc.* 89, 5012 (1967). In this procedure the alkyl mixed anhydride is generated by dissolving a selected carboxylic acid related to $R^3$ in non-polar anhydrous solvent, such as tetrahydrofuran or dichloromethane, and adding one equivalent of a trialkylamine base. The solution is stirred at −78° C. or higher and one equivalent of an alkylchloroformate is added. After formation of the mixed anhydride is complete, a solution of one equivalent each of intermediate (III) and a trialkylamine base is added dropwise. The mixture is stirred with or without cooling until the reaction is complete. The third method preferred for amide formation is the hydroxybenzotriazole/dialkylcarbodiimide method of Koing and Geiger in *Chem. Ber.* 103, 788 (1970). Thus, to (III) and a selected carboxylic acid related to $R^3$, dissolved in an aprotic solvent like N,N-dimethylformamide, dichloromethane or tetrahydrofuran, at −78° C. or higher, is added dialkylcarbodiimide, hydroxybenzotriazole and a trialkylamine base. If necessary, the stirred solution is allowed to thaw to ambient temperature over several hours.

An alternative preparation of N,N-disubstituted amino acids uses α-halo- or α-sulfonate acylesters such as (V) of Scheme 2. Compound (V) can be treated with a primary amine related to $R^{11}$ in the presence of a variety of bases like potassium carbonate, triethyl amine or sodium hydride and in solvents such as ethyl ether, acetone or dimethylformamide at temperatures ranging from −78° C. to the reflux point of the solvent selected. From this reaction can be isolated the N-alkyl aminoacid ester (III) of Scheme 1; the N-alkyl-N-acylamino acid ester (IV) can be prepared from compound (III) by any of the methods outlined in Scheme 1 and the related discussion hereafter.

The preparation of intermediates which will lead to compounds where $R^3$ and $R^{11}$ may be taken together to form a cyclic amide or phthalimide is described in Scheme 2. N,N-Disubstituted α-amino acid subunits (VI) which lead to compounds of this type are best derived by reaction of an appropriate α-haloester (V), where J=Cl, Br, I.

Scheme 2

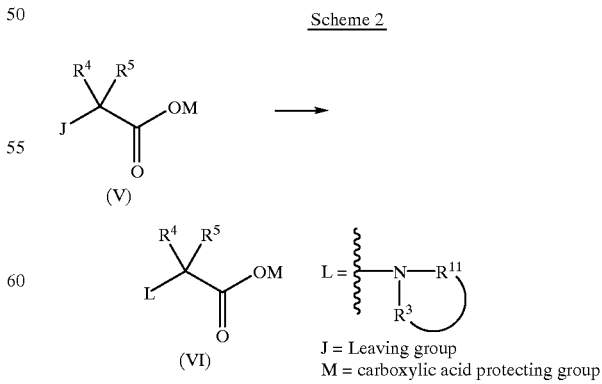

J = Leaving group
M = carboxylic acid protecting group with the alkali metal salt of an amide or phthalimide related to the desired cyclized combination of $R^3$ and $R^{11}$ in a polar aprotic solvent according to the method of Daly et. al.in *J. Med. Chem.* 33, 2818 (1990); Neuberger and Scott, *J. Chem. Soc.* p 1820 (1954). In a typical preparation the alkali metal salt of the required cyclic amide or phthalimide is generated by adding one equivalent of a strong non-nucleophilic base such as sodium or potassium hydride, a lithium dialkylamine, or lithium trimethyl- or lithium triphenyl-methane to a solution of the amide or phthalimide in an anhydrous inert solvent, such as tetrahydrofuran or 1,2-dimethoxyetharle, at −78° C. or higher. When the salt formation is complete, the solvent is removed by distillation and replaced by the appropriate polar aprotic solvent such as acetonitrile, N,N-dimethylformamide or methylsulfoxide. The appropriate α-chloro- or α-bromoester is introduced and the mixture stirred at room temperature or with heating until the haloester is consumed.

It will be recognized by those skilled in the art of organic synthesis that the acid derivatives of the N,N-disubstituted α-amino acid esters (IV) and (VI) are the required precursors for the preparation of the thrombin inhibitors disclosed in this invention. It is recommended that compounds (IV) and (VI) be prepared as either the benzyl, methyl or t-butyl esters because of the ease with which esters of these types may be converted to their corresponding acids. In the case of a benzyl ester (e.g. (IV) or (VI), where M=—$CH_2C_6H_5$), hydrogenolysis of an alcohol solution of the compound may be effected under an atmosphere of hydrogen gas in the presence of platinum or palladium on carbon catalyst according to the reported by Hartney and Simonoff, *Org. React.* VII, 263 (1953); with a methyl ester (IV) or (VI), where M=—$CH_3$, treatment of an ethanol solution of the compound with an aqueous base, such as one equivalent of sodium hydroxide solution, will give the desired acid. The t-butyl ester (IV) or (VI), where M=—$C(CH_3)_3$, is readily cleaved by acid under anhydrous conditions; for example trifluoroacetic acid in dichloromethane solution removes the t-butyl ester of derivatives of (IV) at ambient temperature as reported by Bryan et. al., *J. Am. Chem. Soc.* 99, 2353 (1977). A number of alternative esters and procedures are detailed in Greene and Wuts (1991).

Scheme 3 illustrates the coupling of the acid derivatives of (IV) or (VI) with boropeptide synthons (VII) or (VIII) to give intermediates (IX) or (X).

Scheme 3

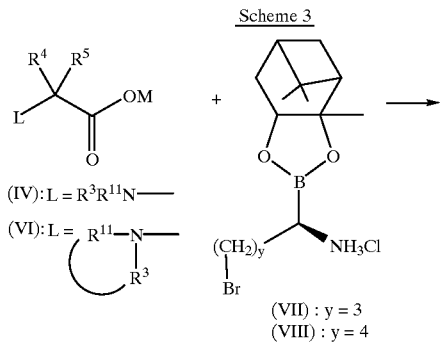

(IV): L = $R^3R^{11}N$——
(VI): L = $R^{11}-N$——
       $\quad\quad R^3$ (VII) : y = 3
(VIII) : y = 4

-continued

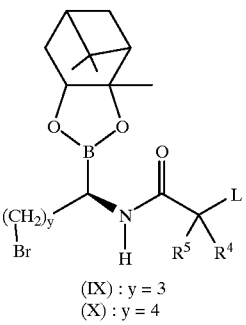

(IX) : y = 3
(X) : y = 4

The preparation of synthons (VII) and (VIII) has been described by Kettner and Shenvi (EP 293 881 A2). It will be recognized by those skilled in the art of organic synthesis that the methodology described by Kettner and Shenvi can be applied to make homologous boropeptide synthons related to (VII) and (VIII). These homologues may be used in the appropriate processes described herein to prepare the corresponding thrombin inhibitors. The coupling of the carboxylic acid derivative of (IV) or (VI) to boropeptide synthon (VII) or (VIII) has been described previously by Kettner et al. in *J. Biol. Chem.* 265 ,18289 (1990) and, in general, the standard amino acid coupling protocols detailed by Bodanszky and Bodanszky (1984) are effective for making the compounds of this invention. Preferred methods are the mixed anhydride procedure of Anderson et al. (1967) and the hydroxybenzotriazole/dialkylcarbodiimide method of Koing and Geiger (1970). In the mixed anhydride procedure, the anhydride is generated by dissolving a carboxylic acid related to (IV) or (VI) in a non polar anhydrous solvent, such as tetrahydrofuran or dichloromethane, and adding one equivalent of a trialkylamine base. The solution is stirred at −78° and up to 0° C. , then one equivalent of an alkylchloroformate is added. After formation of the mixed anhydride is complete, a solution of boropeptide synthon (VII) or (VIII) and a trialkylamine base is added. The mixture is stirred for one hour with cooling followed by several hours at ambient temperature. By the hydroxybenzotriazole/dialkylcarbodiimide method, (VII) or (VIII) and the acids of (IV) or (VI) are dissolved in an aprotic solvent, such as N,N-dimethylformamide, dichloromethane or tetrahydrofuran, at −78° or higher. To this solution one equivalent each of dialkylcarbodiimide, hydroxybenzotriazole and a trialkylamine base are added. If necessary, the solution is allowed to stir and thaw to ambient temperature over several hours.

A process for the preparation of the boropeptide thrombin inhibitors of this invention from intermediates (IX) and (X) is disclosed in Scheme 4. Compound (IX) serves as a starting point for isothiouronium thrombin inhibitors (XI) and (XII). The boronic ester (XI) is prepared by stirring a solution of (IX) and thiourea in an inert polar solvent, such as an alcohol or N,N-dimethylformamide, at temperatures ranging from ambient to the reflux temperature of the selected solvent. It is understood that a boronic acid ester like compound (XI) is an effective thrombin inhibitor, however, it may be transformed to the corresponding free boronic acid (XII) without a loss of biological activity. Compound (XII) is derived from the boron ester (XI) by transesterification under equilibrium conditions.

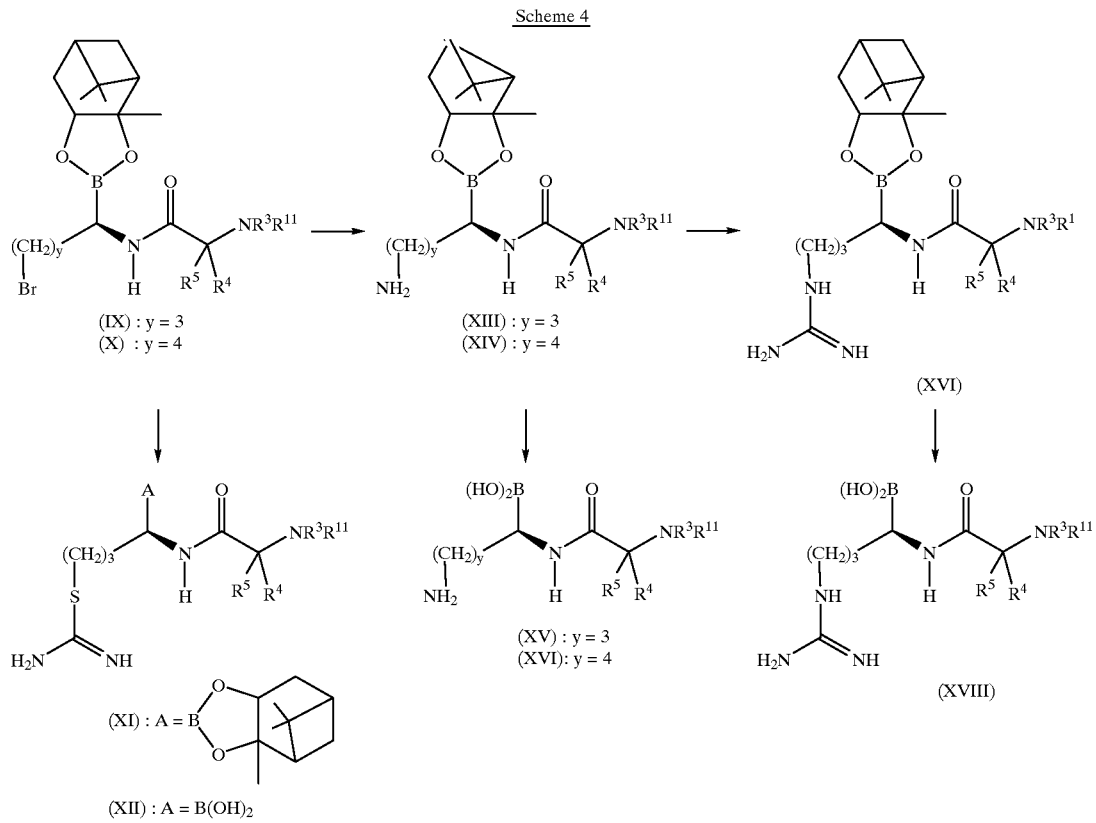

Scheme 4

Thus stirring ester (XI) with an excess of an alkyl- or aryl boric acid in a biphasic mixture of neutral or acidic water and an immiscible solvent, such as ethyl ether or toluene, gives (XII) after several hours at ambient temperature. The conditions generally preferred use 5 to equivalents of phenylboric acid in ethyl ether/water at 10 neutral pH. Thrombin inhibitors (XIII) to (XVI) are obtained by reduction of an azide intermediate prepared from (IX) or (X). The azide intermediate is prepared by heating either (IX) or (X) with an inorganic azide, such as sodium or potassium azide, in an anhydrous polar aprotic solvent, such as acetone, dimethylformamide or methyl sulfoxide at temperatures ranging from ambient to 130° C. Alternatively, phase transfer conditions may be employed to prepare the azide intermediate from (IX) or (X). For example, a tetraalkylammonium azide in a non-polar aprotic solvent, such as tetrahydrofuran or toluene, or a crown ether and inorganic azide in biphasic mixtures of water and an immiscible solvent, such as benzene, toluene or xylene, can be stirred at room temperature or heated up to the reflux point of the selected solvent. The primary amines (XIII) and (XIV) are most conveniently obtained from the catalytic hydrogenation of the azide in an inert solvent, such as an alcohol, ethyl acetate or tetrahydrofuran with a transition metal catalyst such as platinum or palladium on carbon under an atmosphere of hydrogen gas. A variety of alternative methods are also useful and can be found in the monograph by Hudlicky (1984, pp. 76). The acid salt of the resulting amines (XIII) and (XIV) may be formed by the addition of one equivalent of the desired acid to the hydrogenation mixture. Phenylboric acid mediated hydrolysis of esters (XIII) and (XIV) gives the free boronic acid thrombin inhibitors (XV) and (XVI), compounds of formula (I) of the invention.

Compounds containing a primary guanidine or N-alkyl guanidine functionality may be prepared by the alternative process outlined in Scheme 4. As illustrated with primary amine (XIII), the transformation to (XVII) is effected with a guanidinylation agent, such as an S-alkyl thiourea, aminoiminomethane sulfonic acid reported by Miller and *Bischoff Synthesis* 9, 777 (1986), cyanamide reported by Kettner et al. (1990) or- their N-alkyl derivatives. This mixture is stirred at room temperature or higher with a base, such as potassium carbonate, triethylamine or N,N-dimethylaminopyridine in an inert solvent like water, alcohol, N,N-dimethylformamide or acetone. The guanidine boronic acid esters (XVII) can be deesterified to give the corresponding boronic acid (XVIII) by the phenylboric acid procedure described above.

According to Scheme 5, the bromide (X) is converted to the corresponding alkylnitrile (XIX) upon exposure to the cyanide anion under a variety of conditions.

Scheme 5

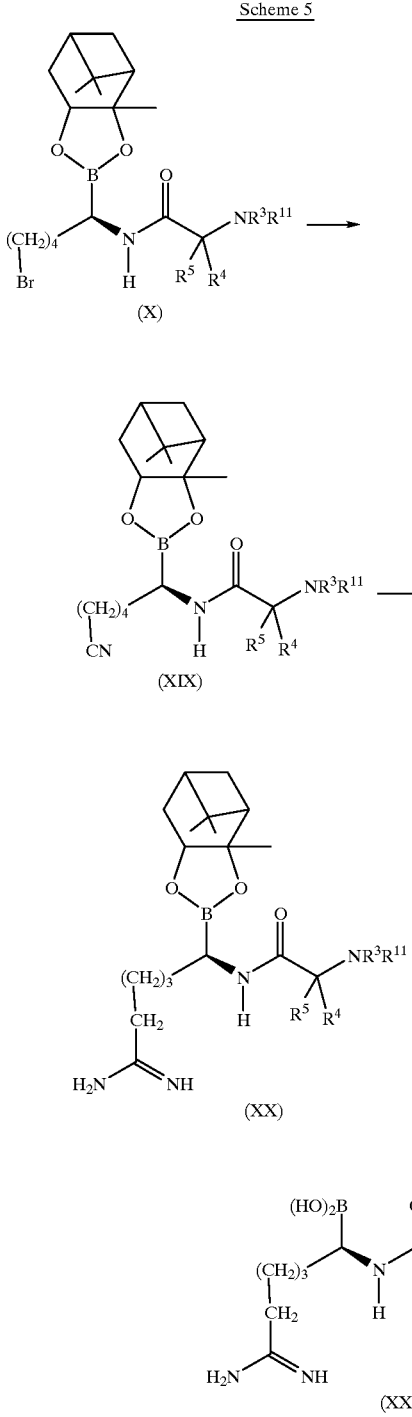

Effective methods include the use of potassium or sodium cyanides in polar aprotic solvents, such as N,N-dimethylformamide, methylsulfoxide, acetone or ethylmethyl ketone, at temperatures ranging from ambient up to the reflux point of the selected solvent. More useful, however, are conditions employing phase transfer agents such as tetrabutylammonium cyanide in a nonpolar aprotic solvent such as tetrahydrofuran or toluene, or a biphasic mixture of a crown ether and an inorganic cyanide in water with an immiscible solvent like benzene, toluene or xylene. These mixtures can be stirred at ambient temperature or heated up to the reflux temperature of the selected solvent. An amidine like (XX) is prepared by first treating nitrile (XIX) with a saturated solution of a mineral acid such as hydrogen chloride in an alcohol solvent at room temperature or lower. The intermediate O-alkylimidate can be exposed to ammonia, or a primary or secondary amine under anhydrous conditions with or without an inert solvent. As illustrated in Scheme 5, compound (XX) is produced by treating the O-alkylimidate formed from (XIX) with neat anhydrous ammonia at reflux. The free boronic acid (XXI) is obtained by transesterification of (XX) with phenylboric acid in a mixture of water and diethyl ether.

The formamidine substituted boronic acid (XXIII) is prepared from alkylamine (XV) as shown in Scheme 6. Compounds of (XV) can be stirred with an O-alkyl or O-aryl formimidate from 0° C. or up to the reflux temperature of an inert anhydrous solvent such as tetrahydrofuran or N,N-dimethylformamide to give formamidine (XXII). Free boronic acid (XXIII) is produced from (XXII) by the phenylboric acid transesterification protocol.

Scheme 6

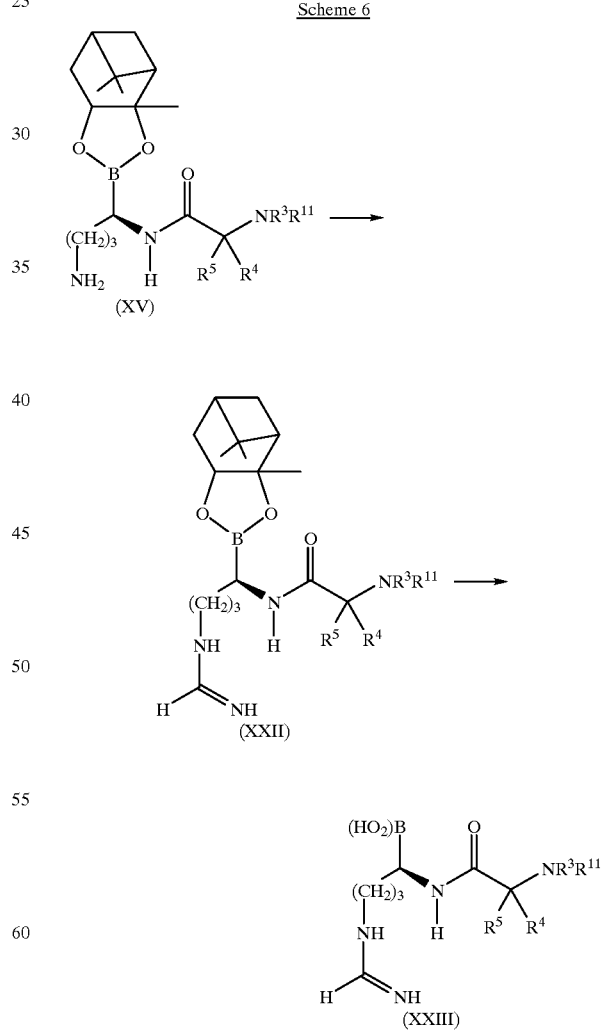

As shown in Scheme 7, the N-cyanoguanidine substituted boronic acid (XXVI), can be prepared by the reaction of (XV) with an N-cyanoisourylation agent such as S,S-dimethyl N-cyanoiminodithiocarbonate or O,O-diphenyl N-cyanodiimino-carbonate. In this general process, compounds of Formula (XV) are combined with a selected iminocarbonate in an inert, anhydrous solvent like tetrahydrofuran or N,N-dimethylformamide. The mixture is stirred at 0° C. or up to the reflux temperature of the chosen solvent until there is obtained an N-cyano-S-isourea or N-cyano-O-isourea of the Formula (XXIV) similar to that reported by Barpill et al., *J. Heterocyclic Chem.* 25, 1698 (1988). This intermediate is treated with an amine such as Scheme 7

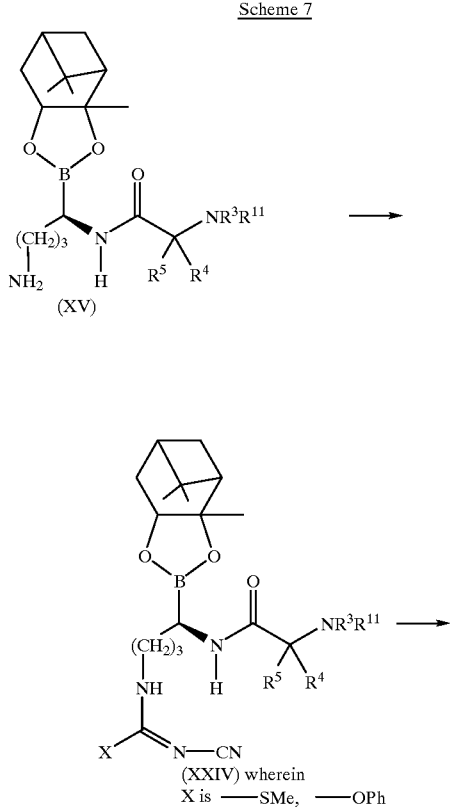

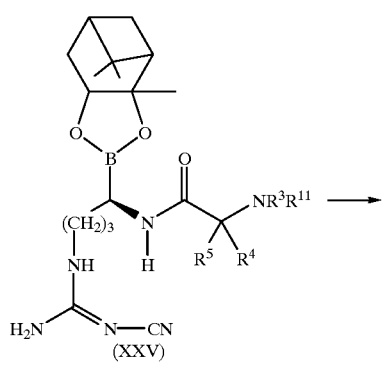

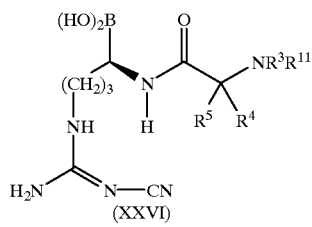

ammonia, or more generally, an alkylamine or an arylamine with or without an inert solvent like water, tetrahydrofuran or an alcohol at temperatures ranging from 0° C. to reflux to give the aminolysis product (XXV). Treatment of (XXV) as described above with phenylboric acid can provide (XXVI).

The N-hydroxyguanidino inhibitors, as shown in Scheme 8, are prepared by treating amine (XV) with cyanogen bromide or cyanogen chloride followed by hydroxylamine in an inert solvent to yield (XXVII) according to Nakahara et. al., *Tetrahedron* 33, 1591 (1977); and Belzecki et al., *J. Chem. Soc. Chem. Commun.* p. 806 (1970). Transesterification of (XXVII) by the phenylboric acid method can provide (XXVIII).

Scheme 8

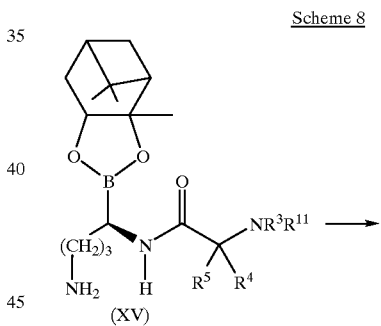

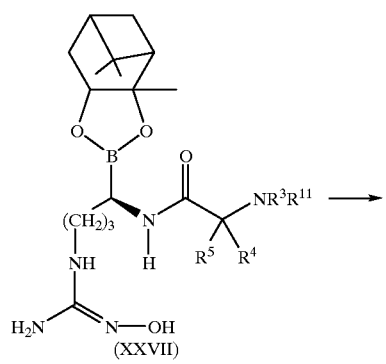

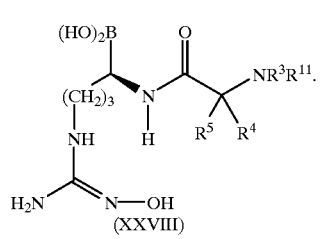

(XXVIII)

A general preparation for the new aromatic boronic acids is illustrated in Scheme 9. Functionalized benzylic anions containing either a halo- or cyano-substituent are obtained with a variety of metalation agents, such as activated zinc metal/CuCN•2LiCl based on the report of Berk et al. *Organometallics* 9, 3053 (1990); or use of lithium metal according to Michel et al., *J. Organometallic Chem.* 204, 1 (1981); or lithium naphthalenide in the presence of zinc chloride based on the report of Zhu et al., *J. Org. Chem.* 56, 1445 (1991) in an inert solvent like tetrahydrofuran or 1,2-dimethoxyethane at temperatures of −78° C. or higher. Dichloromethyl boronic acid pinanediol, prepared by the method described by Tsai et al. in *Organometailics* 2, 1543 (1983), is allowed to react with the transmetallated anion in the selected solvent to give (XXIX). The a-aminoboronic acid, (XXX), can be obtained by treating (XXIX) with the sodium or lithium salt of hexamethyldisilizane in a polar aprotic solvent like acetone, N,N-dimethylformamide or methyl sulfoxide with heating at temperature up to the reflux point of the selected solvent, if necessary The trimethylsilyl protecting groups are removed by treatment with Scheme 9

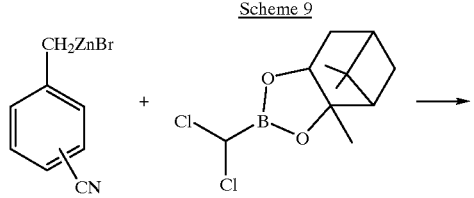

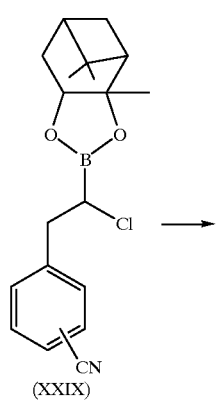

(XXIX)

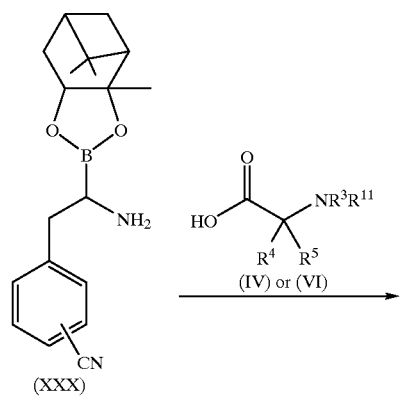

(XXX)

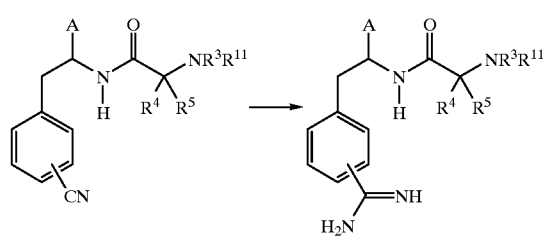

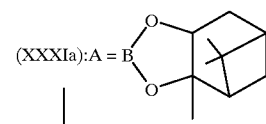     (XXXIIa)

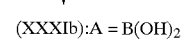     (XXXIIb)

anhydrous acid such as gaseous hydrogen chloride or trifluoroacetic acid in an inert solvent like tetrahydrofuran or dichloromethane at −78° C. or higher. Compound (XXX) was coupled to the N,N-disubstituted a-amino acids (IV) or (VI), using the techniques described in Scheme 3, to give the boronic acid ester (XXXIa). Transesterification of (XXXIa) by the phenylboric acid protocol (vide infra) gives inhibitor (XXXIb). In Scheme 9, the aromatic nitrile (XXXIa) is converted to the amidine (XXXIIa) by methods described for the synthesis of aliphatic amidine (XX) in Scheme 5. Removal of the pinanediol protecting group of (XXXIIa) gives the free boronic acid derivative (XXXIIb).

As detailed in Scheme 10, compound (XXXIa) is a versatile intermediate that can be hydrogenated to yield the aminomethyl derivative (XXXIIIa) under a variety of conditions (Hudlicky, (1984), pp 173).

Scheme 10

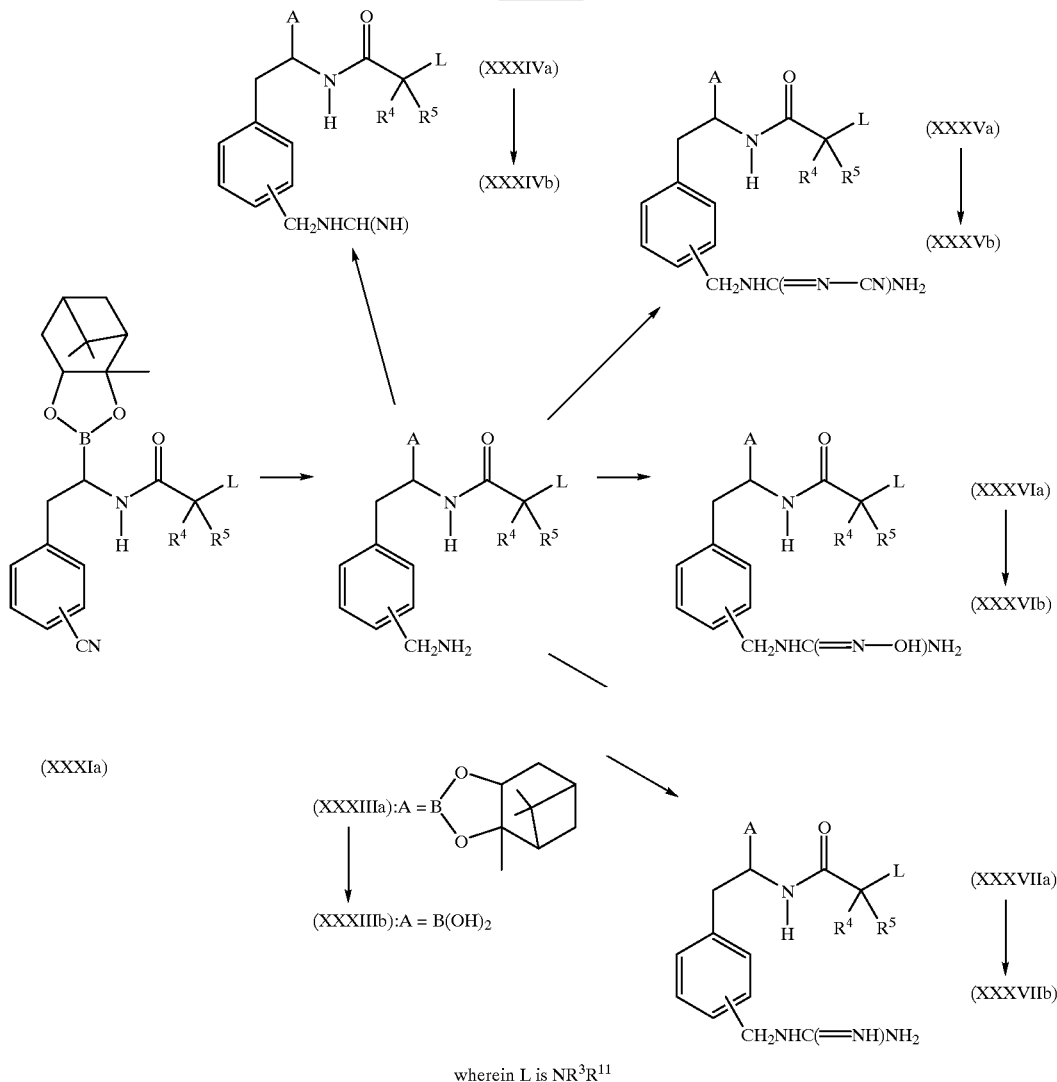

wherein L is $NR^3R^{11}$

Catalysts recommended for this transformation include transition metals like rhodium, Raney nickel, nickel boride, nickel, platinum or palladium; these reductions occur readily under atmospheres of hydrogen or ammonia at pressures ranging from 1 to 300 atmospheres, at room temperature or higher, and in inert solvents such as water, an alcohol, ethyl acetate or tetrahydrofuran. Furthermore, from (XXXIIIa), the formamidino- (XXXIVa), cyanoguanidino- (XXXVa), hydroxyguanidino- (XXXVIa) and guanidino- analogs (XXXVIIa) can prepared by the same procedures described for the aliphatic series in Schemes 4, 6 through 8. The boronic acid esters (XXXIIIa)–(XXXVIIa) can all be transesterified to the corresponding free boronic acid inhibitors (XXXIIIb)–(XXXVIIb) using the phenyl boronic acid method prviously described.

Aromatic boronic acid inhibitors (XLIa,b), with the guanidine functionality substituted directly on the aromatic nucleus, can be prepared from precursor (XXXVIII) according to Scheme 11. Nitration of the aromatic ring of (XXXVIII) according to the method of Olah and Kuhn, J. Amer. Chem. Soc. 84, 3684 (1962) can occur readily with agents such as acetyl nitrate, nitrosonium tetrafluoroborate ($NO_2^+BF_4^-$) and nitrosonium hexafluorophosphate ($NO_2^+$ $PF_6^-$) in inert solvents like tetrahydrofuran or dichloromethane at −78° C. or higher. The products of formula (XXXIX) can be reduced to the aniline derivative (LX) by catalytic hydrogenation. The catalysts recommended for this procedure include iron, zinc, platinum oxide, rhodium— platinum oxide, palladium, Raney nickel, copper chromite, and rhenium sulfide. While reduction occurs readily under an atmosphere of hydrogen gas at pressures range from 1 to 350 atmosphere in an inert solvent like water, an alcohol or ethyl acetate, other reagents which may affect this reaction are transfer agents such as hydrazine, formic acid or triethyl formate (Hudlicky, (1984), pp 73).

Scheme 11

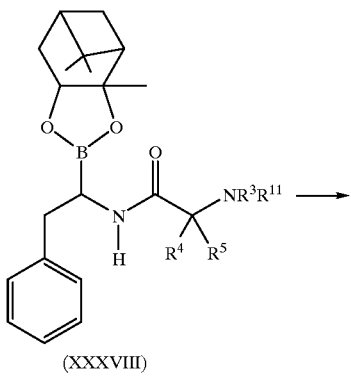

(XXXVIII)

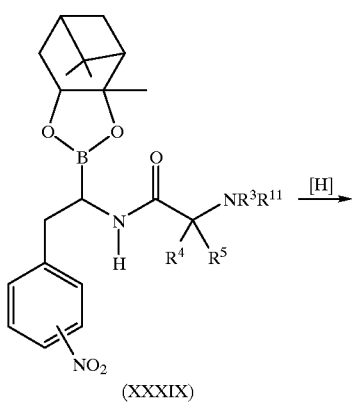

(XXXIX)

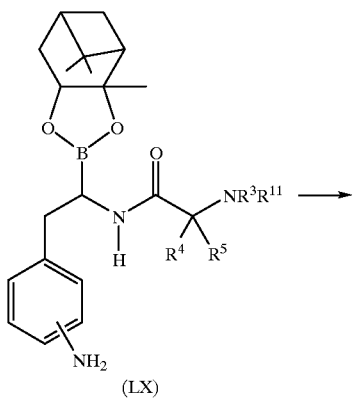

(LX)

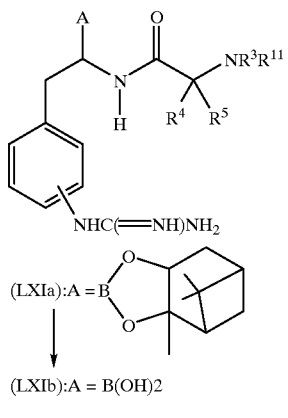

The aniline (LX) can be converted to the phenylguanidine (LXIa) by the procedure described for (XVII) in Scheme 4. The transformation of (LXIa) to the free boronic acid (LXIb) is effected as in Scheme 4.

The several types of inhibitors disclosed in this invention can be broadly classified by their electrophilic functional group A, as defined in Formula (I). The compounds described below, unlike the boron containing peptides, utilize a highly electrophilic carbon atom at A to interact with the active site serine of thrombin. The precursor for the electrophilic carbon inhibitors is the appropriately protected amino acid (LXII) of Scheme 12.

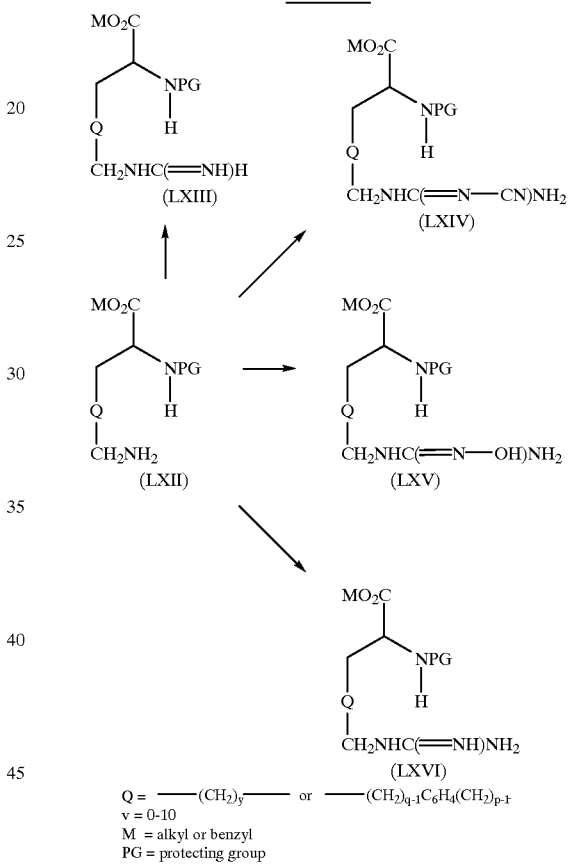

The preparation of (LXII) can be found in the general chemical literature, one such reference being the review by Morrison and Mosher (1976). According to Scheme 12 various terminal functional groups are available from (XLII): the formamidino- (XLIII), cyanoguanidino- (XLIV), hydroxyguanidino- (XLV) and guanidino-analogs (XLVI). These compounds are prepared by the same procedures described for the boropeptide series in Schemes 4, 6–8.

The preparation of amidine derivative (XLVIII) and phenylguanidines of formula (L) from amino acids (XLVII) and (XLIX) is shown in Scheme 13. The conditions used to prepare amidines of formula (XLVIII) is discussed for (XX) of Scheme 5 while the method for formamidinylation of (XLIX) to give (L) is the same as that described to prepare (XVII) of Scheme 4.

Scheme 13

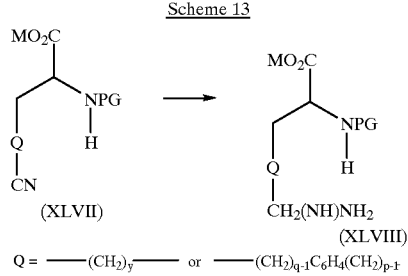

(XLVII) → (XLVIII)

Q = ——(CH$_2$)$_v$—— or ——(CH$_2$)$_{q-1}$C$_6$H$_4$(CH$_2$)$_{p-1}$

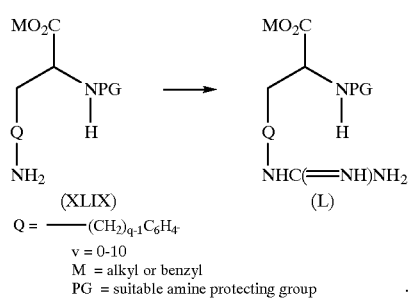

(XLIX) → (L)

Q = ——(CH$_2$)$_{q-1}$C$_6$H$_4$-
v = 0-10
M = alkyl or benzyl
PG = suitable amine protecting group As shown in Scheme 14, appropriately protected derivatives of formulae (XLII)–(L), wherein M is an alkyl or benzyl group can be coupled with N,N-disubstituted acid (IV) or (VI) (wherein M is hydrogen). The methodology to accomplish these transformations is the same as that used to prepare boropeptides (IX) and (X) of Scheme 3. The X group in compounds of formulae (XLII) through (L) and (LI) in Scheme 14, as well as in compounds illustrated in the Schemes to follow, is a protected version of the terminal functional group X, as defined by Formula (I), unless deprotection is indicated to obtain the final compound of the sequence.

Scheme 14

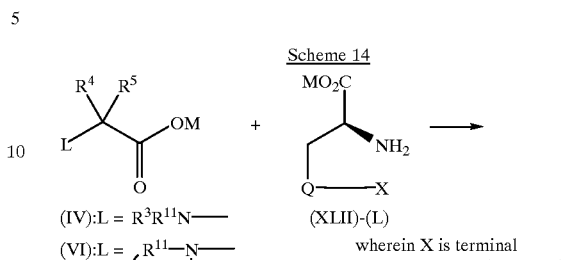

(IV):L = R$^3$R$^{11}$N——
(VI):L = R$^{11}$—N——
              |
              R$^3$ (XLII)-(L)

wherein X is terminal functional group (protected)

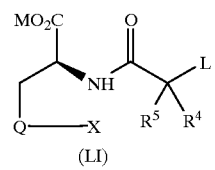

(LI)

It is understood that the protecting group(s) used should compatible with the conditions of the process discussed; a good source for information on protecting group chemistry is Greene and Wuts (1991).

The preparation of the thrombin inhibitors trihalomethyl ketone (LIII) and α-ketoester (LIV) are shown in Scheme 15. The coupled ester (LI), wherein M is alkyl or benzyl can be converted to the acid (M is hydrogen) by the methodology appropriate for the particular ester functionality as described in Greene and Wuts (1984). The aldehyde (LII) can be prepared by selective reduction of the acid (LI, M is hydrogen) to the primary alcohol followed by oxidation.

Scheme 15

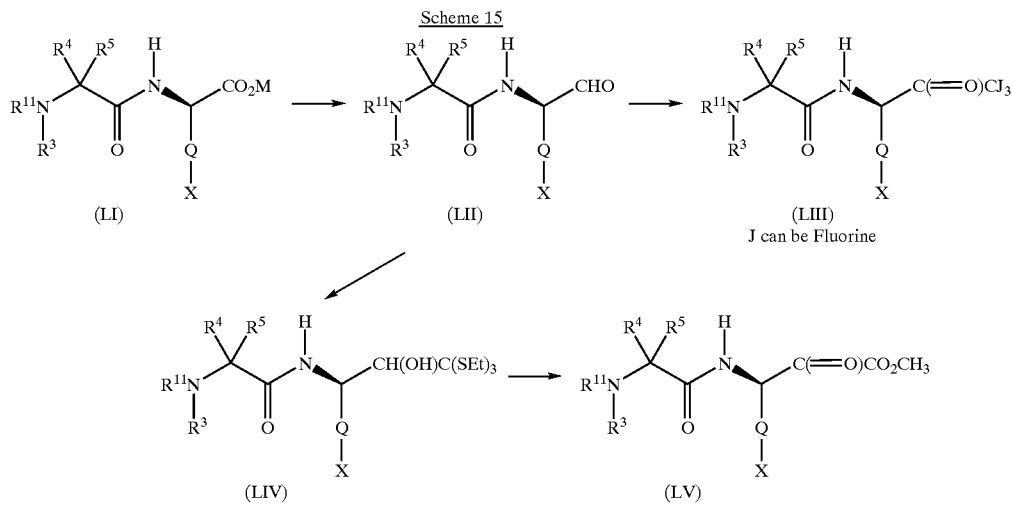

(LI) → (LII) → (LIII)
J can be Fluorine (LIV) → (LV)

To obtain the primary alcohol, the acid can be transformed to the mixed anhydride by condensation of the trialkylammonium salt of the acid with an alkyl- or arylchloroformate in an inert non-polar solvent such as tetrahydrofuran, 1,2-dimethoxyethane or toluene at –78° C. to room temperature.

The solution of the resulting mixed anhydride is filtered and reduced to the peptidyl alcohol with an excess of a borohydride reducing agent in a compatible solvent like water or an alcohol at −78° C. to room temperature according to the method of Rodriguez et. al., *Tetrahedron Lett.* 32, 923 (1991). The peptidyl alcohol can be oxidized to aldehyde (LII) without over oxidation by a variety of procedures, as detailed by Hudlicky in *Oxidations in Organic Chemistry*, American Chemical Society, p. 114 (1991); the preferred methods include Swern oxidation described by Omura and Swern, *Tetrahedron* 34, 1651 (1978); and the Pfitzner-Moffat oxidation described by Fearon et al.in *J. Med. Chem.* 30, 1617 (1987). A two step protocol reported by Edwards, *Tetrahedron Lett.* 33, 4279 (1992) can be used to prepare the trifluoromethyl ketones (LIII) (J is fluorine) from aldehyde (LII). In this procedure a metallated trifluoromethyl anion is generated from an excess of trifluoromethyliodide or -bromide and an active metal such as zinc, magnesium, lithium or cadmium in inert, anhydrous solvents like tetrahydrofuran or N,N-dimethylformamide at temperatures of −100° C. up to the reflux point of the solvent. Alternatively, the metalated trifluoromethyl anion may be generated by the transmetallation of trifluoromethyliodide or -bromide with an organometallic compound such as a Grignard reagent or alkyllithium compound in an inert solvent like tetrahydrofuran, hexane or ether at temperatures ranging from −78° C. up to the reflux point of the selected solvent. Aldehyde (LII) can be added to the solution of the metalated trifluoromethyl anion to form the trifluoroethanol derivative at temperatures of −100° C. or higher. To obtain the trifluoromethyl ketone (LIII) where J is fluoro, the alcohol is oxidized by the Pfitzner-Moffat or Swern procedure. Removal of the protecting group(s) on terminal group X by the appropriate method will provide the thrombin inhibitors of formulae (LIII).

Trihalomethyl analogs of (LIII), where J is fluoro can also be prepared from aldehyde (LII) by a different method. The trihalomethyl ketones are prepared by treating aldehyde (LII) with either the trimethylsilyl trihaloacetate or the potassium or sodium trihaloacetate in a polar solvent such as an alcohol, N,N-dimethylformamide or methylsulfoxide with or without a base such as a trialkyl amine, potassium carbonate or sodium hydroxide at temperatures of −78° C. or higher according to the method of Beaulieu, *Tetrahedron Lett.* 32, 1031 (1991); Shell Int. Res., European Patent Application EP 16504). The resulting a,a,a-trihaloethanol is oxidized and group X can be deprotected as above to give the thrombin inhibitors or formulae (LIII).

The a-ketoester thrombin inhibitors, exemplified by (LV), are prepared according to a route disclosed by Iwanowicz et. al. in *Bioorgan. Med. Chem. Lett.* 12, 1607 (1992). The tris(ethylthio)methyl anion is added to the peptidyl aidehyde (LII) in a solvent such as tetrahydrofuran, 1,2-dimethoxyethane or toluene at −100° C. or higher to give the alcohol (LIV). The a-hydroxyl ester is generated from (LIV) by treatment with a mixture of mercuric salts, such as mercuric chloride and mercuric oxide, in an alcohol or water. Swern or Pfitzner-Moffat oxidation of the a-hydroxyl ester followed by the deprotection of substituent X protecting group provides thrombin inhibitors of formula (LV).

Another method for the preparation of compound (LV) substitutes a 1-lithio-1-alkoxyethene or 1-magnesio-1-alkoxyethene for the tris(ethylthio)methyl anion of Scheme 15 in an addition reaction with peptidyl aldehyde (LII). There can be obtained an adduct analogus to the tris (ethylthio)hydroxyethyl compound (LIV) when excess 1-magnesio- or 1-lithio-1-alkoxyethene anion is stirred at temperatures ranging from −100° C. to ambient temperature with (LII) in anhydrous solvents such as diethyl ether or tetrhydrofuran. This alkoxyolefin product may then be transformed to (LV) by oxidative cleavage with reagents such as ozone or periodate in an inert solvent such as a halohydrocarbon, lower alkyl ketone, an alcohol or water at temperatures ranging from −100° C. to ambient temperature, followed by oxidation of the intervening α-hydroxyester and deprotection as described above.

The preparation of the a,a-dihalomethylketone thrombin inhibitors of this invention is outlined in Scheme 16.

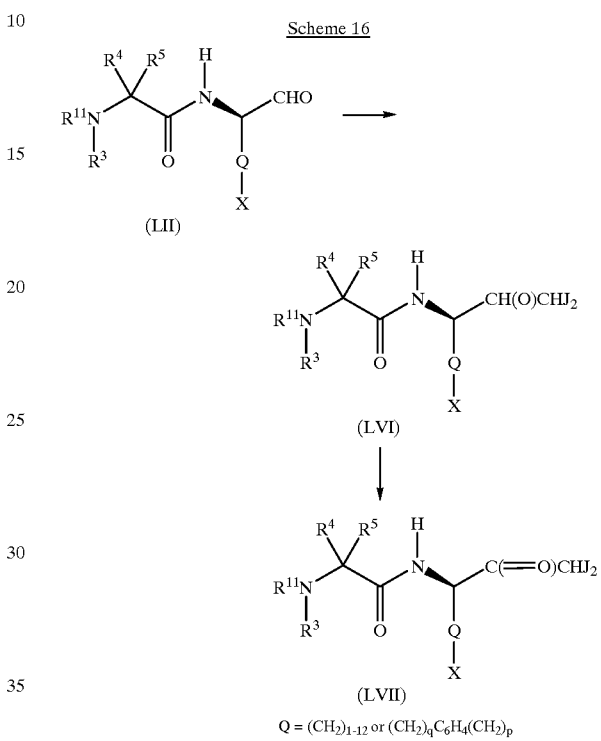

Scheme 16

$Q = (CH_2)_{1-12}$ or $(CH_2)_q C_6H_4 (CH_2)_p$

The a,a-dihalomethylketone (LVII), where J is fluoro can be prepared from the aldehyde (LII) by selective reaction of the aldehyde with the anion of the corresponding dihalomethane. The metalated dihalomethane anion is generated from one equivalent each of a strong hindered base, such as lithium tetramethylpiperidide or Lertbutyllithium, and the selected dihalomethane in an anhydrous, inert solvent like tetrahydrofuran or 1,2-dimethoxyethane at −100° C. or higher according to the method of Taguchi et. al. *Bull. Chem. Soc. Jpn.*, 50, 1588 (1977). The metalated dihalomethane anion can be added to the aldehyde (LII) at −100° C. or higher. Alternatively, the dihalomethane anion is generated from a dihalomethyl(trimethyl)silane and an anhydrous fluoride ion source such as tris(diethylamino)sulfonium difluoromethyl silicate in an inert solvent like benzene, acetonitrile or tetrahydrofuran at −78° C. or higher, then (LII) can be added to give dihaloethanol (LVI) according to the method of Fujita and Hiyama, *J. Am. Chem. Soc.* 107, 4085 (1985). The resulting dihaloethanol can be oxidized to ketone (LVII) by the Swern or Pfitzner-Moffat procedure. Removal of the protecting group(s) on substituent X of (LVII) gives the a,a-dihalomethylketone thrombin inhibitors.

a-Halomethylketone thrombin inhibitors can be prepared by the process illustrated in Scheme 17. The acid chloride (LVIII) can be prepared from acid (LI), wherein M is hydrogen or its trialkylammonium, sodium or potassium salt with a chlorinating agent such as thionyl chloride, oxalyl chloride or dichloromethylmethyl ether in a solvent like tetrahydrofuran or dichloromethane with or without a catalytic amount of N,N-dimethylformamide at −78° C. or higher. Alternatively, the mixed anhydride of (LI) may be prepared as described for (LI) in Scheme 15. Compound (LVIII) or the mixed anhydride of (LI) can be treated with an ether solution of diazomethane and either anhydrous hydrogen fluoride or hydrogen chloride gas according to that described by McPhee and Klingsbury, *Org. Synth. Coll.* III, 119 (1955); or hydrogen bromide according to the method Miescher and Kaji, *Helv. Chim. Acta.* 24, 1471 (1941).

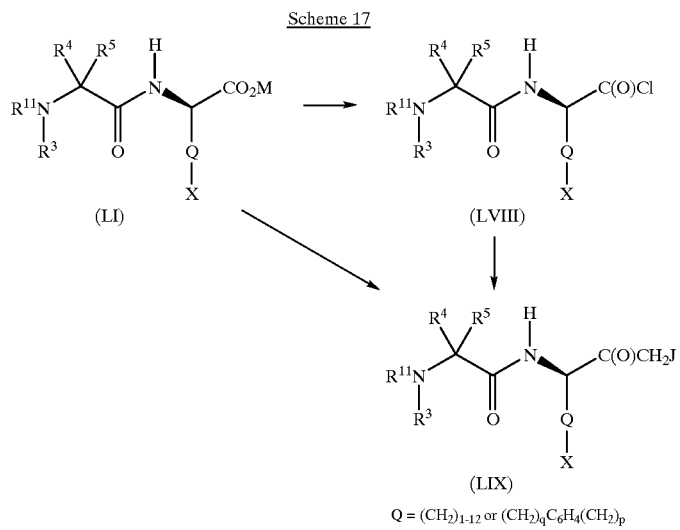

Selection of the hydrogen fluoride gas will give the a-fluoromethylketone analog, (LIX) wherein J is fluoro; and hydrogen chloride gas gives the α-chloromethylketone analog (LIX) wherein J is chloro. Deprotection of X gives the corresponding thrombin inhibitors of (LIX).

The general preparative route for the a,b-diketoester, -amide and -ketone thrombin inhibitors of this invention is exemplified in Scheme 18. Compound (LVIII) or the mixed anhydride of (LI) can be reacted with a Wittig reagent such as methyl (triphenyl-phosphoranylidene)acetate in a solvent like tetrahydrofuran or acetonitrile at temperatures ranging from 0° C. to the reflux point of the solvent to give (LX). Oxidative cleavage of the phosphoranylidene (LX) with an oxidizing agent like ozone or OXONE™ in an inert solvent such as tetrahydrofuran, dichloromethane or water at temperatures of −78° C. or higher gives the vicinal tricarbonyl compound (LXI), analogous to that described by Wasserman and Vu, *Tetrahedron Lett.* 31, 5205 (1990). Cleavage of the protecting group can provide thrombin inhibitors of formula (LXI).

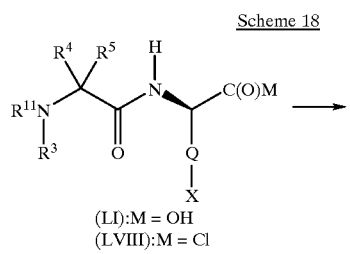

Scheme 18

(LI):M = OH
(LVIII):M = Cl

The preparative routes for the synthesis of the a-mono- and a,a-dihalo-b-ketoester -amide and ketone thrombin inhibitors of this invention are summarized in Scheme 19. The exemplified b-ketoester (LXII) is available from the acid derivative (LI). The acid (LI) can be treated with carbonyl diimidazole in an inert solvent such as tetrahydrofuran or dichloromethane at 0° C. or higher to form the acyl imidazole. This acyl imidazole, or the mixed anhydride of (LI), can be further reacted with lithioethylacetate in solvents such as 1,2-dimethoxyethane or tetrahydrofuran/hexane at temperatures ranging from −100° C. to ambient temperature, according to the method of Dow, *J. Org. Chem.* 55, 386 (1990) to give b-ketoester (LXII).

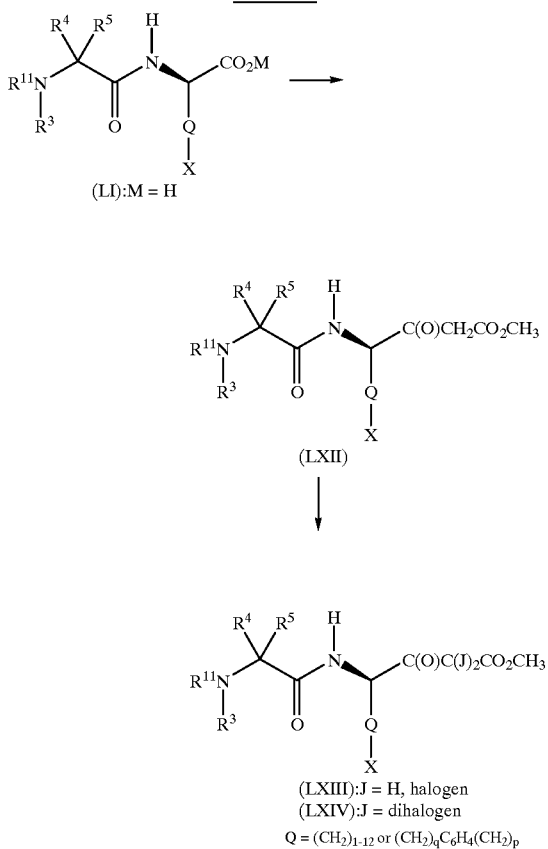

Compound (LXII) serves as a substrate for both mono- and dihalogenation. The α-monochloro analog of (LXIII), where J is each chlorine and hydrogen, can be prepared by controlled halogenation reactions with reagents like N-chlorosuccinimide or thionyl chloride in an inert halogenated solvent and at temperatures ranging from −20° C. to the reflux point of the selected solvent according to the methods of Uhle, *J. Am. Chem. Soc.* 83, 1460 (1961); and DeKimpe et. al., *Synthesis* 2, 188 (1987). The a,a-dihalo analog (LXIV) where J is chloro is available from halogenation with molecular chlorine in a halogenated solvent at temperatures of −20° C. or higher according to the method of Bigelow and Hanslick, *Org. Syn. Coll.* II, 244 (1943). Reagents such as N-fluorobis[(trifluoromethyl)sulfonyl] imide are useful for the preparation of mono- and difluoro analogs (LXIII) and (LXIV) by reacting the appropriate stoichiometry of this reagent with (LXII) in a halogenated solvent at temperatures of −78° C. or higher according to the method of Resnati and DesMarteau, *J. Org. Chem.* 56, 4925 (1991). Deprotection of substituent X of the halogenation products (LXIII) and (LXIV) can provide the corresponding thrombin inhibitors.

Compounds of formula (LXII) also serves as a substrate for the preparation of tricarbonyl derivatives such as (LXI) (Scheme 18). Condensation of (LXII) with an aldehyde, such as benzaldehyde, gives an b-ene-a,g-dione. This enedione can be oxidatively cleaved with reagents like ozone or periodate to give tricarbonyl analog (LXI).

The preparation of the mono- and dihalomethylketone thrombin inhibitors is outlined in Scheme 20. The intermediates formed in the preparation of the a-mono- and a,a-dihalo-b-ketoester thrombin inhibitors of Scheme 19 can be used in these preparations.

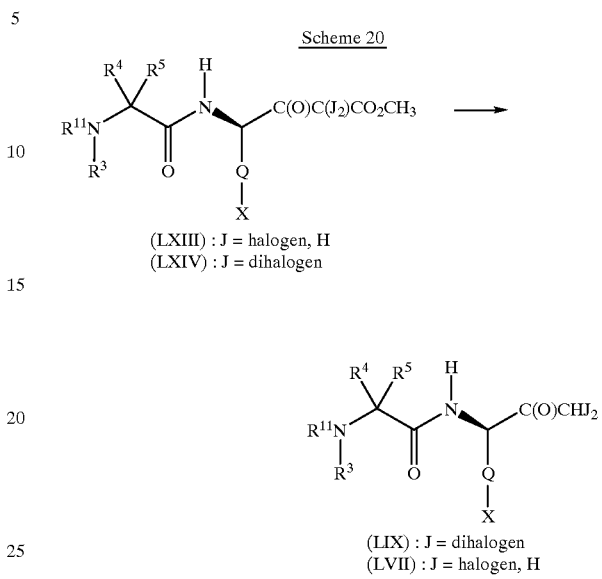

The decarboxylation of these halogenation products, (LXIII) and (LXIV), can be effected by saponification of the ester with mild aqueous base such as potassium carbonate or sodium hydroxide in water miscible solvents like an alcohol, tetrahydrofuran or N,N-dimethylformamide, followed by adjusting the pH to a range of 4 to 6. This mixture can be either stirred at ambient temperatures or heated at various temperatures up to the reflux point of the solvent chosen until the formation of (LVII) or (LIX) is complete and is similar to that reported in Matsuda et. al., *Tetrahedron Lett.* 30, 4259 (1989). Removal of protecting group(s) can provide thrombin inhibitors corresponding to (LVII) or (LIX).

Compounds of the present invention wherein the electrophilic group A is an a-hydroxy ester are prepared according to Scheme 21. The appropriate amino acid (LXVI) is reduced to the corresponding alcohol (LXVII) via NaBH4 treatment of the mixed anhydride. (LXVII) is then oxidized to the aldehyde (LXVIII) utilizing a Swern oxidation. (LXVIII) is converted to the thiocarbinol (XIX) via a lithiated orthoethylthioformate followed by conversion to the a-hydroxy methyl ester (LXX) upon treatment with mercuric salts. (LXX) is readily converted to the peptides of the invention via coupling with (IV) (M=H) to form (LXXI) under the conditions described in Scheme 3.

Scheme 21

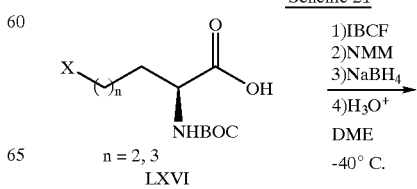

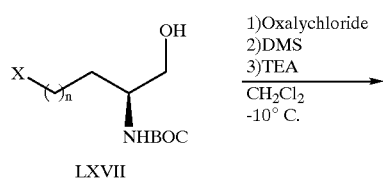
LXVII
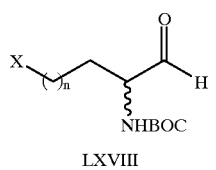
LXVIII
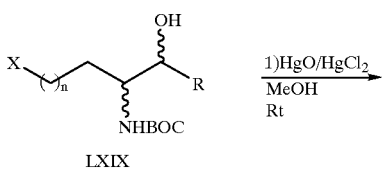
LXIX
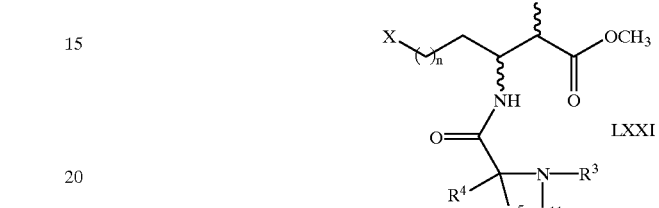
LXX
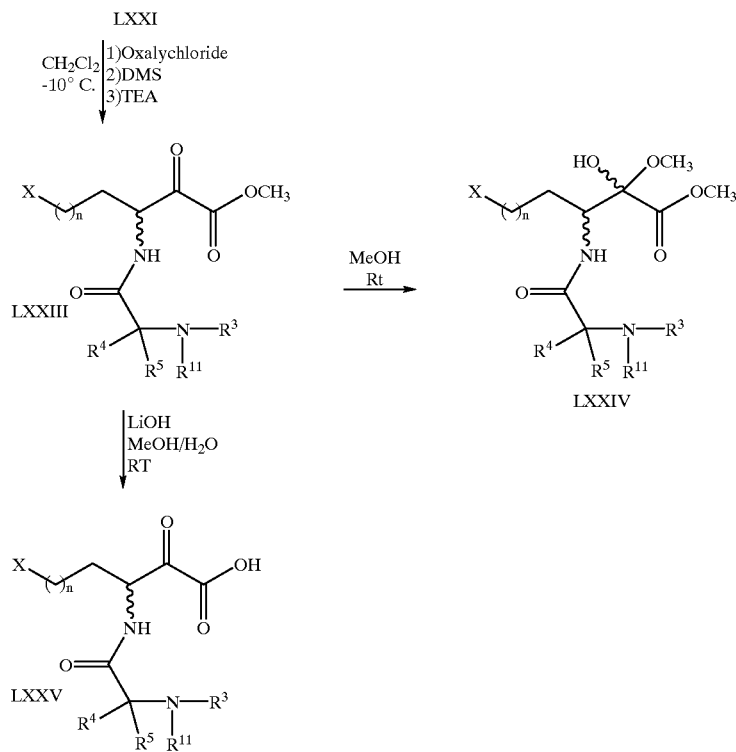
LXXI
The preparation of compounds of the present invention wherein A is an a-keto ester, a-keto acid or a-keto ester hemiacetal is shown in Scheme 22. (LXXI) is converted to the a-keto ester LXXIII via a Swern Oxidation. (LXXIII) is further elaborated to hemiketal (LXXIV) by treating with methanol or to (LXXV) by treatment with hydroxide.
Scheme 22

The compounds of the present invention wherein A is an alkyl carbinol (LXXVII) or an alkyl ketone (LXXVIII) are prepared according to Scheme 23. (LXVIII) is treated with an alkyl-CeCl$_2$ to form the alkyl carbinol (LXXVII) which is then subjected to the Swern oxidation to yield the alkyl ketone (LXXVIII). (LXXVIII) is then further elaborated to the peptide compounds of the present invention (LXXX) by following the conditions outlined in Scheme 3.

Scheme 23

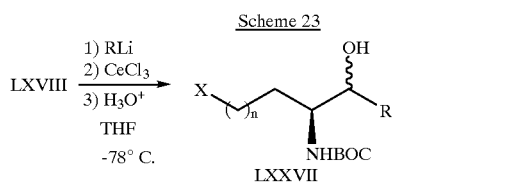

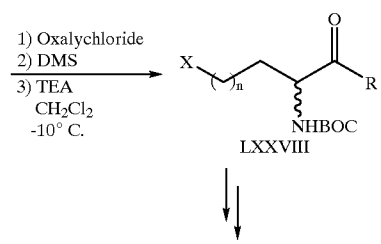

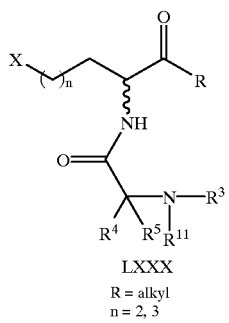

LXXX

R = alkyl
n = 2, 3

Compounds of the present invention wherein R$^3$ is an optionally substituted thiophenylbenzoyl group (LXXXIII) are prepared according to Scheme 24. The desired thiophenol (LXXXII) is coupled to the bromobenzoic acid via a copper promoted coupling reaction to form (LXXXIII). (LXXXIII) is then coupled to (IV) (M=H) under the conditions outlined in Scheme 3 to form (LXXXIV) which is then coupled to (LXXXVI) under the conditions outlined in Scheme 3 to form (LXXXV). It is understood that (LXXXV) need not be in final form and that any or all of the functional groups present may be converted to their desired final form using methods known to the skilled artisan.

Scheme 24

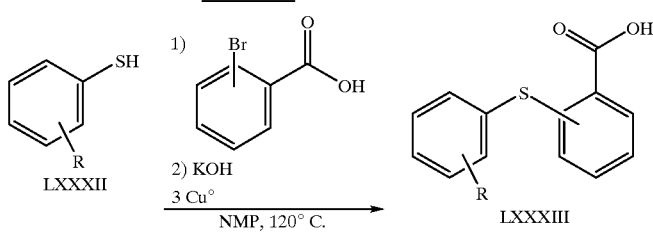

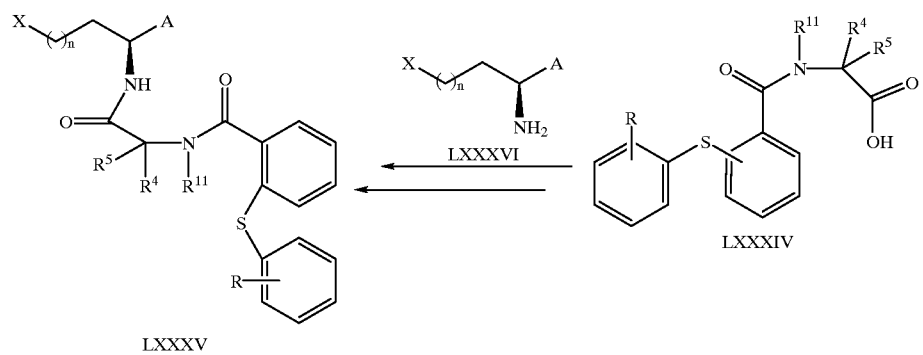

Compounds of the present invention wherein $R^3$ is an optionally substituted benzylbenzoyl group are prepared according to Scheme 25. An optionally substituted bromophenyl compound (LXXXVII) is converted to its phenyl lithium derivative and reacted with a bromobenzaldehyde to form the optionally substituted diphenylmethyl carbinol (LXXXVIII). (LXXXVIII) is further reduced to the substituted diphenylmethane (LXXXIX) with $Et_3SiH$. (LXXXIX) is converted to XC. XC is then further elaborated to XCI arid XCII by following the appropriate outline in previous schemes.

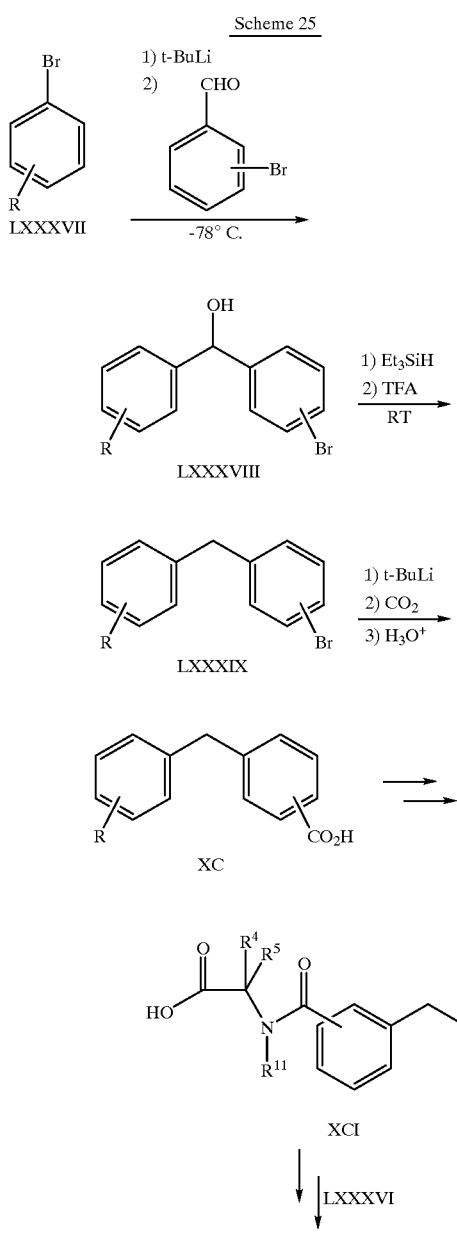

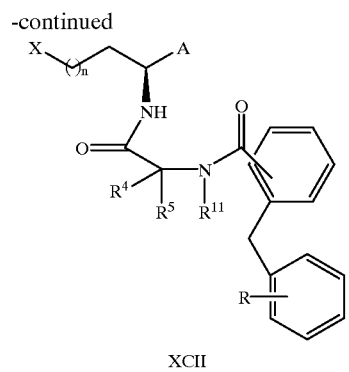

Inhibitors which contain a substituted phenethyl group as $R^{11}$ are easily prepared according to Schemne 26. The appropriate phenylacetate (XCIV) is readily dialkylated with an excess of a small, unbranched alkyl halide ($R^{18}$-X) and a suitable base such as potassium tert-butoxide to form an a,a-bisalkylated ester (XCVa). Reduction of XCVa to the primary alcohol may accomplished with many hydride reducing agents, a preferred agent being lithium aluminum hydride. Oxidation of the alcohol under Swern conditions or with pyridinium chlorochromate affords the aldehyde (XCV). (XCV) is best coupled to the appropriate glycine derivative by reductive amination, a preferred procedure being reduction with sodium cyanoborohydride. The resulting amine (XCVI) is then coupled with $R^3$ by any of several standard amide bond forming reactions familiar to those skilled in the art. A preferred method involves treating the amine with the appropriate acid chloride in the presence of a tertiary amine base, such as N-methylmorpholine or triethylamine. Saponification of the ester affords the carboxylic acid (XCVII).

The acid (XCVII) is then coupled to (LXXXVI) and elaborated to the inhibitors of the present invention by following the procedures outlined in Schemes 3, 4, and 5.

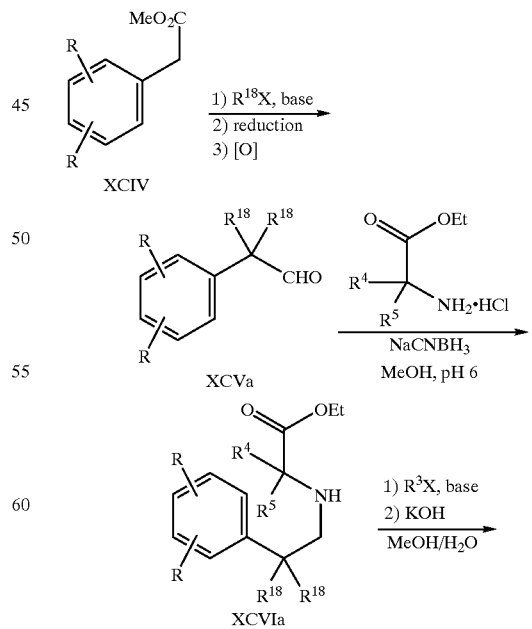

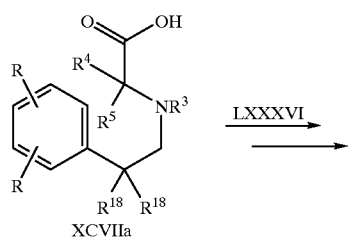

XCVIIa

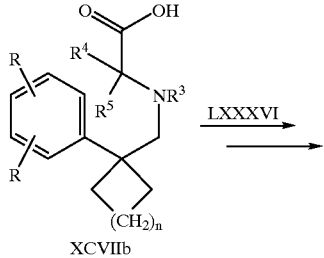

XCVIIb

LXXXVI →→

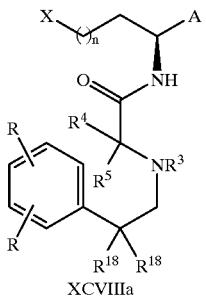

XCVIIIa

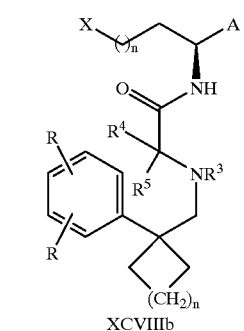

XCVIIIb

Inhibitors which contain a 1,w-alkanediyl substituted phenethyl group (XCVb) as $R^{11}$ are easily prepared according to Scheme 27. This procedure is similar to that of Scheme 26, except that a 1,w-bifunctional alkylating agent (X-$R^{18}$-X) instead of a monofunctional alkylating agent ($R^{18}$-X). In this manner, inhibitors of the present invention with the general formula (XCVIIIb) may be prepared.

Inhibitors in which $R^3$ is an acylalkyl terminated by a carboxylic acid or ester (CI) are prepared by the general route described in Scheme 28. Reaction of a suitably substituted cyclic anhydride (C) with an alkoxide such as sodium benzyl oxide affords a mono-protected diacid (CI).

(CI) is then coupled to an appropriate N-alkylglycine derivative ((IV), (M=H) by any of a number of methods known to the skilled artisan. The choice of ester groups should allow for selective deprotection of the glycine carboxylate. Preferred ester groups are methyl or ethyl on the glycine carboxylate and benzyl on the acylalkyl chain, so that saponification gives the acid (CII). (CII) is then converted to the final products (CIII) following methods described in previous schemes.

Scheme 27

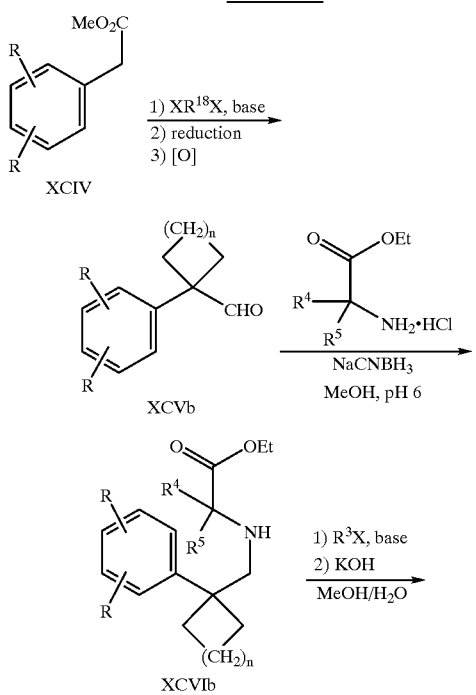

Scheme 28

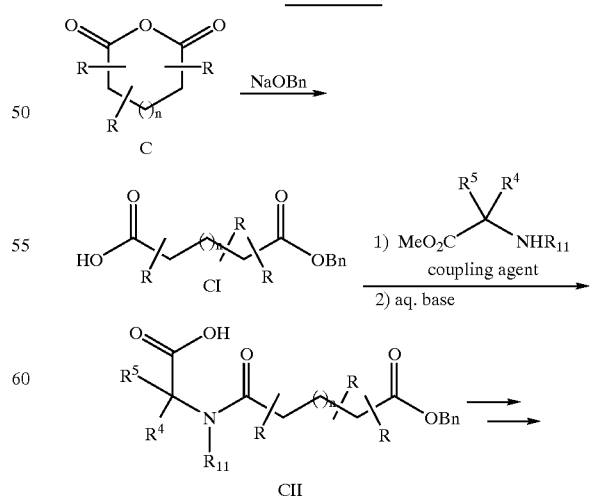

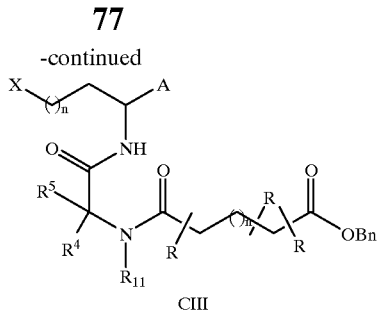

CIII

EXPERIMENTAL SECTION

INTERMEDIATE 1

N-Methyl-N-[(3-phenyl)propionyl]glycine

Part A:

To hydrocinnamic acid (10.0 g, 66.7 mmol) and 4-methylmorpholine (6.74 g, 66.7 mmol) in tetrahydrofuran (THF, 200 mL) at 0° C. was added n-butylchloroformate. The reaction was maintained at 0° C. for 15 minutes, and the hydrochloride salt of sarcosine ethyl ester (10.23 g, 66.7 mmol) followed by triethylamine ($Et_3N$, 16.84 g, 166.8 mmol) was added. The reaction was allowed to thaw to ambient temperature and stirred for 18 hours. After this time, the solvent was removed and the residue partitioned between aqueous hydrochloric acid (HCl, 1 N, 200 mL) and ethyl acetate (EtOAc, 200 mL). The aqueous acid phase was extracted with additional EtOAc (200 mL), the combined organic extracts were washed with HCl (1 N, 100 mL), saturated sodium bicarbonate ($NaHCO_3$, 100 mL) and brine (100 mL). The organic phase was dried over sodium sulfate and evaporated to give ethyl N-methyl-N-[(3-phenyl)propiorlyl]glycine (11.81 g, 71% yield). This material was used in the next step without further purification.

Part B:

To a solution of ethyl N-methyl-N-[(3-phenyl)propionyl]glycine (11.81 g, 47.4 mmol) in ethanol (300 mL) was added aqueous sodium hydroxide (NaOH, 1 N, 94.8 mL, 94.8 mmol). The reaction was stirred at ambient temperature for 18 hour, afterwhich the solvent was removed by distillation in vacuo. The residue was dissolved in HCl (1 N, 100 mL) and the solution extracted with methylene chloride ($CH_2Cl_2$, 2×100 mL). The extracts were dried over sodium sulfate ($Na_2SO_4$), evaporated arid the resulting solid (9.42 g) was recrystallized from EtOAc to give the title compound (7.14 g, 68% yield) as a solid (mp: 123–126° C.).

EXAMPLE 21.1.3

Pinanediol N-{N-methyl-N-[(3-phenyl)propionyl]glycyl}-1-amido-5-aminopentaneboronate, benzenesulfonic acid salt Part A:

A mixture of Intermediate 1 (0.31 g, 1.5 mmol), pinanediol 1-amino-5-bromopentaneboronate (0.57 g, 1.85 mmol), 1-hydroxybenzotriazole (0.20 g, 1.5 mmol), 4-methylmorpholine (0.17 mL, 1.5 mmol), and 1,3-dicyclohexylcarbodiimide (DCC, 0.33 g, 1.5 mmol) were stirred in dry $CH_2Cl_2$ at 0° C. for 1 hour. The reaction was thawed to ambient temperature and stirred an additional 18 hour. After this time, the reaction mixture was diluted with $CH_2Cl_2$ (25 mL) and filtered. The filtrate was washed with aqueous citric acid (10%) and saturated $NaHCO_3$ (25 mL each), dried ($Na_2SO_4$) and evaporated. The intermediate pinanediol N-{N-methyl-N-[(3-phenyl)propionyl]glycyl}-1-amido-5-bromopentaneboronate (0.75 g, 92% yield) was carried on to the next step without further purification.

Part B:

The intermediate from Part A (0.75 g, 1.4 mmol) was heated with sodium azide ($NaN_3$, 0.15 g, 2.3 mmol) in N,N-dimethylformamide (DMF, 10 mL) at 100° C. for 2 hours. The reaction mixture was partitioned between water ($H_2O$) and EtOAc (25 mL each), and the EtOAc layer was washed with additional $H_2O$ (6×15 mL). The organic layer was dried ($Na_2SO_4$) and evaporated to give pinanediol N-{N-methyl-N-[(3-phenyl)propionyl]glycyl}-1-amido-5-azidopentaneboronate (0.67 g) in 95% yield.

Part C:

The azide from Part B (0.48 g, 0.9 mmol) was dissolved in methanol (MeOH, 15 mL) with benzenesulfonic acid (0.15 g, 0.9 mmol) and Pearlman's catalyst (palladium hydroxide on carbon, 0.05 g). This mixture was shaken under an atmosphere of 50 psi of hydrogen for 18 hours at ambient temperature. The reaction mixture was purged with nitrogen and the catalyst was removed by filtration through a pad of diatomaceous earth. The clear filtrate was evaporated and pinanediol N-{N-methyl-N-[(3-phenyl)propionyl]glycyl}-1-amido-5-aminopentaneboronate was obtained as its benzenesulfonate salt (0.51 g) in 88% yield. High Res Mass Spec: found $(M+H)^+$484.334758; calculated $(M+H)^+$=484.334663.

INTERMEDIATE 2

N-[(2-Phenyl)ethyl]-N-[(3-phenyl)propionyl]glycine

Part A:

A mixture of benzyl glycinate, p-toluenesulfonic acid salt (2.68 g, 7.94 mmol), (2-phenyl)bromoethane (0.98 g, 5.29 mmol), and solid $NaHCO_3$ (1.56 g, 18.5 mmol) in acetonitrile (25 mL) were heated at reflux for 18 hour. The reaction was concentrated and diluted with EtOAc (25 mL). The organic solution was washed with $H_2O$ (25 mL) and brine (25 mL), dried ($Na_2SO_4$) and concentrated in vacuo. The residue was purified by elution through a pad of silica gel with a gradient mixture of hexane:EtOAc. The intermediate benzyl N-[(2-phenyl)ethyl]-glycinate (0.82 g) was obtained in 38% yield. Low Res MS: $(M+H)^+$=270.

Part B:

A mixture of intermediate from Part A (0.82 g, 3.04 mmol) and 4-methylmorpholine (0.62 g, 6.08 mmol) in THF (15 mL) at 0° C. was added hydrocinnamoyl chloride (0.51 g, 3.04 mmol). The reaction was thawed to ambient temperature and stirred for 1 hour. The reaction mixture was diluted with EtOAc (50 mL), washed with HCl (10%, 25 mL) and $NaHCO_3$ (saturated, 25 mL), dried ($MgSO_4$) and evaporated. The intermediate benzyl N-[(2-phenyl)ethyl]-N-[(3-phenyl)-propionyl]glycinate (1.2 g) prepared was used in the next procedure without further purification. LRMS: $(M+NH_3)^+$=419.0, $(M+H)^+$=402.1.

Part B

A methanol solution (20 mL) of benzyl N-[(2-phenyl)ethyl]-N-[(3-phenyl)propionyl]glycinate (1.3 g, 3.24 mmol) and palladium on carbon (10%, 180 mg) was stirred under 1 atmosphere of hydrogen gas for 18 hours. The reaction was purged with nitrogen and filtered through a pad of diatomaceous earth and evaporated to give N-[(2-phenyl)ethyl]-N-[(3-phenyl)propionyl]glycine (1.0 g) in quantitative yield. LRMS: $(M+NH_3)^+$=326.

EXAMPLE 23.1.3

Pinanediol N-{N-[(2-phenyl)ethyl]-N-[(3-phenyl) propionyl]glycyl}-1-amido-5- aminopentaneboronate, hydrochloride salt Part A:

To a solution of N-[(2-phenyl)ethyl]-N-[(3-phenyl) propionyl]glycine (1.0 g 3.24 mmol) and 4-methylmorpholine (0.66 g, 6.48 mmol) in THF (15 mL) at 0° C. was added isobutylchloroformate (0.44 g, 3.24 mmol). The reaction was stirred for 15 min at 0° C. , pinanediol 1-amino-5-bromopentaneboronate (1.23 g, 3.24 mmol) was added followed by additional 4-methylmorpholine (0.33 g, 3.24 mmol)and the reaction was stirred at ambient temperature for 18 hours. The reaction was diluted with EtOAc (50 mL), washed sequentially with HCl (10%) and NaHCO$_3$ (saturated) and brine (25 mL each), then dried over magnesium sulfate (MgSO$_4$) and evaporated. The residue was purified by flash chromatography (silica gel) using 3:1 EtOAc:hexane to give pinanediol N-{N-[(2-phenyl)ethyl]-N-[(3-phenyl)propionyl]glycyl}-1-amido-5-bromopentaneboronate (0.8 g) in 43% yield. LRMS: (M+H)$^+$=637/638, (M-HBr)$^+$=557.

Part B:

The intermediate pinanediol N-{N-[(2-phenyl)ethyl]-N-[(3-phenyl)propionyl]glycyl}-1-amido-5-bromopentaneboronate (0.8 g, 1.4 mmol) and NaN$_3$ (0.11 g, 1.7 mmol) in DMF (10 mL) was stirred at 100° C. for 2 h. The cooled reaction mixture was diluted with EtOAc (50 mL), then it was washed with H$_2$O (6×20 mL) and dried (MgSO$_4$). The EtOAc solution was evaporated to give pinanediol N-{N-[(2-phenyl)ethyl]-N-[(3-phenyl) propionyl]glycyl}-1-amido-5-azidopentaneboronate (0.7 g) in 86% yield. LRMS: (M+H)$^+$=600.

Part C:

A mixture of the product from Part B (0.7 g, 1.2 mmol) and Pearlman's catalyst (0.1 g) in HCl (1.2 N, 1 mL, 1.2 mmol) and MeOH (20 mL) was stirred under an atmosphere of hydrogen (1 atm) for 2 hours. The reaction mixture was purged with nitrogen, filtered through a pad of diatomaceous earth and evaporated. The residue was dried by azeotropic distillation with benzene and triturated with hexane to give the title compound (0.45 g) as a yellow powder in 67% yield. LRMS: (M+H)$^+$=574.4.

EXAMPLE 8.1.3

N-{N-[(2-Phenyl)ethyl]-N-[(3-phenyl)propionyl] glycyl}-1-amido-5-aminopentaneboronic acid, hydrogen chloride salt A mixture of Example 23.1.3 (0.45 g, 0.8 mmol) in diethyl ether(Et$_2$O): H$_2$O (15 mL:15 mL) was stirred with phenylboric acid (0.45 g, 3.7 mmol) at ambient temperature for 18 hours. The phases were separated, the Et$_2$O layer was discarded, and the H$_2$O layer was washed with Et$_2$O (15 mL) and 1:1 hexane:EtOAc (15 mL). The H$_2$O solution was concentrated by distillation under reduced pressure and dried by azeotropic distillation with toluene. The dried residue was dissolved in a minimal amount of CH$_2$Cl$_2$ and the title compound was precipitated from solution by the addition of hexane. LRMS: (M+H of glycerol ester)$^+$=496.

INTERMEDIATE 3

N-methyl-N-[(3,4-dichlorophenyl)acetyl]glycine

The title compound was prepared from commercially available sarcosine ethyl ester and 3,4-dichlorophenylacetic acid according to the procedure of Intermediate 1.

EXAMPLE 50

Pinanediol N-{N-methyl-N-[(3,4-dichlorophenyl) acetyl]glycyl}-1-amido-4- formamidinobutaneboronate, hydrochloride salt Part A:

By substituting pinanediol 1-amino-4-bromobutaneboronate for pinanediol 1-amino-5-bromopentaneboronate and coupling with Intermediate 3 according to the procedure in Example 21.1.3, Parts A–C, the amino intermediate was prepared.

Part B:

To an ethanol solution (20 mL) of the product from Part A (600 mg, 1.2 mmol) was added ethylformimidate hydrogen chloride (400 mg, 3.62 mmol) and 4-dimethylamino pyridine (DMAP, 442 mg, 3.62 mmol). This mixture was heated at reflux for 5 hours, and the reaction mixture was evaporated. The residue was chromatographed (Sephedex LH 20, MeOH elutant) to give the title compound as a yellow solid. LRMS: (M+H)$^+$=551.

EXAMPLE 51

Pinanediol N-{N-methyl-N-[(3,4-dichlorophenyl) acetyl]glycyl}-1-amido-4-guanidinobutaneboronate, hydrochloride salt Part A:

The intermediate from Example 50, Part A hydrochloride salt (1.0 g, 2 mmol), formamidine sulfonic acid (0.496 g, 4 mmol) and DMAP (0.488 g, 4 mmol) in ethanol (50 mL) were heated at reflux for 3 hours. The reaction was cooled to ambient temperature, filtered through a pad of Celite, rinsed with chloroform (CHCl$_3$) and evaporated. The residue was dissolved in CHCl$_3$ and washed with HCl (0.1 N) and brine, dried and evaporated. The title compound was obtained as a white solid. HRMS calcd for C$_{26}$H$_{39}$BN$_5$O$_4$Cl$_2$:582.247216$^+$; found: 566.247905.

INTERMEDIATE 4

Pinanediol 1-amino-2-(3-cyanophenyl) ethylboronate, hydrochloride salt

Part A:

The intermediate, Cl-CH[CH$_2$-(m-cyanophenyl)]BO$_2$—C$_{10}$H$_{16}$, was prepared from m-cyanobenzyl bromide and dichloromethyl boronate pinanediol. Zinc dust (1.0 g) in THF (1 mL) was cooled to 0–5° C. and a solution of m-cyanobenzyl bromide (1.37 g, 7.0 mmol) in THF (7 mL) was added dropwise (5 sec/drop). The reaction mixture was allowed to stir at 5° C. for 2 hours. A mixture consisting of lithium bromide (LiBr, 1.22 g, 14 mmol), copper(I) cyanide (CuCN, 0.63 g, 7.0 mmol) and THF (6 mL) was placed in a 50 mL flask and cooled to −40° C.; the benzylic organozinc reagent was added by cannulation. The mixture was allowed to warm to −20° C. and stir for 5 minutes. Following cooling to −78° C., neat dichloromethyl boronic acid pinanediol (1.47 g, 5.6 mmol) was added dropwise and the resulting mixture was stirred at −78° C. for 2 h, and additionally at room temperature for 2 days. Aqueous ammonium chloride (NH$_4$Cl, saturated, 20 mL) was added to the mixture and the aqueous solution was extracted with Et$_2$O (3×20 mL). The combined organic layers was dried over anhydrous MgSO$_4$ and evaporated in vacuo to give crude compound (1.8 g). Purification was carried out using silica gel chromatography where the column was stepwise eluted with hexane (100 mL) and then 15% ether in hexane (200 mL) to give the desired product (0.53 g) in 27% yield. LRMS(NH$_3$-CI) m/e for M+NH$_4^+$ calcd. for C$_{19}$H$_{23}$NO$_2$BCl: 361.2; found: 361.1.

Part B:

To a solution of hexamethyldisilazane (0.21 mL, 0.98 mmol) in THF (2 mL) at −78° C. was added n-butyllithium (1.45 M, 0.67 mL, 0.98 mmol). The solution was allowed to slowly warm to room temperature to ensure the anion generation was complete and recooled to −78° C., upon which a solution of product from Part A (0.33 g, 0.98 mmol) in THF (2 mL) was added. The mixture was allowed to warm to room temperature and to stir overnight. The volatiles were evaporated and hexane (8 mL) was added to give a suspension. Anhydrous hydrogen chloride in dioxane (4.1 N, 1.5 mL, 6.0 mmol) was added at −78° C. and the mixture was slowly warmed to room temperature and stirred for 2 hour. Additional hexane (6 mL) was added and crude product was isolated as a precipitate. This product was dissolved in $CHCl_3$ and insoluble material was removed by filtration. The filtrate was evaporated at a reduced pressure to give an oil (~0.2 g). Final purification was achieved by chromatography on a column of Sephedex™ LH 20 column using MeOH as a solvent. H-boroPhe(m-CN)—CiOH$_{16}$•HCl was obtained as an oil (0.12 g) in 34% yield. HRMS($NH_3$-CI) m/e (M+H)$^+$ calcd. for $C_{19}H_{26}BN_2O_2$: 325.2087; found: 325.2094.

EXAMPLE 52

Pinanediol N-{N-methyl-N-[(3,4-dichlorophenyl) acetyl]glycyl}-1-amido-2-(3-cyanophenyl) ethylboronate Part A:

To Intermediate 3 (0.77 g, 2.8 mmol) and 4-methylmorpholine (0.28 g, 2.8 mmol) in THF (50 mL) at −20° C. was added isobutylchloroformate (0.38 g, 2.8 mmol). After 20 minutes at −20° C., the cold solution was added to a −20° C. solution of Intermediate 4 (1.0 g, 2.8 mmol) and $Et_3N$ (0.28 g, 2.8 mmol) in $CHCl_3$ (50 mL), This mixture was maintained at −20° C. for 5 hours and stirred at ambient temperature for 18 hours. The reaction was filtered and concentrated in vacuo. The residue was dissolved in EtOAc, washed with HCl (0.1N), saturated $NaHCO_3$ and brine. After the solution was dried and evaporated, the resulting yellow solid was applied to a column of Florisil and the desired product eluted with a gradient of $CHCl_3$: MeOH (0% MeOH to 7% MeOH). The title compound was obtained as a white solid. HRMS: calcd. (M+H)$^+$ for $C_{30}H_{35}BN_3O_4Cl_2$: 582.209768; found: 582.209631.

EXAMPLE 53

Pinanediol N-{N-methyl-N-[(3-phenyl)propionyl] glycyl}-1-amido-4-(N-methylguanidino) butylboronate, hydrochloride salt Part A:

Pinanediol N-{A-methyl-N-[(3-phenyl)propionyl] glycyl}-1-amido-4-aminobutylboronate, hydrochloride salt was prepared by the method outlined for Example 21.1.3, wherein pinanediol 1-amino-4-bromobutylboronate hydrochloride was used instead of pinanediol 1-amino-5-bromopentane-boronate hydrochloride.

Part B:

To a solution of the product from Part A (0.45 g, 0.89 mmol) in ethanol (10 mL) was added DMAP (0.22 g, 1.78 mmol)). After 15 minutes at room temperature, N-methylaminoiminomethanesulfonic acid (0.25 g, 1.78 mmol) was added and the resulting suspension stirred at reflux for 5 hours. The reaction was cooled to room temperature, filtered, the precipitate washed with $CHCl_3$ and the combined filtrate concentrated under vacuum. The resulting oil was dissolved in $CHCl_3$ (40 mL) and the organic solution washed with ice cold HCl (0.1 M, 1×10 mL), ice cold $H_2O$ (1×10 mL), brine and dried ($MgSO_4$). The filtered solution was concentrated in vacuc to give of the desired N-methyl guanidino compound (0.35 g) in 70% yield. The material was purified through a florisil column using 10% MeOH/$CHCl_3$ as eluant to give the purified product (0.22 g); LRMS: (M+H)$^+$: 526.

EXAMPLE 54

Ac-(D)Phe-Sar-boroLys—OH

Part A:

Boc-(D)Phe—OH (6.9 g, 26 mmoles)was dissolved in THF (50 mL) and 4-methylmorpholine (2.86 mL, 26 mmoles) was added. The solution was cooled to −20° C. and isobutylchloroformate (3.38 ml, 26 mmoles) was added. After stirring 5 minutes at −20° C., the mixture was added to a cold solution of H-Sar-Bzl•toluenesulfonic acid dissolved in $CHCl_3$ (50 mL), followed by $Et_3N$ (3.6 mL, 26 mmoles). The mixture was allowed to stir for 1 hour at −20° C. and 2 h at room temperature. The solids were removed by filtration and the solvent was removed by evaporation. The residue was dissolved in EtOAc and was washed with HCl (0.20 N), $NaHCO_3$ (5%), and brine. The solution was dried over anhydrous $Na_2SO_4$, filtered, and evaporated to yield Boc-(D)Phe-Sar-O-Bzl as thick oil (10.4 g).

Part B:

The product from Part A (10.4 g) was dissolved in MeOH (100 mL) and the sample was hydrogenated for 2 hour on a Parr apparatus in the presence of palladium on carbon (10%, 0.5 g). The catalysis was removed by filtration and solvent was evaporated to yield Boc-(D)Phe-Sar—OH as a foam (7.8 g).

Part C:

The mixed anhydride of product from Part B (4.42 g, 13.1 mmoles) was prepared as previously described and coupled to $NH_2$—CH[($CH_2$)$_4$Br]$BO_2C_{10}H_{16}$•HCl (5.0 g, 13.1 mmoles) using the procedure described in Part A. The crude product (7.7 g) was purified by chromatography of a 4.2 g portion on a 2.5×100 cm column of Sephedex LH-20 using MeOH as a solvent to give Boc-(D)Phe-Sar—NH—CH[($CH_2$)$_4$-Br]$BO_2C_{10}H_{16}$.

Part D:

The product from Part C(3.5 g, 5.8 mmoles) was dissolved in anhydrous HCl in dioxane (4.1 N, 50 mL) and was stirred for 1 hour at room temperature. Solvent and excess HCl were removed by evaporation. The residue was triturated with hexane to yield H-(D)Phe-Sar—NH—CH[($CH_2$)$_4$-Br]$BO_2C_{10}H_{16}$•HCl (2.9 g).

Part E:

The product from Part D (2.9 g, 4.8 mmoles) was dissolved in 30 mL of a 50% (v/v) solution of dioxane: water and acetic anhydride (0.92 ml, 9.7 mmoles) was added. $NaHCO_3$ (0.81 g, 9.7 mmoles) was added and the solution was allowed to stir 45 minutes at room temperature. Acetic acid (3 ml) was added and solution was concentrated approximately 50% by evaporation. It was diluted to 100 mL with EtOAc and was washed with $NaHCO_3$ (5%), HCl (0.2 N), and brine. The organic phase was dried over anhydrous $Na_2SO_4$, filtered, and evaporated to yield Ac-(D)Phe-Sar—NH—CH[($CH_2$)$_4$-Br]$BO_2C_{10}H_{16}$ as a foam (2.7 g). HRMS calcd for $C_{29}H_{43}N_3O_5BBr$ (M+H): 604.2557; found: 604.2558.

Part F:

The product from Part E (2.5 g, 4.1 mmoles) and $NaN_3$ (0.54 g, 8.3 mmoles) were dissolved in DMF (5 mL) and heated at 100° C. for 1 hour. The reaction was allowed to cool and was diluted with EtOAc (100 mL). The organic phase was washed with H$_2$O and saturated brine, dried over Na$_2$SO$_4$, filtered, and evaporated to yield Ac-(D)Phe-Sar—NH—CH[(CH$_2$)$_4$-N$_3$]BO$_2$C$_{10}$H$_{16}$ as a white foam (2.2 g).
Part G:

The product from Part F (2.0 g, 3.5 mmoles) was dissolved in MeOH (100 mL) arid was hydrogenated on a Parr apparatus in the presence of HCl in dioxane (4.1 N, 1.3 ml, 5.3 mmoles) and palladium on carbon (10%, 0.5 g). The catalysis was removed by filtration and solvent was removed by evaporation. The product, Ac-(D)Phe-Pro-boroLys—C$_{10}$H$_{16}$•HCl (Ac-(D)Phe-Sar—NH—CH[(CH$_2$)$_4$—NH$_2$]BO$_2$C$_{10}$H$_{16}$•HCl), was purified by chromatography on 2.5× 100 cm column of LH-20 in MeOH to yield 1.8 g.
Part H:

The product from Part G (1.5 g, 2.5 mmoles) and phenyl boronic acid (1.5 g, 12 mmoles) was dissolved in H$_2$O and Et$_2$O (15 ml each). The mixture was stoppered and allowed to stir for 3 hour at room temperature. The phases were separated and the aqueous phase was washed extensively with Et$_2$O. The aqueous phase was evaporated, dried in vacuo., and triturated with Et$_2$O to yield the title compound (0.98 g). An analytical sample was prepared as the pinacol ester by treating 4 mg of the boronic acid with 2 equivalents of pinacol in 1.4 ml of MeOH for 5 minutes and evaporating solvent. HRMS calcd for the pinacol ester C$_{25}$H$_{41}$N$_4$O$_5$B (M+H): 489.3248. found: 489.3242.

EXAMPLE 55

Pinanediol N-{N-2-propyl-N-[(3-phenyl)propionyl] glycyl}-1-amido-5-aminopentaneboronate, hydrochloride salt Part A: A mixture of glycine methyl ester hydrochloride (3.83 g, 30.5 mmol), acetone (1.77 g, 30.5 mmol) and NaOH (1.22 g, 30.5 mmol) in MeOH (200 mL) was stirred under an atmosphere of hydrogen (1 atm) in the presence of palladium on carbon (10%, 0.4 g) for 24 hours. The reaction was flushed with nitrogen and filtered through a Celite pad, acidified with HCl (1N), dried (MgSO$_4$) and evaporated. Trituration of the residue with Et$_2$O gave N-2-propylglycine methyl ester hydrochloride (1.0 g) as an off-white solid; LRMS (M+H)$^+$=132.1.
Part B:

To the hydrochloride salt prepared above (1.0 g, 5.97 mmol) and hydrocinnamic acid (0.9 g, 5.97 mmol) in DMF (20 mL) was added O-benzotriazole-N,N,N',N'-tetramethyluronium hexafluorophosphate (2.26 g, 5.97 mmol) followed by N,N-diisopropylethylamine (1.69 g, 13.1 mmol). The reaction was stirred at ambient temperature for 48 hours. The reaction mixture was diluted with 1:1 EtOAc:hexane and washed with H$_2$O (2×), HCl (10%) saturated NaHCO$_3$ and brine. The solution was dried (MgSO$_4$), evaporated, and combined with an additional material obtained by the same acylation procedure. The combined batches were purified by flash chromatography on silica gel with 2:1 hexane:EtOAc as the eluent. There was obtained N-2-propyl-N-[(3-phenyl)propionyl]glycine methyl ester (2.8 g); LRMS (M+H)$^+$=264.0.
Part C:

A mixture of the ester from Part B (2.8 g, 10.52 mmol) and LiOH monohydrate in THF:H$_2$O (20 mL:10 mL) was stirred at ambient temperature for 18 hours. The reaction was diluted with H$_2$O and washed with 1:1 hexane:EtOAc and the organic washings were discarded. The aqueous layer was acidified with HCl (10%) and extracted with EtOAc. The EtOAc extract was washed with brine, dried (MgSO$_4$) and evaporated to give N-2-propyl-N-[(3-phenyl)propionyl] glycine (2.0 g); LRMS (M+H)$^+$=250.1.

Part D:

N-2-propyl-N-[(3-phenyl)propionyl]glycine was reacted with pinanediol 1-amino-5-bromopentaneboronate according to the procedure of Example 23.1.3 to prepare pinanediol N-{N-2-isopropyl-N-[(3-phenyl)propionyl]glycyl}-1-amido-5-bromopentaneboronate; LRMS (M+H)$^+$=575/577.
Part E–F:

This material was reacted with NaN$_3$ according to the procedure in Example 23.1.3 to give pinanediol N-{N-2-isopropyl-N-[(3-phenyl)propionyl]glycyl}-1-amido-5-azidopentaneboronate; LRMS (M+H)$^+$=538.3. The azide was hydrogenated under the conditions in Example 23.1.3 to give the title compound, pinanediol N-{N-2-propyl-N-[(3-phenyl)propionyl]-glycyl}-1-amido-5-aminopentaneboronate hydrochloride; LRMS (M+H)$^+$=512.

EXAMPLE 56

N-{N-2-propyl-N-[(3-phenyl)propionyl]glycyl}-1-amido-5-aminopentaneboronic acid, hydrochloride salt Part A:

N-{N-2-propyl-N-[(3-phenyl)propionyl]glycyl}-1-amido-5-aminopentane-boronic acid, hydrochloride salt, was prepared from pinanediol N-{N-2-propyl-N-[(3-phenyl)propionyl]glycyl}-1-amido-5-aminopentaneboronate, hydrochloride salt by the procedure of Example 8.1.3; LRMS (M+H–H$_2$O)$^+$=360.1, (M+H–2H$_2$O)+342.0.

EXAMPLE 57

Pinanediol N-{N-methyl-N-[2-(methylphenyl) benzoyl]glycyl}-1-amido-5-aminopentaneboronate, hydrochloride salt Part A:

A mixture of 2-(methylphenyl)benzoic acid (3.09 g, 14.55 mmol), sarcosine ethyl ester hydrochloride salt (2.23 g, 14.55 mmol), DCC (3.0 g, 14.55 mmol), HOBT (1.97 g, 14.55 mmol) and Et$_3$N (1.47 g, 14.55 mmol) in THF (50 mL) were stirred at ambient temperature for 48 hours. The reaction was evaporated and the residue dissolved in EtOAc. The EtOAc solution was washed with HCl (10%), saturated NaHCO$_3$ and brine, and dried (MgSO$_4$). The EtOAc solution was filtered through a plug of silica gel follwoed by a second filtration through a plug of neutral alumina. Evaporation of the solution gave N-methyl-N-[2-(methylphenyl) benzoyl]glycine ethyl ester (4.5 g); LRMS (M+H)$^+$=312.2.
Part B:

N-methyl-N-[2-(methylphenyl)benzoyl]glycine ethyl ester (4.5 g, 14.45 mmol) and KOH (2.43 g, 43.4 mmol) in MeOH/H$_2$O (200 mL/50 mL) were heated at reflux for 45 minutes. The solvent was removed and the residue dissolved in H$_2$O. The aqueous solution was washed with Et$_2$O and acidified with HCl (10%). The acidified aqueous layer was extracted with EtOAc, the EtOAc extract was washed with brine (2×), dried over (MgSO$_4$) and evaporated. There was obtained N-methyl-N-[2-(methylphenyl)benzoyl]glycine (2.0 g); LRMS (M+H)+=284.1, (M+NH$_4$)+=301.1
Part C–E:

Pinanediol N-{N-methyl-N-[2-(methylphenyl)benzoyl] glycyl}-1-amido-5-bromopentaneboronate was prepared by reaction of N-methyl-N-[2-(methylphenyl)benzoyl]glycine with pinanediol 1-amino-5-bromopentaneboronate according to the procedure of Example 23.1.3; LRMS (M+H)+= 611.2. Pinanediol N-{N-methyl-N-[2-(methylphenyl) benzoyl]glycyl}-1-amido-5-bromopentaneboronate was reacted withe NaN$_3$ by under the conditions detailed above to give pinanediol N-{N-methyl-N-[2-(methylphenyl)

benzoyl]glycyl}-1-amido-5-azidopentaneboronate; LRMS (M+H)+=572.4. Hydrogenation of the azide was effected by the conditions previously described to give the title compound, pinanediol N-{N-methyl-N-[2-(methylphenyl) benzoyl]glycyl}-1-amido-5-amino-pentaneboronate, hydrochloride acid salt; LRMS (M+H)+=546.3.

EXAMPLE 35.5.3

Part A:

Trimethylsilyl cyanide (5.80 mL, 44.0 mmol) was added dropwise to a solution of benzaldehyde (3.10 g, 29.0 mmol) and zinc iodide (280 mg, 8.80 mmol) at 0° C. The reaction mixture was warmed to room temperature over 18 h then treated with saturated aqueous $NaHCO_3$ (Ca. 100 mL). The layers were separated and the aqueous was extracted with EtOAc (2×75 mL). The combined organics were washed with saturated aqueous NaCl (1×50 mL), dried ($Na_2SO_4$), and concentrated under reduced pressure to give 3.78 g of 2-[(trimethylsilyl)oxy]-phenylacetonitrile as an oil, which was carried on without purification.

Lithium aluminum hydride (2.10 g, 55.0 mmol) was added in portions over 15 min to a solution of [2-(trimethylsilyl)oxy]-phenylacetonitrile (3.75 g, 18.3 mmol) in anhydrous THF (75 mL) at 0° C. The reaction was quenched by the sequential addition of $H_2O$ (2.10 mL), 10% aqueous NaOH (2.10 mL), and $H_2O$ (6.30 mL) then dried ($Na_2SO_4$) and filtered through a pad of Celite using EtOAc (ca. 75 mL). The filtrate was concentrated under reduced pressure to provide an oil which was purified by flash chromatography, elution with 9:1 $CH_2Cl_2$-MeOH containing 2% $Et_3N$, to give 2-hydroxy-1-phenethylamine (2.40 g) as an oil in 95% yield. ($^1$H NMR, 300 MHz) d 7.32 (comp, 5H), 4.66 (dd, 1H, J=7.8, 4.0 Hz), 3.03 (dd, 1H, J=12.5, 4.0 Hz). 2.83 (dd, 1H, J=12.5, 9.1 Hz), 2.46 (br s, 3H). LRMS 155 (M+NH$_4$), 138 (M+H).

Part B:

Phosgene (6.0 mL of a 1.93 M solution in toluene (PhCH$_3$), 12.0 mmol) was added to a solution of 2-hydroxy-1-phenethylamine (1.18 g, 8.60 mmol) in PhCH$_3$ (100 mL) at 0° C. followed by the dropwise additon of Et$_3$N (1.80 mL, 13.0 mmol). The reaction mixture was warmed to room temperature over 48 h and poured into EtOAc (ca. 200 mL). The layers were separated and the aqueous was extracted with EtOAc (1×50 mL). The combined organics were washed with saturated aqueous NaCl (1×100 mL), dried (Na$_2$SO$_4$) and concentrated under reduced pressure to give 5-phenyl-2-oxazolidinone (1.05 g) as a solid in 75% yield. ($^1$H NMR, 300 MHz) d 7.39 (comp, 5H), 5.69 (br s, 1H), 5.63 (dd, 1H, J=8.4, 8.1 Hz), 3.99 (dd, 1H, J=8.4, 8.1 Hz), 3.55 (dd, 1H, J=8.4, 8.1 Hz). LRMS 181 (M+NH$_4$), 164 (M+H).

Part C:

A solution of 5-phenyl-2-oxazolidinone (500 mg, 3.1 mmol) in anhydrous THF was added dropwise to a suspension of NaH (91 mg, 3.7 mmol) in anhydrous THF at 0° C. The reaction mixture was warmed to room temperature over 30 min then heated at reflux for 15 min. Methyl bromoacetate (0.32 mL, 3.4 mmol) was added and the mixtue was heated at reflux for 2 h. The reaction mixture was cooled to room temperature and quenched with H$_2$O (ca. 20 mL). The aqueous was extracted with EtOAc (2×75 mL). The combined organics were washed with saturated aqueous NaCl (1×50 mL), dried (MgSO$_4$), and concentrated under reduced pressure to give an oil which was purified by flash chromatography, elution with 3:1 EtOAc-hexanes, to provide 2-[3-(5-phenyl-2-oxazolidino)]-acetic acid, methyl ester (545 mg) as an oil in 76% yield. ($^1$H NMR, 300 MHz) d 7.42 (comp, 5H), 5.56 (dd, 1H, J=8.4, 8.1 Hz), 4.10 (d, 2H, J=3.0 Hz), 4.06 (dd, 1H, J=8.4, 8.1 Hz), 3.78 (s, 3H), 3.64 (dd, 1H, J=8.4, 8.1 Hz). LRMS 253 (M+NH$_4$, base), 236 (M+H).

Part D:

A solution of 2-[3-(5-phenyl-2-oxazolidino)]acetic acid, methyl ester (540 mg, 2.30 mmol) in MeOH (10 mL) and H$_2$O (10 mL) was treated with NaOH (138 mg, 3.40 mmol) and heated at reflux for 15 min. The reaction mixture was cooled to room temperature, acidified to pH 2 with 2M aqueous HCl, and extracted with EtOAc (3×50 mL). The combined organics were washed with saturated aqueous NaCl (1×25 mL), dried (MgSO$_4$), and concentrated to give 2-[3-(5-Phenyl-2-oxazolidino)]acetic Acid (505 mg) as an oil in 99% yield. ($^1$H NMR, 300 MHz) d 7.41 (comp, 5H), 5.57 (dd, 1H, J=8.0, 8.0 Hz), 4.15 (s, 2H), 4.05 (dd, 1H, J=8.0, 8.0 Hz), 3.65 (dd, 1H, J=8.0, 8.0 Hz). LRMS 239 (M+NH$_4$, base), 222 (M+H).

Part E:

Triethylamine (0.23 mL, 1.60 mmol) was added to a mixture of (2R)-4-bromo-1-aminobutane-1-boronic acid, (+)-pinanediol ester hydrochloride (540 mg, 1.47 mmol), HOBT (200 mg, 1.47 mmol), DCC (300 mg, 1.47 mmol), and 2-[3-(5-phenyl-2-oxazolidino)]acetic acid (325 mg, 1.47 mmol) in anhydrous THF (12 mL) and anhydrous DMF (3 mL) at 0° C. The reaction mixture was warmed to room temperature over 18 h, diluted with Et$_2$O (ca. 30 mL), and filtered through Celite with additional Et$_2$O (ca. 50 mL). The filtrate was washed with H$_2$O (3×25 mL), saturated aqueous NaCl (1×25 mL), dried (Na$_2$SO$_4$), and concentrated under reduced pressure to give (2R)-2-[[3-(5-phenyl-2-oxazolidino)]-acetamido]-4-bromo-1-aminobutane-1-boronic acid, (+)-pinanediol ester (770 mg) as a foam in 98% yield. LRMS 535, 533 (M+H)$_{453}$ (base).

Part F:

A solution of (2R)-2-[[3-(5-phenyl-2-oxazolidino)]-acetamido]-4-bromo-1-aminobutane-1-boronic acid, (+)-pinanediol ester (770 mg, 1.45 mmol) and thiourea (220 mg, 2.90 mmol) in EtOH (15 mL) was heated at reflux for 36 hours then cooled to room temperature and diluted with Et$_2$O (ca. 100 mL) which was decanted. The residue was purified by size exclusion chromatography on Sephadex LH-20, elution with MeOH, to give a foam. The foam was dissolved in 5 mL of anhydrous THF and treated with Et$_2$O (ca. 30 mL) to give a solid that was washed with Et$_2$O (ca. 10 mL) and dried to afford the title compound (180 mg) as a white powder in 21% yield, mp 93–96° C. LRMS 529 (M+1, base); HRMS Calcd for C$_{26}$H$_{38}$BN$_4$O$_5$S: 529.2656. Found: 529.2644.

EXAMPLE 35.6.2

A solution of (2R)-2-[[3-(5-phenethyl-2-oxazolidino)]-acetamido]-4-bromo-1-aminobutane-1-boronic acid, (+)-pinanediol ester (710 mg, 1.27 mmol) was prepared by an analogous method to that reported for Example 35.5.3, however substituting hydrocinnamaldehyde for benzaldehyde. Further reaction with thiourea (190 mg, 2.50 mmol) in EtOH (13 mL) was heated at reflux for 36 h then cooled to room temperature and diluted with Et$_2$O (ca. 200 mL) which was decanted. The residue was purified by size exclusion chromatography on Sephadex LH-20, elution with MeOH, to give a foam. The foam was dissolved in 5 mL of anhydrous THF and treated with Et$_2$O (ca. 40 mL) to give a solid that was washed with Et$_2$O (ca. 10 mL) and dried to afford the title compound (150 mg) as a white powder in 19% yield, mp 93–96° C. LRMS 557 (M+H, base); HRMS Calcd for C$_{28}$H$_{42}$BN$_4$O$_5$S: 557.2969. Found: 557.2965.

EXAMPLE 59

Part A:

A mixture of 1,8-napthalic anhydride (1.0 g, 5.1 mmol), glycine (0.42 g, 5.6 mmol) and camphorsulfonic acid (ca. 100 mg) was suspended in absolute EtOH (60 mL) and DMF (20 mL). The reaction mixture was heated at reflux for 72 h, then the solvent removed by distillation in vacuo. The residue was diluted with $H_2O$ (10 mL), acidified with HCl (1N) to pH=3 and the resulting solid was isolated by filtration and air dried. There was obtained N,N-(1,8-napthyldiimido)-glycine (1.22 g) in 95% yield. LRMS: $(M+H)^+$=256; mp 278–279° C.

An alternative to the above prepartion of N,N-(1,8-napthyldiimido)glycine would be to react the sodium salt of 1,8-napthalic phthalimide with ethyl bromoacetate in dimethylformamide at 60° C. The resulting ester can then be hydrolyzed with 1N sodium hydroxide in ethanol solution to give the title compound.

Part B:

N,N-(1,8-Napthyldiimido)glycine (0.56 g, 2.1 mmol) and N-methylmorpholine (0.53 mL, 4.82 mmol) were dissolved in THF (10 mL) and DMF (1 mL) then cooled to −20° C. Isobutylchloroformate (0.31 mL, 2.32 mmol) was added to the cold solution and the reaction was stirred at −20° C. for 20 min. After this time a THF suspension (5 mL) of pinanediol 1-amino-4-bromobutane-boronate hydrochloride salt (0.80 g, 2.19 mmol) was added to the mixture and the reaction was allowed to warm to room temperature over 3 h. The reaction was partitioned between $H_2O$ (10 mL) and EtOAc (15 mL). The organic layer was washed with $H_2O$ (3×15 mL), then with saturated $NaHCO_3$ (15 mL), and brine (15 mL). After the solution was dried ($MgSO_4$) and evaporated under reduced pressure, there was obtained pinanediol N-[N,N-(1,8-napthyl-diimido)glycyl]-1-amido-4-bromobutaneboronate (1.2 g) in 98% yield. LRMS: $(M+H)^+$=568.

Part C:

To a solution of pinanediol N-[N,N-(1,8-napthyldiimido)glycyl]-1-amido-4-bromobutaneboronate (1.0 g, 1.76 mmol) in MeOH (30 mL) was added thiourea (0.27 g, 3.53 mmol). The reaction mixture was heated at reflux for 4 h, then was allowed to cool to ambient temperature and the solvent was removed by distillation. The resulting viscous liquid was dissolved in a minimal amount of MeOH and passed through a short column (35 g, LH-20 Sephadex) by elution with MeOH. Product containing fractions were combined and concentrated in vacuo, then the resulting foam was dissolved in a minimal amount of MeOH and triturated with $Et_2O$. After solvent was decanted, the residue was rinsed with additional $Et_2O$ and placed under vacuum. There was obtained pinanediol N-[N,N-(1,8-napthyldiimido)glycyl]-1-amido-4-S-thiourylbutane-boronate hydrogen bromide (1.0 g) as an amorphous foam in 100% yield. LRMS: $(M+H)^+$=563.

Part D:

To a solution of pinanediol N-[N,N-(1,8-napthyldiimido)glycyl]-1-amido-4-bromobutaneboronate (1.21 g, 2.13 mmol) in DMF (10 mL) was added $NaN_3$ (0.28 g, 4.27 mmol). The reaction mixture was heated at 65° C. for 8 h, then it was allowed to cool to room temperature and partitioned between $H_2O$ (15 mL) and EtOAc (20 mL). The layers were separated and the organic phase was washed with $H_2O$ (3×20 mL) and brine (20 mL). This solution was dried ($MgSO_4$) and concentrated in vacuo to give pinanediol N-[N,N-(1,8-napthyldiimido)glycyl]-1-amido-4-azidobutaneboronate (0.92 g) in 82% yield. LRMS: $(M+H)^+$=530.

Part D:

A suspension of the azide prepared above (1.19 g, 2.25 mmol) and 10% Pd/C(100 mg) in MeOH (15 mL) was placed under an atmosphere of $H_2$ (1 atm). The reaction mixture was stirred at room temperature for 5 h, then purged with a stream of $N_2$. The catalyst was removed by filtration through a pad of diatomaceous earth and the filtrate was concentrated under reduced pressure to give pinanediol N-[N,N-(1,8-napthyldiimido)glycyl]-1-amido-4-aminobutaneboronate (1.1 g) in 85% yield. LRMS: $(M+H)^+$=504.

Part E:

To a solution of pinanediol N-[N,N-(1,8-napthyldiimido)glycyl]-1-amido-4-aminobutaneboronate (0.51 g, 1.01 mmol) in pyridine (10 mL) was added aminoiminomethanesulfonic acid (0.13 g, 1.01 mmol). The reaction mixture was heated at reflux for 4 h, then was concentrated in vacuo to give pinanediol N-[N,N-(1,8-napthyldiimido)glycyl]-1-amido-4-guanidinobutane-boronate sulfonic acid salt (0.21 g) in 35% yield.

Part F:

Pinanediol N-[N,N-(1,8-napthyldiimido)glycyl]-1-amido-4-guanidinobutane-boronate sulfonic acid salt (0.21 g, 0.35 mmol) was dissolved in MeOH (2 mL) and $Et_2O$ (10 mL). A single portion of phenylboric acid (0.21 g, 1.76 mmol) was added to the solution followed by $H_2O$ (10 mL) and this mixture was stirred for 15 h. The phases were separated and the aqueous layer was washed with $Et_2O$ (6×10 mL). The aqueous layer was concentrated in vacuo and the resulting residue was placed under vacuum to give N-[N,N-(1,8-napthyldiimido)-glycyl]-1-amido-4-guanidinobutane-boronic acid as the sulfonic acid salt (0.16 g) in quantitative yield The following compounds were prepared according to the methods outlined in the Synthesis and Experimental sections. Appropriate physical data to characterize the compounds are provided:

EXAMPLE 52.1.2

Hydrocinnamoyl-[N-(3-methylphenethyl)-Gly]-boroLys—OH hydrochloride salt

Part A. Preparation of 3-methylphenethyl bromide.

To a solution of 3-methylphenethyl alcohol (5.0 g, 36.7 mmol) in methylene chloride at 0° C. was added triphenylphosphine (10.6 g, 40.4 mmol) and carbon tetrabromide (13.4 g, 40.4 mmol). The mixture was allowed to stir with warming to 25° C. for 16 h. The solvent was removed in vacuo and the residue was taken up in ether and filtered through a pad of silica gel. The solvent was removed in vacuo to afford 7.0 g (95%) of the title bromide.

Part B. Preparation of N-(3-methylphenethyl)-Gly-OMe.

To a solution of 3-methylphenethyl bromide (7.0 g, 35.0 mmol) in acetonitrile was added glycine methyl ester hydrochloride (6.6 g, 52.5 mmol) and sodium bicarbonate (10.3 g, 122.5 mmol). The resulting mixture was allowed to stir at 80° C. for 16 h. The reaction mixture was allowed to cool to 25° C. and then was diluted with ethyl acetate. The mixture was washed with water and brine, dried ($MgSO_4$), and concentrated to afford the title compound. MS (CI): m/z 208 (M+H)+. Part C. Preparation of hydrocinnamoyl-[N-(3-methylphenethyl)-Gly]-OMe.

To a solution of N-(3-methylphenethyl)-Gly-OMe (3.15 g, 15.2 mmol) in THF at 0° C. was added N-methylmorpholine (3.34 mL, 30.4 mmol) and hydrocinnamoyl chloride (2.26 mL, 15.2 mmol). The mixture was allowed to stir with warming to 25° C. for 6 h. The solvent was removed in vacuo and the residue was taken up in ethyl acetate and washed with 10% aq HCl, sat'd aq $NaHCO_3$ and brine. The organic layer was dried (MgSO$_4$) and concentrated to afford 4.4 g (86%) of the title compound. MS (CI): m/z 340 (M+H)+.

Part D. Preparation of Hydrocinnamoyl-[N-(3-methylphenethyl)-Gly]—OMe.

To a solution of hydrocinnamoyl-[N-(3-methylphenethyl)-Gly]-OMe (4.4 g, 13.0 mmol) in 50 mL of 2:1 THF/H$_2$O was added lithium hydroxide monohydrate (0.65 g, 15.6 mmol). The reaction mixture was allowed to stir at 25° C. for 4 h and then the THF was removed in vacuo. The basic solution was extracted with 1:1 hexanes/ethyl acetate and the organic layer was discarded. The aqueous layer was acidified with concentrated HCl and then was extracted with ethyl acetate. The ethyl acetate layer was washed with brine, dried (MgSO$_4$) and concentrated to afford the title compound as a white solid. MS (CI): m/z 326 (M+H)+.

Part E. Preparation of Hydrocinnamoyl-[N-(3-methylphenethyl)-Gly]-boroLys—OH hydrochloride salt.

The carboxylic acid hydrocinnamoyl-[N-(3-methylphenethyl)-Gly]—OH was elaborated to the title compound according to the procedures described in Example 54. MS (ES): m/z 454.4 (M+H)+.

EXAMPLE 53.1.1

Hydrocinnamoyl-[N-(2,2-dimethyl)-phenethyl-Gly]-boroLys—OH hydrochloride salt

Part A. Preparation of Methyl 2,2-(dimethyl)-2-phenylacetate.

To a cooled (-78° C.) solution of methyl phenylacetate (1.0 g, 6.7 mmol) in THF was added methyl iodide (0.91 mL, 14.7 mmol) followed by potassium tert-butoxide (14.7 mL of a 1.0 M solution in THF, 14.7 mmol). The reaction mixture was allowed to stir while slowly warming to 25° C. After 1 h the reaction was quenched by addition of saturated aq NH$_4$Cl, diluted with ethyl acetate and washed with brine. The organics were dried (MgSO$_4$) and concentrated to afford 1.1 g (92%) of the title compound.

Part B. Preparation of 2,2-(Dimethyl)-2-phenylethyl alcohol.

To a cooled (0° C.) solution of 1M lithium aluminum hydride in ether (31.1 mL, 31.1 mmol) was added methyl 2,2-(dimethyl)-2-phenylacetate (5.54 g, 31.1 mmol) as a solution in ether. The reaction mixture was allowed to warm to 25° C. and was stirred for 3 h. The mixture was cooled to 0° C. and was quenched by slow sequential addition of 1.2 mL of water, 1.2 mL of 15% aq NaOH and 3.6 mL of water. The resulting slurry was stirred vigorously with warming to 25° C. for 1 h, and then was dried (MgSO$_4$), filtered and concentrated to afford 3.8 g (81%) of the title compound.

Part C. Preparation of 2,2-(Dimethyl)-2-phenylacetaldehyde.

To a solution of 2,2-(dimethyl)-2-phenylethyl alcohol (3.8 g, 25.1 mmol) in methylene chloride was added pyridinium chlorochromate (16.2 g, 75.3 mmol) and the resulting mixture was stirred vigorously at 25° C. for 4 h. The mixture was filtered through a pad of layered silica gel (bottom)/Celite/Florasil (top) and concentrated to the give the title aldehyde.

Part D. Preparation of N-(2,2-dimethyl)-phenethyl-Gly-OEt.

To a solution of glycine ethyl ester hydrochloride (1.7 g, 12.3 mmol) in methanol was added sodium cyanoborohydride (0.77 g, 12.3 mmol) and 2,2-(dimethyl)-2-phenylacetaldehyde (2.0 g, 13.5 mmol). Glacial acetic acid was added if necessary to maintain the pH at 5–6. The mixture was allowed to stir at 25° C. for 16 h. The reaction was quenched by addition of excess satd. aq. K$_2$CO$_3$ and then was diluted with ethyl acetate. The layers were separated and the organic layer was washed with brine (2×), dried (MgSO$_4$) and concentrated to afford 2.5 g (86%) of the title compound. MS (CI): m/z 236 (M+H)+.

Part E. Preparation of Hydrocinnamoyl-N-(2,2-dimethyl)-phenethyl-Gly-OEt.

To a cooled (0° C.) solution of N-(2,2-dimethyl)-phenethyl-Gly-OEt (2.4 g, 10.1 mmol) in THF was added N-methylmorpholine (2.22 mL, 20.2 mtnol) followed by hydrocinnamoyl chloride (1.50 mL, 10.1 mmol). The resulting solution was allowed to warm to 25° C. and was stirred for 3 h. The THF was removed in vacuo and the residue was taken up in ethyl acetate and washed with 10% aq HCl, satd. aq. NaHCO$_3$ and brine. The organics were dried (MgSO4) and concentrated. The residue was purified by silica gel flash chromatography (solvent gradient 7:1 hexanes/ethyl acetate to 3:1 hexanes/ethyl acetate) to afford 2.0 g (54%) of the title compound. MS (CI): m/z 368 (M+H)+.

Part F. Preparation of Hydrocinnamoyl-N-(2,2-dimethyl)-phenethyl-Gly—OH.

To a solution of hydrocinnamoyl-N-(2,2-dimethyl)-phenethyl-Gly-OEt (1.5 g, 4.1 mmol) in 25 mL of 1:1 methanol/water was added potassium hydroxide (0.34 g, 6.1 mmol). The reaction mixture was allowed to stir at reflux for 1 h and then was allowed to cool to 25° C. and the methanol was removed in vacuo. The basic aqueous solution was extracted with 1:1 hexanes/ethyl acetate and the organic layer was discarded. The aqueous layer was acidified with concentrated HCl and then was extracted with ethyl acetate. The ethyl acetate layer was washed with brine, dried (MgSO4) and concentrated to afford the title compound as a white solid. MS (CI): m/z 340 (M+H)+.

Part G. Preparation of Hydrocinnamoyl-[N-(2,2-dimethyl)-phenethyl-Gly]-boroLys—OH hydrochloride salt.

The carboxylic acid hydrocinnamoyl-N-(2,2-dimethyl)-phenethyl-Gly—OH was elaborated to the title compound according to the procedures described in Example 54. MS (ES): m/z 468.4 (M+H)+.

EXAMPLE 1.1.3

N-{N-methyl-N-[(3-phenyl)propionyl]glycyl}-1-amido-4-(guanidino)butylboronate, hydrochloride salt; LRMS (M+H, ethylene glycol ester)$^+$=404

EXAMPLE 6.1.1

N-{N-methyl-N-benzoylglycyl}-1-amido-5-aminopentaneboronate, hydrochloride salt; HRMS calcd: (M+H, ethylene glycol ester)$^+$=348.209462, obs.: (M+H, ethylene glycol ester)$^+$=348.208418

EXAMPLE 6.1.2

N-{N-methyl-N-[phenylacetyl]glycyl}-1-amido-5-aminopentaneboronic acid, hydrochloride salt; LRMS (M+H, ethylene glycol ester)$^+$=362

EXAMPLE 6.1.3

N-{N-methyl-N-[(3-phenyl)propionyl]glycyl}-1-amido-5-aminopentaneboronate; HRMS (M+H)$^+$ calcd: 376.240762, found: 376.240727

EXAMPLE 9.1.2

N-{N-phenyl-N-[phenylacetyl]glycyl}-1-amido-5-aminopentaneboronate, hydrochloride salt; HRMS calcd: (M+H, ethylene glycol ester)$^+$=424.240762, obs.: (M+H, ethylene glycol ester)$^+$=424.242097

EXAMPLE 9.1.3

N-{N-phenyl-N-[(3-phenyl)propionyl]glycyl}-1-amido-5-aminopentaneboronate, hydrochloride salt; HRMS calcd: (M+H, ethylene glycol ester)$^+$= 438.256412, obs.: (M+H, ethylene glycol ester)$^+$= 438.256557

EXAMPLE 15.1.3

Pinanediol N-{N-methyl-N-[(3-phenyl)propionyl]glycyl}-1-amido-4-(guanidino)butylboronate, hydrochloride salt; LRMS (M+H)$^+$=512.3

EXAMPLE 21.1.1

Pinanediol N-{N-methyl-N-benzoylglycyl}-1-amido-5-aminopentaneboronate, hydrochloride salt; HRMS calcd (M+H)$^+$=456.303362, obs.: (M+H)$^+$= 456.302964

EXAMPLE 21.1.2

Pinanediol N-{N-methyl-N-[phenylacetyl]glycyl}-1-amido-5-aminopentaneboronate, hydrochloride salt; LRMS (M+H)$^+$=470

EXAMPLE 21.9.1

Pinanediol N-{N-methyl-N-[2-(phenyl)benzoyl]glycyl}-1-amido-5-amino-pentaneboronate, hydrochloride acid salt; LRMS (M+H)$^+$=532.3

EXAMPLE 24.1.2

Pinanediol N-{N-phenyl-N-[phenylacetyl]glycyl}-1-amido-5-aminopentaneboronate, hydrochloride salt; HRMS calcd: (M+H)$^+$=532.334663, obs.: (M+H)$^+$= 532.334090

EXAMPLE 24.1.3

Pinanediol N-{N-phenyl-N-[(3-phenyl)propionyl]glycyl}-1-amido-5-aminopentaneboronate, hydrochloride salt; HRMS calcd: (M+H)$^+$= 546.350313, obs: (M+H)$^+$=546.352069

EXAMPLE 24.59.1

Pinanediol N-{N-phenyl-N-[N'-methyl-N'-methylphenyl)aminocarbonyl]glycyl}-1-amido-4-isothiouroniumbutylboronate; HRMS (M+H)$^+$ calcd: 606.338533, found: 606.329421

EXAMPLE 26.1.3

Pinanediol N-{N-methyl-N-[(3-phenyl)propionyl]glycyl}-1-amido-4-isothiouroniumbutylboronate; HRMS (M+H)$^+$ calcd: 529.301983, found: 529.302078

EXAMPLE 26.9.1

Pinanediol N-{N-methyl-N-[(2-phenyl)benzoyl]glycyl}-1-amido-4-isothiouroniumbutylboronate; HRMS (M+H)$^+$ calcd: 577.301983, found: 577.302704

EXAMPLE 26.9.3

Pinanediol N-{N-methyl-N-[(3-(2-phenyl)phenyl)propionyl]glycyl}-1-amido-4-isothiouroniumbutylboronate; HRMS (M+H)$^+$ calcd: 605.3333, found: 605.3325

EXAMPLE 26.12.1

Pinanediol N-{N-methyl-N-[(3-(2-phenyl)phenyl)propionyl]glycyl}-1-amido-4-isothiouroniumbutylboronate; HRMS (M+H)$^+$ calcd: 606.3285, found: 606.3294

EXAMPLE 27.1.3

Pinanediol N-{N-[(4-hydroxyphenyl)methyl]-N-[(3-phenyl)propionyl]-glycyl}-1-amido-4-isothiouroniumbutylboronate; HRMS (M+H)$^+$ calcd: 621.328198, found: 621.329437

EXAMPLE 28.1.3

Pinanediol N-{N-[(2-phenyl)ethyl]-N-[(3-phenyl)propionyl]glycyl}-1-amido-4-isothiouroniumbutylboronate; HRMS (M+H)$^+$ calcd: 619.348934, found: 619.348587

EXAMPLE 29.1.3

Pinanediol N-{N-phenyl-N-[(3-phenyl)propionyl]glycyl}-1-amido-4-isothiouroniumbutylboronate; HRMS (M+H)$^+$ calcd: 591.317633, found: 591.316620

EXAMPLE 30.1.3

Pinanediol N-{N-[(naphth-2-yl)methyl]-N-[(3-phenyl)propionyl]glycyl}-1-amido-4-isothiouroniumbutylboronate; HRMS (M+H)$^+$ calcd: 655.348934, found: 655.347870

EXAMPLE 36.6.1

Pinanediol N-{2-[(2-oxo-4-methylphenyl)-4,5-(H)oxazol-3-yl]acetyl}-1-amido-4-isothiouroniumbutylboronate; mp. 120–130° C.; Anal calcd. for $C_{27}H_{39}BN_4O_5S$ HBr % C: 52.02; % H: 6.47; % N: 8.99; % B: 1.73; found: % C: 52.01; % H: 6.43,; % N: 8.84; % B: 1.75

EXAMPLE 49.1.1

Hydrocinnamoyl-[N-(Phenethyl)-Gly]-boroOrn-C10H16HCl; MS (ESI) (M+H)+=560.4

EXAMPLE 49.1.2

Hydrocinnamoyl-[N-(Phenethyl)-Gly]-boroOrn (CH=NH)-C10H16 HCl; MS ($NH_3$-CI) (M+H)+ 587.7

EXAMPLE 49.1.3

Hydrocinnamoyl-[N-(Phenethyl)-Gly]-boroOrn (CH=NH)—OH HCl; MS (ESI) (M+H)+453.1

EXAMPLE 49.2.1

Hydrocinnamoyl-[N-(Phenethyl)-Gly]-boroArg (CH3)-C10H16 HCl; MS (ESI) (M+H)+616.4

EXAMPLE 50.1.1

Hydrocinnamoyl-[N-(N(CH3)$_2$)-Gly]-boroOrn-C10H16 HCl; MS (ESI) (M+H)$^+$499.2

EXAMPLE 50.1.2

Hydrocinnamoyl-[N-(N(CH3)$_2$)-Gly]-boroOrn (CH=NH)-C10H16 HCl; MS (ESI) (M+H)$^+$526.1

EXAMPLE 50.1.3

Hydrocinnamoyl-[N-(N(CH3)$_2$)-Gly]-boroLys—C10H16 HCl; MS ($NH_3$-CI) (M+H)$^+$513.5

EXAMPLE 51.1.1

Hydrocinnamoyl-[N-(3-(Trifluoromethyl)-Phenethyl)-Gly]-boroLys—C10H16 HCl; MS (ESI) (M+H)$^+$642.5

EXAMPLE 51.1.2

Hydrocinnamoyl-[N-(3-(Methyl)-Phenethyl)-Gly]-boroLys-C10H16 HCl; MS (ESI) (M+H)$^+$588.4

EXAMPLE 52.1.1

Hydrocinnamoyl-[N-(3-(Trifluoromethyl)-Phenethyl)-Gly]-boroLys—OH HCl; MS (ESI) (M+H)$^+$534 for ethylene glycol ester

EXAMPLE 61.1.1

Hydrocinnamoyl-Sar-Lys[C(O)$CO_2$H]

Part A:
Preparation of Na-t-Boc-Ne-Cbz-lysine[N(OMe)Me]

A flask was charged 150 ml of anhydrous $CH_2Cl_2$ followed by the addition of Na-t-boc-NE-Cbz-lysine (15.00 grams, 39.43 mmol), N-methylmorpholine (13.0 ml, 118.29 mmol) and was cooled to −78° C. followed by the addition of isobutylchloroformate (5.11 ml, 39.43 mmol). The mixture was stirred for 1 hr at which time the N,O-Dimethylhydroxylamine hydrochloride was added, stirred for 1 hr. and allowed to warm to room temperature. The solvent was removed in vacuo, the residue diluted with EtOAc and washed with 10% aq HCl, sat'd aq $NaHCO_3$ and brine. After drying ($MgSO_4$), the solution was filtered through a pad of silica gel and the solvent removed in vacuo to give the product (16.32 g). MS: ESI, m/z 424.2 (M+H)+.

Part B: Preparation of Part A: Na-t-boc-Ne-Cbz-lysinal

A flask was charged with 200 ml of anhydrous THF followed by the addition of Na-t-boc, NE-Cbz lysine[N(OMe)Me] (4.00 gr, 9.44 mmol), cooled to 0° C. and followed by the addition of Lithium aluminum hydride (450 mg, 11.80 mmol). The solution was stirred for 30 min. and was slowly quenched with a sat'd $KHSO_3$ solution (2.25 gr, 16.53 mmol). The volatiles were removed in vacuo and the residue dissolved in EtOAc and washed with 10% aq HCl, sat'd aq $NaHCO_3$ and brine. After drying ($MgSO_4$), the solution was filtered through a pad of silica gel and the solvent removed in vacuo to give the product (3.29 grams) MS: ESI, m/z 365.2 (M+H)+.

Part C: Preparation of Na-t-boc, Ne-Cbz lysine[C(OH)$CO_2CH_3$]

A flask was charged with 150 ml of anhydrous THF followed by the addition of orthoethylthioformate (6.82 gr, 34.77 mmol), cooled to −78° C. and lithiated with n-butyllithium (2.5 M, 14.0 ml, 34.7 mmol). After stirring for 20 min., Na-t-boc-NE-Cbz-lysinal was added as a THF solution via cannula and continued to stir at −78° C. for and additional 4 hrs; the solution was quenched using sat'd $NH_4Cl$ and the volatiles removed in vacuo. The residue was dissolved in EtOAc and washed twice with brine, dried over $MgSO_4$, filtered and dried in vacuo. The residue was dissolved in 95% MeOH followed by the addition of HgO (12.57 gr, 58.06 mmol) and $HgCl_2$ (40.8 gr, 150.2 mmol) and stirred at rt. for 3 hrs. The solution was filtered through a pad of celite and the volatiles removed in vacuo followed by the addition of chloroform, the solution filtered and the volatiles removed in vacuo. The residue was dissolved in EtOAc and washed with 10% aq HCl, sat'd aq $NaHCO_3$ and brine. After drying ($MgSO_4$), the solution was filtered through a pad of silica gel and the solvent removed in vacuo. The residue was purified by flash chromatography to give the product (1.49 grams) MS: CI m/z 425.2 (M+H)+

Part D: Preparation of NE-Cbz-lysine[C(OH)$CO_2CH_3$] TFA salt

Na-t-boc-Ne-Cbz-lysine[C(OH)$CO_2CH_3$] (1.49 gr, 3.51 mmol) was dissolved in 50 ml of neat TFA and the reaction monitored by TLC. The volatiles were removed in vacuo and the residue dissolved in a minimum amount of $CH_2Cl_2$ followed by the addition of $Et_2O$, cooled to −78° C. and the product ppt. out with hexane (1.36 gr). MS: CI m/z 325.0 (M+H)+.

Part E: Preparation of Hydrocinnamoyl-Sar-ethyl ester

Hydrocinnamic acid was added to 100 ml of anhydrous $CH_2Cl_2$ followed by the addition of N-methylmorpholine (44.0 ml, 400.0 ml), and cooled to −78° C. To the resulting solution was added isobutylchloroformate (17.3 ml, 133.17 mmol) and stirred for 1 hr. The sarcosine ethyl ester hydrochloride (20.00 gr, 133.17 mmol) was added and the solution stirred for and additional hr at −78° C. and allowed to warm to rt. The volatiles were removed in vacuo and the residue was dissolved in EtOAc and washed with 10% aq HCl, sat'd aq NaHCO$_3$ and brine. After drying (MgSO$_4$), the solution was filtered through a pad of silica gel and the solvent removed in vacuo (31.56 gr) MS: CI m/z 250.0 (M+H)+.

Part F: Preparation of Hydrocinnamoyl-Sar—OH

Hydrocinnamoyl-Sar-ethyl ester (31.57 gr, 126.63 mmol) and KOH (21.32 gr, 380 mmol) were combined in a 50/50 methanol-water solution and stirred at rt, the reaction was monitored by TLC. The methanol was removed in vacuo and the organics were extracted using EtOAc. The aq extract was acidified with a 10% HCl solution and the organics extracted with EtOAc and washed with brine. After drying (MgSO$_4$), the solution was filtered and the solvent removed in vacuo to a white solid. MS: CI m/z 222.0 (M+H)+.

Part G: Preparation of Hydrocinnamoyl-Sar-NE-Cbz-lysine [C(OH)CO$_2$CH$_3$]

Hydrocinnamoyl-Sar—OH (690 mg, 3.10 mmol), NE-Cbz lysine[C(OH)CO$_2$CH$_3$] TFA salt (1.36 gr, 3.10 mmol), N-Methyl morpholine (1.0 ml, 9.3 mmol), HOBT (420 mg, 3.10 mmol) and (3-Dimethyl amino propyl)-3 ethyl carbodiimide (600 mg, 3.10 mmol) were dissolved in 50 ml of anhydrous DMF and stirred overnight at rt. The resulting solution was diluted with 300 ml of EtOAc and washed repeatedly with brine. The organic were dried over MgSO$_4$, filtered through a pad of silica gel, and the volatiles dried in vacuo to an oil (1.08 gr). MS: CI m/z 528.4 (M+H)+.

Part H: Preparation of Hydrocinnamoyl-Sar-NE-Cbz-lysine [C(O)CO$_2$CH$_3$]

Anhydrous CH$_2$Cl$_2$ (100 ml) was charged with oxalyl-chloride (20 ml 2.25 mmol) and cooled to −40° C.; this was followed by the addition of anhydrous DMSO (0.35 ml, 4.91 mmol) and stirred for 20 min. Hydrocinnamoyl-Sar-NE-Cbz-lysine[C(OH)CO$_2$CH$_3$] (1.08 gr, 2.04 mmol) was added as a CH$_2$Cl$_2$ solution and stirred for an additional 20 minutes. Triethylamine (1.42 ml, 10.23 mmol) was added to the resulting solution and stirred for an additional 20 min. The volatiles were removed in vacuo and the resulting residue subject to flash chromatography yielding the product as an oil.(73 gr) MS: CI m/z 526.4 (M+H)+.

Part I: Preparation of Hydrocinnamoyl-Sar-NE-Cbz-lysine [C(O)CO$_2$H]

Hydrocinnamoyl-Sar-NE-Cbz lysine[C(O)CO$_2$CH$_3$] (0.73 gr, 1.39 mrol) and LiOH (150 mg, 3.48 mmol) were combined in a 50/50 mixture of methanol/water, stirred at rt and the reaction monitored by TLC. The volatiles were removed in vacuo, the residue dissolved in EtOAc and acidified with 10% HCl. The organics were dried (MgSO$_4$) and the volatiles removed in vacuo to yield 0.57 gr of product MS: CI m/z 468.2 (M+H−CO$_2$)+.

Part J: Hydrocinnamoyl-Sar-Lys[C(O)CO$_2$H]

Hydrocinnamoyl-Sar-Ne-Cbz-lysine[C(O)CO$_2$H] (570 mg, 1.11 mmol) was dissolved in 100 ml of methanol followed by the addition of 20% Pd/C catalyst (60 mg) arid stirred under 1 atm. of H$_2$ at rt for 3 hrs. The solution was filtered through a pad of celite and the volatiles removed in vacuo to give the product MS: CI m/z 380.3 (M+H)+

EXAMPLE 53.1.2

Hydrocinnamoyl-[N-(2-(Cyclopropyl)-Phenethyl)-Gly]-boroLys—OH HCl; MS (ESI) (M+H)$^+$466.3

EXAMPLE 53.2.1

Hydrocinnamoyl-[N-(N-(Methyl)-Phenyl)-Gly]-boroLys—OH HCl; MS (ESI) (M+H)$^+$441.3

EXAMPLE 53.2.2

Hydrocinnamoyl-[N-(N-(Methyl)-Benzyl)-Gly]-boroLys—OH HCl; MS (ESI) (M+H)$^+$455.4

EXAMPLE 53.4.3

Hydrocinnamoyl-[N-(Cyclohexyl)-Gly]-boroLys—OH HCl; MS (ESI) (M+H)$^+$418.3

EXAMPLE 54.1.1

Hydrocinnamoyl-[N-(2,2-(Dimethyl)-Phenethyl)-Gly]-boroLys-C10H16 HCl; MS (ESI) (M+H)$^+$ 616.3

EXAMPLE 54.1.2

Hydrocinnamoyl-[N-(2-(Cyclopropyl)-Phenethyl)-Gly]-boroLys-C10H16 HCl; MS (NH$_3$CI) (M+H)$^+$ 600.5

EXAMPLE 54.1.3

Hydrocinnamoyl-[N-(2,2-(Diethyl)-Phenethyl)-Gly]-boroLys-C10H16 HCl; MS (ESI) (M+H)$^+$630

EXAMPLE 54.2.1

Hydrocinnamoyl-[N-(N-(Methyl)-Phenyl)-Gly]-boroLys-C10H16 HCl; MS (NH$_3$CI) (M+H)$^+$575.4

EXAMPLE 54.2.2

Hydrocinnamoyl-[N-(N-(Methyl)-Benzyl)-Gly]-boroLys-C10H16 HCl; MS (NH$_3$CI) (M+H)$^+$589.4

EXAMPLE 54.2.3

Hydrocinnamoyl-[N-(Succinyl)-Gly]-boroLys-C10H16; MS (ESI) (M+H)$^+$542.5

EXAMPLE 54.3.1

Hydrocinnamoyl-[N-(Methyl Succinyl)-Gly]-boroLys-C10H16 HCl; MS (ESI) (M+H)$^+$556.5

EXAMPLE 54.3.2

Hydrocinnamoyl-[N-(2-(Cyclopentyl)-Phenethyl)-Gly]-boroLys-C10H16 HCl; MS (ESI) (M+H)$^+$ 628.3

EXAMPLE 54.3.3

Hydrocinnamoyl-[N-(2,2-(Dimethyl)-Phenethyl)-Gly]-boroLys-C10H16 HCl; MS (ESI) (M+H)$^+$ 630.4

EXAMPLE 54.4.1

Hydrocinnamoyl-{N-[2-(3,5-dimethylphenyl)-ethyl]-Gly}-boroLys-C10H16 HCl; MS (ESI) (M+H)$^+$ 602.4

EXAMPLE 54.4.2

Hydrocinnamoyl-[N-(Cyclopropyl)-Gly]-boroLys-C10H16 HCl; MS (NH$_3$Cl) (M+H)$^+$510.3

EXAMPLE 54.4.3

Hydrocinnamoyl-[N-(Cyclohexyl)-Gly]-boroLys-C10H16 HCl; MS (NH$_3$Cl) (M+H)$^+$552.4

EXAMPLE 55.1.1

Hydrocinnamoyl-[N-(2,2-(Dimethyl)-Phenethyl)-Gly]-boroArg—OH HCl; MS (ESI) (M+H)$^+$496.4

EXAMPLE 56.1.1

Hydrocinnamoyl-[N-(2,2-(Dimethyl)-Phenethyl)-Gly]-boroArg-C10H16 HCl; MS (ESI) (M+H)$^+$ 630.4

EXAMPLE 56.1.2

Hydrocinnamoyl-[N-(2-(Cyclopropyl)-Phenethyl)—Gly]-boroArg-C10H16 HCl; MS (ESI) (M+H)$^+$ 628.3

EXAMPLE 56.3.3

Hydrocinnamoyl-{N-[2,2-(Dimethyl)-2-(3,5-dimethylphenyl)-ethyl]-Gly}-boroArg-C10H16 HCl; MS (ESI) (M+H)$^+$658.4

EXAMPLE 56.4.1

Hydrocinnamoyl-{N-[2-(3,5-dimethylphenyl)-ethyl]-Gly}-boroArg-C10H16 HCl; MS (ESI) (M+H)$^+$ 630.4

EXAMPLE 57.1.1

Hydrocinnamoyl-[N-(2,2-(Dimethyl)-Phenethyl)-Gly]-boroOrn(CH=NH)—OH HCl; MS (ESI) (M+H)$^+$481.2

EXAMPLE 57.1.2

Hydrocinnamoyl-[N-(2-(Cyclopropyl)-Phenethyl)-Gly]-boroOrn(CH=NH)—OH HCl; MS (ESI) (M+H)$^+$479

EXAMPLE 57.4.2

Hydrocinnamoyl-[N-(Cyclopropyl)-Gly]-boroOrn(CH=NH)—OH HCl; MS (ESI) (M+H)$^+$389.3

EXAMPLE 58

N-{N-methyl-N-[2-(methylphenyl)benzoyl]glycyl}-1-amido-5-aminopentaneboronic acid, hydrochloride salt Using the procedure of Example 8.1.3, however using pinanediol N-{N-methyl-N-[2-(methylphenyl)benzoyl] glycyl}-1-amido-5-aminopentaneboronate, hydrochloride salt, the title compound was prepared; LRMS (M −H$_2$O)$^+$= 394.1, (M−2H$_2$O)$^+$=376.1

EXAMPLE 58.1.1

Hydrocinnamoyl-[N-(2,2-(Dimethyl)-Phernethyl)-Gly]-boroOrn(CH=NH)-C10H16 HCl; MS (ESI) (M+H)$^+$615.4

EXAMPLE 58.3.3

Hydrocinnamoyl-{N-[2,2-(Dimethyl)-2-(3,5-dimethylphenyl)-ethyl]-Gly}-boroOrn(CH=NH)-C10H16 HCl; MS (ESI) (M+H)$^+$643.4

EXAMPLE 58.4.1

Hydrocinnamoyl-{N-[2-(3,5-dimethylphenyl)-ethyl]-Gly}-boroOrn(CH=NH)-C10H16 HCl; MS (ESI) (M+H)$^+$615.4

EXAMPLE 58.4.2

Hydrocinnamoyl-[N-(Cyclopropyl)-Gly]-boroOrn(CH=NH)-C10H16 HCl; MS (NH$_3$Cl) (M+H)$^+$ 524.3

EXAMPLE 59.1.1

Hydrocinnamoyl-[N-(2,2-(Dimethyl)-Phenethyl)-Gly]-boroLys—OH HCl; MS (ESI) (M+H)$^+$482.2

EXAMPLE 59.4.2

Hydrocinnamoyl-[N-(Cyclopropyl)-Gly]-boroLys—OH HCl; MS (ESI) (M+H)$^+$376.2

EXAMPLE 60

Pinanediol N-{N-[((naphth-1-yl)methyl]-N-[(3-phenyl)propionyl]glycyl}-1-amido-4-isothiouroniumbutylboronate; HRMS (M+H)$^+$ calcd: 655.348934, found: 655.349243

EXAMPLE 60.1.1

Hydrocinnamoyl-[N-(2,2-(Dimethyl)-Phenethyl)-Gly]-boroOrn-C10H16 HCl; MS (NH$_3$DCI) (M+H)$^+$602.5

EXAMPLE 60.3.3

Hydrocinnamoyl-[N-(2,2-(Dimethyl)-Phenethyl)-Gly]-boroOrn-C10H16 HCl; MS (ESI) (M+H)$^+$ 616.4

EXAMPLE 60.4.1

Hydrocinnamoyl-{N-[2-(3,5-dimethylphenyl)-ethyl]-Gly}-boroOrn-C10H16 HCl; MS (ESI) (M+H)$^+$ 588.3

EXAMPLE 60.4.2

Hydrocinnamoyl-[N-(Cyclopropyl)-Gly]-boroOrn-C10H16 HCl; MS (NH$_3$CI) (M+H)$^+$496.3

EXAMPLE 61

Pinanediol N-{N-methyl-N-[(3-phenyl-2-(phenyl)methyl)propionyl]-glycyl}-1-amido-5-aminopentylboronate; HRMS (M+H)$^+$ calcd: 560.365963, found: 560.364426

EXAMPLE 61.1.1

Hydrocinnamoyl-Sar-Lys[C(=O)—C(=O)—OH]; MS: ESI m/z 380.3 (M+H)$^+$

EXAMPLE 62.3.3

2-(2-cyanothiophenyl)-benzoyl-Sar-BoroArg C$_{10}$H$_{16}$.HCl

Part A: Preparation of 2-(2-cyanothiophenyl)benzoyl-Sar-ethyl ester 2-(2-cyanothiophenyl)benzoic acid (5.00 gr, 19.58 mmol), sarcosine ethyl ester hydrochloride (3.00 gr, 19.58 mmol), triethylamine (8.2 ml, 58.75 mmol), HOBT (2.64 gr, 19.58 mmol) and 1,3-diisopropylcarbodiimide (3.0 ml, 19.58 mmol) were combined in 100 ml of anhydrous CH$_2$Cl$_2$ and stirred at rt overnight. The volatiles were removed in vacuo, the organics dried over MgSO$_4$, filtered and concentrated. The product was purified by flash chromatography (4.93 gr) MS: CI m/z 355.1 (M+H)+.

Part B: Preparation of 2-(2-cyanothiophenyl)benzoyl-Sar—OH 2-(2-cyanothiophenyl)benzoyl-Sar-ethyl ester (4.93 gr, 14.03 mmol) and KOH (790 mg, 14.03 mmol) were combined in 75 ml of a 50/50 methanol-water solution and stirred at rt, the reaction was monitored by TLC. The methanol was removed in vacuo and the organics were diluted with EtOAc and extracted with H$_2$O. The aq extract was acidified with a 10% HCl solution and the organics extracted with EtOAc, washed with brine. After drying (MgSO$_4$), the solution was filtered and the solvent removed in vacuo to a white solid. MS: CI m/z 327.0 (M+H)+

Part C: Preparation of 2-(2-cyanothiophernyl)benzoyl-Sar—NH—CH[(CH$_2$)$_3$Br]BO$_2$—C$_{10}$H16

2-(2-cyanothiophenyl)benzoyl-Sar—OH (4.23 gr, 12.96 mmol) and NMM (4.3 ml, 38.9 mmol) were dissolved in 150 ml of anhydrous CH$_2$Cl$_2$ and stirred at −78° C. This was followed by the addition of isobutylchloroformate(1.70 ml, 12.96 mmol) and stirred for 1 hr, at which time NH$_2$CH[(CH$_2$)$_3$Br]BO$_2$—C$_{10}$H$_{16}$•HCl (4.75 gr, 12.96 mmol) was added and stirred for an additional hr. and allowed to warm to rt. The volatiles were removed in vacuo, the residue was dissolved in EtOAc and the organics were washed with sat'd NaHCO$_3$, 10% HCl and brine. The residue was dried (MgSO$_4$) and filtered through a pad of florisil and concentrated in vacuo to give the product (6.01 gr) MS: CI m/z 558.2 (M-HBr)+

Part D: Preparation of 2-(2-cyanothiophenyl)benzoyl-Sar—NH—CH[(CH$_2$)$_3$N$_3$]BO$_2$—C$_{10}$H$_{16}$ 2-(2-cyanothiophenyl)benzoyl-Sar—NH—CH[(CH$_2$)$_3$Br]BO$_2$—C$_{10}$H$_{16}$ (6.01 gr, 9.21 mmol) and NaN$_3$ (1.80 gr, 27.64 mmol) were combined in 75 ml of DMF and stirred for 3 hrs. at 110° C. The solution was diluted with EtOAc and washed repeatedly with brine. The organics were dried over MgSO$_4$ and filtered through a pad of florisil and concentrated in vacuo to give the product (5.38 gr).MS: ESI m/z 601.4 (M+H)+

Part E: Preparation of 2-(2-cyanothiophenyl)benzyloyl-Sar-boroOrn—C$_{10}$H$_{16}$.HCl To a solution of 2-(2-cyanothiophenyl)benzyloyl-Sar-NH—CH[(CH$_2$)$_3$N$_3$]BO$_2$—C$_{10}$H$_{16}$ (5.38 gr, 8.96 mmol) in MeOH (75 ml) was added 20% Pd/C catalyst (600 mg). The mixture was stirred under 1 atm of H$_2$ for 2 hrs and then filtered through a pad of celite and concentrated to give the product MS: CI m/z 575.2 (M+H)+.

Part F: Preparation of 2-(2-cyanothiophenyl)benzyloyl-Sar-boroArg—C$_{10}$H$_{16}$.HCl 2-(2-cyanothiophenyl)benzyloyl-Sar-boroOrn—C$_{10}$H$_{16}$.HCl (1.77 gr, 2.90 mmol), DMAP (710 mg, 5.79 mmol) and H$_2$NC(NH)SO$_3$H (720 mg, 5.79 mmol) were combined in 50 ml of absolute EtOH and refluxed overnight. The volatiles were removed and the residue dissolved in CH$_3$Cl and washed with 10% HCl and brine. The organics were dried (NaSO$_4$) and concentrated to give the product MS: CI m/z 617.3 (M+H)+.

EXAMPLE 61.2.1

Hydrocinnamoyl-Sar-Lys—C(=O)—OCH3 HCl; MS: CI m/z 364.2 (M+H)$^+$

EXAMPLE 61.2.3

Hydrocinnamoyl-Sar-Lys—C(=O)—CH3 HCl; MS: CI m/z 348.2 (M+H)$^+$

EXAMPLE 61.4.1

Hydrocinnamoyl-Sar-Lys[CH(OH)(OCH3)—C(=O)—OCH3] HCl; MS: CI m/z 392.3(M+H)$^+$

EXAMPLE 62

Pinanediol N-{N-methyl-N-[(3,4-dichlorophenyl)acetyl]glycyl}-1-amido-5-aminopentaneboronate, hydrochloride salt; LRMS (M+H)$^+$=538

EXAMPLE 62.1.3

(2-(2-Cyano)-Thiophenyl)-Benzoyl-Sar-boroIrg-C10H16 HBr; MS: DCI m/z 648.(M+H)$^+$

EXAMPLE 62.2.2

(2-(2-Cyano)-Thiophenyl)-Benzoyl-Sar-borohomoIrg-C10H16 HBr: MS: ESI m/z 634.4 (M+H)$^+$

EXAMPLE 62.3.2

(2-(2-Cyano)-Thiophenyl)-Benzoyl-Sar-borohomoArg-C10H16 HCl; MS: DCI m/z 631. (M+H)$^+$

EXAMPLE 64.2.3

2-(3-chlorobenzyl)-benzoyl-Sar-Borolys $C_{10}H_{16}$.HCl

Part A: Preparation of 2-bromo-3'-chloro diphenyl methanol

Anhydrous THF (400 ml) was charged with 3-(chloro) bromo benzene (19.63 ml, 167.13 mmol), cooled to −78° C., lithiated with n-BuLi (2.5 M, 66.85 ml, 167.13 mmol) and stirred for 20 minutes. 2-bromobenzaldehyde (19.51 ml, 167.13 mmol) was added and stirred for an additional 30 minutes and allowed to warm to rt. The solution was quenched with sat'd NH$_4$Cl and the volatiles removed in vacuo. The residue was dissolved in EtOAc and washed with brine; the organics were dried over MgSO$_4$, filtered through a pad of silica and the volatiles dried in vacuo. The product was purified by flash chromatography (38.8 gr) MS: CI m/z 281.0 (M+H−H$_2$O)+

Part B: Preparation of 2-bromo-3'-chloro diphenyl methane 2-bromo-3'-chloro diphenyl methanol (38.8 gr, 130.35 mmol) and triethylsilane (31.23 ml, 195.53 mmol) were combined in 200 ml of TFA and stirred overnight at rt. The volatiles were removed in vacuo and the residue purified by flash chromatography (33.32 grams) MS: CI m/z 283.0 (M+H)+.

Part C: Preparation of 3-chlorobenzylbenzoic acid 2-bromo-3'-chloro diphenyl methane was dissolved in 250 ml of anhydrous THF, cooled to −78° C. and lithiated with n-BuLi (2.5 M, 47.5 ml, 118.34 mmol). After stirring for 30 minutes, CO$_2$ was slowly bubbled in for 15 minutes and the solution warmed to rt. The volatiles were removed in vacuo and the residue dissolved in H$_2$O and the organics removed with EtOAc, the aq. layer was acidified with 10% HCl, the organics extracted with EtOAc, washed with brine, dried (MgSO$_4$) and the volatiles removed in vacuo to a white solid MS: CI m/z 264.0 (M+H)+.

Part D: Preparation of 2-(3-chlorobenzyl)benzoyl-Sar ethyl ester 3-chlorobenzylbenzoic acid (10.28 gr, 41.67 mmol), sarcosine ethyl ester hydrochloride (6.40 gr, 41.67 mmol), 1-(3-Dimethyl amino propyl)-3 ethyl carbodiimide (8.0 gr, 41.67 mmol), NMM (13.75 ml, 125.0 mmol) and DMAP (1.27 gr, 10.42 mmol) were combined in anhydrous CH$_2$Cl$_2$ and stirred at rt overnight. The volatiles were removed in vacuo, the residue dissolved in EtOAc, washed with 10% aq HCl, sat'd aq NaHCO$_3$ and brine. After drying (MgSO$_4$), the solution was filtered through a pad of silica gel and the solvent removed in vacuo to give the product (3.19 grams) MS: CI, m/z 346.0 (M+H)+.

Part E: Preparation of 2-(3-chlorobenzyl)benzoyl-Sar—OH 3-chlorobenzylbenzoyl-Sar ethyl ester (3.19 gr, 9.22 mmol) and KOH (2.0 gr, 36.90 mmol) were combined in 75 ml of a 50/50 methanol-water solution and stirred at rt, the reaction was monitored by TLC. The MeOH was removed in vacuo and the organics were diluted with EtOAc and extracted with H$_2$O. The aq extract was acidified with a 10% HCl solution and the organics extracted with EtOAc and washed with brine. After drying (MgSO$_4$), the solution was filtered and the solvent removed in vacuo to a white solid. MS: CI m/z 318.0 (M+H)+

Part F: Preparation of 2-(3-chlorobenzyl)benzyloyl-Sar—NH—CH[(CH$_2$)$_4$Br]BO$_2$—C$_{10}$H$_{16}$ 3-chlorobenzylbenzoyl-Sar—OH (2.66 gr, 8.37 mmol) and NMM (2.76 ml, 25.11 mmol) were dissolved in anhydrous CH$_2$Cl$_2$ and stirred at −78° C. This was followed by the addition of isobutylchloroformate (1.1 ml, 8.37 ml) and stirred for 1 hr, at which time NH$_2$CH[(CH$_2$)$_4$Br]BO$_2$—C$_{10}$H$_{16}$.HCl (3.19 gr, 8.37 mmol) was added and stirred for an additional hr. and allowed to warm to rt. The volatiles were removed in vacuo, the residue was dissolved in EtOAc and the organics were washed with sat'd NaHCO$_3$, 10% HCl and brine. The residue was dried (MgSO$_4$), filtered through a pad of florisil and concentrated in vacuo to give the product (0.4.45 gr) MS: CI m/z 645.5 (M+H)+

Part G: Preparation of 2-(3-chlorobenzyl)benzyloyl-Sar—NH—CH[(CH$_2$)$_4$N$_3$]BO$_2$—C$_{10}$H$_{16}$ 3-chlorobenzylbenzyloyl-Sar—NH—CH[(CH$_2$)$_4$Br]BO$_2$—C$_{10}$H$_{16}$ (4.45 gr, 6.91 mmol) and NaN$_3$ (1.34 gr, 20.73 mmol) were combined in 50 ml of DMF and stirred for 3 hrs. at 110° C. The solution was diluted with EtOAc and washed repeatedly with brine. The organics were dried over MgSO$_4$ and filtered through a pad of florisil and concentrated in vacuo to give the product (3.33 gr) MS: DCI m/z 623.0 (M+NH$_4$)+

Part H: Preparation of 2-(3-chlorobenzyl)benzyloyl-Sar-borolys—C$_{10}$H$_{16}$.HCl To a solution of 3-chlorobenzylbenzyloyl-Sar—NH—CH[(CH$_2$)$_4$N$_3$]BO$_2$—C$_{10}$H$_{16}$ (3.33 gr, 5.49 mmol) in MeOH (75 ml) was added 20% Pd/C catalyst (300 mg). The mixture was stirred under 1 atm of H$_2$ for 2 hrs and then filtered through a pad of celite and concentrated to give the product MS: CI m/z 580.5 (M+H)+.

EXAMPLE 62.4.1

(2-(2-Cyano)-Thiophenyl)-Benzoyl-Sar-boroOrn (CH=NH)-C10H16 HCl; MS: ESI m/z 602.3 (M+H)$^+$

EXAMPLE 62.4.2

(2-(2-Cyano)-Thiophenyl)-Benzoyl-Sar-boroLys (CH=NH)-C10H16 HCl; MS: ESI m/z 616.2 (M+H)$^+$

EXAMPLE 62.4.3

(2-(2-Cyano)-Thiophenyl)-Benzoyl-Sar-boroLys-C10H16 HCl; MS: CI m/z 589.3 (M+H)$^+$

EXAMPLE 63

Pinanediol N-{N-methylphenyl-N-[(3-phenyl)propionyl]glycyl}-1-amido-5-aminopentaneboronate, hydrochloride salt; HRMS calcd: (M+H)$^+$=560.365963, obs: (M+H)$^+$=560.366107

EXAMPLE 63.1.3

2-(Thiophenyl)-Benzoyl-Sar-boroIrg-C10H16 HBr; MS: CI m/z 567.2 (M–H$_2$NCN)$^+$

EXAMPLE 63.3.1

2-(Thiophenyl)-Benzoyl-Sar-boroOrn-C10H16 HCl; MS: CI m/z 550.3 (M+H)$^+$

EXAMPLE 63.4.1

2-(Thiophenyl)-Benzoyl-Sar-boroOrn(CH═NH)-C10H16 HCl; MS: CI m/z 577.3 (M+H)$^+$

EXAMPLE 63.4.2

2-Thiophenyl-Benzoyl-Sar-boroLys(CH═NH)-C10H16; MS: CI m/z 564.2 (M–HCN)$^+$

EXAMPLE 63.5.1

Pinanediol N-{N-methyl-N-[2-(Thiophenyl)-Benzoyl]Sar}-1-amido-5-thiocyanatobutane boronate; MS: CI m/z 592.2 (M+H)$^+$

EXAMPLE 64

N-{N-methylphenyl-N-[(3-phenyl)propionyl]glycyl}-1-amido-5-aminopentaneboronate, hydrochloride salt; HRMS calcd (M+H, ethylene glycol ester)$^+$=452.272062, obs.: (M+H, ethylene glycol ester)$^+$=452.270496

EXAMPLE 64.1.1

2-Benzyl-(N-Benzyl)-Sar-boroLys—C$_{10}$H$_{16}$ HCl; MS: CI m/z 532.5 (M+H)$^+$

EXAMPLE 64.1.2

Acetyl-Gly[N-(2-(Benzyl)-Benzyl)]-boroLys-C10H16 HCl; MS: CI m/z 560.4 (M+H)$^+$

EXAMPLE 64.1.3

Pinanediol N-{N-methyl-N-[2-(pyrrol-1-ylmethyl)-Benzyl]glycyl}-1-amido-5-aminopentaneboronate, hydrochloride salt; MS: CI m/z 535.3 (M+H)$^+$

EXAMPLE 64.2.2

[3-(Trifluoromethyl)-Benzyl]-Benzoyl-Sar-boroLys-C10H16 HCl; MS: CI m/z 614.3 (M+H)$^+$

EXAMPLE 65

Piananediol N-{N-methyl-N-[(4-phenyl)butanoyl]glycyl}-1-amido-5-aminopentaneboronate, hydrochloride salt; HRMS calcd: (M+H)$^+$=498.350313, obs.: (M+H)$^+$=498.350585

EXAMPLE 65.1.3

N-{N-methyl-N-[2-(pyrrol-1-ylmethyl)-Benzyl]glycyl}-1-amido-5-aminopentaneboronic acid, hydrochloride salt; MS: ESI m/z 601.3 (M+H)$^+$

EXAMPLE 66

N-{N-methyl-N-[(4-phenyl)butanoyl]glycyl}-1-amido-5-aminopentaneboronate, hydrochloride salt; HRMS calcd: (M+H, ethylene glycol ester)$^+$=390.256412, obs.: (M+H, ethylene glycol ester)$^+$=390.257428

EXAMPLE 66.1.1

Glutaryl-[N-(Phenethyl)-Gly]-boroLys—OH HCl; MS (ESI) (M+H)$^+$422.3

EXAMPLE 66.1.2

Glutaryl(3,3-Dimethyl)-[N-(Phenethyl)-Gly]-boroLys—OH; MS (ESI) (M+H)$^+$450.5

EXAMPLE 66.1.3

Methyl Glutaryl(3,3-Dimethyl)-[N-(Phenethyl)-Gly]-boroLys—OH HCl; MS (CDI) (M+H)$^+$490

EXAMPLE 66.3.2

Methanesulfonyl-Gly-[N-(N-(Methyl)-Benzyl)-Gly]-boroLys—OH HCl; MS (ESI) (M+H)$^+$458.3

EXAMPLE 67

Pinanediol N-{N-methyl-N-[N-methanesulphonyl-D-phenylalanyl]glycyl}-1-amido-5-aminopentaneboronate, hydrochloride salt; HRMS calcd: (M+H)$^+$=577.323113, obs.: (M+H)$^+$=577.322891

EXAMPLE 67.1.2

Glutaryl(3,3-Dimethyl)-[N-(Phenethyl)-Gly]-boroLys-C10H16; MS (ESI) (M+H)$^+$584.6

EXAMPLE 67.1.3

Methyl Glutaryl(3,3-Dimethyl)-[N-(Phenethyl)-Gly]-boroLys-C10H16 HCl; MS (ESI) (M+H)$^+$ 598.6

EXAMPLE 67.3.2

Methanesylfonyl-Gly-[N-(N-(Methyl)-Benzyl)-Gly]-boroLys-C10H16 HCl; MS (ESI) (M+H)$^+$592.3

EXAMPLE 68

N-{N-methyl-N-[N-methanesulphonyl-D-phenylalanyl]glycyl}-1-amido-5-aminopentaneboronate, hydrochloride salt; HRMS calcd: (M+H, ethylene glycol ester)$^+$=469.229212, obs.: (M+H, ethylene glycol ester)$^+$=469.228962

EXAMPLE 68.2.1

Boc-Glu-[N-(Phenethyl)-Gly]-boroLys—OH

EXAMPLE 68.3.1

Succinyl-[N-(Phenethyl)-Gly]-boroLys—OH; MS (ESI) (M+H)$^+$408.3

EXAMPLE 68.3.3

Methyl Succinyl-[N-(Phenethyl)-Gly]-boroLys—OH HCl; MS (ESI) (M+H)$^+$422.3

EXAMPLE 68.4.1

Methyl Glutaryl-[N-(Phenethyl)-Gly]-boroLys—OH HCl; MS (ESI) (M+H)$^+$336.3

EXAMPLE 68.4.2

Methanesulfonyl-Sar-[N-(Phenethyl)-Glyl-boroLys—OH HCl; MS (ESI) (M+H)$^+$457.0

EXAMPLE 69

Pinanediol N-{N-methyl-N-[3-(4-methylphenyl)propionyl]glycyl}-1-amido-5-aminopentaneboronate, hydrochloride salt; HRMS calcd: (M+H)$^+$=498.350313, obs.: (M+H)$^+$=498.349676

EXAMPLE 69.1.1

Glutaryl-[N-(Phenethyl)-Gly]-boroLys-C10H16; MS (ESI) (M+H)$^+$556.4

EXAMPLE 69.2.1

Boc-Glu-[N-(Phenethyl)-Gly]-boroLys-C10H16; MS (ESI) (M+H)$^+$671.6

EXAMPLE 69.2.2

Boc-Asp-[N-(Phenethyl)-Gly]-boroLys-C10H16; MS (ESI) (M+H)$^+$657.6

EXAMPLE 69.2.3

Boc-Glu(OCH$_3$)-[N-(Phenethyl)-Gly]-boroLys—C10H16 HCl; MS (ESI) (M+H)$^+$685.6

EXAMPLE 69.3.2

Methanesulfonyl-Gly-[N-(Phenethyl)-Gly]-boroLys-C10H16 HCl; MS (NH$_3$Cl) (M+H)$^+$577

EXAMPLE 69.4.1

Methyl Glutaryl-[N-(Phenethyl)-Gly]-boroLys-C10H16 HCl; MS (ESI) (M+H)$^+$570.5

EXAMPLE 69.4.2

Methanesulfonyl-Sar-[N-(Phenethyl)-Gly]-boroLys-C10H16 HCl; MS (NH$_3$Cl) (M+H)$^+$591.4

EXAMPLE 70

N-{N-methyl-N-[3-(4-methylphenyl)propionyl]glycyl}-1-amido-5-aminopentaneboronate, hydrochloride salt; HRMS calcd: (M+H, ethylene glycol ester)$^+$=390.256412, obs.: (M+H, ethylene glycol ester)$^+$=390.256960

EXAMPLE 71

Pinanediol N-{N-methyl-N-[2-(methyl(4-methoxyphenyl))benzoyl]glycyl}-1-amido-5-aminopentaneboronate, hydrochloride acid salt; LRMS (M+H)$^+$=576.3

EXAMPLE 72

Pinanediol N-{N-methyl-N-[2-(methyl(4-methylphenyl))benzoyl]glycyl}-1-amido-5-aminopentaneboronate, hydrochloride acid salt; LRMS (M+H)$^+$=560.5

EXAMPLE 72.1.3

Hydrocinnamoyl-[N-(N(CH3)$_2$)-Gly]-boroLys—OH HCl; MS (ESI) (M+H)$^+$379.0

EXAMPLE 73

Pinanediol N-{N-((O-tert-butyl)methylenecarboxylate)-N-[(3-phenyl)propionyl]-glycyl}-1-amido-5-aminopentaneboronate, hydrochloride salt; LRMS (M+H)⁺=584

EXAMPLE 73.1.2

Succinyl-[N-(3-(Methyl)-Phenethyl)-Gly]-boroLys-C10H16 HCl; MS (ESI) (M+H)⁺556

EXAMPLE 74

Pinanediol N-{N-methyl-N-[(3-phenyl)propionyl]glycyl}-1-amido-4-(formamidino)butylboronate, hydrochloride salt; LRMS (M+H)⁺=497

EXAMPLE 75

N-{N-methyl-N-[(3-phenyl)propionyl]glycyl}-1-amido-4-(N- methylguanidino)butylboronate, hydrochloride salt; LRMS (M+H, ethylene glycol ester)⁺=418.3

EXAMPLE 75.3.1

(2-(2-Cyano)-Thiophenyl)-Benzoyl-Sar-boroArg—OH HCl; MS (ESI) (M+H)⁺483.1

EXAMPLE 76

N-{N-methyl-N-[(3-phenyl)propionyl]glycyl}-1-amido-4-(formamidino)butylboronate, hydrochloride salt; LRMS (M+H, ethylene glycol ester)⁺=389.2

EXAMPLE 76.1.1

Hydrocinnamoyl-[N-(Cyclopropyl)-Gly]-boroLys (CH=NH)—OH HCl; MS (ESI) (M+H)⁺403.0

EXAMPLE 77.1.1

Hydrocinnamoyl-[N-(Cyclopropyl)-Gly]-boroLys (CH=NH)-C10H16 HCl; MS (NH₃Cl) (M+H)⁺ 537.3

EXAMPLE 78.1.2

Phenoxyacetyl-[N-(Cyclopropyl)-Gly]-boroLys—OH HCl; MS (ESI) (M+H)⁺378.3

EXAMPLE 78.1.3

Thiophenacetyl-[N-(Cyclopropyl)-Gly]-boroLys—OH HCl; MS (ESI) (M+H)⁺394.2

EXAMPLE 79.1.2

Phenoxyacetyl-[N-(Cyclopropyl)-Gly]-boroLys-C10H16 HCl; MS (NH₃Cl) (M+H)⁺512.3

EXAMPLE 79.1.3

Thiophenacetyl-[N-(Cyclopropyl)-Gly]-boroLys-C10H16 HCl; MS (NH₃Cl) (M+H)⁺528.3

TABLES 1–79

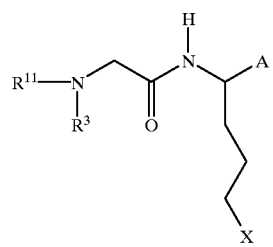
Formula I

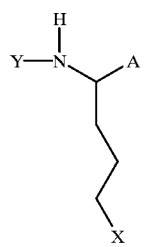
Formula II

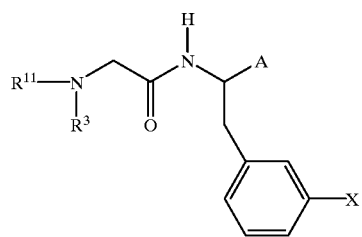
Formula III

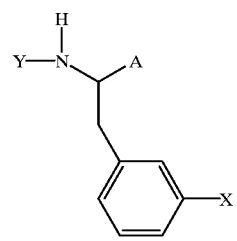
Formula IV

TABLE 1

Formula I: A = —B(OH)₂; X = guanidinyl; $R^3$ = table below; $R^{11}$ = CH₃

| | .1 | .2 | .3 |
|---|---|---|---|
| 1.1 | —C(O)Ph | —C(O)CH₂Ph | —C(O)CH₂CH₂Ph |
| 1.2 | —C(O)CH₂OPh | —C(O)CH₂NHPh | —C(O)CH₂SPh |

TABLE 1-continued

Formula I: A = —B(OH)$_2$; X = guanidinyl; R$^3$ = table below; R$^{11}$ = CH$_3$

| | .1 | .2 | .3 |
|---|---|---|---|
| 1.3 | —C(O)o-PhOH | —C(O)m-PhOH | —C(O)p-PhOH |
| 1.4 | —C(O)o-PhCH$_2$OH | —C(O)m-PhCH$_2$OH | —C(O)p-PhCH$_2$OH |
| 1.5 | —C(O)o-PhCOOH | —C(O)m-PhCOOH | —C(O)p-PhCOOH |
| 1.6 | —C(O)o-PhCH$_2$COOH | —C(O)m-PhCH$_2$COOH | —C(O)p-PhCH$_2$COOH |
| 1.7 | —C(O)naphth-1-yl | —C(O)CH$_2$(naphth-1-yl) | —C(O)CH$_2$CH$_2$(napth-1-yl) |
| 1.8 | —C(O)naphth-2-yl | —C(O)CH$_2$(naphth-2-yl) | —C(O)CH$_2$CH$_2$(napth-2-yl) |
| 1.9 | —C(O)o-biphenyl | —C(O)CH$_2$(o-biphenyl) | —C(O)CH$_2$CH$_2$(o-biphenyl) |
| 1.10 | —C(O)m-biphenyl | —C(O)CH$_2$(m-biphenyl) | —C(O)CH$_2$CH$_2$(m-biphenyl) |
| 1.12 | —C(O)p-biphenyl | —C(O)CH$_2$(p-biphenyl) | —C(O)CH$_2$CH$_2$(p-biphenyl) |
| 1.13 | —C(O)o-PhOPh | —C(O)CH$_2$(o-PhOPh) | —C(O)CH$_2$CH$_2$(o-PhOPh) |
| 1.14 | —C(O)m-PhOPh | —C(O)CH$_2$(m-PhOPh) | —C(O)CH$_2$CH$_2$(m-PhOPh) |
| 1.15 | —C(O)p-PhOPh | —C(O)CH$_2$(p-PhOPh) | —C(O)CH$_2$CH$_2$(p-PhOPh) |
| 1.16 | —C(O)o-PhNHPh | —C(O)CH$_2$(o-PhNHPh) | —C(O)CH$_2$CH$_2$(o-PhNHPh) |
| 1.17 | —C(O)m-PhNHPh | —C(O)CH$_2$(m-PhNHPh) | —C(O)CH$_2$CH$_2$(m-PhNHPh) |
| 1.18 | —C(O)p-PhNHPh | —C(O)CH$_2$(p-PhNHPh) | —C(O)CH$_2$CH$_2$(p-PhNHPh) |
| 1.19 | —C(O)o-PhSPh | —C(O)CH$_2$(o-PhSPh) | —C(O)CH$_2$CH$_2$(o-PhSPh) |
| 1.20 | —C(O)m-PhSPh | —C(O)CH$_2$(m-PhSPh) | —C(O)CH$_2$CH$_2$(m-PhSPh) |
| 1.21 | —C(O)p-PhSPh | —C(O)CH$_2$(p-PhSPh) | —C(O)CH$_2$CH$_2$(p-PhSPh) |
| 1.22 | —C(O)o-PhCH$_2$SPh | —C(O)CH$_2$(o-PhCH$_2$SPh) | —C(O)CH$_2$CH$_2$(o-PhCH$_2$SPh) |
| 1.23 | —C(O)m-PhCH$_2$SPh | —C(O)CH$_2$(m-PhCH$_2$SPh) | —C(O)CH$_2$CH$_2$(m-PhCH$_2$SPh) |
| 1.24 | —C(O)p-PhCH$_2$SPh | —C(O)CH$_2$(p-PhCH$_2$SPh) | —C(O)CH$_2$CH$_2$(p-PhCH$_2$SPh) |
| 1.25 | —C(O)adamantyl | —C(O)CH$_2$(adamantyl) | —C(O)CH$_2$CH$_2$(adamantyl) |
| 1.26 | —C(O)cyclopentyl | —C(O)CH$_2$(cyclopentyl) | —C(O)CH$_2$CH$_2$((cyclopentyl) |
| 1.27 | —C(O)cyclohexyl | —C(O)CH$_2$(cyclohexyl) | —C(O)CH$_2$CH$_2$(cyclohexyl) |
| 1.28 | —C(O)CH$_2$O(cyclopentyl) | —C(O)CH$_2$NH(cyclopentyl) | —C(O)CH$_2$S(cyclopentyl) |
| 1.29 | —C(O)CH$_2$O(cyclohexyl) | —C(O)CH$_2$NH(cyclohexyl) | —C(O)CH$_2$S(cyclohexyl) |
| 1.30 | —C(O)pyridin-2-yl | —C(O)CH$_2$(pyridin-2-yl) | —C(O)CH$_2$CH$_2$(pyridin-2-yl) |
| 1.31 | —C(O)pyridin-3-yl | —C(O)CH$_2$(pyridin-3-yl) | —C(O)CH$_2$CH$_2$(pyridin-3-yl) |
| 1.32 | —C(O)pyridin-4-yl | —C(O)CH$_2$(pyridin-4-yl) | —C(O)CH$_2$CH$_2$(pyridin-4-yl) |
| 1.33 | —C(O)furan-2-yl | —C(O)CH$_2$(furan-2-yl) | —C(O)CH$_2$CH$_2$(furan-2-yl) |
| 1.34 | —C(O)furan-3-yl | —C(O)CH$_2$(furan-3-yl) | —C(O)CH$_2$CH$_2$(furan-3-yl) |
| 1.35 | —C(O)thiophen-2-yl | —C(O)CH$_2$(thiophen-2-yl) | —C(O)CH$_2$CH$_2$(thiophen-2-yl) |
| 1.36 | —C(O)thiophen-2-yl | —C(O)CH$_2$(thiophen-2-yl) | —C(O)CH$_2$CH$_2$(thiophen-2-yl) |
| 1.37 | —C(O)imidazo-2-yl | —C(O)CH$_2$(imidazo-2-yl) | —C(O)CH$_2$CH$_2$(imidazo-2-yl) |
| 1.38 | —C(O)oxazo-2-yl | —C(O)CH$_2$(oxazo-2-yl) | —C(O)CH$_2$CH$_2$(oxazo-2-yl) |
| 1.39 | —C(O)thioazo-2-yl | —C(O)CH$_2$(thioazo-2-yl) | —C(O)CH$_2$CH$_2$(thioazo-2-yl) |
| 1.40 | —C(O)benzofuran-2-yl | —C(O)CH$_2$(benzofuran-2-yl) | —C(O)CH$_2$CH$_2$(benzofuran-2-yl) |
| 1.41 | —C(O)benzofuran-3-yl | —C(O)CH$_2$(benzofuran-3-yl) | —C(O)CH$_2$CH$_2$(benzofuran-3-yl) |
| 1.42 | —C(O)benzothiophen-2-yl | —C(O)CH$_2$(benzothiophen-2-yl) | —C(O)CH$_2$CH$_2$(benzothiophen-2-yl) |
| 1.43 | —C(O)thiophen-2-yl | —C(O)CH$_2$(thiophen-2-yl) | —C(O)CH$_2$CH$_2$(thiophen-2-yl) |
| 1.44 | —C(O)benzimidazo-2-yl | —C(O)CH$_2$(benzimidazo-2-yl) | —C(O)CH$_2$CH$_2$(benzimidazo-2-yl) |
| 1.45 | —C(O)benzoxazo-2-yl | —C(O)CH$_2$(benzoxazo-2-yl) | —C(O)CH$_2$CH$_2$(benzoxazo-2-yl) |
| 1.46 | —C(O)benzothiazo-2-yl | —C(O)CH$_2$(benzothiazo-2-yl) | —C(O)CH$_2$CH$_2$(benzothiazo-2-yl) |
| 1.47 | —C(O)o-Ph(P(O)Ph$_3$) | —C(O)m-Ph(P(O)Ph$_3$) | —C(O)p-Ph(P(O)Ph$_3$) |
| 1.48 | —C(O)Ph-2-(fluoren-9-yl) | —C(O)Ph-3-(fluoren-9-yl) | —C(O)Ph-4-(fluoren-9-yl) |
| 1.49 | —C(O)N-indolin-2-one | —C(O)indolin-2-yl | —C(O)indol-2-yl |
| 1.50 | —C(O)C(CH$_3$)$_2$NHSO$_2$(naphth-2-yl) | —C(O)cyclopentyl-2-(Ph) | —C(O)cyclohexyl-2-(Ph) |
| 1.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 1.52 | —C(O)tetrahydronaphth-1-yl | —C(O)tetrahydronaphth-2-yl | —C(O)cyclopropyl-2,2-(Ph$_2$) |
| 1.53 | —C(O)tetrahydroisoquinolin-1-yl | —C(O)tetrahydroisoquinolin-3-yl | —C(O)CH$_2$((2-oxo)indolin-3-yl) |
| 1.54 | —C(O)CH$_2$(N-benzimidazol-2-one) | —C(O)CH$_2$(N-benzoxazol-2-one) | —C(O)CH$_2$(N-benzothiazol-2-one) |
| 1.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 1.56 | | | |

TABLE 1-continued

Formula I: A = —B(OH)₂; X = guanidinyl; R³ = table below; R¹¹ = CH₃

| | .1 | .2 | .3 |
|---|---|---|---|
| 1.57 | 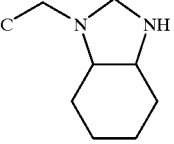 |  | 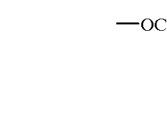 |
| 1.58 | 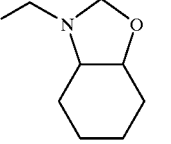 | 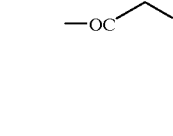 | 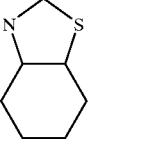 |
| 1.59 | —C(O)N(CH₃)CH₂Ph | —C(O)N(C₂H₅)CH₂Ph | —C(O)N(C₃H₇)CH₂Ph |
| 1.60 | —C(O)pyridin-3-yl-5-(Ph) | —C(O)Ph-3-(CH₂(thiophen-2-yl)) | —C(O)Ph-3-(CH₂Ph) |
| 1.61 | —C(O)C(CH₃)₂OPh | —C(O)CH(C₂H₅)OPh | —C(O)CH₂OCH₂Ph |
| 1.62 | —C(O)CH₂O(o-PhCH₂OH) | —C(O)CH₂O(m-PhCH₂OH) | —C(O)CH₂O(p-PhCH₂OH) |
| 1.63 | —C(O)CH₂O(o-PhCOOH) | —C(O)CH₂O(m-PhCOOH) | —C(O)CH₂O(p-PhCOOH) |
| 1.64 | —C(O)CH₂O(o-PhCOOCH₃) | —C(O)CH₂O(m-PhCOOCH₃) | —C(O)CH₂O(p-PhCOOCH₃) |
| 1.65 | —C(O)CH₂O(o-PhCH₂COOH) | —C(O)CH₂O(m-PhCH₂COOH) | —C(O)CH₂O(p-PhCH₂COOH) |
| 1.66 | 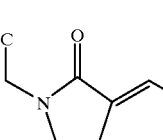 | | |

TABLE 2

Formula I: A = —B(OH)₂; X = guanidinyl; R³ = table below; R¹¹ = CH₂(p-PhOH).

| | .1 | .2 | .3 |
|---|---|---|---|
| 2.1 | —C(O)Ph | —C(O)CH₂Ph | —C(O)CH₂CH₂Ph |
| 2.2 | —C(O)CH₂OPh | —C(O)CH₂NHPh | —C(O)CH₂SPh |
| 2.3 | —C(O)o-PhOH | —C(O)m-PhOH | —C(O)p-PhOH |
| 2.4 | —C(O)o-PhCH₂OH | —C(O)m-PhCH₂OH | —C(O)p-PhCH₂OH |
| 2.5 | —C(O)o-PhCOOH | —C(O)m-PhCOOH | —C(O)p-PhCOOH |
| 2.6 | —C(O)o-PhCH₂COOH | —C(O)m-PhCH₂COOH | —C(O)p-PhCH₂COOH |
| 2.7 | —C(O)naphth-1-yl | —C(O)CH₂(naphth-1-yl) | —C(O)CH₂CH₂(napth-1-yl) |
| 2.8 | —C(O)naphth-2-yl | —C(O)CH₂(naphth-2-yl) | —C(O)CH₂CH₂(napth-2-yl) |
| 2.9 | —C(O)o-biphenyl | —C(O)CH₂(o-biphenyl) | —C(O)CH₂CH₂(o-biphenyl) |
| 2.10 | —C(O)m-biphenyl | —C(O)CH₂(m-biphenyl) | —C(O)CH₂CH₂(m-biphenyl) |
| 2.12 | —C(O)p-biphenyl | —C(O)CH₂(p-biphenyl) | —C(O)CH₂CH₂(p-biphenyl) |
| 2.13 | —C(O)o-PhOPh | —C(O)CH₂(o-PhOPh) | —C(O)CH₂CH₂(o-PhOPh) |
| 2.14 | —C(O)m-PhOPh | —C(O)CH₂(m-PhOPh) | —C(O)CH₂CH₂(m-PhOPh) |
| 2.15 | —C(O)p-PhOPh | —C(O)CH₂(p-PhOPh) | —C(O)CH₂CH₂(p-PhOPh) |
| 2.16 | —C(O)o-PhNHPh | —C(O)CH₂(o-PhNHPh) | —C(O)CH₂CH₂(o-PhNHPh) |
| 2.17 | —C(O)m-PhNHPh | —C(O)CH₂(m-PhNHPh) | —C(O)CH₂CH₂(m-PhNHPh) |
| 2.18 | —C(O)p-PhNHPh | —C(O)CH₂(p-PhNHPh) | —C(O)CH₂CH₂(p-PhNHPh) |
| 2.19 | —C(O)o-PhSPh | —C(O)CH₂(o-PhSPh) | —C(O)CH₂CH₂(o-PhSPh) |
| 2.20 | —C(O)m-PhSPh | —C(O)CH₂(m-PhSPh) | —C(O)CH₂CH₂(m-PhSPh) |

TABLE 2-continued

Formula I: A = —B(OH)$_2$; X = guanidinyl; R$^3$ = table below; R$^{11}$ = CH$_2$(p-PhOH).

| | .1 | .2 | .3 |
|---|---|---|---|
| 2.21 | —C(O)p-PhSPh | —C(O)CH$_2$(p-PhSPh) | —C(O)CH$_2$CH$_2$(p-PhSPh) |
| 2.22 | —C(O)o-PhCH$_2$SPh | —C(O)CH$_2$(o-PhCH$_2$SPh) | —C(O)CH$_2$CH$_2$(o-PhCH$_2$SPh) |
| 2.23 | —C(O)m-PhCH$_2$SPh | —C(O)CH$_2$(m-PhCH$_2$SPh) | —C(O)CH$_2$CH$_2$(m-PhCH$_2$SPh) |
| 2.24 | —C(O)p-PhCH$_2$SPh | —C(O)CH$_2$(p-PhCH$_2$SPh) | —C(O)CH$_2$CH$_2$(p-PhCH$_2$SPh) |
| 2.25 | —C(O)adamantyl | —C(O)CH$_2$(adamantyl) | —C(O)CH$_2$CH$_2$(adamantyl) |
| 2.26 | —C(O)cyclopentyl | —C(O)CH$_2$(cyclopentyl) | —C(O)CH$_2$CH$_2$((cyclopentyl) |
| 2.27 | —C(O)cyclohexyl | —C(O)CH$_2$(cyclohexyl) | —C(O)CH$_2$CH$_2$(cyclohexyl) |
| 2.28 | —C(O)CH$_2$O(cyclopentyl) | —C(O)CH$_2$NH(cyclopentyl) | —C(O)CH$_2$S(cyclopentyl) |
| 2.29 | —C(O)CH$_2$O(cyclohexyl) | —C(O)CH$_2$NH(cyclohexyl) | —C(O)CH$_2$S(cyclohexyl) |
| 2.30 | —C(O)pyridin-2-yl | —C(O)CH$_2$(pyridin-2-yl) | —C(O)CH$_2$CH$_2$(pyridin-2-yl) |
| 2.31 | —C(O)pyridin-3-yl | —C(O)CH$_2$(pyridin-3-yl) | —C(O)CH$_2$CH$_2$(pyridin-3-yl) |
| 2.32 | —C(O)pyridin-4-yl | —C(O)CH$_2$(pyridin-4-yl) | —C(O)CH$_2$CH$_2$(pyridin-4-yl) |
| 2.33 | —C(O)furan-2-yl | —C(O)CH$_2$(furan-2-yl) | —C(O)CH$_2$CH$_2$(furan-2-yl) |
| 2.34 | —C(O)furan-3-yl | —C(O)CH$_2$(furan-3-yl) | —C(O)CH$_2$CH$_2$(furan-3-yl) |
| 2.35 | —C(O)thiophen-2-yl | —C(O)CH$_2$(thiophen-2-yl) | —C(O)CH$_2$CH$_2$(thiophen-2-yl) |
| 2.36 | —C(O)thiophen-2-yl | —C(O)CH$_2$(thiophen-2-yl) | —C(O)CH$_2$CH$_2$(thiophen-2-yl) |
| 2.37 | —C(O)imidazo-2-yl | —C(O)CH$_2$(imidazo-2-yl) | —C(O)CH$_2$CH$_2$(imidazo-2-yl) |
| 2.38 | —C(O)oxazo-2-yl | —C(O)CH$_2$(oxazo-2-yl) | —C(O)CH$_2$CH$_2$(oxazo-2-yl) |
| 2.39 | —C(O)thioazo-2-yl | —C(O)CH$_2$(thioazo-2-yl) | —C(O)CH$_2$CH$_2$(thioazo-2-yl) |
| 2.40 | —C(O)benzofuran-2-yl | —C(O)CH$_2$(benzofuran-2-yl) | —C(O)CH$_2$CH$_2$(benzofuran-2-yl) |
| 2.41 | —C(O)benzofuran-3-yl | —C(O)CH$_2$(benzofuran-3-yl) | —C(O)CH$_2$CH$_2$(benzofuran-3-yl) |
| 2.42 | —C(O)benzothiophen-2-yl | —C(O)CH$_2$(benzothiophen-2-yl) | —C(O)CH$_2$CH$_2$(benzothiophen-2-yl) |
| 2.43 | —C(O)thiophen-2-yl | —C(O)CH$_2$(thiophen-2-yl) | —C(O)CH$_2$CH$_2$(thiophen-2-yl) |
| 2.44 | —C(O)benzimidazo-2-yl | —C(O)CH$_2$(benzimidazo-2-yl) | —C(O)CH$_2$CH$_2$(benzimidazo-2-yl) |
| 2.45 | —C(O)benzoxazo-2-yl | —C(O)CH$_2$(benzoxazo-2-yl) | —C(O)CH$_2$CH$_2$(benzoxazo-2-yl) |
| 2.46 | —C(O)benzothiazo-2-yl | —C(O)CH$_2$(benzothiazo-2-yl) | —C(O)CH$_2$CH$_2$(benzothiazo-2-yl) |
| 2.47 | —C(O)o-Ph(P(O)Ph$_3$) | —C(O)m-Ph(P(O)Ph$_3$) | —C(O)p-Ph(P(O)Ph$_3$) |
| 2.48 | —C(O)Ph-2-(fluoren-9-yl) | —C(O)Ph-3-(fluoren-9-yl) | —C(O)Ph-4(fluoren-9-yl) |
| 2.49 | —C(O)N-indolin-2-one | —C(O)indolin-2-yl | —C(O)indol-2-yl |
| 2.50 | —C(O)C(CH$_3$)$_2$NHSO$_2$(naphth-2-yl) | —C(O)cyclopentyl-2-(Ph) | —C(O)cyclohexyl-2-(Ph) |
| 2.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 2.52 | —C(O)tetrahydronaphth-1-yl | —C(O)tetrahydronaphth-2-yl | —C(O)cyclopropyl-2,2-(Ph$_2$) |
| 2.53 | —C(O)tetrahydroisoquinolin-1-yl | —C(O)tetrahydroisoquinolin-3-yl | —C(O)CH$_2$((2-oxo)indolin-3-yl) |
| 2.54 | —C(O)CH$_2$(N-benzimidazol-2-one) | —C(O)CH$_2$(N-benzoxazol-2-one) | —C(O)CH$_2$(N-benzothiazol-2-one) |
| 2.55 | —C(O)CH$_2$(N-dihydroimidazol-2-one) | —C(O)CH$_2$(N-dihydrooxazol-2-one) | —C(O)CH$_2$(N-dihydrothiazol-2-one) |

2.56

2.57

TABLE 2-continued

Formula I: A = —B(OH)$_2$; X = guanidinyl; R$^3$ = table below; R$^{11}$ = CH$_2$(p-PhOH).

| | .1 | .2 | .3 |
|---|---|---|---|
| 2.58 | —OCH$_2$-(3-benzylidene-2-oxoindolin-1-yl) | —OCH$_2$-(4-phenylpiperazin-1-yl) | —OCH$_2$-(5-phenyl-2-oxooxazolidin-3-yl) |
| 2.59 | —C(O)N(CH$_3$)CH$_2$Ph | —C(O)N(C$_2$H$_5$)CH$_2$Ph | —C(O)N(C$_3$H$_7$)CH$_2$Ph |
| 2.60 | —C(O)pyridin-3-yl-5-(Ph) | —C(O)Ph-3-(CH$_2$(thiophen-2-yl)) | —C(O)Ph-3-(CH$_2$Ph) |
| 2.61 | —C(O)C(CH$_3$)$_2$OPh | —C(O)CH(C$_2$H$_5$)OPh | —C(O)CH$_2$OCH$_2$Ph |
| 2.62 | —C(O)CH$_2$O(o-PhCH$_2$OH) | —C(O)CH$_2$O(m-PhCH$_2$OH) | —C(O)CH$_2$O(p-PhCH$_2$OH) |
| 2.63 | —C(O)CH$_2$O(o-PhCOOH) | —C(O)CH$_2$O(m-PhCOOH) | —C(O)CH$_2$O(p-PhCOOH) |
| 2.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 2.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 2.66 | —OCH$_2$-(4-benzyl-2-oxooxazolidin-3-yl) | | |

TABLE 3

Formula I: A = —B(OH)$_2$; X = guanidinyl; R$^3$ = table below; R$^{11}$ = —CH$_2$CH$_2$Ph.

| | .1 | .2 | .3 |
|---|---|---|---|
| 3.1 | —C(O)Ph | —C(O)CH$_2$Ph | —C(O)CH$_2$CH$_2$Ph |
| 3.2 | —C(O)CH$_2$OPh | —C(O)CH$_2$NHPh | —C(O)CH$_2$SPh |
| 3.3 | —C(O)o-PhOH | —C(O)m-PhOH | —C(O)p-PhOH |
| 3.4 | —C(O)o-PhCH$_2$OH | —C(O)m-PhCH$_2$OH | —C(O)p-PhCH$_2$OH |
| 3.5 | —C(O)o-PhCOOH | —C(O)m-PhCOOH | —C(O)p-PhCOOH |
| 3.6 | —C(O)o-PhCH$_2$COOH | —C(O)m-PhCH$_2$COOH | —C(O)p-PhCH$_2$COOH |
| 3.7 | —C(O)naphth-1-yl | —C(O)CH$_2$(naphth-1-yl) | —C(O)CH$_2$CH$_2$(napth-1-yl) |
| 3.8 | —C(O)naphth-2-yl | —C(O)CH$_2$(naphth-2-yl) | —C(O)CH$_2$CH$_2$(napth-2-yl) |
| 3.9 | —C(O)o-biphenyl | —C(O)CH$_2$(o-biphenyl) | —C(O)CH$_2$CH$_2$(o-biphenyl) |
| 3.10 | —C(O)m-biphenyl | —C(O)CH$_2$(m-biphenyl) | —C(O)CH$_2$CH$_2$(m-biphenyl) |
| 3.12 | —C(O)p-biphenyl | —C(O)CH$_2$(p-biphenyl) | —C(O)CH$_2$CH$_2$(p-biphenyl) |
| 3.13 | —C(O)o-PhOPh | —C(O)CH$_2$(o-PhOPh) | —C(O)CH$_2$CH$_2$(o-PhOPh) |
| 3.14 | —C(O)m-PhOPh | —C(O)CH$_2$(m-PhOPh) | —C(O)CH$_2$CH$_2$(m-PhOPh) |
| 3.15 | —C(O)p-PhOPh | —C(O)CH$_2$(p-PhOPh) | —C(O)CH$_2$CH$_2$(p-PhOPh) |
| 3.16 | —C(O)o-PhNHPh | —C(O)CH$_2$(o-PhNHPh) | —C(O)CH$_2$CH$_2$(o-PhNHPh) |
| 3.17 | —C(O)m-PhNHPh | —C(O)CH$_2$(m-PhNHPh) | —C(O)CH$_2$CH$_2$(m-PhNHPh) |
| 3.18 | —C(O)p-PhNHPh | —C(O)CH$_2$(p-PhNHPh) | —C(O)CH$_2$CH$_2$(p-PhNHPh) |
| 3.19 | —C(O)o-PhSPh | —C(O)CH$_2$(o-PhSPh) | —C(O)CH$_2$CH$_2$(o-PhSPh) |
| 3.20 | —C(O)m-PhSPh | —C(O)CH$_2$(m-PhSPh) | —C(O)CH$_2$CH$_2$(m-PhSPh) |
| 3.21 | —C(O)p-PhSPh | —C(O)CH$_2$(p-PhSPh) | —C(O)CH$_2$CH$_2$(p-PhSPh) |
| 3.22 | —C(O)o-PhCH$_2$SPh | —C(O)CH$_2$(o-PhCH$_2$SPh) | —C(O)CH$_2$CH$_2$(o-PhCH$_2$SPh) |
| 3.23 | —C(O)m-PhCH$_2$SPh | —C(O)CH$_2$(m-PhCH$_2$SPh) | —C(O)CH$_2$CH$_2$(m-PhCH$_2$SPh) |
| 3.24 | —C(O)p-PhCH$_2$SPh | —C(O)CH$_2$(p-PhCH$_2$SPh) | —C(O)CH$_2$CH$_2$(p-PhCH$_2$SPh) |
| 3.25 | —C(O)adamantyl | —C(O)CH$_2$(adamantyl) | —C(O)CH$_2$CH$_2$(adamantyl) |
| 3.26 | —C(O)cyclopentyl | —C(O)CH$_2$(cyclopentyl) | —C(O)CH$_2$CH$_2$((cyclopentyl) |
| 3.27 | —C(O)cyclohexyl | —C(O)CH$_2$(cyclohexyl) | —C(O)CH$_2$CH$_2$(cyclohexyl) |
| 3.28 | —C(O)CH$_2$O(cyclopentyl) | —C(O)CH$_2$NH(cyclopentyl) | —C(O)CH$_2$S(cyclopentyl) |
| 3.29 | —C(O)CH$_2$O(cyclohexyl) | —C(O)CH$_2$NH(cyclohexyl) | —C(O)CH$_2$S(cyclohexyl) |
| 3.30 | —C(O)pyridin-2-yl | —C(O)CH$_2$(pyridin-2-yl) | —C(O)CH$_2$CH$_2$(pyridin-2-yl) |

TABLE 3-continued

Formula I: A = —B(OH)₂; X = guanidinyl; R³ = table below; R¹¹ = —CH₂CH₂Ph.

| | .1 | .2 | .3 |
|---|---|---|---|
| 3.31 | —C(O)pyridin-3-yl | —C(O)CH₂(pyridin-3-yl) | —C(O)CH₂CH₂(pyridin-3-yl) |
| 3.32 | —C(O)pyridin-4-yl | —C(O)CH₂(pyridin-4-yl) | —C(O)CH₂CH₂(pyridin-4-yl) |
| 3.33 | —C(O)furan-2-yl | —C(O)CH₂(furan-2-yl) | —C(O)CH₂CH₂(furan-2-yl) |
| 3.34 | —C(O)furan-3-yl | —C(O)CH₂(furan-3-yl) | —C(O)CH₂CH₂(furan-3-yl) |
| 3.35 | —C(O)thiophen-2-yl | —C(O)CH₂(thiophen-2-yl) | —C(O)CH₂CH₂(thiophen-2-yl) |
| 3.36 | —C(O)thiophen-2-yl | —C(O)CH₂(thiophen-2-yl) | —C(O)CH₂CH₂(thiophen-2-yl) |
| 3.37 | —C(O)imidazo-2-yl | —C(O)CH₂(imidazo-2-yl) | —C(O)CH₂CH₂(imidazo-2-yl) |
| 3.38 | —C(O)oxazo-2-yl | —C(O)CH₂(oxazo-2-yl) | —C(O)CH₂CH₂(oxazo-2-yl) |
| 3.39 | —C(O)thioazo-2-yl | —C(O)CH₂(thioazo-2-yl) | —C(O)CH₂CH₂(thioazo-2-yl) |
| 3.40 | —C(O)benzofuran-2-yl | —C(O)CH₂(benzofuran-2-yl) | —C(O)CH₂CH₂(benzofuran-2-yl) |
| 3.41 | —C(O)benzofuran-3-yl | —C(O)CH₂(benzofuran-3-yl) | —C(O)CH₂CH₂(benzofuran-3-yl) |
| 3.42 | —C(O)benzothiophen-2-yl | —C(O)CH₂(benzothiophen-2-yl) | —C(O)CH₂CH₂(benzothiophen-2-yl |
| 3.43 | —C(O)thiophen-2-yl | —C(O)CH₂(thiophen-2-yl) | —C(O)CH₂CH₂(thiophen-2-yl) |
| 3.44 | —C(O)benzimidazo-2-yl | —C(O)CH₂(benzimidazo-2-yl) | —C(O)CH₂CH₂(benzimidazo-2-yl) |
| 3.45 | —C(O)benzoxazo-2-yl | —C(O)CH₂(benzoxazo-2-yl) | —C(O)CH₂CH₂(benzoxazo-2-yl) |
| 3.46 | —C(O)benzothiazo-2-yl | —C(O)CH₂(benzothiazo-2-yl) | —C(O)CH₂CH₂(benzothiazo-2-yl) |
| 3.47 | —C(O)p-Ph(P(O)Ph₃) | —C(O)m-Ph(P(O)Ph₃) | —C(O)p-Ph(P(O)Ph₃) |
| 3.48 | —C(O)Ph-2-(fluoren-9-yl) | —C(O)Ph-3-(fluoren-9-yl) | —C(O)Ph-4-(fluoren-9-yl) |
| 3.49 | —C(O)N-indolin-2-one | —C(O)indolin-2-yl | —C(O)indol-2-yl |
| 3.50 | —C(O)C(CH₃)₂NHSO₂(naphth-2-yl) | —C(O)cyclopentyl-2-(Ph) | —C(O)cyclohexyl-2-Ph) |
| 3.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 3.52 | —C(O)tetrahydronaphth-1-yl | —C(O)tetrahydronaphth-2-yl | —C(O)cyclopropyl-2,2-(Ph₂) |
| 3.53 | —C(O)tetrahydroisoquinolin-1-yl | —C(O)tetrahydroisoquinolin-3-yl | —C(O)CH₂((2-oxo)indolin-3-yl) |
| 3.54 | —C(O)CH₂(N-benzimidazol-2-one) | —C(O)CH₂(N-benzoxazol-2-one) | —C(O)CH₂(N-benzothiazol-2-one) |
| 3.55 | —C(O)CH₂(N-dihydroimidazol-2-one) | —C(O)CH₂(N-dihydrooxazol-2-one) | —C(O)CH₂(N-dihydrothiazol-2-one) |
| 3.56 | | | |
| 3.57 | | | |
| 3.58 | | | |
| 3.59 | —C(O)N(CH₃)CH₂Ph | —C(O)N(C₂H₅)CH₂Ph | —C(O)N(C₃H₇)CH₂Ph |
| 3.60 | —C(O)pyridin-3-yl-5-(Ph) | —C(O)Ph-3-(CH₂(thiophen-2-yl)) | —C(O)Ph-3-(CH₂Ph) |
| 3.61 | —C(O)C(CH₃)₂OPh | —C(O)CH(C₂H₅)OPh | —C(O)CH₂OCH₂Ph |
| 3.62 | —C(O)CH₂O(o-PhCH₂OH) | —C(O)CH₂O(m-PhCH₂OH) | —C(O)CH₂O(p-PhCH₂OH) |
| 3.63 | —C(O)CH₂O(o-PhCOOH) | —C(O)CH₂O(m-PhCOOH) | —C(O)CH₂O(p-PhCOOH) |
| 3.64 | —C(O)CH₂O(o-PhCOOCH₃) | —C(O)CH₂O(m-PhCOOCH₃) | —C(O)CH₂O(p-PhCOOCH₃) |

TABLE 3-continued

Formula I: A = —B(OH)$_2$; X = guanidinyl; R$^3$ = table below; R$^{11}$ = —CH$_2$CH$_2$Ph.

| | .1 | .2 | .3 |
|---|---|---|---|
| 3.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 3.66 | —OC(O)CH$_2$-N(oxazolidin-2-one-4-yl-CH$_2$Ph) | | |

TABLE 4

Formula I: A = —B(OH)$_2$; X = guanidinyl; R$^3$ = table below; R$^{11}$ = —Ph.

| | .1 | .2 | .3 |
|---|---|---|---|
| 4.1 | —C(O)Ph | —C(O)CH$_2$Ph | —C(O)CH$_2$CH$_2$Ph |
| 4.2 | —C(O)CH$_2$OPh | —C(O)CH$_2$NHPh | —C(O)CH$_2$SPh |
| 4.3 | —C(O)o-PhOH | —C(O)m-PhOH | —C(O)p-PhOH |
| 4.4 | —C(O)o-PhCH$_2$OH | —C(O)m-PhCH$_2$OH | —C(O)p-PhCH$_2$OH |
| 4.5 | —C(O)o-PhCOOH | —C(O)m-PhCOOH | —C(O)p-PhCOOH |
| 4.6 | —C(O)o-PhCH$_2$COOH | —C(O)m-PhCH$_2$COOH | —C(O)p-PhCH$_2$COOH |
| 4.7 | —C(O)naphth-1-yl | —C(O)CH$_2$(naphth-1-yl) | —C(O)CH$_2$CH$_2$(napth-1-yl) |
| 4.8 | —C(O)naphth-2-yl | —C(O)CH$_2$(naphth-2-yl | —C(O)CH$_2$CH$_2$(napth-2-yl) |
| 4.9 | —C(O)o-biphenyl | —C(O)CH$_2$(o-biphenyl) | —C(O)CH$_2$CH$_2$(o-biphenyl) |
| 4.10 | —C(O)m-biphenyl | —C(O)CH$_2$(m-biphenyl) | —C(O)CH$_2$CH$_2$(m-biphenyl) |
| 4.12 | —C(O)p-biphenyl | —C(O)CH$_2$(p-biphenyl) | —C(O)CH$_2$CH$_2$(p-biphenyl) |
| 4.13 | —C(O)o-PhOPh | —C(O)CH$_2$(o-PhOPh) | —C(O)CH$_2$CH$_2$(o-PhOPh) |
| 4.14 | —C(O)m-PhOPh | —C(O)CH$_2$(m-PhOPh) | —C(O)CH$_2$CH$_2$(m-PhOPh) |
| 4.15 | —C(O)p-PhOPh | —C(O)CH$_2$(p-PhOPh) | —C(O)CH$_2$CH$_2$(p-PhOPh) |
| 4.16 | —C(O)o-PhNHPh | —C(O)CH$_2$(o-PhNHPh) | —C(O)CH$_2$CH$_2$(o-PhNHPh) |
| 4.17 | —C(O)m-PhNHPh | —C(O)CH$_2$(m-PhNHPh) | —C(O)CH$_2$CH$_2$(m-PhNHPh) |
| 4.18 | —C(O)p-PhNHPh | —C(O)CH$_2$(p-PhNHPh) | —C(O)CH$_2$CH$_2$(p-PhNHPh) |
| 4.19 | —C(O)o-PhSPh | —C(O)CH$_2$(o-PhSPh) | —C(O)CH$_2$CH$_2$(o-PhSPh) |
| 4.20 | —C(O)m-PhSPh | —C(O)CH$_2$(m-PhSPh) | —C(O)CH$_2$CH$_2$(m-PhSPh) |
| 4.21 | —C(O)p-PhSPh | —C(O)CH$_2$(p-PhSPh) | —C(O)CH$_2$CH$_2$(p-PhSPh) |
| 4.22 | —C(O)o-PhCH$_2$SPh | —C(O)CH$_2$(o-PhCH$_2$SPh) | —C(O)CH$_2$CH$_2$(o-PhCH$_2$SPh) |
| 4.23 | —C(O)m-PhCH$_2$SPh | —C(O)CH$_2$(m-PhCH$_2$SPh) | —C(O)CH$_2$CH$_2$(m-PhCH$_2$SPh) |
| 4.24 | —C(O)p-PhCH$_2$SPh | —C(O)CH$_2$(p-PhCH$_2$SPh) | —C(O)CH$_2$CH$_2$(p-PhCH$_2$SPh) |
| 4.25 | —C(O)adamantyl | —C(O)CH$_2$(adamantyl) | —C(O)CH$_2$CH$_2$(adamantyl) |
| 4.26 | —C(O)cyclopentyl | —C(O)CH$_2$(cyclopentyl) | —C(O)CH$_2$CH$_2$((cyclopentyl) |
| 4.27 | —C(O)cyclohexyl | —C(O)CH$_2$(cyclohexyl) | —C(O)CH$_2$CH$_2$(cyclohexyl) |
| 4.28 | —C(O)CH$_2$O(cyclopentyl) | —C(O)CH$_2$NH(cyclopentyl) | —C(O)CH$_2$S(cyclopentyl) |
| 4.29 | —C(O)CH$_2$O(cyclohexyl) | —C(O)CH$_2$NH(cyclohexyl) | —C(O)CH$_2$S(cyclohexyl) |
| 4.30 | —C(O)pyridin-2-yl | —C(O)CH$_2$(pyridin-2-yl) | —C(O)CH$_2$CH$_2$(pyridin-2-yl) |
| 4.31 | —C(O)pyridin-3-yl | —C(O)CH$_2$(pyridin-3-yl) | —C(O)CH$_2$CH$_2$(pyridin-3-yl) |
| 4.32 | —C(O)pyridin-4-yl | —C(O)CH$_2$(pyridin-4-yl) | —C(O)CH$_2$CH$_2$(pyridin-4-yl) |
| 4.33 | —C(O)furan-2-yl | —C(O)CH$_2$(furan-2-yl) | —C(O)CH$_2$CH$_2$(furan-2-yl) |
| 4.34 | —C(O)furan-3-yl | —C(O)CH$_2$(furan-3-yl) | —C(O)CH$_2$CH$_2$(furan-3-yl) |
| 4.35 | —C(O)thiophen-2-yl | —C(O)CH$_2$(thiophen-2-yl) | —C(O)CH$_2$CH$_2$(thiophen-2-yl) |
| 4.36 | —C(O)thiophen-2-yl | —C(O)CH$_2$(thiophen-2-yl) | —C(O)CH$_2$CH$_2$(thiophen-2-yl) |
| 4.37 | —C(O)imidazo-2-yl | —C(O)CH$_2$(imidazo-2-yl) | —C(O)CH$_2$CH$_2$(imidazo-2-yl) |
| 4.38 | —C(O)oxazo-2-yl | —C(O)CH$_2$(oxazo-2-yl) | —C(O)CH$_2$CH$_2$(oxazo-2-yl) |
| 4.39 | —C(O)thioazo-2-yl | —C(O)CH$_2$(thioazo-2-yl) | —C(O)CH$_2$CH$_2$(thioazo-2-yl) |
| 4.40 | —C(O)benzofuran-2-yl | —C(O)CH$_2$(benzofuran-2-yl) | —C(O)CH$_2$CH$_2$(benzofuran-2-yl) |
| 4.41 | —C(O)benzofuran-3-yl | —C(O)CH$_2$(benzofuran-3-yl) | —C(O)CH$_2$CH$_2$(benzofuran-3-yl) |
| 4.42 | —C(O)benzothiophen-2-yl | —C(O)CH$_2$(benzothiophen-2-yl) | —C(O)CH$_2$CH$_2$(benzothiophen-2-yl) |
| 4.43 | —C(O)thiophen-2-yl | —C(O)CH$_2$(thiophen-2-yl) | —C(O)CH$_2$CH$_2$(thiophen-2-yl) |
| 4.44 | —C(O)benzimidazo-2-yl | —C(O)CH$_2$(benzimidazo-2-yl) | —C(O)CH$_2$CH$_2$(benzimidazo-2-yl) |
| 4.45 | —C(O)benzoxazo-2-yl | —C(O)CH$_2$(benzoxazo-2-yl) | —C(O)CH$_2$CH$_2$(benzoxazo-2-yl) |
| 4.46 | —C(O)benzothiazo-2-yl | —C(O)CH$_2$(benzothiazo-2-yl) | —C(O)CH$_2$CH$_2$(benzothiazo-2-yl) |
| 4.47 | —C(O)o-Ph(P(O)Ph$_3$) | —C(O)m-Ph(P(O)Ph$_3$) | —C(O)p-Ph(P(O)Ph$_3$) |
| 4.48 | —C(O)Ph-2-(fluoren-9-yl) | —C(O)Ph-3-(fluoren-9-yl) | —C(O)Ph-4-(fluoren-9-yl) |
| 4.49 | —C(O)N-indolin-2-one | —C(O)indolin-2-yl | —C(O)indol-2-yl |

TABLE 4-continued

Formula I: A = —B(OH)$_2$; X = guanidinyl; R$^3$ = table below; R$^{11}$ = —Ph.

| | .1 | .2 | .3 |
|---|---|---|---|
| 4.50 | —C(O)C(CH$_3$)$_2$NHSO$_2$(naphth-2-yl) | —C(O)cyclopentyl-2-(Ph) | —C(O)cyclohexyl-2-Ph) |
| 4.51 | —C(O)pyrrolidin-3-yl-4-Ph) | —C(O)tetrahydrofuran-3-yl-4-(Ph) | —C(O)tetrahydrothiophen-3-yl-4-(Ph) |
| 4.52 | —C(O)tetrahydronaphth-1-yl | —C(O)tetrahydronaphth-2-yl | —C(O)cyclopropyl-2,-2-(Ph$_2$) |
| 4.53 | —C(O)tetrahydroisoquinolin-1-yl | —C(O)tetrahydroisoquinolin-3-yl | —C(O)CH$_2$((-2-oxo)indolin-3-yl) |
| 4.54 | —C(O)CH$_2$(N-benzimidazol-2-one) | —C(O)CH$_2$(N-benzoxazol-2-one) | —C(O)CH$_2$(N-benzothiazol-2-one) |
| 4.55 | —C(O)CH$_2$(N-dihydroimidazol 2-one) | —C(O)CH$_2$(N-dihydrooxazol-2-one) | —C(O)CH$_2$(N-dihydrothiazol-2-one) |
| 4.56 | *[structure]* | *[structure]* | *[structure]* |
| 4.57 | *[structure]* | *[structure]* | *[structure]* |
| 4.58 | *[structure]* | *[structure]* | *[structure]* |
| 4.59 | —C(O)N(CH$_3$)CH$_2$Ph | —C(O)N(C$_2$H$_5$)CH$_2$Ph | —C(O)N(C$_3$H$_7$)CH$_2$Ph |
| 4.60 | —C(O)pyridin-3-yl-5-(Ph) | —C(O)Ph-3-(CH$_2$(thiophen-2-yl)) | —C(O)Ph-3-(CH$_2$Ph) |
| 4.61 | —C(O)C(CH$_3$)$_2$OPh | —C(O)CH(C$_2$H$_5$)OPh | —C(O)CH$_2$OCH$_2$Ph |
| 4.62 | —C(O)CH$_2$O(o-PhCH$_2$OH) | —C(O)CH$_2$O(m-PhCH$_2$OH) | —C(O)CH$_2$O(p-PhCH$_2$OH) |
| 4.63 | —C(O)CH$_2$O(o-PhCOOH) | —C(O)CH$_2$O(m-PhCOOH) | —C(O)CH$_2$O(p-PhCOOH) |
| 4.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 4.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 4.66 | *[structure]* | | |

TABLE 5

Formula I: A = —B(OH)$_2$; X = guanidinyl; R$^3$ = table below; R$^{11}$ = —CH$_2$(naphth-2-yl).

| | .1 | .2 | .3 |
|---|---|---|---|
| 5.1 | —C(O)Ph | —C(O)CH$_2$Ph | —C(O)CH$_2$CH$_2$Ph |
| 5.2 | —C(O)CH$_2$OPh | —C(O)CH$_2$NHPh | —C(O)CH$_2$SPh |
| 5.3 | —C(O)o-PhOH | —C(O)m-PhOH | —C(O)p-PhOH |
| 5.4 | —C(O)o-PhCH$_2$OH | —C(O)m-PhCH$_2$OH | —C(O)p-PhCH$_2$OH |
| 5.5 | —C(O)o-PhCOOH | —C(O)m-PhCOOH | —C(O)p-PhCOOH |
| 5.6 | —C(O)o-PhCH$_2$COOH | —C(O)m-PhCH$_2$COOH | —C(O)p-PhCH$_2$COOH |
| 5.7 | —C(O)naphth-1-yl | —C(O)CH$_2$(napth-1-yl) | —C(O)CH$_2$CH$_2$(napth-1-yl) |
| 5.8 | —C(O)naphth-2-yl | —C(O)CH$_2$(naphth-2-yl) | —C(O)CH$_2$CH$_2$(napth-2-yl) |
| 5.9 | —C(O)o-biphenyl | —C(O)CH$_2$(o-biphenyl) | —C(O)CH$_2$CH$_2$(o-biphenyl) |
| 5.10 | —C(O)m-biphenyl | —C(O)CH$_2$(m-biphenyl) | —C(O)CH$_2$CH$_2$(m-biphenyl) |
| 5.12 | —C(O)p-biphenyl | —C(O)CH$_2$(p-biphenyl) | —C(O)CH$_2$CH$_2$(p-biphenyl) |
| 5.13 | —C(O)o-PhOPh | —C(O)CH$_2$(o-PhOPh) | —C(O)CH$_2$CH$_2$(o-PhOPh) |
| 5.14 | —C(O)m-PhOPh | —C(O)CH$_2$(m-PhOPh) | —C(O)CH$_2$CH$_2$(m-PhOPh) |
| 5.15 | —C(O)p-PhOPh | —C(O)CH$_2$(p-PhOPh) | —C(O)CH$_2$CH$_2$(p-PhOPh) |
| 5.16 | —C(O)o-PhNHPh | —C(O)CH$_2$(o-PhNHPh) | —C(O)CH$_2$CH$_2$(o-PhNHPh) |
| 5.17 | —C(O)m-PhNHPh | —C(O)CH$_2$(m-PhNHPh) | —C(O)CH$_2$CH$_2$(m-PhNHPh) |
| 5.18 | —C(O)p-PhNHPh | —C(O)CH$_2$(p-PhNHPh) | —C(O)CH$_2$CH$_2$(p-PhNHPh) |
| 5.19 | —C(O)o-PhSPh | —C(O)CH$_2$(o-PhSPh) | —C(O)CH$_2$CH$_2$(o-PhSPh) |
| 5.20 | —C(O)m-PhSPh | —C(O)CH$_2$(m-PhSPh) | —C(O)CH$_2$CH$_2$(m-PhSPh) |
| 5.21 | —C(O)p-PhSPh | —C(O)CH$_2$(p-PhSPh) | —C(O)CH$_2$CH$_2$(p-PhSPh) |
| 5.22 | —C(O)o-PhCH$_2$SPh | —C(O)CH$_2$(o-PhCH$_2$SPh) | —C(O)CH$_2$CH$_2$(o-PhCH$_2$SPh) |
| 5.23 | —C(O)m-PhCH$_2$SPh | —C(O)CH$_2$(m-PhCH$_2$SPh) | —C(O)CH$_2$CH$_2$(m-PhCH$_2$SPh) |
| 5.24 | —C(O)p-PhCH$_2$SPh | —C(O)CH$_2$(p-PhCH$_2$SPh) | —C(O)CH$_2$CH$_2$(p-PhCH$_2$SPh) |
| 5.25 | —C(O)adamantyl | —C(O)CH$_2$(adamantyl) | —C(O)CH$_2$CH$_2$(adamantyl) |
| 5.26 | —C(O)cyclopentyl | —C(O)CH$_2$(cyclopentyl) | —C(O)CH$_2$CH$_2$((cyclopentyl) |
| 5.27 | —C(O)cyclohexyl | —C(O)CH$_2$(cyclohexyl) | —C(O)CH$_2$CH$_2$(cyclohexyl) |
| 5.28 | —C(O)CH$_2$O(cyclopentyl) | —C(O)CH$_2$NH(cyclopentyl) | —C(O)CH$_2$S(cyclopentyl) |
| 5.29 | —C(O)CH$_2$O(cyclohexyl) | —C(O)CH$_2$NH(cyclohexyl) | —C(O)CH$_2$S(cyclohexyl) |
| 5.30 | —C(O)pyridin-2-yl | —C(O)CH$_2$(pyridin-2-yl) | —C(O)CH$_2$CH$_2$(pyridin-2-yl) |
| 5.31 | —C(O)pyridin-3-yl | —C(O)CH$_2$(pyridin-3-yl) | —C(O)CH$_2$CH$_2$(pyridin-3-yl) |
| 5.32 | —C(O)pyridin-4-yl | —C(O)CH$_2$(pyridin-4-yl) | —C(O)CH$_2$CH$_2$(pyridin-4-yl) |
| 5.33 | —C(O)furan-2-yl | —C(O)CH$_2$(furan-2-yl) | —C(O)CH$_2$CH$_2$(furan-2-yl) |
| 5.34 | —C(O)furan-3-yl | —C(O)CH$_2$(furan-3-yl) | —C(O)CH$_2$CH$_2$(furan-3-yl) |
| 5.35 | —C(O)thiophen-2-yl | —C(O)CH$_2$(thiophen-2-yl) | —C(O)CH$_2$CH$_2$(thiophen-2-yl) |
| 5.36 | —C(O)thiophen-2-yl | —C(O)CH$_2$(thiophen-2-yl) | —C(O)CH$_2$CH$_2$(thiophen-2-yl) |
| 5.37 | —C(O)imidazo-2-yl | —C(O)CH$_2$(imidazo-2-yl) | —C(O)CH$_2$CH$_2$(imidazo-2-yl) |
| 5.38 | —C(O)oxazo-2-yl | —C(O)CH$_2$(oxazo-2-yl) | —C(O)CH$_2$CH$_2$(oxazo-2-yl) |
| 5.39 | —C(O)thioazo-2-yl | —C(O)CH$_2$(thioazo-2-yl) | —C(O)CH$_2$CH$_2$(thioazo-2-yl) |
| 5.40 | —C(O)benzofuran-2-yl | —C(O)CH$_2$(benzofuran-2-yl) | —C(O)CH$_2$CH$_2$(benzofuran-2-yl) |
| 5.41 | —C(O)benzofuran-3-yl | —C(O)CH$_2$(benzofuran-3-yl) | —C(O)CH$_2$CH$_2$(benzofuran-3-yl) |
| 5.42 | —C(O)benzothiophen-2-yl | —C(O)CH$_2$(benzothiophen-2-yl) | —C(O)CH$_2$CH$_2$(benzothiophen-2-yl) |
| 5.43 | —C(O)thiophen-2-yl | —C(O)CH$_2$(thiophen-2-yl) | —C(O)CH$_2$CH$_2$(thiophen-2-yl) |
| 5.44 | —C(O)benzimidazo-2-yl | —C(O)CH$_2$(benzimidazo-2-yl) | —C(O)CH$_2$CH$_2$(benzimidazo-2-yl) |
| 5.45 | —C(O)benzoxazo-2-yl | —C(O)CH$_2$(benzoxazo-2-yl) | —C(O)CH$_2$CH$_2$(benzoxazo-2-yl) |
| 5.46 | —C(O)benzothiazo-2-yl | —C(O)CH$_2$(benzothiazo-2-yl) | —C(O)CH$_2$CH$_2$(benzothiazo-2-yl) |
| 5.47 | —C(O)o-Ph(P(O)Ph$_3$) | —C(O)m-Ph(P(O)Ph$_3$) | —C(O)p-Ph(P(O)Ph$_3$) |
| 5.48 | —C(O)Ph-2-(fluoren-9-yl) | —C(O)Ph-3-(fluoren-9-yl) | —C(O)Ph-4-(fluoren-9-yl) |
| 5.49 | —C(O)N-indolin-2-one | —C(O)indolin-2-yl | —C(O)indol-2-yl |
| 5.50 | —C(O)C(CH$_3$)$_2$NHSO$_2$(naphth-2-yl) | —C(O)cyclopentyl-2-(Ph) | —C(O)cyclohexyl-2-(Ph) |
| 5.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 5.52 | —C(O)tetrahydronaphth-1-yl | —C(O)tetrahydronaphth-2-yl | —C(O)cyclopropyl-2,2-(Ph$_2$) |
| 5.53 | —C(O)tetrahydroisoquinolin-1-yl | —C(O)tetrahydroisoquinolin-3-yl | —C(O)CH$_2$((2-oxo)indolin-3-yl) |
| 5.54 | —C(O)CH$_2$(N-benzimidazol-2-one) | —C(O)CH$_2$(N-benzoxazol-2-one) | —C(O)CH$_2$(N-benzothiazol-2-one) |
| 5.55 | —C(O)CH$_2$(N-dihydroimidazol-2-one) | —C(O)CH$_2$(N-dihydrooxazol-2-one) | —C(O)CH$_2$(N-dihydrothiazol-2-one) |

TABLE 5-continued

Formula I: A = —B(OH)₂; X = guanidinyl; R³ = table below; R¹¹ = —CH₂(naphth-2-yl).

| | .1 | .2 | .3 |
|---|---|---|---|
| 5.56 | (structure) | (structure) | (structure) |
| 5.57 | (structure) | (structure) | (structure) |
| 5.58 | (structure) | (structure) | (structure) |
| 5.59 | —C(O)N(CH₃)CH₂Ph | —C(O)N(C₂H₅)CH₂Ph | —C(O)N(C₃H₇)CH₂Ph |
| 5.60 | —C(O)pyridin-3-yl-5-(Ph) | —C(O)Ph-3-(CH₂(thiophen-2-yl)) | —C(O)Ph-3-(CH₂Ph) |
| 5.61 | —C(O)C(CH₃)₂OPh | —C(O)CH(C₂H₅)OPh | —C(O)CH₂OCH₂Ph |
| 5.62 | —C(O)CH₂O(o-PhCH₂OH) | —C(O)CH₂O(m-PhCH₂OH) | —C(O)CH₂O(p-PhCH₂OH) |
| 5.63 | —C(O)CH₂O(o-PhCOOH) | —C(O)CH₂O(m-PhCOOH) | —C(O)CH₂O(p-PhCOOH) |
| 5.64 | —C(O)CH₂O(o-PhCOOCH₃) | —C(O)CH₂O(m-PhCOOCH₃) | —C(O)CH₂O(p-PhCOOCH₃) |
| 5.65 | —C(O)CH₂O(o-PhCH₂COOH) | —C(O)CH₂O(m-PhCH₂COOH) | —C(O)CH₂O(p-PhCH₂COOH) |
| 5.66 | (structure) | | |

TABLE 6

Formula I: A = —B(OH)₂; X = —CH₂NH₂; R³ = table below; R¹¹ = CH₃

| | .1 | .2 | .3 |
|---|---|---|---|
| 6.1 | —C(O)Ph | —C(O)CH₂Ph | —C(O)CH₂CH₂Ph |
| 6.2 | —C(O)CH₂OPh | —C(O)CH₂NHPh | —C(O)CH₂SPh |
| 6.3 | —C(O)o-PhOH | —C(O)m-PhOH | —C(O)p-PhOH |
| 6.4 | —C(O)o-PhCH₂OH | —C(O)m-PhCH₂OH | —C(O)p-PhCH₂OH |

TABLE 6-continued

Formula I: A = —B(OH)$_2$; X = —CH$_2$NH$_2$; R$^3$ = table below; R$^{11}$ = CH$_3$

| | .1 | .2 | .3 |
|---|---|---|---|
| 6.5 | —C(O)o-PhCOOH | —C(O)m-PhCOOH | —C(O)p-PhCOOH |
| 6.6 | —C(O)o-PhCH$_2$COOH | —C(O)m-PhCH$_2$COOH | —C(O)p-PhCH$_2$COOH |
| 6.7 | —C(O)naphth-1-yl | —C(O)CH$_2$(naphth-1-yl) | —C(O)CH$_2$CH$_2$(napth-1-yl) |
| 6.8 | —C(O)naphth-2-yl | —C(O)CH$_2$(naphth-2-yl) | —C(O)CH$_2$CH$_2$(napth-2-yl) |
| 6.9 | —C(O)o-biphenyl | —C(O)CH$_2$(o-biphenyl) | —C(O)CH$_2$CH$_2$(o-biphenyl) |
| 6.10 | —C(O)m-biphenyl | —C(O)CH$_2$(m-biphenyl) | —C(O)CH$_2$CH$_2$(m-biphenyl) |
| 6.12 | —C(O)p-biphenyl | —C(O)CH$_2$(p-biphenyl) | —C(O)CH$_2$CH$_2$(p-biphenyl) |
| 6.13 | —C(O)o-PhOPh | —C(O)CH$_2$(o-PhOPh) | —C(O)CH$_2$CH$_2$(o-PhOPh) |
| 6.14 | —C(O)m-PhOPh | —C(O)CH$_2$(m-PhOPh) | —C(O)CH$_2$CH$_2$(m-PhOPh) |
| 6.15 | —C(O)p-PhOPh | —C(O)CH$_2$(p-PhOPh) | —C(O)CH$_2$CH$_2$(p-PhOPh) |
| 6.16 | —C(O)o-PhNHPh | —C(O)CH$_2$(o-PhNHPh) | —C(O)CH$_2$CH$_2$(o-PhNHPh) |
| 6.17 | —C(O)m-PhNHPh | —C(O)CH$_2$(m-PhNHPh) | —C(O)CH$_2$CH$_2$(m-PhNHPh) |
| 6.18 | —C(O)p-PhNHPh | —C(O)CH$_2$(p-PhNHPh) | —C(O)CH$_2$CH$_2$(p-PhNHPh) |
| 6.19 | —C(O)o-PhSPh | —C(O)CH$_2$(o-PhSPh) | —C(O)CH$_2$CH$_2$(o-PhSPh) |
| 6.20 | —C(O)m-PhSPh | —C(O)CH$_2$(m-PhSPh) | —C(O)CH$_2$CH$_2$(m-PhSPh) |
| 6.21 | —C(O)p-PhSPh | —C(O)CH$_2$(p-PhSPh) | —C(O)CH$_2$CH$_2$(p-PhSPh) |
| 6.22 | —C(O)o-PhCH$_2$SPh | —C(O)CH$_2$(o-PhCH$_2$SPh) | —C(O)CH$_2$CH$_2$(o-PhCH$_2$SPh) |
| 6.23 | —C(O)m-PhCH$_2$SPh | —C(O)CH$_2$(m-PhCH$_2$SPh) | —C(O)CH$_2$CH$_2$(m-PhCH$_2$SPh) |
| 6.24 | —C(O)p-PhCH$_2$SPh | —C(O)CH$_2$(p-PhCH$_2$SPh) | —C(O)CH$_2$CH$_2$(p-PhCH$_2$SPh) |
| 6.25 | —C(O)adamantyl | —C(O)CH$_2$(adamantyl) | —C(O)CH$_2$CH$_2$(adamantyl) |
| 6.26 | —C(O)cyclopentyl | —C(O)CH$_2$(cyclopentyl) | —C(O)CH$_2$CH$_2$((cyclopentyl) |
| 6.27 | —C(O)cyclohexyl | —C(O)CH$_2$(cyclohexyl) | —C(O)CH$_2$CH$_2$(cyclohexyl) |
| 6.28 | —C(O)CH$_2$O(cyclopentyl) | —C(O)CH$_2$NH(cyclopentyl) | —C(O)CH$_2$S(cyclopentyl) |
| 6.29 | —C(O)CH$_2$O(cyclohexyl) | —C(O)CH$_2$NH(cyclohexyl) | —C(O)CH$_2$S(cyclohexyl) |
| 6.30 | —C(O)pyridin-2-yl | —C(O)CH$_2$(pyridin-2-yl) | —C(O)CH$_2$CH$_2$(pyridin-2-yl) |
| 6.31 | —C(O)pyridin-3-yl | —C(O)CH$_2$(pyridin-3-yl) | —C(O)CH$_2$CH$_2$(pyridin-3-yl) |
| 6.32 | —C(O)pyridin-4-yl | —C(O)CH$_2$(pyridin-4-yl) | —C(O)CH$_2$CH$_2$(pyridin-4-yl) |
| 6.33 | —C(O)furan-2-yl | —C(O)CH$_2$(furan-2-yl) | —C(O)CH$_2$CH$_2$(furan-2-yl) |
| 6.34 | —C(O)furan-3-yl | —C(O)CH$_2$(furan-3-yl) | —C(O)CH$_2$CH$_2$(furan-3-yl) |
| 6.35 | —C(O)thiophen-2-yl | —C(O)CH$_2$(thiophen-2-yl) | —C(O)CH$_2$CH$_2$(thiophen-2-yl) |
| 6.36 | —C(O)thiophen-2-yl | —C(O)CH$_2$(thiophen-2-yl) | —C(O)CH$_2$CH$_2$(thiophen-2-yl) |
| 6.37 | —C(O)imidazo-2-yl | —C(O)CH$_2$(imidazo-2-yl) | —C(O)CH$_2$CH$_2$(imidazo-2-yl) |
| 6.38 | —C(O)oxazo-2-yl | —C(O)CH$_2$(oxazo-2-yl) | —C(O)CH$_2$CH$_2$(oxazo-2-yl) |
| 6.39 | —C(O)thioazo-2-yl | —C(O)CH$_2$(thioazo-2-yl) | —C(O)CH$_2$CH$_2$(thioazo-2-yl) |
| 6.40 | —C(O)benzofuran-2-yl | —C(O)CH$_2$(benzofuran-2-yl) | —C(O)CH$_2$CH$_2$(benzofuran-2-yl) |
| 6.41 | —C(O)benzofuran-3-yl | —C(O)CH$_2$(benzofuran-3-yl) | —C(O)CH$_2$CH$_2$(benzofuran-3-yl) |
| 6.42 | —C(O)benzothiophen-2-yl | —C(O)CH$_2$(benzothiophen-2-yl) | —C(O)CH$_2$CH$_2$(benzothiophen-2-yl) |
| 6.43 | —C(O)thiophen-2-yl | —C(O)CH$_2$(thiophen-2-yl) | —C(O)CH$_2$CH$_2$(thiophen-2-yl) |
| 6.44 | —C(O)benzimidazo-2-yl | —C(O)CH$_2$(benzimidazo-2-yl) | —C(O)CH$_2$CH$_2$(benzimidazo-2-yl) |
| 6.45 | —C(O)benzoxazo-2-yl | —C(O)CH$_2$(benzoxazo-2-yl) | —C(O)CH$_2$CH$_2$(benzoxazo-2-yl) |
| 6.46 | —C(O)benzothiazo-2-yl | —C(O)CH$_2$(benzothiazo-2-yl) | —C(O)CH$_2$CH$_2$(benzothiazo-2-yl) |
| 6.47 | —C(O)o-Ph(P(O)Ph$_3$) | —C(O)m-Ph(P(O)Ph$_3$) | —C(O)p-Ph(P(O)Ph$_3$) |
| 6.48 | —C(O)Ph-2-(fluoren-9-yl) | —C(O)Ph-3-(fluoren-9-yl) | —C(O)Ph-4-(fluoren-9-yl) |
| 6.49 | —C(O)N-indolin-2-one | —C(O)indolin-2-yl | —C(O)indol-2-yl |
| 6.50 | —C(O)C(CH$_3$)$_2$NHSO$_2$(naphth-2-yl) | —C(O)cyclopentyl-2-(Ph) | —C(O)cyclohexyl-2-(Ph) |
| 6.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 6.52 | —C(O)tetrahydronaphth-1-yl | —C(O)tetrahydronaphth-2-yl | —C(O)cyclopropyl-2,2-(Ph$_2$) |
| 6.53 | —C(O)tetrahydroisoquinolin-1-yl | —C(O)tetrahydroisoquinolin-3-yl | —C(O)CH$_2$((2-oxo)indolin-3-yl) |
| 6.54 | —C(O)CH$_2$(N-benzimidazol-2-one) | —C(O)CH$_2$(N-benzoxazol-2-one) | —C(O)CH$_2$(N-benzothiazol-2-one) |
| 6.55 | —C(O)CH$_2$(N-dihydroimidazol-2-one) | —C(O)CH$_2$(N-dihydrooxazol-2-one) | —C(O)CH$_2$(N-dihydrothiazol-2-one) |

6.56

6.57

TABLE 6-continued

Formula I: A = —B(OH)$_2$; X = —CH$_2$NH$_2$; R$^3$ = table below; R$^{11}$ = CH$_3$

| | .1 | .2 | .3 |
|---|---|---|---|
| 6.58 | [structure: —OC-CH$_2$-N-(3-benzylidene-2-oxoindolin-1-yl)] | [structure: —OC-CH$_2$-N(4-phenylpiperazin-1-yl)] | [structure: —OC-CH$_2$-N-(5-phenyl-2-oxo-oxazolidin-3-yl)] |
| 6.59 | —C(O)N(CH$_3$)CH$_2$Ph | —C(O)N(C$_2$H$_5$)CH$_2$Ph | —C(O)N(C$_3$H$_7$)CH$_2$Ph |
| 6.60 | —C(O)pyridin-3-yl-5-(Ph) | —C(O)Ph-3-(CH$_2$(thiophen-2-yl)) | —C(O)Ph-3-(CH$_2$Ph) |
| 6.61 | —C(O)C(CH$_3$)$_2$OPh | —C(O)CH(C$_2$H$_5$)OPh | —C(O)CH$_2$OCH$_2$Ph |
| 6.62 | —C(O)CH$_2$O(o-PhCH$_2$OH) | —C(O)CH$_2$O(m-PhCH$_2$OH) | —C(O)CH$_2$O(p-PhCH$_2$OH) |
| 6.63 | —C(O)CH$_2$O(o-PhCOOH) | —C(O)CH$_2$O(m-PhCOOH) | —C(O)CH$_2$O(p-PhCOOH) |
| 6.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 6.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 6.66 | [structure: —OC-CH$_2$-N-(4-benzyl-2-oxo-oxazolidin-3-yl)] | | |

TABLE 7

Formula I: A = —B(OH)$_2$; X = —CH$_2$NH$_2$; R$^3$ = table below; R$^{11}$ = —CH$_2$(p-PhOH).

| | .1 | .2 | .3 |
|---|---|---|---|
| 7.1 | —C(O)Ph | —C(O)CH$_2$Ph | —C(O)CH$_2$CH$_2$Ph |
| 7.2 | —C(O)CH$_2$OPh | —C(O)CH$_2$NHPh | —C(O)CH$_2$SPh |
| 7.3 | —C(O)o-PhOH | —C(O)m-PhOH | —C(O)p-PhOH |
| 7.4 | —C(O)o-PhCH$_2$OH | —C(O)m-PhCH$_2$OH | —C(O)p-PhCH$_2$OH |
| 7.5 | —C(O)o-PhCOOH | —C(O)m-PhCOOH | —C(O)p-PhCOOH |
| 7.6 | —C(O)o-PhCH$_2$COOH | —C(O)m-PhCH$_2$COOH | —C(O)p-PhCH$_2$COOH |
| 7.7 | —C(O)naphth-1-yl | —C(O)CH$_2$(naphth-1-yl) | —C(O)CH$_2$CH$_2$(napth-1-yl) |
| 7.8 | —C(O)naphth-2-yl | —C(O)CH$_2$(naphth-2-yl) | —C(O)CH$_2$CH$_2$(napth-2-yl) |
| 7.9 | —C(O)o-biphenyl | —C(O)CH$_2$(o-biphenyl) | —C(O)CH$_2$CH$_2$(o-biphenyl) |
| 7.10 | —C(O)m-biphenyl | —C(O)CH$_2$(m-biphenyl) | —C(O)CH$_2$CH$_2$(m-biphenyl) |
| 7.12 | —C(O)p-biphenyl | —C(O)CH$_2$(p-biphenyl) | —C(O)CH$_2$CH$_2$(p-biphenyl) |
| 7.13 | —C(O)o-PhOPh | —C(O)CH$_2$(o-PhOPh) | —C(O)CH$_2$CH$_2$(o-PhOPh) |
| 7.14 | —C(O)m-PhOPh | —C(O)CH$_2$(m-PhOPh) | —C(O)CH$_2$CH$_2$(m-PhOPh) |
| 7.15 | —C(O)p-PhOPh | —C(O)CH$_2$(p-PhOPh) | —C(O)CH$_2$CH$_2$(p-PhOPh) |
| 7.16 | —C(O)o-PhNHPh | —C(O)CH$_2$(o-PhNHPh) | —C(O)CH$_2$CH$_2$(o-PhNHPh) |
| 7.17 | —C(O)m-PhNHPh | —C(O)CH$_2$(m-PhNHPh) | —C(O)CH$_2$CH$_2$(m-PhNHPh) |
| 7.18 | —C(O)p-PhNHPh | —C(O)CH$_2$(p-PhNHPh) | —C(O)CH$_2$CH$_2$(p-PhNHPh) |
| 7.19 | —C(O)o-PhSPh | —C(O)CH$_2$(o-PhSPh) | —C(O)CH$_2$CH$_2$(o-PhSPh) |
| 7.20 | —C(O)m-PhSPh | —C(O)CH$_2$(m-PhSPh) | —C(O)CH$_2$CH$_2$(m-PhSPh) |
| 7.21 | —C(O)p-PhSPh | —C(O)CH$_2$(p-PhSPh) | —C(O)CH$_2$CH$_2$(p-PhSPh) |
| 7.22 | —C(O)o-PhCH$_2$SPh | —C(O)CH$_2$(o-PhCH$_2$SPh) | —C(O)CH$_2$CH$_2$(o-PhCH$_2$SPh) |
| 7.23 | —C(O)m-PhCH$_2$SPh | —C(O)CH$_2$(m-PhCH$_2$SPh) | —C(O)CH$_2$CH$_2$(m-PhCH$_2$SPh) |
| 7.24 | —C(O)p-PhCH$_2$SPh | —C(O)CH$_2$(p-PhCH$_2$SPh) | —C(O)CH$_2$CH$_2$(p-PhCH$_2$SPh) |
| 7.25 | —C(O)adamantyl | —C(O)CH$_2$(adamantyl) | —C(O)CH$_2$CH$_2$(adamantyl) |
| 7.26 | —C(O)cyclopentyl | —C(O)CH$_2$(cyclopentyl) | —C(O)CH$_2$CH$_2$((cyclopentyl) |
| 7.27 | —C(O)cyclohexyl | —C(O)CH$_2$(cyclohexyl) | —C(O)CH$_2$CH$_2$(cyclohexyl) |
| 7.28 | —C(O)CH$_2$O(cyclopentyl) | —C(O)CH$_2$NH(cyclopentyl) | —C(O)CH$_2$S(cyclopentyl) |
| 7.29 | —C(O)CH$_2$O(cyclohexyl) | —C(O)CH$_2$NH(cyclohexyl) | —C(O)CH$_2$S(cyclohexyl) |
| 7.30 | —C(O)pyridin-2-yl | —C(O)CH$_2$(pyridin-2-yl) | —C(O)CH$_2$CH$_2$(pyridin-2-yl) |

TABLE 7-continued

Formula I: A = —B(OH)₂; X = —CH₂NH₂; R³ = table below; R¹¹ = —CH₂(p-PhOH).

| | .1 | .2 | .3 |
|---|---|---|---|
| 7.31 | —C(O)pyridin-3-yl | —C(O)CH₂(pyridin-3-yl) | —C(O)CH₂CH₂(pyridin-3-yl) |
| 7.32 | —C(O)pyridin-4-yl | —C(O)CH₂(pyridin-4-yl) | —C(O)CH₂CH₂(pyridin-4-yl) |
| 7.33 | —C(O)furan-2-yl | —C(O)CH₂(furan-2-yl) | —C(O)CH₂CH₂(furan-2-yl) |
| 7.34 | —C(O)furan-3-yl | —C(O)CH₂(furan-3-yl) | —C(O)CH₂CH₂(furan-3-yl) |
| 7.35 | —C(O)thiophen-2-yl | —C(O)CH₂(thiophen-2-yl) | —C(O)CH₂CH₂(thiophen-2-yl) |
| 7.36 | —C(O)thiophen-2-yl | —C(O)CH₂(thiophen-2-yl) | —C(O)CH₂CH₂(thiophen-2-yl) |
| 7.37 | —C(O)imidazo-2-yl | —C(O)CH₂(imidazo-2-yl) | —C(O)CH₂CH₂(imidazo-2-yl) |
| 7.38 | —C(O)oxazo-2-yl | —C(O)CH₂(oxazo-2-yl) | —C(O)CH₂CH₂(oxazo-2-yl) |
| 7.39 | —C(O)thioazo-2-yl | —C(O)CH₂(thioazo-2-yl) | —C(O)CH₂CH₂(thioazo-2-yl) |
| 7.40 | —C(O)benzofuran-2-yl | —C(O)CH₂(benzofuran-2-yl) | —C(O)CH₂CH₂(benzofuran-2-yl) |
| 7.41 | —C(O)benzofuran-3-yl | —C(O)CH₂(benzofuran-3-yl) | —C(O)CH₂CH₂(benzofuran-3-yl) |
| 7.42 | —C(O)benzothiophen-2-yl | —C(O)CH₂(benzothiophen-2-yl) | —C(O)CH₂CH₂(benzothiophen-2-yl) |
| 7.43 | —C(O)thiophen-2-yl | —C(O)CH₂(thiophen-2-yl) | —C(O)CH₂CH₂(thiophen-2-yl) |
| 7.44 | —C(O)benzimidazo-2-yl | —C(O)CH₂(benzimidazo-2-yl) | —C(O)CH₂CH₂(benzimidazo-2-yl) |
| 7.45 | —C(O)benzoxazo-2-yl | —C(O)CH₂(benzoxazo-2-yl) | —C(O)CH₂CH₂(benzoxazo-2-yl) |
| 7.46 | —C(O)benzothiazo-2-yl | —C(O)CH₂(benzothiazo-2-yl) | —C(O)CH₂CH₂(benzothiazo-2-yl) |
| 7.47 | —C(O)o-Ph(P(O)Ph₃) | —C(O)m-Ph(P(O)Ph₃) | —C(O)p-Ph(P(O)Ph₃) |
| 7.48 | —C(O)Ph-2-(fluoren-9-yl) | —C(O)Ph-3-(fluoren-9-yl) | —C(O)Ph-4-(fluoren-9-yl) |
| 7.49 | —C(O)N-indolin-2-one | —C(O)indolin-2-yl | —C(O)indol-2-yl |
| 7.50 | —C(O)C(CH₃)₂NHSO₂(naphth-2-yl) | —C(O)cyclopentyl-2-(Ph) | —C(O)cyclohexyl-2-(Ph) |
| 7.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 7.52 | —C(O)tetrahydronaphth-1-yl | —C(O)tetrahydronaphth-2-yl | —C(O)cyclopropyl-2,2-(Ph₂) |
| 7.53 | —C(O)tetrahydroisoquinolin-1-yl | —C(O)tetrahydroisoquinolin-3-yl | —C(O)CH₂((2-oxo)indolin-3-yl) |
| 7.54 | —C(O)CH₂(N-benzimidazol-2-one) | —C(O)CH₂(N-benzoxazol-2-one) | —C(O)CH₂(N-benzothiazol-2-one) |
| 7.55 | —C(O)CH₂(N-dihydroimidazol-2-one) | —C(O)CH₂(N-dihydrooxazol-2-one) | —C(O)CH₂(N-dihydrothiazol-2-one) |
| 7.56 | [structure] | [structure] | [structure] |
| 7.57 | [structure] | [structure] | [structure] |
| 7.58 | [structure] | [structure] | [structure] |
| 7.59 | —C(O)N(CH₃)CH₂Ph | —C(O)N(C₂H₅)CH₂Ph | —C(O)N(C₃H₇)CH₂Ph |
| 7.60 | —C(O)pyridin-3-yl-5-(Ph) | —C(O)Ph-3-(CH₂(thiophen-2-yl)) | —C(O)Ph-3-(CH₂Ph) |
| 7.61 | —C(O)C(CH₃)₂OPh | —C(O)CH(C₂H₅)OPh | —C(O)CH₂OCH₂Ph |
| 7.62 | —C(O)CH₂O(o-PhCH₂OH) | —C(O)CH₂O(m-PhCH₂OH) | —C(O)CH₂O(p-PhCH₂OH) |
| 7.63 | —C(O)CH₂O(o-PhCOOH) | —C(O)CH₂O(m-PhCOOH) | —C(O)CH₂O(p-PhCOOH) |
| 7.64 | —C(O)CH₂O(o-PhCOOCH₃) | —C(O)CH₂O(m-PhCOOCH₃) | —C(O)CH₂O(p-PhCOOCH₃) |

TABLE 7-continued

Formula I: A = —B(OH)$_2$; X = —CH$_2$NH$_2$; R$^3$ = table below; R$^{11}$ = —CH$_2$(p-PhOH).

| | .1 | .2 | .3 |
|---|---|---|---|
| 7.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 7.66 | —OCH$_2$-(4-benzyl-oxazolidin-2-one) | | |

TABLE 8

Formula I: A = —B(OH)$_2$; X = CH$_2$NH$_2$; R$^3$ = table below; R$^{11}$ = —CH$_2$CH$_2$Ph.

| | .1 | .2 | .3 |
|---|---|---|---|
| 8.1 | —C(O)Ph | —C(O)CH$_2$Ph | —C(O)CH$_2$CH$_2$Ph |
| 8.2 | —C(O)CH$_2$OPh | —C(O)CH$_2$NHPh | —C(O)CH$_2$SPh |
| 8.3 | —C(O)o-PhOH | —C(O)m-PhOH | —C(O)p-PhOH |
| 8.4 | —C(O)o-PhCH$_2$OH | —C(O)m-PhCH$_2$OH | —C(O)p-PhCH$_2$OH |
| 8.5 | —C(O)o-PhCOOH | —C(O)m-PhCOOH | —C(O)p-PhCOOH |
| 8.6 | —C(O)o-PhCH$_2$COOH | —C(O)m-PhCH$_2$COOH | —C(O)p-PhCH$_2$COOH |
| 8.7 | —C(O)naphth-1-yl | —C(O)CH$_2$(naphth-1-yl) | —C(O)CH$_2$CH$_2$(napth-1-yl) |
| 8.8 | —C(O)naphth-2-yl | —C(O)CH$_2$(naphth-2-yl) | —C(O)CH$_2$CH$_2$(napth-2-yl) |
| 8.9 | —C(O)o-biphenyl | —C(O)CH$_2$(o-biphenyl) | —C(O)CH$_2$CH$_2$(o-biphenyl) |
| 8.10 | —C(O)m-biphenyl | —C(O)CH$_2$(m-biphenyl) | —C(O)CH$_2$CH$_2$(m-biphenyl) |
| 8.12 | —C(O)p-biphenyl | —C(O)CH$_2$(p-biphenyl) | —C(O)CH$_2$CH$_2$(p-biphenyl) |
| 8.13 | —C(O)o-PhOPh | —C(O)CH$_2$(o-PhOPh) | —C(O)CH$_2$CH$_2$(o-PhOPh) |
| 8.14 | —C(O)m-PhOPh | —C(O)CH$_2$(m-PhOPh) | —C(O)CH$_2$CH$_2$(m-PhOPh) |
| 8.15 | —C(O)p-PhOPh | —C(O)CH$_2$(p-PhOPh) | —C(O)CH$_2$CH$_2$(p-PhOPh) |
| 8.16 | —C(O)o-PhNHPh | —C(O)CH$_2$(o-PhNHPh) | —C(O)CH$_2$CH$_2$(o-PhNHPh) |
| 8.17 | —C(O)m-PhNHPh | —C(O)CH$_2$(m-PhNHPh) | —C(O)CH$_2$CH$_2$(m-PhNHPh) |
| 8.18 | —C(O)p-PhNHPh | —C(O)CH$_2$(p-PhNHPh) | —C(O)CH$_2$CH$_2$(p-PhNHPh) |
| 8.19 | —C(O)o-PhSPh | —C(O)CH$_2$(o-PhSPh) | —C(O)CH$_2$CH$_2$(o-PhSPh) |
| 8.20 | —C(O)m-PhSPh | —C(O)CH$_2$(m-PhSPh) | —C(O)CH$_2$CH$_2$(m-PhSPh) |
| 8.21 | —C(O)p-PhSPh | —C(O)CH$_2$(p-PhSPh) | —C(O)CH$_2$CH$_2$(p-PhSPh) |
| 8.22 | —C(O)o-PhCH$_2$SPh | —C(O)CH$_2$(o-PhCH$_2$SPh) | —C(O)CH$_2$CH$_2$(o-PhCH$_2$SPh) |
| 8.23 | —C(O)m-PhCH$_2$SPh | —C(O)CH$_2$(m-PhCH$_2$SPh) | —C(O)CH$_2$CH$_2$(m-PhCH$_2$SPh) |
| 8.24 | —C(O)p-PhCH$_2$SPh | —C(O)CH$_2$(p-PhCH$_2$SPh) | —C(O)CH$_2$CH$_2$(p-PhCH$_2$SPh) |
| 8.25 | —C(O)adamantyl | —C(O)CH$_2$(adamantyl) | —C(O)CH$_2$CH$_2$(adamantyl) |
| 8.26 | —C(O)cyclopentyl | —C(O)CH$_2$(cyclopentyl) | —C(O)CH$_2$CH$_2$((cyclopentyl) |
| 8.27 | —C(O)cyclohexyl | —C(O)CH$_2$(cyclohexyl) | —C(O)CH$_2$CH$_2$(cyclohexyl) |
| 8.28 | —C(O)CH$_2$O(cyclopentyl) | —C(O)CH$_2$NH(cyclopentyl) | —C(O)CH$_2$S(cyclopentyl) |
| 8.29 | —C(O)CH$_2$O(cyclohexyl) | —C(O)CH$_2$NH(cyclohexyl) | —C(O)CH$_2$S(cyclohexyl) |
| 8.30 | —C(O)pyridin-2-yl | —C(O)CH$_2$(pyridin-2-yl) | —C(O)CH$_2$CH$_2$(pyridin-2-yl) |
| 8.31 | —C(O)pyridin-3-yl | —C(O)CH$_2$(pyridin-3-yl) | —C(O)CH$_2$CH$_2$(pyridin-3-yl) |
| 8.32 | —C(O)pyridin-4-yl | —C(O)CH$_2$(pyridin-4-yl) | —C(O)CH$_2$CH$_2$(pyridin-4-yl) |
| 8.33 | —C(O)furan-2-yl | —C(O)CH$_2$(furan-2-yl) | —C(O)CH$_2$CH$_2$(furan-2-yl) |
| 8.34 | —C(O)furan-3-yl | —C(O)CH$_2$(furan-3-yl) | —C(O)CH$_2$CH$_2$(furan-3-yl) |
| 8.35 | —C(O)thiophen-2-yl | —C(O)CH$_2$(thiophen-2-yl) | —C(O)CH$_2$CH$_2$(thiophen-2-yl) |
| 8.36 | —C(O)thiophen-2-yl | —C(O)CH$_2$(thiophen-2-yl) | —C(O)CH$_2$CH$_2$(thiophen-2-yl) |
| 8.37 | —C(O)imidazo-2-yl | —C(O)CH$_2$(imidazo-2-yl) | —C(O)CH$_2$CH$_2$(imidazo-2-yl) |
| 8.38 | —C(O)oxazo-2-yl | —C(O)CH$_2$(oxazo-2-yl) | —C(O)CH$_2$CH$_2$(oxazo-2-yl) |
| 8.39 | —C(O)thioazo-2-yl | —C(O)CH$_2$(thioazo-2-yl) | —C(O)CH$_2$CH$_2$(thioazo-2-yl) |
| 8.40 | —C(O)benzofuran-2-yl | —C(O)CH$_2$(benzofuran-2-yl) | —C(O)CH$_2$CH$_2$(benzofuran-2-yl) |
| 8.41 | —C(O)benzofuran-3-yl | —C(O)CH$_2$(benzofuran-3-yl) | —C(O)CH$_2$CH$_2$(benzofuran-3-yl) |
| 8.42 | —C(O)benzothiophen-2-yl | —C(O)CH$_2$(benzothiophen-2-yl) | —C(O)CH$_2$CH$_2$(benzothiophen-2-yl) |
| 8.43 | —C(O)thiophen-2-yl | —C(O)CH$_2$(thiophen-2-yl) | —C(O)CH$_2$CH$_2$(thiophen-2-yl) |
| 8.44 | —C(O)benzimidazo-2-yl | —C(O)CH$_2$(benzimidazo-2-yl) | —C(O)CH$_2$CH$_2$(benzimidazo-2-yl) |
| 8.45 | —C(O)benzoxazo-2-yl | —C(O)CH$_2$(benzoxazo-2-yl) | —C(O)CH$_2$CH$_2$(benzoxazo-2-yl) |
| 8.46 | —C(O)benzothiazo-2-yl | —C(O)CH$_2$(benzothiazo-2-yl) | —C(O)CH$_2$CH$_2$(benzothiazo-2-yl) |
| 8.47 | —C(O)o-Ph(P(O)Ph$_3$) | —C(O)m-Ph(P(O)Ph$_3$) | —C(O)p-Ph(P(O)Ph$_3$) |
| 8.48 | —C(O)Ph-2-(fluoren-9-yl) | —C(O)Ph-3-(fluoren-9-yl) | —C(O)Ph-4-(fluoren-9-yl) |

TABLE 8-continued

Formula I: A = —B(OH)$_2$; X = CH$_2$NH$_2$; R$^3$ = table below; R$^{11}$ = —CH$_2$CH$_2$Ph.

|  | .1 | .2 | .3 |
|---|---|---|---|
| 8.49 | —C(O)N-indolin-2-one | —C(O)indolin-2-yl | —C(O)indol-2-yl |
| 8.50 | —C(O)C(CH$_3$)$_2$NHSO$_2$(naphth-2-yl) | —C(O)cyclopentyl-2-(Ph) | —C(O)cyclohexyl-2-(Ph) |
| 8.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 8.52 | —C(O)tetrahydronaphth-1-yl | —C(O)tetrahydronaphth-2-yl | —C(O)cyclopropyl-2,2-(Ph$_2$) |
| 8.53 | —C(O)tetrahydroisoquinolin-1-yl | —C(O)tetrahydroisoquinolin-3-yl | —C(O)CH$_2$((2-oxo)indolin-3-yl) |
| 8.54 | —C(O)CH$_2$(N-benzimidazol-2-one) | —C(O)CH$_2$(N-benzoxazol-2-one) | —C(O)CH$_2$(N-benzothiazol-2-one) |
| 8.55 | —C(O)CH$_2$(N-dihydroimidazol-2-one) | —C(O)CH$_2$(N-dihydrooxazol-2-one) | —C(O)CH$_2$(N-dihydrothiazol-2-one) |

8.56

8.57

8.58

| 8.59 | —C(O)N(CH$_3$)CH$_2$Ph | —C(O)N(C$_2$H$_5$)CH$_2$Ph | —C(O)N(C$_3$H$_7$)CH$_2$Ph |
|---|---|---|---|
| 8.60 | —C(O)pyridin-3-yl-5-(Ph) | —C(O)Ph-3-(CH$_2$(thiophen-2-yl)) | —C(O)Ph-3-(CH$_2$Ph) |
| 8.61 | —C(O)C(CH$_3$)$_2$OPh | —C(O)CH(C$_2$H$_5$)OPh | —C(O)CH$_2$OCH$_2$Ph |
| 8.62 | —C(O)CH$_2$O(o-PhCH$_2$OH) | —C(O)CH$_2$O(m-PhCH$_2$OH) | —C(O)CH$_2$O(p-PhCH$_2$OH) |
| 8.63 | —C(O)CH$_2$O(o-PhCOOH) | —C(O)CH$_2$O(m-PhCOOH) | —C(O)CH$_2$O(p-PhCOOH) |
| 8.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 8.65 | —C(O)CH$_2$O(o-PhCH$_2$COOH) | —C(O)CH$_2$O(m-PhCH$_2$COOH) | —C(O)CH$_2$O(p-PhCH$_2$COOH) |

8.66

TABLE 9

Formula I: A = —B(OH)$_2$; X = CH$_2$NH$_2$; R$^3$ = table below; R$^{11}$ = —Ph.

| | .1 | .2 | .3 |
|---|---|---|---|
| 9.1 | —C(O)Ph | —C(O)CH$_2$Ph | —C(O)CH$_2$CH$_2$Ph |
| 9.2 | —C(O)CH$_2$OPh | —C(O)CH$_2$NHPh | —C(O)CH$_2$SPh |
| 9.3 | —C(O)o-PhOH | —C(O)m-PhOH | —C(O)p-PhOH |
| 9.4 | —C(O)o-PhCH$_2$OH | —C(O)m-PhCH$_2$OH | —C(O)p-PhCH$_2$OH |
| 9.5 | —C(O)o-PhCOOH | —C(O)m-PhCOOH | —C(O)p-PhCOOH |
| 9.6 | —C(O)o-PhCH$_2$COOH | —C(O)m-PhCH$_2$COOH | —C(O)p-PhCH$_2$COOH |
| 9.7 | —C(O)naphth-1-yl | —C(O)CH$_2$(naphth-1-yl) | —C(O)CH$_2$CH$_2$(napth-1-yl) |
| 9.8 | —C(O)naphth-2-yl | —C(O)CH$_2$(naphth-2-yl) | —C(O)CH$_2$CH$_2$(napth-2-yl) |
| 9.9 | —C(O)o-biphenyl | —C(O)CH$_2$(o-biphenyl) | —C(O)CH$_2$CH$_2$(o-biphenyl) |
| 9.10 | —C(O)m-biphenyl | —C(O)CH$_2$(m-biphenyl) | —C(O)CH$_2$CH$_2$(m-biphenyl) |
| 9.12 | —C(O)p-biphenyl | —C(O)CH$_2$(p-biphenyl) | —C(O)CH$_2$CH$_2$(p-biphenyl) |
| 9.13 | —C(O)o-PhOPh | —C(O)CH$_2$(o-PhOPh) | —C(O)CH$_2$CH$_2$(o-PhOPh) |
| 9.14 | —C(O)m-PhOPh | —C(O)CH$_2$(m-PhOPh) | —C(O)CH$_2$CH$_2$(m-PhOPh) |
| 9.15 | —C(O)p-PhOPh | —C(O)CH$_2$(p-PhOPh) | —C(O)CH$_2$CH$_2$(p-PhOPh) |
| 9.16 | —C(O)o-PhNHPh | —C(O)CH$_2$(o-PhNHPh) | —C(O)CH$_2$CH$_2$(o-PhNHPh) |
| 9.17 | —C(O)m-PhNHPh | —C(O)CH$_2$(m-PhNHPh) | —C(O)CH$_2$CH$_2$(m-PhNHPh) |
| 9.18 | —C(O)p-PhNHPh | —C(O)CH$_2$(p-PhNHPh) | —C(O)CH$_2$CH$_2$(p-PhNHPh) |
| 9.19 | —C(O)o-PhSPh | —C(O)CH$_2$(o-PhSPh) | —C(O)CH$_2$CH$_2$(o-PhSPh) |
| 9.20 | —C(O)m-PhSPh | —C(O)CH$_2$(m-PhSPh) | —C(O)CH$_2$CH$_2$(m-PhSPh) |
| 9.21 | —C(O)p-PhSPh | —C(O)CH$_2$(p-PhSPh) | —C(O)CH$_2$CH$_2$(p-PhSPh) |
| 9.22 | —C(O)o-PhCH$_2$SPh | —C(O)CH$_2$(o-PhCH$_2$SPh) | —C(O)CH$_2$CH$_2$(o-PhCH$_2$SPh) |
| 9.23 | —C(O)m-PhCH$_2$SPh | —C(O)CH$_2$(m-PhCH$_2$SPh) | —C(O)CH$_2$CH$_2$(m-PhCH$_2$SPh) |
| 9.24 | —C(O)p-PhCH$_2$SPh | —C(O)CH$_2$(p-PhCH$_2$SPh) | —C(O)CH$_2$CH$_2$(p-PhCH$_2$SPh) |
| 9.25 | —C(O)adamantyl | —C(O)CH$_2$(adamantyl) | —C(O)CH$_2$CH$_2$(adamantyl) |
| 9.26 | —C(O)cyclopentyl | —C(O)CH$_2$(cyclopentyl) | —C(O)CH$_2$CH$_2$((cyclopentyl) |
| 9.27 | —C(O)cyclohexyl | —C(O)CH$_2$(cyclohexyl) | —C(O)CH$_2$CH$_2$(cyclohexyl) |
| 9.28 | —C(O)CH$_2$O(cyclopentyl) | —C(O)CH$_2$NH(cyclopentyl) | —C(O)CH$_2$S(cyclopentyl) |
| 9.29 | —C(O)CH$_2$O(cyclohexyl) | —C(O)CH$_2$NH(cyclohexyl) | —C(O)CH$_2$S(cyclohexyl) |
| 9.30 | —C(O)pyridin-2-yl | —C(O)CH$_2$(pyridin-2-yl) | —C(O)CH$_2$CH$_2$(pyridin-2-yl) |
| 9.31 | —C(O)pyridin-3-yl | —C(O)CH$_2$(pyridin-3-yl) | —C(O)CH$_2$CH$_2$(pyridin-3-yl) |
| 9.32 | —C(O)pyridin-4-yl | —C(O)CH$_2$(pyridin-4-yl) | —C(O)CH$_2$CH$_2$(pyridin-4-yl) |
| 9.33 | —C(O)furan-2-yl | —C(O)CH$_2$(furan-2-yl) | —C(O)CH$_2$CH$_2$(furan-2-yl) |
| 9.34 | —C(O)furan-3-yl | —C(O)CH$_2$(furan-3-yl) | —C(O)CH$_2$CH$_2$(furan-3-yl) |
| 9.35 | —C(O)thiophen-2-yl | —C(O)CH$_2$(thiophen-2-yl) | —C(O)CH$_2$CH$_2$(thiophen-2-yl) |
| 9.36 | —C(O)thiophen-2-yl | —C(O)CH$_2$(thiophen-2-yl) | —C(O)CH$_2$CH$_2$(thiophen-2-yl) |
| 9.37 | —C(O)imidazo-2-yl | —C(O)CH$_2$(imidazo-2-yl) | —C(O)CH$_2$CH$_2$(imidazo-2-yl) |
| 9.38 | —C(O)oxazo-2-yl | —C(O)CH$_2$(oxazo-2-yl) | —C(O)CH$_2$CH$_2$(oxazo-2-yl) |
| 9.39 | —C(O)thioazo-2-yl | —C(O)CH$_2$(thioazo-2-yl) | —C(O)CH$_2$CH$_2$(thioazo-2-yl) |
| 9.40 | —C(O)benzofuran-2-yl | —C(O)CH$_2$(benzofuran-2-yl) | —C(O)CH$_2$CH$_2$(benzofuran-2-yl) |
| 9.41 | —C(O)benzofuran-3-yl | —C(O)CH$_2$(benzofuran-3-yl) | —C(O)CH$_2$CH$_2$(benzofuran-3-yl) |
| 9.42 | —C(O)benzothiophen-2-yl | —C(O)CH$_2$(benzothiophen-2-yl) | —C(O)CH$_2$CH$_2$(benzothiophen-2-yl) |
| 9.43 | —C(O)thiophen-2-yl | —C(O)CH$_2$(thiophen-2-yl) | —C(O)CH$_2$CH$_2$(thiophen-2-yl) |
| 9.44 | —C(O)benzimidazo-2-yl | —C(O)CH$_2$(benzimidazo-2-yl) | —C(O)CH$_2$CH$_2$(benzimidazo-2-yl) |
| 9.45 | —C(O)benzoxazo-2-yl | —C(O)CH$_2$(benzoxazo-2-yl) | —C(O)CH$_2$CH$_2$(benzoxazo-2-yl) |
| 9.46 | —C(O)benzothiazo-2-yl | —C(O)CH$_2$(benzothiazo-2-yl) | —C(O)CH$_2$CH$_2$(benzothiazo-2-yl) |
| 9.47 | —C(O)o-Ph(P(O)Ph$_3$) | —C(O)m-Ph(P(O)Ph$_3$) | —C(O)p-Ph(P(O)Ph$_3$) |
| 9.48 | —C(O)Ph-2-(fluoren-9-yl) | —C(O)Ph-3-(fluoren-9-yl) | —C(O)Ph-4-(fluoren-9-yl) |
| 9.49 | —C(O)N-indolin-2-one | —C(O)indolin-2-yl | —C(O)indol-2-yl |
| 9.50 | —C(O)C(CH$_3$)$_2$NHSO$_2$(naphth-2-yl) | —C(O)cyclopentyl-2-(Ph) | —C(O)cyclohexyl-2-(Ph) |
| 9.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 9.52 | —C(O)tetrahydronaphth-1-yl | —C(O)tetrahydronaphth-2-yl | —C(O)cyclopropyl-2,2-(Ph$_2$) |
| 9.53 | —C(O)tetrahydroisoquinolin-1-yl | —C(O)tetrahydroisoquinolin-3-yl | —C(O)CH$_2$((2-oxo)indolin-3-yl) |
| 9.54 | —C(O)CH$_2$(N-benzimidazol-2-one) | —C(O)CH$_2$(N-benzoxazol-2-one) | —C(O)CH$_2$(N-benzothiazol-2-one) |
| 9.55 | —C(O)CH$_2$(N-dihydroimidazol-2-one) | —C(O)CH$_2$(N-dihydrooxazol-2-one) | —C(O)CH$_2$(N-dihydrothiazol-2-one) |

9.56

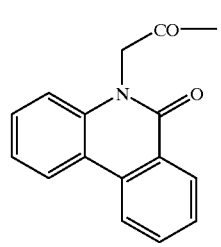 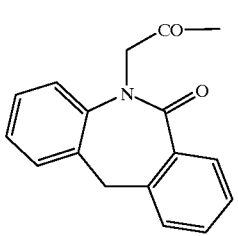 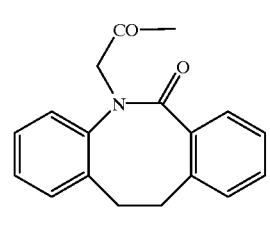

TABLE 9-continued

Formula I: A = —B(OH)₂; X = CH₂NH₂; R³ = table below; R¹¹ = —Ph.

| | .1 | .2 | .3 |
|---|---|---|---|
| 9.57 | ![structure] | ![structure] | ![structure] |
| 9.58 | ![structure] | ![structure] | ![structure] |
| 9.59 | —C(O)N(CH₃)CH₂Ph | —C(O)N(C₂H₅)CH₂Ph | —C(O)N(C₃H₇)CH₂Ph |
| 9.60 | —C(O)pyridin-3-yl-5-(Ph) | —C(O)Ph-3-(CH₂(thiophen-2-yl)) | —C(O)Ph-3-(CH₂Ph) |
| 9.61 | —C(O)C(CH₃)₂OPh | —C(O)CH(C₂H₅)OPh | —C(O)CH₂OCH₂Ph |
| 9.62 | —C(O)CH₂O(o-PhCH₂OH) | —C(O)CH₂O(m-PhCH₂OH) | —C(O)CH₂O(p-PhCH₂OH) |
| 9.63 | —C(O)CH₂O(o-PhCOOH) | —C(O)CH₂O(m-PhCOOH) | —C(O)CH₂O(p-PhCOOH) |
| 9.64 | —C(O)CH₂O(o-PhCOOCH₃) | —C(O)CH₂O(m-PhCOOCH₃) | —C(O)CH₂O(p-PhCOOCH₃) |
| 9.65 | —C(O)CH₂O(o-PhCH₂COOH) | —C(O)CH₂O(m-PhCH₂COOH) | —C(O)CH₂O(p-PhCH₂COOH) |
| 9.66 | ![structure] | | |

TABLE 10

Formula I: A = —B(OH)₂; X = —CH₂NH₂; R³ = table below; R¹¹ = —CH₂(naphth-2-yl)

| | .1 | .2 | .3 |
|---|---|---|---|
| 10.1 | —C(O)Ph | —C(O)CH₂Ph | —C(O)CH₂CH₂Ph |
| 10.2 | —C(O)CH₂OPh | —C(O)CH₂NHPh | —C(O)CH₂SPh |
| 10.3 | —C(O)o-PhOH | —C(O)m-PhOH | —C(O)p-PhOH |
| 10.4 | —C(O)o-PhCH₂OH | —C(O)m-PhCH₂OH | —C(O)p-PhCH₂OH |
| 10.5 | —C(O)o-PhCOOH | —C(O)m-PhCOOH | —C(O)p-PhCOOH |
| 10.6 | —C(O)o-PhCH₂COOH | —C(O)m-PhCH₂COOH | —C(O)p-PhCH₂COOH |
| 10.7 | —C(O)naphth-1-yl | —C(O)CH₂(naphth-1-yl) | —C(O)CH₂CH₂(napth-1-yl) |
| 10.8 | —C(O)naphth-2-yl | —C(O)CH₂(naphth-2-yl) | —C(O)CH₂CH₂(napth-2-yl) |
| 10.9 | —C(O)o-biphenyl | —C(O)CH₂(o-biphenyl) | —C(O)CH₂CH₂(o-biphenyl) |
| 10.10 | —C(O)m-biphenyl | —C(O)CH₂(m-biphenyl) | —C(O)CH₂CH₂(m-biphenyl) |
| 10.12 | —C(O)p-biphenyl | —C(O)CH₂(p-biphenyl) | —C(O)CH₂CH₂(p-biphenyl) |
| 10.13 | —C(O)o-PhOPh | —C(O)CH₂(o-PhOPh) | —C(O)CH₂CH₂(o-PhOPh) |
| 10.14 | —C(O)m-PhOPh | —C(O)CH₂(m-PhOPh) | —C(O)CH₂CH₂(m-PhOPh) |
| 10.15 | —C(O)p-PhOPh | —C(O)CH₂(p-PhOPh) | —C(O)CH₂CH₂(p-PhOPh) |
| 10.16 | —C(O)o-PhNHPh | —C(O)CH₂(o-PhNHPh) | —C(O)CH₂CH₂(o-PhNHPh) |
| 10.17 | —C(O)m-PhNHPh | —C(O)CH₂(m-PhNHPh) | —C(O)CH₂CH₂(m-PhNHPh) |
| 10.18 | —C(O)p-PhNHPh | —C(O)CH₂(p-PhNHPh) | —C(O)CH₂CH₂(p-PhNHPh) |
| 10.19 | —C(O)o-PhSPh | —C(O)CH₂(o-PhSPh) | —C(O)CH₂CH₂(o-PhSPh) |

TABLE 10-continued

Formula I: A = —B(OH)₂; X = —CH₂NH₂; R³ = table below; R¹¹ = —CH₂(naphth-2-yl)

| | .1 | .2 | .3 |
|---|---|---|---|
| 10.20 | —C(O)m-PhSPh | —C(O)CH₂(m-PhSPh) | —C(O)CH₂CH₂(m-PhSPh) |
| 10.21 | —C(O)p-PhSPh | —C(O)CH₂(p-PhSPh) | —C(O)CH₂CH₂(p-PhSPh) |
| 10.22 | —C(O)o-PhCH₂SPh | —C(O)CH₂(o-PhCH₂SPh) | —C(O)CH₂CH₂(o-PhCH₂SPh) |
| 10.23 | —C(O)m-PhCH₂SPh | —C(O)CH₂(m-PhCH₂SPh) | —C(O)CH₂CH₂(m-PhCH₂SPh) |
| 10.24 | —C(O)p-PhCH₂SPh | —C(O)CH₂(p-PhCH₂SPh) | —C(O)CH₂CH₂(p-PhCH₂SPh) |
| 10.25 | —C(O)adamantyl | —C(O)CH₂(adamantyl) | —C(O)CH₂CH₂(adamantyl) |
| 10.26 | —C(O)cyclopentyl | —C(O)CH₂(cyclopentyl) | —C(O)CH₂CH₂((cyclopentyl) |
| 10.27 | —C(O)cyclohexyl | —C(O)CH₂(cyclohexyl) | —C(O)CH₂CH₂(cyclohexyl) |
| 10.28 | —C(O)CH₂O(cyclopentyl) | —C(O)CH₂NH(cyclopentyl) | —C(O)CH₂S(cyclopentyl) |
| 10.29 | —C(O)CH₂O(cyclohexyl) | —C(O)CH₂NH(cyclohexyl) | —C(O)CH₂S(cyclohexyl) |
| 10.30 | —C(O)pyridin-2-yl | —C(O)CH₂(pyridin-2-yl) | —C(O)CH₂CH₂(pyridin-2-yl) |
| 10.31 | —C(O)pyridin-3-yl | —C(O)CH₂(pyridin-3-yl) | —C(O)CH₂CH₂(pyridin-3-yl) |
| 10.32 | —C(O)pyridin-4-yl | —C(O)CH₂(pyridin-4-yl) | —C(O)CH₂CH₂(pyridin-4-yl) |
| 10.33 | —C(O)furan-2-yl | —C(O)CH₂(furan-2-yl) | —C(O)CH₂CH₂(furan-2-yl) |
| 10.34 | —C(O)furan-3-yl | —C(O)CH₂(furan-3-yl) | —C(O)CH₂CH₂(furan-3-yl) |
| 10.35 | —C(O)thiophen-2-yl | —C(O)CH₂(thiophen-2-yl) | —C(O)CH₂CH₂(thiophen-2-yl) |
| 10.36 | —C(O)thiophen-2-yl | —C(O)CH₂(thiophen-2-yl) | —C(O)CH₂CH₂(thiophen-2-yl) |
| 10.37 | —C(O)imidazo-2-yl | —C(O)CH₂(imidazo-2-yl) | —C(O)CH₂CH₂(imidazo-2-yl) |
| 10.38 | —C(O)oxazo-2-yl | —C(O)CH₂(oxazo-2-yl) | —C(O)CH₂CH₂(oxazo-2-yl) |
| 10.39 | —C(O)thioazo-2-yl | —C(O)CH₂(thioazo-2-yl) | —C(O)CH₂CH₂(thioazo-2-yl) |
| 10.40 | —C(O)benzofuran-2-yl | —C(O)CH₂(benzofuran-2-yl) | —C(O)CH₂CH₂(benzofuran-2-yl) |
| 10.41 | —C(O)benzofuran-3-yl | —C(O)CH₂(benzofuran-3-yl) | —C(O)CH₂CH₂(benzofuran-3-yl) |
| 10.42 | —C(O)benzothiophen-2-yl | —C(O)CH₂(benzothiophen-2-yl) | —C(O)CH₂CH₂(benzothiophen-2-yl) |
| 10.43 | —C(O)thiophen-2-yl | —C(O)CH₂(thiophen-2-yl) | —C(O)CH₂CH₂(thiophen-2-yl) |
| 10.44 | —C(O)benzimidazo-2-yl | —C(O)CH₂(benzimidazo-2-yl) | —C(O)CH₂CH₂(benzimidazo-2-yl) |
| 10.45 | —C(O)benzoxazo-2-yl | —C(O)CH₂(benzoxazo-2-yl) | —C(O)CH₂CH₂(benzoxazo-2-yl) |
| 10.46 | —C(O)benzothiazo-2-yl | —C(O)CH₂(benzothiazo-2-yl) | —C(O)CH₂CH₂(benzothiazo-2-yl) |
| 10.47 | —C(O)o-Ph(P(O)Ph₃) | —C(O)m-Ph(P(O)Ph₃) | —C(O)p-Ph(P(O)Ph₃) |
| 10.48 | —C(O)Ph-2-(fluoren-9-yl) | —C(O)Ph-3-(fluoren-9-yl) | —C(O)Ph-4-(fluoren-9-yl) |
| 10.49 | —C(O)N-indolin-2-one | —C(O)indolin-2-yl | —C(O)indol-2-yl |
| 10.50 | —C(O)C(CH₃)₂NHSO₂(naphth-2-yl) | —C(O)cyclopentyl-2-(Ph) | —C(O)cyclohexyl-2-(Ph) |
| 10.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 10.52 | —C(O)tetrahydronaphth-1-yl | —C(O)tetrahydronaphth-2-yl | —C(O)cyclopropyl-2,2-(Ph₂) |
| 10.53 | —C(O)tetrahydroisoquinolin-1-yl | —C(O)tetrahydroisoquinolin-3-yl | —C(O)CH₂((2-oxo)indolin-3-yl) |
| 10.54 | —C(O)CH₂(N-benzimidazol-2-one) | —C(O)CH₂(N-benzoxazol-2-one) | —C(O)CH₂(N-benzothiazol-2-one) |
| 10.55 | —C(O)CH₂(N-dihydroimidazol-2-one) | —C(O)CH₂(N-dihydrooxazol-2-one) | —C(O)CH₂(N-dihydrothiazol-2-one) |

10.56

10.57

10.58

TABLE 10-continued

Formula I: A = —B(OH)₂; X = —CH₂NH₂; R³ = table below; R¹¹ = —CH₂(naphth-2-yl)

| | .1 | .2 | .3 |
|---|---|---|---|
| 10.59 | —C(O)N(CH₃)CH₂Ph | —C(O)N(C₂H₅)CH₂Ph | —C(O)N(C₃H₇)CH₂Ph |
| 10.60 | —C(O)pyridin-3-yl-5-(Ph) | —C(O)Ph-3-(CH₂(thiophen-2-yl)) | —C(O)Ph-3-(CH₂Ph) |
| 10.61 | —C(O)C(CH₃)₂OPh | —C(O)CH(C₂H₅)OPh | —C(O)CH₂OCH₂Ph |
| 10.62 | —C(O)CH₂O(o-PhCH₂OH) | —C(O)CH₂O(m-PhCH₂OH) | —C(O)CH₂O(p-PhCH₂OH) |
| 10.63 | —C(O)CH₂O(o-PhCOOH) | —C(O)CH₂O(m-PhCOOH) | —C(O)CH₂O(p-PhCOOH) |
| 10.64 | —C(O)CH₂O(o-PhCOOCH₃) | —C(O)CH₂O(m-PhCOOCH₃) | —C(O)CH₂O(p-PhCOOCH₃) |
| 10.65 | —C(O)CH₂O(o-PhCH₂COOH) | —C(O)CH₂O(m-PhCH₂COOH) | —C(O)CH₂O(p-PhCH₂COOH) |
| 10.66 | 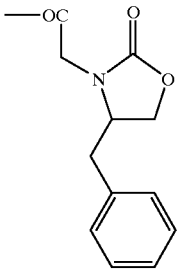 | | |

TABLE 11

Formula I: A = —B(OH)₂; X = —SC(=NH)NH2; R³ = table below; R¹¹ = CH₃

| | .1 | .2 | .3 |
|---|---|---|---|
| 11.1 | —C(O)Ph | —C(O)CH₂Ph | —C(O)CH₂CH₂Ph |
| 11.2 | —C(O)CH₂OPh | —C(O)CH₂NHPh | —C(O)CH₂SPh |
| 11.3 | —C(O)o-PhOH | —C(O)m-PhOH | —C(O)p-PhOH |
| 11.4 | —C(O)o-PhCH₂OH | —C(O)m-PhCH₂OH | —C(O)p-PhCH₂OH |
| 11.5 | —C(O)o-PhCOOH | —C(O)m-PhCOOH | —C(O)p-PhCOOH |
| 11.6 | —C(O)o-PhCH₂COOH | —C(O)m-PhCH₂COOH | —C(O)p-PhCH₂COOH |
| 11.7 | —C(O)naphth-1-yl | —C(O)CH₂(naphth-1-yl) | —C(O)CH₂CH₂(napth-1-yl) |
| 11.8 | —C(O)naphth-2-yl | —C(O)CH₂(naphth-2-yl) | —C(O)CH₂CH₂(napth-2-yl) |
| 11.9 | —C(O)o-biphenyl | —C(O)CH₂(o-biphenyl) | —C(O)CH₂CH₂(o-biphenyl) |
| 11.10 | —C(O)m-biphenyl | —C(O)CH₂(m-biphenyl) | —C(O)CH₂CH₂(m-biphenyl) |
| 11.12 | —C(O)p-biphenyl | —C(O)CH₂(p-biphenyl) | —C(O)CH₂CH₂(p-biphenyl) |
| 11.13 | —C(O)o-PhOPh | —C(O)CH₂(o-PhOPh) | —C(O)CH₂CH₂(o-PhOPh) |
| 11.14 | —C(O)m-PhOPh | —C(O)CH₂(m-PhOPh) | —C(O)CH₂CH₂(m-PhOPh) |
| 11.15 | —C(O)p-PhOPh | —C(O)CH₂(p-PhOPh) | —C(O)CH₂CH₂(p-PhOPh) |
| 11.16 | —C(O)o-PhNHPh | —C(O)CH₂(o-PhNHPh) | —C(O)CH₂CH₂(o-PhNHPh) |
| 11.17 | —C(O)m-PhNHPh | —C(O)CH₂(m-PhNHPh) | —C(O)CH₂CH₂(m-PhNHPh) |
| 11.18 | —C(O)p-PhNHPh | —C(O)CH₂(p-PhNHPh) | —C(O)CH₂CH₂(p-PhNHPh) |
| 11.19 | —C(O)o-PhSPh | —C(O)CH₂(o-PhSPh) | —C(O)CH₂CH₂(o-PhSPh) |
| 11.20 | —C(O)m-PhSPh | —C(O)CH₂(m-PhSPh) | —C(O)CH₂CH₂(m-PhSPh) |
| 11.21 | —C(O)p-PhSPh | —C(O)CH₂(p-PhSPh) | —C(O)CH₂CH₂(p-PhSPh) |
| 11.22 | —C(O)o-PhCH₂SPh | —C(O)CH₂(o-PhCH₂SPh) | —C(O)CH₂CH₂(o-PhCH₂SPh) |
| 11.23 | —C(O)m-PhCH₂SPh | —C(O)CH₂(m-PhCH₂SPh) | —C(O)CH₂CH₂(m-PhCH₂SPh) |
| 11.24 | —C(O)p-PhCH₂SPh | —C(O)CH₂(p-PhCH₂SPh) | —C(O)CH₂CH₂(p-PhCH₂SPh) |
| 11.25 | —C(O)adamantyl | —C(O)CH₂(adamantyl) | —C(O)CH₂CH₂(adamantyl) |
| 11.26 | —C(O)cyclopentyl | —C(O)CH₂(cyclopentyl) | —C(O)CH₂CH₂((cyclopentyl) |
| 11.27 | —C(O)cyclohexyl | —C(O)CH₂(cyclohexyl) | —C(O)CH₂CH₂(cyclohexyl) |
| 11.28 | —C(O)CH₂O(cyclopentyl) | —C(O)CH₂NH(cyclopentyl) | —C(O)CH₂S(cyclopentyl) |
| 11.29 | —C(O)CH₂O(cyclohexyl) | —C(O)CH₂NH(cyclohexyl) | —C(O)CH₂S(cyclohexyl) |
| 11.30 | —C(O)pyridin-2-yl | —C(O)CH₂(pyridin-2-yl) | —C(O)CH₂CH₂(pyridin-2-yl) |
| 11.31 | —C(O)pyridin-3-yl | —C(O)CH₂(pyridin-3-yl) | —C(O)CH₂CH₂(pyridin-3-yl) |
| 11.32 | —C(O)pyridin-4-yl | —C(O)CH₂(pyridin-4-yl) | —C(O)CH₂CH₂(pyridin-4-yl) |
| 11.33 | —C(O)furan-2-yl | —C(O)CH₂(furan-2-yl) | —C(O)CH₂CH₂(furan-2-yl) |
| 11.34 | —C(O)furan-3-yl | —C(O)CH₂(furan-3-yl) | —C(O)CH₂CH₂(furan-3-yl) |
| 11.35 | —C(O)thiophen-2-yl | —C(O)CH₂(thiophen-2-yl) | —C(O)CH₂CH₂(thiophen-2-yl) |
| 11.36 | —C(O)thiophen-2-yl | —C(O)CH₂(thiophen-2-yl) | —C(O)CH₂CH₂(thiophen-2-yl) |
| 11.37 | —C(O)imidazo-2-yl | —C(O)CH₂(imidazo-2-yl) | —C(O)CH₂CH₂(imidazo-2-yl) |
| 11.38 | —C(O)oxazo-2-yl | —C(O)CH₂(oxazo-2-yl) | —C(O)CH₂CH₂(oxazo-2-yl) |
| 11.39 | —C(O)thioazo-2-yl | —C(O)CH₂(thioazo-2-yl) | —C(O)CH₂CH₂(thioazo-2-yl) |
| 11.40 | —C(O)benzofuran-2-yl | —C(O)CH₂(benzofuran-2-yl) | —C(O)CH₂CH₂(benzofuran-2-yl) |
| 11.41 | —C(O)benzofuran-3-yl | —C(O)CH₂(benzofuran-3-yl) | —C(O)CH₂CH₂(benzofuran-3-yl) |
| 11.42 | —C(O)benzothiophen-2-yl | —C(O)CH₂(benzothiophen-2-yl) | —C(O)CH₂CH₂(benzothiophen-2-yl) |
| 11.43 | —C(O)thiophen-2-yl | —C(O)CH₂(thiophen-2-yl) | —C(O)CH₂CH₂(thiophen-2-yl) |
| 11.44 | —C(O)benzimidazo-2-yl | —C(O)CH₂(benzimidazo-2-yl) | —C(O)CH₂CH₂(benzimidazo-2-yl) |
| 11.45 | —C(O)benzoxazo-2-yl | —C(O)CH₂(benzoxazo-2-yl) | —C(O)CH₂CH₂(benzoxazo-2-yl) |

TABLE 11-continued

Formula I: A = —B(OH)$_2$; X = —SC(=NH)NH2; R$^3$ = table below; R$^{11}$ = CH$_3$

| | .1 | .2 | .3 |
|---|---|---|---|
| 11.46 | —C(O)benzothiazo-2-yl | —C(O)CH$_2$(benzothiazo-2-yl) | —C(O)CH$_2$CH$_2$(benzothiazo-2-yl) |
| 11.47 | —C(O)o-Ph(P(O)Ph$_3$) | —C(O)m-Ph(P(O)Ph$_3$) | —C(O)p-Ph(P(O)Ph$_3$) |
| 11.48 | —C(O)Ph-2-(fluoren-9-yl) | —C(O)Ph-3-(fluoren-9-yl) | —C(O)Ph-4-(fluoren-9-yl) |
| 11.49 | —C(O)N-indolin-2-one | —C(O)indolin-2-yl | —C(O)indol-2-yl |
| 11.50 | —C(O)C(CH$_3$)$_2$NHSO$_2$(naphth-2-yl) | —C(O)cyclopentyl-2-(Ph) | —C(O)cyclohexyl-2-(Ph) |
| 11.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 11.52 | —C(O)tetrahydronaphth-1-yl | —C(O)tetrahydronaphth-2-yl | —C(O)cyclopropyl-2,2-(Ph$_2$) |
| 11.53 | —C(O)tetrahydroisoquinolin-1-yl | —C(O)tetrahydroisoquinolin-3-yl | —C(O)CH$_2$((2-oxo)indolin-3-yl) |
| 11.54 | —C(O)CH$_2$(N-benzimidazol-2-one) | —C(O)CH$_2$(N-benzoxazol-2-one) | —C(O)CH$_2$(N-benzothiazol-2-one) |
| 11.55 | —C(O)CH$_2$(N-dihydroimidazol-2-one) | —C(O)CH$_2$(N-dihydrooxazol-2-one) | —C(O)CH$_2$(N-dihydrothiazol-2-one) |

11.56 [structures: phenanthridinone-N-CH$_2$CO—, dibenzazepinone-N-CH$_2$CO—, dibenzazocinone-N-CH$_2$CO—]

11.57 [structures: —OCCH$_2$-(hexahydrobenzimidazol-2-one), —OCCH$_2$-(hexahydrobenzoxazol-2-one), —OCCH$_2$-(hexahydrobenzothiazol-2-one)]

11.58 [structures: —OCCH$_2$-(3-benzylidene-2-oxoindolin-1-yl), —OCCH$_2$-(4-phenylpiperazin-1-yl), —OCCH$_2$-(5-phenyloxazolidin-2-one-3-yl)]

| 11.59 | —C(O)N(CH$_3$)CH$_2$Ph | —C(O)N(C$_2$H$_5$)CH$_2$Ph | —C(O)N(C$_3$H$_7$)CH$_2$Ph |
| 11.60 | —C(O)pyridin-3-yl-5-(Ph) | —C(O)Ph-3-(CH$_2$(thiophen-2-yl)) | —C(O)Ph-3-(CH$_2$Ph) |
| 11.61 | —C(O)C(CH$_3$)$_2$OPh | —C(O)CH(C$_2$H$_5$)OPh | —C(O)CH$_2$OCH$_2$Ph |
| 11.62 | —C(O)CH$_2$O(o-PhCH$_2$OH) | —C(O)CH$_2$O(m-PhCH$_2$OH) | —C(O)CH$_2$O(p-PhCH$_2$OH) |
| 11.63 | —C(O)CH$_2$O(o-PhCOOH) | —C(O)CH$_2$O(m-PhCOOH) | —C(O)CH$_2$O(p-PhCOOH) |
| 11.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 11.65 | —C(O)CH$_2$O(o-PhCH$_2$COOH) | —C(O)CH$_2$O(m-PhCH$_2$COOH) | —C(O)CH$_2$O(p-PhCH$_2$COOH) |

11.66 [structure: —OCCH$_2$-(4-benzyloxazolidin-2-one-3-yl)]

TABLE 12

Formula I: A = —B(OH)$_2$; X = —SC(=NH)NH$_2$; R$^3$ = table below; R$^{11}$ = —CH$_2$(p-PhOH)

| | .1 | .2 | .3 |
|---|---|---|---|
| 12.1 | —C(O)Ph | —C(O)CH$_2$Ph | —C(O)CH$_2$CH$_2$Ph |
| 12.2 | —C(O)CH$_2$OPh | —C(O)CH$_2$NHPh | —C(O)CH$_2$SPh |
| 12.3 | —C(O)o-PhOH | —C(O)m-PhOH | —C(O)p-PhOH |
| 12.4 | —C(O)o-PhCH$_2$OH | —C(O)m-PhCH$_2$OH | —C(O)p-PhCH$_2$OH |
| 12.5 | —C(O)o-PhCOOH | —C(O)m-PhCOOH | —C(O)p-PhCOOH |
| 12.6 | —C(O)o-PhCH$_2$COOH | —C(O)m-PhCH$_2$COOH | —C(O)p-PhCH$_2$COOH |
| 12.7 | —C(O)naphth-1-yl | —C(O)CH$_2$(naphth-1-yl) | —C(O)CH$_2$CH$_2$(napth-1-yl) |
| 12.8 | —C(O)naphth-2-yl | —C(O)CH$_2$(naphth-2-yl) | —C(O)CH$_2$CH$_2$(napth-2-yl) |
| 12.9 | —C(O)o-biphenyl | —C(O)CH$_2$(o-biphenyl) | —C(O)CH$_2$CH$_2$(o-biphenyl) |
| 12.10 | —C(O)m-biphenyl | —C(O)CH$_2$(m-biphenyl) | —C(O)CH$_2$CH$_2$(m-biphenyl) |
| 12.12 | —C(O)p-biphenyl | —C(O)CH$_2$(p-biphenyl) | —C(O)CH$_2$CH$_2$(p-biphenyl) |
| 12.13 | —C(O)o-PhOPh | —C(O)CH$_2$(o-PhOPh) | —C(O)CH$_2$CH$_2$(o-PhOPh) |
| 12.14 | —C(O)m-PhOPh | —C(O)CH$_2$(m-PhOPh) | —C(O)CH$_2$CH$_2$(m-PhOPh) |
| 12.15 | —C(O)p-PhOPh | —C(O)CH$_2$(p-PhOPh) | —C(O)CH$_2$CH$_2$(p-PhOPh) |
| 12.16 | —C(O)o-PhNHPh | —C(O)CH$_2$(o-PhNHPh) | —C(O)CH$_2$CH$_2$(o-PhNHPh) |
| 12.17 | —C(O)m-PhNHPh | —C(O)CH$_2$(m-PhNHPh) | —C(O)CH$_2$CH$_2$(m-PhNHPh) |
| 12.18 | —C(O)p-PhNHPh | —C(O)CH$_2$(p-PhNHPh) | —C(O)CH$_2$CH$_2$(p-PhNHPh) |
| 12.19 | —C(O)o-PhSPh | —C(O)CH$_2$(o-PhSPh) | —C(O)CH$_2$CH$_2$(o-PhSPh) |
| 12.20 | —C(O)m-PhSPh | —C(O)CH$_2$(m-PhSPh) | —C(O)CH$_2$CH$_2$(m-PhSPh) |
| 12.21 | —C(O)p-PhSPh | —C(O)CH$_2$(p-PhSPh) | —C(O)CH$_2$CH$_2$(p-PhSPh) |
| 12.22 | —C(O)o-PhCH$_2$SPh | —C(O)CH$_2$(o-PhCH$_2$SPh) | —C(O)CH$_2$CH$_2$(o-PhCH$_2$SPh) |
| 12.23 | —C(O)m-PhCH$_2$SPh | —C(O)CH$_2$(m-PhCH$_2$SPh) | —C(O)CH$_2$CH$_2$(m-PhCH$_2$SPh) |
| 12.24 | —C(O)p-PhCH$_2$SPh | —C(O)CH$_2$(p-PhCH$_2$SPh) | —C(O)CH$_2$CH$_2$(p-PhCH$_2$SPh) |
| 12.25 | —C(O)adamantyl | —C(O)CH$_2$(adamantyl) | —C(O)CH$_2$CH$_2$(adamantyl) |
| 12.26 | —C(O)cyclopentyl | —C(O)CH$_2$(cyclopentyl) | —C(O)CH$_2$CH$_2$((cyclopentyl) |
| 12.27 | —C(O)cyclohexyl | —C(O)CH$_2$(cyclohexyl) | —C(O)CH$_2$CH$_2$(cyclohexyl) |
| 12.28 | —C(O)CH$_2$O(cyclopentyl) | —C(O)CH$_2$NH(cyclopentyl) | —C(O)CH$_2$S(cyclopentyl) |
| 12.29 | —C(O)CH$_2$O(cyclohexyl) | —C(O)CH$_2$NH(cyclohexyl) | —C(O)CH$_2$S(cyclohexyl) |
| 12.30 | —C(O)pyridin-2-yl | —C(O)CH$_2$(pyridin-2-yl) | —C(O)CH$_2$CH$_2$(pyridin-2-yl) |
| 12.31 | —C(O)pyridin-3-yl | —C(O)CH$_2$(pyridin-3-yl) | —C(O)CH$_2$CH$_2$(pyridin-3-yl) |
| 12.32 | —C(O)pyridin-4-yl | —C(O)CH$_2$(pyridin-4-yl) | —C(O)CH$_2$CH$_2$(pyridin-4-yl) |
| 12.33 | —C(O)furan-2-yl | —C(O)CH$_2$(furan-2-yl) | —C(O)CH$_2$CH$_2$(furan-2-yl) |
| 12.34 | —C(O)furan-3-yl | —C(O)CH$_2$(furan-3-yl) | —C(O)CH$_2$CH$_2$(furan-3-yl) |
| 12.35 | —C(O)thiophen-2-yl | —C(O)CH$_2$(thiophen-2-yl) | —C(O)CH$_2$CH$_2$(thiophen-2-yl) |
| 12.36 | —C(O)thiophen-2-yl | —C(O)CH$_2$(thiophen-2-yl) | —C(O)CH$_2$CH$_2$(thiophen-2-yl) |
| 12.37 | —C(O)imidazo-2-yl | —C(O)CH$_2$(imidazo-2-yl) | —C(O)CH$_2$CH$_2$(imidazo-2-yl) |
| 12.38 | —C(O)oxazo-2-yl | —C(O)CH$_2$(oxazo-2-yl) | —C(O)CH$_2$CH$_2$(oxazo-2-yl) |
| 12.39 | —C(O)thioazo-2-yl | —C(O)CH$_2$(thioazo-2-yl) | —C(O)CH$_2$CH$_2$(thioazo-2-yl) |
| 12.40 | —C(O)benzofuran-2-yl | —C(O)CH$_2$(benzofuran-2-yl) | —C(O)CH$_2$CH$_2$(benzofuran-2-yl) |
| 12.41 | —C(O)benzofuran-3-yl | —C(O)CH$_2$(benzofuran-3-yl) | —C(O)CH$_2$CH$_2$(benzofuran-3-yl) |
| 12.42 | —C(O)benzothiophen-2-yl | —C(O)CH$_2$(benzothiophen-2-yl) | —C(O)CH$_2$CH$_2$(benzothiophen-2-yl) |
| 12.43 | —C(O)thiophen-2-yl | —C(O)CH$_2$(thiophen-2-yl) | —C(O)CH$_2$CH$_2$(thiophen-2-yl) |
| 12.44 | —C(O)benzimidazo-2-yl | —C(O)CH$_2$(benzimidazo-2-yl) | —C(O)CH$_2$CH$_2$(benzimidazo-2-yl) |
| 12.45 | —C(O)benzoxazo-2-yl | —C(O)CH$_2$(benzoxazo-2-yl) | —C(O)CH$_2$CH$_2$(benzoxazo-2-yl) |
| 12.46 | —C(O)benzothiazo-2-yl | —C(O)CH$_2$(benzothiazo-2-yl) | —C(O)CH$_2$CH$_2$(benzothiazo-2-yl) |
| 12.47 | —C(O)o-Ph(P(O)Ph$_3$) | —C(O)m-Ph(P(O)Ph$_3$) | —C(O)p-Ph(P(O)Ph$_3$) |
| 12.48 | —C(O)Ph-2-(fluoren-9-yl) | —C(O)Ph-3-(fluoren-9-yl) | —C(O)Ph-4-(fluoren-9-yl) |
| 12.49 | —C(O)N-indolin-2-one | —C(O)indolin-2-yl | —C(O)indol-2-yl |
| 12.50 | —C(O)C(CH$_3$)$_2$NHSO$_2$(naphth-2-yl) | —C(O)cyclopentyl-2-(Ph) | —C(O)cyclohexyl-2-(Ph) |
| 12.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 12.52 | —C(O)tetrahydronaphth-1-yl | —C(O)tetrahydronaphth-2-yl | —C(O)cyclopropyl-2,2-(Ph$_2$) |
| 12.53 | —C(O)tetrahydroisoquinolin-1-yl | —C(O)tetrahydroisoquinolin-3-yl | —C(O)CH$_2$((2-oxo)indolin-3-yl) |
| 12.54 | —C(O)CH$_2$(N-benzimidazol-2-one) | —C(O)CH$_2$(N-benzoxazol-2-one) | —C(O)CH$_2$(N-benzothiazol-2-one) |
| 12.55 | —C(O)CH$_2$(N-dihydroimidazol-2-one) | —C(O)CH$_2$(N-dihydrooxazol-2-one) | —C(O)CH$_2$(N-dihydrothiazol-2-one) |

12.56

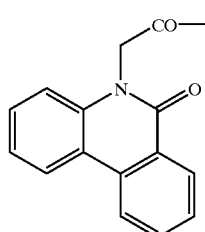 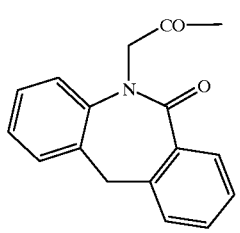 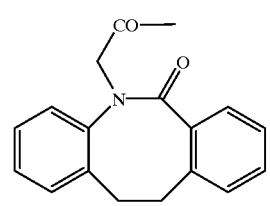

TABLE 12-continued

Formula I: A = —B(OH)₂; X = —SC(=NH)NH₂; R³ = table below; R¹¹ = —CH₂(p-PhOH)

| | .1 | .2 | .3 |
|---|---|---|---|
| 12.57 | (structure) | (structure) | (structure) |
| 12.58 | (structure) | (structure) | (structure) |
| 12.59 | —C(O)N(CH₃)CH₂Ph | —C(O)N(C₂H₅)CH₂Ph | —C(O)N(C₃H₇)CH₂Ph |
| 12.60 | —C(O)pyridin-3-yl-5-(Ph) | —C(O)Ph-3-(CH₂(thiophen-2-yl)) | —C(O)Ph-3-(CH₂Ph) |
| 12.61 | —C(O)C(CH₃)₂OPh | —C(O)CH(C₂H₅)OPh | —C(O)CH₂OCH₂Ph |
| 12.62 | —C(O)CH₂O(o-PhCH₂OH) | —C(O)CH₂O(m-PhCH₂OH) | —C(O)CH₂O(p-PhCH₂OH) |
| 12.63 | —C(O)CH₂O(o-PhCOOH) | —C(O)CH₂O(m-PhCOOH) | —C(O)CH₂O(p-PhCOOH) |
| 12.64 | —C(O)CH₂O(o-PhCOOCH₃) | —C(O)CH₂O(m-PhCOOCH₃) | —C(O)CH₂O(p-PhCOOCH₃) |
| 12.65 | —C(O)CH₂O(o-PhCH₂COOH) | —C(O)CH₂O(m-PhCH₂COOH) | —C(O)CH₂O(p-PhCH₂COOH) |
| 12.66 | (structure) | | |

TABLE 13

Formula I: A = —B(OH)₂; X = —SC(=NH)NH₂; R³ = table below; R¹¹ = —CH₂CH₂Ph

| | .1 | .2 | .3 |
|---|---|---|---|
| 13.1 | —C(O)Ph | —C(O)CH₂Ph | —C(O)CH₂CH₂Ph |
| 13.2 | —C(O)CH₂OPh | —C(O)CH₂NHPh | —C(O)CH₂SPh |
| 13.3 | —C(O)o-PhOH | —C(O)m-PhOH | —C(O)p-PhOH |
| 13.4 | —C(O)o-PhCH₂OH | —C(O)m-PhCH₂OH | —C(O)p-PhCH₂OH |
| 13.5 | —C(O)o-PhCOOH | —C(O)m-PhCOOH | —C(O)p-PhCOOH |
| 13.6 | —C(O)o-PhCH₂COOH | —C(O)m-PhCH₂COOH | —C(O)p-PhCH₂COOH |
| 13.7 | —C(O)naphth-1-yl | —C(O)CH₂(naphth-1-yl) | —C(O)CH₂CH₂(napth-1-yl) |
| 13.8 | —C(O)naphth-2-yl | —C(O)CH₂(naphth-2-yl) | —C(O)CH₂CH₂(napth-2-yl) |
| 13.9 | —C(O)o-biphenyl | —C(O)CH₂(o-biphenyl) | —C(O)CH₂CH₂(o-biphenyl) |
| 13.10 | —C(O)m-biphenyl | —C(O)CH₂(m-biphenyl) | —C(O)CH₂CH₂(m-biphenyl) |
| 13.12 | —C(O)p-biphenyl | —C(O)CH₂(p-biphenyl) | —C(O)CH₂CH₂(p-biphenyl) |
| 13.13 | —C(O)o-PhOPh | —C(O)CH₂(o-PhOPh) | —C(O)CH₂CH₂(o-PhOPh) |
| 13.14 | —C(O)m-PhOPh | —C(O)CH₂(m-PhOPh) | —C(O)CH₂CH₂(m-PhOPh) |
| 13.15 | —C(O)p-PhOPh | —C(O)CH₂(p-PhOPh) | —C(O)CH₂CH₂(p-PhOPh) |
| 13.16 | —C(O)o-PhNHPh | —C(O)CH₂(o-PhNHPh) | —C(O)CH₂CH₂(o-PhNHPh) |
| 13.17 | —C(O)m-PhNHPh | —C(O)CH₂(m-PhNHPh) | —C(O)CH₂CH₂(m-PhNHPh) |
| 13.18 | —C(O)p-PhNHPh | —C(O)CH₂(p-PhNHPh) | —C(O)CH₂CH₂(p-PhNHPh) |
| 13.19 | —C(O)o-PhSPh | —C(O)CH₂(o-PhSPh) | —C(O)CH₂CH₂(o-PhSPh) |

TABLE 13-continued

Formula I: A = —B(OH)$_2$; X = —SC(=NH)NH$_2$; R$^3$ = table below; R$^{11}$ = —CH$_2$CH$_2$Ph

| | .1 | .2 | .3 |
|---|---|---|---|
| 13.20 | —C(O)m-PhSPh | —C(O)CH$_2$(m-PhSPh) | —C(O)CH$_2$CH$_2$(m-PhSPh) |
| 13.21 | —C(O)p-PhSPh | —C(O)CH$_2$(p-PhSPh) | —C(O)CH$_2$CH$_2$(p-PhSPh) |
| 13.22 | —C(O)o-PhCH$_2$SPh | —C(O)CH$_2$(o-PhCH$_2$SPh) | —C(O)CH$_2$CH$_2$(o-PhCH$_2$SPh) |
| 13.23 | —C(O)m-PhCH$_2$SPh | —C(O)CH$_2$(m-PhCH$_2$SPh) | —C(O)CH$_2$CH$_2$(m-PhCH$_2$SPh) |
| 13.24 | —C(O)p-PhCH$_2$SPh | —C(O)CH$_2$(p-PhCH$_2$SPh) | —C(O)CH$_2$CH$_2$(p-PhCH$_2$SPh) |
| 13.25 | —C(O)adamantyl | —C(O)CH$_2$(adamantyl) | —C(O)CH$_2$CH$_2$(adamantyl) |
| 13.26 | —C(O)cyclopentyl | —C(O)CH$_2$(cyclopentyl) | —C(O)CH$_2$CH$_2$((cyclopentyl) |
| 13.27 | —C(O)cyclohexyl | —C(O)CH$_2$(cyclohexyl) | —C(O)CH$_2$CH$_2$(cyclohexyl) |
| 13.28 | —C(O)CH$_2$O(cyclopentyl) | —C(O)CH$_2$NH(cyclopentyl) | —C(O)CH$_2$S(cyclopentyl) |
| 13.29 | —C(O)CH$_2$O(cyclohexyl) | —C(O)CH$_2$NH(cyclohexyl) | —C(O)CH$_2$S(cyclohexyl) |
| 13.30 | —C(O)pyridin-2-yl | —C(O)CH$_2$(pyridin-2-yl) | —C(O)CH$_2$CH$_2$(pyridin-2-yl) |
| 13.31 | —C(O)pyridin-3-yl | —C(O)CH$_2$(pyridin-3-yl) | —C(O)CH$_2$CH$_2$(pyridin-3-yl) |
| 13.32 | —C(O)pyridin-4-yl | —C(O)CH$_2$(pyridin-4-yl) | —C(O)CH$_2$CH$_2$(pyridin-4-yl) |
| 13.33 | —C(O)furan-2-yl | —C(O)CH$_2$(furan-2-yl) | —C(O)CH$_2$CH$_2$(furan-2-yl) |
| 13.34 | —C(O)furan-3-yl | —C(O)CH$_2$(furan-3-yl) | —C(O)CH$_2$CH$_2$(furan-3-yl) |
| 13.35 | —C(O)thiophen-2-yl | —C(O)CH$_2$(thiophen-2-yl) | —C(O)CH$_2$CH$_2$(thiophen-2-yl) |
| 13.36 | —C(O)thiophen-2-yl | —C(O)CH$_2$(thiophen-2-yl) | —C(O)CH$_2$CH$_2$(thiophen-2-yl) |
| 13.37 | —C(O)imidazo-2-yl | —C(O)CH$_2$(imidazo-2-yl) | —C(O)CH$_2$CH$_2$(imidazo-2-yl) |
| 13.38 | —C(O)oxazo-2-yl | —C(O)CH$_2$(oxazo-2-yl) | —C(O)CH$_2$CH$_2$(oxazo-2-yl) |
| 13.39 | —C(O)thioazo-2-yl | —C(O)CH$_2$(thioazo-2-yl) | —C(O)CH$_2$CH$_2$(thioazo-2-yl) |
| 13.40 | —C(O)benzofuran-2-yl | —C(O)CH$_2$(benzofuran-2-yl) | —C(O)CH$_2$CH$_2$(benzofuran-2-yl) |
| 13.41 | —C(O)benzofuran-3-yl | —C(O)CH$_2$(benzofuran-3-yl) | —C(O)CH$_2$CH$_2$(benzofuran-3-yl) |
| 13.42 | —C(O)benzothiophen-2-yl | —C(O)CH$_2$(benzothiophen-2-yl) | —C(O)CH$_2$CH$_2$(benzothiophen-2-yl) |
| 13.43 | —C(O)thiophen-2-yl | —C(O)CH$_2$(thiophen-2-yl) | —C(O)CH$_2$CH$_2$(thiophen-2-yl) |
| 13.44 | —C(O)benzimidazo-2-yl | —C(O)CH$_2$(benzimidazo-2-yl) | —C(O)CH$_2$CH$_2$(benzimidazo-2-yl) |
| 13.45 | —C(O)benzoxazo-2-yl | —C(O)CH$_2$(benzoxazo-2-yl) | —C(O)CH$_2$CH$_2$(benzoxazo-2-yl) |
| 13.46 | —C(O)benzothiazo-2-yl | —C(O)CH$_2$(benzothiazo-2-yl) | —C(O)CH$_2$CH$_2$(benzothiazo-2-yl) |
| 13.47 | —C(O)o-Ph(P(O)Ph$_3$) | —C(O)m-Ph(P(O)Ph$_3$) | —C(O)p-Ph(P(O)Ph$_3$) |
| 13.48 | —C(O)Ph-2-(fluoren-9-yl) | —C(O)Ph-3-(fluoren-9-yl) | —C(O)Ph-4-(fluoren-9-yl) |
| 13.49 | —C(O)N-indolin-2-one | —C(O)indolin-2-yl | —C(O)indol-2-yl |
| 13.50 | —C(O)C(CH$_3$)$_2$NHSO$_2$(naphth-2-yl) | —C(O)cyclopentyl-2-(Ph) | —C(O)cyclohexyl-2-(Ph) |
| 13.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 13.52 | —C(O)tetrahydronaphth-1-yl | —C(O)tetrahydronaphth-2-yl | —C(O)cyclopropyl-2,2-(Ph$_2$) |
| 13.53 | —C(O)tetrahydroisoquinolin-1-yl | —C(O)tetrahydroisoquinolin-3-yl | —C(O)CH$_2$((2-oxo)indolin-3-yl) |
| 13.54 | —C(O)CH$_2$(N-benzimidazol-2-one) | —C(O)CH$_2$(N-benzoxazol-2-one) | —C(O)CH$_2$(N-benzothiazol-2-one) |
| 13.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 13.56 | 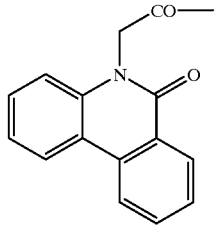 | 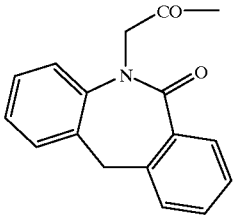 | 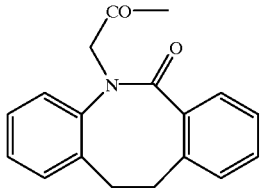 |
| 13.57 | 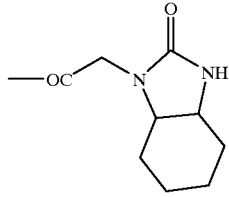 | 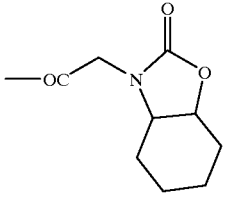 | 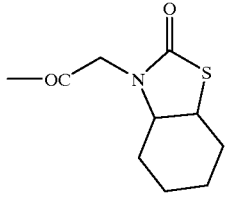 |
| 13.58 | 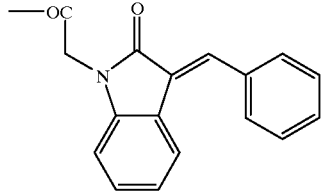 | 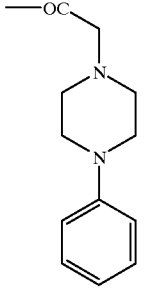 | 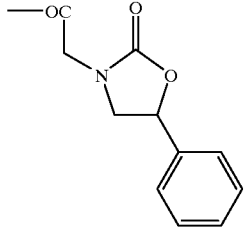 |

TABLE 13-continued

Formula I: A = —B(OH)$_2$; X = —SC(=NH)NH$_2$; R$^3$ = table below; R$^{11}$ = —CH$_2$CH$_2$Ph

| | .1 | .2 | .3 |
|---|---|---|---|
| 13.59 | —C(O)N(CH$_3$)CH$_2$Ph | —C(O)N(C$_2$H$_5$)CH$_2$Ph | —C(O)N(C$_3$H$_7$)CH$_2$Ph |
| 13.60 | —C(O)pyridin-3-yl-5-(Ph) | —C(O)Ph-3-(CH$_2$(thiophen-2-yl)) | —C(O)Ph-3-(CH$_2$Ph) |
| 13.61 | —C(O)C(CH$_3$)$_2$OPh | —C(O)CH(C$_2$H$_5$)OPh | —C(O)CH$_2$OCH$_2$Ph |
| 13.62 | —C(O)CH$_2$O(o-PhCH$_2$OH) | —C(O)CH$_2$O(m-PhCH$_2$OH) | —C(O)CH$_2$O(p-PhCH$_2$OH) |
| 13.63 | —C(O)CH$_2$O(o-PhCOOH) | —C(O)CH$_2$O(m-PhCOOH) | —C(O)CH$_2$O(p-PhCOOH) |
| 13.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 13.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 13.66 | —OCH$_2$-(3-benzyl-oxazolidin-2-one) | | |

TABLE 14

Formula I: A = —B(OH)$_2$; X = —SC(=NH)NH$_2$; R$^3$ = table below; R$^{11}$ = —Ph

| | .1 | .2 | .3 |
|---|---|---|---|
| 14.1 | —C(O)Ph | —C(O)CH$_2$Ph | —C(O)CH$_2$CH$_2$Ph |
| 14.2 | —C(O)CH$_2$OPh | —C(O)CH$_2$NHPh | —C(O)CH$_2$SPh |
| 14.3 | —C(O)o-PhOH | —C(O)m-PhOH | —C(O)p-PhOH |
| 14.4 | —C(O)o-PhCH$_2$OH | —C(O)m-PhCH$_2$OH | —C(O)p-PhCH$_2$OH |
| 14.5 | —C(O)o-PhCOOH | —C(O)m-PhCOOH | —C(O)p-PhCOOH |
| 14.6 | —C(O)o-PhCH$_2$COOH | —C(O)m-PhCH$_2$COOH | —C(O)p-PhCH$_2$COOH |
| 14.7 | —C(O)naphth-1-yl | —C(O)CH$_2$(naphth-1-yl) | —C(O)CH$_2$CH$_2$(napth-1-yl) |
| 14.8 | —C(O)naphth-2-yl | —C(O)CH$_2$(naphth-2-yl) | —C(O)CH$_2$CH$_2$(napth-2-yl) |
| 14.9 | —C(O)o-biphenyl | —C(O)CH$_2$(o-biphenyl) | —C(O)CH$_2$CH$_2$(o-biphenyl) |
| 14.10 | —C(O)m-biphenyl | —C(O)CH$_2$(m-biphenyl) | —C(O)CH$_2$CH$_2$(m-biphenyl) |
| 14.12 | —C(O)p-biphenyl | —C(O)CH$_2$(p-biphenyl) | —C(O)CH$_2$CH$_2$(p-biphenyl) |
| 14.13 | —C(O)o-PhOPh | —C(O)CH$_2$(o-PhOPh) | —C(O)CH$_2$CH$_2$(o-PhOPh) |
| 14.14 | —C(O)m-PhOPh | —C(O)CH$_2$(m-PhOPh) | —C(O)CH$_2$CH$_2$(m-PhOPh) |
| 14.15 | —C(O)p-PhOPh | —C(O)CH$_2$(p-PhOPh) | —C(O)CH$_2$CH$_2$(p-PhOPh) |
| 14.16 | —C(O)o-PhNHPh | —C(O)CH$_2$(o-PhNHPh) | —C(O)CH$_2$CH$_2$(o-PhNHPh) |
| 14.17 | —C(O)m-PhNHPh | —C(O)CH$_2$(m-PhNHPh) | —C(O)CH$_2$CH$_2$(m-PhNHPh) |
| 14.18 | —C(O)p-PhNHPh | —C(O)CH$_2$(p-PhNHPh) | —C(O)CH$_2$CH$_2$(p-PhNHPh) |
| 14.19 | —C(O)o-PhSPh | —C(O)CH$_2$(o-PhSPh) | —C(O)CH$_2$CH$_2$(o-PhSPh) |
| 14.20 | —C(O)m-PhSPh | —C(O)CH$_2$(m-PhSPh) | —C(O)CH$_2$CH$_2$(m-PhSPh) |
| 14.21 | —C(O)p-PhSPh | —C(O)CH$_2$(p-PhSPh) | —C(O)CH$_2$CH$_2$(p-PhSPh) |
| 14.22 | —C(O)o-PhCH$_2$SPh | —C(O)CH$_2$(o-PhCH$_2$SPh) | —C(O)CH$_2$CH$_2$(o-PhCH$_2$SPh) |
| 14.23 | —C(O)m-PhCH$_2$SPh | —C(O)CH$_2$(m-PhCH$_2$SPh) | —C(O)CH$_2$CH$_2$(m-PhCH$_2$SPh) |
| 14.24 | —C(O)p-PhCH$_2$SPh | —C(O)CH$_2$(p-PhCH$_2$SPh) | —C(O)CH$_2$CH$_2$(p-PhCH$_2$SPh) |
| 14.25 | —C(O)adamantyl | —C(O)CH$_2$(adamantyl) | —C(O)CH$_2$CH$_2$(adamantyl) |
| 14.26 | —C(O)cyclopentyl | —C(O)CH$_2$(cyclopentyl) | —C(O)CH$_2$CH$_2$((cyclopentyl) |
| 14.27 | —C(O)cyclohexyl | —C(O)CH$_2$(cyclohexyl) | —C(O)CH$_2$CH$_2$(cyclohexyl) |
| 14.28 | —C(O)CH$_2$O(cyclopentyl) | —C(O)CH$_2$NH(cyclopentyl) | —C(O)CH$_2$S(cyclopentyl) |
| 14.29 | —C(O)CH$_2$O(cyclohexyl) | —C(O)CH$_2$NH(cyclohexyl) | —C(O)CH$_2$S(cyclohexyl) |
| 14.30 | —C(O)pyridin-2-yl | —C(O)CH$_2$(pyridin-2-yl) | —C(O)CH$_2$CH$_2$(pyridin-2-yl) |
| 14.31 | —C(O)pyridin-3-yl | —C(O)CH$_2$(pyridin-3-yl) | —C(O)CH$_2$CH$_2$(pyridin-3-yl) |
| 14.32 | —C(O)pyridin-4-yl | —C(O)CH$_2$(pyridin-4-yl) | —C(O)CH$_2$CH$_2$(pyridin-4-yl) |
| 14.33 | —C(O)furan-2-yl | —C(O)CH$_2$(furan-2-yl) | —C(O)CH$_2$CH$_2$(furan-2-yl) |
| 14.34 | —C(O)furan-3-yl | —C(O)CH$_2$(furan-3-yl) | —C(O)CH$_2$CH$_2$(furan-3-yl) |
| 14.35 | —C(O)thiophen-2-yl | —C(O)CH$_2$(thiophen-2-yl) | —C(O)CH$_2$CH$_2$(thiophen-2-yl) |
| 14.36 | —C(O)thiophen-2-yl | —C(O)CH$_2$(thiophen-2-yl) | —C(O)CH$_2$CH$_2$(thiophen-2-yl) |
| 14.37 | —C(O)imidazo-2-yl | —C(O)CH$_2$(imidazo-2-yl) | —C(O)CH$_2$CH$_2$(imidazo-2-yl) |
| 14.38 | —C(O)oxazo-2-yl | —C(O)CH$_2$(oxazo-2-yl) | —C(O)CH$_2$CH$_2$(oxazo-2-yl) |
| 14.39 | —C(O)thioazo-2-yl | —C(O)CH$_2$(thioazo-2-yl) | —C(O)CH$_2$CH$_2$(thioazo-2-yl) |
| 14.40 | —C(O)benzofuran-2-yl | —C(O)CH$_2$(benzofuran-2-yl) | —C(O)CH$_2$CH$_2$(benzofuran-2-yl) |
| 14.41 | —C(O)benzofuran-3-yl | —C(O)CH$_2$(benzofuran-3-yl) | —C(O)CH$_2$CH$_2$(benzofuran-3-yl) |
| 14.42 | —C(O)benzothiophen-2-yl | —C(O)CH$_2$(benzothiophen-2-yl) | —C(O)CH$_2$CH$_2$(benzothiophen-2-yl) |
| 14.43 | —C(O)thiophen-2-yl | —C(O)CH$_2$(thiophen-2-yl) | —C(O)CH$_2$CH$_2$(thiophen-2-yl) |
| 14.44 | —C(O)benzimidazo-2-yl | —C(O)CH$_2$(benzimidazo-2-yl) | —C(O)CH$_2$CH$_2$(benzimidazo-2-yl) |
| 14.45 | —C(O)benzoxazo-2-yl | —C(O)CH$_2$(benzoxazo-2-yl) | —C(O)CH$_2$CH$_2$(benzoxazo-2-yl) |

TABLE 14-continued

Formula I: A = —B(OH)$_2$; X = —SC(=NH)NH$_2$; R$^3$ = table below; R$^{11}$ = —Ph

| | .1 | .2 | .3 |
|---|---|---|---|
| 14.46 | —C(O)benzothiazo-2-yl | —C(O)CH$_2$(benzothiazo-2-yl) | —C(O)CH$_2$CH$_2$(benzothiazo-2-yl) |
| 14.47 | —C(O)o-Ph(P(O)Ph$_3$) | —C(O)m-Ph(P(O)Ph$_3$) | —C(O)p-Ph(P(O)Ph$_3$) |
| 14.48 | —C(O)Ph-2-(fluoren-9-yl) | —C(O)Ph-3-(fluoren-9-yl) | —C(O)Ph-4-(fluoren-9-yl) |
| 14.49 | —C(O)N-indolin-2-one | —C(O)indolin-2-yl | —C(O)indol-2-yl |
| 14.50 | —C(O)C(CH$_3$)$_2$NHSO$_2$(naphth-2-yl) | —C(O)cyclopentyl-2-(Ph) | —C(O)cyclohexyl-2-(Ph) |
| 14.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 14.52 | —C(O)tetrahydronaphth-1-yl | —C(O)tetrahydronaphth-2-yl | —C(O)cyclopropyl-2,2-(Ph$_2$) |
| 14.53 | —C(O)tetrahydroisoquinolin-1-yl | —C(O)tetrahydroisoquinolin-3-yl | —C(O)CH$_2$((2-oxo)indolin-3-yl) |
| 14.54 | —C(O)CH$_2$(N-benzimidazol-2-one) | —C(O)CH$_2$(N-benzoxazol-2-one) | —C(O)CH$_2$(N-benzothiazol-2-one) |
| 14.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 14.59 | —C(O)N(CH$_3$)CH$_2$Ph | —C(O)N(C$_2$H$_5$)CH$_2$Ph | —C(O)N(C$_3$H$_7$)CH$_2$Ph |
| 14.60 | —C(O)pyridin-3-yl-5-(Ph) | —C(O)Ph-3-(CH$_2$(thiophen-2-yl)) | —C(O)Ph-3-(CH$_2$Ph) |
| 14.61 | —C(O)C(CH$_3$)$_2$OPh | —C(O)CH(C$_2$H$_5$)OPh | —C(O)CH$_2$OCH$_2$Ph |
| 14.62 | —C(O)CH$_2$O(o-PhCH$_2$OH) | —C(O)CH$_2$O(m-PhCH$_2$OH) | —C(O)CH$_2$O(p-PhCH$_2$OH) |
| 14.63 | —C(O)CH$_2$O(o-PhCOOH) | —C(O)CH$_2$O(m-PhCOOH) | —C(O)CH$_2$O(p-PhCOOH) |
| 14.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 14.65 | —C(O)CH$_2$O(o-PhCH$_2$COOH) | —C(O)CH$_2$O(m-PhCH$_2$COOH) | —C(O)CH$_2$O(p-PhCH$_2$COOH) |

14.56, 14.57, 14.58, 14.66: [structures]

TABLE 15

Formula I: A = —B(OH)$_2$; X = —SC(=NH)NH$_2$; R$^3$ = table below; R$^{11}$ = —CH$_2$(naphth-2-yl)

| | .1 | .2 | .3 |
|---|---|---|---|
| 15.1 | —C(O)Ph | —C(O)CH$_2$Ph | —C(O)CH$_2$CH$_2$Ph |
| 15.2 | —C(O)CH$_2$OPh | —C(O)CH$_2$NHPh | —C(O)CH$_2$SPh |
| 15.3 | —C(O)o-PhOH | —C(O)m-PhOH | —C(O)p-PhOH |
| 15.4 | —C(O)o-PhCH$_2$OH | —C(O)m-PhCH$_2$OH | —C(O)p-PhCH$_2$OH |
| 15.5 | —C(O)o-PhCOOH | —C(O)m-PhCOOH | —C(O)p-PhCOOH |
| 15.6 | —C(O)o-PhCH$_2$COOH | —C(O)m-PhCH$_2$COOH | —C(O)p-PhCH$_2$COOH |
| 15.7 | —C(O)naphth-1-yl | —C(O)CH$_2$(naphth-1-yl) | —C(O)CH$_2$CH$_2$(napth-1-yl) |
| 15.8 | —C(O)naphth-2-yl | —C(O)CH$_2$(naphth-2-yl) | —C(O)CH$_2$CH$_2$(napth-2-yl) |
| 15.9 | —C(O)o-biphenyl | —C(O)CH$_2$(o-biphenyl) | —C(O)CH$_2$CH$_2$(o-biphenyl) |
| 15.10 | —C(O)m-biphenyl | —C(O)CH$_2$(m-biphenyl) | —C(O)CH$_2$CH$_2$(m-biphenyl) |
| 15.12 | —C(O)p-biphenyl | —C(O)CH$_2$(p-biphenyl) | —C(O)CH$_2$CH$_2$(p-biphenyl) |
| 15.13 | —C(O)o-PhOPh | —C(O)CH$_2$(o-PhOPh) | —C(O)CH$_2$CH$_2$(o-PhOPh) |
| 15.14 | —C(O)m-PhOPh | —C(O)CH$_2$(m-PhOPh) | —C(O)CH$_2$CH$_2$(m-PhOPh) |
| 15.15 | —C(O)p-PhOPh | —C(O)CH$_2$(p-PhOPh) | —C(O)CH$_2$CH$_2$(p-PhOPh) |
| 15.16 | —C(O)o-PhNHPh | —C(O)CH$_2$(o-PhNHPh) | —C(O)CH$_2$CH$_2$(o-PhNHPh) |
| 15.17 | —C(O)m-PhNHPh | —C(O)CH$_2$(m-PhNHPh) | —C(O)CH$_2$CH$_2$(m-PhNHPh) |
| 15.18 | —C(O)p-PhNHPh | —C(O)CH$_2$(p-PhNHPh) | —C(O)CH$_2$CH$_2$(p-PhNHPh) |
| 15.19 | —C(O)o-PhSPh | —C(O)CH$_2$(o-PhSPh) | —C(O)CH$_2$CH$_2$(o-PhSPh) |
| 15.20 | —C(O)m-PhSPh | —C(O)CH$_2$(m-PhSPh) | —C(O)CH$_2$CH$_2$(m-PhSPh) |
| 15.21 | —C(O)p-PhSPh | —C(O)CH$_2$(p-PhSPh) | —C(O)CH$_2$CH$_2$(p-PhSPh) |
| 15.22 | —C(O)o-PhCH$_2$SPh | —C(O)CH$_2$(o-PhCH$_2$SPh) | —C(O)CH$_2$CH$_2$(o-PhCH$_2$SPh) |
| 15.23 | —C(O)m-PhCH$_2$SPh | —C(O)CH$_2$(m-PhCH$_2$SPh) | —C(O)CH$_2$CH$_2$(m-PhCH$_2$SPh) |
| 15.24 | —C(O)p-PhCH$_2$SPh | —C(O)CH$_2$(p-PhCH$_2$SPh) | —C(O)CH$_2$CH$_2$(p-PhCH$_2$SPh) |
| 15.25 | —C(O)adamantyl | —C(O)CH$_2$(adamantyl) | —C(O)CH$_2$CH$_2$(adamantyl) |
| 15.26 | —C(O)cyclopentyl | —C(O)CH$_2$(cyclopentyl) | —C(O)CH$_2$CH$_2$((cyclopentyl) |
| 15.27 | —C(O)cyclohexyl | —C(O)CH$_2$(cyclohexyl) | —C(O)CH$_2$CH$_2$(cyclohexyl) |
| 15.28 | —C(O)CH$_2$O(cyclopentyl) | —C(O)CH$_2$NH(cyclopentyl) | —C(O)CH$_2$S(cyclopentyl) |
| 15.29 | —C(O)CH$_2$O(cyclohexyl) | —C(O)CH$_2$NH(cyclohexyl) | —C(O)CH$_2$S(cyclohexyl) |
| 15.30 | —C(O)pyridin-2-yl | —C(O)CH$_2$(pyridin-2-yl) | —C(O)CH$_2$CH$_2$(pyridin-2-yl) |
| 15.31 | —C(O)pyridin-3-yl | —C(O)CH$_2$(pyridin-3-yl) | —C(O)CH$_2$CH$_2$(pyridin-3-yl) |
| 15.32 | —C(O)pyridin-4-yl | —C(O)CH$_2$(pyridin-4-yl) | —C(O)CH$_2$CH$_2$(pyridin-4-yl) |
| 15.33 | —C(O)furan-2-yl | —C(O)CH$_2$(furan-2-yl) | —C(O)CH$_2$CH$_2$(furan-2-yl) |
| 15.34 | —C(O)furan-3-yl | —C(O)CH$_2$(furan-3-yl) | —C(O)CH$_2$CH$_2$(furan-3-yl) |
| 15.35 | —C(O)thiophen-2-yl | —C(O)CH$_2$(thiophen-2-yl) | —C(O)CH$_2$CH$_2$(thiophen-2-yl) |
| 15.36 | —C(O)thiophen-2-yl | —C(O)CH$_2$(thiophen-2-yl) | —C(O)CH$_2$CH$_2$(thiophen-2-yl) |
| 15.37 | —C(O)imidazo-2-yl | —C(O)CH$_2$(imidazo-2-yl) | —C(O)CH$_2$CH$_2$(imidazo-2-yl) |
| 15.38 | —C(O)oxazo-2-yl | —C(O)CH$_2$(oxazo-2-yl) | —C(O)CH$_2$CH$_2$(oxazo-2-yl) |
| 15.39 | —C(O)thioazo-2-yl | —C(O)CH$_2$(thioazo-2-yl) | —C(O)CH$_2$CH$_2$(thioazo-2-yl) |
| 15.40 | —C(O)benzofuran-2-yl | —C(O)CH$_2$(benzofuran-2-yl) | —C(O)CH$_2$CH$_2$(benzofuran-2-yl) |
| 15.41 | —C(O)benzofuran-3-yl | —C(O)CH$_2$(benzofuran-3-yl) | —C(O)CH$_2$CH$_2$(benzofuran-3-yl) |
| 15.42 | —C(O)benzothiophen-2-yl | —C(O)CH$_2$(benzothiophen-2-yl) | —C(O)CH$_2$CH$_2$(benzothiophen-2-yl) |
| 15.43 | —C(O)thiophen-2-yl | —C(O)CH$_2$(thiophen-2-yl) | —C(O)CH$_2$CH$_2$(thiophen-2-yl) |
| 15.44 | —C(O)benzimidazo-2-yl | —C(O)CH$_2$(benzimidazo-2-yl) | —C(O)CH$_2$CH$_2$(benzimidazo-2-yl) |
| 15.45 | —C(O)benzoxazo-2-yl | —C(O)CH$_2$(benzoxazo-2-yl) | —C(O)CH$_2$CH$_2$(benzoxazo-2-yl) |
| 15.46 | —C(O)benzothiazo-2-yl | —C(O)CH$_2$(benzothiazo-2-yl) | —C(O)CH$_2$CH$_2$(benzothiazo-2-yl) |
| 15.47 | —C(O)o-Ph(P(O)Ph$_3$) | —C(O)m-Ph(P(O)Ph$_3$) | —C(O)p-Ph(P(O)Ph$_3$) |
| 15.48 | —C(O)Ph-2-(fluoren-9-yl) | —C(O)Ph-3-(fluoren-9-yl) | —C(O)Ph-4-(fluoren-9-yl) |
| 15.49 | —C(O)N-indolin-2-one | —C(O)indolin-2-yl | —C(O)indol-2-yl |
| 15.50 | —C(O)C(CH$_3$)$_2$NHSO$_2$(naphth-2-yl) | —C(O)cyclopentyl-2-(Ph) | —C(O)cyclohexyl-2-(Ph) |
| 15.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 15.52 | —C(O)tetrahydronaphth-1-yl | —C(O)tetrahydronaphth-2-yl | —C(O)cyclopropyl-2,2-(Ph$_2$) |
| 15.53 | —C(O)tetrahydroisoquinolin-1-yl | —C(O)tetrahydroisoquinolin-3-yl | —C(O)CH$_2$((2-oxo)indolin-3-yl) |
| 15.54 | —C(O)CH$_2$(N-benzimidazol-2-one) | —C(O)CH$_2$(N-benzoxazol-2-one) | —C(O)CH$_2$(N-benzothiazol-2-one) |
| 15.55 | —C(O)CH$_2$(N-dihydroimidazol-2-one) | —C(O)CH$_2$(N-dihydrooxazol-2-one) | —C(O)CH$_2$(N-dihydrothiazol-2-one) |

15.56

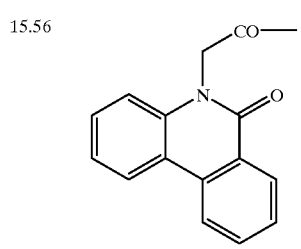 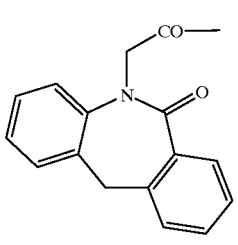 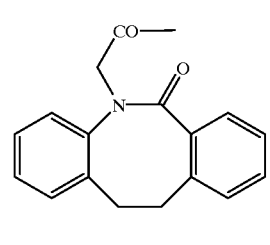

TABLE 15-continued

Formula I: A = —B(OH)$_2$; X = —SC(=NH)NH$_2$; R$^3$ = table below; R$^{11}$ = —CH$_2$(naphth-2-yl)

|   | .1 | .2 | .3 |
|---|---|---|---|
| 15.57 | (structure) | (structure) | (structure) |
| 15.58 | (structure) | (structure) | (structure) |
| 15.59 | —C(O)N(CH$_3$)CH$_2$Ph | —C(O)N(C$_2$H$_5$)CH$_2$Ph | —C(O)N(C$_3$H$_7$)CH$_2$Ph |
| 15.60 | —C(O)pyridin-3-yl-5-(Ph) | —C(O)Ph-3-(CH$_2$(thiophen-2-yl)) | —C(O)Ph-3-(CH$_2$Ph) |
| 15.61 | —C(O)C(CH$_3$)$_2$OPh | —C(O)CH(C$_2$H$_5$)OPh | —C(O)CH$_2$OCH$_2$Ph |
| 15.62 | —C(O)CH$_2$O(o-PhCH$_2$OH) | —C(O)CH$_2$O(m-PhCH$_2$OH) | —C(O)CH$_2$O(p-PhCH$_2$OH) |
| 15.63 | —C(O)CH$_2$O(o-PhCOOH) | —C(O)CH$_2$O(m-PhCOOH) | —C(O)CH$_2$O(p-PhCOOH) |
| 15.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 15.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 15.66 | (structure) | | |

TABLE 16

Formula I: A = —B(pinanediol); X = guanidinyl; R$^3$ = table below; R$^{11}$ = CH$_3$

|   | .1 | .2 | .3 |
|---|---|---|---|
| 16.1 | —C(O)Ph | —C(O)CH$_2$Ph | —C(O)CH$_2$CH$_2$Ph |
| 16.2 | —C(O)CH$_2$OPh | —C(O)CH$_2$NHPh | —C(O)CH$_2$SPh |
| 16.3 | —C(O)o-PhOH | —C(O)m-PhOH | —C(O)p-PhOH |
| 16.4 | —C(O)o-PhCH$_2$OH | —C(O)m-PhCH$_2$OH | —C(O)p-PhCH$_2$OH |
| 16.5 | —C(O)o-PhCOOH | —C(O)m-PhCOOH | —C(O)p-PhCOOH |
| 16.6 | —C(O)o-PhCH$_2$COOH | —C(O)m-PhCH$_2$COOH | —C(O)p-PhCH$_2$COOH |
| 16.7 | —C(O)naphth-1-yl | —C(O)CH$_2$(naphth-1-yl) | —C(O)CH$_2$CH$_2$(napth-1-yl) |
| 16.8 | —C(O)naphth-2-yl | —C(O)CH$_2$(naphth-2-yl) | —C(O)CH$_2$CH$_2$(napth-2-yl) |
| 16.9 | —C(O)o-biphenyl | —C(O)CH$_2$(o-biphenyl) | —C(O)CH$_2$CH$_2$(o-biphenyl) |
| 16.10 | —C(O)m-biphenyl | —C(O)CH$_2$(m-biphenyl) | —C(O)CH$_2$CH$_2$(m-biphenyl) |
| 16.12 | —C(O)p-biphenyl | —C(O)CH$_2$(p-biphenyl) | —C(O)CH$_2$CH$_2$(p-biphenyl) |
| 16.13 | —C(O)o-PhOPh | —C(O)CH$_2$(o-PhOPh) | —C(O)CH$_2$CH$_2$(o-PhOPh) |
| 16.14 | —C(O)m-PhOPh | —C(O)CH$_2$(m-PhOPh) | —C(O)CH$_2$CH$_2$(m-PhOPh) |
| 16.15 | —C(O)p-PhOPh | —C(O)CH$_2$(p-PhOPh) | —C(O)CH$_2$CH$_2$(p-PhOPh) |
| 16.16 | —C(O)o-PhNHPh | —C(O)CH$_2$(o-PhNHPh) | —C(O)CH$_2$CH$_2$(o-PhNHPh) |
| 16.17 | —C(O)m-PhNHPh | —C(O)CH$_2$(m-PhNHPh) | —C(O)CH$_2$CH$_2$(m-PhNHPh) |
| 16.18 | —C(O)p-PhNHPh | —C(O)CH$_2$(p-PhNHPh) | —C(O)CH$_2$CH$_2$(p-PhNHPh) |
| 16.19 | —C(O)o-PhSPh | —C(O)CH$_2$(o-PhSPh) | —C(O)CH$_2$CH$_2$(o-PhSPh) |

TABLE 16-continued

Formula I: A = —B(pinanediol); X = guanidinyl; R³ = table below; R¹¹ = CH₃

| | .1 | .2 | .3 |
|---|---|---|---|
| 16.20 | —C(O)m-PhSPh | —C(O)CH₂(m-PhSPh) | —C(O)CH₂CH₂(m-PhSPh) |
| 16.21 | —C(O)p-PhSPh | —C(O)CH₂(p-PhSPh) | —C(O)CH₂CH₂(p-PhSPh) |
| 16.22 | —C(O)o-PhCH₂SPh | —C(O)CH₂(o-PhCH₂SPh) | —C(O)CH₂CH₂(o-PhCH₂SPh) |
| 16.23 | —C(O)m-PhCH₂SPh | —C(O)CH₂(m-PhCH₂SPh) | —C(O)CH₂CH₂(m-PhCH₂SPh) |
| 16.24 | —C(O)p-PhCH₂SPh | —C(O)CH₂(p-PhCH₂SPh) | —C(O)CH₂CH₂(p-PhCH₂SPh) |
| 16.25 | —C(O)adamantyl | —C(O)CH₂(adamantyl) | —C(O)CH₂CH₂(adamantyl) |
| 16.26 | —C(O)cyclopentyl | —C(O)CH₂(cyclopentyl) | —C(O)CH₂CH₂((cyclopentyl) |
| 16.27 | —C(O)cyclohexyl | —C(O)CH₂(cyclohexyl) | —C(O)CH₂CH₂(cyclohexyl) |
| 16.28 | —C(O)CH₂O(cyclopentyl) | —C(O)CH₂NH(cyclopentyl) | —C(O)CH₂S(cyclopentyl) |
| 16.29 | —C(O)CH₂O(cyclohexyl) | —C(O)CH₂NH(cyclohexyl) | —C(O)CH₂S(cyclohexyl) |
| 16.30 | —C(O)pyridin-2-yl | —C(O)CH₂(pyridin-2-yl) | —C(O)CH₂CH₂(pyridin-2-yl) |
| 16.31 | —C(O)pyridin-3-yl | —C(O)CH₂(pyridin-3-yl) | —C(O)CH₂CH₂(pyridin-3-yl) |
| 16.32 | —C(O)pyridin-4-yl | —C(O)CH₂(pyridin-4-yl) | —C(O)CH₂CH₂(pyridin-4-yl) |
| 16.33 | —C(O)furan-2-yl | —C(O)CH₂(furan-2-yl) | —C(O)CH₂CH₂(furan-2-yl) |
| 16.34 | —C(O)furan-3-yl | —C(O)CH₂(furan-3-yl) | —C(O)CH₂CH₂(furan-3-yl) |
| 16.35 | —C(O)thiophen-2-yl | —C(O)CH₂(thiophen-2-yl) | —C(O)CH₂CH₂(thiophen-2-yl) |
| 16.36 | —C(O)thiophen-2-yl | —C(O)CH₂(thiophen-2-yl) | —C(O)CH₂CH₂(thiophen-2-yl) |
| 16.37 | —C(O)imidazo-2-yl | —C(O)CH₂(imidazo-2-yl) | —C(O)CH₂CH₂(imidazo-2-yl) |
| 16.38 | —C(O)oxazo-2-yl | —C(O)CH₂(oxazo-2-yl) | —C(O)CH₂CH₂(oxazo-2-yl) |
| 16.39 | —C(O)thioazo-2-yl | —C(O)CH₂(thioazo-2-yl) | —C(O)CH₂CH₂(thioazo-2-yl) |
| 16.40 | —C(O)benzofuran-2-yl | —C(O)CH₂(benzofuran-2-yl) | —C(O)CH₂CH₂(benzofuran-2-yl) |
| 16.41 | —C(O)benzofuran-3-yl | —C(O)CH₂(benzofuran-3-yl) | —C(O)CH₂CH₂(benzofuran-3-yl) |
| 16.42 | —C(O)benzothiophen-2-yl | —C(O)CH₂(benzothiophen-2-yl) | —C(O)CH₂CH₂(benzothiophen-2-yl) |
| 16.43 | —C(O)thiophen-2-yl | —C(O)CH₂(thiophen-2-yl) | —C(O)CH₂CH₂(thiophen-2-yl) |
| 16.44 | —C(O)benzimidazo-2-yl | —C(O)CH₂(benzimidazo-2-yl) | —C(O)CH₂CH₂(benzimidazo-2-yl) |
| 16.45 | —C(O)benzoxazo-2-yl | —C(O)CH₂(benzoxazo-2-yl) | —C(O)CH₂CH₂(benzoxazo-2-yl) |
| 16.46 | —C(O)benzothiazo-2-yl | —C(O)CH₂(benzothiazo-2-yl) | —C(O)CH₂CH₂(benzothiazo-2-yl) |
| 16.47 | —C(O)o-Ph(P(O)Ph₃) | —C(O)m-Ph(P(O)Ph₃) | —C(O)p-Ph(P(O)Ph₃) |
| 16.48 | —C(O)Ph-2-(fluoren-9-yl) | —C(O)Ph-3-(fluoren-9-yl) | —C(O)Ph-4-(fluoren-9-yl) |
| 16.49 | —C(O)N-indolin-2-one | —C(O)indolin-2-yl | —C(O)indol-2-yl |
| 16.50 | —C(O)C(CH₃)₂NHSO₂(naphth-2-yl) | —C(O)cyclopentyl-2-(Ph) | —C(O)cyclohexyl-2-(Ph) |
| 16.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 16.52 | —C(O)tetrahydronaphth-1-yl | —C(O)tetrahydronaphth-2-yl | —C(O)cyclopropyl-2,2-(Ph₂) |
| 16.53 | —C(O)tetrahydroisoquinolin-1-yl | —C(O)tetrahydroisoquinolin-3-yl | —C(O)CH₂((2-oxo)indolin-3-yl) |
| 16.54 | —C(O)CH₂(N-benzimidazol-2-one) | —C(O)CH₂(N-benzoxazol-2-one) | —C(O)CH₂(N-benzothiazol-2-one) |
| 16.55 | —C(O)CH₂(N-dihydroimidazol-2-one) | —C(O)CH₂(N-dihydrooxazol-2-one) | —C(O)CH₂(N-dihydrothiazol-2-one) |
| 16.56 | ![structure] | ![structure] | ![structure] |
| 16.57 | ![structure] | ![structure] | ![structure] |
| 16.58 | ![structure] | ![structure] | ![structure] |

TABLE 16-continued

Formula I: A = —B(pinanediol); X = guanidinyl; R$^3$ = table below; R$^{11}$ = CH$_3$

| | .1 | .2 | .3 |
|---|---|---|---|
| 16.59 | —C(O)N(CH$_3$)CH$_2$Ph | —C(O)N(C$_2$H$_5$)CH$_2$Ph | —C(O)N(C$_3$H$_7$)CH$_2$Ph |
| 16.60 | —C(O)pyridin-3-yl-5-(Ph) | —C(O)Ph-3-(CH$_2$(thiophen-2-yl)) | —C(O)Ph-3-(CH$_2$Ph) |
| 16.61 | —C(O)C(CH$_3$)$_2$OPh | —C(O)CH(C$_2$H$_5$)OPh | —C(O)CH$_2$OCH$_2$Ph |
| 16.62 | —C(O)CH$_2$O(o-PhCH$_2$OH) | —C(O)CH$_2$O(m-PhCH$_2$OH) | —C(O)CH$_2$O(p-PhCH$_2$OH) |
| 16.63 | —C(O)CH$_2$O(o-PhCOOH) | —C(O)CH$_2$O(m-PhCOOH) | —C(O)CH$_2$O(p-PhCOOH) |
| 16.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 16.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 16.66 | (4-benzyl-2-oxo-oxazolidin-3-yl)methoxycarbonyl structure | | |

TABLE 17

Formula I: A = —B(pinanediol); X = guanidinyl; R$^3$ = table below; R$^{11}$ = —CH$_2$(p-PhOH)

| | .1 | .2 | .3 |
|---|---|---|---|
| 17.1 | —C(O)Ph | —C(O)CH$_2$Ph | —C(O)CH$_2$CH$_2$Ph |
| 17.2 | —C(O)CH$_2$OPh | —C(O)CH$_2$NHPh | —C(O)CH$_2$SPh |
| 17.3 | —C(O)o-PhOH | —C(O)m-PhOH | —C(O)p-PhOH |
| 17.4 | —C(O)o-PhCH$_2$OH | —C(O)m-PhCH$_2$OH | —C(O)p-PhCH$_2$OH |
| 17.5 | —C(O)o-PhCOOH | —C(O)m-PhCOOH | —C(O)p-PhCOOH |
| 17.6 | —C(O)o-PhCH$_2$COOH | —C(O)m-PhCH$_2$COOH | —C(O)p-PhCH$_2$COOH |
| 17.7 | —C(O)naphth-1-yl | —C(O)CH$_2$(naphth-1-yl) | —C(O)CH$_2$CH$_2$(napth-1-yl) |
| 17.8 | —C(O)naphth-2-yl | —C(O)CH$_2$(naphth-2-yl) | —C(O)CH$_2$CH$_2$(napth-2-yl) |
| 17.9 | —C(O)o-biphenyl | —C(O)CH$_2$(o-biphenyl) | —C(O)CH$_2$CH$_2$(o-biphenyl) |
| 17.10 | —C(O)m-biphenyl | —C(O)CH$_2$(m-biphenyl) | —C(O)CH$_2$CH$_2$(m-biphenyl) |
| 17.12 | —C(O)p-biphenyl | —C(O)CH$_2$(p-biphenyl) | —C(O)CH$_2$CH$_2$(p-biphenyl) |
| 17.13 | —C(O)o-PhOPh | —C(O)CH$_2$(o-PhOPh) | —C(O)CH$_2$CH$_2$(o-PhOPh) |
| 17.14 | —C(O)m-PhOPh | —C(O)CH$_2$(m-PhOPh) | —C(O)CH$_2$CH$_2$(m-PhOPh) |
| 17.15 | —C(O)p-PhOPh | —C(O)CH$_2$(p-PhOPh) | —C(O)CH$_2$CH$_2$(p-PhOPh) |
| 17.16 | —C(O)o-PhNHPh | —C(O)CH$_2$(o-PhNHPh) | —C(O)CH$_2$CH$_2$(o-PhNHPh) |
| 17.17 | —C(O)m-PhNHPh | —C(O)CH$_2$(m-PhNHPh) | —C(O)CH$_2$CH$_2$(m-PhNHPh) |
| 17.18 | —C(O)p-PhNHPh | —C(O)CH$_2$(p-PhNHPh) | —C(O)CH$_2$CH$_2$(p-PhNHPh) |
| 17.19 | —C(O)o-PhSPh | —C(O)CH$_2$(o-PhSPh) | —C(O)CH$_2$CH$_2$(o-PhSPh) |
| 17.20 | —C(O)m-PhSPh | —C(O)CH$_2$(m-PhSPh) | —C(O)CH$_2$CH$_2$(m-PhSPh) |
| 17.21 | —C(O)p-PhSPh | —C(O)CH$_2$(p-PhSPh) | —C(O)CH$_2$CH$_2$(p-PhSPh) |
| 17.22 | —C(O)o-PhCH$_2$SPh | —C(O)CH$_2$(o-PhCH$_2$SPh) | —C(O)CH$_2$CH$_2$(o-PhCH$_2$SPh) |
| 17.23 | —C(O)m-PhCH$_2$SPh | —C(O)CH$_2$(m-PhCH$_2$SPh) | —C(O)CH$_2$CH$_2$(m-PhCH$_2$SPh) |
| 17.24 | —C(O)p-PhCH$_2$SPh | —C(O)CH$_2$(p-PhCH$_2$SPh) | —C(O)CH$_2$CH$_2$(p-PhCH$_2$SPh) |
| 17.25 | —C(O)adamantyl | —C(O)CH$_2$(adamantyl) | —C(O)CH$_2$CH$_2$(adamantyl) |
| 17.26 | —C(O)cyclopentyl | —C(O)CH$_2$(cyclopentyl) | —C(O)CH$_2$CH$_2$((cyclopentyl) |
| 17.27 | —C(O)cyclohexyl | —C(O)CH$_2$(cyclohexyl) | —C(O)CH$_2$CH$_2$(cyclohexyl) |
| 17.28 | —C(O)CH$_2$O(cyclopentyl) | —C(O)CH$_2$NH(cyclopentyl) | —C(O)CH$_2$S(cyclopentyl) |
| 17.29 | —C(O)CH$_2$O(cyclohexyl) | —C(O)CH$_2$NH(cyclohexyl) | —C(O)CH$_2$S(cyclohexyl) |
| 17.30 | —C(O)pyridin-2-yl | —C(O)CH$_2$(pyridin-2-yl) | —C(O)CH$_2$CH$_2$(pyridin-2-yl) |
| 17.31 | —C(O)pyridin-3-yl | —C(O)CH$_2$(pyridin-3-yl) | —C(O)CH$_2$CH$_2$(pyridin-3-yl) |
| 17.32 | —C(O)pyridin-4-yl | —C(O)CH$_2$(pyridin-4-yl) | —C(O)CH$_2$CH$_2$(pyridin-4-yl) |
| 17.33 | —C(O)furan-2-yl | —C(O)CH$_2$(furan-2-yl) | —C(O)CH$_2$CH$_2$(furan-2-yl) |
| 17.34 | —C(O)furan-3-yl | —C(O)CH$_2$(furan-3-yl) | —C(O)CH$_2$CH$_2$(furan-3-yl) |
| 17.35 | —C(O)thiophen-2-yl | —C(O)CH$_2$(thiophen-2-yl) | —C(O)CH$_2$CH$_2$(thiophen-2-yl) |
| 17.36 | —C(O)thiophen-2-yl | —C(O)CH$_2$(thiophen-2-yl) | —C(O)CH$_2$CH$_2$(thiophen-2-yl) |
| 17.37 | —C(O)imidazo-2-yl | —C(O)CH$_2$(imidazo-2-yl) | —C(O)CH$_2$CH$_2$(imidazo-2-yl) |
| 17.38 | —C(O)oxazo-2-yl | —C(O)CH$_2$(oxazo-2-yl) | —C(O)CH$_2$CH$_2$(oxazo-2-yl) |
| 17.39 | —C(O)thioazo-2-yl | —C(O)CH$_2$(thioazo-2-yl) | —C(O)CH$_2$CH$_2$(thioazo-2-yl) |
| 17.40 | —C(O)benzofuran-2-yl | —C(O)CH$_2$(benzofuran-2-yl) | —C(O)CH$_2$CH$_2$(benzofuran-2-yl) |
| 17.41 | —C(O)benzofuran-3-yl | —C(O)CH$_2$(benzofuran-3-yl) | —C(O)CH$_2$CH$_2$(benzofuran-3-yl) |
| 17.42 | —C(O)benzothiophen-2-yl | —C(O)CH$_2$(benzothiophen-2-yl) | —C(O)CH$_2$CH$_2$(benzothiophen-2-yl) |
| 17.43 | —C(O)thiophen-2-yl | —C(O)CH$_2$(thiophen-2-yl) | —C(O)CH$_2$CH$_2$(thiophen-2-yl) |
| 17.44 | —C(O)benzimidazo-2-yl | —C(O)CH$_2$(benzimidazo-2-yl) | —C(O)CH$_2$CH$_2$(benzimidazo-2-yl) |
| 17.45 | —C(O)benzoxazo-2-yl | —C(O)CH$_2$(benzoxazo-2-yl) | —C(O)CH$_2$CH$_2$(benzoxazo-2-yl) |

TABLE 17-continued

Formula I: A = —B(pinanediol); X = guanidinyl; $R^3$ = table below; $R^{11}$ = —CH$_2$(p-PhOH)

| | .1 | .2 | .3 |
|---|---|---|---|
| 17.46 | —C(O)benzothiazo-2-yl | —C(O)CH$_2$(benzothiazo-2-yl) | —C(O)CH$_2$CH$_2$(benzothiazo-2-yl) |
| 17.47 | —C(O)o-Ph(P(O)Ph$_3$) | —C(O)m-Ph(P(O)Ph$_3$) | —C(O)p-Ph(P(O)Ph$_3$) |
| 17.48 | —C(O)Ph-2-(fluoren-9-yl) | —C(O)Ph-3-(fluoren-9-yl) | —C(O)Ph-4-(fluoren-9-yl) |
| 17.49 | —C(O)N-indolin-2-one | —C(O)indolin-2-yl | —C(O)indol-2-yl |
| 17.50 | —C(O)C(CH$_3$)$_2$NHSO$_2$(naphth-2-yl) | —C(O)cyclopentyl-2-(Ph) | —C(O)cyclohexyl-2-(Ph) |
| 17.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 17.52 | —C(O)tetrahydronaphth-1-yl | —C(O)tetrahydronaphth-2-yl | —C(O)cyclopropyl-2,2-(Ph$_2$) |
| 17.53 | —C(O)tetrahydroisoquinolin-1-yl | —C(O)tetrahydroisoquinolin-3-yl | —C(O)CH$_2$((2-oxo)indolin-3-yl) |
| 17.54 | —C(O)CH$_2$(N-benzimidazol-2-one) | —C(O)CH$_2$(N-benzoxazol-2-one) | —C(O)CH$_2$(N-benzothiazol-2-one) |
| 17.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 17.56 | 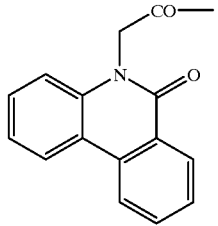 | 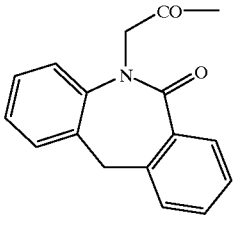 | 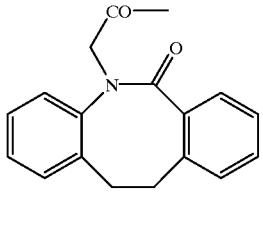 |
| 17.57 | 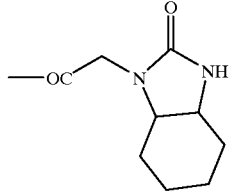 | 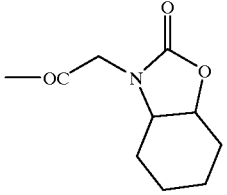 | 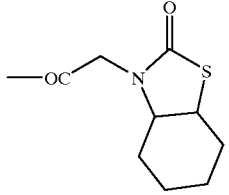 |
| 17.58 | 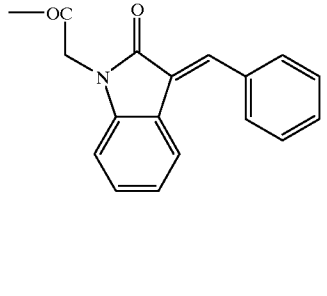 | 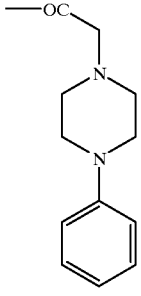 | 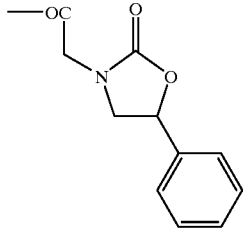 |
| 17.59 | —C(O)N(CH$_3$)CH$_2$Ph | —C(O)N(C$_2$H$_5$)CH$_2$Ph | —C(O)N(C$_3$H$_7$)CH$_2$Ph |
| 17.60 | —C(O)pyridin-3-yl-5-(Ph) | —C(O)Ph-3-(CH$_2$(thiophen-2-yl)) | —C(O)Ph-3-(CH$_2$Ph) |
| 17.61 | —C(O)C(CH$_3$)$_2$OPh | —C(O)CH(C$_2$H$_5$)OPh | —C(O)CH$_2$OCH$_2$Ph |
| 17.62 | —C(O)CH$_2$O(o-PhCH$_2$OH) | —C(O)CH$_2$O(m-PhCH$_2$OH) | —C(O)CH$_2$O(p-PhCH$_2$OH) |
| 17.63 | —C(O)CH$_2$O(o-PhCOOH) | —C(O)CH$_2$O(m-PhCOOH) | —C(O)CH$_2$O(p-PhCOOH) |
| 17.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 17.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 17.66 | 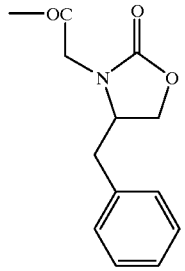 | | |

TABLE 18

Formula I: A = —B(pinanediol); X = guanidinyl; $R^3$ = table below; $R^{11}$ = —CH$_2$CH$_2$Ph

| | .1 | .2 | .3 |
|---|---|---|---|
| 18.1 | —C(O)Ph | —C(O)CH$_2$Ph | —C(O)CH$_2$CH$_2$Ph |
| 18.2 | —C(O)CH$_2$OPh | —C(O)CH$_2$NHPh | —C(O)CH$_2$SPh |
| 18.3 | —C(O)o-PhOH | —C(O)m-PhOH | —C(O)p-PhOH |
| 18.4 | —C(O)o-PhCH$_2$OH | —C(O)m-PhCH$_2$OH | —C(O)p-PhCH$_2$OH |
| 18.5 | —C(O)o-PhCOOH | —C(O)m-PhCOOH | —C(O)p-PhCOOH |
| 18.6 | —C(O)o-PhCH$_2$COOH | —C(O)m-PhCH$_2$COOH | —C(O)p-PhCH$_2$COOH |
| 18.7 | —C(O)naphth-1-yl | —C(O)CH$_2$(naphth-1-yl) | —C(O)CH$_2$CH$_2$(napth-1-yl) |
| 18.8 | —C(O)naphth-2-yl | —C(O)CH$_2$(naphth-2-yl) | —C(O)CH$_2$CH$_2$(napth-2-yl) |
| 18.9 | —C(O)o-biphenyl | —C(O)CH$_2$(o-biphenyl) | —C(O)CH$_2$CH$_2$(o-biphenyl) |
| 18.10 | —C(O)m-biphenyl | —C(O)CH$_2$(m-biphenyl) | —C(O)CH$_2$CH$_2$(m-biphenyl) |
| 18.12 | —C(O)p-biphenyl | —C(O)CH$_2$(p-biphenyl) | —C(O)CH$_2$CH$_2$(p-biphenyl) |
| 18.13 | —C(O)o-PhOPh | —C(O)CH$_2$(o-PhOPh) | —C(O)CH$_2$CH$_2$(o-PhOPh) |
| 18.14 | —C(O)m-PhOPh | —C(O)CH$_2$(m-PhOPh) | —C(O)CH$_2$CH$_2$(m-PhOPh) |
| 18.15 | —C(O)p-PhOPh | —C(O)CH$_2$(p-PhOPh) | —C(O)CH$_2$CH$_2$(p-PhOPh) |
| 18.16 | —C(O)o-PhNHPh | —C(O)CH$_2$(o-PhNHPh) | —C(O)CH$_2$CH$_2$(o-PhNHPh) |
| 18.17 | —C(O)m-PhNHPh | —C(O)CH$_2$(m-PhNHPh) | —C(O)CH$_2$CH$_2$(m-PhNHPh) |
| 18.18 | —C(O)p-PhNHPh | —C(O)CH$_2$(p-PhNHPh) | —C(O)CH$_2$CH$_2$(p-PhNHPh) |
| 18.19 | —C(O)o-PhSPh | —C(O)CH$_2$(o-PhSPh) | —C(O)CH$_2$CH$_2$(o-PhSPh) |
| 18.20 | —C(O)m-PhSPh | —C(O)CH$_2$(m-PhSPh) | —C(O)CH$_2$CH$_2$(m-PhSPh) |
| 18.21 | —C(O)p-PhSPh | —C(O)CH$_2$(p-PhSPh) | —C(O)CH$_2$CH$_2$(p-PhSPh) |
| 18.22 | —C(O)o-PhCH$_2$SPh | —C(O)CH$_2$(o-PhCH$_2$SPh) | —C(O)CH$_2$CH$_2$(o-PhCH$_2$SPh) |
| 18.23 | —C(O)m-PhCH$_2$SPh | —C(O)CH$_2$(m-PhCH$_2$SPh) | —C(O)CH$_2$CH$_2$(m-PhCH$_2$SPh) |
| 18.24 | —C(O)p-PhCH$_2$SPh | —C(O)CH$_2$(p-PhCH$_2$SPh) | —C(O)CH$_2$CH$_2$(p-PhCH$_2$SPh) |
| 18.25 | —C(O)adamantyl | —C(O)CH$_2$(adamantyl) | —C(O)CH$_2$CH$_2$(adamantyl) |
| 18.26 | —C(O)cyclopentyl | —C(O)CH$_2$(cyclopentyl) | —C(O)CH$_2$CH$_2$((cyclopentyl) |
| 18.27 | —C(O)cyclohexyl | —C(O)CH$_2$(cyclohexyl) | —C(O)CH$_2$CH$_2$(cyclohexyl) |
| 18.28 | —C(O)CH$_2$O(cyclopentyl) | —C(O)CH$_2$NH(cyclopentyl) | —C(O)CH$_2$S(cyclopentyl) |
| 18.29 | —C(O)CH$_2$O(cyclohexyl) | —C(O)CH$_2$NH(cyclohexyl) | —C(O)CH$_2$S(cyclohexyl) |
| 18.30 | —C(O)pyridin-2-yl | —C(O)CH$_2$(pyridin-2-yl) | —C(O)CH$_2$CH$_2$(pyridin-2-yl) |
| 18.31 | —C(O)pyridin-3-yl | —C(O)CH$_2$(pyridin-3-yl) | —C(O)CH$_2$CH$_2$(pyridin-3-yl) |
| 18.32 | —C(O)pyridin-4-yl | —C(O)CH$_2$(pyridin-4-yl) | —C(O)CH$_2$CH$_2$(pyridin-4-yl) |
| 18.33 | —C(O)furan-2-yl | —C(O)CH$_2$(furan-2-yl) | —C(O)CH$_2$CH$_2$(furan-2-yl) |
| 18.34 | —C(O)furan-3-yl | —C(O)CH$_2$(furan-3-yl) | —C(O)CH$_2$CH$_2$(furan-3-yl) |
| 18.35 | —C(O)thiophen-2-yl | —C(O)CH$_2$(thiophen-2-yl) | —C(O)CH$_2$CH$_2$(thiophen-2-yl) |
| 18.36 | —C(O)thiophen-2-yl | —C(O)CH$_2$(thiophen-2-yl) | —C(O)CH$_2$CH$_2$(thiophen-2-yl) |
| 18.37 | —C(O)imidazo-2-yl | —C(O)CH$_2$(imidazo-2-yl) | —C(O)CH$_2$CH$_2$(imidazo-2-yl) |
| 18.38 | —C(O)oxazo-2-yl | —C(O)CH$_2$(oxazo-2-yl) | —C(O)CH$_2$CH$_2$(oxazo-2-yl) |
| 18.39 | —C(O)thioazo-2-yl | —C(O)CH$_2$(thioazo-2-yl) | —C(O)CH$_2$CH$_2$(thioazo-2-yl) |
| 18.40 | —C(O)benzofuran-2-yl | —C(O)CH$_2$(benzofuran-2-yl) | —C(O)CH$_2$CH$_2$(benzofuran-2-yl) |
| 18.41 | —C(O)benzofuran-3-yl | —C(O)CH$_2$(benzofuran-3-yl) | —C(O)CH$_2$CH$_2$(benzofuran-3-yl) |
| 18.42 | —C(O)benzothiophen-2-yl | —C(O)CH$_2$(benzothiophen-2-yl) | —C(O)CH$_2$CH$_2$(benzothiophen-2-yl) |
| 18.43 | —C(O)thiophen-2-yl | —C(O)CH$_2$(thiophen-2-yl) | —C(O)CH$_2$CH$_2$(thiophen-2-yl) |
| 18.44 | —C(O)benzimidazo-2-yl | —C(O)CH$_2$(benzimidazo-2-yl) | —C(O)CH$_2$CH$_2$(benzimidazo-2-yl) |
| 18.45 | —C(O)benzoxazo-2-yl | —C(O)CH$_2$(benzoxazo-2-yl) | —C(O)CH$_2$CH$_2$(benzoxazo-2-yl) |
| 18.46 | —C(O)benzothiazo-2-yl | —C(O)CH$_2$(benzothiazo-2-yl) | —C(O)CH$_2$CH$_2$(benzothiazo-2-yl) |
| 18.47 | —C(O)o-Ph(P(O)Ph$_3$) | —C(O)m-Ph(P(O)Ph$_3$) | —C(O)p-Ph(P(O)Ph$_3$) |
| 18.48 | —C(O)Ph-2-(fluoren-9-yl) | —C(O)Ph-3-(fluoren-9-yl) | —C(O)Ph-4-(fluoren-9-yl) |
| 18.49 | —C(O)N-indolin-2-one | —C(O)indolin-2-yl | —C(O)indol-2-yl |
| 18.50 | —C(O)C(CH$_3$)$_2$NHSO$_2$(naphth-2-yl) | —C(O)cyclopentyl-2-(Ph) | —C(O)cyclohexyl-2-(Ph) |
| 18.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 18.52 | —C(O)tetrahydronaphth-1-yl | —C(O)tetrahydronaphth-2-yl | —C(O)cyclopropyl-2,2-(Ph$_2$) |
| 18.53 | —C(O)tetrahydroisoquinolin-1-yl | —C(O)tetrahydroisoquinolin-3-yl | —C(O)CH$_2$((2-oxo)indolin-3-yl) |
| 18.54 | —C(O)CH$_2$(N-benzimidazol-2-one) | —C(O)CH$_2$(N-benzoxazol-2-one) | —C(O)CH$_2$(N-benzothiazol-2-one) |
| 18.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 18.56 | 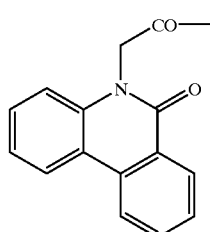 | 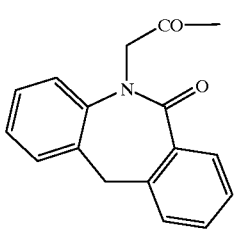 | 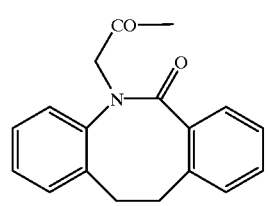 |

TABLE 18-continued

Formula I: A = —B(pinanediol); X = guanidinyl; R$^3$ = table below; R$^{11}$ = —CH$_2$CH$_2$Ph

| | .1 | .2 | .3 |
|---|---|---|---|
| 18.57 | (structure) | (structure) | (structure) |
| 18.58 | (structure) | (structure) | (structure) |
| 18.59 | —C(O)N(CH$_3$)CH$_2$Ph | —C(O)N(C$_2$H$_5$)CH$_2$Ph | —C(O)N(C$_3$H$_7$)CH$_2$Ph |
| 18.60 | —C(O)pyridin-3-yl-5-(Ph) | —C(O)Ph-3-(CH$_2$(thiophen-2-yl)) | —C(O)Ph-3-(CH$_2$Ph) |
| 18.61 | —C(O)C(CH$_3$)$_2$OPh | —C(O)CH(C$_2$H$_5$)OPh | —C(O)CH$_2$OCH$_2$Ph |
| 18.62 | —C(O)CH$_2$O(o-PhCH$_2$OH) | —C(O)CH$_2$O(m-PhCH$_2$OH) | —C(O)CH$_2$O(p-PhCH$_2$OH) |
| 18.63 | —C(O)CH$_2$O(o-PhCOOH) | —C(O)CH$_2$O(m-PhCOOH) | —C(O)CH$_2$O(p-PhCOOH) |
| 18.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 18.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 18.66 | (structure) | | |

TABLE 19

Formula I: A = —B(pinanediol); X = guanidinyl; R$^3$ = table below; R$^{11}$ = —Ph

| | .1 | .2 | .3 |
|---|---|---|---|
| 19.1 | —C(O)Ph | —C(O)CH$_2$Ph | —C(O)CH$_2$CH$_2$Ph |
| 19.2 | —C(O)CH$_2$OPh | —C(O)CH$_2$NHPh | —C(O)CH$_2$SPh |
| 19.3 | —C(O)o-PhOH | —C(O)m-PhOH | —C(O)p-PhOH |
| 19.4 | —C(O)o-PhCH$_2$OH | —C(O)m-PhCH$_2$OH | —C(O)p-PhCH$_2$OH |
| 19.5 | —C(O)o-PhCOOH | —C(O)m-PhCOOH | —C(O)p-PhCOOH |
| 19.6 | —C(O)o-PhCH$_2$COOH | —C(O)m-PhCH$_2$COOH | —C(O)p-PhCH$_2$COOH |
| 19.7 | —C(O)naphth-1-yl | —C(O)CH$_2$(naphth-1-yl) | —C(O)CH$_2$CH$_2$(napth-1-yl) |
| 19.8 | —C(O)naphth-2-yl | —C(O)CH$_2$(naphth-2-yl) | —C(O)CH$_2$CH$_2$(napth-2-yl) |
| 19.9 | —C(O)o-biphenyl | —C(O)CH$_2$(o-biphenyl) | —C(O)CH$_2$CH$_2$(o-biphenyl) |
| 19.10 | —C(O)m-biphenyl | —C(O)CH$_2$(m-biphenyl) | —C(O)CH$_2$CH$_2$(m-biphenyl) |
| 19.12 | —C(O)p-biphenyl | —C(O)CH$_2$(p-biphenyl) | —C(O)CH$_2$CH$_2$(p-biphenyl) |
| 19.13 | —C(O)o-PhOPh | —C(O)CH$_2$(o-PhOPh) | —C(O)CH$_2$CH$_2$(o-PhOPh) |
| 19.14 | —C(O)m-PhOPh | —C(O)CH$_2$(m-PhOPh) | —C(O)CH$_2$CH$_2$(m-PhOPh) |
| 19.15 | —C(O)p-PhOPh | —C(O)CH$_2$(p-PhOPh) | —C(O)CH$_2$CH$_2$(p-PhOPh) |
| 19.16 | —C(O)o-PhNHPh | —C(O)CH$_2$(o-PhNHPh) | —C(O)CH$_2$CH$_2$(o-PhNHPh) |
| 19.17 | —C(O)m-PhNHPh | —C(O)CH$_2$(m-PhNHPh) | —C(O)CH$_2$CH$_2$(m-PhNHPh) |
| 19.18 | —C(O)p-PhNHPh | —C(O)CH$_2$(p-PhNHPh) | —C(O)CH$_2$CH$_2$(p-PhNHPh) |
| 19.19 | —C(O)o-PhSPh | —C(O)CH$_2$(o-PhSPh) | —C(O)CH$_2$CH$_2$(o-PhSPh) |

TABLE 19-continued

Formula I: A = —B(pinanediol); X = guanidinyl; $R^3$ = table below; $R^{11}$ = —Ph

| | .1 | .2 | .3 |
|---|---|---|---|
| 19.20 | —C(O)m-PhSPh | —C(O)CH$_2$(m-PhSPh) | —C(O)CH$_2$CH$_2$(m-PhSPh) |
| 19.21 | —C(O)p-PhSPh | —C(O)CH$_2$(p-PhSPh) | —C(O)CH$_2$CH$_2$(p-PhSPh) |
| 19.22 | —C(O)o-PhCH$_2$SPh | —C(O)CH$_2$(o-PhCH$_2$SPh) | —C(O)CH$_2$CH$_2$(o-PhCH$_2$SPh) |
| 19.23 | —C(O)m-PhCH$_2$SPh | —C(O)CH$_2$(m-PhCH$_2$SPh) | —C(O)CH$_2$CH$_2$(m-PhCH$_2$SPh) |
| 19.24 | —C(O)p-PhCH$_2$SPh | —C(O)CH$_2$(p-PhCH$_2$SPh) | —C(O)CH$_2$CH$_2$(p-PhCH$_2$SPh) |
| 19.25 | —C(O)adamantyl | —C(O)CH$_2$(adamantyl) | —C(O)CH$_2$CH$_2$(adamantyl) |
| 19.26 | —C(O)cyclopentyl | —C(O)CH$_2$(cyclopentyl) | —C(O)CH$_2$CH$_2$((cyclopentyl) |
| 19.27 | —C(O)cyclohexyl | —C(O)CH$_2$(cyclohexyl) | —C(O)CH$_2$CH$_2$(cyclohexyl) |
| 19.28 | —C(O)CH$_2$O(cyclopentyl) | —C(O)CH$_2$NH(cyclopentyl) | —C(O)CH$_2$S(cyclopentyl) |
| 19.29 | —C(O)CH$_2$O(cyclohexyl) | —C(O)CH$_2$NH(cyclohexyl) | —C(O)CH$_2$S(cyclohexyl) |
| 19.30 | —C(O)pyridin-2-yl | —C(O)CH$_2$(pyridin-2-yl) | —C(O)CH$_2$CH$_2$(pyridin-2-yl) |
| 19.31 | —C(O)pyridin-3-yl | —C(O)CH$_2$(pyridin-3-yl) | —C(O)CH$_2$CH$_2$(pyridin-3-yl) |
| 19.32 | —C(O)pyridin-4-yl | —C(O)CH$_2$(pyridin-4-yl) | —C(O)CH$_2$CH$_2$(pyridin-4-yl) |
| 19.33 | —C(O)furan-2-yl | —C(O)CH$_2$(furan-2-yl) | —C(O)CH$_2$CH$_2$(furan-2-yl) |
| 19.34 | —C(O)furan-3-yl | —C(O)CH$_2$(furan-3-yl) | —C(O)CH$_2$CH$_2$(furan-3-yl) |
| 19.35 | —C(O)thiophen-2-yl | —C(O)CH$_2$(thiophen-2-yl) | —C(O)CH$_2$CH$_2$(thiophen-2-yl) |
| 19.36 | —C(O)thiophen-2-yl | —C(O)CH$_2$(thiophen-2-yl) | —C(O)CH$_2$CH$_2$(thiophen-2-yl) |
| 19.37 | —C(O)imidazo-2-yl | —C(O)CH$_2$(imidazo-2-yl) | —C(O)CH$_2$CH$_2$(imidazo-2-yl) |
| 19.38 | —C(O)oxazo-2-yl | —C(O)CH$_2$(oxazo-2-yl) | —C(O)CH$_2$CH$_2$(oxazo-2-yl) |
| 19.39 | —C(O)thioazo-2-yl | —C(O)CH$_2$(thioazo-2-yl) | —C(O)CH$_2$CH$_2$(thioazo-2-yl) |
| 19.40 | —C(O)benzofuran-2-yl | —C(O)CH$_2$(benzofuran-2-yl) | —C(O)CH$_2$CH$_2$(benzofuran-2-yl) |
| 19.41 | —C(O)benzofuran-3-yl | —C(O)CH$_2$(benzofuran-3-yl) | —C(O)CH$_2$CH$_2$(benzofuran-3-yl) |
| 19.42 | —C(O)benzothiophen-2-yl | —C(O)CH$_2$(benzothiophen-2-yl) | —C(O)CH$_2$CH$_2$(benzothiophen-2-yl) |
| 19.43 | —C(O)thiophen-2-yl | —C(O)CH$_2$(thiophen-2-yl) | —C(O)CH$_2$CH$_2$(thiophen-2-yl) |
| 19.44 | —C(O)benzimidazo-2-yl | —C(O)CH$_2$(benzimidazo-2-yl) | —C(O)CH$_2$CH$_2$(benzimidazo-2-yl) |
| 19.45 | —C(O)benzoxazo-2-yl | —C(O)CH$_2$(benzoxazo-2-yl) | —C(O)CH$_2$CH$_2$(benzoxazo-2-yl) |
| 19.46 | —C(O)benzothiazo-2-yl | —C(O)CH$_2$(benzothiazo-2-yl) | —C(O)CH$_2$CH$_2$(benzothiazo-2-yl) |
| 19.47 | —C(O)o-Ph(P(O)Ph$_3$) | —C(O)m-Ph(P(O)Ph$_3$) | —C(O)p-Ph(P(O)Ph$_3$) |
| 19.48 | —C(O)Ph-2-(fluoren-9-yl) | —C(O)Ph-3-(fluoren-9-yl) | —C(O)Ph-4-(fluoren-9-yl) |
| 19.49 | —C(O)N-indolin-2-one | —C(O)indolin-2-yl | —C(O)indol-2-yl |
| 19.50 | —C(O)C(CH$_3$)$_2$NHSO$_2$(naphth-2-yl) | —C(O)cyclopentyl-2-(Ph) | —C(O)cyclohexyl-2-(Ph) |
| 19.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 19.52 | —C(O)tetrahydronaphth-1-yl | —C(O)tetrahydronaphth-2-yl | —C(O)cyclopropyl-2,2-(Ph$_2$) |
| 19.53 | —C(O)tetrahydroisoquinolin-1-yl | —C(O)tetrahydroisoquinolin-3-yl | —C(O)CH$_2$((2-oxo)indolin-3-yl) |
| 19.54 | —C(O)CH$_2$(N-benzimidazol-2-one) | —C(O)CH$_2$(N-benzoxazol-2-one) | —C(O)CH$_2$(N-benzothiazol-2-one) |
| 19.55 | —C(O)CH$_2$(N-dihydroimidazol-2-one) | —C(O)CH$_2$(N-dihydrooxazol-2-one) | —C(O)CH$_2$(N-dihydrothiazol-2-one) |

19.56

19.57

19.58

TABLE 19-continued

Formula I: A = —B(pinanediol); X = guanidinyl; $R^3$ = table below; $R^{11}$ = —Ph

| | .1 | .2 | .3 |
|---|---|---|---|
| 19.59 | —C(O)N(CH₃)CH₂Ph | —C(O)N(C₂H₅)CH₂Ph | —C(O)N(C₃H₇)CH₂Ph |
| 19.60 | —C(O)pyridin-3-yl-5-(Ph) | —C(O)Ph-3-(CH₂(thiophen-2-yl)) | —C(O)Ph-3-(CH₂Ph) |
| 19.61 | —C(O)C(CH₃)₂OPh | —C(O)CH(C₂H₅)OPh | —C(O)CH₂OCH₂Ph |
| 19.62 | —C(O)CH₂O(o-PhCH₂OH) | —C(O)CH₂O(m-PhCH₂OH) | —C(O)CH₂O(p-PhCH₂OH) |
| 19.63 | —C(O)CH₂O(o-PhCOOH) | —C(O)CH₂O(m-PhCOOH) | —C(O)CH₂O(p-PhCOOH) |
| 19.64 | —C(O)CH₂O(o-PhCOOCH₃) | —C(O)CH₂O(m-PhCOOCH₃) | —C(O)CH₂O(p-PhCOOCH₃) |
| 19.65 | —C(O)CH₂O(o-PhCH₂COOH) | —C(O)CH₂O(m-PhCH₂COOH) | —C(O)CH₂O(p-PhCH₂COOH) |
| 19.66 | 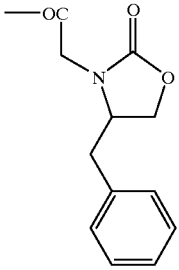 | | |

TABLE 20

Formula I: A = —B(pinanediol) ; X = guanidinyl; $R^3$ = table below; $R^{11}$ = —CH₂(naphth-2-yl).

| | .1 | .2 | .3 |
|---|---|---|---|
| 20.1 | —C(O)Ph | —C(O)CH₂Ph | —C(O)CH₂CH₂Ph |
| 20.2 | —C(O)CH₂OPh | —C(O)CH₂NHPh | —C(O)CH₂SPh |
| 20.3 | —C(O)o-PhOH | —C(O)m-PhOH | —C(O)p-PhOH |
| 20.4 | —C(O)o-PhCH₂OH | —C(O)m-PhCH₂OH | —C(O)p-PhCH₂OH |
| 20.5 | —C(O)o-PhCOOH | —C(O)m-PhCOOH | —C(O)p-PhCOOH |
| 20.6 | —C(O)o-PhCH₂COOH | —C(O)m-PhCH₂COOH | —C(O)p-PhCH₂COOH |
| 20.7 | —C(O)naphth-1-yl | —C(O)CH₂(naphth-1-yl) | —C(O)CH₂CH₂(naphth-1-yl) |
| 20.8 | —C(O)naphth-2-yl | —C(O)CH₂(naphth-2-yl) | —C(O)CH₂CH₂(napth-2-yl) |
| 20.9 | —C(O)o-biphenyl | —C(O)CH₂(o-biphenyl) | —C(O)CH₂CH₂(o-biphenyl) |
| 20.10 | —C(O)m-biphenyl | —C(O)CH₂(m-biphenyl) | —C(O)CH₂CH₂(m-biphenyl) |
| 20.12 | —C(O)p-biphenyl | —C(O)CH₂-p-biphenyl) | —C(O)CH₂CH₂(p-biphenyl) |
| 20.13 | —C(O)o-PhOPh | —C(O)CH₂(o-PhOPh) | —C(O)CH₂CH₂(o-PhOPh) |
| 20.14 | —C(O)m-PhOPh | —C(O)CH₂(m-PhOPh) | —C(O)CH₂CH₂(m-PhOPh) |
| 20.15 | —C(O)p-PhOPh | —C(O)CH₂(p-PhOPh) | —C(O)CH₂CH₂(p-PhOPh) |
| 20.16 | —C(O)o-PhNHPh | —C(O)CH₂(o-PhNHPh) | —C(O)CH₂CH₂(o-PhNHPh) |
| 20.17 | —C(O)m-PhNHPh | —C(O)CH₃(m-PhNHPh) | —C(O)CH₂CH₂(m-PhNHPh) |
| 20.18 | —C(O)p-PhNHPh | —C(O)CH₂(p-PhNHPh) | —C(O)CH₂CH₂(p-PhNHPh) |
| 20.19 | —C(O)o-PhSPh | —C(O)CH₂(o-PhSPh) | —C(O)CH₂CH₂(o-PhSPh) |
| 20.20 | —C(O)m-PhSPh | —C(O)CH₂(m-PhSPh) | —C(O)CH₂CH₂(m-PhSPh) |
| 20.21 | —C(O)p-PhSPh | —C(O)CH₂(p-PhSPh) | —C(O)CH₂CH₂(p-PhSPh) |
| 20.22 | —C(O)o-PhCH₂SPh | —C(O)CH₂(o-PhCH₂SPh) | —C(O)CH₂CH₂(o-PhCH₂SPh) |
| 20.23 | —C(O)m-PhCH₂SPh | —C(O)CH₃(m-PhCH₂SPh) | —C(O)CH₂CH₂(m-PhCH₂SPh) |
| 20.24 | —C(O)p-PhCH₂SPh | —C(O)CH₂(p-PhCH₂SPh) | —C(O)CH₂CH₂(p-PhCH₂SPh) |
| 20.25 | —C(O)adamantyl | —C(O)CH₂(adamantyl) | —C(O)CH₂CH₂(adamantyl) |
| 20.26 | —C(O)cyclopentyl | —C(O)CH₂(cyclopentyl) | —C(O)CH₂CH₂((cyclopentyl) |
| 20.27 | —C(O)cyclohexyl | —C(O)CH₂(cyclohexyl) | —C(O)CH₂CH₂(cyclohexyl) |
| 20.28 | —C(O)CH₂O(cyclopentyl) | —C(O)CH₂NH(cyclopentyl) | —C(O)CH₂S(cyclopentyl) |
| 20.29 | —C(O)CH₂O(cyclohexyl) | —C(O)CH₂NH(cyclohexyl) | —C(O)CH₂S(cyclohexyl) |
| 20.30 | —C(O)pyridin-2-yl | —C(O)CH₂(pyridin-2-yl) | —C(O)CH₂CH₂(pyridin-2-yl) |
| 20.31 | —C(O)pyridin-3-yl | —C(O)CH₂(pyridin-3-yl) | —C(O)CH₂CH₂(pyridin-3-yl) |
| 20.32 | —C(O)pyridin-4-yl | —C(O)CH₂(pyridin-4-yl) | —C(O)CH₂CH₂(pyridin-4-yl) |
| 20.33 | —C(O)furan-2-yl | —C(O)CH₂(furan-2-yl) | —C(O)CH₂CH₂(furan-2-yl) |
| 20.34 | —C(O)furan-3-yl | —C(O)CH₂(furan-3-yl) | —C(O)CH₂CH₂(furan-3-yl) |
| 20.35 | —C(O)thiophen-2-yl | —C(O)CH₂(thiophen-2-yl) | —C(O)CH₂CH₂(thiophen-2-yl) |
| 20.36 | —C(O)thiophen-2-yl | —C(O)CH₂(thiophen-2-yl) | —C(O)CH₂CH₂(thiophen-2-yl) |
| 20.37 | —C(O)imidazo-2-yl | —C(O)CH₂(imidazo-2-yl) | —C(O)CH₂CH₂(imidazo-2-yl) |
| 20.38 | —C(O)oxazo-2-yl | —C(O)CH₂(oxazo-2-yl) | —C(O)CH₂CH₂(oxazo-2-yl) |
| 20.39 | —C(O)thioazo-2-yl | —C(O)CH₂(thioazo-2-yl) | —C(O)CH₂CH₂(thioazo-2-yl) |
| 20.40 | —C(O)benzofuran-2-yl | —C(O)CH₂(benzofuran-2-yl) | —C(O)CH₂CH₂(benzofuran-2-yl) |
| 20.41 | —C(O)benzofuran-3-yl | —C(O)CH₂(benzofuran-3-yl) | —C(O)CH₂CH₂(benzofuran-3-yl) |
| 20.42 | —C(O)benzothiophen-2-yl | —C(O)CH₂(benzothiophen-2-yl) | —C(O)CH₂CH₂(benzothiophen-2-yl) |
| 20.43 | —C(O)thiophen-2-yl | —C(O)CH₂(thiophen-2-yl) | —C(O)CH₂CH₂(thiophen-2-yl) |

TABLE 20-continued

Formula I: A = —B(pinanediol) ; X = guanidinyl; R³ = table below; R¹¹ = —CH₂(naphth-2-yl).

| .1 | .2 | .3 |
|---|---|---|
| 20.44 —C(O)benzimidazo-2-yl | —C(O)CH₂(benzimidazo-2-yl) | —C(O)CH₂CH₂(benzimidazo-2-yl) |
| 20.45 —C(O)benzoxazo-2-yl | —C(O)CH₂(benzoxazo-2-yl) | —C(O)CH₂CH₂(benzoxazo-2-yl) |
| 20.46 —C(O)benzothiazo-2-yl | —C(O)CH₂(benzothiazo-2-yl) | —C(O)CH₂CH₂(benzothiazo-2-yl) |
| 20.47 —C(O)o-Ph(P(O)Ph₃) | —C(O)m-Ph(P(O)Ph₃) | —C(O)p-Ph(P(O)Ph₃) |
| 20.48 —C(O)Ph-2-(fluoren-9-yl) | —C(O)Ph-3-(fluoren-9-yl) | —C(O)Ph-4-(fluoren-9-yl) |
| 20.49 —C(O)N-indolin-2-one | —C(O)indolin-2-yl | —C(O)indol-2-yl |
| 20.50 —C(O)C(CH₃)₂NHSO₂(naphth-2-yl) | —C(O)cyclopentyl-2-(Ph) | —C(O)cyclohexyl-2-(Ph) |
| 20.51 —C(O)pyrrolidin-3-yl-4-(Ph) | —C(O)tetrahydrofuran-3-yl-4-(Ph) | —C(O)tetrahydrothiophen-3-yl-4-(Ph) |
| 20.52 —C(O)tetrahydronaphth-1-yl | —C(O)tetrahydronaphth-2-yl | —C(O)cyclopropyl-2,2-(Ph₂) |
| 20.53 —C(O)tetrahydroisoquinolin-1-yl | —C(O)tetrahydroisoquinolin-3-yl | —C(O)CH₂((2-oxo)indolin-3-yl) |
| 20.54 —C(O)CH₂(N-benzimidazol-2-one) | —C(O)CH₂(N-benzoxazol-2-one) | —C(O)CH₂(N-benzothiazol-2-one) |
| 20.55 —C(O)CH₂(N-dihydroimidazol-2-one) | —C(O)CH₂(N-dihydrooxazol-2-one) | —C(O)CH₂(N-dihydrothiazol-2-one) |

20.56

20.57

20.58

| 20.59 —C(O)N(CH₃)CH₂Ph | —C(O)N(C₂H₅)CH₂Ph | —C(O)N(C₃H₇)CH₂Ph |
| 20.60 —C(O)pyridin-3-yl-5-(Ph) | —C(O)Ph-3-(CH₂(thiophen-2-yl)) | —C(O)Ph-3-(CH₂Ph) |
| 20.61 —C(O)C(CH₃)₂OPh | —C(O)CH(C₂H₅)OPh | —C(O)CH₂OCH₂Ph |
| 20.62 —C(O)CH₂O(o-PhCH₂OH) | —C(O)CH₂O(m-PhCH₂OH) | —C(O)CH₂O(p-PhCH₂OH) |
| 20.63 —C(O)CH₂O(o-PhCOOH) | —C(O)CH₂O(m-PhCOOH) | —C(O)CH₂O(p-PhCOOH) |
| 20.64 —C(O)CH₂O(o-PhCOOCH₃) | —C(O)CH₂O(m-PhCOOCH₃) | —C(O)CH₂O(p-PhCOOCH₃) |

TABLE 20-continued

Formula I: A = —B(pinanediol) ; X = guanidinyl; $R^3$ = table below; $R^{11}$ = —CH$_2$(naphth-2-yl).

| .1 | .2 | .3 |
|---|---|---|
| 20.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 20.66 (structure: —OC(O)CH$_2$-N-oxazolidinone-benzyl) | | |

TABLE 21

Formula I: A = —B(pinanediol) ; X = —CH$_2$NH$_2$; $R^3$ = table below; $R^{11}$ = =CH$_3$

| .1 | .2 | .3 |
|---|---|---|
| 21.1 —C(O)Ph | —C(O)CH$_2$Ph | —C(O)CH$_2$CH$_2$Ph |
| 21.2 —C(O)CH$_2$OPh | —C(O)CH$_2$NHPh | —C(O)CH$_2$SPh |
| 21.3 —C(O)o-PhOH | —C(O)m-PhOH | —C(O)p-PhOH |
| 21.4 —C(O)o-PhCH$_2$OH | —C(O)m-PhCH$_2$OH | —C(O)p-PhCH$_2$OH |
| 21.5 —C(O)o-PhCOOH | —C(O)m-PhCOOH | —C(O)p-PhCOOH |
| 21.6 —C(O)o-PhCH$_2$COOH | —C(O)m-PhCH$_2$COOH | —C(O)p-PhCH$_2$COOH |
| 21.7 —C(O)naphth-1-yl | —C(O)CH$_2$(naphth-1-yl) | —C(O)CH$_2$CH$_2$(napth-1-yl) |
| 21.8 —C(O)naphth-2-yl | —C(O)CH$_2$(naphth-2-yl | —C(O)CH$_2$CH$_2$(napth-2-yl) |
| 21.9 —C(O)o-biphenyl | —C(O)CH$_2$(o-biphenyl) | —C(O)CH$_2$CH$_2$(o-biphenyl) |
| 21.10 —C(O)m-biphenyl | —C(O)CH$_2$(m-biphenyl) | —C(O)CH$_2$CH$_2$(m-biphenyl) |
| 21.12 —C(O)p-biphenyl | —C(O)CH$_2$-p-biphenyl) | —C(O)CH$_2$CH$_2$(p-biphenyl) |
| 21.13 —C(O)o-PhOPh | —C(O)CH$_2$(o-PhOPh) | —C(O)CH$_2$CH$_2$(o-PhOPh) |
| 21.14 —C(O)m-PhOPh | —C(O)CH$_2$(m-PhOPh) | —C(O)CH$_2$CH$_2$(m-PhOPh) |
| 21.15 —C(O)p-PhOPh | —C(O)CH$_2$(p-PhOPh) | —C(O)CH$_2$CH$_2$(p-PhOPh) |
| 21.16 —C(O)o-PhNHPh | —C(O)CH$_2$(o-PhNHPh) | —C(O)CH$_2$CH$_2$(o-PhNHPh) |
| 21.17 —C(O)m-PhNHPh | —C(O)CH$_2$(m-PhNHPh) | —C(O)CH$_2$CH$_2$(m-PhNHPh) |
| 21.18 —C(O)p-PhNHPh | —C(O)CH$_2$(p-PhNHPh) | —C(O)CH$_2$CH$_2$(p-PhNHPh) |
| 21.19 —C(O)o-PhSPh | —C(O)CH$_2$(o-PhSPh) | —C(O)CH$_2$CH$_2$(o-PhSPh) |
| 21.20 —C(O)m-PhSPh | —C(O)CH$_2$(m-PhSPh) | —C(O)CH$_2$CH$_2$(m-PhSPh) |
| 21.21 —C(O)p-PhSPh | —C(O)CH$_2$(p-PhSPh) | —C(O)CH$_2$CH$_2$(p-PhSPh) |
| 21.22 —C(O)o-PhCH$_2$SPh | —C(O)CH$_2$(o-PhCH$_2$SPh) | —C(O)CH$_2$CH$_2$(o-PhCH$_2$SPh) |
| 21.23 —C(O)m-PhCH$_2$SPh | —C(O)CH$_2$(m-PhCH$_2$SPh) | —C(O)CH$_2$CH$_2$(m-PhCH$_2$SPh) |
| 21.24 —C(O)p-PhCH$_2$SPh | —C(O)CH$_2$(p-PhCH$_2$SPh) | —C(O)CH$_2$CH$_2$(p-PhCH$_2$SPh) |
| 21.25 —C(O)adamantyl | —C(O)CH$_2$(adamantyl) | —C(O)CH$_2$CH$_2$(adamantyl) |
| 21.26 —C(O)cyclopentyl | —C(O)CH$_2$(cyclopentyl) | —C(O)CH$_2$CH$_2$((cyclopentyl) |
| 21.27 —C(O)cyclohexyl | —C(O)CH$_2$(cyclohexyl) | —C(O)CH$_2$CH$_2$(cyclohexyl) |
| 21.28 —C(O)CH$_2$O(cyclopentyl) | —C(O)CH$_2$NH(cyclopentyl) | —C(O)CH$_2$S(cyclopentyl) |
| 21.29 —C(O)CH$_2$O(cyclohexyl) | —C(O)CH$_2$NH(cyclohexyl) | —C(O)CH$_2$S(cyclohexyl) |
| 21.30 —C(O)pyridin-2-yl | —C(O)CH$_2$(pyridin-2-yl) | —C(O)CH$_2$CH$_2$(pyridin-2-yl) |
| 21.31 —C(O)pyridin-3-yl | —C(O)CH$_2$(pyridin-3-yl) | —C(O)CH$_2$CH$_2$(pyridin-3-yl) |
| 21.32 —C(O)pyridin-4-yl | —C(O)CH$_2$(pyridin-4-yl) | —C(O)CH$_2$CH$_2$(pyridin-4-yl) |
| 21.33 —C(O)furan-2-yl | —C(O)CH$_2$(furan-2-yl) | —C(O)CH$_2$CH$_2$(furan-2-yl) |
| 21.34 —C(O)furan-3-yl | —C(O)CH$_2$(furan-3-yl) | —C(O)CH$_2$CH$_2$(furan-3-yl) |
| 21.35 —C(O)thiophen-2-yl | —C(O)CH$_2$(thiophen-2-yl) | —C(O)CH$_2$CH$_2$(thiophen-2-yl) |
| 21.36 —C(O)thiophen-2-yl | —C(O)CH$_2$(thiophen-2-yl) | —C(O)CH$_2$CH$_2$(thiophen-2-yl) |
| 21.37 —C(O)imidazo-2-yl | —C(O)CH$_2$(imidazo-2-yl) | —C(O)CH$_2$CH$_2$(imidazo-2-yl) |
| 21.38 —C(O)oxazo-2-yl | —C(O)CH$_2$(oxazo-2-yl) | —C(O)CH$_2$CH$_2$(oxazo-2-yl) |
| 21.39 —C(O)thioazo-2-yl | —C(O)CH$_2$(thioazo-2-yl) | —C(O)CH$_2$CH$_2$(thioazo-2-yl) |
| 21.40 —C(O)benzofuran-2-yl | —C(O)CH$_2$(benzofuran-2-yl) | —C(O)CH$_2$CH$_2$(benzofuran-2-yl) |
| 21.41 —C(O)benzofuran-3-yl | —C(O)CH$_2$(benzofuran-3-yl) | —C(O)CH$_2$CH$_2$(benzofuran-3-yl) |
| 21.42 —C(O)benzothiophen-2-yl | —C(O)CH$_2$(benzothiophen-2-yl) | —C(O)CH$_2$CH$_2$(benzothiophen-2-yl |
| 21.43 —C(O)thiophen-2-yl | —C(O)CH$_2$(thiophen-2-yl) | —C(O)CH$_2$CH$_2$(thiophen-2-yl) |
| 21.44 —C(O)benzimidazo-2-yl | —C(O)CH$_2$(benzimidazo-2-yl) | —C(O)CH$_2$CH$_2$(benzimidazo-2-yl) |
| 21.45 —C(O)benzoxazo-2-yl | —C(O)CH$_2$(benzoxazo-2-yl) | —C(O)CH$_2$CH$_2$(benzoxazo-2-yl) |
| 21.46 —C(O)benzothiazo-2-yl | —C(O)CH$_2$(benzothiazo-2-yl) | —C(O)CH$_2$CH$_2$(benzothiazo-2-yl) |
| 21.47 —C(O)o-Ph(P(O)Ph$_3$) | —C(O)m-Ph(P(O)Ph$_3$) | —C(O)p-Ph(P(O)Ph$_3$) |
| 21.48 —C(O)Ph-2-(fluoren-9-yl) | —C(O)Ph-3-(fluoren-9-yl) | —C(O)Ph-4-(fluoren-9-yl) |
| 21.49 —C(O)N-indolin-2-one | —C(O)indolin-2-yl | —C(O)indol-2-yl |
| 21.50 —C(O)C(CH$_3$)$_2$NHSO$_2$(naphth-2-yl) | —C(O)cyclopentyl-2-(Ph) | —C(O)cyclohexyl-2-(Ph) |
| 21.51 —C(O)pyrrolidin-3-yl-4-(Ph) | —C(O)tetrahydrofuran-3-yl-4- | —C(O)tetrahydrothiophen-3-yl-4- |

TABLE 21-continued

Formula I: A = —B(pinanediol) ; X = —CH$_2$NH$_2$; R$^3$ = table below; R$^{11}$ = =CH$_3$

| .1 | .2 | .3 |
|---|---|---|
| | (Ph) | (Ph) |
| 21.52 —C(O)tetrahydronaphth-1-yl | —C(O)tetrahydronaphth-2-yl | —C(O)cyclopropyl-2,2-(Ph$_2$) |
| 21.53 —C(O)tetrahydroisoquinolin-1-yl | —C(O)tetrahydroisoquinolin-3-yl | —C(O)CH$_2$((2-oxo)indolin-3-yl) |
| 21.54 —C(O)CH$_2$(N-benzimidazol-2-one) | —C(O)CH$_2$(N-benzoxazol-2-one) | —C(O)CH$_2$(N-benzothiazol-2-one) |
| 21.55 —C(O)CH$_2$(N-dihydroimidazol-2-one) | —C(O)CH$_2$(N-dihydrooxazol-2-one) | —C(O)CH$_2$(N-dihydrothiazol-2-one) |

21.56

21.57

21.58

| 21.59 —C(O)N(CH$_3$)CH$_2$Ph | —C(O)N(C$_2$H$_5$)CH$_2$Ph | —C(O)N(C$_3$H$_7$)CH$_2$Ph |
|---|---|---|
| 21.60 —C(O)pyridin-3-yl-5-(Ph) | —C(O)Ph-3-(CH$_2$(thiophen-2-yl)) | —C(O)Ph-3-(CH$_2$Ph) |
| 21.61 —C(O)C(CH$_3$)$_2$OPh | —C(O)CH(C$_2$H$_5$)OPh | —C(O)CH$_2$OCH$_2$Ph |
| 21.62 —C(O)CH$_2$O(o-PhCH$_2$OH) | —C(O)CH$_2$O(m-PhCH$_2$OH) | —C(O)CH$_2$O(p-PhCH$_2$OH) |
| 21.63 —C(O)CH$_2$O(o-PhCOOH) | —C(O)CH$_2$O(m-PhCOOH) | —C(O)CH$_2$O(p-PhCOOH) |
| 21.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 21.65 —C(O)CH$_2$O(o-PhCH$_2$COOH) | —C(O)CH$_2$O(m-PhCH$_2$COOH) | —C(O)CH$_2$O(p-PhCH$_2$COOH) |

21.66

TABLE 22

Formula I: A = —B(pinanediol) ; X = —CH$_2$NH$_2$; R$^3$ = table below; R$^{11}$ = —CH$_2$(p-PhOH).

| | .1 | .2 | .3 |
|---|---|---|---|
| 22.1 | —C(O)Ph | —C(O)CH$_2$Ph | —C(O)CH$_2$CH$_2$Ph |
| 22.2 | —C(O)CH$_2$OPh | —C(O)CH$_2$NHPh | —C(O)CH$_2$SPh |
| 22.3 | —C(O)o-PhOH | —C(O)m-PhOH | —C(O)p-PhOH |
| 22.4 | —C(O)o-PhCH$_2$OH | —C(O)m-PhCH$_2$OH | —C(O)p-PhCH$_2$OH |
| 22.5 | —C(O)o-PhCOOH | —C(O)m-PhCOOH | —C(O)p-PhCOOH |
| 22.6 | —C(O)o-PhCH$_2$COOH | —C(O)m-PhCH$_2$COOH | —C(O)p-PhCH$_2$COOH |
| 22.7 | —C(O)naphth-1-yl | —C(O)CH$_2$(naphth-1-yl) | —C(O)CH$_2$CH$_2$(napth-1-yl) |
| 22.8 | —C(O)naphth-2-yl | —C(O)CH$_2$(naphth-2-yl) | —C(O)CH$_2$CH$_2$(napth-2-yl) |
| 22.9 | —C(O)o-biphenyl | —C(O)CH$_2$(o-biphenyl) | —C(O)CH$_2$CH$_2$(o-biphenyl) |
| 22.10 | —C(O)m-biphenyl | —C(O)CH$_2$(m-biphenyl) | —C(O)CH$_2$CH$_2$(m-biphenyl) |
| 22.12 | —C(O)p-biphenyl | —C(O)CH$_2$-p-biphenyl) | —C(O)CH$_2$CH$_2$(p-biphenyl) |
| 22.13 | —C(O)o-PhOPh | —C(O)CH$_2$(o-PhOPh) | —C(O)CH$_2$CH$_2$(o-PhOPh) |
| 22.14 | —C(O)m-PhOPh | —C(O)CH$_2$(m-PhOPh) | —C(O)CH$_2$CH$_2$(m-PhOPh) |
| 22.15 | —C(O)p-PhOPh | —C(O)CH$_2$(p-PhOPh) | —C(O)CH$_2$CH$_2$(p-PhOPh) |
| 22.16 | —C(O)o-PhNHPh | —C(O)CH$_2$(o-PhNHPh) | —C(O)CH$_2$CH$_2$(o-PhNHPh) |
| 22.17 | —C(O)m-PhNHPh | —C(O)CH$_2$(m-PhNHPh) | —C(O)CH$_2$CH$_2$(m-PhNHPh) |
| 22.18 | —C(O)p-PhNHPh | —C(O)CH$_2$(p-PhNHPh) | —C(O)CH$_2$CH$_2$(p-PhNHPh) |
| 22.19 | —C(O)o-PhSPh | —C(O)CH$_2$(o-PhSPh) | —C(O)CH$_2$CH$_2$(o-PhSPh) |
| 22.20 | —C(O)m-PhSPh | —C(O)CH$_2$(m-PhSPh) | —C(O)CH$_2$CH$_2$(m-PhSPh) |
| 22.21 | —C(O)p-PhSPh | —C(O)CH$_2$(p-PhSPh) | —C(O)CH$_2$CH$_2$(p-PhSPh) |
| 22.22 | —C(O)o-PhCH$_2$SPh | —C(O)CH$_2$(o-PhCH$_2$SPh) | —C(O)CH$_2$CH$_2$(o-PhCH$_2$SPh) |
| 22.23 | —C(O)m-PhCH$_2$SPh | —C(O)CH$_2$(m-PhCH$_2$SPh) | —C(O)CH$_2$CH$_2$(m-PhCH$_2$SPh) |
| 22.24 | —C(O)p-PhCH$_2$SPh | —C(O)CH$_2$(p-PhCH$_2$SPh) | —C(O)CH$_2$CH$_2$(p-PhCH$_2$SPh) |
| 22.25 | —C(O)adamantyl | —C(O)CH$_2$(adamantyl) | —C(O)CH$_2$CH$_2$(adamantyl) |
| 22.26 | —C(O)cyclopentyl | —C(O)CH$_2$(cyclopentyl) | —C(O)CH$_2$CH$_2$((cyclopentyl) |
| 22.27 | —C(O)cyclohexyl | —C(O)CH$_2$(cyclohexyl) | —C(O)CH$_2$CH$_2$(cyclohexyl) |
| 22.28 | —C(O)CH$_2$O(cyclopentyl) | —C(O)CH$_2$NH(cyclopentyl) | —C(O)CH$_2$S(cyclopentyl) |
| 22.29 | —C(O)CH$_2$O(cyclohexyl) | —C(O)CH$_2$NH(cyclohexyl) | —C(O)CH$_2$S(cyclohexyl) |
| 22.30 | —C(O)pyridin-2-yl | —C(O)CH$_2$(pyridin-2-yl) | —C(O)CH$_2$CH$_2$(pyridin-2-yl) |
| 22.31 | —C(O)pyridin-3-yl | —C(O)CH$_2$(pyridin-3-yl) | —C(O)CH$_2$CH$_2$(pyridin-3-yl) |
| 22.32 | —C(O)pyridin-4-yl | —C(O)CH$_2$(pyridin-4-yl) | —C(O)CH$_2$CH$_2$(pyridin-4-yl) |
| 22.33 | —C(O)furan-2-yl | —C(O)CH$_2$(furan-2-yl) | —C(O)CH$_2$CH$_2$(furan-2-yl) |
| 22.34 | —C(O)furan-3-yl | —C(O)CH$_2$(furan-3-yl) | —C(O)CH$_2$CH$_2$(furan-3-yl) |
| 22.35 | —C(O)thiophen-2-yl | —C(O)CH$_2$(thiophen-2-yl) | —C(O)CH$_2$CH$_2$(thiophen-2-yl) |
| 22.36 | —C(O)thiophen-2-yl | —C(O)CH$_2$(thiophen-2-yl) | —C(O)CH$_2$CH$_2$(thiophen-2-yl) |
| 22.37 | —C(O)imidazo-2-yl | —C(O)CH$_2$(imidazo-2-yl) | —C(O)CH$_2$CH$_2$(imidazo-2-yl) |
| 22.38 | —C(O)oxazo-2-yl | —C(O)CH$_2$(oxazo-2-yl) | —C(O)CH$_2$CH$_2$(oxazo-2-yl) |
| 22.39 | —C(O)thioazo-2-yl | —C(O)CH$_2$(thioazo-2-yl) | —C(O)CH$_2$CH$_2$(thioazo-2-yl) |
| 22.40 | —C(O)benzofuran-2-yl | —C(O)CH$_2$(benzofuran-2-yl) | —C(O)CH$_2$CH$_2$(benzofuran-2-yl) |
| 22.41 | —C(O)benzofuran-3-yl | —C(O)CH$_2$(benzofuran-3-yl) | —C(O)CH$_2$CH$_2$(benzofuran-3-yl) |
| 22.42 | —C(O)benzothiophen-2-yl | —C(O)CH$_2$(benzothiophen-2-yl) | —C(O)CH$_2$CH$_2$(benzothiophen-2-yl |
| 22.43 | —C(O)thiophen-2-yl | —C(O)CH$_2$(thiophen-2-yl) | —C(O)CH$_2$CH$_2$(thiophen-2-yl) |
| 22.44 | —C(O)benzimidazo-2-yl | —C(O)CH$_2$(benzimidazo-2-yl) | —C(O)CH$_2$CH$_2$(benzimidazo-2-yl) |
| 22.45 | —C(O)benzoxazo-2-yl | —C(O)CH$_2$(benzoxazo-2-yl) | —C(O)CH$_2$CH$_2$(benzoxazo-2-yl) |
| 22.46 | —C(O)benzothiazo-2-yl | —C(O)CH$_2$(benzothiazo-2-yl) | —C(O)CH$_2$CH$_2$(benzothiazo-2-yl) |
| 22.47 | —C(O)o-Ph(P(O)Ph$_3$) | —C(O)m-Ph(P(O)Ph$_3$) | —C(O)p-Ph(P(O)Ph$_3$) |
| 22.48 | —C(O)Ph-2-(fluoren-9-yl) | —C(O)Ph-3-(fluoren-9-yl) | —C(O)Ph-4-(fluoren-9-yl) |
| 22.49 | —C(O)N-indolin-2-one | —C(O)indolin-2-yl | —C(O)indol-2-yl |
| 22.50 | —C(O)C(CH$_3$)$_2$NHSO$_2$(naphth-2-yl) | —C(O)cyclopentyl-2-(Ph) | —C(O)cyclohexyl-2-(Ph) |
| 22.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 22.52 | —C(O)tetrahydronaphth-1-yl | —C(O)tetrahydronaphth-2-yl | —C(O)cyclopropyl-2,2-(Ph$_2$) |
| 22.53 | —C(O)tetrahydroisoquinolin-1-yl | —C(O)tetrahydroisoquinolin-3-yl | —C(O)CH$_2$((2-oxo)indolin-3-yl) |
| 22.54 | —C(O)CH$_2$(N-benzimidazol-2-one) | —C(O)CH$_2$(N-benzoxazol-2-one) | —C(O)CH$_2$(N-benzothiazol-2-one) |
| 22.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 22.56 | 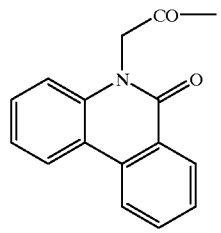 | 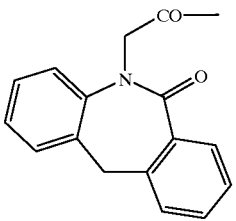 |  |

TABLE 22-continued

Formula I: A = —B(pinanediol) ; X = —CH$_2$NH$_2$; R$^3$ = table below; R$^{11}$ = —CH$_2$(p-PhOH).

| .1 | .2 | .3 |
|---|---|---|
| 22.57 | | |
| 22.58 | | |
| 22.59 —C(O)N(CH$_3$)CH$_2$Ph | —C(O)N(C$_2$H$_5$)CH$_2$Ph | —C(O)N(C$_3$H$_7$)CH$_2$Ph |
| 22.60 —C(O)pyridin-3-yl-5-(Ph) | —C(O)Ph-3-(CH$_2$(thiophen-2-yl)) | —C(O)Ph-3-(CH$_2$Ph) |
| 22.61 —C(O)C(CH$_3$)$_2$OPh | —C(O)CH(C$_2$H$_5$)OPh | —C(O)CH$_2$OCH$_2$Ph |
| 22.62 —C(O)CH$_2$O(o-PhCH$_2$OH) | —C(O)CH$_2$O(m-PhCH$_2$OH) | —C(O)CH$_2$O(p-PhCH$_2$OH) |
| 22.63 —C(O)CH$_2$O(o-PhCOOH) | —C(O)CH$_2$O(m-PhCOOH) | —C(O)CH$_2$O(p-PhCOOH) |
| 22.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 22.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 22.66 | | |

TABLE 23

Formula I: A = —B(pinanediol) ; X = CH$_2$NH$_2$; R$^3$ = table below; R$^{11}$ = —CH$_2$CH$_2$Ph.

| .1 | .2 | .3 |
|---|---|---|
| 23.1 —C(O)Ph | —C(O)CH$_2$Ph | —C(O)CH$_2$CH$_2$Ph |
| 23.2 —C(O)CH$_2$OPh | —C(O)CH$_2$NHPh | —C(O)CH$_2$SPh |
| 23.3 —C(O)o-PhOH | —C(O)m-PhOH | —C(O)p-PhOH |
| 23.4 —C(O)o-PhCH$_2$OH | —C(O)m-PhCH$_2$OH | —C(O)p-PhCH$_2$OH |
| 23.5 —C(O)o-PhCOOH | —C(O)m-PhCOOH | —C(O)p-PhCOOH |
| 23.6 —C(O)o-PhCH$_2$COOH | —C(O)m-PhCH$_2$COOH | —C(O)p-PhCH$_2$COOH |
| 23.7 —C(O)naphth-1-yl | —C(O)CH$_2$(naphth-1-yl) | —C(O)CH$_2$CH$_2$(napth-1-yl) |
| 23.8 —C(O)naphth-2-yl | —C(O)CH$_2$(naphth-2-yl | —C(O)CH$_2$CH$_2$(napth-2-yl) |
| 23.9 —C(O)o-biphenyl | —C(O)CH$_2$(o-biphenyl) | —C(O)CH$_2$CH$_2$(o-biphenyl) |
| 23.10 —C(O)m-biphenyl | —C(O)CH$_2$(m-biphenyl) | —C(O)CH$_2$CH$_2$(m-biphenyl) |
| 23.12 —C(O)p-biphenyl | —C(O)CH$_2$-p-biphenyl) | —C(O)CH$_2$CH$_2$(p-biphenyl) |
| 23.13 —C(O)o-PhOPh | —C(O)CH$_2$(o-PhOPh) | —C(O)CH$_2$CH$_2$(o-PhOPh) |
| 23.14 —C(O)m-PhOPh | —C(O)CH$_2$(m-PhOPh) | —C(O)CH$_2$CH$_2$(m-PhOPh) |
| 23.15 —C(O)p-PhOPh | —C(O)CH$_2$(p-PhOPh) | —C(O)CH$_2$CH$_2$(p-PhOPh) |
| 23.16 —C(O)o-PhNHPh | —C(O)CH$_2$(o-PhNHPh) | —C(O)CH$_2$CH$_2$(o-PhNHPh) |
| 23.17 —C(O)m-PhNHPh | —C(O)CH$_2$(m-PhNHPh) | —C(O)CH$_2$CH$_2$(m-PhNHPh) |
| 23.18 —C(O)p-PhNHPh | —C(O)CH$_2$(p-PhNHPh) | —C(O)CH$_2$CH$_2$(p-PhNHPh) |

TABLE 23-continued

Formula I: A = —B(pinanediol) ; X = CH$_2$NH$_2$; R$^3$ = table below; R$^{11}$ = —CH$_2$CH$_2$Ph.

| .1 | .2 | .3 |
|---|---|---|
| 23.19 —C(O)o-PhSPh | —C(O)CH$_2$(o-PhSPh) | —C(O)CH$_2$CH$_2$(o-PhSPh) |
| 23.20 —C(O)m-PhSPh | —C(O)CH$_2$(m-PhSPh) | —C(O)CH$_2$CH$_2$(m-PhSPh) |
| 23.21 —C(O)p-PhSPh | —C(O)CH$_2$(p-PhSPh) | —C(O)CH$_2$CH$_2$(p-PhSPh) |
| 23.22 —C(O)o-PhCH$_2$SPh | —C(O)CH$_2$(o-PhCH$_2$SPh) | —C(O)CH$_2$CH$_2$(o-PhCH$_2$SPh) |
| 23.23 —C(O)m-PhCH$_2$SPh | —C(O)CH$_2$(m-PhCH$_2$SPh) | —C(O)CH$_2$CH$_2$(m-PhCH$_2$SPh) |
| 23.24 —C(O)p-PhCH$_2$SPh | —C(O)CH$_2$(p-PhCH$_2$SPh) | —C(O)CH$_2$CH$_2$(p-PhCH$_2$SPh) |
| 23.25 —C(O)adamantyl | —C(O)CH$_2$(adamantyl) | —C(O)CH$_2$CH$_2$(adamantyl) |
| 23.26 —C(O)cyclopentyl | —C(O)CH$_2$(cyclopentyl) | —C(O)CH$_2$CH$_2$((cyclopentyl) |
| 23.27 —C(O)cyclohexyl | —C(O)CH$_2$(cyclohexyl) | —C(O)CH$_2$CH$_2$(cyclohexyl) |
| 23.28 —C(O)CH$_2$O(cyclopentyl) | —C(O)CH$_2$NH(cyclopentyl) | —C(O)CH$_2$S(cyclopentyl) |
| 23.29 —C(O)CH$_2$O(cyclohexyl) | —C(O)CH$_2$NH(cyclohexyl) | —C(O)CH$_2$S(cyclohexyl) |
| 23.30 —C(O)pyridin-2-yl | —C(O)CH$_2$(pyridin-2-yl) | —C(O)CH$_2$CH$_2$(pyridin-2-yl) |
| 23.31 —C(O)pyridin-3-yl | —C(O)CH$_2$(pyridin-3-yl) | —C(O)CH$_2$CH$_2$(pyridin-3-yl) |
| 23.32 —C(O)pyridin-4-yl | —C(O)CH$_2$(pyridin-4-yl) | —C(O)CH$_2$CH$_2$(pyridin-4-yl) |
| 23.33 —C(O)furan-2-yl | —C(O)CH$_2$(furan-2-yl) | —C(O)CH$_2$CH$_2$(furan-2-yl) |
| 23.34 —C(O)furan-3-yl | —C(O)CH$_2$(furan-3-yl) | —C(O)CH$_2$CH$_2$(furan-3-yl) |
| 23.35 —C(O)thiophen-2-yl | —C(O)CH$_2$(thiophen-2-yl) | —C(O)CH$_2$CH$_2$(thiophen-2-yl) |
| 23.36 —C(O)thiophen-2-yl | —C(O)CH$_2$(thiophen-2-yl) | —C(O)CH$_2$CH$_2$(thiophen-2-yl) |
| 23.37 —C(O)imidazo-2-yl | —C(O)CH$_2$(imidazo-2-yl) | —C(O)CH$_2$CH$_2$(imidazo-2-yl) |
| 23.38 —C(O)oxazo-2-yl | —C(O)CH$_2$(oxazo-2-yl) | —C(O)CH$_2$CH$_2$(oxazo-2-yl) |
| 23.39 —C(O)thioazo-2-yl | —C(O)CH$_2$(thioazo-2-yl) | —C(O)CH$_2$CH$_2$(thioazo-2-yl) |
| 23.40 —C(O)benzofuran-2-yl | —C(O)CH$_2$(benzofuran-2-yl) | —C(O)CH$_2$CH$_2$(benzofuran-2-yl) |
| 23.41 —C(O)benzofuran-3-yl | —C(O)CH$_2$(benzofuran-3-yl) | —C(O)CH$_2$CH$_2$(benzofuran-3-yl) |
| 23.42 —C(O)benzothiophen-2-yl | —C(O)CH$_2$(benzothiophen-2-yl) | —C(O)CH$_2$CH$_2$(benzothiophen-2-yl |
| 23.43 —C(O)thiophen-2-yl | —C(O)CH$_2$(thiophen-2-yl) | —C(O)CH$_2$CH$_2$(thiophen-2-yl) |
| 23.44 —C(O)benzimidazo-2-yl | —C(O)CH$_2$(benzimidazo-2-yl) | —C(O)CH$_2$CH$_2$(benzimidazo-2-yl) |
| 23.45 —C(O)benzoxazo-2-yl | —C(O)CH$_2$(benzoxazo-2-yl) | —C(O)CH$_2$CH$_2$(benzoxazo-2-yl) |
| 23.46 —C(O)benzothiazo-2-yl | —C(O)CH$_2$(benzothiazo-2-yl) | —C(O)CH$_2$CH$_2$(benzothiazo-2-yl) |
| 23.47 —C(O)o-Ph(P(O)Ph$_3$) | —C(O)m-Ph(P(O)Ph$_3$) | —C(O)p-Ph(P(O)Ph$_3$) |
| 23.48 —C(O)Ph-2-(fluoren-9-yl) | —C(O)Ph-3-(fluoren-9-yl) | —C(O)Ph-4-(fluoren-9-yl) |
| 23.49 —C(O)N-indolin-2-one | —C(O)indolin-2-yl | —C(O)indol-2-yl |
| 23.50 —C(O)C(CH$_3$)$_2$NHSO$_2$(naphth-2-yl) | —C(O)cyclopentyl-2-(Ph) | —C(O)cyclohexyl-2-(Ph) |
| 23.51 —C(O)pyrrolidin-3-yl-4-(Ph) | —C(O)tetrahydrofuran-3-yl-4-(Ph) | —C(O)tetrahydrothiophen-3-yl-4-(Ph) |
| 23.52 —C(O)tetrahydronaphth-1-yl | —C(O)tetrahydronaphth-2-yl | —C(O)cyclopropyl-2,2-(Ph$_2$) |
| 23.53 —C(O)tetrahydroisoquinolin-1-yl | —C(O)tetrahydroisoquinolin-3-yl | —C(O)CH$_2$((2-oxo)indolin-3-yl) |
| 23.54 —C(O)CH$_2$(N-benzimidazol-2-one) | —C(O)CH$_2$(N-benzoxazol-2-one) | —C(O)CH$_2$(N-benzothiazol-2-one) |
| 23.55 —C(O)CH$_2$(N-dihydroimidazol-2-one) | —C(O)CH$_2$(N-dihydrooxazol-2-one) | —C(O)CH$_2$(N-dihydrothiazol-2-one) |

23.56

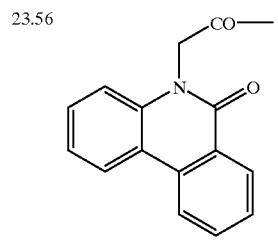 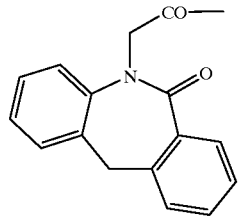 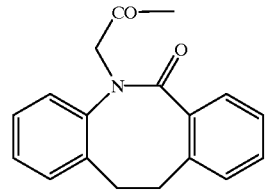

23.57

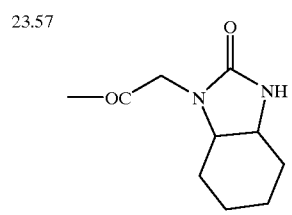 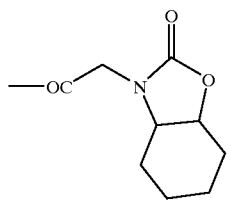 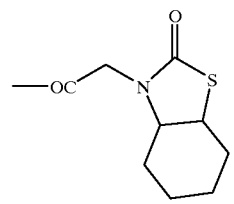

TABLE 23-continued

Formula I: A = —B(pinanediol) ; X = CH$_2$NH$_2$; R$^3$ = table below; R$^{11}$ = —CH$_2$CH$_2$Ph.

| .1 | .2 | .3 |
|---|---|---|
| 23.58 (N-benzylidene-oxindole-N-CH$_2$-OC—) | (4-phenylpiperazin-1-yl-CH$_2$-OC—) | (5-phenyl-oxazolidin-2-one-N-CH$_2$-OC—) |
| 23.59 —C(O)N(CH$_3$)CH$_2$Ph | —C(O)N(C$_2$H$_5$)CH$_2$Ph | —C(O)N(C$_3$H$_7$)CH$_2$Ph |
| 23.60 —C(O)pyridin-3-yl-5-(Ph) | —C(O)Ph-3-(CH$_2$(thiophen-2-yl)) | —C(O)Ph-3-(CH$_2$Ph) |
| 23.61 —C(O)C(CH$_3$)$_2$OPh | —C(O)CH(C$_2$H$_5$)OPh | —C(O)CH$_2$OCH$_2$Ph |
| 23.62 —C(O)CH$_2$O(o-PhCH$_2$OH) | —C(O)CH$_2$O(m-PhCH$_2$OH) | —C(O)CH$_2$O(p-PhCH$_2$OH) |
| 23.63 —C(O)CH$_2$O(o-PhCOOH) | —C(O)CH$_2$O(m-PhCOOH) | —C(O)CH$_2$O(p-PhCOOH) |
| 23.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 23.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 23.66 (4-benzyl-oxazolidin-2-one-N-CH$_2$-OC—) | | |

TABLE 24

Formula I: A = —B(pinanediol) ; X = CH$_2$NH$_2$; R$^3$ = table below; R$^{11}$ = —Ph.

| .1 | .2 | .3 |
|---|---|---|
| 24.1 —C(O)Ph | —C(O)CH$_2$Ph | —C(O)CH$_2$CH$_2$Ph |
| 24.2 —C(O)CH$_2$OPh | —C(O)CH$_2$NHPh | —C(O)CH$_2$SPh |
| 24.3 —C(O)o-PhOH | —C(O)m-PhOH | —C(O)p-PhOH |
| 24.4 —C(O)o-PhCH$_2$OH | —C(O)m-PhCH$_2$OH | —C(O)p-PhCH$_2$OH |
| 24.5 —C(O)o-PhCOOH | —C(O)m-PhCOOH | —C(O)p-PhCOOH |
| 24.6 —C(O)o-PhCH$_2$COOH | —C(O)m-PhCH$_2$COOH | —C(O)p-PhCH$_2$COOH |
| 24.7 —C(O)naphth-1-yl | —C(O)CH$_2$(naphth-1-yl) | —C(O)CH$_2$CH$_2$(napth-1-yl) |
| 24.8 —C(O)naphth-2-yl | —C(O)CH$_2$(naphth-2-yl | —C(O)CH$_2$CH$_2$(napth-2-yl) |
| 24.9 —C(O)o-biphenyl | —C(O)CH$_2$(o-biphenyl) | —C(O)CH$_2$CH$_2$(o-biphenyl) |
| 24.10 —C(O)m-biphenyl | —C(O)CH$_2$(m-biphenyl) | —C(O)CH$_2$CH$_2$(m-biphenyl) |
| 24.12 —C(O)p-biphenyl | —C(O)CH$_2$-p-biphenyl) | —C(O)CH$_2$CH$_2$(p-biphenyl) |
| 24.13 —C(O)o-PhOPh | —C(O)CH$_2$(o-PhOPh) | —C(O)CH$_2$CH$_2$(o-PhOPh) |
| 24.14 —C(O)m-PhOPh | —C(O)CH$_2$(m-PhOPh) | —C(O)CH$_2$CH$_2$(m-PhOPh) |
| 24.15 —C(O)p-PhOPh | —C(O)CH$_2$(p-PhOPh) | —C(O)CH$_2$CH$_2$(p-PhOPh) |
| 24.16 —C(O)o-PhNHPh | —C(O)CH$_2$(o-PhNHPh) | —C(O)CH$_2$CH$_2$(o-PhNHPh) |
| 24.17 —C(O)m-PhNHPh | —C(O)CH$_2$(m-PhNHPh) | —C(O)CH$_2$CH$_2$(m-PhNHPh) |
| 24.18 —C(O)p-PhNHPh | —C(O)CH$_2$(p-PhNHPh) | —C(O)CH$_2$CH$_2$(p-PhNHPh) |
| 24.19 —C(O)o-PhSPh | —C(O)CH$_2$(o-PhSPh) | —C(O)CH$_2$CH$_2$(o-PhSPh) |
| 24.20 —C(O)m-PhSPh | —C(O)CH$_2$(m-PhSPh) | —C(O)CH$_2$CH$_2$(m-PhSPh) |
| 24.21 —C(O)p-PhSPh | —C(O)CH$_2$(p-PhSPh) | —C(O)CH$_2$CH$_2$(p-PhSPh) |
| 24.22 —C(O)o-PhCH$_2$SPh | —C(O)CH$_2$(o-PhCH$_2$SPh) | —C(O)CH$_2$CH$_2$(o-PhCH$_2$SPh) |
| 24.23 —C(O)m-PhCH$_2$SPh | —C(O)CH$_2$(m-PhCH$_2$SPh) | —C(O)CH$_2$CH$_2$(m-PhCH$_2$SPh) |
| 24.24 —C(O)p-PhCH$_2$SPh | —C(O)CH$_2$(p-PhCH$_2$SPh) | —C(O)CH$_2$CH$_2$(p-PhCH$_2$SPh) |
| 24.25 —C(O)adamantyl | —C(O)CH$_2$(adamantyl) | —C(O)CH$_2$CH$_2$(adamantyl) |
| 24.26 —C(O)cyclopentyl | —C(O)CH$_2$(cyclopentyl) | —C(O)CH$_2$CH$_2$((cyclopentyl) |
| 24.27 —C(O)cyclohexyl | —C(O)CH$_2$(cyclohexyl) | —C(O)CH$_2$CH$_2$(cyclohexyl) |
| 24.28 —C(O)CH$_2$O(cyclopentyl) | —C(O)CH$_2$NH(cyclopentyl) | —C(O)CH$_2$S(cyclopentyl) |
| 24.29 —C(O)CH$_2$O(cyclohexyl) | —C(O)CH$_2$NH(cyclohexyl) | —C(O)CH$_2$S(cyclohexyl) |

TABLE 24-continued

Formula I: A = —B(pinanediol) ; X = CH$_2$NH$_2$; R$^3$ = table below; R$^{11}$ = —Ph.

| .1 | .2 | .3 |
|---|---|---|
| 24.30 —C(O)pyridin-2-yl | —C(O)CH$_2$(pyridin-2-yl) | —C(O)CH$_2$CH$_2$(pyridin-2-yl) |
| 24.31 —C(O)pyridin-3-yl | —C(O)CH$_2$(pyridin-3-yl) | —C(O)CH$_2$CH$_2$(pyridin-3-yl) |
| 24.32 —C(O)pyridin-4-yl | —C(O)CH$_2$(pyridin-4-yl) | —C(O)CH$_2$CH$_2$(pyridin-4-yl) |
| 24.33 —C(O)furan-2-yl | —C(O)CH$_2$(furan-2-yl) | —C(O)CH$_2$CH$_2$(furan-2-yl) |
| 24.34 —C(O)furan-3-yl | —C(O)CH$_2$(furan-3-yl) | —C(O)CH$_2$CH$_2$(furan-3-yl) |
| 24.35 —C(O)thiophen-2-yl | —C(O)CH$_2$(thiophen-2-yl) | —C(O)CH$_2$CH$_2$(thiophen-2-yl) |
| 24.36 —C(O)thiophen-2-yl | —C(O)CH$_2$(thiophen-2-yl) | —C(O)CH$_2$CH$_2$(thiophen-2-yl) |
| 24.37 —C(O)imidazo-2-yl | —C(O)CH$_2$(imidazo-2-yl) | —C(O)CH$_2$CH$_2$(imidazo-2-yl) |
| 24.38 —C(O)oxazo-2-yl | —C(O)CH$_2$(oxazo-2-yl) | —C(O)CH$_2$CH$_2$(oxazo-2-yl) |
| 24.39 —C(O)thioazo-2-yl | —C(O)CH$_2$(thioazo-2-yl) | —C(O)CH$_2$CH$_2$(thioazo-2-yl) |
| 24.40 —C(O)benzofuran-2-yl | —C(O)CH$_2$(benzofuran-2-yl) | —C(O)CH$_2$CH$_2$(benzofuran-2-yl) |
| 24.41 —C(O)benzofuran-3-yl | —C(O)CH$_2$(benzofuran-3-yl) | —C(O)CH$_2$CH$_2$(benzofuran-3-yl) |
| 24.42 —C(O)benzothiophen-2-yl | —C(O)CH$_2$(benzothiophen-2-yl) | —C(O)CH$_2$CH$_2$(benzothiophen-2-yl |
| 24.43 —C(O)thiophen-2-yl | —C(O)CH$_2$(thiophen-2-yl) | —C(O)CH$_2$CH$_2$(thiophen-2-yl) |
| 24.44 —C(O)benzimidazo-2-yl | —C(O)CH$_2$(benzimidazo-2-yl) | —C(O)CH$_2$CH$_2$(benzimidazo-2-yl) |
| 24.45 —C(O)benzoxazo-2-yl | —C(O)CH$_2$(benzoxazo-2-yl) | —C(O)CH$_2$CH$_2$(benzoxazo-2-yl) |
| 24.46 —C(O)benzothiazo-2-yl | —C(O)CH$_2$(benzothiazo-2-yl) | —C(O)CH$_2$CH$_2$(benzothiazo-2-yl) |
| 24.47 —C(O)o-Ph(P(O)Ph$_3$) | —C(O)m-Ph(P(O)Ph$_3$) | —C(O)p-Ph(P(O)Ph$_3$) |
| 24.48 —C(O)Ph-2-(fluoren-9-yl) | —C(O)Ph-3-(fluoren-9-yl) | —C(O)Ph-4-(fluoren-9-yl) |
| 24.49 —C(O)N-indolin-2-one | —C(O)indolin-2-yl | —C(O)indol-2-yl |
| 24.50 —C(O)C(CH$_3$)$_2$NHSO$_2$(naphth-2-yl) | —C(O)cyclopentyl-2-(Ph) | —C(O)cyclohexyl-2-(Ph) |
| 24.51 —C(O)pyrrolidin-3-yl-4-(Ph) | —C(O)tetrahydrofuran-3-yl-4-(Ph) | —C(O)tetrahydrothiophen-3-yl-4-(Ph) |
| 24.52 —C(O)tetrahydronaphth-1-yl | —C(O)tetrahydronaphth-2-yl | —C(O)cyclopropyl-2,2-(Ph$_2$) |
| 24.53 —C(O)tetrahydroisoquinolin-1-yl | —C(O)tetrahydroisoquinolin-3-yl | —C(O)CH$_2$((2-oxo)indolin-3-yl) |
| 24.54 —C(O)CH$_2$(N-benzimidazol-2-one) | —C(O)CH$_2$(N-benzoxazol-2-one) | —C(O)CH$_2$(N-benzothiazol-2-one) |
| 24.55 —C(O)CH$_2$(N-dihydroimidazol-2-one) | —C(O)CH$_2$(N-dihydrooxazol-2-one) | —C(O)CH$_2$(N-dihydrothiazol-2-one) |
| 24.56 | | |
| 24.57 | | |
| 24.58 | | |
| 24.59 —C(O)N(CH$_3$)CH$_2$Ph | —C(O)N(C$_2$H$_5$)CH$_2$Ph | —C(O)N(C$_3$H$_7$)CH$_2$Ph |
| 24.60 —C(O)pyridin-3-yl-5-(Ph) | —C(O)Ph-3-(CH$_2$(thiophen-2-yl)) | —C(O)Ph-3-(CH$_2$Ph) |
| 24.61 —C(O)C(CH$_3$)$_2$OPh | —C(O)CH(C$_2$H$_5$)OPh | —C(O)CH$_2$OCH$_2$Ph |
| 24.62 —C(O)CH$_2$O(o-PhCH$_2$OH) | —C(O)CH$_2$O(m-PhCH$_2$OH) | —C(O)CH$_2$O(p-PhCH$_2$OH) |
| 24.63 —C(O)CH$_2$O(o-PhCOOH) | —C(O)CH$_2$O(m-PhCOOH) | —C(O)CH$_2$O(p-PhCOOH) |

TABLE 24-continued

Formula I: A = —B(pinanediol) ; X = CH$_2$NH$_2$; R$^3$ = table below; R$^{11}$ = —Ph.

| .1 | .2 | .3 |
|---|---|---|
| 24.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 24.65 —C(O)CH$_2$O(o-PhCH$_2$COOH) | —C(O)CH$_2$O(m-PhCH$_2$COOH) | —C(O)CH$_2$O(p-PhCH$_2$COOH) |

24.66 —OC—CH$_2$—N(benzyl-oxazolidinone) [structure: —OC—CH$_2$—N of an oxazolidin-2-one ring with benzyl substituent at the 4-position]

TABLE 25

Formula I: A = —B(pinanediol) ; X = —CH$_2$NH$_2$; R$^3$ = table below; R$^{11}$ = —CH$_2$(naphth-2-yl).

| | .1 | .2 | .3 |
|---|---|---|---|
| 25.1 | —C(O)Ph | —C(O)CH$_2$Ph | —C(O)CH$_2$CH$_2$Ph |
| 25.2 | —C(O)CH$_2$OPh | —C(O)CH$_2$NHPh | —C(O)CH$_2$SPh |
| 25.3 | —C(O)o-PhOH | —C(O)m-PhOH | —C(O)p-PhOH |
| 25.4 | —C(O)o-PhCH$_2$OH | —C(O)m-PhCH$_2$OH | —C(O)p-PhCH$_2$OH |
| 25.5 | —C(O)o-PhCOOH | —C(O)m-PhCOOH | —C(O)p-PhCOOH |
| 25.6 | —C(O)o-PhCH$_2$COOH | —C(O)m-PhCH$_2$COOH | —C(O)p-PhCH$_2$COOH |
| 25.7 | —C(O)naphth-1-yl | —C(O)CH$_2$(naphth-1-yl) | —C(O)CH$_2$CH$_2$(napth-1-yl) |
| 25.8 | —C(O)naphth-2-yl | —C(O)CH$_2$(naphth-2-yl | —C(O)CH$_2$CH$_2$(napth-2-yl) |
| 25.9 | —C(O)o-biphenyl | —C(O)CH$_2$(o-biphenyl) | —C(O)CH$_2$CH$_2$(o-biphenyl) |
| 25.10 | —C(O)m-biphenyl | —C(O)CH$_2$(m-biphenyl) | —C(O)CH$_2$CH$_2$(m-biphenyl) |
| 25.12 | —C(O)p-biphenyl | —C(O)CH$_2$-p-biphenyl) | —C(O)CH$_2$CH$_2$(p-biphenyl) |
| 25.13 | —C(O)o-PhOPh | —C(O)CH$_2$(o-PhOPh) | —C(O)CH$_2$CH$_2$(o-PhOPh) |
| 25.14 | —C(O)m-PhOPh | —C(O)CH$_2$(m-PhOPh) | —C(O)CH$_2$CH$_2$(m-PhOPh) |
| 25.15 | —C(O)p-PhOPh | —C(O)CH$_2$(p-PhOPh) | —C(O)CH$_2$CH$_2$(p-PhOPh) |
| 25.16 | —C(O)o-PhNHPh | —C(O)CH$_2$(o-PhNHPh) | —C(O)CH$_2$CH$_2$(o-PhNHPh) |
| 25.17 | —C(O)m-PhNHPh | —C(O)CH$_2$(m-PhNHPh) | —C(O)CH$_2$CH$_2$(m-PhNHPh) |
| 25.18 | —C(O)p-PhNHPh | —C(O)CH$_2$(p-PhNHPh) | —C(O)CH$_2$CH$_2$(p-PhNHPh) |
| 25.19 | —C(O)o-PhSPh | —C(O)CH$_2$(o-PhSPh) | —C(O)CH$_2$CH$_2$(o-PhSPh) |
| 25.20 | —C(O)m-PhSPh | —C(O)CH$_2$(m-PhSPh) | —C(O)CH$_2$CH$_2$(m-PhSPh) |
| 25.21 | —C(O)p-PhSPh | —C(O)CH$_2$(p-PhSPh) | —C(O)CH$_2$CH$_2$(p-PhSPh) |
| 25.22 | —C(O)o-PhCH$_2$SPh | —C(O)CH$_2$(o-PhCH$_2$SPh) | —C(O)CH$_2$CH$_2$(o-PhCH$_2$SPh) |
| 25.23 | —C(O)m-PhCH$_2$SPh | —C(O)CH$_2$(m-PhCH$_2$SPh) | —C(O)CH$_2$CH$_2$(m-PhCH$_2$SPh) |
| 25.24 | —C(O)p-PhCH$_2$SPh | —C(O)CH$_2$(p-PhCH$_2$SPh) | —C(O)CH$_2$CH$_2$(p-PhCH$_2$SPh) |
| 25.25 | —C(O)adamantyl | —C(O)CH$_2$(adamantyl) | —C(O)CH$_2$CH$_2$(adamantyl) |
| 25.26 | —C(O)cyclopentyl | —C(O)CH$_2$(cyclopentyl) | —C(O)CH$_2$CH$_2$((cyclopentyl) |
| 25.27 | —C(O)cyclohexyl | —C(O)CH$_2$(cyclohexyl) | —C(O)CH$_2$CH$_2$(cyclohexyl) |
| 25.28 | —C(O)CH$_2$O(cyclopentyl) | —C(O)CH$_2$NH(cyclopentyl) | —C(O)CH$_2$S(cyclopentyl) |
| 25.29 | —C(O)CH$_2$O(cyclohexyl) | —C(O)CH$_2$NH(cyclohexyl) | —C(O)CH$_2$S(cyclohexyl) |
| 25.30 | —C(O)pyridin-2-yl | —C(O)CH$_2$(pyridin-2-yl) | —C(O)CH$_2$CH$_2$(pyridin-2-yl) |
| 25.31 | —C(O)pyridin-3-yl | —C(O)CH$_2$(pyridin-3-yl) | —C(O)CH$_2$CH$_2$(pyridin-3-yl) |
| 25.32 | —C(O)pyridin-4-yl | —C(O)CH$_2$(pyridin-4-yl) | —C(O)CH$_2$CH$_2$(pyridin-4-yl) |
| 25.33 | —C(O)furan-2-yl | —C(O)CH$_2$(furan-2-yl) | —C(O)CH$_2$CH$_2$(furan-2-yl) |
| 25.34 | —C(O)furan-3-yl | —C(O)CH$_2$(furan-3-yl) | —C(O)CH$_2$CH$_2$(furan-3-yl) |
| 25.35 | —C(O)thiophen-2-yl | —C(O)CH$_2$(thiophen-2-yl) | —C(O)CH$_2$CH$_2$(thiophen-2-yl) |
| 25.36 | —C(O)thiophen-2-yl | —C(O)CH$_2$(thiophen-2-yl) | —C(O)CH$_2$CH$_2$(thiophen-2-yl) |
| 25.37 | —C(O)imidazo-2-yl | —C(O)CH$_2$(imidazo-2-yl) | —C(O)CH$_2$CH$_2$(imidazo-2-yl) |
| 25.38 | —C(O)oxazo-2-yl | —C(O)CH$_2$(oxazo-2-yl) | —C(O)CH$_2$CH$_2$(oxazo-2-yl) |
| 25.39 | —C(O)thioazo-2-yl | —C(O)CH$_2$(thioazo-2-yl) | —C(O)CH$_2$CH$_2$(thioazo-2-yl) |
| 25.40 | —C(O)benzofuran-2-yl | —C(O)CH$_2$(benzofuran-2-yl) | —C(O)CH$_2$CH$_2$(benzofuran-2-yl) |
| 25.41 | —C(O)benzofuran-3-yl | —C(O)CH$_2$(benzofuran-3-yl) | —C(O)CH$_2$CH$_2$(benzofuran-3-yl) |
| 25.42 | —C(O)benzothiophen-2-yl | —C(O)CH$_2$(benzothiophen-2-yl) | —C(O)CH$_2$CH$_2$(benzothiophen-2-yl |
| 25.43 | —C(O)thiophen-2-yl | —C(O)CH$_2$(thiophen-2-yl) | —C(O)CH$_2$CH$_2$(thiophen-2-yl) |
| 25.44 | —C(O)benzimidazo-2-yl | —C(O)CH$_2$(benzimidazo-2-yl) | —C(O)CH$_2$CH$_2$(benzimidazo-2-yl) |
| 25.45 | —C(O)benzoxazo-2-yl | —C(O)CH$_2$(benzoxazo-2-yl) | —C(O)CH$_2$CH$_2$(benzoxazo-2-yl) |
| 25.46 | —C(O)benzothiazo-2-yl | —C(O)CH$_2$(benzothiazo-2-yl) | —C(O)CH$_2$CH$_2$(benzothiazo-2-yl) |
| 25.47 | —C(O)o-Ph(P(O)Ph$_3$) | —C(O)m-Ph(P(O)Ph$_3$) | —C(O)p-Ph(P(O)Ph$_3$) |
| 25.48 | —C(O)Ph-2-(fluoren-9-yl) | —C(O)Ph-3-(fluoren-9-yl) | —C(O)Ph-4-(fluoren-9-yl) |
| 25.49 | —C(O)N-indolin-2-one | —C(O)indolin-2-yl | —C(O)indol-2-yl |
| 25.50 | —C(O)C(CH$_3$)$_2$NHSO$_2$(naphth-2-yl) | —C(O)cyclopentyl-2-(Ph) | —C(O)cyclohexyl-2-(Ph) |

TABLE 25-continued

Formula I: A = —B(pinanediol) ; X = —CH$_2$NH$_2$; R$^3$ = table below; R$^{11}$ = —CH$_2$(naphth-2-yl).

| .1 | .2 | .3 |
|---|---|---|
| 25.51 —C(O)pyrrolidin-3-yl-4-(Ph) | —C(O)tetrahydrofuran-3-yl-4-(Ph) | —C(O)tetrahydrothiophen-3-yl-4-(Ph) |
| 25.52 —C(O)tetrahydronaphth-1-yl | —C(O)tetrahydronaphth-2-yl | —C(O)cyclopropyl-2,2-(Ph$_2$) |
| 25.53 —C(O)tetrahydroisoquinolin-1-yl | —C(O)tetrahydroisoquinolin-3-yl | —C(O)CH$_2$((2-oxo)indolin-3-yl) |
| 25.54 —C(O)CH$_2$(N-benzimidazol-2-one) | —C(O)CH$_2$(N-benzoxazol-2-one) | —C(O)CH$_2$(N-benzothiazol-2-one) |
| 25.55 —C(O)CH$_2$(N-dihydroimidazol-2-one) | —C(O)CH$_2$(N-dihydrooxazol-2-one) | —C(O)CH$_2$(N-dihydrothiazol-2-one) |
| 25.56 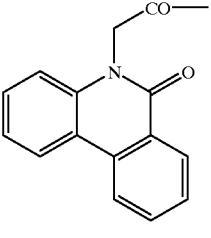 | 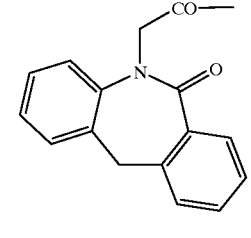 | 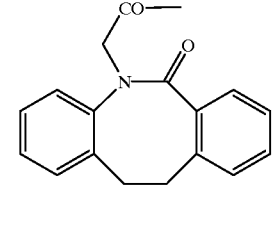 |
| 25.57 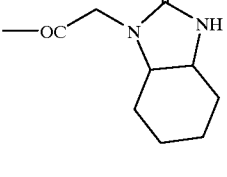 | 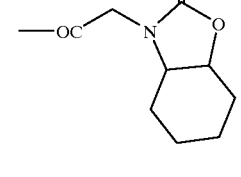 | 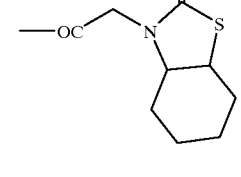 |
| 25.58 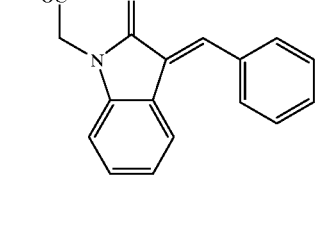 | 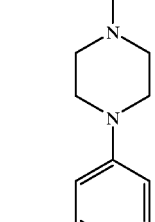 | 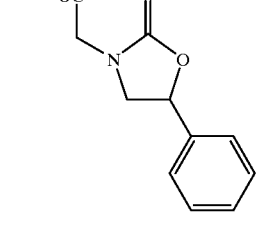 |
| 25.59 —C(O)N(CH$_3$)CH$_2$Ph | —C(O)N(C$_2$H$_5$)CH$_2$Ph | —C(O)N(C$_3$H$_7$)CH$_2$Ph |
| 25.60 —C(O)pyridin-3-yl-5-(Ph) | —C(O)Ph-3-(CH$_2$(thiophen-2-yl)) | —C(O)Ph-3-(CH$_2$Ph) |
| 25.61 —C(O)C(CH$_3$)$_2$OPh | —C(O)CH(C$_2$H$_5$)OPh | —C(O)CH$_2$OCH$_2$Ph |
| 25.62 —C(O)CH$_2$O(o-PhCH$_2$OH) | —C(O)CH$_2$O(m-PhCH$_2$OH) | —C(O)CH$_2$O(p-PhCH$_2$OH) |
| 25.63 —C(O)CH$_2$O(o-PhCOOH) | —C(O)CH$_2$O(m-PhCOOH) | —C(O)CH$_2$O(p-PhCOOH) |
| 25.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 25.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 25.66 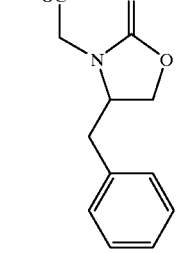 | | |

TABLE 26

Formula I: A = —B(pinanediol) ; X = —SC(=NH)NH2; R³ = table below; R¹¹ = —CH₃

| | .1 | .2 | .3 |
|---|---|---|---|
| 26.1 | —C(O)Ph | —C(O)CH₂Ph | —C(O)CH₂CH₂Ph |
| 26.2 | —C(O)CH₂OPh | —C(O)CH₂NHPh | —C(O)CH₂SPh |
| 26.3 | —C(O)o-PhOH | —C(O)m-PhOH | —C(O)p-PhOH |
| 26.4 | —C(O)o-PhCH₂OH | —C(O)m-PhCH₂OH | —C(O)p-PhCH₂OH |
| 26.5 | —C(O)o-PhCOOH | —C(O)m-PhCOOH | —C(O)p-PhCOOH |
| 26.6 | —C(O)o-PhCH₂COOH | —C(O)m-PhCH₂COOH | —C(O)p-PhCH₂COOH |
| 26.7 | —C(O)naphth-1-yl | —C(O)CH₂(naphth-1-yl) | —C(O)CH₂CH₂(napth-1-yl) |
| 26.8 | —C(O)naphth-2-yl | —C(O)CH₂(naphth-2-yl) | —C(O)CH₂CH₂(napth-2-yl) |
| 26.9 | —C(O)o-biphenyl | —C(O)CH₂(o-biphenyl) | —C(O)CH₂CH₂(o-biphenyl) |
| 26.10 | —C(O)m-biphenyl | —C(O)CH₂(m-biphenyl) | —C(O)CH₂CH₂(m-biphenyl) |
| 26.11 | —C(O)p-biphenyl | —C(O)CH₂-(p-biphenyl) | —C(O)CH₂CH₂(p-biphenyl) |
| 26.13 | —C(O)o-PhOPh | —C(O)CH₂(o-PhOPh) | —C(O)CH₂CH₂(o-PhOPh) |
| 26.14 | —C(O)m-PhOPh | —C(O)CH₂(m-PhOPh) | —C(O)CH₂CH₂(m-PhOPh) |
| 26.15 | —C(O)p-PhOPh | —C(O)CH₂(p-PhOPh) | —C(O)CH₂CH₂(p-PhOPh) |
| 26.16 | —C(O)o-PhNHPh | —C(O)CH₂(o-PhNHPh) | —C(O)CH₂CH₂(o-PhNHPh) |
| 26.17 | —C(O)m-PhNHPh | —C(O)CH₂(m-PhNHPh) | —C(O)CH₂CH₂(m-PhNHPh) |
| 26.18 | —C(O)p-PhNHPh | —C(O)CH₂(p-PhNHPh) | —C(O)CH₂CH₂(p-PhNHPh) |
| 26.19 | —C(O)o-PhSPh | —C(O)CH₂(o-PhSPh) | —C(O)CH₂CH₂(o-PhSPh) |
| 26.20 | —C(O)m-PhSPh | —C(O)CH₂(m-PhSPh) | —C(O)CH₂CH₂(m-PhSPh) |
| 26.21 | —C(O)p-PhSPh | —C(O)CH₂(p-PhSPh) | —C(O)CH₂CH₂(p-PhSPh) |
| 26.22 | —C(O)o-PhCH₂SPh | —C(O)CH₂(o-PhCH₂SPh) | —C(O)CH₂CH₂(o-PhCH₂SPh) |
| 26.23 | —C(O)m-PhCH₂SPh | —C(O)CH₂(m-PhCH₂SPh) | —C(O)CH₂CH₂(m-PhCH₂SPh) |
| 26.24 | —C(O)p-PhCH₂SPh | —C(O)CH₂(p-PhCH₂SPh) | —C(O)CH₂CH₂(p-PhCH₂SPh) |
| 26.25 | —C(O)adamantyl | —C(O)CH₂(adamantyl) | —C(O)CH₂CH₂(adamantyl) |
| 26.26 | —C(O)cyclopentyl | —C(O)CH₂(cyclopentyl) | —C(O)CH₂CH₂((cyclopentyl) |
| 26.27 | —C(O)cyclohexyl | —C(O)CH₂(cyclohexyl) | —C(O)CH₂CH₂(cyclohexyl) |
| 26.28 | —C(O)CH₂O(cyclopentyl) | —C(O)CH₂NH(cyclopentyl) | —C(O)CH₂S(cyclopentyl) |
| 26.29 | —C(O)CH₂O(cyclohexyl) | —C(O)CH₂NH(cyclohexyl) | —C(O)CH₂S(cyclohexyl) |
| 26.30 | —C(O)pyridin-2-yl | —C(O)CH₂(pyridin-2-yl) | —C(O)CH₂CH₂(pyridin-2-yl) |
| 26.31 | —C(O)pyridin-3-yl | —C(O)CH₂(pyridin-3-yl) | —C(O)CH₂CH₂(pyridin-3-yl) |
| 26.32 | —C(O)pyridin-4-yl | —C(O)CH₂(pyridin-4-yl) | —C(O)CH₂CH₂(pyridin-4-yl) |
| 26.33 | —C(O)furan-2-yl | —C(O)CH₂(furan-2-yl) | —C(O)CH₂CH₂(furan-2-yl) |
| 26.34 | —C(O)furan-3-yl | —C(O)CH₂(furan-3-yl) | —C(O)CH₂CH₂(furan-3-yl) |
| 26.35 | —C(O)thiophen-2-yl | —C(O)CH₂(thiophen-2-yl) | —C(O)CH₂CH₂(thiophen-2-yl) |
| 26.36 | —C(O)thiophen-2-yl | —C(O)CH₂(thiophen-2-yl) | —C(O)CH₂CH₂(thiophen-2-yl) |
| 26.37 | —C(O)imidazo-2-yl | —C(O)CH₂(imidazo-2-yl) | —C(O)CH₂CH₂(imidazo-2-yl) |
| 26.38 | —C(O)oxazo-2-yl | —C(O)CH₂(oxazo-2-yl) | —C(O)CH₂CH₂(oxazo-2-yl) |
| 26.39 | —C(O)thioazo-2-yl | —C(O)CH₂(thioazo-2-yl) | —C(O)CH₂CH₂(thioazo-2-yl) |
| 26.40 | —C(O)benzofuran-2-yl | —C(O)CH₂(benzofuran-2-yl) | —C(O)CH₂CH₂(benzofuran-2-yl) |
| 26.41 | —C(O)benzofuran-3-yl | —C(O)CH₂(benzofuran-3-yl) | —C(O)CH₂CH₂(benzofuran-3-yl) |
| 26.42 | —C(O)benzothiophen-2-yl | —C(O)CH₂(benzothiophen-2-yl) | —C(O)CH₂CH₂(benzothiophen-2-yl) |
| 26.43 | —C(O)thiophen-2-yl | —C(O)CH₂(thiophen-2-yl) | —C(O)CH₂CH₂(thiophen-2-yl) |
| 26.44 | —C(O)benzimidazo-2-yl | —C(O)CH₂(benzimidazo-2-yl) | —C(O)CH₂CH₂(benzimidazo-2-yl) |
| 26.45 | —C(O)benzoxazo-2-yl | —C(O)CH₂(benzoxazo-2-yl) | —C(O)CH₂CH₂(benzoxazo-2-yl) |
| 26.46 | —C(O)benzothiazo-2-yl | —C(O)CH₂(benzothiazo-2-yl) | —C(O)CH₂CH₂(benzothiazo-2-yl) |
| 26.47 | —C(O)o-Ph(P(O)Ph₃) | —C(O)m-Ph(P(O)Ph₃) | —C(O)p-Ph(P(O)Ph₃) |
| 26.48 | —C(O)Ph-2-(fluoren-9-yl) | —C(O)Ph-3-(fluoren-9-yl) | —C(O)Ph-4-(fluoren-9-yl) |
| 26.49 | —C(O)N-indolin-2-one | —C(O)indolin-2-yl | —C(O)indol-2-yl |
| 26.50 | —C(O)C(CH₃)₂NHSO₂(naphth-2-yl) | —C(O)cyclopentyl-2-(Ph) | —C(O)cyclohexyl-2-(Ph) |
| 26.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 26.52 | —C(O)tetrahydronaphth-1-yl | —C(O)tetrahydronaphth-2-yl | —C(O)cyclopropyl-2,2-(Ph₂) |
| 26.53 | —C(O)tetrahydroisoquinolin-1-yl | —C(O)tetrahydroisoquinolin-3-yl | —C(O)CH₂((2-oxo)indolin-3-yl) |
| 26.54 | —C(O)CH₂(N-benzimidazol-2-one) | —C(O)CH₂(N-benzoxazol-2-one) | —C(O)CH₂(N-benzothiazol-2-one) |
| 26.55 | —C(O)CH₂(N-dihydroimidazol-2-one) | —C(O)CH₂(N-dihydrooxazol-2-one) | —C(O)CH₂(N-dihydrothiazol-2-one) |
| 26.56 | 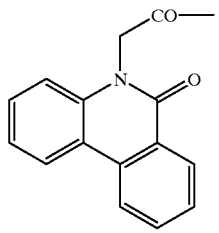 | 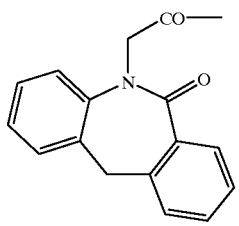 | 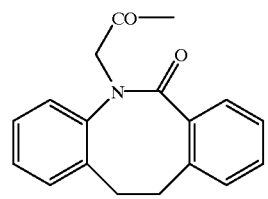 |

TABLE 26-continued

Formula I: A = —B(pinanediol) ; X = —SC(=NH)NH2; R³ = table below; R¹¹ = —CH₃

| .1 | .2 | .3 |
|---|---|---|
| 26.57 | | |
| 26.58 | | |

| | | |
|---|---|---|
| 26.59 —C(O)N(CH₃)CH₂Ph | —C(O)N(C₂H₅)CH₂Ph | —C(O)N(C₃H₇)CH₂Ph |
| 26.60 —C(O)pyridin-3-yl-5-(Ph) | —C(O)Ph-3-(CH₂(thiophen-2-yl)) | —C(O)Ph-3-(CH₂Ph) |
| 26.61 —C(O)C(CH₃)₂OPh | —C(O)CH(C₂H₅)OPh | —C(O)CH₂OCH₂Ph |
| 26.62 —C(O)CH₂O(o-PhCH₂OH) | —C(O)CH₂O(m-PhCH₂OH) | —C(O)CH₂O(p-PhCH₂OH) |
| 26.63 —C(O)CH₂O(o-PhCOOH) | —C(O)CH₂O(m-PhCOOH) | —C(O)CH₂O(p-PhCOOH) |
| 26.64 —C(O)CH₂O(o-PhCOOCH₃) | —C(O)CH₂O(m-PhCOOCH₃) | —C(O)CH₂O(p-PhCOOCH₃) |
| 26.65 —C(O)CH₂O(o-PhCH₂COOH) | —C(O)CH₂O(m-PhCH₂COOH) | —C(O)CH₂O(p-PhCH₂COOH) |
| 26.66 | | |

TABLE 27

Formula I: A = —B(pinanediol) ; X = —SC(=NH)NH₂; R³ = table below; R¹¹ = —CH₂(p-PhOH).

| .1 | .2 | .3 |
|---|---|---|
| 27.1 —C(O)Ph | —C(O)CH₂Ph | —C(O)CH₂CH₂Ph |
| 27.2 —C(O)CH₂OPh | —C(O)CH₂NHPh | —C(O)CH₂SPh |
| 27.3 —C(O)o-PhOH | —C(O)m-PhOH | —C(O)p-PhOH |
| 27.4 —C(O)o-PhCH₂OH | —C(O)m-PhCH₂OH | —C(O)p-PhCH₂OH |
| 27.5 —C(O)o-PhCOOH | —C(O)m-PhCOOH | —C(O)p-PhCOOH |
| 27.6 —C(O)o-PhCH₂COOH | —C(O)m-PhCH₂COOH | —C(O)p-PhCH₂COOH |
| 27.7 —C(O)naphth-1-yl | —C(O)CH₂(naphth-1-yl) | —C(O)CH₂CH₂(napth-1-yl) |
| 27.8 —C(O)naphth-2-yl | —C(O)CH₂(naphth-2-yl | —C(O)CH₂CH₂(napth-2-yl) |
| 27.9 —C(O)o-biphenyl | —C(O)CH₂(o-biphenyl) | —C(O)CH₂CH₂(o-biphenyl) |
| 27.10 —C(O)m-biphenyl | —C(O)CH₂(m-biphenyl) | —C(O)CH₂CH₂(m-biphenyl) |
| 27.12 —C(O)p-biphenyl | —C(O)CH₂-(p-biphenyl) | —C(O)CH₂CH₂(p-biphenyl) |
| 27.13 —C(O)o-PhOPh | —C(O)CH₂(o-PhOPh) | —C(O)CH₂CH₂(o-PhOPh) |
| 27.14 —C(O)m-PhOPh | —C(O)CH₂(m-PhOPh) | —C(O)CH₂CH₂(m-PhOPh) |
| 27.15 —C(O)p-PhOPh | —C(O)CH₂(p-PhOPh) | —C(O)CH₂CH₂(p-PhOPh) |
| 27.16 —C(O)o-PhNHPh | —C(O)CH₂(o-PhNHPh) | —C(O)CH₂CH₂(o-PhNHPh) |
| 27.17 —C(O)m-PhNHPh | —C(O)CH₂(m-PhNHPh) | —C(O)CH₂CH₂(m-PhNHPh) |
| 27.18 —C(O)p-PhNHPh | —C(O)CH₂(p-PhNHPh) | —C(O)CH₂CH₂(p-PhNHPh) |

TABLE 27-continued

Formula I: A = —B(pinanediol) ; X = —SC(=NH)NH$_2$; R$^3$ = table below; R$^{11}$ = —CH$_2$(p-PhOH).

| .1 | .2 | .3 |
|---|---|---|
| 27.19 —C(O)o-PhSPh | —C(O)CH$_2$(o-PhSPh) | —C(O)CH$_2$CH$_2$(o-PhSPh) |
| 27.20 —C(O)m-PhSPh | —C(O)CH$_2$(m-PhSPh) | —C(O)CH$_2$CH$_2$(m-PhSPh) |
| 27.21 —C(O)p-PhSPh | —C(O)CH$_2$(p-PhSPh) | —C(O)CH$_2$CH$_2$(p-PhSPh) |
| 27.22 —C(O)o-PhCH$_2$SPh | —C(O)CH$_2$(o-PhCH$_2$SPh) | —C(O)CH$_2$CH$_2$(o-PhCH$_2$SPh) |
| 27.23 —C(O)m-PhCH$_2$SPh | —C(O)CH$_2$(m-PhCH$_2$SPh) | —C(O)CH$_2$CH$_2$(m-PhCH$_2$SPh) |
| 27.24 —C(O)p-PhCH$_2$SPh | —C(O)CH$_2$(p-PhCH$_2$SPh) | —C(O)CH$_2$CH$_2$(p-PhCH$_2$SPh) |
| 27.25 —C(O)adamantyl | —C(O)CH$_2$(adamantyl) | —C(O)CH$_2$CH$_2$(adamantyl) |
| 27.26 —C(O)cyclopentyl | —C(O)CH$_2$(cyclopentyl) | —C(O)CH$_2$CH$_2$((cyclopentyl) |
| 27.27 —C(O)cyclohexyl | —C(O)CH$_2$(cyclohexyl) | —C(O)CH$_2$CH$_2$(cyclohexyl) |
| 27.28 —C(O)CH$_2$O(cyclopentyl) | —C(O)CH$_2$NH(cyclopentyl) | —C(O)CH$_2$S(cyclopentyl) |
| 27.29 —C(O)CH$_2$O(cyclohexyl) | —C(O)CH$_2$NH(cyclohexyl) | —C(O)CH$_2$S(cyclohexyl) |
| 27.30 —C(O)pyridin-2-yl | —C(O)CH$_2$(pyridin-2-yl) | —C(O)CH$_2$CH$_2$(pyridin-2-yl) |
| 27.31 —C(O)pyridin-3-yl | —C(O)CH$_2$(pyridin-3-yl) | —C(O)CH$_2$CH$_2$(pyridin-3-yl) |
| 27.32 —C(O)pyridin-4-yl | —C(O)CH$_2$(pyridin-4-yl) | —C(O)CH$_2$CH$_2$(pyridin-4-yl) |
| 27.33 —C(O)furan-2-yl | —C(O)CH$_2$(furan-2-yl) | —C(O)CH$_2$CH$_2$(furan-2-yl) |
| 27.34 —C(O)furan-3-yl | —C(O)CH$_2$(furan-3-yl) | —C(O)CH$_2$CH$_2$(furan-3-yl) |
| 27.35 —C(O)thiophen-2-yl | —C(O)CH$_2$(thiophen-2-yl) | —C(O)CH$_2$CH$_2$(thiophen-2-yl) |
| 27.36 —C(O)thiophen-2-yl | —C(O)CH$_2$(thiophen-2-yl) | —C(O)CH$_2$CH$_2$(thiophen-2-yl) |
| 27.37 —C(O)imidazo-2-yl | —C(O)CH$_2$(imidazo-2-yl) | —C(O)CH$_2$CH$_2$(imidazo-2-yl) |
| 27.38 —C(O)oxazo-2-yl | —C(O)CH$_2$(oxazo-2-yl) | —C(O)CH$_2$CH$_2$(oxazo-2-yl) |
| 27.39 —C(O)thioazo-2-yl | —C(O)CH$_2$(thioazo-2-yl) | —C(O)CH$_2$CH$_2$(thioazo-2-yl) |
| 27.40 —C(O)benzofuran-2-yl | —C(O)CH$_2$(benzofuran-2-yl) | —C(O)CH$_2$CH$_2$(benzofuran-2-yl) |
| 27.41 —C(O)benzofuran-3-yl | —C(O)CH$_2$(benzofuran-3-yl) | —C(O)CH$_2$CH$_2$(benzofuran-3-yl) |
| 27.42 —C(O)benzothiophen-2-yl | —C(O)CH$_2$(benzothiophen-2-yl) | —C(O)CH$_2$CH$_2$(benzothiophen-2-yl) |
| 27.43 —C(O)thiophen-2-yl | —C(O)CH$_2$(thiophen-2-yl) | —C(O)CH$_2$CH$_2$(thiophen-2-yl) |
| 27.44 —C(O)benzimidazo-2-yl | —C(O)CH$_2$(benzimidazo-2-yl) | —C(O)CH$_2$CH$_2$(benzimidazo-2-yl) |
| 27.45 —C(O)benzoxazo-2-yl | —C(O)CH$_2$(benzoxazo-2-yl) | —C(O)CH$_2$CH$_2$(benzoxazo-2-yl) |
| 27.46 —C(O)benzothiazo-2-yl | —C(O)CH$_2$(benzothiazo-2-yl) | —C(O)CH$_2$CH$_2$(benzothiazo-2-yl) |
| 27.47 —C(O)o-Ph(P(O)Ph$_3$) | —C(O)m-Ph(P(O)Ph$_3$) | —C(O)p-Ph(P(O)Ph$_3$) |
| 27.48 —C(O)Ph-2-(fluoren-9-yl) | —C(O)Ph-3-(fluoren-9-yl) | —C(O)Ph-4-(fluoren-9-yl) |
| 27.49 —C(O)N-indolin-2-one | —C(O)indolin-2-yl | —C(O)indol-2-yl |
| 27.50 —C(O)C(CH$_3$)$_2$NHSO$_2$(naphth-2-yl) | —C(O)cyclopentyl-2-(Ph) | —C(O)cyclohexyl-2-(Ph) |
| 27.51 —C(O)pyrrolidin-3-yl-4-(Ph) | —C(O)tetrahydrofuran-3-yl-4-(Ph) | —C(O)tetrahydrothiophen-3-yl-4-(Ph) |
| 27.52 —C(O)tetrahydronaphth-1-yl | —C(O)tetrahydronaphth-2-yl | —C(O)cyclopropyl-2,2-(Ph$_2$) |
| 27.53 —C(O)tetrahydroisoquinolin-1-yl | —C(O)tetrahydroisoquinolin-3-yl | —C(O)CH$_2$((2-oxo)indolin-3-yl) |
| 27.54 —C(O)CH$_2$(N-benzimidazol-2-one) | —C(O)CH$_2$(N-benzoxazol-2-one) | —C(O)CH$_2$(N-benzothiazol-2-one) |
| 27.55 —C(O)CH$_2$(N-dihydroimidazol-2-one) | —C(O)CH$_2$(N-dihydrooxazol-2-one) | —C(O)CH$_2$(N-dihydrothiazol-2-one) |

TABLE 27-continued

Formula I: A = —B(pinanediol) ; X = —SC(=NH)NH₂; R³ = table below; R¹¹ = —CH₂(p-PhOH).

| | .1 | .2 | .3 |
|---|---|---|---|
| 27.58 | (N-CH₂-C(O)O- attached 3-benzylidene-oxindole) | (N-CH₂-C(O)O- attached 4-phenylpiperazine) | (N-CH₂-C(O)O- attached 5-phenyl-oxazolidin-2-one) |
| 27.59 | —C(O)N(CH₃)CH₂Ph | —C(O)N(C₂H₅)CH₂Ph | —C(O)N(C₃H₇)CH₂Ph |
| 27.60 | —C(O)pyridin-3-yl-5-(Ph) | —C(O)Ph-3-(CH₂(thiophen-2-yl)) | —C(O)Ph-3-(CH₂Ph) |
| 27.61 | —C(O)C(CH₃)₂OPh | —C(O)CH(C₂H₅)OPh | —C(O)CH₂OCH₂Ph |
| 27.62 | —C(O)CH₂O(o-PhCH₂OH) | —C(O)CH₂O(m-PhCH₂OH) | —C(O)CH₂O(p-PhCH₂OH) |
| 27.63 | —C(O)CH₂O(o-PhCOOH) | —C(O)CH₂O(m-PhCOOH) | —C(O)CH₂O(p-PhCOOH) |
| 27.64 | —C(O)CH₂O(o-PhCOOCH₃) | —C(O)CH₂O(m-PhCOOCH₃) | —C(O)CH₂O(p-PhCOOCH₃) |
| 27.65 | —C(O)CH₂O(o-PhCH₂COOH) | —C(O)CH₂O(m-PhCH₂COOH) | —C(O)CH₂O(p-PhCH₂COOH) |
| 27.66 | (N-CH₂-C(O)O- attached 4-benzyl-oxazolidin-2-one) | | |

TABLE 28

Formula I: A = —B(pinanediol) ; X = —SC(=NH)NH₂; R³ = table below; R¹¹ = —CH₂CH₂Ph.

| | .1 | .2 | .3 |
|---|---|---|---|
| 28.1 | —C(O)Ph | —C(O)CH₂Ph | —C(O)CH₂CH₂Ph |
| 28.2 | —C(O)CH₂OPh | —C(O)CH₂NHPh | —C(O)CH₂SPh |
| 28.3 | —C(O)o-PhOH | —C(O)m-PhOH | —C(O)p-PhOH |
| 28.4 | —C(O)o-PhCH₂OH | —C(O)m-PhCH₂OH | —C(O)p-PhCH₂OH |
| 28.5 | —C(O)o-PhCOOH | —C(O)m-PhCOOH | —C(O)p-PhCOOH |
| 28.6 | —C(O)o-PhCH₂COOH | —C(O)m-PhCH₂COOH | —C(O)p-PhCH₂COOH |
| 28.7 | —C(O)naphth-1-yl | —C(O)CH₂(naphth-1-yl) | —C(O)CH₂CH₂(napth-1-yl) |
| 28.8 | —C(O)naphth-2-yl | —C(O)CH₂(naphth-2-yl | —C(O)CH₂CH₂(napth-2-yl) |
| 28.9 | —C(O)o-biphenyl | —C(O)CH₂(o-biphenyl) | —C(O)CH₂CH₂(o-biphenyl) |
| 28.10 | —C(O)m-biphenyl | —C(O)CH₂(m-biphenyl) | —C(O)CH₂CH₂(m-biphenyl) |
| 28.12 | —C(O)p-biphenyl | —C(O)CH₂-(p-biphenyl) | —C(O)CH₂CH₂(p-biphenyl) |
| 28.13 | —C(O)o-PhOPh | —C(O)CH₂(o-PhOPh) | —C(O)CH₂CH₂(o-PhOPh) |
| 28.14 | —C(O)m-PhOPh | —C(O)CH₂(m-PhOPh) | —C(O)CH₂CH₂(m-PhOPh) |
| 28.15 | —C(O)p-PhOPh | —C(O)CH₂(p-PhOPh) | —C(O)CH₂CH₂(p-PhOPh) |
| 28.16 | —C(O)o-PhNHPh | —C(O)CH₂(o-PhNHPh) | —C(O)CH₂CH₂(o-PhNHPh) |
| 28.17 | —C(O)m-PhNHPh | —C(O)CH₂(m-PhNHPh) | —C(O)CH₂CH₂(m-PhNHPh) |
| 28.18 | —C(O)p-PhNHPh | —C(O)CH₂(p-PhNHPh) | —C(O)CH₂CH₂(p-PhNHPh) |
| 28.19 | —C(O)o-PhSPh | —C(O)CH₂(o-PhSPh) | —C(O)CH₂CH₂(o-PhSPh) |
| 28.20 | —C(O)m-PhSPh | —C(O)CH₂(m-PhSPh) | —C(O)CH₂CH₂(m-PhSPh) |
| 28.21 | —C(O)p-PhSPh | —C(O)CH₂(p-PhSPh) | —C(O)CH₂CH₂(p-PhSPh) |
| 28.22 | —C(O)o-PhCH₂SPh | —C(O)CH₂(o-PhCH₂SPh) | —C(O)CH₂CH₂(o-PhCH₂SPh) |
| 28.23 | —C(O)m-PhCH₂SPh | —C(O)CH₂(m-PhCH₂SPh) | —C(O)CH₂CH₂(m-PhCH₂SPh) |
| 28.24 | —C(O)p-PhCH₂SPh | —C(O)CH₂(p-PhCH₂SPh) | —C(O)CH₂CH₂(p-PhCH₂SPh) |
| 28.25 | —C(O)adamantyl | —C(O)CH₂(adamantyl) | —C(O)CH₂CH₂(adamantyl) |
| 28.26 | —C(O)cyclopentyl | —C(O)CH₂(cyclopentyl) | —C(O)CH₂CH₂((cyclopentyl) |
| 28.27 | —C(O)cyclohexyl | —C(O)CH₂(cyclohexyl) | —C(O)CH₂CH₂(cyclohexyl) |
| 28.28 | —C(O)CH₂O(cyclopentyl) | —C(O)CH₂NH(cyclopentyl) | —C(O)CH₂S(cyclopentyl) |
| 28.29 | —C(O)CH₂O(cyclohexyl) | —C(O)CH₂NH(cyclohexyl) | —C(O)CH₂S(cyclohexyl) |

TABLE 28-continued

Formula I: A = —B(pinanediol) ; X = —SC(=NH)NH$_2$; R$^3$ = table below; R$^{11}$ = —CH$_2$CH$_2$Ph.

| .1 | .2 | .3 |
|---|---|---|
| 28.30 —C(O)pyridin-2-yl | —C(O)CH$_2$(pyridin-2-yl) | —C(O)CH$_2$CH$_2$(pyridin-2-yl) |
| 28.31 —C(O)pyridin-3-yl | —C(O)CH$_2$(pyridin-3-yl) | —C(O)CH$_2$CH$_2$(pyridin-3-yl) |
| 28.32 —C(O)pyridin-4-yl | —C(O)CH$_2$(pyridin-4-yl) | —C(O)CH$_2$CH$_2$(pyridin-4-yl) |
| 28.33 —C(O)furan-2-yl | —C(O)CH$_2$(furan-2-yl) | —C(O)CH$_2$CH$_2$(furan-2-yl) |
| 28.34 —C(O)furan-3-yl | —C(O)CH$_2$(furan-3-yl) | —C(O)CH$_2$CH$_2$(furan-3-yl) |
| 28.35 —C(O)thiophen-2-yl | —C(O)CH$_2$(thiophen-2-yl) | —C(O)CH$_2$CH$_2$(thiophen-2-yl) |
| 28.36 —C(O)thiophen-2-yl | —C(O)CH$_2$(thiophen-2-yl) | —C(O)CH$_2$CH$_2$(thiophen-2-yl) |
| 28.37 —C(O)imidazo-2-yl | —C(O)CH$_2$(imidazo-2-yl) | —C(O)CH$_2$CH$_2$(imidazo-2-yl) |
| 28.38 —C(O)oxazo-2-yl | —C(O)CH$_2$(oxazo-2-yl) | —C(O)CH$_2$CH$_2$(oxazo-2-yl) |
| 28.39 —C(O)thioazo-2-yl | —C(O)CH$_2$(thioazo-2-yl) | —C(O)CH$_2$CH$_2$(thioazo-2-yl) |
| 28.40 —C(O)benzofuran-2-yl | —C(O)CH$_2$(benzofuran-2-yl) | —C(O)CH$_2$CH$_2$(benzofuran-2-yl) |
| 28.41 —C(O)benzofuran-3-yl | —C(O)CH$_2$(benzofuran-3-yl) | —C(O)CH$_2$CH$_2$(benzofuran-3-yl) |
| 28.42 —C(O)benzothiophen-2-yl | —C(O)CH$_2$(benzothiophen-2-yl) | —C(O)CH$_2$CH$_2$(benzothiophen-2-yl) |
| 28.43 —C(O)thiophen-2-yl | —C(O)CH$_2$(thiophen-2-yl) | —C(O)CH$_2$CH$_2$(thiophen-2-yl) |
| 28.44 —C(O)benzimidazo-2-yl | —C(O)CH$_2$(benzimidazo-2-yl) | —C(O)CH$_2$CH$_2$(benzimidazo-2-yl) |
| 28.45 —C(O)benzoxazo-2-yl | —C(O)CH$_2$(benzoxazo-2-yl) | —C(O)CH$_2$CH$_2$(benzoxazo-2-yl) |
| 28.46 —C(O)benzothiazo-2-yl | —C(O)CH$_2$(benzothiazo-2-yl) | —C(O)CH$_2$CH$_2$(benzothiazo-2-yl) |
| 28.47 —C(O)o-Ph(P(O)Ph$_3$) | —C(O)m-Ph(P(O)Ph$_3$) | —C(O)p-Ph(P(O)Ph$_3$) |
| 28.48 —C(O)Ph-2-(fluoren-9-yl) | —C(O)Ph-3-(fluoren-9-yl) | —C(O)Ph-4-(fluoren-9-yl) |
| 28.49 —C(O)N-indolin-2-one | —C(O)indolin-2-yl | —C(O)indol-2-yl |
| 28.50 —C(O)C(CH$_3$)$_2$NHSO$_2$(naphth-2-yl) | —C(O)cyclopentyl-2-(Ph) | —C(O)cyclohexyl-2-(Ph) |
| 28.51 —C(O)pyrrolidin-3-yl-4-(Ph) | —C(O)tetrahydrofuran-3-yl-4-(Ph) | —C(O)tetrahydrothiophen-3-yl-4-(Ph) |
| 28.52 —C(O)tetrahydronaphth-1-yl | —C(O)tetrahydronaphth-2-yl | —C(O)cyclopropyl-2,2-(Ph$_2$) |
| 28.53 —C(O)tetrahydroisoquinolin-1-yl | —C(O)tetrahydroisoquinolin-3-yl | —C(O)CH$_2$((2-oxo)indolin-3-yl) |
| 28.54 —C(O)CH$_2$(N-benzimidazol-2-one) | —C(O)CH$_2$(N-benzoxazol-2-one) | —C(O)CH$_2$(N-benzothiazol-2-one) |
| 28.55 —C(O)CH$_2$(N-dihydroimidazol-2-one) | —C(O)CH$_2$(N-dihydrooxazol-2-one) | —C(O)CH$_2$(N-dihydrothiazol-2-one) |

28.56

28.57

28.58

| 28.59 —C(O)N(CH$_3$)CH$_2$Ph | —C(O)N(C$_2$H$_5$)CH$_2$Ph | —C(O)N(C$_3$H$_7$)CH$_2$Ph |
| 28.60 —C(O)pyridin-3-yl-5-(Ph) | —C(O)Ph-3-(CH$_2$(thiophen-2-yl)) | —C(O)Ph-3-(CH$_2$Ph) |
| 28.61 —C(O)C(CH$_3$)$_2$OPh | —C(O)CH(C$_2$H$_5$)OPh | —C(O)CH$_2$OCH$_2$Ph |
| 28.62 —C(O)CH$_2$O(o-PhCH$_2$OH) | —C(O)CH$_2$O(m-PhCH$_2$OH) | —C(O)CH$_2$O(p-PhCH$_2$OH) |
| 28.63 —C(O)CH$_2$O(o-PhCOOH) | —C(O)CH$_2$O(m-PhCOOH) | —C(O)CH$_2$O(p-PhCOOH) |

TABLE 28-continued

Formula I: A = —B(pinanediol) ; X = —SC(=NH)NH$_2$; R$^3$ = table below; R$^{11}$ = —CH$_2$CH$_2$Ph.

| .1 | .2 | .3 |
|---|---|---|
| 28.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 28.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 28.66 (4-benzyl-2-oxo-oxazolidin-3-ylmethyl)carbonyl- | | |

TABLE 29

Formula I: A = —B(pinanediol) ; X = —SC(=NH)NH$_2$; R$^3$ = table below; R$^{11}$ = —Ph.

| .1 | .2 | .3 |
|---|---|---|
| 29.1 —C(O)Ph | —C(O)CH$_2$Ph | —C(O)CH$_2$CH$_2$Ph |
| 29.2 —C(O)CH$_2$OPh | —C(O)CH$_2$NHPh | —C(O)CH$_2$SPh |
| 29.3 —C(O)o-PhOH | —C(O)m-PhOH | —C(O)p-PhOH |
| 29.4 —C(O)o-PhCH$_2$OH | —C(O)m-PhCH$_2$OH | —C(O)p-PhCH$_2$OH |
| 29.5 —C(O)o-PhCOOH | —C(O)m-PhCOOH | —C(O)p-PhCOOH |
| 29.6 —C(O)o-PhCH$_2$COOH | —C(O)m-PhCH$_2$COOH | —C(O)p-PhCH$_2$COOH |
| 29.7 —C(O)naphth-1-yl | —C(O)CH$_2$(naphth-1-yl) | —C(O)CH$_2$CH$_2$(napth-1-yl) |
| 29.8 —C(O)naphth-2-yl | —C(O)CH$_2$(naphth-2-yl) | —C(O)CH$_2$CH$_2$(napth-2-yl) |
| 29.9 —C(O)o-biphenyl | —C(O)CH$_2$(o-biphenyl) | —C(O)CH$_2$CH$_2$(o-biphenyl) |
| 29.10 —C(O)m-biphenyl | —C(O)CH$_2$(m-biphenyl) | —C(O)CH$_2$CH$_2$(m-biphenyl) |
| 29.12 —C(O)p-biphenyl | —C(O)CH$_2$-(p-biphenyl) | —C(O)CH$_2$CH$_2$(p-biphenyl) |
| 29.13 —C(O)o-PhOPh | —C(O)CH$_2$(o-PhOPh) | —C(O)CH$_2$CH$_2$(o-PhOPh) |
| 29.14 —C(O)m-PhOPh | —C(O)CH$_2$(m-PhOPh) | —C(O)CH$_2$CH$_2$(m-PhOPh) |
| 29.15 —C(O)p-PhOPh | —C(O)CH$_2$(p-PhOPh) | —C(O)CH$_2$CH$_2$(p-PhOPh) |
| 29.16 —C(O)o-PhNHPh | —C(O)CH$_2$(o-PhNHPh) | —C(O)CH$_2$CH$_2$(o-PhNHPh) |
| 29.17 —C(O)m-PhNHPh | —C(O)CH$_2$(m-PhNHPh) | —C(O)CH$_2$CH$_2$(m-PhNHPh) |
| 29.18 —C(O)p-PhNHPh | —C(O)CH$_2$(p-PhNHPh) | —C(O)CH$_2$CH$_2$(p-PhNHPh) |
| 29.19 —C(O)o-PhSPh | —C(O)CH$_2$(o-PhSPh) | —C(O)CH$_2$CH$_2$(o-PhSPh) |
| 29.20 —C(O)m-PhSPh | —C(O)CH$_2$(m-PhSPh) | —C(O)CH$_2$CH$_2$(m-PhSPh) |
| 29.21 —C(O)p-PhSPh | —C(O)CH$_2$(p-PhSPh) | —C(O)CH$_2$CH$_2$(p-PhSPh) |
| 29.22 —C(O)o-PhCH$_2$SPh | —C(O)CH$_2$(o-PhCH$_2$SPh) | —C(O)CH$_2$CH$_2$(o-PhCH$_2$SPh) |
| 29.23 —C(O)m-PhCH$_2$SPh | —C(O)CH$_2$(m-PhCH$_2$SPh) | —C(O)CH$_2$CH$_2$(m-PhCH$_2$SPh) |
| 29.24 —C(O)p-PhCH$_2$SPh | —C(O)CH$_2$(p-PhCH$_2$SPh) | —C(O)CH$_2$CH$_2$(p-PhCH$_2$SPh) |
| 29.25 —C(O)adamantyl | —C(O)CH$_2$(adamantyl) | —C(O)CH$_2$CH$_2$(adamantyl) |
| 29.26 —C(O)cyclopentyl | —C(O)CH$_2$(cyclopentyl) | —C(O)CH$_2$CH$_2$((cyclopentyl) |
| 29.27 —C(O)cyclohexyl | —C(O)CH$_2$(cyclohexyl) | —C(O)CH$_2$CH$_2$(cyclohexyl) |
| 29.28 —C(O)CH$_2$O(cyclopentyl) | —C(O)CH$_2$NH(cyclopentyl) | —C(O)CH$_2$S(cyclopentyl) |
| 29.29 —C(O)CH$_2$O(cyclohexyl) | —C(O)CH$_2$NH(cyclohexyl) | —C(O)CH$_2$S(cyclohexyl) |
| 29.30 —C(O)pyridin-2-yl | —C(O)CH$_2$(pyridin-2-yl) | —C(O)CH$_2$CH$_2$(pyridin-2-yl) |
| 29.31 —C(O)pyridin-3-yl | —C(O)CH$_2$(pyridin-3-yl) | —C(O)CH$_2$CH$_2$(pyridin-3-yl) |
| 29.32 —C(O)pyridin-4-yl | —C(O)CH$_2$(pyridin-4-yl) | —C(O)CH$_2$CH$_2$(pyridin-4-yl) |
| 29.33 —C(O)furan-2-yl | —C(O)CH$_2$(furan-2-yl) | —C(O)CH$_2$CH$_2$(furan-2-yl) |
| 29.34 —C(O)furan-3-yl | —C(O)CH$_2$(furan-3-yl) | —C(O)CH$_2$CH$_2$(furan-3-yl) |
| 29.35 —C(O)thiophen-2-yl | —C(O)CH$_2$(thiophen-2-yl) | —C(O)CH$_2$CH$_2$(thiophen-2-yl) |
| 29.36 —C(O)thiophen-2-yl | —C(O)CH$_2$(thiophen-2-yl) | —C(O)CH$_2$CH$_2$(thiophen-2-yl) |
| 29.37 —C(O)imidazo-2-yl | —C(O)CH$_2$(imidazo-2-yl) | —C(O)CH$_2$CH$_2$(imidazo-2-yl) |
| 29.38 —C(O)oxazo-2-yl | —C(O)CH$_2$(oxazo-2-yl) | —C(O)CH$_2$CH$_2$(oxazo-2-yl) |
| 29.39 —C(O)thioazo-2-yl | —C(O)CH$_2$(thioazo-2-yl) | —C(O)CH$_2$CH$_2$(thioazo-2-yl) |
| 29.40 —C(O)benzofuran-2-yl | —C(O)CH$_2$(benzofuran-2-yl) | —C(O)CH$_2$CH$_2$(benzofuran-2-yl) |
| 29.41 —C(O)benzofuran-3-yl | —C(O)CH$_2$(benzofuran-3-yl) | —C(O)CH$_2$CH$_2$(benzofuran-3-yl) |
| 29.42 —C(O)benzothiophen-2-yl | —C(O)CH$_2$(benzothiophen-2-yl) | —C(O)CH$_2$CH$_2$(benzothiophen-2-yl) |
| 29.43 —C(O)thiophen-2-yl | —C(O)CH$_2$(thiophen-2-yl) | —C(O)CH$_2$CH$_2$(thiophen-2-yl) |
| 29.44 —C(O)benzimidazo-2-yl | —C(O)CH$_2$(benzimidazo-2-yl) | —C(O)CH$_2$CH$_2$(benzimidazo-2-yl) |
| 29.45 —C(O)benzoxazo-2-yl | —C(O)CH$_2$(benzoxazo-2-yl) | —C(O)CH$_2$CH$_2$(benzoxazo-2-yl) |
| 29.46 —C(O)benzothiazo-2-yl | —C(O)CH$_2$(benzothiazo-2-yl) | —C(O)CH$_2$CH$_2$(benzothiazo-2-yl) |
| 29.47 —C(O)o-Ph(P(O)Ph$_3$) | —C(O)m-Ph(P(O)Ph$_3$) | —C(O)p-Ph(P(O)Ph$_3$) |
| 29.48 —C(O)Ph-2-(fluoren-9-yl) | —C(O)Ph-3-(fluoren-9-yl) | —C(O)Ph-4-(fluoren-9-yl) |
| 29.49 —C(O)N-indolin-2-one | —C(O)indolin-2-yl | —C(O)indol-2-yl |
| 29.50 —C(O)C(CH$_3$)$_2$NHSO$_2$(naphth-2-yl) | —C(O)cyclopentyl-2-(Ph) | —C(O)cyclohexyl-2-(Ph) |

TABLE 29-continued

Formula I: A = —B(pinanediol) ; X = —SC(=NH)NH$_2$; R$^3$ = table below; R$^{11}$ = —Ph.

|  | .1 | .2 | .3 |
|---|---|---|---|
| 29.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 29.52 | —C(O)tetrahydronaphth-1-yl | —C(O)tetrahydronaphth-2-yl | —C(O)cyclopropyl-2,2-(Ph$_2$) |
| 29.53 | —C(O)tetrahydroisoquinolin-1-yl | —C(O)tetrahydroisoquinolin-3-yl | —C(O)CH$_2$((2-oxo)indolin-3-yl) |
| 29.54 | —C(O)CH$_2$(N-benzimidazol-2-one) | —C(O)CH$_2$(N-benzoxazol-2-one) | —C(O)CH$_2$(N-benzothiazol-2-one) |
| 29.55 | —C(O)CH$_2$(N-dihydroimidazol-2-one) | —C(O)CH$_2$(N-dihydrooxazol-2-one) | —C(O)CH$_2$(N-dihydrothiazol-2-one) |

29.56 [structures]

29.57 [structures]

29.58 [structures]

| 29.59 | —C(O)N(CH$_3$)CH$_2$Ph | —C(O)N(C$_2$H$_5$)CH$_2$Ph | —C(O)N(C$_3$H$_7$)CH$_2$Ph |
| 29.60 | —C(O)pyridin-3-yl-5-(Ph) | —C(O)Ph-3-(CH$_2$(thiophen-2-yl)) | —C(O)Ph-3-(CH$_2$Ph) |
| 29.61 | —C(O)C(CH$_3$)$_2$OPh | —C(O)CH(C$_2$H$_5$)OPh | —C(O)CH$_2$OCH$_2$Ph |
| 29.62 | —C(O)CH$_2$O(o-PhCH$_2$OH) | —C(O)CH$_2$O(m-PhCH$_2$OH) | —C(O)CH$_2$O(p-PhCH$_2$OH) |
| 29.63 | —C(O)CH$_2$O(o-PhCOOH) | —C(O)CH$_2$O(m-PhCOOH) | —C(O)CH$_2$O(p-PhCOOH) |
| 29.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 29.65 | —C(O)CH$_2$O(o-PhCH$_2$COOH) | —C(O)CH$_2$O(m-PhCH$_2$COOH) | —C(O)CH$_2$O(p-PhCH$_2$COOH) |

29.66 [structure]

TABLE 30

Formula I: A = —B(pinanediol) ; X = —SC(=NH)NH$_2$; R$^3$ = table below; R$^{11}$ = —CH$_2$(naphth-2-yl).

| | .1 | .2 | .3 |
|---|---|---|---|
| 30.1 | —C(O)Ph | —C(O)CH$_2$Ph | —C(O)CH$_2$CH$_2$Ph |
| 30.2 | —C(O)CH$_2$OPh | —C(O)CH$_2$NHPh | —C(O)CH$_2$SPh |
| 30.3 | —C(O)o-PhOH | —C(O)m-PhOH | —C(O)p-PhOH |
| 30.4 | —C(O)o-PhCH$_2$OH | —C(O)m-PhCH$_2$OH | —C(O)p-PhCH$_2$OH |
| 30.5 | —C(O)o-PhCOOH | —C(O)m-PhCOOH | —C(O)p-PhCOOH |
| 30.6 | —C(O)o-PhCH$_2$COOH | —C(O)m-PhCH$_2$COOH | —C(O)p-PhCH$_2$COOH |
| 30.7 | —C(O)naphth-1-yl | —C(O)CH$_2$(naphth-1-yl) | —C(O)CH$_2$CH$_2$(napth-1-yl) |
| 30.8 | —C(O)naphth-2-yl | —C(O)CH$_2$(naphth-2-yl | —C(O)CH$_2$CH$_2$(napth-2-yl) |
| 30.9 | —C(O)o-biphenyl | —C(O)CH$_2$(o-biphenyl) | —C(O)CH$_2$CH$_2$(o-biphenyl) |
| 30.10 | —C(O)m-biphenyl | —C(O)CH$_2$(m-biphenyl) | —C(O)CH$_2$CH$_2$(m-biphenyl) |
| 30.12 | —C(O)p-biphenyl | —C(O)CH$_2$-(p-biphenyl) | —C(O)CH$_2$CH$_2$(p-biphenyl) |
| 30.13 | —C(O)o-PhOPh | —C(O)CH$_2$(o-PhOPh) | —C(O)CH$_2$CH$_2$(o-PhOPh) |
| 30.14 | —C(O)m-PhOPh | —C(O)CH$_2$(m-PhOPh) | —C(O)CH$_2$CH$_2$(m-PhOPh) |
| 30.15 | —C(O)p-PhOPh | —C(O)CH$_2$(p-PhOPh) | —C(O)CH$_2$CH$_2$(p-PhOPh) |
| 30.16 | —C(O)o-PhNHPh | —C(O)CH$_2$(o-PhNHPh) | —C(O)CH$_2$CH$_2$(o-PhNHPh) |
| 30.17 | —C(O)m-PhNHPh | —C(O)CH$_2$(m-PhNHPh) | —C(O)CH$_2$CH$_2$(m-PhNHPh) |
| 30.18 | —C(O)p-PhNHPh | —C(O)CH$_2$(p-PhNHPh) | —C(O)CH$_2$CH$_2$(p-PhNHPh) |
| 30.19 | —C(O)o-PhSPh | —C(O)CH$_2$(o-PhSPh) | —C(O)CH$_2$CH$_2$(o-PhSPh) |
| 30.20 | —C(O)m-PhSPh | —C(O)CH$_2$(m-PhSPh) | —C(O)CH$_2$CH$_2$(m-PhSPh) |
| 30.21 | —C(O)p-PhSPh | —C(O)CH$_2$(p-PhSPh) | —C(O)CH$_2$CH$_2$(p-PhSPh) |
| 30.22 | —C(O)o-PhCH$_2$SPh | —C(O)CH$_2$(o-PhCH$_2$SPh) | —C(O)CH$_2$CH$_2$(o-PhCH$_2$SPh) |
| 30.23 | —C(O)m-PhCH$_2$SPh | —C(O)CH$_2$(m-PhCH$_2$SPh) | —C(O)CH$_2$CH$_2$(m-PhCH$_2$SPh) |
| 30.24 | —C(O)p-PhCH$_2$SPh | —C(O)CH$_2$(p-PhCH$_2$SPh) | —C(O)CH$_2$CH$_2$(p-PhCH$_2$SPh) |
| 30.25 | —C(O)adamantyl | —C(O)CH$_2$(adamantyl) | —C(O)CH$_2$CH$_2$(adamantyl) |
| 30.26 | —C(O)cyclopentyl | —C(O)CH$_2$(cyclopentyl) | —C(O)CH$_2$CH$_2$((cyclopentyl) |
| 30.27 | —C(O)cyclohexyl | —C(O)CH$_2$(cyclohexyl) | —C(O)CH$_2$CH$_2$(cyclohexyl) |
| 30.28 | —C(O)CH$_2$O(cyclopentyl) | —C(O)CH$_2$NH(cyclopentyl) | —C(O)CH$_2$S(cyclopentyl) |
| 30.29 | —C(O)CH$_2$O(cyclohexyl) | —C(O)CH$_2$NH(cyclohexyl) | —C(O)CH$_2$S(cyclohexyl) |
| 30.30 | —C(O)pyridin-2-yl | —C(O)CH$_2$(pyridin-2-yl) | —C(O)CH$_2$CH$_2$(pyridin-2-yl) |
| 30.31 | —C(O)pyridin-3-yl | —C(O)CH$_2$(pyridin-3-yl) | —C(O)CH$_2$CH$_2$(pyridin-3-yl) |
| 30.32 | —C(O)pyridin-4-yl | —C(O)CH$_2$(pyridin-4-yl) | —C(O)CH$_2$CH$_2$(pyridin-4-yl) |
| 30.33 | —C(O)furan-2-yl | —C(O)CH$_2$(furan-2-yl) | —C(O)CH$_2$CH$_2$(furan-2-yl) |
| 30.34 | —C(O)furan-3-yl | —C(O)CH$_2$(furan-3-yl) | —C(O)CH$_2$CH$_2$(furan-3-yl) |
| 30.35 | —C(O)thiophen-2-yl | —C(O)CH$_2$(thiophen-2-yl) | —C(O)CH$_2$CH$_2$(thiophen-2-yl) |
| 30.36 | —C(O)thiophen-2-yl | —C(O)CH$_2$(thiophen-2-yl) | —C(O)CH$_2$CH$_2$(thiophen-2-yl) |
| 30.37 | —C(O)imidazo-2-yl | —C(O)CH$_2$(imidazo-2-yl) | —C(O)CH$_2$CH$_2$(imidazo-2-yl) |
| 30.38 | —C(O)oxazo-2-yl | —C(O)CH$_2$(oxazo-2-yl) | —C(O)CH$_2$CH$_2$(oxazo-2-yl) |
| 30.39 | —C(O)thioazo-2-yl | —C(O)CH$_2$(thioazo-2-yl) | —C(O)CH$_2$CH$_2$(thioazo-2-yl) |
| 30.40 | —C(O)benzofuran-2-yl | —C(O)CH$_2$(benzofuran-2-yl) | —C(O)CH$_2$CH$_2$(benzofuran-2-yl) |
| 30.41 | —C(O)benzofuran-3-yl | —C(O)CH$_2$(benzofuran-3-yl) | —C(O)CH$_2$CH$_2$(benzofuran-3-yl) |
| 30.42 | —C(O)benzothiophen-2-yl | —C(O)CH$_2$(benzothiophen-2-yl) | —C(O)CH$_2$CH$_2$(benzothiophen-2-yl) |
| 30.43 | —C(O)thiophen-2-yl | —C(O)CH$_2$(thiophen-2-yl) | —C(O)CH$_2$CH$_2$(thiophen-2-yl) |
| 30.44 | —C(O)benzimidazo-2-yl | —C(O)CH$_2$(benzimidazo-2-yl) | —C(O)CH$_2$CH$_2$(benzimidazo-2-yl) |
| 30.45 | —C(O)benzoxazo-2-yl | —C(O)CH$_2$(benzoxazo-2-yl) | —C(O)CH$_2$CH$_2$(benzoxazo-2-yl) |
| 30.46 | —C(O)benzothiazo-2-yl | —C(O)CH$_2$(benzothiazo-2-yl) | —C(O)CH$_2$CH$_2$(benzothiazo-2-yl) |
| 30.47 | —C(O)o-Ph(P(O)Ph$_3$) | —C(O)m-Ph(P(O)Ph$_3$) | —C(O)p-Ph(P(O)Ph$_3$) |
| 30.48 | —C(O)Ph-2-(fluoren-9-yl) | —C(O)Ph-3-(fluoren-9-yl) | —C(O)Ph-4-(fluoren-9-yl) |
| 30.49 | —C(O)N-indolin-2-one | —C(O)indolin-2-yl | —C(O)indol-2-yl |
| 30.50 | —C(O)C(CH$_3$)$_2$NHSO$_2$(naphth-2-yl) | —C(O)cyclopentyl-2-(Ph) | —C(O)cyclohexyl-2-(Ph) |
| 30.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 30.52 | —C(O)tetrahydronaphth-1-yl | —C(O)tetrahydronaphth-2-yl | —C(O)cyclopropyl-2,2-(Ph$_2$) |
| 30.53 | —C(O)tetrahydroisoquinolin-1-yl | —C(O)tetrahydroisoquinolin-3-yl | —C(O)CH$_2$((2-oxo)indolin-3-yl) |
| 30.54 | —C(O)CH$_2$(N-benzimidazol-2-one) | —C(O)CH$_2$(N-benzoxazol-2-one) | —C(O)CH$_2$(N-benzothiazol-2-one) |
| 30.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 30.56 | 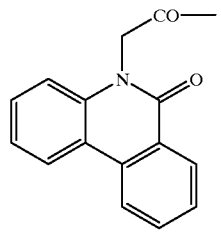 | 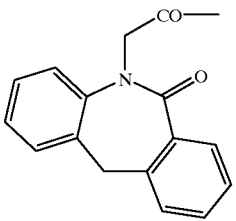 | |

TABLE 30-continued

Formula I: A = —B(pinanediol) ; X = —SC(=NH)NH$_2$; R$^3$ = table below; R$^{11}$ = —CH$_2$(naphth-2-yl).

| .1 | .2 | .3 |
|---|---|---|
| 30.57 | | |
| 30.58 | | |
| 30.59 —C(O)N(CH$_3$)CH$_2$Ph | —C(O)N(C$_2$H$_5$)CH$_2$Ph | —C(O)N(C$_3$H$_7$)CH$_2$Ph |
| 30.60 —C(O)pyridin-3-yl-5-(Ph) | —C(O)Ph-3-(CH$_2$(thiophen-2-yl)) | —C(O)Ph-3-(CH$_2$Ph) |
| 30.61 —C(O)C(CH$_3$)$_2$OPh | —C(O)CH(C$_2$H$_5$)OPh | —C(O)CH$_2$OCH$_2$Ph |
| 30.62 —C(O)CH$_2$O(o-PhCH$_2$OH) | —C(O)CH$_2$O(m-PhCH$_2$OH) | —C(O)CH$_2$O(p-PhCH$_2$OH) |
| 30.63 —C(O)CH$_2$O(o-PhCOOH) | —C(O)CH$_2$O(m-PhCOOH) | —C(O)CH$_2$O(p-PhCOOH) |
| 30.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 30.65 —C(O)CH$_2$O(o-PhCH$_2$COOH) | —C(O)CH$_2$O(m-PhCH$_2$COOH) | —C(O)CH$_2$O(p-PhCH$_2$COOH) |
| 30.66 | | |

TABLE 31

Formula II: A = —B(OH)$_2$; X = guanidinyl; Y = table below.

| .1 | .2 | .3 |
|---|---|---|
| 31.1 —C(O)CH$_2$(N-benzimidazol-2-one) | —C(O)CH$_2$(N-benzoxazol-2-one) | —C(O)CH$_2$(N-benzothiazol-2-one) |
| 31.2 —C(O)CH$_2$(N-dihydroimidazol-2-one) | —C(O)CH$_2$(N-dihydrooxazol-2-one) | —C(O)CH$_2$(N-dihydrothiazol-2-one) |
| 31.3 | | |

TABLE 31-continued
Formula II: A = —B(OH)₂; X = guanidinyl; Y = table below.
| .1 | .2 | .3 |
|---|---|---|
| 31.4 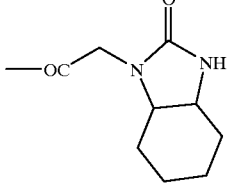 | 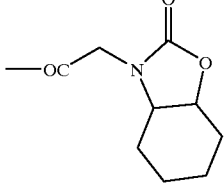 | 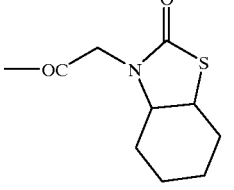 |
| 31.5 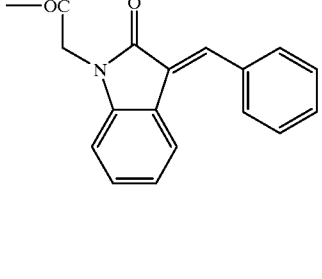 | 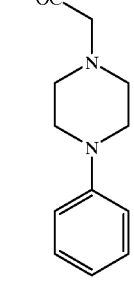 | 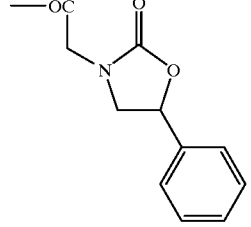 |
| 31.6 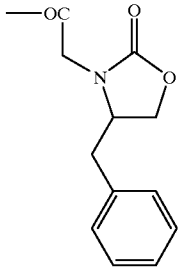 | 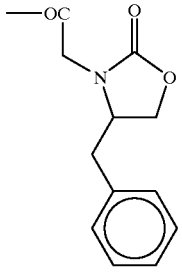 | |
TABLE 32
Formula II: A = —B(OH)₂; X = —CH₂NH₂; Y = table below
| | .1 | .2 | .3 |
|---|---|---|---|
| 32.1 | —C(O)CH₂(N-benzimidazol-2-one) | —C(O)CH₂(N-benzoxazol-2-one) | —C(O)CH₂(N-benzothiazol-2-one) |
| 32.2 | —C(O)CH₂(N-dihydroimidazol-2-one) | —C(O)CH₂(N-dihydrooxazol-2-one) | —C(O)CH₂(N-dihydrothiazol-2-one) |
| 32.3 | 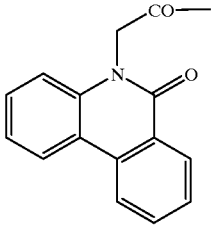 | 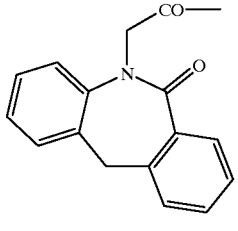 | 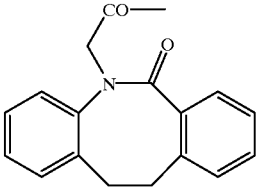 |
| 32.4 | 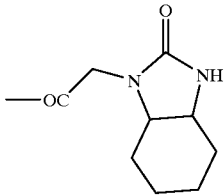 | 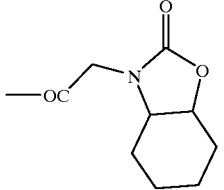 | 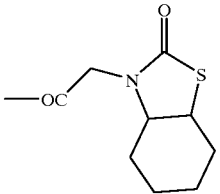 |

TABLE 32-continued
Formula II: A = —B(OH)$_2$; X = —CH$_2$NH$_2$; Y = table below
| | .1 | .2 | .3 |
|---|---|---|---|
| 32.5 | 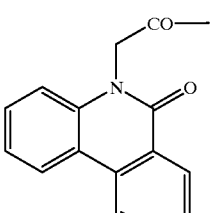 | 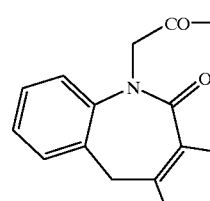 | 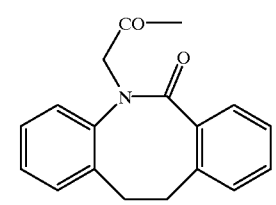 |
| 32.6 | 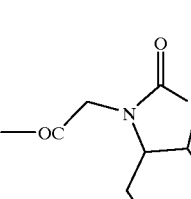 | | |
TABLE 33
Formula II: A = —B(OH)$_2$; X = —SC(=NH)NH$_2$; Y = table below
| | .1 | .2 | .3 |
|---|---|---|---|
| 33.1 | —C(O)CH$_2$(N-benzimidazol-2-one) | —C(O)CH$_2$(N-benzoxazol-2-one) | —C(O)CH$_2$(N-benzothiazol-2-one) |
| 33.2 | —C(O)CH$_2$(N-dihydroimidazol-2-one) | —C(O)CH$_2$(N-dihydrooxazol-2-one) | —C(O)CH$_2$(N-dihydrothiazol-2-one) |
| 33.3 | 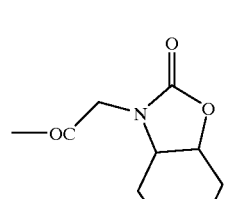 | | |
| 33.4 | 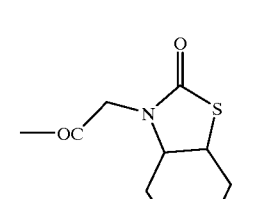 | | |

TABLE 33-continued
Formula II: A = —B(OH)₂; X = —SC(=NH)NH₂; Y = table below
| | .1 | .2 | .3 |
|---|---|---|---|
| 33.5 | | | |
| 33.6 | | | |
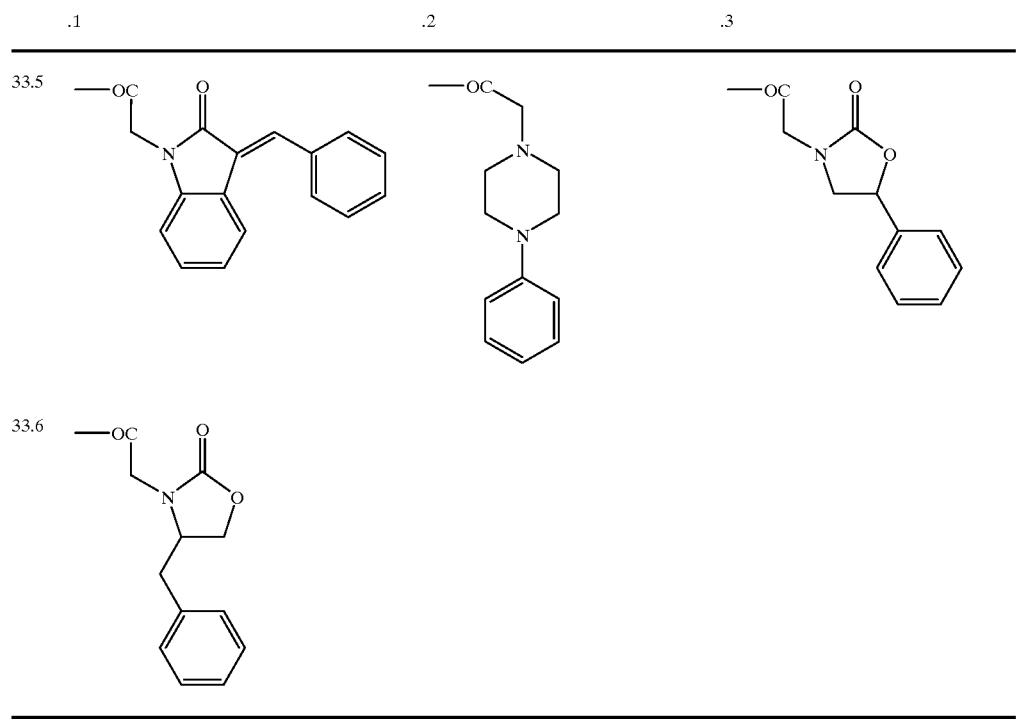
TABLE 34
Formula II: A = —B(pinanediol); X = guanidinyl; Y = table below
| | .1 | .2 | .3 |
|---|---|---|---|
| 34.1 | —C(O)CH₂(N-benzimidazol-2-one) | —C(O)CH₂(N-benzoxazol-2-one) | —C(O)CH₂(N-benzothiazol-2-one) |
| 34.2 | —C(O)CH₂(N-dihydroimidazol-2-one) | —C(O)CH₂(N-dihydrooxazol-2-one) | —C(O)CH₂(N-dihydrothiazol-2-one) |
| 34.3 | | | |
| 34.4 | | | |
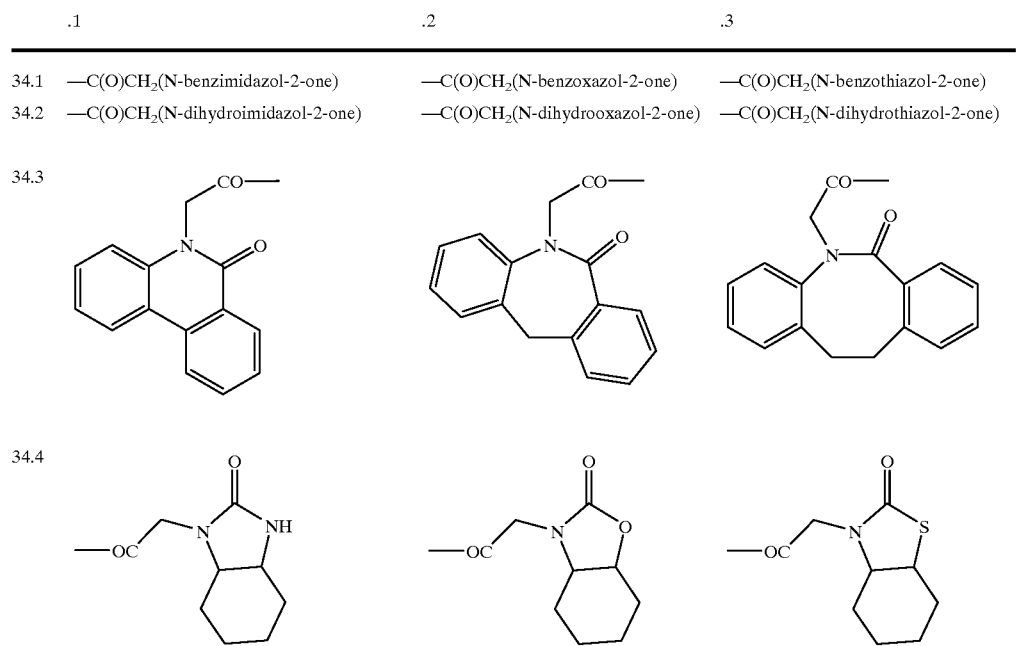

TABLE 34-continued

Formula II: A = —B(pinanediol); X = guanidinyl; Y = table below

| | .1 | .2 | .3 |
|---|---|---|---|
| 34.5 | —OC—CH₂-(3-benzylidene-indolin-2-one-N-yl) | —OC—CH₂-(4-phenylpiperazin-1-yl) | —OC—CH₂-(5-phenyl-oxazolidin-2-one-N-yl) |
| 34.6 | —OC—CH₂-(4-benzyl-oxazolidin-2-one-N-yl) | | |

TABLE 35

Formula II: A = —B(pinanediol); X = —CH₂NH₂; Y = table below

| | .1 | .2 | .3 |
|---|---|---|---|
| 35.1 | —C(O)CH₂(N-benzimidazol-2-one) | —C(O)CH₂(N-benzoxazol-2-one) | —C(O)CH₂(N-benzothiazol-2-one) |
| 35.2 | —C(O)CH₂(N-dihydroimidazol-2-one) | —C(O)CH₂(N-dihydrooxazol-2-one) | —C(O)CH₂(N-dihydrothiazol-2-one) |
| 35.3 | phenanthridinone-N-CH₂CO— | dibenzazepinone-N-CH₂CO— | dibenzazocinone-N-CH₂CO— |
| 35.4 | —OC—CH₂-(hexahydrobenzimidazol-2-one-N-yl) | —OC—CH₂-(hexahydrobenzoxazol-2-one-N-yl) | —OC—CH₂-(hexahydrobenzothiazol-2-one-N-yl) |

TABLE 35-continued

Formula II: A = —B(pinanediol); X = —CH$_2$NH$_2$; Y = table below

| | .1 | .2 | .3 |
|---|---|---|---|
| 35.5 | (3-benzylidene-indolin-2-one, N-CH$_2$C(O)O—) | (4-phenyl-piperazin-1-yl-CH$_2$C(O)O—) | (5-phenyl-oxazolidin-2-one, N-CH$_2$C(O)O—) |
| 35.6 | (4-benzyl-oxazolidin-2-one, N-CH$_2$C(O)O—) | | |

TABLE 36

Formula II: A = —B(pinanediol); X = —SC(=NH)NH$_2$; Y = table below

| | .1 | .2 | .3 |
|---|---|---|---|
| 36.1 | —C(O)CH$_2$(N-benzimidazol-2-one) | —C(O)CH$_2$(N-benzoxazol-2-one) | —C(O)CH$_2$(N-benzothiazol-2-one) |
| 36.2 | —C(O)CH$_2$(N-dihydroimidazol-2-one) | —C(O)CH$_2$(N-dihydrooxazol-2-one) | —C(O)CH$_2$(N-dihydrothiazol-2-one) |
| 36.3 | (phenanthridin-6(5H)-one, N-CH$_2$CO—) | (dibenzazepin-one, N-CH$_2$CO—) | (dibenzazocin-one, N-CH$_2$CO—) |
| 36.4 | (hexahydro-benzimidazol-2-one, N-CH$_2$CO—) | (hexahydro-benzoxazol-2-one, N-CH$_2$CO—) | (hexahydro-benzothiazol-2-one, N-CH$_2$CO—) |

TABLE 36-continued

Formula II: A = —B(pinanediol); X = —SC(=NH)NH$_2$; Y = table below

| | .1 | .2 | .3 |
|---|---|---|---|
| 36.5 | —OC—CH$_2$—N(3-benzylidene-2-oxoindolin-1-yl) | —OC—CH$_2$—(4-phenylpiperazin-1-yl) | —OC—CH$_2$—N(5-phenyl-2-oxooxazolidin-3-yl) |
| 36.6 | —OC—CH$_2$—N(4-benzyl-2-oxooxazolidin-3-yl) | | |

TABLE 37

Formula III: A = —B(OH)$_2$; X = —CN; R$^3$ = table below; R$^{11}$ = CH$_3$

| | .1 | .2 | .3 |
|---|---|---|---|
| 37.1 | —C(O)Ph | —C(O)CH$_2$Ph | —C(O)CH$_2$CH$_2$Ph |
| 37.2 | —C(O)CH$_2$OPh | —C(O)CH$_2$NHPh | —C(O)CH$_2$SPh |
| 37.3 | —C(O)o-PhOH | —C(O)m-PhOH | —C(O)p-PhOH |
| 37.4 | —C(O)o-PhCH$_2$OH | —C(O)m-PhCH$_2$OH | —C(O)p-PhCH$_2$OH |
| 37.5 | —C(O)o-PhCOOH | —C(O)m-PhCOOH | —C(O)p-PhCOOH |
| 37.6 | —C(O)o-PhCH$_2$COOH | —C(O)m-PhCH$_2$COOH | —C(O)p-PhCH$_2$COOH |
| 37.7 | —C(O)naphth-1-yl | —C(O)CH$_2$(naphth-1-yl) | —C(O)CH$_2$CH$_2$(napth-1-yl) |
| 37.8 | —C(O)naphth-2-yl | —C(O)CH$_2$(naphth-2-yl) | —C(O)CH$_2$CH$_2$(napth-2-yl) |
| 37.9 | —C(O)o-biphenyl | —C(O)CH$_2$(o-biphenyl) | —C(O)CH$_2$CH$_2$(o-biphenyl) |
| 37.10 | —C(O)m-biphenyl | —C(O)CH$_2$(m-biphenyl) | —C(O)CH$_2$CH$_2$(m-biphenyl) |
| 37.12 | —C(O)p-biphenyl | —C(O)CH$_2$(p-biphenyl) | —C(O)CH$_2$CH$_2$(p-biphenyl) |
| 37.13 | —C(O)o-PhOPh | —C(O)CH$_2$(o-PhOPh) | —C(O)CH$_2$CH$_2$(o-PhOPh) |
| 37.14 | —C(O)m-PhOPh | —C(O)CH$_2$(m-PhOPh) | —C(O)CH$_2$CH$_2$(m-PhOPh) |
| 37.15 | —C(O)p-PhOPh | —C(O)CH$_2$(p-PhOPh) | —C(O)CH$_2$CH$_2$(p-PhOPh) |
| 37.16 | —C(O)o-PhNHPh | —C(O)CH$_2$(o-PhNHPh) | —C(O)CH$_2$CH$_2$(o-PhNHPh) |
| 37.17 | —C(O)m-PhNHPh | —C(O)CH$_2$(m-PhNHPh) | —C(O)CH$_2$CH$_2$(m-PhNHPh) |
| 37.18 | —C(O)p-PhNHPh | —C(O)CH$_2$(p-PhNHPh) | —C(O)CH$_2$CH$_2$(p-PhNHPh) |
| 37.19 | —C(O)o-PhSPh | —C(O)CH$_2$(o-PhSPh) | —C(O)CH$_2$CH$_2$(o-PhSPh) |
| 37.20 | —C(O)m-PhSPh | —C(O)CH$_2$(m-PhSPh) | —C(O)CH$_2$CH$_2$(m-PhSPh) |
| 37.21 | —C(O)p-PhSPh | —C(O)CH$_2$(p-PhSPh) | —C(O)CH$_2$CH$_2$(p-PhSPh) |
| 37.22 | —C(O)o-PhCH$_2$SPh | —C(O)CH$_2$(o-PhCH$_2$SPh) | —C(O)CH$_2$CH$_2$(o-PhCH$_2$SPh) |
| 37.23 | —C(O)m-PhCH$_2$SPh | —C(O)CH$_2$(m-PhCH$_2$SPh) | —C(O)CH$_2$CH$_2$(m-PhCH$_2$SPh) |
| 37.24 | —C(O)p-PhCH$_2$SPh | —C(O)CH$_2$(p-PhCH$_2$SPh) | —C(O)CH$_2$CH$_2$(p-PhCH$_2$SPh) |
| 37.25 | —C(O)adamantyl | —C(O)CH$_2$(adamantyl) | —C(O)CH$_2$CH$_2$(adamantyl) |
| 37.26 | —C(O)cyclopentyl | —C(O)CH$_2$(cyclopentyl) | —C(O)CH$_2$CH$_2$((cyclopentyl) |
| 37.27 | —C(O)cyclohexyl | —C(O)CH$_2$(cyclohexyl) | —C(O)CH$_2$CH$_2$(cyclohexyl) |
| 37.28 | —C(O)CH$_2$O(cyclopentyl) | —C(O)CH$_2$NH(cyclopentyl) | —C(O)CH$_2$S(cyclopentyl) |
| 37.29 | —C(O)CH$_2$O(cyclohexyl) | —C(O)CH$_2$NH(cyclohexyl) | —C(O)CH$_2$S(cyclohexyl) |
| 37.30 | —C(O)pyridin-2-yl | —C(O)CH$_2$(pyridin-2-yl) | —C(O)CH$_2$CH$_2$(pyridin-2-yl) |
| 37.31 | —C(O)pyridin-3-yl | —C(O)CH$_2$(pyridin-3-yl) | —C(O)CH$_2$CH$_2$(pyridin-3-yl) |
| 37.32 | —C(O)pyridin-4-yl | —C(O)CH$_2$(pyridin-4-yl) | —C(O)CH$_2$CH$_2$(pyridin-4-yl) |
| 37.33 | —C(O)furan-2-yl | —C(O)CH$_2$(furan-2-yl) | —C(O)CH$_2$CH$_2$(furan-2-yl) |
| 37.34 | —C(O)furan-3-yl | —C(O)CH$_2$(furan-3-yl) | —C(O)CH$_2$CH$_2$(furan-3-yl) |
| 37.35 | —C(O)thiophen-2-yl | —C(O)CH$_2$(thiophen-2-yl) | —C(O)CH$_2$CH$_2$(thiophen-2-yl) |
| 37.36 | —C(O)thiophen-2-yl | —C(O)CH$_2$(thiophen-2-yl) | —C(O)CH$_2$CH$_2$(thiophen-2-yl) |
| 37.37 | —C(O)imidazo-2-yl | —C(O)CH$_2$(imidazo-2-yl) | —C(O)CH$_2$CH$_2$(imidazo-2-yl) |
| 37.38 | —C(O)oxazo-2-yl | —C(O)CH$_2$(oxazo-2-yl) | —C(O)CH$_2$CH$_2$(oxazo-2-yl) |

TABLE 37-continued

Formula III: A = —B(OH)₂; X = —CN; R³ = table below; R¹¹ = CH₃

| | .1 | .2 | .3 |
|---|---|---|---|
| 37.39 | —C(O)thioazo-2-yl | —C(O)CH₂(thioazo-2-yl) | —C(O)CH₂CH₂(thioazo-2-yl) |
| 37.40 | —C(O)benzofuran-2-yl | —C(O)CH₂(benzofuran-2-yl) | —C(O)CH₂CH₂(benzofuran-2-yl) |
| 37.41 | —C(O)benzofuran-3-yl | —C(O)CH₂(benzofuran-3-yl) | —C(O)CH₂CH₂(benzofuran-3-yl) |
| 37.42 | —C(O)benzothiophen-2-yl | —C(O)CH₂(benzothiophen-2-yl) | —C(O)CH₂CH₂(benzothiophen-2-yl) |
| 37.43 | —C(O)thiophen-2-yl | —C(O)CH₂(thiophen-2-yl) | —C(O)CH₂CH₂(thiophen-2-yl) |
| 37.44 | —C(O)benzimidazo-2-yl | —C(O)CH₂(benzimidazo-2-yl) | —C(O)CH₂CH₂(benzimidazo-2-yl) |
| 37.45 | —C(O)benzoxazo-2-yl | —C(O)CH₂(benzoxazo-2-yl) | —C(O)CH₂CH₂(benzoxazo-2-yl) |
| 37.46 | —C(O)benzothiazo-2-yl | —C(O)CH₂(benzothiazo-2-yl) | —C(O)CH₂CH₂(benzothiazo-2-yl) |
| 37.47 | —C(O)o-Ph(P(O)Ph₃) | —C(O)m-Ph(P(O)Ph₃) | —C(O)p-Ph(P(O)Ph₃) |
| 37.48 | —C(O)Ph-2-(fluoren-9-yl) | —C(O)Ph-3-(fluoren-9-yl) | —C(O)Ph-4-(fluoren-9-yl) |
| 37.49 | —C(O)N-indolin-2-one | —C(O)indolin-2-yl | —C(O)indol-2-yl |
| 37.50 | —C(O)C(CH₃)₂NHSO₂(naphth-2-yl) | —C(O)cyclopentyl-2-(Ph) | —C(O)cyclohexyl-2-(Ph) |
| 37.51 | —C(O)pyrrolidin-3-yl-4(Ph) | —C(O)tetrahydrofuran-3-yl-4-(Ph) | —C(O)tetrahydrothiophen-3-yl-4-(Ph) |
| 37.52 | —C(O)tetrahydronaphth-1-yl | —C(O)tetrahydronaphth-2-yl | —C(O)cyclopropyl-2,2-(Ph₂) |
| 37.53 | —C(O)tetrahydroisoquinolin-1-yl | —C(O)tetrahydroisoquinolin-3-yl | —C(O)CH₂((2-oxo)indolin-3-yl) |
| 37.54 | —C(O)CH₂(N-benzimidazol-2-one) | —C(O)CH₂(N-benzoxazol-2-one) | —C(O)CH₂(N-benzothiazol-2-one) |
| 37.55 | —C(O)CH₂(N-dihydroimidazol-2-one) | —C(O)CH₂(N-dihydrooxazol-2-one) | —C(O)CH₂(N-dihydrothiazol-2-one) |

37.56

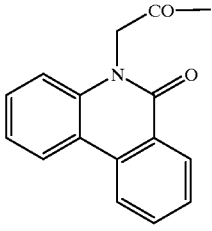

37.57

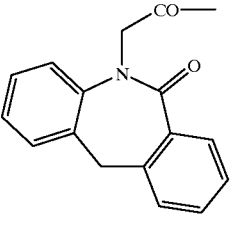

37.58

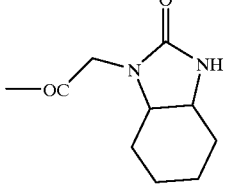

| | | | |
|---|---|---|---|
| 37.59 | —C(O)N(CH₃)CH₂Ph | —C(O)N(C₂H₅)CH₂Ph | —C(O)N(C₃H₇)CH₂Ph |
| 37.60 | —C(O)pyridin-3-yl-5-(Ph) | —C(O)Ph-3-(CH₂(thiophen-2-yl)) | —C(O)Ph-3-(CH₂Ph) |
| 37.61 | —C(O)C(CH₃)₂OPh | —C(O)CH(C₂H₅)OPh | —C(O)CH₂OCH₂Ph |
| 37.62 | —C(O)CH₂O(o-PhCH₂OH) | —C(O)CH₂O(m-PhCH₂OH) | —C(O)CH₂O(p-PhCH₂OH) |
| 37.63 | —C(O)CH₂O(o-PhCOOH) | —C(O)CH₂O(m-PhCOOH) | —C(O)CH₂O(p-PhCOOH) |
| 37.64 | —C(O)CH₂O(o-PhCOOCH₃) | —C(O)CH₂O(m-PhCOOCH₃) | —C(O)CH₂O(p-PhCOOCH₃) |

TABLE 37-continued

Formula III: A = —B(OH)$_2$; X = —CN; R$^3$ = table below; R$^{11}$ = CH$_3$

| | .1 | .2 | .3 |
|---|---|---|---|
| 37.65 | —C(O)CH$_2$O(o-PhCH$_2$COOH) | —C(O)CH$_2$O(m-PhCH$_2$COOH) | —C(O)CH$_2$O(p-PhCH$_2$COOH) |
| 37.66 | 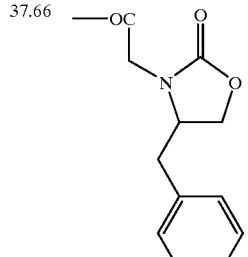 | | |

TABLE 38

Formula III: A = —B(OH)$_2$; X = —CN; R$^3$ = table below; R$^{11}$ = —CH$_2$CH$_2$Ph

| | .1 | .2 | .3 |
|---|---|---|---|
| 38.1 | —C(O)Ph | —C(O)CH$_2$Ph | —C(O)CH$_2$CH$_2$Ph |
| 38.2 | —C(O)CH$_2$OPh | —C(O)CH$_2$NHPh | —C(O)CH$_2$SPh |
| 38.3 | —C(O)o-PhOH | —C(O)m-PhOH | —C(O)p-PhOH |
| 38.4 | —C(O)o-PhCH$_2$OH | —C(O)m-PhCH$_2$OH | —C(O)p-PhCH$_2$OH |
| 38.5 | —C(O)o-PhCOOH | —C(O)m-PhCOOH | —C(O)p-PhCOOH |
| 38.6 | —C(O)o-PhCH$_2$COOH | —C(O)m-PhCH$_2$COOH | —C(O)p-PhCH$_2$COOH |
| 38.7 | —C(O)naphth-1-yl | —C(O)CH$_2$(naphth-1-yl) | —C(O)CH$_2$CH$_2$(napth-1-yl) |
| 38.8 | —C(O)naphth-2-yl | —C(O)CH$_2$(naphth-2-yl) | —C(O)CH$_2$CH$_2$(napth-2-yl) |
| 38.9 | —C(O)o-biphenyl | —C(O)CH$_2$(o-biphenyl) | —C(O)CH$_2$CH$_2$(o-biphenyl) |
| 38.10 | —C(O)m-biphenyl | —C(O)CH$_2$(m-biphenyl) | —C(O)CH$_2$CH$_2$(m-biphenyl) |
| 38.12 | —C(O)p-biphenyl | —C(O)CH$_2$(p-biphenyl) | —C(O)CH$_2$CH$_2$(p-biphenyl) |
| 38.13 | —C(O)o-PhOPh | —C(O)CH$_2$(o-PhOPh) | —C(O)CH$_2$CH$_2$(o-PhOPh) |
| 38.14 | —C(O)m-PhOPh | —C(O)CH$_2$(m-PhOPh) | —C(O)CH$_2$CH$_2$(m-PhOPh) |
| 38.15 | —C(O)p-PhOPh | —C(O)CH$_2$(p-PhOPh) | —C(O)CH$_2$CH$_2$(p-PhOPh) |
| 38.16 | —C(O)o-PhNHPh | —C(O)CH$_2$(o-PhNHPh) | —C(O)CH$_2$CH$_2$(o-PhNHPh) |
| 38.17 | —C(O)m-PhNHPh | —C(O)CH$_2$(m-PhNHPh) | —C(O)CH$_2$CH$_2$(m-PhNHPh) |
| 38.18 | —C(O)p-PhNHPh | —C(O)CH$_2$(p-PhNHPh) | —C(O)CH$_2$CH$_2$(p-PhNHPh) |
| 38.19 | —C(O)o-PhSPh | —C(O)CH$_2$(o-PhSPh) | —C(O)CH$_2$CH$_2$(o-PhSPh) |
| 38.20 | —C(O)m-PhSPh | —C(O)CH$_2$(m-PhSPh) | —C(O)CH$_2$CH$_2$(m-PhSPh) |
| 38.21 | —C(O)p-PhSPh | —C(O)CH$_2$(p-PhSPh) | —C(O)CH$_2$CH$_2$(p-PhSPh) |
| 38.22 | —C(O)o-PhCH$_2$SPh | —C(O)CH$_2$(o-PhCH$_2$SPh) | —C(O)CH$_2$CH$_2$(o-PhCH$_2$SPh) |
| 38.23 | —C(O)m-PhCH$_2$SPh | —C(O)CH$_2$(m-PhCH$_2$SPh) | —C(O)CH$_2$CH$_2$(m-PhCH$_2$SPh) |
| 38.24 | —C(O)p-PhCH$_2$SPh | —C(O)CH$_2$(p-PhCH$_2$SPh) | —C(O)CH$_2$CH$_2$(p-PhCH$_2$SPh) |
| 38.25 | —C(O)adamantyl | —C(O)CH$_2$(adamantyl) | —C(O)CH$_2$CH$_2$(adamantyl) |
| 38.26 | —C(O)cyclopentyl | —C(O)CH$_2$(cyclopentyl) | —C(O)CH$_2$CH$_2$((cyclopentyl) |
| 38.27 | —C(O)cyclohexyl | —C(O)CH$_2$(cyclohexyl) | —C(O)CH$_2$CH$_2$(cyclohexyl) |
| 38.28 | —C(O)CH$_2$O(cyclopentyl) | —C(O)CH$_2$NH(cyclopentyl) | —C(O)CH$_2$S(cyclopentyl) |
| 38.29 | —C(O)CH$_2$O(cyclohexyl) | —C(O)CH$_2$NH(cyclohexyl) | —C(O)CH$_2$S(cyclohexyl) |
| 38.30 | —C(O)pyridin-2-yl | —C(O)CH$_2$(pyridin-2-yl) | —C(O)CH$_2$CH$_2$(pyridin-2-yl) |
| 38.31 | —C(O)pyridin-3-yl | —C(O)CH$_2$(pyridin-3-yl) | —C(O)CH$_2$CH$_2$(pyridin-3-yl) |
| 38.32 | —C(O)pyridin-4-yl | —C(O)CH$_2$(pyridin-4-yl) | —C(O)CH$_2$CH$_2$(pyridin-4-yl) |
| 38.33 | —C(O)furan-2-yl | —C(O)CH$_2$(furan-2-yl) | —C(O)CH$_2$CH$_2$(furan-2-yl) |
| 38.34 | —C(O)furan-3-yl | —C(O)CH$_2$(furan-3-yl) | —C(O)CH$_2$CH$_2$(furan-3-yl) |
| 38.35 | —C(O)thiophen-2-yl | —C(O)CH$_2$(thiophen-2-yl) | —C(O)CH$_2$CH$_2$(thiophen-2-yl) |
| 38.36 | —C(O)thiophen-2-yl | —C(O)CH$_2$(thiophen-2-yl) | —C(O)CH$_2$CH$_2$(thiophen-2-yl) |
| 38.37 | —C(O)imidazo-2-yl | —C(O)CH$_2$(imidazo-2-yl) | —C(O)CH$_2$CH$_2$(imidazo-2-yl) |
| 38.38 | —C(O)oxazo-2-yl | —C(O)CH$_2$(oxazo-2-yl) | —C(O)CH$_2$CH$_2$(oxazo-2-yl) |
| 38.39 | —C(O)thioazo-2-yl | —C(O)CH$_2$(thioazo-2-yl) | —C(O)CH$_2$CH$_2$(thioazo-2-yl) |
| 38.40 | —C(O)benzofuran-2-yl | —C(O)CH$_2$(benzofuran-2-yl) | —C(O)CH$_2$CH$_2$(benzofuran-2-yl) |
| 38.41 | —C(O)benzofuran-3-yl | —C(O)CH$_2$(benzofuran-3-yl) | —C(O)CH$_2$CH$_2$(benzofuran-3-yl) |
| 38.42 | —C(O)benzothiophen-2-yl | —C(O)CH$_2$(benzothiophen-2-yl) | —C(O)CH$_2$CH$_2$(benzothiophen-2-yl) |
| 38.43 | —C(O)thiophen-2-yl | —C(O)CH$_2$(thiophen-2-yl) | —C(O)CH$_2$CH$_2$(thiophen-2-yl) |
| 38.44 | —C(O)benzimidazo-2-yl | —C(O)CH$_2$(benzimidazo-2-yl) | —C(O)CH$_2$CH$_2$(benzimidazo-2-yl) |
| 38.45 | —C(O)benzoxazo-2-yl | —C(O)CH$_2$(benzoxazo-2-yl) | —C(O)CH$_2$CH$_2$(benzoxazo-2-yl) |
| 38.46 | —C(O)benzothiazo-2-yl | —C(O)CH$_2$(benzothiazo-2-yl) | —C(O)CH$_2$CH$_2$(benzothiazo-2-yl) |
| 38.47 | —C(O)o-Ph(P(O)Ph$_3$) | —C(O)m-Ph(P(O)Ph$_3$) | —C(O)p-Ph(P(O)Ph$_3$) |
| 38.48 | —C(O)Ph-2-(fluoren-9-yl) | —C(O)Ph-3-(fluoren-9-yl) | —C(O)Ph-4-(fluoren-9-yl) |
| 38.49 | —C(O)N-indolin-2-one | —C(O)indolin-2-yl | —C(O)indol-2-yl |
| 38.50 | —C(O)C(CH$_3$)$_2$NHSO$_2$(naphth-2-yl) | —C(O)cyclopentyl-2-(Ph) | —C(O)cyclohexyl-2-(Ph) |
| 38.51 | —C(O)pyrrolidin-3-yl-4(Ph) | —C(O)tetrahydrofuran-3-yl-4-(Ph) | —C(O)tetrahydrothiophen-3-yl-4-(Ph) |

TABLE 38-continued

Formula III: A = —B(OH)$_2$; X = —CN; R$^3$ = table below; R$^{11}$ = —CH$_2$CH$_2$Ph

| .1 | .2 | .3 |
|---|---|---|
| 38.52 —C(O)tetrahydronaphth-1-yl | —C(O)tetrahydronaphth-2-yl | —C(O)cyclopropyl-2,2-(Ph$_2$) |
| 38.53 —C(O)tetrahydroisoquinolin-1-yl | —C(O)tetrahydroisoquinolin-3-yl | —C(O)CH$_2$((2-oxo)indolin-3-yl) |
| 38.54 —C(O)CH$_2$(N-benzimidazol-2-one) | —C(O)CH$_2$(N-benzoxazol-2-one) | —C(O)CH$_2$(N-benzothiazol-2-one) |
| 38.55 —C(O)CH$_2$(N-dihydroimidazol-2-one) | —C(O)CH$_2$(N-dihydrooxazol-2-one) | —C(O)CH$_2$(N-dihydrothiazol-2-one) |

38.56 [structures]

38.57 [structures]

38.58 [structures]

| 38.59 —C(O)N(CH$_3$)CH$_2$Ph | —C(O)N(C$_2$H$_5$)CH$_2$Ph | —C(O)N(C$_3$H$_7$)CH$_2$Ph |
|---|---|---|
| 38.60 —C(O)pyridin-3-yl-5-(Ph) | —C(O)Ph-3-(CH$_2$(thiophen-2-yl)) | —C(O)Ph-3-(CH$_2$Ph) |
| 38.61 —C(O)C(CH$_3$)$_2$OPh | —C(O)CH(C$_2$H$_5$)OPh | —C(O)CH$_2$OCH$_2$Ph |
| 38.62 —C(O)CH$_2$O(o-PhCH$_2$OH) | —C(O)CH$_2$O(m-PhCH$_2$OH) | —C(O)CH$_2$O(p-PhCH$_2$OH) |
| 38.63 —C(O)CH$_2$O(o-PhCOOH) | —C(O)CH$_2$O(m-PhCOOH) | —C(O)CH$_2$O(p-PhCOOH) |
| 38.64 —C(O)CH$_2$O(o-PhCOOCH$_3$) | —C(O)CH$_2$O(m-PhCOOCH$_3$) | —C(O)CH$_2$O(p-PhCOOCH$_3$) |
| 38.65 —C(O)CH$_2$O(o-PhCH$_2$COOH) | —C(O)CH$_2$O(m-PhCH$_2$COOH) | —C(O)CH$_2$O(p-PhCH$_2$COOH) |

38.66 [structure]

TABLE 39

Formula III: A = —B(OH)$_2$; X = —CH$_2$NH$_2$; R$^3$ = table below; R$^{11}$ = CH$_3$

| | .1 | .2 | .3 |
|---|---|---|---|
| 39.1 | —C(O)Ph | —C(O)CH$_2$Ph | —C(O)CH$_2$CH$_2$Ph |
| 39.2 | —C(O)CH$_2$OPh | —C(O)CH$_2$NHPh | —C(O)CH$_2$SPh |
| 39.3 | —C(O)o-PhOH | —C(O)m-PhOH | —C(O)p-PhOH |
| 39.4 | —C(O)o-PhCH$_2$OH | —C(O)m-PhCH$_2$OH | —C(O)p-PhCH$_2$OH |
| 39.5 | —C(O)o-PhCOOH | —C(O)m-PhCOOH | —C(O)p-PhCOOH |
| 39.6 | —C(O)o-PhCH$_2$COOH | —C(O)m-PhCH$_2$COOH | —C(O)p-PhCH$_2$COOH |
| 39.7 | —C(O)naphth-1-yl | —C(O)CH$_2$(naphth-1-yl) | —C(O)CH$_2$CH$_2$(napth-1-yl) |
| 39.8 | —C(O)naphth-2-yl | —C(O)CH$_2$(naphth-2-yl) | —C(O)CH$_2$CH$_2$(napth-2-yl) |
| 39.9 | —C(O)o-biphenyl | —C(O)CH$_2$(o-biphenyl) | —C(O)CH$_2$CH$_2$(o-biphenyl) |
| 39.10 | —C(O)m-biphenyl | —C(O)CH$_2$(m-biphenyl) | —C(O)CH$_2$CH$_2$(m-biphenyl) |
| 39.12 | —C(O)p-biphenyl | —C(O)CH$_2$(p-biphenyl) | —C(O)CH$_2$CH$_2$(p-biphenyl) |
| 39.13 | —C(O)o-PhOPh | —C(O)CH$_2$(o-PhOPh) | —C(O)CH$_2$CH$_2$(o-PhOPh) |
| 39.14 | —C(O)m-PhOPh | —C(O)CH$_2$(m-PhOPh) | —C(O)CH$_2$CH$_2$(m-PhOPh) |
| 39.15 | —C(O)p-PhOPh | —C(O)CH$_2$(p-PhOPh) | —C(O)CH$_2$CH$_2$(p-PhOPh) |
| 39.16 | —C(O)o-PhNHPh | —C(O)CH$_2$(o-PhNHPh) | —C(O)CH$_2$CH$_2$(o-PhNHPh) |
| 39.17 | —C(O)m-PhNHPh | —C(O)CH$_2$(m-PhNHPh) | —C(O)CH$_2$CH$_2$(m-PhNHPh) |
| 39.18 | —C(O)p-PhNHPh | —C(O)CH$_2$(p-PhNHPh) | —C(O)CH$_2$CH$_2$(p-PhNHPh) |
| 39.19 | —C(O)o-PhSPh | —C(O)CH$_2$(o-PhSPh) | —C(O)CH$_2$CH$_2$(o-PhSPh) |
| 39.20 | —C(O)m-PhSPh | —C(O)CH$_2$(m-PhSPh) | —C(O)CH$_2$CH$_2$(m-PhSPh) |
| 39.21 | —C(O)p-PhSPh | —C(O)CH$_2$(p-PhSPh) | —C(O)CH$_2$CH$_2$(p-PhSPh) |
| 39.22 | —C(O)o-PhCH$_2$SPh | —C(O)CH$_2$(o-PhCH$_2$SPh) | —C(O)CH$_2$CH$_2$(o-PhCH$_2$SPh) |
| 39.23 | —C(O)m-PhCH$_2$SPh | —C(O)CH$_2$(m-PhCH$_2$SPh) | —C(O)CH$_2$CH$_2$(m-PhCH$_2$SPh) |
| 39.24 | —C(O)p-PhCH$_2$SPh | —C(O)CH$_2$(p-PhCH$_2$SPh) | —C(O)CH$_2$CH$_2$(p-PhCH$_2$SPh) |
| 39.25 | —C(O)adamantyl | —C(O)CH$_2$(adamantyl) | —C(O)CH$_2$CH$_2$(adamantyl) |
| 39.26 | —C(O)cyclopentyl | —C(O)CH$_2$(cyclopentyl) | —C(O)CH$_2$CH$_2$((cyclopentyl) |
| 39.27 | —C(O)cyclohexyl | —C(O)CH$_2$(cyclohexyl) | —C(O)CH$_2$CH$_2$(cyclohexyl) |
| 39.28 | —C(O)CH$_2$O(cyclopentyl) | —C(O)CH$_2$NH(cyclopentyl) | —C(O)CH$_2$S(cyclopentyl) |
| 39.29 | —C(O)CH$_2$O(cyclohexyl) | —C(O)CH$_2$NH(cyclohexyl) | —C(O)CH$_2$S(cyclohexyl) |
| 39.30 | —C(O)pyridin-2-yl | —C(O)CH$_2$(pyridin-2-yl) | —C(O)CH$_2$CH$_2$(pyridin-2-yl) |
| 39.31 | —C(O)pyridin-3-yl | —C(O)CH$_2$(pyridin-3-yl) | —C(O)CH$_2$CH$_2$(pyridin-3-yl) |
| 39.32 | —C(O)pyridin-4-yl | —C(O)CH$_2$(pyridin-4-yl) | —C(O)CH$_2$CH$_2$(pyridin-4-yl) |
| 39.33 | —C(O)furan-2-yl | —C(O)CH$_2$(furan-2-yl) | —C(O)CH$_2$CH$_2$(furan-2-yl) |
| 39.34 | —C(O)furan-3-yl | —C(O)CH$_2$(furan-3-yl) | —C(O)CH$_2$CH$_2$(furan-3-yl) |
| 39.35 | —C(O)thiophen-2-yl | —C(O)CH$_2$(thiophen-2-yl) | —C(O)CH$_2$CH$_2$(thiophen-2-yl) |
| 39.36 | —C(O)thiophen-2-yl | —C(O)CH$_2$(thiophen-2-yl) | —C(O)CH$_2$CH$_2$(thiophen-2-yl) |
| 39.37 | —C(O)imidazo-2-yl | —C(O)CH$_2$(imidazo-2-yl) | —C(O)CH$_2$CH$_2$(imidazo-2-yl) |
| 39.38 | —C(O)oxazo-2-yl | —C(O)CH$_2$(oxazo-2-yl) | —C(O)CH$_2$CH$_2$(oxazo-2-yl) |
| 39.39 | —C(O)thioazo-2-yl | —C(O)CH$_2$(thioazo-2-yl) | —C(O)CH$_2$CH$_2$(thioazo-2-yl) |
| 39.40 | —C(O)benzofuran-2-yl | —C(O)CH$_2$(benzofuran-2-yl) | —C(O)CH$_2$CH$_2$(benzofuran-2-yl) |
| 39.41 | —C(O)benzofuran-3-yl | —C(O)CH$_2$(benzofuran-3-yl) | —C(O)CH$_2$CH$_2$(benzofuran-3-yl) |
| 39.42 | —C(O)benzothiophen-2-yl | —C(O)CH$_2$(benzothiophen-2-yl) | —C(O)CH$_2$CH$_2$(benzothiophen-2-yl) |
| 39.43 | —C(O)thiophen-2-yl | —C(O)CH$_2$(thiophen-2-yl) | —C(O)CH$_2$CH$_2$(thiophen-2-yl) |
| 39.44 | —C(O)benzimidazo-2-yl | —C(O)CH$_2$(benzimidazo-2-yl) | —C(O)CH$_2$CH$_2$(benzimidazo-2-yl) |
| 39.45 | —C(O)benzoxazo-2-yl | —C(O)CH$_2$(benzoxazo-2-yl) | —C(O)CH$_2$CH$_2$(benzoxazo-2-yl) |
| 39.46 | —C(O)benzothiazo-2-yl | —C(O)CH$_2$(benzothiazo-2-yl) | —C(O)CH$_2$CH$_2$(benzothiazo-2-yl) |
| 39.47 | —C(O)o-Ph(P(O)Ph$_3$) | —C(O)m-Ph(P(O)Ph$_3$) | —C(O)p-Ph(P(O)Ph$_3$) |
| 39.48 | —C(O)Ph-2-(fluoren-9-yl) | —C(O)Ph-3-(fluoren-9-yl) | —C(O)Ph-4-(fluoren-9-yl) |
| 39.49 | —C(O)N-indolin-2-one | —C(O)indolin-2-yl | —C(O)indol-2-yl |
| 39.50 | —C(O)C(CH$_3$)$_2$NHSO$_2$(naphth-2-yl) | —C(O)cyclopentyl-2-(Ph) | —C(O)cyclohexyl-2-(Ph) |
| 39.51 | —C(O)pyrrolidin-3-yl-4(Ph) | —C(O)tetrahydrofuran-3-yl-4-(Ph) | —C(O)tetrahydrothiophen-3-yl-4-(Ph) |
| 39.52 | —C(O)tetrahydronaphth-1-yl | —C(O)tetrahydronaphth-2-yl | —C(O)cyclopropyl-2,2-(Ph$_2$) |
| 39.53 | —C(O)tetrahydroisoquinolin-1-yl | —C(O)tetrahydroisoquinolin-3-yl | —C(O)CH$_2$((2-oxo)indolin-3-yl) |
| 39.54 | —C(O)CH$_2$(N-benzimidazol-2-one) | —C(O)CH$_2$(N-benzoxazol-2-one) | —C(O)CH$_2$(N-benzothiazol-2-one) |
| 39.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 39.56 | 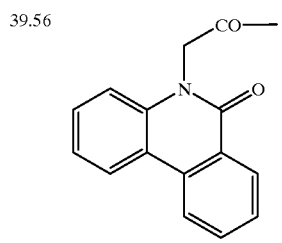 | 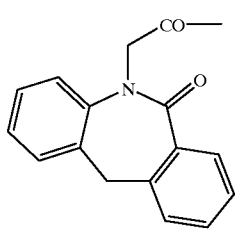 | 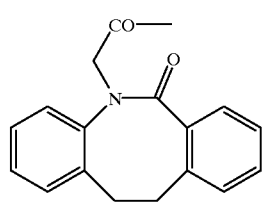 |

TABLE 39-continued

Formula III: A = —B(OH)$_2$; X = —CH$_2$NH$_2$; R$^3$ = table below; R$^{11}$ = CH$_3$

| | .1 | .2 | .3 |
|---|---|---|---|

39.57, 39.58, 39.66: (structures)

| | .1 | .2 | .3 |
|---|---|---|---|
| 39.59 | —C(O)N(CH$_3$)CH$_2$Ph | —C(O)N(C$_2$H$_5$)CH$_2$Ph | —C(O)N(C$_3$H$_7$)CH$_2$Ph |
| 39.60 | —C(O)pyridin-3-yl-5-(Ph) | —C(O)Ph-3-(CH$_2$(thiophen-2-yl)) | —C(O)Ph-3-(CH$_2$Ph) |
| 39.61 | —C(O)C(CH$_3$)$_2$OPh | —C(O)CH(C$_2$H$_5$)OPh | —C(O)CH$_2$OCH$_2$Ph |
| 39.62 | —C(O)CH$_2$O(o-PhCH$_2$OH) | —C(O)CH$_2$O(m-PhCH$_2$OH) | —C(O)CH$_2$O(p-PhCH$_2$OH) |
| 39.63 | —C(O)CH$_2$O(o-PhCOOH) | —C(O)CH$_2$O(m-PhCOOH) | —C(O)CH$_2$O(p-PhCOOH) |
| 39.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 39.65 | —C(O)CH$_2$O(o-PhCH$_2$COOH) | —C(O)CH$_2$O(m-PhCH$_2$COOH) | —C(O)CH$_2$O(p-PhCH$_2$COOH) |

TABLE 40

Formula III: A = —B(OH)$_2$; X = CH$_2$NH$_2$; R$^3$ = table below; R$^{11}$ = —CH$_2$CH$_2$Ph

| | .1 | .2 | .3 |
|---|---|---|---|
| 40.1 | —C(O)Ph | —C(O)CH$_2$Ph | —C(O)CH$_2$CH$_2$Ph |
| 40.2 | —C(O)CH$_2$OPh | —C(O)CH$_2$NHPh | —C(O)CH$_2$SPh |
| 40.3 | —C(O)o-PhOH | —C(O)m-PhOH | —C(O)p-PhOH |
| 40.4 | —C(O)o-PhCH$_2$OH | —C(O)m-PhCH$_2$OH | —C(O)p-PhCH$_2$OH |
| 40.5 | —C(O)o-PhCOOH | —C(O)m-PhCOOH | —C(O)p-PhCOOH |
| 40.6 | —C(O)o-PhCH$_2$COOH | —C(O)m-PhCH$_2$COOH | —C(O)p-PhCH$_2$COOH |
| 40.7 | —C(O)naphth-1-yl | —C(O)CH$_2$(naphth-1-yl) | —C(O)CH$_2$CH$_2$(napth-1-yl) |
| 40.8 | —C(O)naphth-2-yl | —C(O)CH$_2$(naphth-2-yl) | —C(O)CH$_2$CH$_2$(napth-2-yl) |
| 40.9 | —C(O)o-biphenyl | —C(O)CH$_2$(o-biphenyl) | —C(O)CH$_2$CH$_2$(o-biphenyl) |
| 40.10 | —C(O)m-biphenyl | —C(O)CH$_2$(m-biphenyl) | —C(O)CH$_2$CH$_2$(m-biphenyl) |
| 40.12 | —C(O)p-biphenyl | —C(O)CH$_2$(p-biphenyl) | —C(O)CH$_2$CH$_2$(p-biphenyl) |
| 40.13 | —C(O)o-PhOPh | —C(O)CH$_2$(o-PhOPh) | —C(O)CH$_2$CH$_2$(o-PhOPh) |
| 40.14 | —C(O)m-PhOPh | —C(O)CH$_2$(m-PhOPh) | —C(O)CH$_2$CH$_2$(m-PhOPh) |
| 40.15 | —C(O)p-PhOPh | —C(O)CH$_2$(p-PhOPh) | —C(O)CH$_2$CH$_2$(p-PhOPh) |
| 40.16 | —C(O)o-PhNHPh | —C(O)CH$_2$(o-PhNHPh) | —C(O)CH$_2$CH$_2$(o-PhNHPh) |
| 40.17 | —C(O)m-PhNHPh | —C(O)CH$_2$(m-PhNHPh) | —C(O)CH$_2$CH$_2$(m-PhNHPh) |
| 40.18 | —C(O)p-PhNHPh | —C(O)CH$_2$(p-PhNHPh) | —C(O)CH$_2$CH$_2$(p-PhNHPh) |
| 40.19 | —C(O)o-PhSPh | —C(O)CH$_2$(o-PhSPh) | —C(O)CH$_2$CH$_2$(o-PhSPh) |

TABLE 40-continued

Formula III: A = —B(OH)$_2$; X = CH$_2$NH$_2$; R$^3$ = table below; R$^{11}$ = —CH$_2$CH$_2$Ph

| | .1 | .2 | .3 |
|---|---|---|---|
| 40.20 | —C(O)m-PhSPh | —C(O)CH$_2$(m-PhSPh) | —C(O)CH$_2$CH$_2$(m-PhSPh) |
| 40.21 | —C(O)p-PhSPh | —C(O)CH$_2$(p-PhSPh) | —C(O)CH$_2$CH$_2$(p-PhSPh) |
| 40.22 | —C(O)o-PhCH$_2$SPh | —C(O)CH$_2$(o-PhCH$_2$SPh) | —C(O)CH$_2$CH$_2$(o-PhCH$_2$SPh) |
| 40.23 | —C(O)m-PhCH$_2$SPh | —C(O)CH$_2$(m-PhCH$_2$SPh) | —C(O)CH$_2$CH$_2$(m-PhCH$_2$SPh) |
| 40.24 | —C(O)p-PhCH$_2$SPh | —C(O)CH$_2$(p-PhCH$_2$SPh) | —C(O)CH$_2$CH$_2$(p-PhCH$_2$SPh) |
| 40.25 | —C(O)adamantyl | —C(O)CH$_2$(adamantyl) | —C(O)CH$_2$CH$_2$(adamantyl) |
| 40.26 | —C(O)cyclopentyl | —C(O)CH$_2$(cyclopentyl) | —C(O)CH$_2$CH$_2$((cyclopentyl) |
| 40.27 | —C(O)cyclohexyl | —C(O)CH$_2$(cyclohexyl) | —C(O)CH$_2$CH$_2$(cyclohexyl) |
| 40.28 | —C(O)CH$_2$O(cyclopentyl) | —C(O)CH$_2$NH(cyclopentyl) | —C(O)CH$_2$S(cyclopentyl) |
| 40.29 | —C(O)CH$_2$O(cyclohexyl) | —C(O)CH$_2$NH(cyclohexyl) | —C(O)CH$_2$S(cyclohexyl) |
| 40.30 | —C(O)pyridin-2-yl | —C(O)CH$_2$(pyridin-2-yl) | —C(O)CH$_2$CH$_2$(pyridin-2-yl) |
| 40.31 | —C(O)pyridin-3-yl | —C(O)CH$_2$(pyridin-3-yl) | —C(O)CH$_2$CH$_2$(pyridin-3-yl) |
| 40.32 | —C(O)pyridin-4-yl | —C(O)CH$_2$(pyridin-4-yl) | —C(O)CH$_2$CH$_2$(pyridin-4-yl) |
| 40.33 | —C(O)furan-2-yl | —C(O)CH$_2$(furan-2-yl) | —C(O)CH$_2$CH$_2$(furan-2-yl) |
| 40.34 | —C(O)furan-3-yl | —C(O)CH$_2$(furan-3-yl) | —C(O)CH$_2$CH$_2$(furan-3-yl) |
| 40.35 | —C(O)thiophen-2-yl | —C(O)CH$_2$(thiophen-2-yl) | —C(O)CH$_2$CH$_2$(thiophen-2-yl) |
| 40.36 | —C(O)thiophen-2-yl | —C(O)CH$_2$(thiophen-2-yl) | —C(O)CH$_2$CH$_2$(thiophen-2-yl) |
| 40.37 | —C(O)imidazo-2-yl | —C(O)CH$_2$(imidazo-2-yl) | —C(O)CH$_2$CH$_2$(imidazo-2-yl) |
| 40.38 | —C(O)oxazo-2-yl | —C(O)CH$_2$(oxazo-2-yl) | —C(O)CH$_2$CH$_2$(oxazo-2-yl) |
| 40.39 | —C(O)thioazo-2-yl | —C(O)CH$_2$(thioazo-2-yl) | —C(O)CH$_2$CH$_2$(thioazo-2-yl) |
| 40.40 | —C(O)benzofuran-2-yl | —C(O)CH$_2$(benzofuran-2-yl) | —C(O)CH$_2$CH$_2$(benzofuran-2-yl) |
| 40.41 | —C(O)benzofuran-3-yl | —C(O)CH$_2$(benzofuran-3-yl) | —C(O)CH$_2$CH$_2$(benzofuran-3-yl) |
| 40.42 | —C(O)benzothiophen-2-yl | —C(O)CH$_2$(benzothiophen-2-yl) | —C(O)CH$_2$CH$_2$(benzothiophen-2-yl) |
| 40.43 | —C(O)thiophen-2-yl | —C(O)CH$_2$(thiophen-2-yl) | —C(O)CH$_2$CH$_2$(thiophen-2-yl) |
| 40.44 | —C(O)benzimidazo-2-yl | —C(O)CH$_2$(benzimidazo-2-yl) | —C(O)CH$_2$CH$_2$(benzimidazo-2-yl) |
| 40.45 | —C(O)benzoxazo-2-yl | —C(O)CH$_2$(benzoxazo-2-yl) | —C(O)CH$_2$CH$_2$(benzoxazo-2-yl) |
| 40.46 | —C(O)benzothiazo-2-yl | —C(O)CH$_2$(benzothiazo-2-yl) | —C(O)CH$_2$CH$_2$(benzothiazo-2-yl) |
| 40.47 | —C(O)o-Ph(P(O)Ph$_3$) | —C(O)m-Ph(P(O)Ph$_3$) | —C(O)p-Ph(P(O)Ph$_3$) |
| 40.48 | —C(O)Ph-2-(fluoren-9-yl) | —C(O)Ph-3-(fluoren-9-yl) | —C(O)Ph-4-(fluoren-9-yl) |
| 40.49 | —C(O)N-indolin-2-one | —C(O)indolin-2-yl | —C(O)indol-2-yl |
| 40.50 | —C(O)C(CH$_3$)$_2$NHSO$_2$(naphth-2-yl) | —C(O)cyclopentyl-2-(Ph) | —C(O)cyclohexyl-2-(Ph) |
| 40.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 40.52 | —C(O)tetrahydronaphth-1-yl | —C(O)tetrahydronaphth-2-yl | —C(O)cyclopropyl-2,2-(Ph$_2$) |
| 40.53 | —C(O)tetrahydroisoquinolin-1-yl | —C(O)tetrahydroisoquinolin-3-yl | —C(O)CH$_2$((2-oxo)indolin-3-yl) |
| 40.54 | —C(O)CH$_2$(N-benzimidazol-2-one) | —C(O)CH$_2$(N-benzoxazol-2-one) | —C(O)CH$_2$(N-benzothiazol-2-one) |
| 40.55 | —C(O)CH$_2$(N-dihydroimidazol-2-one) | —C(O)CH$_2$(N-dihydrooxazol-2-one) | —C(O)CH$_2$(N-dihydrothiazol-2-one) |

40.56

40.57

40.58

TABLE 40-continued

Formula III: A = —B(OH)₂; X = CH₂NH₂; R³ = table below; R¹¹ = —CH₂CH₂Ph

| .1 | .2 | .3 |
|---|---|---|
| 40.59 —C(O)N(CH)CH₂Ph | —C(O)N(C₂H₅)CH₂Ph | —C(O)N(C₃H₇)CH₂Ph |
| 40.60 —C(O)pyridin-3-yl-5-(Ph) | —C(O)Ph-3-(CH₂(thiophen-2-yl)) | —C(O)Ph-3-(CH₂Ph) |
| 40.61 —C(O)C(CH₃)₂OPh | —C(O)CH(C₂H₅)OPh | —C(O)CH₂OCH₂Ph |
| 40.62 —C(O)CH₂O(o-PhCH₂OH) | —C(O)CH₂O(m-PhCH₂OH) | —C(O)CH₂O(p-PhCH₂OH) |
| 40.63 —C(O)CH₂O(o-PhCOOH) | —C(O)CH₂O(m-PhCOOH) | —C(O)CH₂O(p-PhCOOH) |
| 40.64 —C(O)CH₂O(o-PhCOOCH₃) | —C(O)CH₂O(m-PhCOOCH₃) | —C(O)CH₂O(p-PhCOOCH₃) |
| 40.65 —C(O)CH₂O(o-PhCH₂COOH) | —C(O)CH₂O(m-PhCH₂COOH) | —C(O)CH₂O(p-PhCH₂COOH) |

40.66

[structure: —OC(O)CH₂-N of a 4-benzyl-oxazolidin-2-one]

TABLE 41

Formula III: A = —B(pinanediol); X = —CN; R³ = table below; R¹¹ = CH₃

| | .1 | .2 | .3 |
|---|---|---|---|
| 41.1 | —C(O)Ph | —C(O)CH₂Ph | —C(O)CH₂CH₂Ph |
| 41.2 | —C(O)CH₂OPh | —C(O)CH₂NHPh | —C(O)CH₂SPh |
| 41.3 | —C(O)o-PhOH | —C(O)m-PhOH | —C(O)p-PhOH |
| 41.4 | —C(O)o-PhCH₂OH | —C(O)m-PhCH₂OH | —C(O)p-PhCH₂OH |
| 41.5 | —C(O)o-PhCOOH | —C(O)m-PhCOOH | —C(O)p-PhCOOH |
| 41.6 | —C(O)o-PhCH₂COOH | —C(O)m-PhCH₂COOH | —C(O)p-PhCH₂COOH |
| 41.7 | —C(O)naphth-1-yl | —C(O)CH₂(naphth-1-yl) | —C(O)CH₂CH₂(napth-1-yl) |
| 41.8 | —C(O)naphth-2-yl | —C(O)CH₂(naphth-2-yl | —C(O)CH₂CH₂(napth-2-yl) |
| 41.9 | —C(O)o-biphenyl | —C(O)CH₂(o-biphenyl) | —C(O)CH₂CH₂(o-biphenyl) |
| 41.10 | —C(O)m-biphenyl | —C(O)CH₂(m-biphenyl) | —C(O)CH₂CH₂(m-biphenyl) |
| 41.12 | —C(O)p-biphenyl | —C(O)CH₂(p-biphenyl) | —C(O)CH₂CH₂(p-biphenyl) |
| 41.13 | —C(O)o-PhOPh | —C(O)CH₂(o-PhOPh) | —C(O)CH₂CH₂(o-PhOPh) |
| 41.14 | —C(O)m-PhOPh | —C(O)CH₂(m-PhOPh) | —C(O)CH₂CH₂(m-PhOPh) |
| 41.15 | —C(O)p-PhOPh | —C(O)CH₂(p-PhOPh) | —C(O)CH₂CH₂(p-PhOPh) |
| 41.16 | —C(O)o-PhNHPh | —C(O)CH₂(o-PhNHPh) | —C(O)CH₂CH₂(o-PhNHPh) |
| 41.17 | —C(O)m-PhNHPh | —C(O)CH₂(m-PhNHPh) | —C(O)CH₂CH₂(m-PhNHPh) |
| 41.18 | —C(O)p-PhNHPh | —C(O)CH₂(p-PhNHPh) | —C(O)CH₂CH₂(p-PhNHPh) |
| 41.19 | —C(O)o-PhSPh | —C(O)CH₂(o-PhSPh) | —C(O)CH₂CH₂(o-PhSPh) |
| 41.20 | —C(O)m-PhSPh | —C(O)CH₂(m-PhSPh) | —C(O)CH₂CH₂(m-PhSPh) |
| 41.21 | —C(O)p-PhSPh | —C(O)CH₂(p-PhSPh) | —C(O)CH₂CH₂(p-PhSPh) |
| 41.22 | —C(O)o-PhCH₂SPh | —C(O)CH₂(o-PhCH₂SPh) | —C(O)CH₂CH₂(o-PhCH₂SPh) |
| 41.23 | —C(O)m-PhCH₂SPh | —C(O)CH₂(m-PhCH₂SPh) | —C(O)CH₂CH₂(m-PhCH₂SPh) |
| 41.24 | —C(O)p-PhCH₂SPh | —C(O)CH₂(p-PhCH₂SPh) | —C(O)CH₂CH₂(p-PhCH₂SPh) |
| 41.25 | —C(O)adamantyl | —C(O)CH₂(adamantyl) | —C(O)CH₂CH₂(adamantyl) |
| 41.26 | —C(O)cyclopentyl | —C(O)CH₂(cyclopentyl) | —C(O)CH₂CH₂((cyclopentyl) |
| 41.27 | —C(O)cyclohexyl | —C(O)CH₂(cyclohexyl) | —C(O)CH₂CH₂(cyclohexyl) |
| 41.28 | —C(O)CH₂O(cyclopentyl) | —C(O)CH₂NH(cyclopentyl) | —C(O)CH₂S(cyclopentyl) |
| 41.29 | —C(O)CH₂O(cyclohexyl) | —C(O)CH₂NH(cyclohexyl) | —C(O)CH₂S(cyclohexyl) |
| 41.30 | —C(O)pyridin-2-yl | —C(O)CH₂(pyridin-2-yl) | —C(O)CH₂CH₂(pyridin-2-yl) |
| 41.31 | —C(O)pyridin-3-yl | —C(O)CH₂(pyridin-3-yl) | —C(O)CH₂CH₂(pyridin-3-yl) |
| 41.32 | —C(O)pyridin-4-yl | —C(O)CH₂(pyridin-4-yl) | —C(O)CH₂CH₂(pyridin-4-yl) |
| 41.33 | —C(O)furan-2-yl | —C(O)CH₂(furan-2-yl) | —C(O)CH₂CH₂(furan-2-yl) |
| 41.34 | —C(O)furan-3-yl | —C(O)CH₂(furan-3-yl) | —C(O)CH₂CH₂(furan-3-yl) |
| 41.35 | —C(O)thiophen-2-yl | —C(O)CH₂(thiophen-2-yl) | —C(O)CH₂CH₂(thiophen-2-yl) |
| 41.36 | —C(O)thiophen-2-yl | —C(O)CH₂(thiophen-2-yl) | —C(O)CH₂CH₂(thiophen-2-yl) |
| 41.37 | —C(O)imidazo-2-yl | —C(O)CH₂(imidazo-2-yl) | —C(O)CH₂CH₂(imidazo-2-yl) |
| 41.38 | —C(O)oxazo-2-yl | —C(O)CH₂(oxazo-2-yl) | —C(O)CH₂CH₂(oxazo-2-yl) |
| 41.39 | —C(O)thioazo-2-yl | —C(O)CH₂(thioazo-2-yl) | —C(O)CH₂CH₂(thioazo-2-yl) |
| 41.40 | —C(O)benzofuran-2-yl | —C(O)CH₂(benzofuran-2-yl) | —C(O)CH₂CH₂(benzofuran-2-yl) |
| 41.41 | —C(O)benzofuran-3-yl | —C(O)CH₂(benzofuran-3-yl) | —C(O)CH₂CH₂(benzofuran-3-yl) |
| 41.42 | —C(O)benzothiophen-2-yl | —C(O)CH₂(benzothiophen-2-yl) | —C(O)CH₂CH₂(benzothiophen-2-yl) |
| 41.43 | —C(O)thiophen-2-yl | —C(O)CH₂(thiophen-2-yl) | —C(O)CH₂CH₂(thiophen-2-yl) |
| 41.44 | —C(O)benzimidazo-2-yl | —C(O)CH₂(benzimidazo-2-yl) | —C(O)CH₂CH₂(benzimidazo-2-yl) |
| 41.45 | —C(O)benzoxazo-2-yl | —C(O)CH₂(benzoxazo-2-yl) | —C(O)CH₂CH₂(benzoxazo-2-yl) |

TABLE 41-continued

Formula III: A = —B(pinanediol); X = —CN; R³ = table below; R¹¹ = CH₃

| .1 | .2 | .3 |
|---|---|---|
| 41.46 —C(O)benzothiazo-2-yl | —C(O)CH₂(benzothiazo-2-yl) | —C(O)CH₂CH₂(benzothiazo-2-yl) |
| 41.47 —C(O)o-Ph(P(O)Ph₃) | —C(O)m-Ph(P(O)Ph₃) | —C(O)p-Ph(P(O)Ph₃) |
| 41.48 —C(O)Ph-2-(fluoren-9-yl) | —C(O)Ph-3-(fluoren-9-yl) | —C(O)Ph-4-(fluoren-9-yl) |
| 41.49 —C(O)N-indolin-2-one | —C(O)indolin-2-yl | —C(O)indol-2-yl |
| 41.50 —C(O)C(CH₃)₂NHSO₂(naphth-2-yl) | —C(O)cyclopentyl-2-(Ph) | —C(O)cyclohexyl-2-(Ph) |
| 41.51 —C(O)pyrrolidin-3-yl-4-(Ph) | —C(O)tetrahydrofuran-3-yl-4-(Ph) | —C(o)tetrahydrothiophen-3-yl-4-(Ph) |
| 41.52 —C(O)tetrahydronaphth-1-yl | —C(O)tetrahydronaphth-2-yl | —C(O)cyclopropyl-2,2-(Ph₂) |
| 41.53 —C(O)tetrahydroisoquinolin-1-yl | —C(O)tetrahydroisoquinolin-3-yl | —C(O)CH₂((2-oxo)indolin-3-yl) |
| 41.54 —C(O)CH₂(N-benzimidazol-2-one) | —C(O)CH₂(N-benzoxazol-2-one) | —C(O)CH₂(N-benzothiazol-2-one) |
| 41.55 —C(O)CH₂(N-dihydroimidazol-2-one) | —C(O)CH₂(N-dihydrooxazol-2-one) | —C(O)CH₂(N-dihydrothiazol-2-one) |

41.56

41.57

41.58

| 41.59 —C(O)N(CH₃)CH₂Ph | —C(O)N(C₂H₅)CH₂Ph | —C(O)N(C₃H₇)CH₂Ph |
| 41.60 —C(O)pyridin-3-yl-5-(Ph) | —C(O)Ph-3-(CH₂(thiophen-2-yl)) | —C(O)Ph-3-(CH₂Ph) |
| 41.61 —C(O)CH(CH₃)₂OPh | —C(O)CH(C₂H₅)OPh | —C(O)CH₂OCH₂Ph |
| 41.62 —C(O)CH₂O(o-PhCH₂OH) | —C(O)CH₂O(m-PhCH₂OH) | —C(O)CH₂O(p-PhCH₂OH) |
| 41.63 —C(O)CH₂O(o-PhCOOH) | —C(O)CH₂O(m-PhCOOH) | —C(O)CH₂O(p-PhCOOH) |
| 41.64 —C(O)CH₂O(o-PhCOOCH₃) | —C(O)CH₂O(m-PhCOOCH₃) | —C(O)CH₂O(p-PhCOOCH₃) |
| 41.65 —C(O)CH₂O(o-PhCH₂COOH) | —C(O)CH₂O(m-PhCH₂COOH) | —C(O)CH₂O(p-PhCH₂COOH) |

41.66

TABLE 42

Formula III: A = —B(pinanediol); X = —CN; $R^3$ = table below; $R^{11}$ = —CH$_2$CH$_2$Ph

| | .1 | .2 | .3 |
|---|---|---|---|
| 42.1 | —C(O)Ph | —C(O)CH$_2$Ph | —C(O)CH$_2$CH$_2$Ph |
| 42.2 | —C(O)CH$_2$OPh | —C(O)CH$_2$NHPh | —C(O)CH$_2$SPh |
| 42.3 | —C(O)o-PhOH | —C(O)m-PhOH | —C(O)p-PhOH |
| 42.4 | —C(O)o-PhCH$_2$OH | —C(O)m-PhCH$_2$OH | —C(O)p-PhCH$_2$OH |
| 42.5 | —C(O)o-PhCOOH | —C(O)m-PhCOOH | —C(O)p-PhCOOH |
| 42.6 | —C(O)o-PhCH$_2$COOH | —C(O)m-PhCH$_2$COOH | —C(O)p-PhCH$_2$COOH |
| 42.7 | —C(O)naphth-1-yl | —C(O)CH$_2$(naphth-1-yl) | —C(O)CH$_2$CH$_2$(napth-1-yl) |
| 42.8 | —C(O)naphth-2-yl | —C(O)CH$_2$(naphth-2-yl) | —C(O)CH$_2$CH$_2$(napth-2-yl) |
| 42.9 | —C(O)o-biphenyl | —C(O)CH$_2$(o-biphenyl) | —C(O)CH$_2$CH$_2$(o-biphenyl) |
| 42.10 | —C(O)m-biphenyl | —C(O)CH$_2$(m-biphenyl) | —C(O)CH$_2$CH$_2$(m-biphenyl) |
| 42.12 | —C(O)p-biphenyl | —C(O)CH$_2$(p-biphenyl) | —C(O)CH$_2$CH$_2$(p-biphenyl) |
| 42.13 | —C(O)o-PhOPh | —C(O)CH$_2$(o-PhOPh) | —C(O)CH$_2$CH$_2$(o-PhOPh) |
| 42.14 | —C(O)m-PhOPh | —C(O)CH$_2$(m-PhOPh) | —C(O)CH$_2$CH$_2$(m-PhOPh) |
| 42.15 | —C(O)p-PhOPh | —C(O)CH$_2$(p-PhOPh) | —C(O)CH$_2$CH$_2$(p-PhOPh) |
| 42.16 | —C(O)o-PhNHPh | —C(O)CH$_2$(o-PhNHPh) | —C(O)CH$_2$CH$_2$(o-PhNHPh) |
| 42.17 | —C(O)m-PhNHPh | —C(O)CH$_2$(m-PhNHPh) | —C(O)CH$_2$CH$_2$(m-PhNHPh) |
| 42.18 | —C(O)p-PhNHPh | —C(O)CH$_2$(p-PhNHPh) | —C(O)CH$_2$CH$_2$(p-PhNHPh) |
| 42.19 | —C(O)o-PhSPh | —C(O)CH$_2$(o-PhSPh) | —C(O)CH$_2$CH$_2$(o-PhSPh) |
| 42.20 | —C(O)m-PhSPh | —C(O)CH$_2$(m-PhSPh) | —C(O)CH$_2$CH$_2$(m-PhSPh) |
| 42.21 | —C(O)p-PhSPh | —C(O)CH$_2$(p-PhSPh) | —C(O)CH$_2$CH$_2$(p-PhSPh) |
| 42.22 | —C(O)o-PhCH$_2$SPh | —C(O)CH$_2$(o-PhCH$_2$SPh) | —C(O)CH$_2$CH$_2$(o-PhCH$_2$SPh) |
| 42.23 | —C(O)m-PhCH$_2$SPh | —C(O)CH$_2$(m-PhCH$_2$SPh) | —C(O)CH$_2$CH$_2$(m-PhCH$_2$SPh) |
| 42.24 | —C(O)p-PhCH$_2$SPh | —C(O)CH$_2$(p-PhCH$_2$SPh) | —C(O)CH$_2$CH$_2$(p-PhCH$_2$SPh) |
| 42.25 | —C(O)adamantyl | —C(O)CH$_2$(adamantyl) | —C(O)CH$_2$CH$_2$(adamantyl) |
| 42.26 | —C(O)cyclopentyl | —C(O)CH$_2$(cyclopentyl) | —C(O)CH$_2$CH$_2$((cyclopentyl) |
| 42.27 | —C(O)cyclohexyl | —C(O)CH$_2$(cyclohexyl) | —C(O)CH$_2$CH$_2$(cyclohexyl) |
| 42.28 | —C(O)CH$_2$O(cyclopentyl) | —C(O)CH$_2$NH(cyclopentyl) | —C(O)CH$_2$S(cyclopentyl) |
| 42.29 | —C(O)CH$_2$O(cyclohexyl) | —C(O)CH$_2$NH(cyclohexyl) | —C(O)CH$_2$S(cyclohexyl) |
| 42.30 | —C(O)pyridin-2-yl | —C(O)CH$_2$(pyridin-2-yl) | —C(O)CH$_2$CH$_2$(pyridin-2-yl) |
| 42.31 | —C(O)pyridin-3-yl | —C(O)CH$_2$(pyridin-3-yl) | —C(O)CH$_2$CH$_2$(pyridin-3-yl) |
| 42.32 | —C(O)pyridin-4-yl | —C(O)CH$_2$(pyridin-4-yl) | —C(O)CH$_2$CH$_2$(pyridin-4-yl) |
| 42.33 | —C(O)furan-2-yl | —C(O)CH$_2$(furan-2-yl) | —C(O)CH$_2$CH$_2$(furan-2-yl) |
| 42.34 | —C(O)furan-3-yl | —C(O)CH$_2$(furan-3-yl) | —C(O)CH$_2$CH$_2$(furan-3-yl) |
| 42.35 | —C(O)thiophen-2-yl | —C(O)CH$_2$(thiophen-2-yl) | —C(O)CH$_2$CH$_2$(thiophen-2-yl) |
| 42.36 | —C(O)thiophen-2-yl | —C(O)CH$_2$(thiophen-2-yl) | —C(O)CH$_2$CH$_2$(thiophen-2-yl) |
| 42.37 | —C(O)imidazo-2-yl | —C(O)CH$_2$(imidazo-2-yl) | —C(O)CH$_2$CH$_2$(imidazo-2-yl) |
| 42.38 | —C(O)oxazo-2-yl | —C(O)CH$_2$(oxazo-2-yl) | —C(O)CH$_2$CH$_2$(oxazo-2-yl) |
| 42.39 | —C(O)thioazo-2-yl | —C(O)CH$_2$(thioazo-2-yl) | —C(O)CH$_2$CH$_2$(thioazo-2-yl) |
| 42.40 | —C(O)benzofuran-2-yl | —C(O)CH$_2$(benzofuran-2-yl) | —C(O)CH$_2$CH$_2$(benzofuran-2-yl) |
| 42.41 | —C(O)benzofuran-3-yl | —C(O)CH$_2$(benzofuran-3-yl) | —C(O)CH$_2$CH$_2$(benzofuran-3-yl) |
| 42.42 | —C(O)benzothiophen-2-yl | —C(O)CH$_2$(benzothiophen-2-yl) | —C(O)CH$_2$CH$_2$(benzothiophen-2-yl) |
| 42.43 | —C(O)thiophen-2-yl | —C(O)CH$_2$(thiophen-2-yl) | —C(O)CH$_2$CH$_2$(thiophen-2-yl) |
| 42.44 | —C(O)benzimidazo-2-yl | —C(O)CH$_2$(benzimidazo-2-yl) | —C(O)CH$_2$CH$_2$(benzimidazo-2-yl) |
| 42.45 | —C(O)benzoxazo-2-yl | —C(O)CH$_2$(benzoxazo-2-yl) | —C(O)CH$_2$CH$_2$(benzoxazo-2-yl) |
| 42.46 | —C(O)benzothiazo-2-yl | —C(O)CH$_2$(benzothiazo-2-yl) | —C(O)CH$_2$CH$_2$(benzothiazo-2-yl) |
| 42.47 | —C(O)o-Ph(P(O)Ph$_3$) | —C(O)m-Ph(P(O)Ph$_3$) | —C(O)p-Ph(P(O)Ph$_3$) |
| 42.48 | —C(O)Ph-2-(fluoren-9-yl) | —C(O)Ph-3-(fluoren-9-yl) | —C(O)Ph-4-(fluoren-9-yl) |
| 42.49 | —C(O)N-indolin-2-one | —C(O)indolin-2-yl | —C(O)indol-2-yl |
| 42.50 | —C(O)C(CH$_3$)$_2$NHSO$_2$(naphth-2-yl) | —C(O)cyclopentyl-2-(Ph) | —C(O)cyclohexyl-2-(Ph) |
| 42.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 42.52 | —C(O)tetrahydronaphth-1-yl | —C(O)tetrahydronaphth-2-yl | —C(O)cyclopropyl-2,2-(Ph$_2$) |
| 42.53 | —C(O)tetrahydroisoquinolin-1-yl | —C(O)tetrahydroisoquinolin-3-yl | —C(O)CH$_2$((2-oxo)indolin-3-yl) |
| 42.54 | —C(O)CH$_2$(N-benzimidazol-2-one) | —C(O)CH$_2$(N-benzoxazol-2-one) | —C(O)CH$_2$(N-benzothiazol-2-one) |
| 42.55 | —C(O)CH$_2$(N-dihydroimidazol-2-one) | —C(O)CH$_2$(N-dihydrooxazol-2-one) | —C(O)CH$_2$(N-dihydrothiazol-2-one) |
| 42.56 | 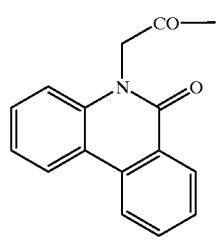 | 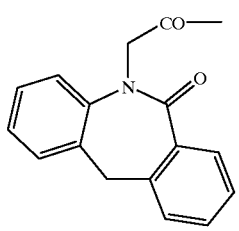 | 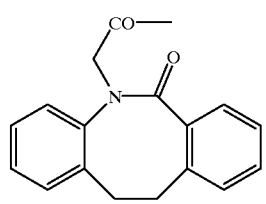 |

TABLE 42-continued

Formula III: A = —B(pinanediol); X = —CN; R³ = table below; R¹¹ = —CH₂CH₂Ph

| | .1 | .2 | .3 |
|---|---|---|---|
| 42.57 | | | |
| 42.58 | | | |

| 42.59 | —C(O)N(CH₃)CH₂Ph | —C(O)N(C₂H₅)CH₂Ph | —C(O)N(C₃H₇)CH₂Ph |
| 42.60 | —C(O)pyridin-3-yl-5-(Ph) | —C(O)Ph-3-(CH₂(thiophen-2-yl)) | —C(O)Ph-3-(CH₂Ph) |
| 42.61 | —C(O)C(CH₃)₂OPh | —C(O)CH(C₂H₅)OPh | —C(O)CH₂OCH₂Ph |
| 42.62 | —C(O)CH₂O(o-PhCH₂OH) | —C(O)CH₂O(m-PhCH₂OH) | —C(O)CH₂O(p-PhCH₂OH) |
| 42.63 | —C(O)CH₂O(o-PhCOOH) | —C(O)CH₂O(m-PhCOOH) | —C(O)CH₂O(p-PhCOOH) |
| 42.64 | —C(O)CH₂O(o-PhCOOCH₃) | —C(O)CH₂O(m-PhCOOCH₃) | —C(O)CH₂O(p-PhCOOCH₃) |
| 42.65 | —C(O)CH₂O(o-PhCH₂COOH) | —C(O)CH₂O(m-PhCH₂COOH) | —C(O)CH₂O(p-PhCH₂COOH) |

42.66

TABLE 43

Formula III: A = —B(pinanediol); X = —CH₂NH₂; R³ = table below; R¹¹ = CH₃

| | .1 | .2 | .3 |
|---|---|---|---|
| 43.1 | —C(O)Ph | —C(O)CH₂Ph | —C(O)CH₂CH₂Ph |
| 43.2 | —C(O)CH₂OPh | —C(O)CH₂NHPh | —C(O)CH₂SPh |
| 43.3 | —C(O)o-PhOH | —C(O)m-PhOH | —C(O)p-PhOH |
| 43.4 | —C(O)o-PhCH₂OH | —C(O)m-PhCH₂OH | —C(O)p-PhCH₂OH |
| 43.5 | —C(O)o-PhCOOH | —C(O)m-PhCOOH | —C(O)p-PhCOOH |
| 43.6 | —C(O)o-PhCH₂COOH | —C(O)m-PhCH₂COOH | —C(O)p-PhCH₂COOH |
| 43.7 | —C(O)naphth-1-yl | —C(O)CH₂(naphth-1-yl) | —C(O)CH₂CH₂(napth-1-yl) |
| 43.8 | —C(O)naphth-2-yl | —C(O)CH₂(naphth-2-yl) | —C(O)CH₂CH₂(napth-2-yl) |
| 43.9 | —C(O)o-biphenyl | —C(O)CH₂(o-biphenyl) | —C(O)CH₂CH₂(o-biphenyl) |
| 43.10 | —C(O)m-biphenyl | —C(O)CH₂(m-biphenyl) | —C(O)CH₂CH₂(m-biphenyl) |
| 43.12 | —C(O)p-biphenyl | —C(O)CH₂(p-biphenyl) | —C(O)CH₂CH₂(p-biphenyl) |
| 43.13 | —C(O)o-PhOPh | —C(O)CH₂(o-PhOPh) | —C(O)CH₂CH₂(o-PhOPh) |
| 43.14 | —C(O)m-PhOPh | —C(O)CH₂(m-PhOPh) | —C(O)CH₂CH₂(m-PhOPh) |
| 43.15 | —C(O)p-PhOPh | —C(O)CH₂(p-PhOPh) | —C(O)CH₂CH₂(p-PhOPh) |
| 43.16 | —C(O)o-PhNHPh | —C(O)CH₂(o-PhNHPh) | —C(O)CH₂CH₂(o-PhNHPh) |
| 43.17 | —C(O)m-PhNHPh | —C(O)CH₂(m-PhNHPh) | —C(O)CH₂CH₂(m-PhNHPh) |
| 43.18 | —C(O)p-PhNHPh | —C(O)CH₂(p-PhNHPh) | —C(O)CH₂CH₂(p-PhNHPh) |
| 43.19 | —C(O)o-PhSPh | —C(O)CH₂(o-PhSPh) | —C(O)CH₂CH₂(o-PhSPh) |

TABLE 43-continued

Formula III: A = —B(pinanediol); X = —CH₂NH₂; R³ = table below; R¹¹ = CH₃

| .1 | .2 | .3 |
|---|---|---|
| 43.20 —C(O)m-PhSPh | —C(O)CH₂(m-PhSPh) | —C(O)CH₂CH₂(m-PhSPh) |
| 43.21 —C(O)p-PhSPh | —C(O)CH₂(p-PhSPh) | —C(O)CH₂CH₂(p-PhSPh) |
| 43.22 —C(O)o-PhCH₂SPh | —C(O)CH₂(o-PhCH₂SPh) | —C(O)CH₂CH₂(o-PhCH₂SPh) |
| 43.23 —C(O)m-PhCH₂SPh | —C(O)CH₂(m-PhCH₂SPh) | —C(O)CH₂CH₂(m-PhCH₂SPh) |
| 43.24 —C(O)p-PhCH₂SPh | —C(O)CH₂(p-PhCH₂SPh) | —C(O)CH₂CH₂(p-PhCH₂SPh) |
| 43.25 —C(O)adamantyl | —C(O)CH₂(adamantyl) | —C(O)CH₂CH₂(adamantyl) |
| 43.26 —C(O)cyclopentyl | —C(O)CH₂(cyclopentyl) | —C(O)CH₂CH₂((cyclopentyl) |
| 43.27 —C(O)cyclohexyl | —C(O)CH₂(cyclohexyl) | —C(O)CH₂CH₂(cyclohexyl) |
| 43.28 —C(O)CH₂O(cyclopentyl) | —C(O)CH₂NH(cyclopentyl) | —C(O)CH₂S(cyclopentyl) |
| 43.29 —C(O)CH₂O(cyclohexyl) | —C(O)CH₂NH(cyclohexyl) | —C(O)CH₂S(cyclohexyl) |
| 43.30 —C(O)pyridin-2-yl | —C(O)CH₂(pyridin-2-yl) | —C(O)CH₂CH₂(pyridin-2-yl) |
| 43.31 —C(O)pyridin-3-yl | —C(O)CH₂(pyridin-3-yl) | —C(O)CH₂CH₂(pyridin-3-yl) |
| 43.32 —C(O)pyridin-4-yl | —C(O)CH₂(pyridin-4-yl) | —C(O)CH₂CH₂(pyridin-4-yl) |
| 43.33 —C(O)furan-2-yl | —C(O)CH₂(furan-2-yl) | —C(O)CH₂CH₂(furan-2-yl) |
| 43.34 —C(O)furan-3-yl | —C(O)CH₂(furan-3-yl) | —C(O)CH₂CH₂(furan-3-yl) |
| 43.35 —C(O)thiophen-2-yl | —C(O)CH₂(thiophen-2-yl) | —C(O)CH₂CH₂(thiophen-2-yl) |
| 43.36 —C(O)thiophen-2-yl | —C(O)CH₂(thiophen-2-yl) | —C(O)CH₂CH₂(thiophen-2-yl) |
| 43.37 —C(O)imidazo-2-yl | —C(O)CH₂(imidazo-2-yl) | —C(O)CH₂CH₂(imidazo-2-yl) |
| 43.38 —C(O)oxazo-2-yl | —C(O)CH₂(oxazo-2-yl) | —C(O)CH₂CH₂(oxazo-2-yl) |
| 43.39 —C(O)thioazo-2-yl | —C(O)CH₂(thioazo-2-yl) | —C(O)CH₂CH₂(thioazo-2-yl) |
| 43.40 —C(O)benzofuran-2-yl | —C(O)CH₂(benzofuran-2-yl) | —C(O)CH₂CH₂(benzofuran-2-yl) |
| 43.41 —C(O)benzofuran-3-yl | —C(O)CH₂(benzofuran-3-yl) | —C(O)CH₂CH₂(benzofuran-3-yl) |
| 43.42 —C(O)benzothiophen-2-yl | —C(O)CH₂(benzothiophen-2-yl) | —C(O)CH₂CH₂(benzothiophen-2-yl) |
| 43.43 —C(O)thiophen-2-yl | —C(O)CH₂(thiophen-2-yl) | —C(O)CH₂CH₂(thiophen-2-yl) |
| 43.44 —C(O)benzimidazo-2-yl | —C(O)CH₂(benzimidazo-2-yl) | —C(O)CH₂CH₂(benzimidazo-2-yl) |
| 43.45 —C(O)benzoxazo-2-yl | —C(O)CH₂(benzoxazo-2-yl) | —C(O)CH₂CH₂(benzoxazo-2-yl) |
| 43.46 —C(O)benzothiazo-2-yl | —C(O)CH₂(benzothiazo-2-yl) | —C(O)CH₂CH₂(benzothiazo-2-yl) |
| 43.47 —C(O)o-Ph(P(O)Ph₃) | —C(O)m-Ph(P(O)Ph₃) | —C(O)p-Ph(P(O)Ph₃) |
| 43.48 —C(O)Ph-2-(fluoren-9-yl) | —C(O)Ph-3-(fluoren-9-yl) | —C(O)Ph-4-(fluoren-9-yl) |
| 43.49 —C(O)N-indolin-2-one | —C(O)indolin-2-yl | —C(O)indol-2-yl |
| 43.50 —C(O)C(CH₃)₂NHSO₂(naphth-2-yl) | —C(O)cyclopentyl-2-(Ph) | —C(O)cyclohexyl-2-(Ph) |
| 43.51 —C(O)pyrrolidin-3-yl-4-(Ph) | —C(O)tetrahydrofuran-3-yl-4-(Ph) | —C(O)tetrahydrothiophen-3-yl-4-(Ph) |
| 43.52 —C(O)tetrahydronaphth-1-yl | —C(O)tetrahydronaphth-2-yl | —C(O)cyclopropyl-2,2-(Ph₂) |
| 43.53 —C(O)tetrahydroisoquinolin-1-yl | —C(O)tetrahydroisoquinolin-3-yl | —C(O)CH₂((2-oxo)indolin-3-yl) |
| 43.54 —C(O)CH₂(N-benzimidazol-2-one) | —C(O)CH₂(N-benzoxazol-2-one) | —C(O)CH₂(N-benzothiazol-2-one) |
| 43.55 —C(O)CH₂(N-dihydroimidazol-2-one) | —C(O)CH₂(N-dihydrooxazol-2-one) | —C(O)CH₂(N-dihydrothiazol-2-one) |

43.56

43.57

43.58

TABLE 43-continued

Formula III: A = —B(pinanediol); X = —CH₂NH₂; R³ = table below; R¹¹ = CH₃

| .1 | .2 | .3 |
|---|---|---|
| 43.59 —C(O)N(CH₃)CH₂Ph | —C(O)N(C₂H₅)CH₂Ph | —C(O)N(C₃H₇)CH₂Ph |
| 43.60 —C(O)pyridin-3-yl-5-(Ph) | —C(O)Ph-3-(CH₂(thiophen-2-yl)) | —C(O)Ph-3-(CH₂Ph) |
| 43.61 —C(O)C(CH₃)₂OPh | —C(O)CH(C₂H₅)OPh | —C(O)CH₂OCH₂Ph |
| 43.62 —C(O)CH₂O(o-PhCH₂OH) | —C(O)CH₂O(m-PhCH₂OH) | —C(O)CH₂O(p-PhCH₂OH) |
| 43.63 —C(O)CH₂O(o-PhCOOH) | —C(O)CH₂O(m-PhCOOH) | —C(O)CH₂O(p-PhCOOH) |
| 43.64 —C(O)CH₂O(o-PhCOOCH₃) | —C(O)CH₂O(m-PhCOOCH₃) | —C(O)CH₂O(p-PhCOOCH₃) |
| 43.65 —C(O)CH₂O(o-PhCH₂COOH) | —C(O)CH₂O(m-PhCH₂COOH) | —C(O)CH₂O(p-PhCH₂COOH) |

43.66

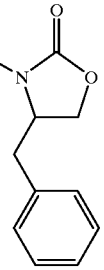

TABLE 44

Formula III: A = —B(pinanediol); X = CH₂NH₂; R³ = table below; R¹¹ = —CH₂CH₂Ph

| .1 | .2 | .3 |
|---|---|---|
| 44.1 —C(O)Ph | —C(O)CH₂Ph | —C(O)CH₂CH₂Ph |
| 44.2 —C(O)CH₂OPh | —C(O)CH₂NHPh | —C(O)CH₂SPh |
| 44.3 —C(O)o-PhOH | —C(O)m-PhOH | —C(O)p-PhOH |
| 44.4 —C(O)o-PhCH₂OH | —C(O)m-PhCH₂OH | —C(O)p-PhCH₂OH |
| 44.5 —C(O)o-PhCOOH | —C(O)m-PhCOOH | —C(O)p-PhCOOH |
| 44.6 —C(O)o-PhCH₂COOH | —C(O)m-PhCH₂COOH | —C(O)p-PhCH₂COOH |
| 44.7 —C(O)naphth-1-yl | —C(O)CH₂(naphth-1-yl) | —C(O)CH₂CH₂(napth-1-yl) |
| 44.8 —C(O)naphth-2-yl | —C(O)CH₂(naphth-2-yl | —C(O)CH₂CH₂(napth-2-yl) |
| 44.9 —C(O)o-biphenyl | —C(O)CH₂(o-biphenyl) | —C(O)CH₂CH₂(o-biphenyl) |
| 44.10 —C(O)m-biphenyl | —C(O)CH₂(m-biphenyl) | —C(O)CH₂CH₂(m-biphenyl) |
| 44.12 —C(O)p-biphenyl | —C(O)CH₂(p-biphenyl) | —C(O)CH₂CH₂(p-biphenyl) |
| 44.13 —C(O)o-PhOPh | —C(O)CH₂(o-PhOPh) | —C(O)CH₂CH₂(o-PhOPh) |
| 44.14 —C(O)m-PhOPh | —C(O)CH₂(m-PhOPh) | —C(O)CH₂CH₂(m-PhOPh) |
| 44.15 —C(O)p-PhOPh | —C(O)CH₂(p-PhOPh) | —C(O)CH₂CH₂(p-PhOPh) |
| 44.16 —C(O)o-PhNHPh | —C(O)CH₂(o-PhNHPh) | —C(O)CH₂CH₂(o-PhNHPh) |
| 44.17 —C(O)m-PhNHPh | —C(O)CH₂(m-PhNHPh) | —C(O)CH₂CH₂(m-PhNHPh) |
| 44.18 —C(O)p-PhNHPh | —C(O)CH₂(p-PhNHPh) | —C(O)CH₂CH₂(p-PhNHPh) |
| 44.19 —C(O)o-PhSPh | —C(O)CH₂(o-PhSPh) | —C(O)CH₂CH₂(o-PhSPh) |
| 44.20 —C(O)m-PhSPh | —C(O)CH₂(m-PhSPh) | —C(O)CH₂CH₂(m-PhSPh) |
| 44.21 —C(O)p-PhSPh | —C(O)CH₂(p-PhSPh) | —C(O)CH₂CH₂(p-PhSPh) |
| 44.22 —C(O)o-PhCH₂SPh | —C(O)CH₂(o-PhCH₂SPh) | —C(O)CH₂CH₂(o-PhCH₂SPh) |
| 44.23 —C(O)m-PhCH₂SPh | —C(O)CH₂(m-PhCH₂SPh) | —C(O)CH₂CH₂(m-PhCH₂SPh) |
| 44.24 —C(O)p-PhCH₂SPh | —C(O)CH₂(p-PhCH₂SPh) | —C(O)CH₂CH₂(p-PhCH₂SPh) |
| 44.25 —C(O)adamantyl | —C(O)CH₂(adamantyl) | —C(O)CH₂CH₂(adamantyl) |
| 44.26 —C(O)cyclopentyl | —C(O)CH₂(cyclopentyl) | —C(O)CH₂CH₂((cyclopentyl) |
| 44.27 —C(O)cyclohexyl | —C(O)CH₂(cyclohexyl) | —C(O)CH₂CH₂(cyclohexyl) |
| 44.28 —C(O)CH₂O(cyclopentyl) | —C(O)CH₂NH(cyclopentyl) | —C(O)CH₂S(cyclopentyl) |
| 44.29 —C(O)CH₂O(cyclohexyl) | —C(O)CH₂NH(cyclohexyl) | —C(O)CH₂S(cyclohexyl) |
| 44.30 —C(O)pyridin-2-yl | —C(O)CH₂(pyridin-2-yl) | —C(O)CH₂CH₂(pyridin-2-yl) |
| 44.31 —C(O)pyridin-3-yl | —C(O)CH₂(pyridin-3-yl) | —C(O)CH₂CH₂(pyridin-3-yl) |
| 44.32 —C(O)pyridin-4-yl | —C(O)CH₂(pyridin-4-yl) | —C(O)CH₂CH₂(pyridin-4-yl) |
| 44.33 —C(O)furan-2-yl | —C(O)CH₂(furan-2-yl) | —C(O)CH₂CH₂(furan-2-yl) |
| 44.34 —C(O)furan-3-yl | —C(O)CH₂(furan-3-yl) | —C(O)CH₂CH₂(furan-3-yl) |
| 44.35 —C(O)thiophen-2-yl | —C(O)CH₂(thiophen-2-yl) | —C(O)CH₂CH₂(thiophen-2-yl) |
| 44.36 —C(O)thiophen-2-yl | —C(O)CH₂(thiophen-2-yl) | —C(O)CH₂CH₂(thiophen-2-yl) |
| 44.37 —C(O)imidazo-2-yl | —C(O)CH₂(imidazo-2-yl) | —C(O)CH₂CH₂(imidazo-2-yl) |
| 44.38 —C(O)oxazo-2-yl | —C(O)CH₂(oxazo-2-yl) | —C(O)CH₂CH₂(oxazo-2-yl) |
| 44.39 —C(O)thioazo-2-yl | —C(O)CH₂(thioazo-2-yl) | —C(O)CH₂CH₂(thioazo-2-yl) |
| 44.40 —C(O)benzofuran-2-yl | —C(O)CH₂(benzofuran-2-yl) | —C(O)CH₂CH₂(benzofuran-2-yl) |
| 44.41 —C(O)benzofuran-3-yl | —C(O)CH₂(benzofuran-3-yl) | —C(O)CH₂CH₂(benzofuran-3-yl) |
| 44.42 —C(O)benzothiophen-2-yl | —C(O)CH₂(benzothiophen-2-yl) | —C(O)CH₂CH₂(benzothiophen-2-yl) |
| 44.43 —C(O)thiophen-2-yl | —C(O)CH₂(thiophen-2-yl) | —C(O)CH₂CH₂(thiophen-2-yl) |
| 44.44 —C(O)benzimidazo-2-yl | —C(O)CH₂(benzimidazo-2-yl) | —C(O)CH₂CH₂(benzimidazo-2-yl) |
| 44.45 —C(O)benzoxazo-2-yl | —C(O)CH₂(benzoxazo-2-yl) | —C(O)CH₂CH₂(benzoxazo-2-yl) |

TABLE 44-continued

Formula III: A = —B(pinanediol); X = CH$_2$NH$_2$; R$^3$ = table below; R$^{11}$ = —CH$_2$CH$_2$Ph

| | .1 | .2 | .3 |
|---|---|---|---|
| 44.46 | —C(O)benzothiazo-2-yl | —C(O)CH$_2$(benzothiazo-2-yl) | —C(O)CH$_2$CH$_2$(benzothiazo-2-yl) |
| 44.47 | —C(O)o-Ph(P(O)Ph$_3$) | —C(O)m-Ph(P(O)Ph$_3$) | —C(O)p-Ph(P(O)Ph$_3$) |
| 44.48 | —C(O)Ph-2-(fluoren-9-yl) | —C(O)Ph-3-(fluoren-9-yl) | —C(O)Ph-4-(fluoren-9-yl) |
| 44.49 | —C(O)N-indolin-2-one | —C(O)indolin-2-yl | —C(O)indol-2-yl |
| 44.50 | —C(O)C(CH$_3$)$_2$NHSO$_2$(naphth-2-yl) | —C(O)cyclopentyl-2-(Ph) | —C(O)cyclohexyl-2-(Ph) |
| 44.51 | —C(O)pyrrolidin-3-yl-4-(Ph) | —C(O)tetrahydrofuran-3-yl-4-(Ph) | —C(O)tetrahydrothiophen-3-yl-4-(Ph) |
| 44.52 | —C(O)tetrahydronaphth-1-yl | —C(O)tetrahydronaphth-2-yl | —C(O)cyclopropyl-2,2-(Ph$_2$) |
| 44.53 | —C(O)tetrahydroisoquinolin-1-yl | —C(O)tetrahydroisoquinolin-3-yl | —C(O)CH$_2$((2-oxo)indolin-3-yl) |
| 44.54 | —C(O)CH$_2$(N-benzimidazol-2-one) | —C(O)CH$_2$(N-benzoxazol-2-one) | —C(O)CH$_2$(N-benzothiazol-2-one) |
| 44.55 | —C(O)CH$_2$(N-dihydroimidazol-2-one) | —C(O)CH$_2$(N-dihydrooxazol-2-one) | —C(O)CH$_2$(N-dihydrothiazol-2-one) |

44.56 [structure] [structure] [structure]

44.57 [structure] [structure] [structure]

44.58 [structure] [structure] [structure]

| 44.59 | —C(O)N(CH$_3$)CH$_2$Ph | —C(O)N(C$_2$H$_5$)CH$_2$Ph | —C(O)N(C$_3$H$_7$)CH$_2$Ph |
| 44.60 | —C(O)pyridin-3-yl-5-(Ph) | —C(O)Ph-3-(CH$_2$(thiophen-2-yl)) | —C(O)Ph-3-(CH$_2$Ph) |
| 44.61 | —C(O)CH(CH$_3$)$_2$OPh | —C(O)CH(C$_2$H$_5$)OPh | —C(O)CH$_2$OCH$_2$Ph |
| 44.62 | —C(O)CH$_2$O(o-PhCH$_2$OH) | —C(O)CH$_2$O(m-PhCH$_2$OH) | —C(O)CH$_2$O(p-PhCH$_2$OH) |
| 44.63 | —C(O)CH$_2$O(o-PhCOOH) | —C(O)CH$_2$O(m-PhCOOH) | —C(O)CH$_2$O(p-PhCOOH) |
| 44.64 | —C(O)CH$_2$O(o-PhCOOCH$_3$) | —C(O)CH$_2$O(m-PhCOOCH$_3$) | —C(O)CH$_2$O(p-PhCOOCH$_3$) |
| 44.65 | —C(O)CH$_2$O(o-PhCH$_2$COOH) | —C(O)CH$_2$O(m-PhCH$_2$COOH) | —C(O)CH$_2$O(p-PhCH$_2$COOH) |

44.66 [structure]

TABLE 45

Formula IV: A = —B(OH)$_2$; X = —CN; Y = table below

| | .1 | .2 | .3 |
|---|---|---|---|
| 45.1 | —C(O)CH$_2$(N-benzimidazol-2-one) | —C(O)CH$_2$(N-benzoxazol-2-one) | —C(O)CH$_2$(N-benzothiazol-2-one) |
| 45.2 | —C(O)CH$_2$(N-dihydroimidazol-2-one) | —C(O)CH$_2$(N-dihydrooxazol-2-one) | —C(O)CH$_2$(N-dihydrothiazol-2-one) |
| 45.3 | *structure* | *structure* | *structure* |
| 45.4 | *structure* | *structure* | *structure* |
| 45.5 | *structure* | *structure* | *structure* |
| 45.6 | *structure* | | |

TABLE 46

Formula IV: A = —B(OH)$_2$; X = —CH$_2$NH$_2$; Y = table below

| | .1 | .2 | .3 |
|---|---|---|---|
| 46.1 | —C(O)CH$_2$(N-benzimidazol-2-one) | —C(O)CH$_2$(N-benzoxazol-2-one) | —C(O)CH$_2$(N-benzothiazol-2-one) |
| 46.2 | —C(O)CH$_2$(N-dihydroimidazol-2-one) | —C(O)CH$_2$(N-dihydrooxazol-2-one) | —C(O)CH$_2$(N-dihydrothiazol-2-one) |

TABLE 46-continued

Formula IV: A = —B(OH)$_2$; X = —CH$_2$NH$_2$; Y = table below

| | .1 | .2 | .3 |
|---|---|---|---|
| 46.3 | [structure: phenanthridinone with N-CH$_2$CO—] | [structure: dibenzazepinone with N-CH$_2$CO—] | [structure: dibenzazocinone with N-CH$_2$CO—] |
| 46.4 | [structure: hexahydrobenzimidazol-2-one with N-CH$_2$CO—] | [structure: hexahydrobenzoxazol-2-one with N-CH$_2$CO—] | [structure: hexahydrobenzothiazol-2-one with N-CH$_2$CO—] |
| 46.5 | [structure: 3-benzylidene-indolin-2-one with N-CH$_2$CO—] | [structure: 4-phenylpiperazine with N-CH$_2$CO—] | [structure: 5-phenyl-oxazolidin-2-one with N-CH$_2$CO—] |
| 46.6 | [structure: 4-benzyl-oxazolidin-2-one with N-CH$_2$CO—] | | |

TABLE 47

Formula IV: A = —B(pinanediol); X = —CN; Y = table below

| | .1 | .2 | .3 |
|---|---|---|---|
| 47.1 | —C(O)CH$_2$(N-benzimidazol-2-one) | —C(O)CH$_2$(N-benzoxazol-2-one) | —C(O)CH$_2$(N-benzothiazol-2-one) |
| 47.2 | —C(O)CH$_2$(N-dihydroimidazol-2-one) | —C(O)CH$_2$(N-dihydrooxazol-2-one) | —C(O)CH$_2$(N-dihydrothiazol-2-one) |
| 47.3 | [structure: phenanthridinone with N-CH$_2$CO—] | [structure: dibenzazepinone with N-CH$_2$CO—] | [structure: dibenzazocinone with N-CH$_2$CO—] |

TABLE 47-continued

Formula IV: A = —B(pinanediol); X = —CN; Y = table below

| | .1 | .2 | .3 |
|---|---|---|---|
| 47.4 | (structure) | (structure) | (structure) |
| 47.5 | (structure) | (structure) | (structure) |
| 47.6 | (structure) | | |

TABLE 48

Formula IV: A = —B(pinanediol); X = —CH₂NH₂; Y = table below

| | .1 | .2 | .3 |
|---|---|---|---|
| 48.1 | —C(O)CH₂(N-benzimidazol-2-one) | —C(O)CH₂(N-benzoxazol-2-one) | —C(O)CH₂(N-benzothiazol-2-one) |
| 48.2 | —C(O)CH₂(N-dihydroimidazol-2-one) | —C(O)CH₂(N-dihydrooxazol-2-one) | —C(O)CH₂(N-dihydrothiazol-2-one) |
| 48.3 | (structure) | (structure) | (structure) |
| 48.4 | (structure) | (structure) | (structure) |

TABLE 48-continued

Formula IV: A = —B(pinanediol); X = —CH$_2$NH$_2$; Y = table below

| .1 | .2 | .3 |
|---|---|---|
| 48.5 [structure] | [structure] | [structure] |
| 48.6 [structure] | | |

TABLE 49

Formula I: A = —B(pinanediol); X = See Table below;
R$^3$ = hydrocinnamoyl; R$^{11}$ = —CH$_2$CH$_2$Ph

| Example No. | .1 | .2 | .3 |
|---|---|---|---|
| 49.1 | —NH$_2$ | —NHCH(=NH)H | —CH$_2$NHC(=NH)NH$_2$ |
| 49.2 | —NHC(=NH)NH$_2$ | —CH$_2$NH$_2$ | |

TABLE 50

Formula I: A = —B(pinanediol); X = See Table below;
R$^3$ = hydrocinnamoyl; R$^{11}$ = —N(CH$_3$)$_2$

| Example No. | .1 | .2 | .3 |
|---|---|---|---|
| 50.1 | —NH$_2$ | —NHCH(=NH)H | —CH$_2$NH$_2$ |
| 50.2 | —CH$_2$NHC(=NH)NH$_2$ | —NHC(=NH)NH$_2$ | |

TABLE 51

Formula I: A = —B(pinanediol); X = —CH$_2$NH$_2$;
R$^3$ = hydrocinnamoyl; R$^{11}$ = See Table below

| Example No. | .1 | .2 | .3 |
|---|---|---|---|
| 51.1 | —CH$_2$(m-PhCF$_3$) | —CH$_2$(m-PhCH$_3$) | |

TABLE 52

Formula I: A = —B(OH)$_2$; X = —CH$_2$NH$_2$;
R$^3$ = hydrocinnamoyl; R$^{11}$ = See Table below

| Example No. | .1 | .2 | .3 |
|---|---|---|---|
| 52.1 | —CH$_2$(m-PhCF$_3$) | —CH$_2$(m-PhCH$_3$) | |

TABLE 53

Formula I: A = —B(OH)$_2$; X = —CH$_2$NH$_2$;
R$^3$ = hydrocinnamoyl; R$^{11}$ = See Table below

| Example No. | .1 | .2 | .3 |
|---|---|---|---|
| 53.1 | -(2,2-dimethyl-2-phenyl)ethyl | -(2,2-ethanediyl-2-phenyl)ethyl | -(2,2-diethyl-2-phenyl)ethyl |
| 53.2 | -N-phenyl-N-methyl | -N-benzyl-N-methyl | —C(=O)CH$_2$CH$_2$CO$_2$H |
| 53.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 53.4 | -2-(3,5-dimethyl)phenyl ethyl | -cyclopropyl | -cyclohexyl |

TABLE 54

Formula I: A = —B(pinanediol); X = —CH$_2$NH$_2$;
R$^3$ = hydrocinnamoyl; R$^{11}$ = See Table below

| Example No. | .1 | .2 | .3 |
|---|---|---|---|
| 54.1 | -(2,2-dimethyl-2-phenyl)ethyl | -(2,2-ethanediyl-2-phenyl)ethyl | -(2,2-diethyl-2-phenyl)ethyl |
| 54.2 | -N-phenyl-N-methyl | -N-benzyl-N-methyl | —C(=O)CH$_2$CH$_2$CO$_2$H |
| 54.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 54.4 | -2-(3,5-dimethyl)phenylethyl | -cyclopropyl | -cyclohexyl |

TABLE 55

Formula I: A = —B(OH)$_2$; X = —NHC(=NH)NH$_2$;
R$^3$ = hydrocinnamoyl; R$^{11}$ = See Table below

| Example No. | .1 | .2 | .3 |
|---|---|---|---|
| 55.1 | -(2,2-dimethyl-2-phenyl)ethyl | -(2,2-ethanediyl-2-phenyl)ethyl | -(2,2-diethyl-2-phenyl)ethyl |
| 55.2 | -N-phenyl-N-methyl | -N-benzyl-N-methyl | —C(=O)CH$_2$CH$_2$CO$_2$H |
| 55.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 55.4 | -2-(3,5-dimethyl)phenylethyl | -cyclopropyl | -cyclohexyl |

TABLE 56

Formula I: A = —B(pinanediol); X = —NHC(=NH)NH$_2$;
R$^3$ = hydrocinnamoyl; R$^{11}$ = See Table below

| Example No. | .1 | .2 | .3 |
|---|---|---|---|
| 56.1 | -(2,2-dimethyl-2-phenyl)ethyl | -(2,2-ethanediyl-2-phenyl)ethyl | -(2,2-diethyl-2-phenyl)ethyl |
| 56.2 | -N-phenyl-N-methyl | -N-benzyl-N-methyl | —C(=O)CH$_2$CH$_2$CO$_2$H |
| 56.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 56.4 | -2-(3,5-dimethyl)phenylethyl | -cyclopropyl | -cyclohexyl |

TABLE 57

Formula I: A = —B(OH)$_2$; X = —NHC(=NH)H;
R$^3$ = hydrocinnamoyl; R$^{11}$ = See Table below

| Example No. | .1 | .2 | .3 |
|---|---|---|---|
| 57.1 | -(2,2-dimethyl-2-phenyl)ethyl | -(2,2-ethanediyl-2-phenyl)ethyl | -(2,2-diethyl-2-phenyl)ethyl |
| 57.2 | -N-phenyl-N-methyl | -N-benzyl-N-methyl | —C(=O)CH$_2$CH$_2$CO$_2$H |
| 57.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 57.4 | -2-(3,5-dimethyl)phenylethyl | -cyclopropyl | -cyclohexyl |

TABLE 58

Formula I: A = —B(pinanediol); X = —NHC(=NH)H;
R$^3$ = hydrocinnamoyl; R$^{11}$ = See Table below

| Example No. | .1 | .2 | .3 |
|---|---|---|---|
| 58.1 | -(2,2-dimethyl-2-phenyl)ethyl | -(2,2-ethanediyl-2-phenyl)ethyl | -(2,2-diethyl-2-phenyl)ethyl |
| 58.2 | -N-phenyl-N-methyl | -N-benzyl-N-methyl | —C(=O)CH$_2$CH$_2$CO$_2$H |
| 58.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 58.4 | -2-(3,5-dimethyl)phenylethyl | -cyclopropyl | -cyclohexyl |

TABLE 59

Formula I: A = —B(OH)$_2$; X = —NH$_2$;
R$^3$ = hydrocinnamoyl; R$^{11}$ = See Table below

| Example No. | .1 | .2 | .3 |
|---|---|---|---|
| 59.1 | -(2,2-dimethyl-2-phenyl)ethyl | -(2,2-ethanediyl-2-phenyl)ethyl | -(2,2-diethyl-2-phenyl)ethyl |
| 59.2 | -N-phenyl-N-methyl | -N-benzyl-N-methyl | —C(=O)CH$_2$CH$_2$CO$_2$H |
| 59.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 59.4 | -2-(3,5-dimethyl)phenylethyl | -cyclopropyl | -cyclohexyl |

TABLE 60

Formula I: A = —B(pinanediol); X = —NH$_2$;
R$^3$ = hydrocinnamoyl; R$^{11}$ = See Table below

| Example No. | .1 | .2 | .3 |
|---|---|---|---|
| 60.1 | -(2,2-dimethyl-2-phenyl)ethyl | -(2,2-ethanediyl-2-phenyl)ethyl | -(2,2-diethyl-2-phenyl)ethyl |
| 60.2 | -N-phenyl-N-methyl | -N-benzyl-N-methyl | —C(=O)CH$_2$CH$_2$CO$_2$H |
| 60.3 | —C(=O)CH$_2$CH$_2$—CO$_2$CH$_3$ | -(2,2-butanediyl-2-phenyl)ethyl | -[2,2-dimethyl-2-(3,5-dimethyl)-phenyl]ethyl |
| 60.4 | -2-(3,5-dimethyl)phenyl ethyl | -cyclopropyl | -cyclohexyl |

TABLE 61

Formula I: A = See Table below; X = —CH$_2$NH$_2$;
R$^3$ = hydrocinnamoyl; R$^{11}$ = —CH$_3$

| Example No. | .1 | .2 | .3 |
|---|---|---|---|
| 61.1 | —C(=O)CO$_2$H | —C(=O)OCH$_2$CH$_2$—NHCbz | —C(=O)OCH$_2$CH$_2$—NH$_2$ |
| 61.2 | —C(=O)OCH$_3$ HCL | —C(=O)OCH$_3$ free base | —C(=O)CH$_3$ |
| 61.3 | —CH$_2$OH | —CH$_2$OH; X = —CH$_2$NHCbz | —C(=O)OH; X = —CH$_2$NHCbz |
| 61.4 | —C(OH)(OCH$_3$)—C(=O)OCH$_3$ | —C(=O)NHNH$_2$ | |

TABLE 62

Formula I: A = —B(pinanediol); X = See Table below;
R$^3$ = 2-(2-cyanothiophenyl)-benzoyl; R$^{11}$ = —CH$_3$

| Example No. | .1 | .2 | .3 |
|---|---|---|---|
| 62.1 | —Br | —CH$_2$Br | —SC(=NH)NH$_2$ |
| 62.2 | —N$_3$ | —CH$_2$SC(=NH)NH$_2$ | —CH$_2$N$_3$ |
| 62.3 | —NH$_2$ | —CH$_2$NHC(=NH)NH$_2$ | —NHC(=NH)NH$_2$ |
| 62.4 | —NHC(=NH)H | —CH$_2$NHC(=NH)H | —CH$_2$NH$_2$ |
| 62.4 | —SCN | | |

TABLE 63

Formula I: A = —B(pinanediol); X = See Table below;
R$^3$ = 2-(thiophenyl)benzoyl; R$^{11}$ = —CH$_3$

| Example No. | .1 | .2 | .3 |
|---|---|---|---|
| 63.1 | —Br | —CH$_2$Br | —SC(=NH)NH$_2$ |
| 63.2 | —N$_3$ | —CH$_2$SC(=NH)NH$_2$ | —CH$_2$N$_3$ |
| 63.3 | —NH$_2$ | —CH$_2$NHC(=NH)NH$_2$ | —NHC(=NH)NH$_2$ |
| 63.4 | —NHC(=NH)H | —CH$_2$NHC(=NH)H | —CH$_2$NH$_2$ |
| 63.5 | —SCN | | |

TABLE 64

Formula I: A = —B(pinanediol); X = —CH$_2$NH$_2$;
R$^3$ = See Table below; R$^{11}$ = —CH$_3$

| Example No. | .1 | .2 | .3 |
|---|---|---|---|
| 64.1 | 2-(benzyl)-benzyl | 2-(benzyl)-benzyl; R$^{11}$ = —C(=O)CH | 2-(pyrrol-1-ylmethyl)benzyl |

TABLE 64-continued

Formula I: A = —B(pinanediol); X = —CH$_2$NH$_2$;
R$^3$ = See Table below; R$^{11}$ = —CH$_3$

| Example No. | .1 | .2 | .3 |
|---|---|---|---|
| 64.2 | 2-(2-methylbenzyl)-benzoyl | 3-(3-trifluoro-methylbenzyl)-benzoyl | 3-(3-chlorobenzyl)-benzoyl |
| 64.3 | 2-(2-cyano-benzyl)benzoyl | | |

TABLE 65

Formula I: A = —B(OH)$_2$; X = —CH$_2$NH$_2$;
R$^3$ = See Table below; R$^{11}$ = —CH$_3$

| Example No. | .1 | .2 | .3 |
|---|---|---|---|
| 65.1 | 2-(benzyl)-benzyl | 2-(benzyl)-benzyl; R$^{11}$ = —C(=O)CH | 2-(pyrrol-1-ylmethyl)benzyl |
| 65.2 | 2-(2-methylbenzyl)-benzoyl | 3-(3-trifluoro-methylbenzyl)-benzoyl | 3-(3-chlorobenzyl)-benzoyl |
| 65.3 | 2-(2-cyano-benzyl)benzoyl | | |

TABLE 66

Formula I: A = —B(OH)$_2$; X = —CH$_2$NH$_2$;
R$^3$ = See Table below; R$^{11}$ = —N(CH$_3$)CH$_2$Ph

| Example No. | .1 | .2 | .3 |
|---|---|---|---|
| 66.1 | —C(=O)CH$_2$CH$_2$—CH$_2$CO$_2$H | —C(=O)CH$_2$C—(CH$_3$)$_2$CH$_2$CO$_2$H | —C(=O)CH$_2$C—(CH$_3$)$_2$CH$_2$CO$_2$CH$_3$ |
| 66.2 | —C(=O)CH—(NHBOC)—CH$_2$CH$_2$CO$_2$H | —C(=O)CH—(NHBOC)CH$_2$CO$_2$H | —C(=O)CH—(NHBOC)—CH$_2$CH$_2$CO$_2$CH$_3$ |
| 66.3 | —C(=O)CH$_2$CH$_2$CO$_2$H | —C(=O)CH$_2$NH—S(O)$_2$CH$_3$ | —C(=O)CH$_2$CH$_2$—CO$_2$CH$_3$ |
| 66.4 | —C(=O)CH$_2$CH$_2$—CH$_2$CO$_2$CH$_3$ | —C(=O)CH$_2$N—(CH$_3$)S(O)$_2$CH$_3$ | |

TABLE 67

Formula I: A = —B(pinanediol); X = —CH$_2$NH$_2$;
R$^3$ = See Table below; R$^{11}$ = —N(CH$_3$)CH$_2$Ph

| Example No. | .1 | .2 | .3 |
|---|---|---|---|
| 67.1 | —C(=O)CH$_2$CH$_2$—CH$_2$CO$_2$H | —C(=O)CH$_2$C—(CH$_3$)$_2$CH$_2$CO$_2$H | —C(=O)CH$_2$C—(CH$_3$)$_2$CH$_2$CO$_2$CH$_3$ |
| 67.2 | —C(=O)CH—(NHBOC)—CH$_2$CH$_2$CO$_2$H | —C(=O)CH—(NHBOC)CH$_2$CO$_2$H | —C(=O)CH—(NHBOC)—CH$_2$CH$_2$CO$_2$CH$_3$ |
| 67.3 | —C(=O)CH$_2$CH$_2$CO$_2$H | —C(=O)CH$_2$NH—S(O)$_2$CH$_3$ | —C(=O)CH$_2$CH$_2$—CO$_2$CH$_3$ |
| 67.4 | —C(=O)CH$_2$CH$_2$—CH$_2$CO$_2$CH$_3$ | —C(=O)CH$_2$N—(CH$_3$)S(O)$_2$CH$_3$ | |

TABLE 68

Formula I: A = —B(OH)$_2$; X = —CH$_2$NH$_2$;
R$^3$ = See Table below; R$^{11}$ = —CH$_2$CH$_2$Ph

| Example No. | .1 | .2 | .3 |
|---|---|---|---|
| 68.1 | —C(=O)CH$_2$CH$_2$—CH$_2$CO$_2$H | —C(=O)CH$_2$C—(CH$_3$)$_2$CH$_2$CO$_2$H | —C(=O)CH$_2$C—(CH$_3$)$_2$CH$_2$CO$_2$CH$_3$ |
| 68.2 | —C(=O)CH—(NHBOC)—CH$_2$CH$_2$CO$_2$H | —C(=O)CH—(NHBOC)CH$_2$CO$_2$H | —C(=O)CH—(NHBOC)—CH$_2$CH$_2$CO$_2$CH$_3$ |
| 68.3 | —C(=O)CH$_2$CH$_2$CO$_2$H | —C(=O)CH$_2$NH—S(O)$_2$CH$_3$ | —C(=O)CH$_2$CH$_2$—CO$_2$CH$_3$ |

TABLE 68-continued

Formula I: A = —B(OH)$_2$; X = —CH$_2$NH$_2$;
R$^3$ = See Table below; R$^{11}$ = —CH$_2$CH$_2$Ph

| Example No. | .1 | .2 | .3 |
|---|---|---|---|
| 68.4 | —C(=O)CH$_2$CH$_2$—CH$_2$CO$_2$CH$_3$ | —C(=O)CH$_2$N—(CH$_3$)S(O)$_2$CH$_3$ | |

TABLE 69

Formula I: A = —B(pinanediol); X = —CH$_2$NH$_2$;
R$^3$ = See Table below; R$^{11}$ = —CH$_2$CH$_2$Ph

| Example No. | .1 | .2 | .3 |
|---|---|---|---|
| 69.1 | —C(=O)CH$_2$CH$_2$—CH$_2$CO$_2$H | —C(=O)CH$_2$C—(CH$_3$)$_2$CH$_2$CO$_2$H | —C(=O)CH$_2$C—(CH$_3$)$_2$CH$_2$CO$_2$CH$_3$ |
| 69.2 | —C(=O)CH—(NHBOC)—CH$_2$CH$_2$CO$_2$H | —C(=O)CH—(NHBOC)CH$_2$CO$_2$H | —C(=O)CH—(NHBOC)—CH$_2$CH$_2$CO$_2$CH$_3$ |
| 69.3 | —C(=O)CH$_2$CH$_2$CO$_2$H | —C(=O)CH$_2$NH—S(O)$_2$CH$_3$ | —C(=O)CH$_2$CH$_2$—CO$_2$CH$_3$ |
| 69.4 | —C(=O)CH$_2$CH$_2$—CH$_2$CO$_2$CH$_3$ | —C(=O)CH$_2$N—(CH$_3$)S(O)$_2$CH$_3$ | |

TABLE 70

Formula I: A = See Table below; X = —CH$_2$NH$_2$;
R$^3$ = 2-(benzyl)benzoyl; R$^{11}$ = —CH$_3$

| Example No. | .1 | .2 | .3 |
|---|---|---|---|
| 70.1 | —C(=O)CO$_2$H | —C(=O)OCH$_2$CH$_2$—NHCbz | —C(=O)OCH$_2$CH$_2$—NH$_2$ |
| 70.2 | —C(=O)OCH$_3$ HCL | —C(=O)OCH$_3$ free base | —C(=O)CH$_3$ |
| 70.3 | —CH$_2$OH | —CH$_2$OH; X = —CH$_2$NHCbz | —C(=O)OH; X = —CH$_2$NHCbz |
| 70.4 | —C(OH)(OCH$_3$)—C(=O)OCH$_3$ | —C(=O)NHNH$_2$ | |

TABLE 71

Formula I: A = See Table below; X = —CH$_2$NH$_2$;
R$^3$ = 2-(2-trifluoromethylbenzyl)benzoyl; R$^{11}$ = —CH$_3$

| Example No. | .1 | .2 | .3 |
|---|---|---|---|
| 71.1 | —C(=O)CO$_2$H | —C(=O)OCH$_2$CH$_2$—NHCbz | —C(=O)OCH$_2$CH$_2$—NH$_2$ |
| 71.2 | —C(=O)OCH$_3$ HCL | —C(=O)OCH$_3$ free base | —C(=O)CH$_3$ |
| 71.3 | —CH$_2$OH | —CH$_2$OH; X = —CH$_2$NHCbz | —C(=O)OH; X = —CH$_2$NHCbz |
| 71.4 | —C(OH)(OCH$_3$)—C(=O)OCH$_3$ | —C(=O)NHNH$_2$ | |

TABLE 72

Formula I: A = —B(OH)$_2$; X = See Table below;
R$^3$ = hydrocinnamoyl; R$^{11}$ = —N(CH$_3$)$_2$

| Example No. | .1 | .2 | .3 |
|---|---|---|---|
| 72.1 | —NH$_2$ | —NHCH(=NH)H | —CH$_2$NH$_2$ |
| 72.2 | —CH$_2$NHC(=NH)NH$_2$ | —NHC(=NH)NH$_2$ | |

TABLE 73

Formula I: A = —B(pinanediol); X = —CH$_2$NH$_2$;
R$^3$ = —C(=O)CH$_2$CH$_2$CO$_2$H; R$^{11}$ = See Table below

| Example No. | .1 | .2 | .3 |
|---|---|---|---|
| 73.1 | —CH$_2$(m-PhCF$_3$) | —CH$_2$(m-PhCH$_3$) | |

TABLE 74

Formula I: A = —B(pinanediol); X = —NHC(=NH)NH$_2$;
R$^3$ = See Table below; R$^{11}$ = —CH$_3$

| Example No. | .1 | .2 | .3 |
|---|---|---|---|
| 74.1 | 2-(benzyl)benzyl | 2-(benzyl)benzyl; R$^{11}$ = —C(=O)CH | 2-(pyrrol-1-ylmethyl)benzyl |
| 74.2 | 2-(2-methylbenzyl)benzoyl | 3-(3-trifluoromethylbenzyl)benzoyl | 3-(3-chlorobenzyl)benzoyl |
| 74.3 | 2-(2-cyanobenzyl)benzoyl | | |

TABLE 75

Formula I: A = —B(OH)$_2$; X = —NHC(=NH)NH$_2$;
R$^3$ = See Table below; R$^{11}$ = —CH$_3$

| Example No. | .1 | .2 | .3 |
|---|---|---|---|
| 75.1 | 2-(benzyl)benzyl | 2-(benzyl)benzyl; R$^{11}$ = —C(=O)CH | 2-(pyrrol-1-ylmethyl)benzyl |
| 75.2 | 2-(2-methylbenzyl)benzoyl | 3-(3-trifluoromethylbenzyl)benzoyl | 3-(3-chlorobenzyl)benzoyl |
| 75.3 | 2-(2-cyanobenzyl)benzoyl | | |

TABLE 76

Formula I: A = —B(OH)$_2$; X = —CH$_2$NHC(=NH)H;
R$^3$ = See Table below; R$^{11}$ = -cyclopropyl

| Example No. | .1 | .2 | .3 |
|---|---|---|---|
| 76.1 | hydrocinnamoyl | —C(=O)CH$_2$OPh | —C(=O)CH$_2$SPh |

TABLE 77

Formula I: A = —B(pinanediol); X = —CH$_2$NHC(=NH)H;
R$^3$ = See Table below; R$^{11}$ = -cyclopropyl

| Example No. | .1 | .2 | .3 |
|---|---|---|---|
| 77.1 | hydrocinnamoyl | —C(=O)CH$_2$OPh | —C(=O)CH$_2$SPh |

TABLE 78

Formula I: A = —B(OH)$_2$; X = —CH$_2$NH$_2$;
R$^3$ = See Table below; R$^{11}$ = -cyclopropyl

| Example No. | .1 | .2 | .3 |
|---|---|---|---|
| 78.1 | hydrocinnamoyl | —C(=O)CH$_2$OPh | —C(=O)CH$_2$SPh |

TABLE 79

Formula I: A = —B(pinanediol); X = —CH$_2$NH$_2$;
R$^3$ = See Table below; R$^{11}$ = -cyclopropyl

| Example No. | .1 | .2 | .3 |
|---|---|---|---|
| 79.1 | hydrocinnamoyl | —C(=O)CH$_2$OPh | —C(=O)CH$_2$SPh |

UTILITY

The compounds which are described in the present invention represent a novel class of potent, reversible inhibitors of trypsin-like enzymes. Trypsin-like enzymes are a group of proteases which hydrolyzed peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Enzymes of the complement system, acrosin (required for fertilization), pancreatic trypsin are also in this group. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. Intervention by a synthetic inhibitor would clearly be valuable. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infractions and other clotting disorders. However, a low molecular weight thrombin inhibitor, containing a different functionality, was effective in blocking arterial thrombosis (Hanson and Harker, *Proc. Natl. Acad. Sci. U.S.A.* 85, 3184 (1988). Therefore, we have chosen to demonstrate utility of compounds in the inhibition of thrombin, both as in buffered solutions and in plasma. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention are expected to be effective in the control of aberrant proteolysis and a number of accompanying disease states such as inflammation, pancretitis, and heritary angioedema.

The effectiveness of compounds of the present invention as inhibitors of blood coagulation proteases was determined using purified human proteases and synthetic substrates following procedures similar to those described in Kettner et al. (1990).

For these assays, the rate of enzymatic (thrombin, Factor Xa, and Factor VIIa) hydrolysis of chromogenic substrates (S2238 (H-D-Phe-Pip-Arg-pNA), S2222, and S2288, respectively; Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Thrombin and Xa determinations were made in 0.10 M sodium phosphate buffer, pH 7.5, containing 0.20 M NaCl, and 0.5% PEG 8000. VIIa determinations were made in 0.05 M tris buffer, pH 7.6, containing 0.10 M NaCl, 4 mM $CaCl_2$, and 0.1% bovine serum albumin. The Michaelis constant, $K_m$, for substrate hydrolysis was determined at 25° C. using the method of Lineweaver and Burk.

Values of $K_i$ were determined by allowing 0.2–0.5 nM human thrombin or human factor Xa (Enzyme Research Laboratories, South Bend, Ind.), or 50 nM human factor VIIa (BioSPacific, Emeryville, Calif.) react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_O - v_S}{v_S} = \frac{I}{K_i(1 + S/K_m)}$$

where:

$v_o$ is the velocity of the control in the absence of inhibitor;

$v_s$ is the velocity in the presence of inhibitor;

I is the concentration of inhibitor;

$K_i$ is the dissociation constant of the enzyme: inhibitor complex;

S is the concentration of substrate;

$K_m$ is the Michaelis constant.

Using the methodology described above, representative compounds of this invention were evaluated and found to exhibit a $K_i$ of less 500 μM thereby confirming the utility of compounds of the invention as effective inhibitors of human blood coagulation proteases. The results of these assays are summarized in Table 80, where +++ indicates a $K_i$<500 nM; ++ indicates a $K_i$<50,000 nM; and + indicates a $K_i$ 500,000<nM; − indicates inactive.

TABLE 80

$K_i$ values for inhibition of Serine Proteases by compounds of the present invention.

| Ex No. | Trombin | Factor Xa | Factor VIIa | $IC_{50}$ Thrombin time |
|---|---|---|---|---|
| 49.1.1 | +++ | ++ | inactive | NT |
| 49.1.2 | +++ | NT | NT | +++ |
| 49.1.3 | +++ | +++ | NT | +++ |
| 49.2.1 | +++ | +++ | NT | ++ |
| 50.1.1 | NT | NT | NT | NT |
| 50.1.2 | +++ | NT | NT | +++ |
| 50.1.3 | +++ | NT | NT | NT |
| 51.1.1 | +++ | +++ | ++ | NT |
| 51.1.2 | +++ | NT | NT | NT |
| 52.1.1 | +++ | +++ | ++ | NT |
| 52.1.2 | +++ | +++ | ++ | +++ |
| 53.1.1 | +++ | +++ | +++ | +++ |
| 53.1.2 | +++ | +++ | +++ | +++ |
| 53.2.1 | +++ | NT | NT | ++ |
| 53.2.2 | +++ | +++ | +++ | NT |
| 53.4.3 | +++ | ++ | +++ | NT |
| 54.1.1 | +++ | NT | NT | NT |
| 54.1.2 | +++ | ++ | +++ | +++ |
| 54.1.3 | +++ | ++ | +++ | NT |
| 54.2.1 | +++ | NT | NT | ++ |
| 54.2.2 | +++ | NT | NT | ++ |
| 54.2.3 | +++ | ++ | ++ | NT |
| 54.3.1 | +++ | ++ | ++ | NT |
| 54.3.2 | +++ | ++ | +++ | NT |
| 54.3.3 | NT | ++ | +++ | NT |
| 54.4.1 | NT | ++ | ++ | NT |
| 54.4.2 | +++ | ++ | +++ | +++ |
| 54.4.3 | +++ | ++ | +++ | ++ |
| 55.1.1 | +++ | +++ | +++ | NT |
| 56.1.1 | +++ | +++ | +++ | NT |
| 56.1.2 | +++ | +++ | +++ | NT |
| 56.3.3 | +++ | +++ | +++ | NT |
| 56.4.1 | NT | NT | NT | NT |
| 57.1.1 | +++ | +++ | +++ | NT |
| 57.1.2 | +++ | +++ | +++ | NT |
| 57.4.2 | +++ | ++ | NT | +++ |
| 58.1.1 | +++ | +++ | +++ | NT |
| 58.3.3 | NT | NT | NT | NT |
| 58.4.1 | NT | NT | NT | NT |
| 58.4.2 | ++ | NT | NT | NT |
| 59.1.1 | +++ | ++ | +++ | NT |
| 59.4.2 | +++ | ++ | NT | +++ |
| 60.1.1 | +++ | ++ | NT | NT |
| 60.3.3 | +++ | ++ | ++ | NT |
| 60.4.1 | +++ | ++ | ++ | NT |
| 60.4.2 | +++ | NT | NT | NT |
| 61.1.1 | +++ | ++ | ++ | NT |
| 61.1.2 | ++ | Inactive | Inactive | NT |
| 61.1.3 | ++ | ++ | Inactive | NT |
| 61.2.1 | ++ | ++ | ++ | NT |
| 61.2.2 | ++ | Inactive | Inactive | NT |
| 61.2.3 | NT | Inactive | Inactive | NT |
| 61.3.1 | ++ | Inactive | Inactive | NT |
| 61.3.2 | ++ | Inactive | Inactive | NT |
| 61.3.3 | ++ | ++ | inactive | NT |
| 61.4.1 | +++ | ++ | ++ | ++ |
| 62.1.1 | ++ | ++ | ++ | NT |
| 62.1.2 | ++ | ++ | ++ | NT |
| 62.1.3 | +++ | +++ | +++ | NT |
| 62.2.1 | ++ | ++ | ++ | NT |
| 62.2.2 | +++ | +++ | ++ | NT |
| 62.2.3 | ++ | ++ | ++ | NT |
| 62.3.1 | ++ | ++ | ++ | NT |
| 62.3.2 | +++ | +++ | ++ | NT |
| 62.3.3 | +++ | +++ | +++ | NT |
| 62.4.1 | +++ | +++ | +++ | NT |
| 62.4.2 | +++ | +++ | ++ | NT |
| 62.4.3 | +++ | +++ | ++ | ++ |
| 63.1.3 | +++ | +++ | ++ | NT |
| 63.3.1 | +++ | ++ | inactive | NT |
| 63.4.1 | +++ | +++ | ++ | +++ |
| 63.4.2 | +++ | +++ | ++ | ++ |
| 63.5.1 | ++ | ++ | inactive | NT |

TABLE 80-continued $K_i$ values for inhibition of Serine Proteases by compounds of the present invention.

| Ex No. | Trombin | Factor Xa | Factor VIIa | IC$_{50}$ Thrombin time |
|---|---|---|---|---|
| 64.1.1 | +++ | ++ | ++ | Inactive |
| 64.1.2 | +++ | ++ | +++ | NT |
| 64.1.3 | +++ | NT | NT | ++ |
| 64.2.2 | +++ | +++ | ++ | NT |
| 64.2.3 | +++ | +++ | +++ | NT |
| 65.1.3 | +++ | NT | NT | ++ |
| 66.1.1 | +++ | +++ | ++ | ++ |
| 66.1.2 | +++ | NT | ++ | NT |
| 66.1.3 | +++ | NT | ++ | NT |
| 66.3.2 | +++ | +++ | +++ | +++ |
| 67.1.2 | +++ | ++ | ++ | NT |
| 67.1.3 | +++ | +++ | ++ | NT |
| 67.3.2 | +++ | NT | NT | NT |
| 68.2.1 | +++ | ++ | ++ | NT |
| 68.3.1 | +++ | ++ | ++ | NT |
| 68.3.3 | +++ | ++ | ++ | ++ |
| 68.4.1 | +++ | +++ | ++ | ++ |
| 68.4.2 | +++ | NT | NT | NT |
| 69.1.1 | +++ | +++ | ++ | ++ |
| 69.2.1 | +++ | NT | +++ | NT |
| 69.2.2 | +++ | NT | +++ | NT |
| 69.2.3 | +++ | NT | ++ | NT |
| 69.3.2 | +++ | +++ | +++ | +++ |
| 69.4.1 | +++ | ++ | ++ | NT |
| 69.4.2 | +++ | NT | NT | NT |
| 70.4.2 | ++ | ++ | inactive | NT |
| 71.4.2 | ++ | NT | NT | NT |
| 72.1.3 | +++ | NT | NT | +++ |
| 73.1.2 | +++ | +++ | ++ | NT |
| 75.3.1 | NT | NT | +++ | NT |
| 76.1.1 | +++ | NT | NT | NT |
| 77.1.1 | +++ | NT | NT | NT |
| 78.1.2 | +++ | NT | NT | +++ |
| 78.1.3 | +++ | NT | NT | +++ |
| 79.1.2 | +++ | NT | NT | +++ |
| 79.1.3 | +++ | NT | NT | +++ |

What is claimed is:

1. A compound of formula (I)

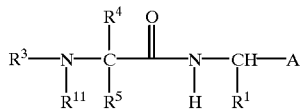

or a pharmaceutically acceptable salt thereof, wherein:

$R^1$ is
a) —($C_1$–$C_{12}$ alkyl)—X, a
b) —($C_1$–$C_{12}$ alkenyl)—X, or c)
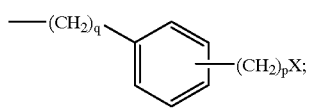

x is
a) halogen,
b) —CN,
c) —$NO_2$,
d) —$CF_3$,
e) —$NH_2$,
f) —$NHOR^2$,
g) —NHC(=NH)$R^2$,
h) —NHC(=NH)NHOH,
i) —NHC(=NH)NH$NH_2$,
j) —NHC(=NH)NHCN,
k) —NHC(=NH)$NHR^2$,
l) —NHC(=NH)NHCO$R^2$,
m) —C(=NH)$NHR^2$,
n) —C(=NH)NHCO$R^2$,
o) —C(=O)$NHR^2$,
p) —$CO_2R^2$,
q) —$OR^2$,
r) —$OCF_3$,
s) —S(O)$_r R^2$,
t) —SC(=NH)$NHR^2$, or
u) —SC(=NH)NHC(=O)$R^2$;

$R^2$ is
a) hydrogen, or
b) $C_1$–$C_4$ alkyl;

$R^3$ is
a) —C(=O)—($CH_2$)$_p$—$CR^6R^7$—($CH_2$)$_q$-aryl,
b) —C(=O)—W—$CR^8R^9$-aryl, with the proviso that W cannot be a bivalent oxygen atom,
c) —C(=O)—$CR^8R^9$—W—($CH_2$)$_r$-aryl, with the proviso that W cannot be —$NR^4$— or —NC(=O)$R^4$—,
d) —C(=O)—W—$CR^8R^9$-heteroaryl,
e) —C(=O)—$CR^8R^9$—W—($CH_2$)$_r$-heteroaryl, with the proviso that W cannot be —$NR^4$— or —NC(=O)$R^4$—,
f) —C(=O)—W—$CR^8R^9$-heterocycle,
g) —C(=O)—$CR^8R^9$—W—($CH_2$)$_r$-heterocycle, with the proviso that W cannot be —$NR^4$— or —NCO$R^4$—, h) —C(=O)—($CH_2$)$_r$—W—($C_5$–$C_7$ cycloalkyl), i)
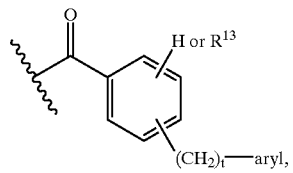

wherein aryl is limited to phenyl, j)
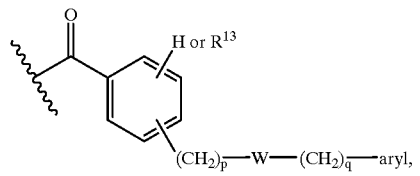

wherein aryl is limited to phenyl, k)
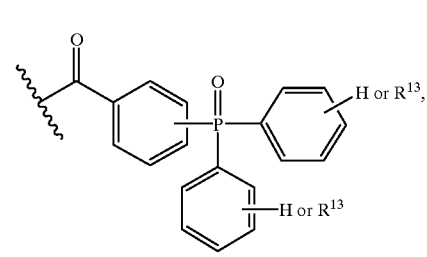

l)
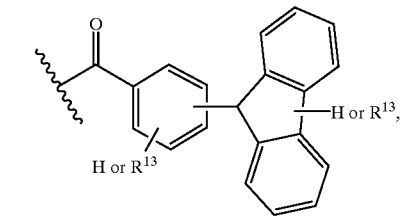

m)
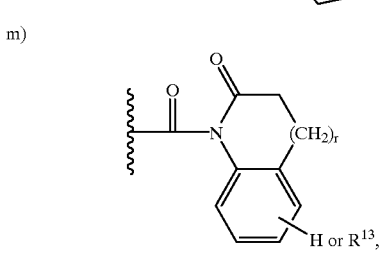

n) 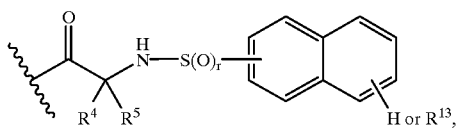

with the proviso that $R^{13}$ cannot be —N($C_1$–$C_4$ alkyl)$_2$ when A is —C(=O)$R^{14}$, o) 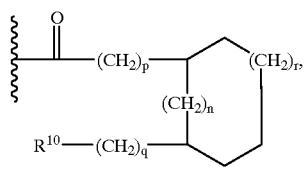

p) 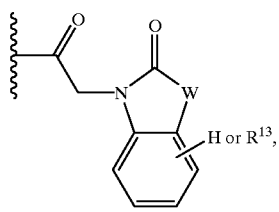

q) 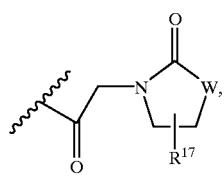

r) 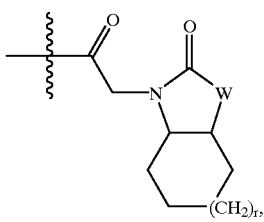

s) 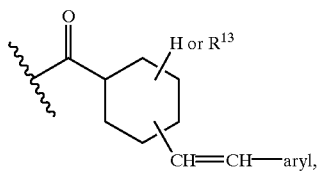

wherein aryl is limited to phenyl, t) —C(=O)—(CR$^8$R$^9$)—NHS(O)$_r$R$^8$, u) 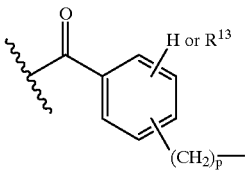

$R^4$ and $R^5$ are independently selected at each occurrence from the group consisting of:
a) hydrogen,
b) $C_1$–$C_4$ alkyl,
c) —($C_1$–$C_4$ alkyl)-aryl, or
d) $C_5$–$C_7$ cycloalkyl;

$R^8$ and $R^9$ are independently selected at each occurrence from the group consisting of:
a) hydrogen,
b) $C_1$–$C_4$ alkyl,
c) $C_1$–$C_4$ alkoxy,
d) aryl,
e) —($C_1$–$C_4$ alkyl)-aryl,
f) —($C_1$–$C_4$ alkyl)-heterocycle,
g) —O-aryl,
h) —(CH$_2$)$_p$—CO$_2$R$^4$,
i) $R^8$ and $R^9$ can be taken together to form a ($C_2$–$C_7$) alkyl;

$R^{10}$ is:
phenyl, wherein phenyl is optionally substituted with one to three substituents selected from the group consisting of halogen, $C_1$–$C_4$ alkyl, $C_1$–$C_4$ alkoxy, $C_7$–$C_{15}$ alkylaryl, $C_7$–$C_{15}$ alkoxyaryl, methylenedioxy, —NO$_2$, —CF$_3$, —SH, —S(O)$_r$—($C_1$–$C_4$ alkyl), CN, —OH, —NH$_2$, —NH($C_1$–$C_4$ alkyl), —N($C_1$–$C_4$ alkyl)$_2$, —NHCOR$^4$, —(CH$_2$)$_p$—CO$_2$R$^4$;

$R^{11}$ is:
a) —OR$^4$,
b) —NR$^{15}$R$^{16}$,
c) —NC(=O)R$^{15}$R$^{16}$,
d) —NR$^{15}$C(=O)OR$^4$,
e) aryl,
f) —($C_1$–$C_4$ alkyl)-aryl,
g) heteroaryl,
h) —($C_1$–$C_4$ alkyl)-heteroaryl,
i) —($C_1$–$C_4$ alkyl)—CO$_2$R$^4$,
j) heterocycle,
k) —($C_1$–$C_4$ alkyl)heterocycle, l) 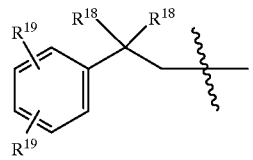

or m) 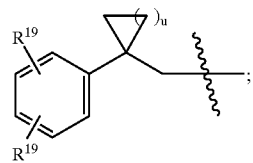

$R^3$ and $R^{11}$, when taken together to form a ring bonded to the nitrogen:

a) 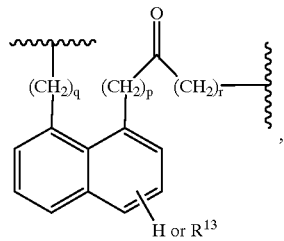, b) 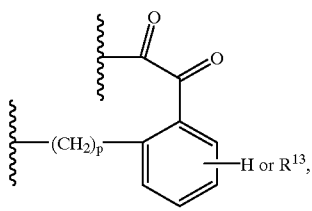, c) 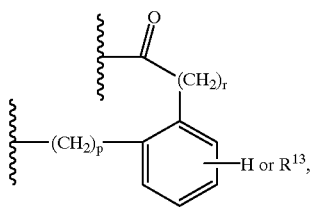, d) 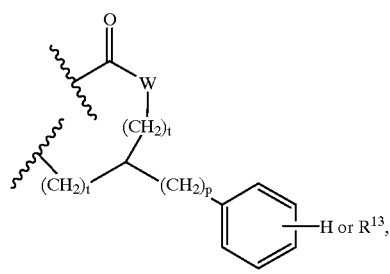, e) 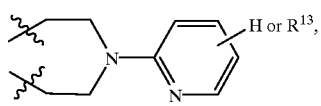, f) 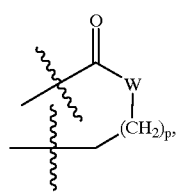

g) 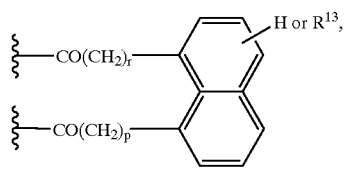

h) 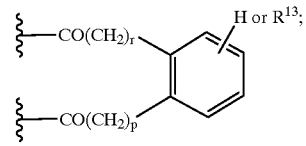;

$R^{13}$ is independently selected at each occurrence from the group consisting of:
a) hydrogen
b) halogen,
c) $C_1$–$C_4$ alkyl,
d) $C_1$–$C_4$ alkoxy,
e) methylenedioxy,
f) —$NO_2$,
g) —$CF_3$,
h) —SH,
i) —$S(O)_r$—($C_1$–$C_4$ alkyl),
j) —CN,
k) —OH,
l) —$NH_2$,
m) —NH($C_1$–$C_4$ alkyl),
n) —N($C_1$–$C_4$ alkyl)$_2$,
o) —NHC(=O)$R^4$, or
p) —$(CH_2)_p$—$CO_2R^4$;

$R^{14}$ is:
a) —$CF_3$,
b) —$CHF_2$,
c) —$CH_2F$,
d) —$CH_2Cl$,
e) —C(=O)$OR^4$,
f) —C(=O)$NR^{15}R^{16}$,
g) —C(=O)$R^4$,
h) —C(=O)$COOR^4$,
i) —C(=O)C(=O)$NR^{15}R^{16}$,
j) —C(=O)C(=O)$R^4$,
k) —$CY^3Y^4COOR^4$,
l) —$CY^3Y^4$C(=O)$NR^{15}R^{16}$, or
m) —$CY^3Y^4$C(=O)$R^4$;

$R^{15}$ and $R^{16}$ are independently selected at each occurrence from the group consisting of:
a) hydrogen,
b) $C_1$–$C_4$ alkyl,
c) —($C_1$–$C_4$ alkyl)-aryl,
d) $C_5$–$C_7$ cycloalkyl, or
e) phenyl, unsubstituted or substituted by $R^{13}$;

$R^{15}$ and $R^{16}$ taken together to form a ring can also include:

a) 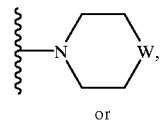

or

-continued b)

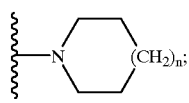

$R^{17}$ is:
a) hydrogen,
b) $C_1-C_4$ alkyl,
c) aryl,
d) —($C_1-C_4$ alkyl)-aryl, or
e) $C_5-C_7$ cycloalkyl;

$R^{18}$ is:
a) hydrogen,
b) —($C_1-C_5$) alkyl, or
c) —($C_1-C_5$) haloalkyl,
d) —($C_1-C_5$) alkoxy;

$R^{19}$ is:
a) hydrogen,
b) —($C_1-C_5$) alkyl,
c) halo, or
d) —($C_1-C_5$) haloalkyl,
e) —$NO_2$,
f) —$NR^4R^5$,
g) —CN,
h) —($C_1-C_5$) alkoxy;

A is:
—$BY^1Y^2$ ;

W is
a) —O—,
b) —S(O)$_r$—,
c) —$NR^4$—, or
d) —NC(=O)$R^4$—;

$Y^1$ and $Y^2$ are
a) —OH,
b) —F,
c) —$NR^4R^5$,
d) $C_1-C_8$ alkoxy, or
when taken together $Y^1$ and $Y^2$ form:
e) a cyclic boron ester where said chain or ring contains from 2 to 20 carbon atoms and, optionally, 1–3 heteroatoms which can be N, S, or O,
f) a cyclic boron amide where said chain or ring contains from 2 to 20 carbon atoms and, optionally, 1–3 heteroatoms which can be N, S, or O,
g) a cyclic boron amide-ester where said chain or ring contains from 2 to 20 carbon atoms and, optionally, 1–3 heteroatoms which can be N, S, or O;

$Y^3$ and $Y^4$ are
a) —OH or
b) —F;

n is 0 or 1;
p is 0 to 3;
q is 0 to 4;
r is 0 to 2;
t is 1 to 3;
v is 1 to 17;

wherein aryl is defined as phenyl, fluorenyl, biphenyl and naphthyl, which may be unsubstituted or include optional substitution with one to three substituents;

heteroaryl is 2-, or 3-, or 4-pyridyl; 2- or 3-furyl; 2- or 3-benzofuranyl; 2-, or 3-thiophenyl; 2- or 3-benzo[b]thiophenyl; 2-, or 3-, or 4-quinolinyl; 1-, or 3-, or 4-isoquinolinyl; 2- or 3-pyrrolyl; 1- or 2- or 3-indolyl; 2-, or 4-, or 5-oxazolyl; 2-benzoxazolyl; 2- or 4- or 5-imidazolyl; 1- or 2-benzimidazolyl; 2- or 4- or 5-thiazolyl; 2-benzothiazolyl; 3- or 4- or 5-isoxazolyl; 3- or 4- or 5-pyrazolyl; 3- or 4-or 5-isothiazolyl; 3- or 4-pyridazinyl; 2- or 4- or 5-pyrimidinyl; 2-pyrazinyl; 2-triazinyl; 3- or 4-cinnolinyl; 1-phthalazinyl; 2- or 4-quinazolinyl; or 2-quinoxalinyl ring; said ring(s) may be unsubstituted or include optional substitution with one to three substituents;

heterocycle is tetrahydroisoquinoline, tetrahydroquinoline, tetrahydrofuran, tetrahydrothiophene, piperidine, piperazine, morpholino; said ring(s) may be unsubstituted or include optional substitution with one to three substituents;

the substituents that may be attached to the aryl, heteroaryl and heterocycle ring(s) may be independently selected at each occurrence from the group consisting of:

halogen, $C_1-C_4$ alkyl, $C_1-C_4$ alkoxy, methylenedioxy, —$NO_2$, —$CF_3$, —SH, —S(O)$_r$—($C_1-C_4$ alkyl)—CN, —OH, —$NH_2$, —NH($C_1-C_4$ alkyl) —N($C_1-C_4$ alkyl)$_2$, —NHC(=O)$R^4$, —$(CH_2)_p$—$CO_2R^4$, phenyl which may be unsubstituted or substituted with $R^{13}$.

2. A compound of claim 1 wherein heteroaryl is 2-, 3-, or 4-pyridyl; 2-, or 3-furyl; 2-, or 3-thiophenyl; 2-, 3-, or 4-quinolinyl; or 1-, 3-, or 4-isoquinolinyl which may be unsubstitued or include optional substitution with one to three substituents; and heterocycle is 1-, 3-, or 4-tetrahydroisoquinolinyl, 2- or 3-pyrrolidinyl, and 2-, 3- or 4-piperidinyl which may be unsubstituted or include optional substitution with one to three substituents.

3. A compound of claim 2 wherein $R^3$ is
a) —C(=O)—$(CH_2)_p$—$CR^6R^7$—$(CH_2)_q$-aryl, b)

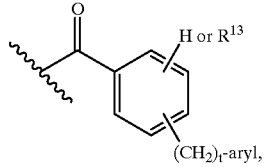

wherein aryl is limited to phenyl;

c)

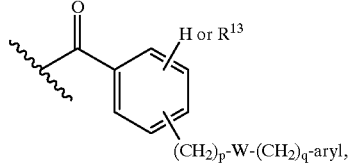

wherein aryl is limited to phenyl; or d)

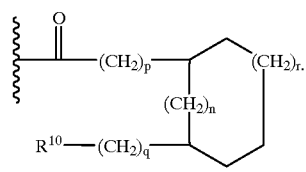

4. A compound of claim 3 wherein $R^3$ is hydrocinnamoyl and $R^{11}$ is

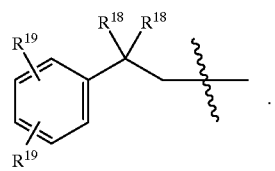

5. A compound of claim 4 wherein $R^4$ and $R^5$ are both H.

6. A compound of claim 1 selected from the group consisting of:

Hydrocinnamoyl-[N-(Phenethyl)-Gly]-boroOrn-C10H16 HCl
Hydrocinnamoyl-[N-(Phenethyl)-Gly]-boroOrn(CH=NH)-C10H16 HCl
Hydrocinnamoyl-[N-(Phenethyl)-Gly]-boroOrn(CH=NH)—OH HCl
Hydrocinnamoyl-[N-(Phenethyl)-Gly]-boroArg(CH3)-C10H16 HCl
Hydrocinnamoyl-[N-(N(CH3)$_2$)-Gly]-boroLys-C10H16 HCl
Hydrocinnamoyl-[N-(N(CH3)$_2$)-Gly]-boroLys—OH HCl
Hydrocinnamoyl-[N-(N(CH3)$_2$)-Gly]-boroOrn-C10H16 HCl
Hydrocinnamoyl-[N-(N(CH3)$_2$)-Gly]-boroOrn(CH=NH)-C10H16 HCl
Methanesulfonyl-Gly-[N-(Phenethyl)-Gly]-boroLys-C10H16 HCl
Hydrocinnamoyl-[N-(3-(Trifluoromethyl)-Phenethyl)-Gly]-boroLys-C10H16 HCl
Hydrocinnamoyl-[N-(3-(Trifluoromethyl)-Phenethyl)-Gly]-boroLys—OH HCl
Hydrocinnamoyl-[N-(3-(Methyl)-Phenethyl)-Gly]-boroLys-C10H16 HCl
Hydrocinnamoyl-[N-(3-(Methyl)-Phenethyl)-Gly]-boroLys—OH HCl
Succinyl-[N-(3-(Methyl)-Phenethyl)-Gly]-boroLys-C10H16 HCl
Hydrocinnamoyl-[N-(2,2-(Dimethyl)-Phenethyl)-Gly]-boroLys—OH HCl
Hydrocinnamoyl-[N-(2-(Cyclopropyl)-Phenethyl)-Gly]-boroLys-C10H16 HCl
Hydrocinnamoyl-[N-(2-(Cyclopropyl)-Phenethyl)-Gly]-boroLys—OH HCl
Hydrocinnamoyl-[N-(2-(Cyclopropyl)-Phenethyl)-Gly]-boroOrn(CH=NH)—OH HCl
Hydrocinnamoyl-[N-(2,2-(Diethyl)-Phenethyl)-Gly]-boroLys-C10H16 HCl
Acetyl-Gly[N-(2-(Benzyl)-Benzyl)]-boroLys-C10H16 HCl
Pinanediol N-{N-methyl-N-[2-(pyrrol-1-ylmethyl)-Benzyl]glycyl}-1-amido-5-aminopentaneboronate, hydrochloride salt
Phenoxyacetyl-[N-(Cyclopropyl)-Gly]-boroLys-C10H16 HCl
Thiophenacetyl-[N-(Cyclopropyl)-Gly]-boroLys-C10H16 HCl
Phenoxyacetyl-[N-(Cyclopropyl)-Gly]-boroLys—OH HCl
Thiophenacetyl-[N-(Cyclopropyl)-Gly]-boroLys—OH HCl
Glutaryl-[N-(Phenethyl)-Gly]-boroLys—OH HCl
Glutaryl(3,3-Dimethyl)-[N-(Phenethyl)-Gly]-boroLys-C10H16
Methyl Glutaryl(3,3-Dimethyl)-[N-(Phenethyl)-Gly]-boroLys-C10H16 HCl
Glutaryl(3,3-Dimethyl)-[N-(Phenethyl)-Gly]-boroLys—OH
Methyl Glutaryl(3,3-Dimethyl)-[N-(Phenethyl)-Gly]-boroLys—OH HCl
Boc-Asp-[N-(Phenethyl)-Gly]-boroLys-C10H16
Boc-Glu-[N-(Phenethyl)-Gly]-boroLys-C10H16
Boc-Glu(OCH3)-[N-(Phenethyl)-Gly]-boroLys-C10H16 HCl
Boc-Glu-[N-(Phenethyl-Gly)-boroLys—OH
Methanesylfonyl-Gly-[N-(N-(Methyl)-Benzyl)-Gly]-boroLys-C10H16 HCl
Methanesulfonyl-Gly-[N-(N-(Methyl)-Benzyl)-Gly]-boroLys—OH HCl
Succinyl-[N-(Phenethyl)-Gly]-boroLys—OH
Methyl Succinyl-[N-(Phenethyl)-Gly]-boroLys—OH HCl
Glutaryl-[N-(Phenethyl)-Gly]-boroLys-C10H16
Methyl Glutaryl-[N-(Phenethyl)-Gly]-boroLys-C10H16 HCl
Methyl Glutaryl-[N-(Phenethyl)-Gly]-boroLys—OH HCl.

7. A pharmaceutical composition comprising a pharmaceutically suitable carrier and a therapeutically effective amount of a compound of claim 1.

8. A pharmaceutical composition comprising a pharmaceutically suitable carrier and a therapeutically effective amount of a compound of claim 2.

9. A pharmaceutical composition comprising a pharmaceutically suitable carrier and a therapeutically effective amount of a compound of claim 6.

10. A method of treating a physiological disorder in a warm blooded animal catalyzed by trypsin-like enzymes comprising administering to an animal in need such treatment an effective amount of a compound of claim 1.

11. A method of treating a physiological disorder in a warm blooded animal catalyzed by trypsin-like enzymes comprising administering to an animal in need such treatment an effective amount of a compound of claim 2.

12. A method of treating a physiological disorder in a warm blooded animal catalyzed by trypsin-like enzymes comprising administering to an animal in need such treatment an effective amount of a compound of claim 6.

* * * * *